(12) United States Patent
Ito et al.

(10) Patent No.: US 11,107,999 B2
(45) Date of Patent: Aug. 31, 2021

(54) CONDENSED CYCLIC COMPOUND AND AN ORGANIC LIGHT-EMITTING DEVICE INCLUDING THE SAME

(71) Applicant: SAMSUNG DISPLAY CO., LTD., Yongin-si (KR)

(72) Inventors: Naoyuki Ito, Yongin-si (KR); Seulong Kim, Yongin-si (KR); Younsun Kim, Yongin-si (KR); Dongwoo Shin, Yongin-si (KR); Jungsub Lee, Yongin-si (KR); Jino Lim, Yongin-si (KR)

(73) Assignee: SAMSUNG DISPLAY CO., LTD., Yongin-si (KR)

( * ) Notice: Subject to any disclaimer, the term of this patent is extended or adjusted under 35 U.S.C. 154(b) by 93 days.

(21) Appl. No.: 15/399,349

(22) Filed: Jan. 5, 2017

(65) Prior Publication Data

US 2017/0194573 A1    Jul. 6, 2017

(30) Foreign Application Priority Data

Jan. 5, 2016  (KR) .................. 10-2016-0001115
Jan. 5, 2016  (KR) .................. 10-2016-0001122
Jan. 20, 2016 (KR) .................. 10-2016-0006995
Jan. 20, 2016 (KR) .................. 10-2016-0006996

(51) Int. Cl.
| H01L 51/54 | (2006.01) |
| H01L 51/00 | (2006.01) |
| C07D 307/77 | (2006.01) |
| C09K 11/02 | (2006.01) |
| C07D 333/50 | (2006.01) |

(Continued)

(52) U.S. Cl.
CPC ........ H01L 51/0073 (2013.01); C07D 307/77 (2013.01); C07D 307/91 (2013.01); C07D 333/50 (2013.01); C07D 405/10 (2013.01); C07D 493/04 (2013.01); C07D 495/04 (2013.01); C09K 11/025 (2013.01); C09K 11/06 (2013.01); H01L 51/006 (2013.01); H01L 51/0052 (2013.01); H01L 51/0058 (2013.01); H01L 51/0074 (2013.01); H01L 51/5265 (2013.01); C09K 2211/1007 (2013.01); C09K 2211/1011 (2013.01); C09K 2211/1014 (2013.01); H01L 51/0054 (2013.01); H01L 51/5012 (2013.01); H01L 51/5016 (2013.01); H01L 51/5056 (2013.01);

(Continued)

(58) Field of Classification Search
CPC .. C07D 307/77; C07D 307/91; C07D 333/50; C07D 405/00; C07D 405/10; C07D 493/00; C07D 493/04; C07D 495/00; C07D 495/02; C07D 495/04; C09K 11/025; C09K 11/06; C09K 2211/00; C09K 2211/10; C09K 2211/1011; C09K 2211/1014; C09K 2211/1007; H01L 51/0032; H01L 51/005; H01L 51/0052; H01L 51/0054; H01L 51/0058; H01L 51/006; H01L 51/0072; H01L 51/0073; H01L 51/0074; H01L 51/50; H01L 51/5012; H01L 51/5016; H01L 51/5056; H01L 51/5206; H01L 51/5265
USPC ....... 428/690, 691, 917, 411.4, 336; 427/58, 427/66; 313/500–512; 257/40, 88–104, 257/E51.001–E51.052; 252/301.16–301.35
See application file for complete search history.

(56) References Cited

U.S. PATENT DOCUMENTS 7,839,074 B2   11/2010   Ikeda et al.
8,241,763 B2   8/2012    Buesing et al.
(Continued)

FOREIGN PATENT DOCUMENTS

KR   10-2008-0049770    6/2008
KR   10-2008-0109000    12/2008
(Continued)

OTHER PUBLICATIONS

Machine translation of KR2015-0128583. (Year: 2015).*
(Continued)

*Primary Examiner* — Andrew K Bohaty
(74) *Attorney, Agent, or Firm* — F. Chau & Associates, LLC

(57) ABSTRACT

A condensed cyclic compound represented by Formula 1-1 or Formula 1-2 and an organic light-emitting device including the same.

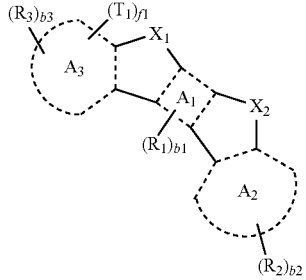

[Formula 1-1]

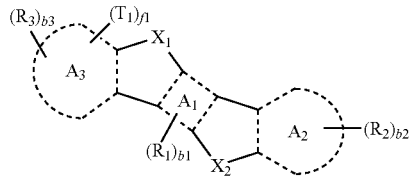

[Formula 1-2]

18 Claims, 4 Drawing Sheets

(51) Int. Cl.

| | | |
|---|---|---|
| *C07D 307/91* | (2006.01) | |
| *C07D 493/04* | (2006.01) | |
| *C07D 495/04* | (2006.01) | |
| *C09K 11/06* | (2006.01) | |
| *C07D 405/10* | (2006.01) | |
| *H01L 51/52* | (2006.01) | |
| *H01L 51/50* | (2006.01) | |

(52) U.S. Cl.
CPC ...... *H01L 51/5072* (2013.01); *H01L 51/5206* (2013.01); *H01L 51/5221* (2013.01)

(56) References Cited

U.S. PATENT DOCUMENTS

| | | | |
|---|---|---|---|
| 2006/0043858 A1 | 3/2006 | Ikeda et al. | |
| 2008/0193797 A1 | 8/2008 | Heil et al. | |
| 2009/0261717 A1 | 10/2009 | Buesing et al. | |
| 2010/0032658 A1 | 2/2010 | Lee et al. | |
| 2011/0156016 A1 | 6/2011 | Kawamura et al. | |
| 2012/0138914 A1* | 6/2012 | Kawamura | C07D 307/79 257/40 |
| 2013/0069523 A1 | 3/2013 | Matsuura et al. | |
| 2014/0332793 A1 | 11/2014 | Park et al. | |
| 2015/0372237 A1 | 12/2015 | Kawamura et al. | |

FOREIGN PATENT DOCUMENTS

| | | | |
|---|---|---|---|
| KR | 10-2009-0065201 | | 6/2009 |
| KR | 10-2010-0007780 | | 1/2010 |
| KR | 10-2011-0043625 | | 4/2011 |
| KR | 10-2011-0047278 | | 5/2011 |
| KR | 10-2012-0003692 | | 1/2012 |
| KR | 10-2012-0038402 | | 4/2012 |
| KR | 10-2013-0075982 | | 7/2013 |
| KR | 10-2014-0049186 | | 4/2014 |
| KR | 20150128583 A | * | 11/2015 |
| WO | 2010137285 | | 12/2010 |
| WO | 2010151006 | | 12/2010 |
| WO | 2014061963 | | 4/2014 |

OTHER PUBLICATIONS

Office Action for U.S. Appl. No. 15/399,255 dated Apr. 18, 2018 in related application.
Office Action issued in corresponding U.S. Appl. No. 15/399,155 dated Apr. 29, 2019.
Office Action issued in corresponding U.S. Appl. No. 15/399,414 dated May 2, 2019.
Notice of Allowance issued in corresponding U.S. Appl. No. 15/399,255 dated Sep. 18, 2019.
Office Action issued in corresponding U.S. Appl. No. 15/399,414 dated May 21, 2020.

* cited by examiner

| 190 |
| 150 |
| 110 |

| 190 |
|-----|
| 150 |
| 110 |
| 210 |

| 220 |
|-----|
| 190 |
| 150 |
| 110 |

| 220 |
|---|
| 190 |
| 150 |
| 110 |
| 210 |

CONDENSED CYCLIC COMPOUND AND AN ORGANIC LIGHT-EMITTING DEVICE INCLUDING THE SAME

CROSS-REFERENCE TO RELATED APPLICATION

This application claims the benefit of Korean Patent Application Nos.: 10-2016-0001115, filed on Jan. 5, 2016; 10-2016-0001122, filed on Jan. 5, 2016; 10-2016-0006996, filed on Jan. 20, 2016; 10-2016-0006995, filed on Jan. 20, 2016 in the Korean Intellectual Property Office. The above-referenced disclosures are incorporated by reference herein.

This application claims the benefit of Korean Patent Application No. 10-2016-001115, filed on Jan. 5, 2016 in the Korean Intellectual Property Office, the disclosure of which is incorporated by reference herein in its entirety.

TECHNICAL FIELD

Exemplary embodiments of the present invention relate to a condensed cyclic compound, and more particularly to an organic light-emitting device including the same.

DISCUSSION OF RELATED ART

Organic light-emitting devices may be self-emission devices. Organic light-emitting devices may produce full-color images. Organic light-emitting devices may have relatively wide viewing angles, relatively high contrast ratios, and relatively short response times, and increased brightness, driving voltage, and response speed characteristics.

Organic light-emitting devices may include a first electrode disposed on a substrate. Organic light-emitting devices may include a hole transport region, an emission layer, an electron transport region, and a second electrode sequentially disposed on the first electrode. Holes provided from the first electrode may move toward the emission layer through the hole transport region. Electrons provided from the second electrode may move toward the emission layer through the electron transport region. Carriers, such as holes and electrons, may recombine in the emission layer to produce excitons. The excitons may transition from an excited state to a ground state, thus generating light.

SUMMARY

One or more exemplary embodiments of the present invention may include a condensed cyclic compound and an organic light-emitting device including the same.

According to an exemplary embodiment of the present invention, a condensed cyclic compound is represented by Formula 1-1 or 1-2:

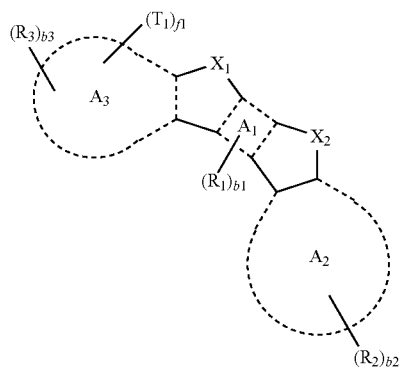

<Formula 1-1>

<Formula 1-2>

In Formulae 1-1 and 1-2,
ring $A_1$ is a benzene group,
ring $A_2$ is selected from a $C_6$-$C_{60}$ aromatic ring and a $C_1$-$C_{60}$ heteroaromatic ring,
ring $A_3$ is selected from a $C_7$-$C_{60}$ aromatic ring and a $C_1$-$C_{60}$ heteroaromatic ring,
$X_1$ is selected from $C(R_{11})(R_{12})$, O, and S,
$X_2$ is selected from $C(R_{13})(R_{14})$, O, and S,
$R_1$ to $R_3$ and $R_{11}$ to $R_{14}$ are each independently selected from hydrogen, deuterium (-D), —F, —Cl, —Br, —I, a hydroxyl group, a cyano group, a nitro group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), —N($Q_1$)($Q_2$), —B($Q_1$)($Q_2$), —C(=O)($Q_1$), —S(=O)$_2$($Q_1$), and —P(=O)($Q_1$)($Q_2$),
b1 is an integer selected from 0 to 2, and
b2 and b3 are each independently an integer selected from 0 to 10,
$T_1$ is a group represented by Formula 2,

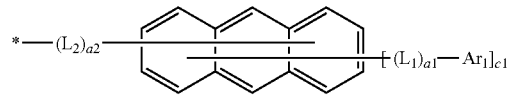

<Formula 2>

In Formula 2, $L_1$ and $L_2$ are each independently selected from a substituted or unsubstituted $C_3$-$C_{10}$ cycloalkylene, a substituted or unsubstituted $C_1$-$C_{10}$ heterocycloalkylene, a substituted or unsubstituted $C_3$-$C_{10}$ cycloalkenylene, a substituted or unsubstituted $C_1$-$C_{10}$ heterocycloalkenylene, a substituted or unsubstituted $C_6$-$C_{60}$ arylene, a substituted or unsubstituted $C_1$-$C_{60}$ heteroarylene, a substituted or unsubstituted divalent non-aromatic condensed polycyclic group, and a substituted or unsubstituted divalent non-aromatic condensed heteropolycyclic group, a1 is an integer selected from 0, 1, 2, and 3, and a2 is an integer selected from 1, 2, and 3, $Ar_1$ is selected from hydrogen, deuterium (-D), —F, —Cl, —Br, —I, a hydroxyl group, a cyano group, a nitro group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_4$)($Q_5$)($Q_6$), —N($Q_4$)($Q_5$), —B($Q_4$)($Q_5$), —C(=O)($Q_4$), —S(=O)$_2$($Q_4$), and —P(=O)($Q_4$)($Q_5$), c1 is an integer selected from 1 to 9, f1 is an integer selected from 1 to 3, at least one substituent selected from a substituent(s) of the substituted $C_3$-$C_{10}$ cycloalkylene group, the substituted $C_1$-$C_{10}$ heterocycloalkylene group, the substituted $C_3$-$C_{10}$ cycloalkenylene group, the substituted $C_1$-$C_{10}$ heterocycloalkenylene group, the substituted $C_6$-$C_{60}$ arylene group, the substituted $C_1$-$C_{60}$ heteroarylene group, the substituted divalent non-aromatic condensed polycyclic group, the substituted divalent non-aromatic condensed heteropolycyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group is selected from:

deuterium (-D), —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amidino group, a hydrazino group, a hydrazono group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{11}$)($Q_{12}$)($Q_{13}$), —N($Q_{11}$)($Q_{12}$), —B($Q_{11}$)($Q_{12}$), —C(=O)($Q_{11}$), —S(=O)$_2$($Q_{11}$), and —P(=O)($Q_{11}$)($Q_{12}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{21}$)($Q_{22}$)($Q_{23}$), —N($Q_{21}$)($Q_{22}$), —B($Q_{21}$)($Q_{22}$), —C(=O)($Q_{21}$), —S(=O)$_2$($Q_{21}$), and —P(=O)($Q_{21}$)($Q_{22}$); and —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$), $Q_1$ to $Q_6$, $Q_{11}$ to $Q_{13}$, $Q_{21}$ to $Q_{23}$, and $Q_{31}$ to $Q_{33}$ are each independently selected from hydrogen, deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, a monovalent non-aromatic condensed heteropolycyclic group, a biphenyl group, and a terphenyl group, and

* indicates a binding site to a neighboring atom.

According to an exemplary embodiment of the present invention, an organic light-emitting device includes a first electrode; a second electrode facing the first electrode; and an organic layer disposed between the first electrode and the second electrode. The organic layer includes an emission layer. The organic layer includes at least one of the condensed cyclic compounds represented by Formula 1-1 or Formula 1-2.

BRIEF DESCRIPTION OF THE DRAWINGS

The above and other features of the present invention will become more apparent by describing in detail exemplary embodiments thereof, with reference to the accompanying drawings, in which:

FIG. 1 is a schematic cross-sectional diagram illustrating an organic light-emitting device according to an exemplary embodiment of the present invention;

FIG. 2 is a schematic cross-sectional diagram illustrating an organic light-emitting device according to an exemplary embodiment of the present invention;

FIG. 3 is a schematic cross-sectional diagram illustrating an organic light-emitting device according to an exemplary embodiment of the present invention; and FIG. 4 is a schematic cross-sectional diagram illustrating an organic light-emitting device according to an exemplary embodiment of the present invention.

DETAILED DESCRIPTION OF THE EMBODIMENTS

A condensed cyclic compound according to an exemplary embodiment of the present invention may be represented by Formula 1-1 or 1-2:

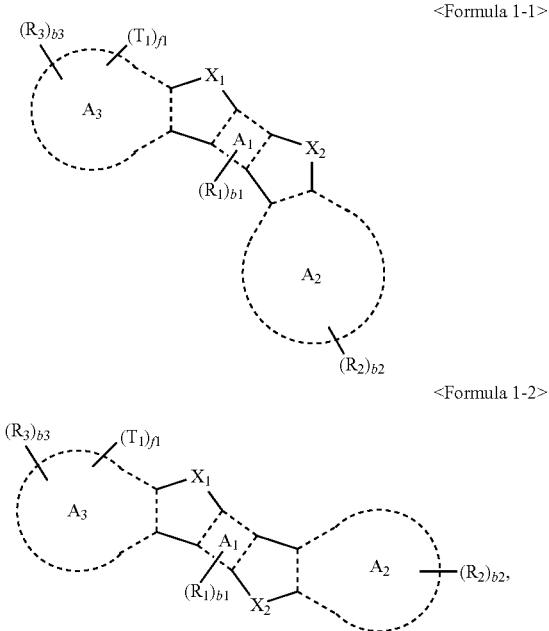

<Formula 1-1>

<Formula 1-2>

In Formulae 1-1 and 1-2, ring $A_1$ may be a benzene.

In Formulae 1-1 and 1-2, ring $A_2$ may be a $C_6$-$C_{60}$ aromatic ring or a $C_1$-$C_{60}$ heteroaromatic ring, and ring $A_3$ may be a $C_7$-$C_{60}$ aromatic ring or a $C_1$-$C_{60}$ heteroaromatic ring.

For example, in Formulae 1-1 and 1-2, ring $A_2$ may be selected from a benzene group, a naphthalene group, an anthracene group, a phenanthrene group, and a triphenylene group, and ring $A_3$ may be selected from a naphthalene, an anthracene, a phenanthrene, and a triphenylene.

According to one or more exemplary embodiments of the present invention, in Formulae 1-1 and 1-2, ring $A_2$ may be a benzene group, and ring $A_3$ may be naphthalene.

In Formulae 1-1 and 1-2, $X_1$ may be selected from $C(R_{11})(R_{12})$, O, and S, and $X_2$ may be selected from $C(R_{13})(R_{14})$, O, and S. $R_{11}$ to $R_{14}$ may be the same as described herein.

According to one or more exemplary embodiments of the present invention, in Formulae 1-1 and 1-2, $X_1$ and $X_2$ may be S;

$X_1$ may be $C(R_{11})(R_{12})$ and $X_2$ may be S;

$X_1$ may be S and $X_2$ may be $C(R_{13})(R_{14})$;

$X_1$ may be O and $X_2$ may be S;

$X_1$ and $X_2$ may be O;

$X_1$ may be $C(R_{11})(R_{12})$ and $X_2$ may be O;

$X_1$ may be O and $X_2$ may be $C(R_{13})(R_{14})$; or $X_1$ may be S and $X_2$ may be O.

In Formulae 1-1 and 1-2, $R_1$ to $R_3$ and $R_{11}$ to $R_{14}$ may each independently be selected from hydrogen, deuterium (-D), —F, —Cl, —Br, —I, a hydroxyl group, a cyano group, a nitro group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), —N($Q_1$)($Q_2$), —B($Q_1$)($Q_2$), —C(=O)($Q_1$), —S(=O)$_2$($Q_1$), and —P(=O)($Q_1$)($Q_2$).

$Q_1$ to $Q_3$ may be the same as described herein.

According to one or more exemplary embodiments of the present invention, $R_1$ to $R_3$ and $R_{11}$ to $R_{14}$ in Formulae 1-1 and 1-2 may each independently be selected from:

hydrogen, deuterium (-D), —F, —Cl, —Br, —I, a hydroxyl group, a cyano group, a nitro group, an amidino group, a hydrazino group, a hydrazono group, a $C_1$-$C_{20}$ alkyl group, and a $C_1$-$C_{20}$ alkoxy group;

a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, a benzofuranyl group, a benzothiophenyl group, a dibenzofuranyl group, a dibenzothiophenyl group, a benzocarbazolyl group, a dibenzocarbazolyl group, or a dibenzosilolyl group; or a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, a benzofuranyl group, a benzothiophenyl group, a dibenzofuranyl group, a dibenzothiophenyl group, a benzocarbazolyl group, a dibenzocarbazolyl group, and a dibenzosilolyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and —Si($Q_{31}$)($Q_{32}$)($Q_{33}$).

$Q_{31}$ to $Q_{33}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a pyrenyl group, a chrysenyl group, and a carbazolyl group.

According to one or more exemplary embodiments of the present invention, in Formulae 1-1 and 1-2, $R_1$ to $R_3$ and $R_{11}$ to $R_{14}$ may each independently be selected from:

hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, and a $C_1$-$C_{20}$ alkoxy group;

a phenyl group, a biphenyl group, a terphenyl group, a naphthyl group, a fluorenyl group, a phenanthrenyl group, an anthracenyl group, a fluoranthenyl group, a triphenylenyl group, a pyrenyl group, a chrysenyl group, a thiophenyl group, a furanyl group, a carbazolyl group, a benzofuranyl group, a benzothiophenyl group, a dibenzofuranyl group, a dibenzothiophenyl group, a benzocarbazolyl group, and a dibenzocarbazolyl group; and a phenyl group, a biphenyl group, a terphenyl group, a naphthyl group, a fluorenyl group, a phenanthrenyl group, an anthracenyl group, a fluoranthenyl group, a triphenylenyl group, a pyrenyl group, a chrysenyl group, a thiophenyl group, a furanyl group, a carbazolyl group, a dibenzofuranyl group, a dibenzothiophenyl group, a benzocarbazolyl group, and a dibenzocarbazolyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a phenanthrenyl group, an anthracenyl group, a fluoranthenyl group, a triphenylenyl group, a pyrenyl group, a chrysenyl group, a thiophenyl group, a furanyl group, a carbazolyl group, a dibenzofuranyl group, a dibenzothiophenyl group, a benzocarbazolyl group, a dibenzocarbazolyl group, and —Si($Q_{31}$)($Q_{32}$)($Q_{33}$).

$Q_{31}$ to $Q_{33}$ may each independently be selected from a $C_1$-$C_{10}$ alkyl group, a $C_1$-$C_{10}$ alkoxy group, a phenyl group, a biphenyl group, a terphenyl group, and a naphthyl group.

According to one or more exemplary embodiments of the present invention, in Formulae 1-1 and 1-2, $R_1$ to $R_3$ and $R_{11}$ to $R_{14}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, and a $C_1$-$C_{20}$ alkoxy group.

In Formulae 1-1 and 1-2, b1 may be an integer selected from 0 to 2, and b2 and b3 may each independently be an integer selected from 0 to 10.

b1 in Formulae 1-1 and 1-2 may indicate the number of $R_1$(s). When b1 is 2 or greater, at least two $R_1$(s) may be the same as or different from each other. b2 and b3 may be the same as described herein with reference to b1 and the structures of Formulae 1-1 and 1-2.

According to one or more exemplary embodiments of the present invention, in Formulae 1-1 and 1-2, b1 may be an integer selected from 0 to 2, b2 may be an integer selected from 0 to 4, and b3 may be an integer selected from 0 to 5; however, exemplary embodiments of the present invention are not limited thereto.

$T_1$ in Formulae 1-1 and 1-2 may be a group represented by Formula 2:

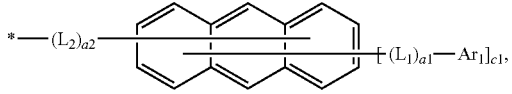

<Formula 2>

In Formula 2, $L_1$ and $L_2$ may each independently be selected from a substituted or unsubstituted $C_3$-$C_{10}$ cycloalkylene, a substituted or unsubstituted heterocycloalkylene, a substituted or unsubstituted $C_3$-$C_{10}$ cycloalkenylene, a substituted or unsubstituted $C_1$-$C_{10}$ heterocycloalkenylene, a substituted or unsubstituted $C_6$-$C_{60}$ arylene, a substituted or unsubstituted $C_1$-$C_{60}$ heteroarylene, a substituted or unsubstituted divalent non-aromatic condensed polycyclic group, or a substituted and unsubstituted divalent non-aromatic condensed heteropolycyclic group.

According to one or more exemplary embodiments of the present invention, in Formula 2, $L_1$ and $L_2$ may each independently be selected from:

a phenylene group, a pentalenylene group, an indenylene group, a naphthylene group, an azulenylene group, a heptalenylene group, an indacenylene group, an acenaphthylene group, a fluorenylene group, a spiro-bifluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a pyrrolylene group, a thiophenylene group, a furanylene group, a carbazolylene group, a benzofuranylene group, a benzothiophenylene group, a dibenzofuranylene group, a dibenzothiophenylene group, a benzocarbazolylene group, and a dibenzocarbazolylene group; and a phenylene group, a pentalenylene group, an indenylene group, a naphthylene group, an azulenylene group, a heptalenylene group, an indacenylene group, an acenaphthylene group, a fluorenylene group, a spiro-bifluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a pyrrolylene group, a thiophenylene group, a furanylene group, a carbazolylene group, a benzofuranylene group, a benzothiophenylene group, a dibenzofuranylene group, a dibenzothiophenylene group, a benzocarbazolylene group, and a dibenzocarbazolylene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, a benzofuranyl group, a benzothiophenyl group, a dibenzofuranyl group, a dibenzothiophenyl group, a benzocarbazolyl group, and a dibenzocarbazolyl group.

According to one or more exemplary embodiments of the present invention, $L_1$ and $L_2$ in Formula 2 may each independently be selected from groups represented by Formulae 3-1 to 3-22; however, exemplary embodiments of the present invention are not limited thereto:

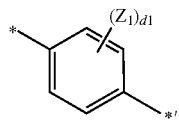

3-1

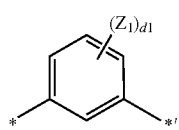

3-2

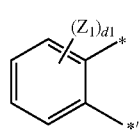

3-3

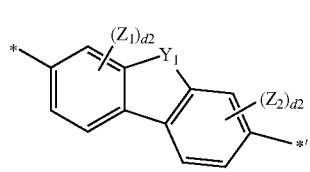

3-4

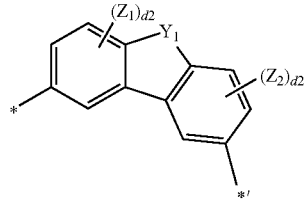

3-5

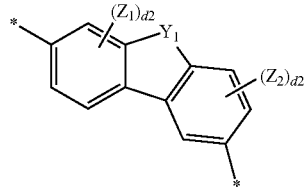

3-6

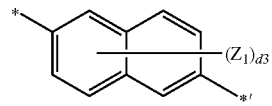

3-7

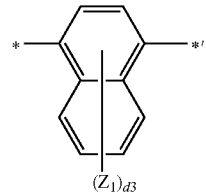

3-8

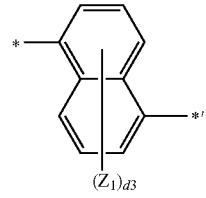

3-9

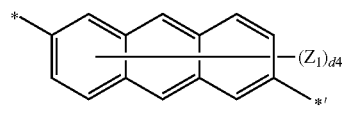

3-10

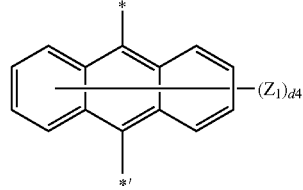

3-11

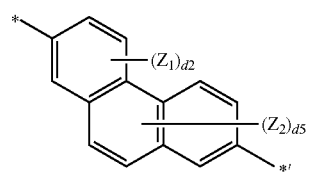

3-12

11
-continued 3-13
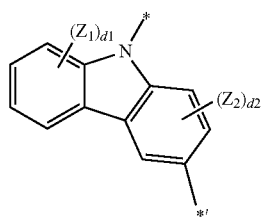

3-14
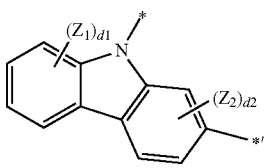

3-15
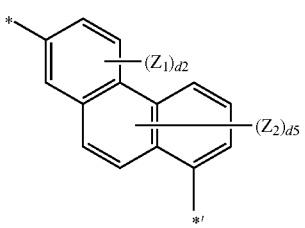

3-16
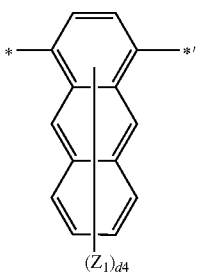

3-17
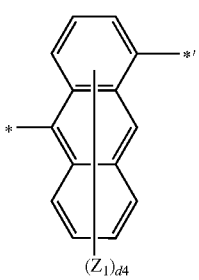

3-18
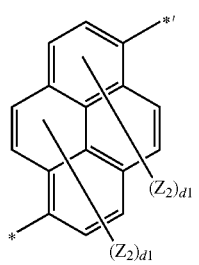

12
-continued 3-19
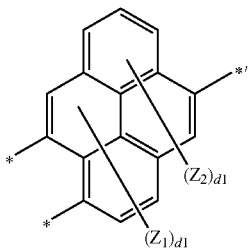

3-20
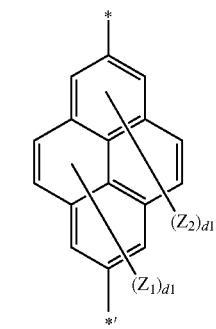

3-21
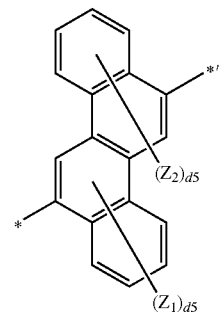

3-22
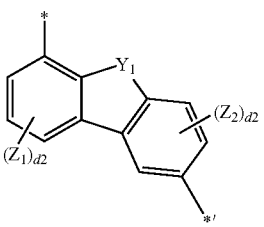

In Formulae 3-1 to 3-22:

$Y_1$ may be selected from O, S, $C(Z_3)(Z_4)$, $N(Z_5)$, and $Si(Z_6)(Z_7)$.

$Z_1$ to $Z_7$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a carbazolyl group, and —$Si(Q_{31})(Q_{32})(Q_{33})$, wherein $Q_{31}$ to $Q_{33}$ may each independently be selected from a $C_1$-$C_{10}$ alkyl group, a $C_1$-$C_{10}$ alkoxy group, a phenyl group, a naphthyl group, a biphenyl group, and a terphenyl group.

d1 may be an integer selected from 1 to 4.

d2 may be an integer selected from 1 to 3.

d3 may be an integer selected from 1 to 6.
d4 may be an integer selected from 1 to 8.
d5 may be an integer selected from 1 to 5.
The symbols * and *′ each indicate a binding site to a neighboring atom.
According to one or more exemplary embodiments of the present invention, $L_1$ and $L_2$ in Formula 2 may each independently be selected from groups represented by Formulae 4-1 to 4-35:
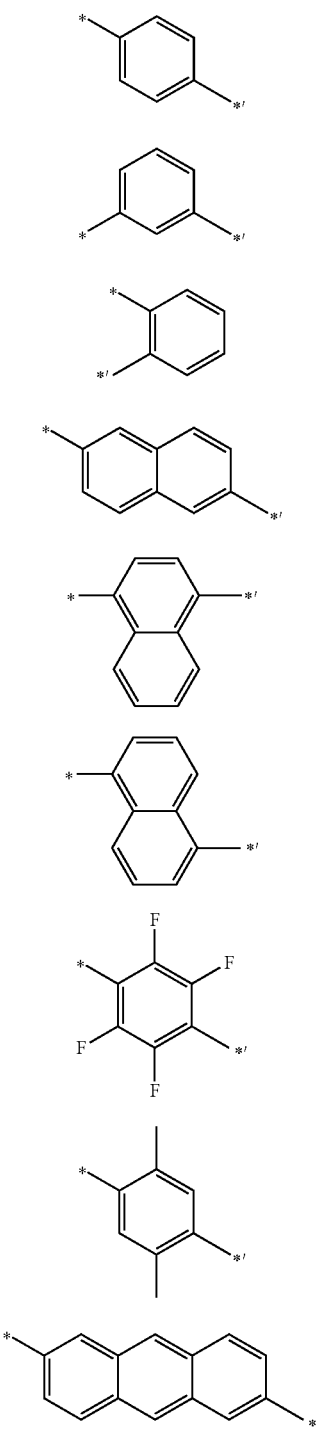
4-1
4-2
4-3
4-4
4-5
4-6
4-7
4-8
4-9
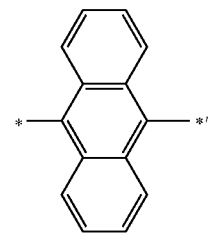
4-10
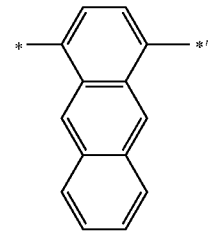
4-11
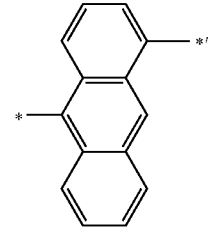
4-12
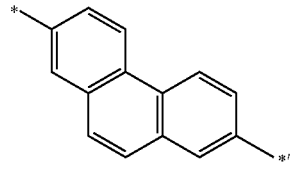
4-13
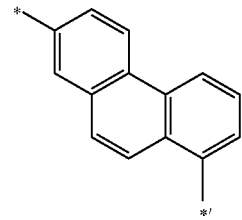
4-14
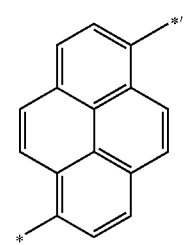
4-15
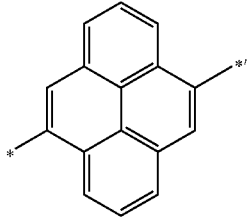
4-16

4-17 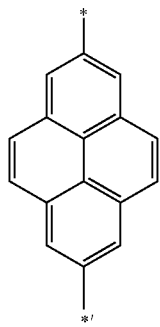
4-18 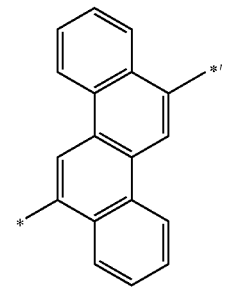
4-19 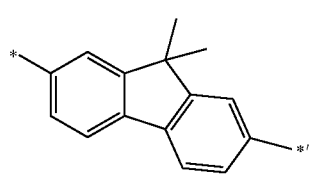
4-20 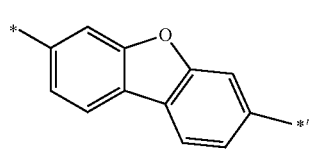
4-21 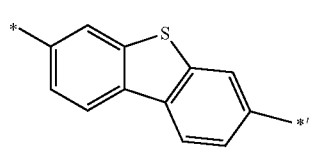
4-22 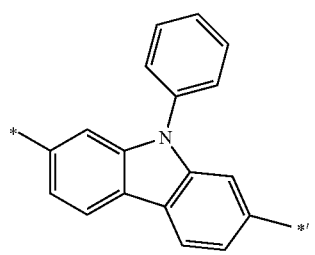
4-23 
4-24 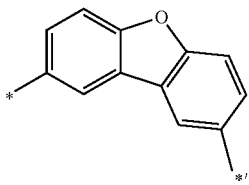
4-25 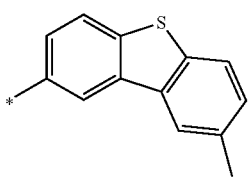
4-26 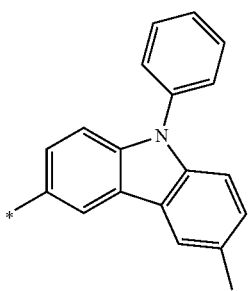
4-27 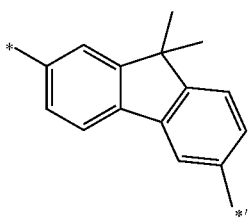
4-28 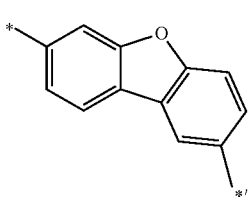
4-29 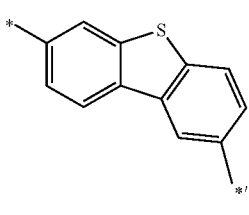

-continued

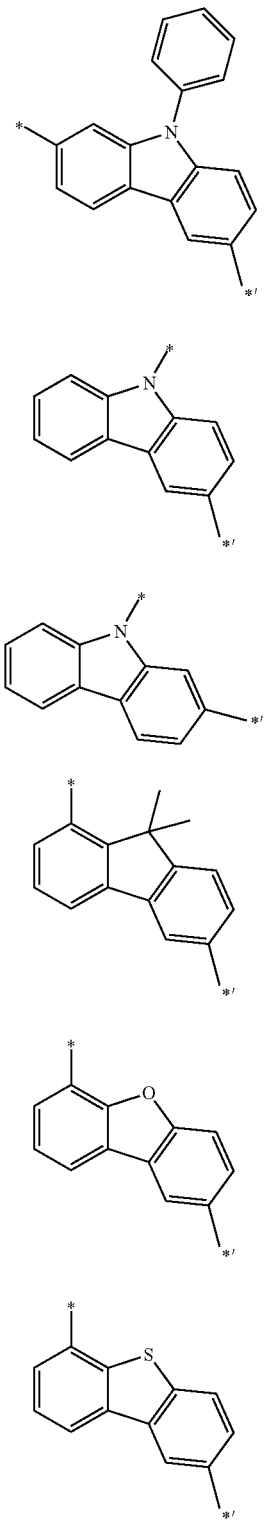

The symbols * and *' in Formulae 4-1 and 4-35 may each indicate a binding site to a neighboring atom.

a1 in Formula 2 may indicate the number of $L_1$(s). a1 in Formula 2 may be an integer selected from 0, 1, 2, and 3. For example, a1 in Formula 2 may be 0 or 1; however, exemplary embodiments of the present invention are not limited thereto. When a1 is 0, *-$(L_1)_{a1}$-*' may be a single bond. When a1 is 2 or greater, at least two $L_1$(s) may be the same as or different from each other.

a2 in Formula 2 may indicate the number of $L_2$(s). a2 in Formula 2 may be an integer selected from 1, 2, and 3. For example, a2 in Formula 2 may be 1 or 2. When a2 is 2 or greater, at least two $L_2$(s) may be the same as or different from each other.

For example, in Formula 2, a1 may be 0 or 1, and a2 may be 1; however, exemplary embodiments of the present invention are not limited thereto.

$Ar_1$ in Formula 2 may be selected from hydrogen, deuterium, —F, —Cl, —Br, —I, a hydroxyl group, a cyano group, a nitro group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_4$)($Q_5$)($Q_6$), —N($Q_4$)($Q_5$), —B($Q_4$)($Q_5$), —C(=O)($Q_4$), —S(=O)$_2$($Q_4$), and —P(=O)($Q_4$)($Q_5$).

According to one or more exemplary embodiments of the present invention, $Ar_1$ in Formula 2 may be selected from:
hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, and a $C_1$-$C_{20}$ alkoxy group;
a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, a benzofuranyl group, a benzothiophenyl group, a dibenzofuranyl group, a dibenzothiophenyl group, a benzocarbazolyl group, a dibenzocarbazolyl group, and a dibenzosilolyl group; and
a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, a benzofuranyl group, a benzothiophenyl group, a dibenzofuranyl group, a dibenzothiophenyl group, a benzocarbazolyl group, a dibenzocarbazolyl group, and a dibenzosilolyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and —Si($Q_{31}$)($Q_{32}$)($Q_{33}$).

$Q_{31}$ to $Q_{33}$ may each independently be selected from a $C_1$-$C_{10}$ alkyl group, a $C_1$-$C_{10}$ alkoxy group, a phenyl group, a naphthyl group, a biphenyl group, and a terphenyl group.

According to one or more exemplary embodiments of the present invention, $Ar_1$ in Formula 2 may be selected from:

hydrogen, deuterium, —F, —Cl, —Br, —I, a hydroxyl group, a cyano group, a nitro group, an amidino group, a hydrazino group, a hydrazono group, a $C_1$-$C_{10}$ alkyl group, and a $C_1$-$C_{10}$ alkoxy group; and groups represented by Formulae 5-1 to 5-16; however, exemplary embodiments of the present invention are not limited thereto:

5-1
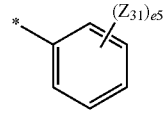

5-2
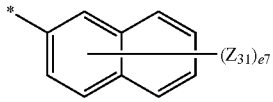

5-3
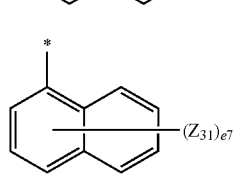

5-4
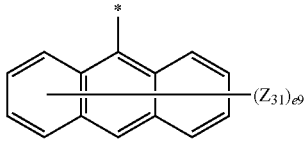

5-5
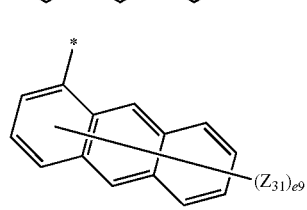

5-6
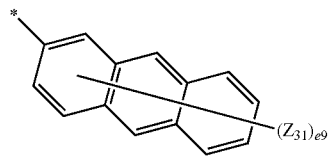

5-7
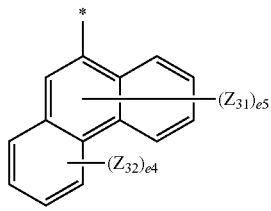

5-8
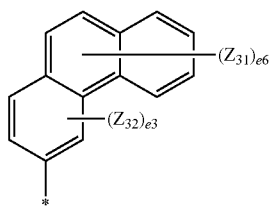

5-9
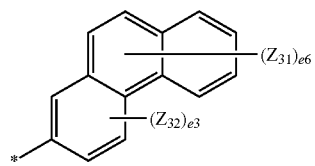

5-10
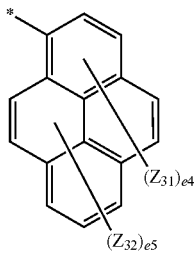

5-11
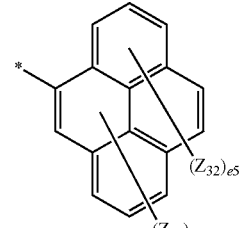

5-12
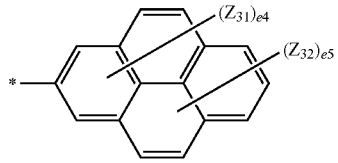

5-13
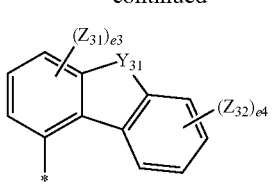

5-14
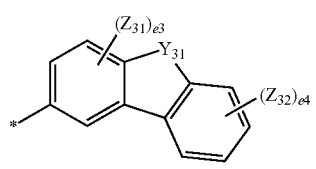

5-15
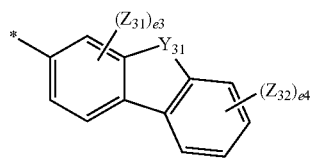

5-16
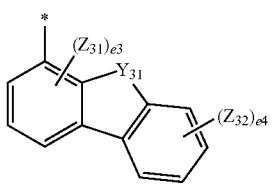

In Formulae 5-1 to 5-16, $Y_{31}$ may be selected from O, S, $C(Z_{33})(Z_{34})$, $N(Z_{35})$, and $Si(Z_{36})(Z_{37})$, $Z_{31}$ to $Z_{37}$ may each independently be selected from:

hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, and a $C_1$-$C_{20}$ alkoxy group;

a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a triphenylenyl group, a pyrenyl group, a chrysenyl group, a thiophenyl group, a furanyl group, a carbazolyl group, a benzofuranyl group, a benzothiophenyl group, a dibenzofuranyl group, and a dibenzothiophenyl group; and a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a triphenylenyl group, a pyrenyl group, a chrysenyl group, a thiophenyl group, a furanyl group, a carbazolyl group, a benzofuranyl group, a benzothiophenyl group, a dibenzofuranyl group, and a dibenzothiophenyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a triphenylenyl group, a pyrenyl group, a chrysenyl group, a thiophenyl group, a furanyl group, a carbazolyl group, a benzofuranyl group, a benzothiophenyl group, a dibenzofuranyl group, and a dibenzothiophenyl group.

e3 may be an integer selected from 1 to 3.

e4 may be an integer selected from 1 to 4.

e5 may be an integer selected from 1 to 5.

e6 may be an integer selected from 1 to 6.

e7 may be an integer selected from 1 to 7.

e9 may be an integer selected from 1 to 9.

According to one or more exemplary embodiments of the present invention, $Ar_1$ in Formula 2 may be selected from:

hydrogen, deuterium, —F, —Cl, —Br, —I, a hydroxyl group, a cyano group, a nitro group, an amidino group, a hydrazino group, a hydrazono group, a $C_1$-$C_{10}$ alkyl group, and a $C_1$-$C_{10}$ alkoxy group; and groups represented by Formulae 6-1 to 6-44; however, exemplary embodiments of the present invention are not limited thereto:

6-1
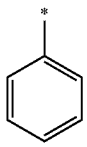

6-2
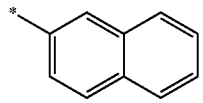

6-3
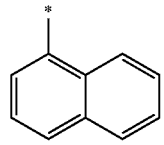

6-4
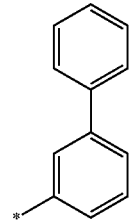

6-5
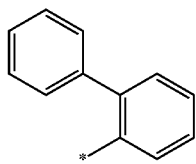

6-6
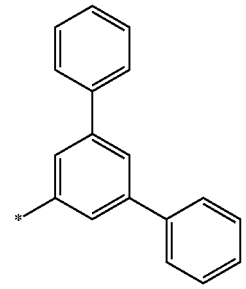

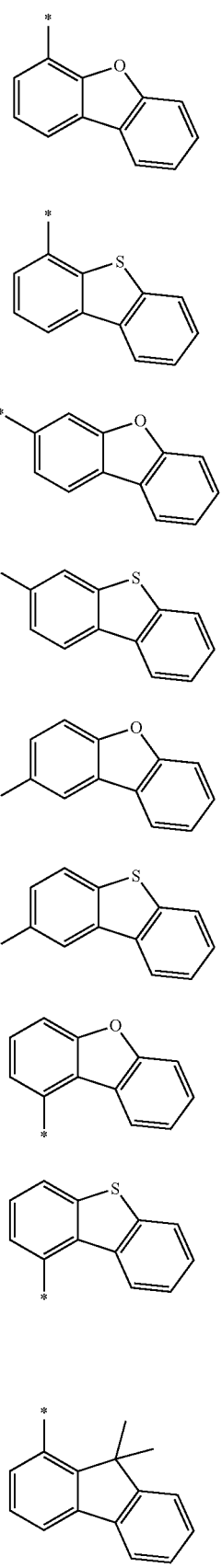
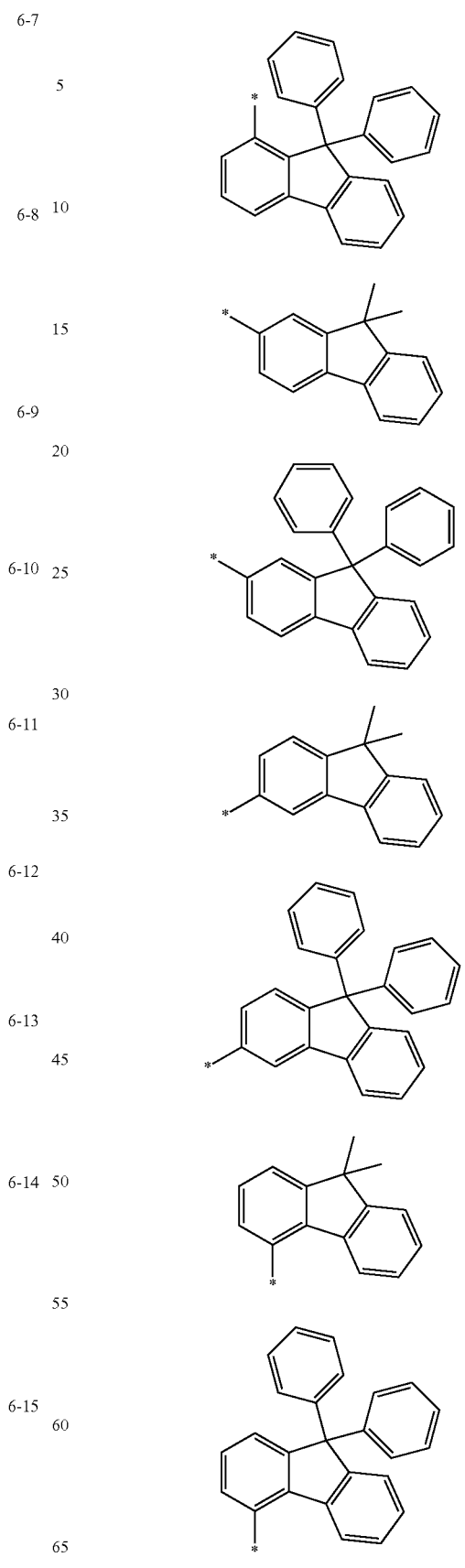

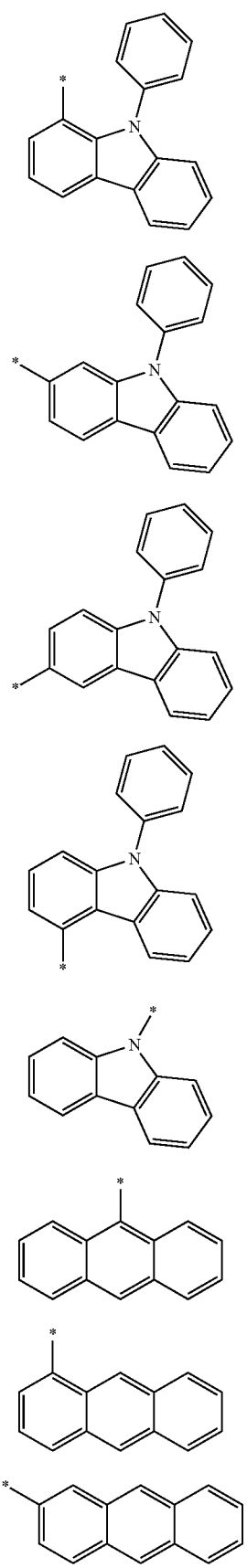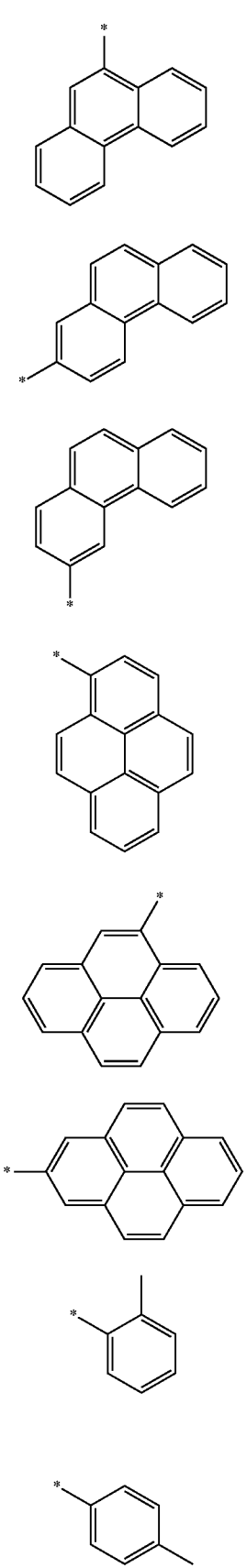

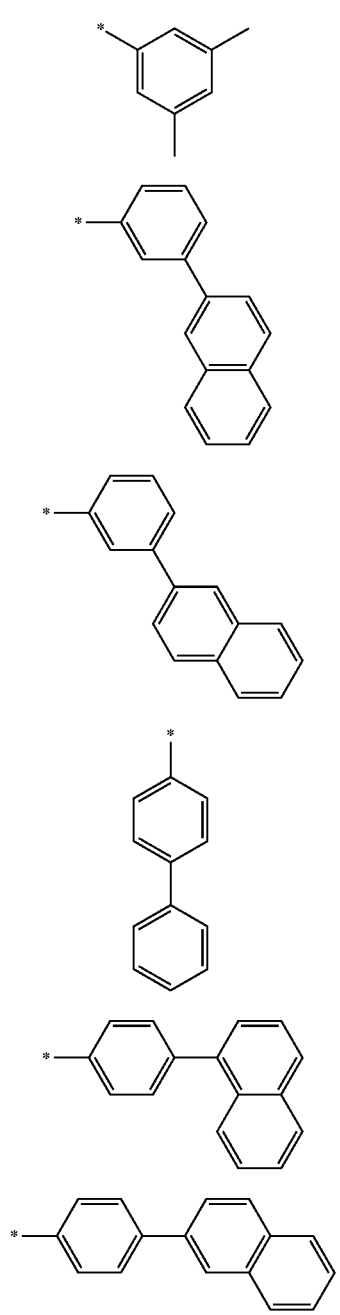

The symbol * in Formulae 6-1 to 6-44 may indicate a binding site to a neighboring atom.

According to one or more exemplary embodiments of the present invention, in Formula 2, $Ar_1$ may be selected from:

a phenyl group, a biphenyl group, a terphenyl group, a naphthyl group, a fluorenyl group, a phenanthrenyl group, an anthracenyl group, a triphenylenyl group, a pyrenyl group, a chrysenyl group, a carbazolyl group, a dibenzofuranyl group, or a dibenzothiophenyl group; and a phenyl group, a biphenyl group, a terphenyl group, a naphthyl group, a fluorenyl group, a phenanthrenyl group, an anthracenyl group, a triphenylenyl group, a pyrenyl group, a chrysenyl group, a carbazolyl group, a dibenzofuranyl group, and a dibenzothiophenyl group, each substituted with at least one selected from deuterium, —F, —Cl, —Br, —I, a hydroxyl group, a cyano group, a nitro group, an amidino group, a hydrazino group, a hydrazono group, a $C_1$-$C_{10}$ alkyl group, a $C_1$-$C_{10}$ alkoxy group, a phenyl group, and a naphthyl group.

c1 in Formula 2 may be an integer selected from 1 to 9.

c1 in Formula 2 may indicate the number of -[$(L_1)_{a1}$-$Ar_1$](s). When c1 is 2 or greater, at least two -[$(L_1)_{a1}$-$Ar_1$](s) may be the same as or different from each other. For example, c1 may be an integer selected from 1 to 4. According to one or more exemplary embodiments of the present invention, c1 in Formula 2 may be 1 or 2.

f1 in Formulae 1-1 and 1-2 may indicate the number of $T_1$(s). f1 in Formulae 1-1 and 1-2 may be an integer selected from 1 to 3. When f1 is 2 or greater, at least two or more $T_1$(s) may be the same as or different from each other. For example, f1 may be 1.

According to one or more exemplary embodiments of the present invention, $T_1$ in Formulae 1-1 and 1-2 may be represented by Formula 2A:

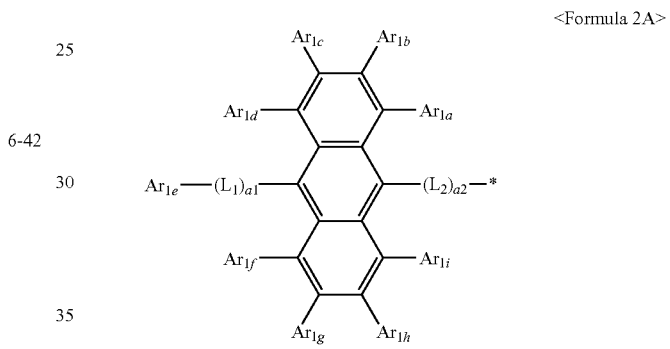

<Formula 2A>

In Formula 2A, $L_1$, $L_2$, a1, and a2 may be the same as described above.

$Ar_{1a}$ to $Ar_{1i}$ may be the same as $Ar_1$.

The symbol * may indicate a binding site to a neighboring atom.

According to one or more exemplary embodiments of the present invention, $Ar_{1a}$ to $Ar_{1i}$ in Formula 2A may each independently be selected from:

hydrogen, deuterium, —F, —Cl, —Br, —I, a hydroxyl group, a cyano group, a nitro group, an amidino group, a hydrazino group, a hydrazono group, a $C_1$-$C_{10}$ alkyl group, and a $C_1$-$C_{10}$ alkoxy group; and groups represented by Formulae 6-1 to 6-44.

According to one or more exemplary embodiments of the present invention, $T_1$ in Formulae 1-1 and 1-2 may be represented by Formula 2A(1):

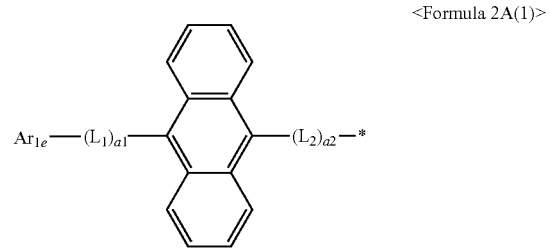

<Formula 2A(1)>

In Formula 2A(1), $L_1$, $L_2$, a1, and a2 may be the same as described above.

$Ar_{1e}$ may be the same as $Ar_1$.

The symbol * may indicate a binding site to a neighboring atom.

According to one or more exemplary embodiments of the present invention, $Ar_{1e}$ in Formula 2A(1) may be selected from groups represented by Formulae 6-1 to 6-44.

According to one or more exemplary embodiments of the present invention, $Ar_{1e}$ in Formula 2A(1) may be selected from:

a phenyl group, a biphenyl group, a terphenyl group, a naphthyl group, a fluorenyl group, a phenanthrenyl group, an anthracenyl group, a triphenylenyl group, a pyrenyl group, a chrysenyl group, a carbazolyl group, a dibenzofuranyl group, and a dibenzothiophenyl group; and a phenyl group, a biphenyl group, a terphenyl group, a naphthyl group, a fluorenyl group, a phenanthrenyl group, an anthracenyl group, a triphenylenyl group, a pyrenyl group, a chrysenyl group, a carbazolyl group, a dibenzofuranyl group, and a dibenzothiophenyl group, each substituted with at least one selected from deuterium, —F, —Cl, —Br, —I, a hydroxyl group, a cyano group, a nitro group, an amidino group, a hydrazino group, a hydrazono group, a $C_1$-$C_{10}$ alkyl group, a $C_1$-$C_{10}$ alkoxy group, a phenyl group, and a naphthyl group.

According to one or more exemplary embodiments of the present invention, the condensed cyclic compound may be represented by one selected from Formulae 1(1) to 1(18):

1(1)
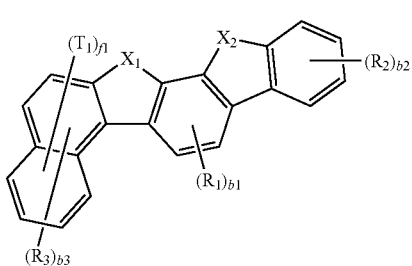

1(2)
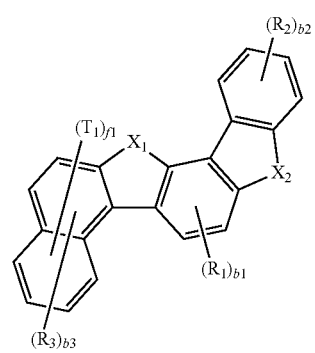

1(3)
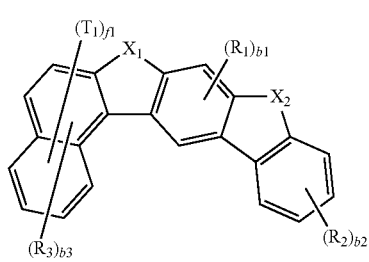

1(4)
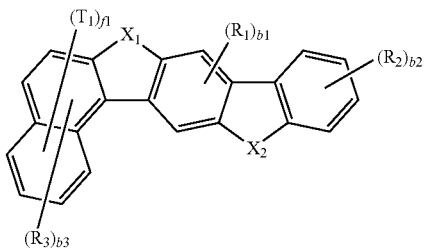

1(5)
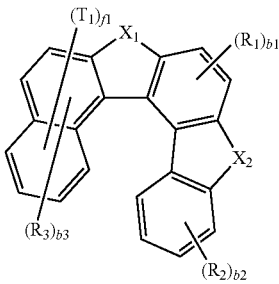

1(6)
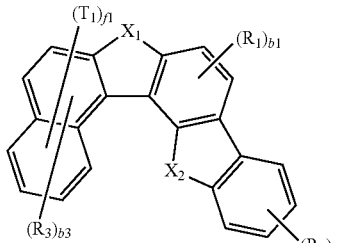

1(7)
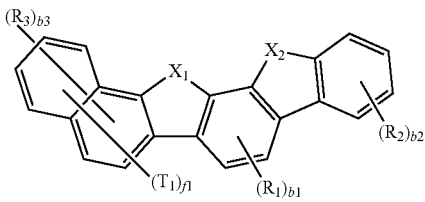

1(8)
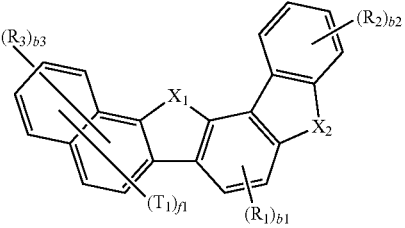

1(9)
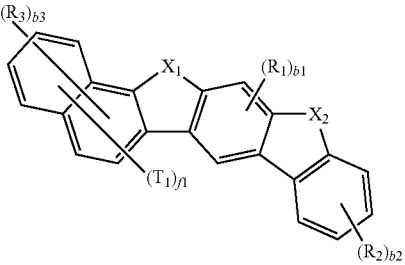

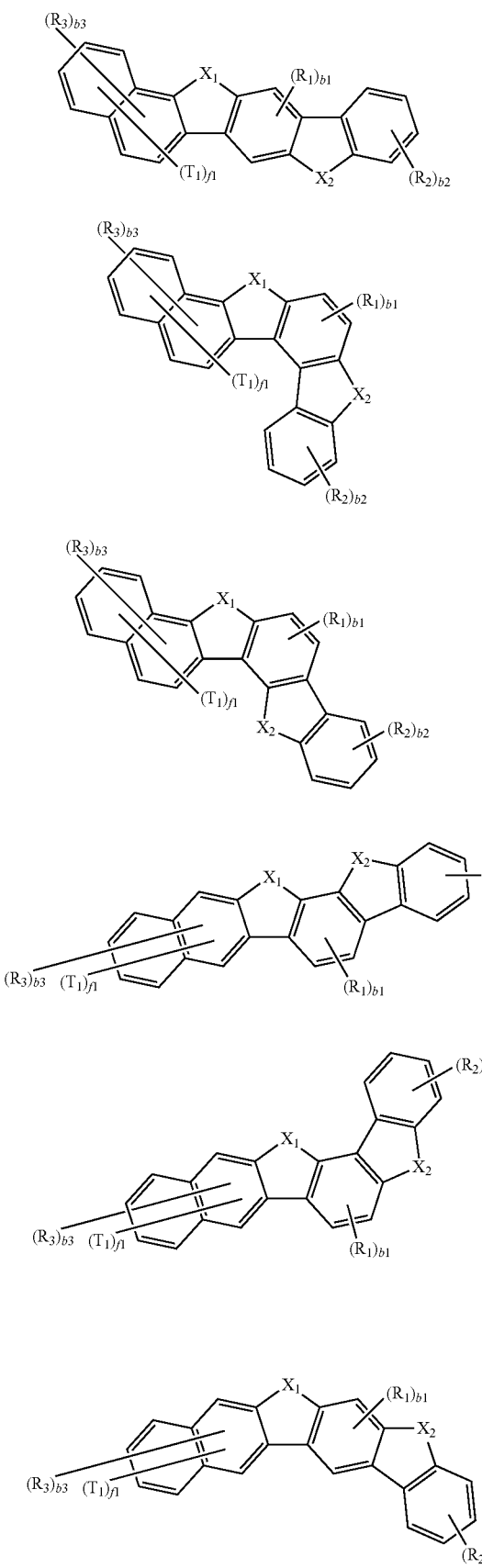
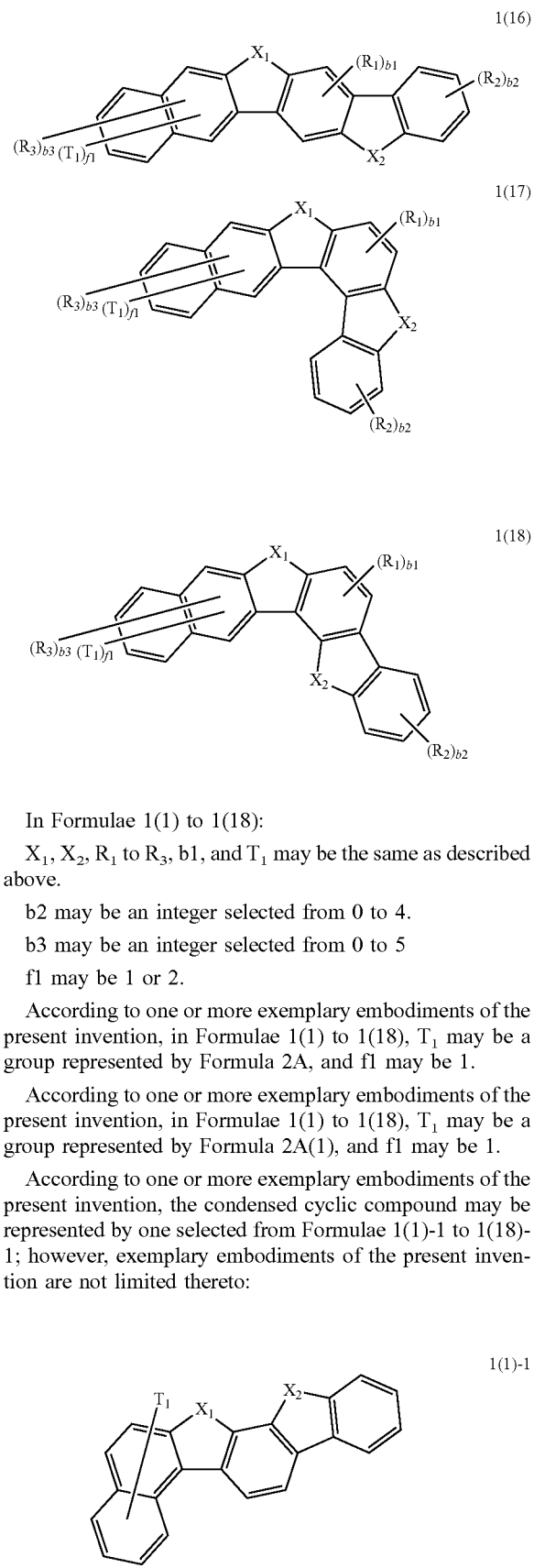

In Formulae 1(1) to 1(18):

$X_1$, $X_2$, $R_1$ to $R_3$, b1, and $T_1$ may be the same as described above.

b2 may be an integer selected from 0 to 4.

b3 may be an integer selected from 0 to 5 f1 may be 1 or 2.

According to one or more exemplary embodiments of the present invention, in Formulae 1(1) to 1(18), $T_1$ may be a group represented by Formula 2A, and f1 may be 1.

According to one or more exemplary embodiments of the present invention, in Formulae 1(1) to 1(18), $T_1$ may be a group represented by Formula 2A(1), and f1 may be 1.

According to one or more exemplary embodiments of the present invention, the condensed cyclic compound may be represented by one selected from Formulae 1(1)-1 to 1(18)-1; however, exemplary embodiments of the present invention are not limited thereto:

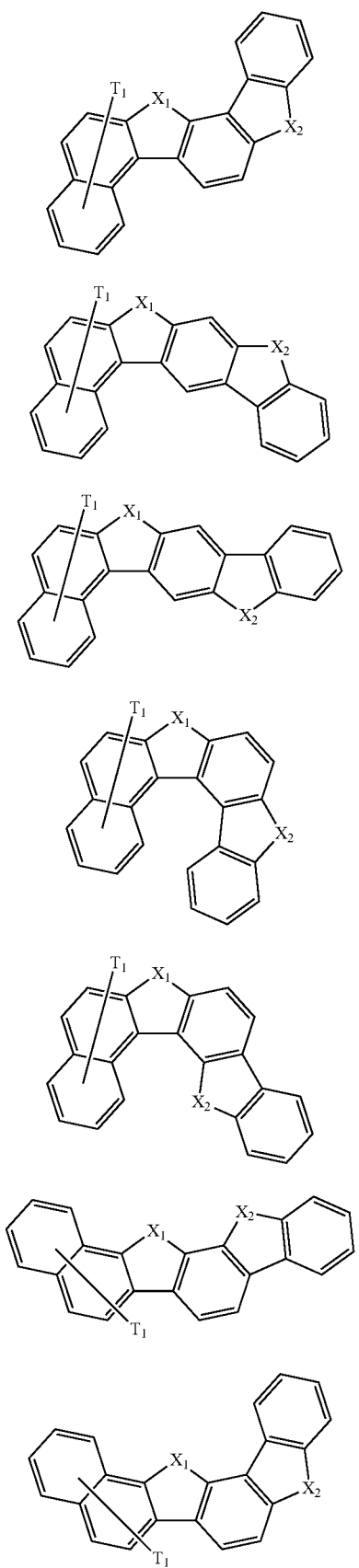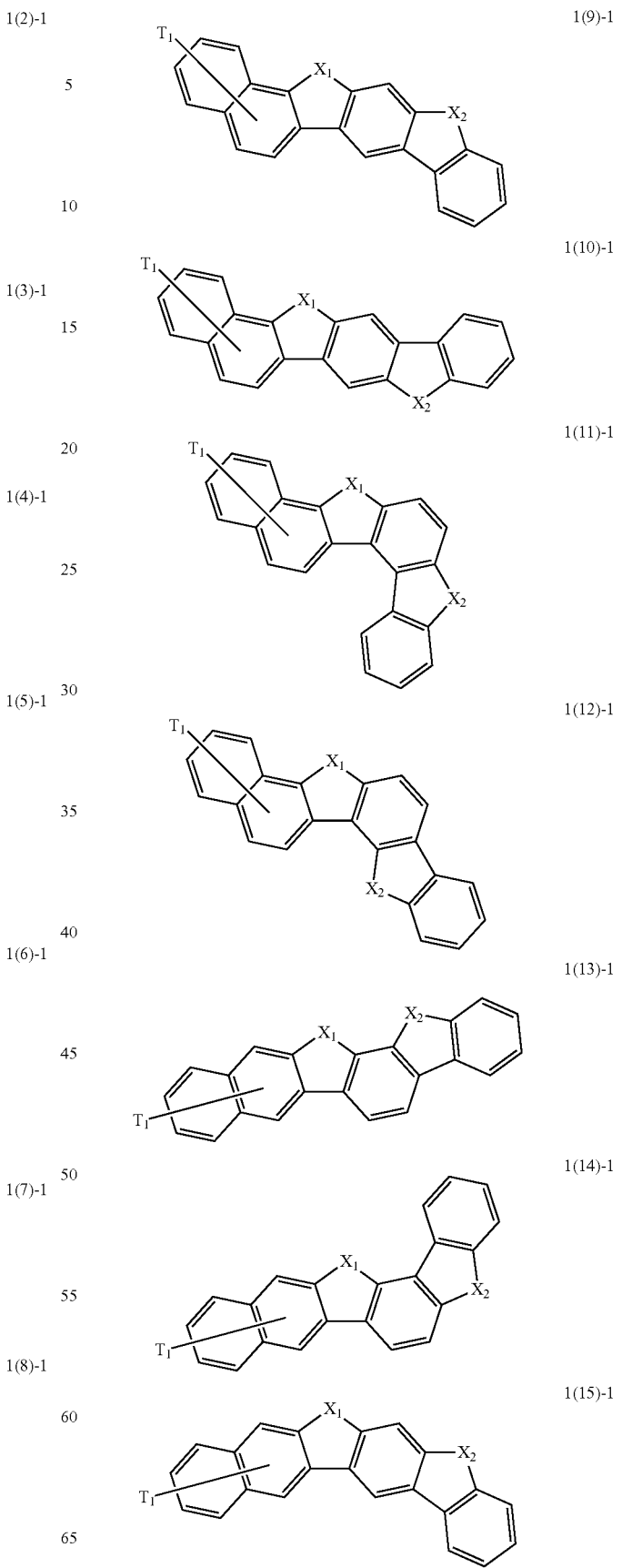

-continued

1(16)-1

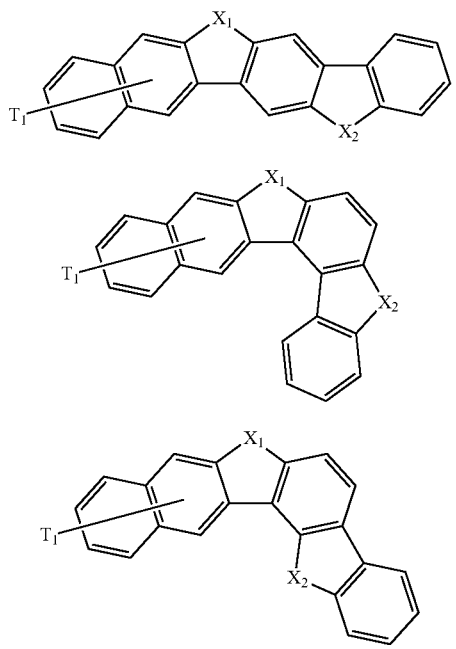

1(17)-1

1(18)-1

$X_1$, $X_2$, and $T_1$ in Formulae 1(1)-1 to 1(18)-1 may be the same as described above.

According to one or more exemplary embodiments of the present invention, $T_1$ in Formulae 1(1)-1 to 1(18)-1 may be a group represented by Formula 2A.

According to one or more exemplary embodiments of the present invention, $T_1$ in Formulae 1(1)-1 to 1(18)-1 may be a group represented by Formula 2A(1).

According to one or more exemplary embodiments of the present invention, in Formulae 1(1)-1 to 1(18)-1:

$X_1$ and $X_2$ may be S;

$X_1$ may be $C(R_{11})(R_{12})$ and $X_2$ may be S;

$X_1$ may be S and $X_2$ may be $C(R_{13})(R_{14})$;

$X_1$ may be O and $X_2$ may be S;

$X_1$ and $X_2$ may be O;

$X_1$ may be $C(R_{11})(R_{12})$ and $X_2$ may be O;

$X_1$ may be O and $X_2$ may be $C(R_{13})(R_{14})$; or $X_1$ may be S and $X_2$ may be O; however, exemplary embodiments of the present invention are not limited thereto.

According to one or more exemplary embodiments of the present invention, the condensed cyclic compound may be selected from compounds illustrated below; however, exemplary embodiments of the present invention are not limited thereto:

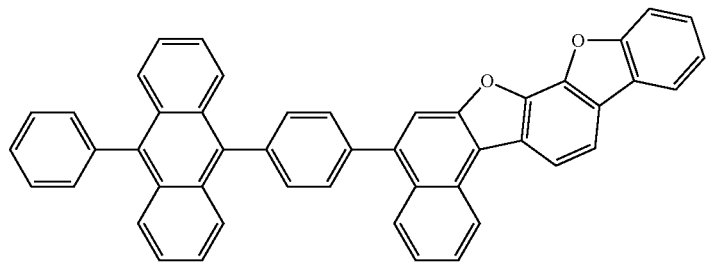

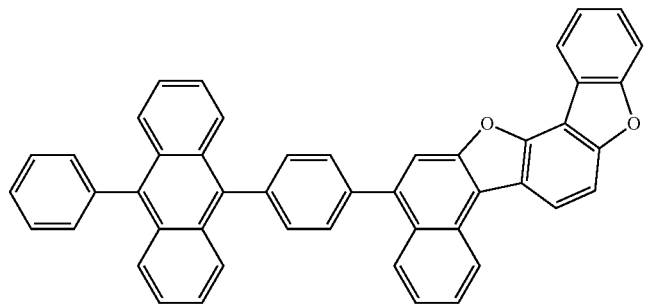

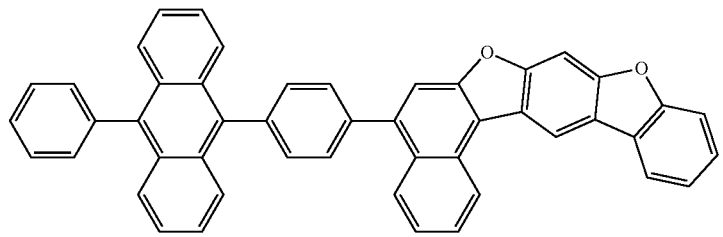

-continued
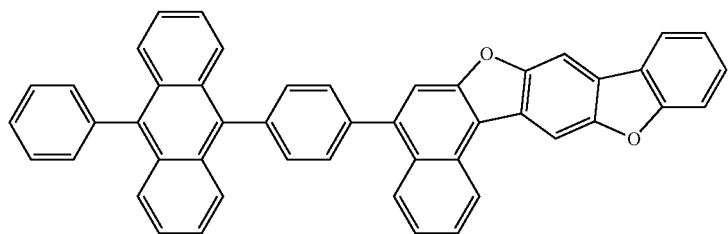
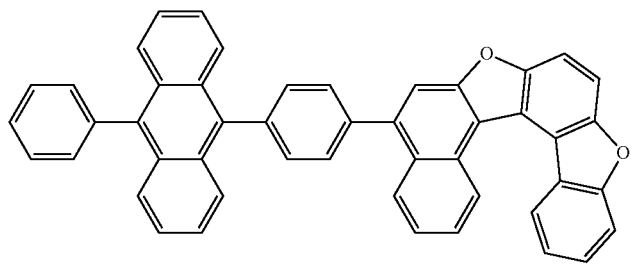
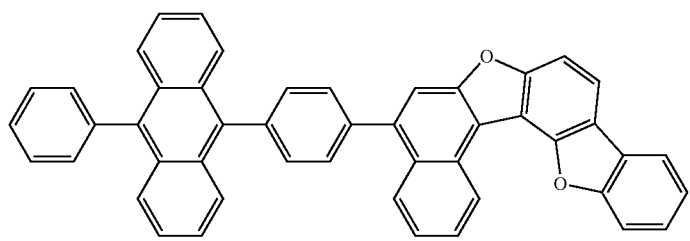
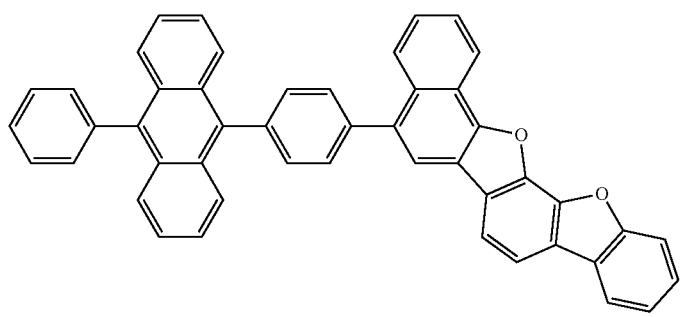
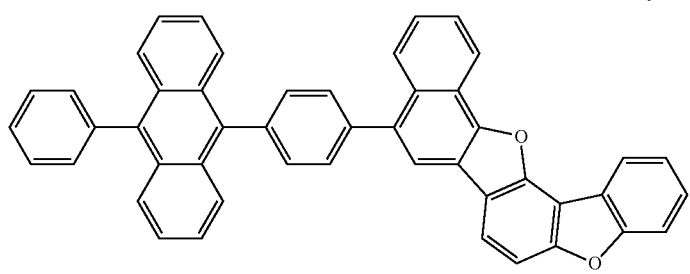
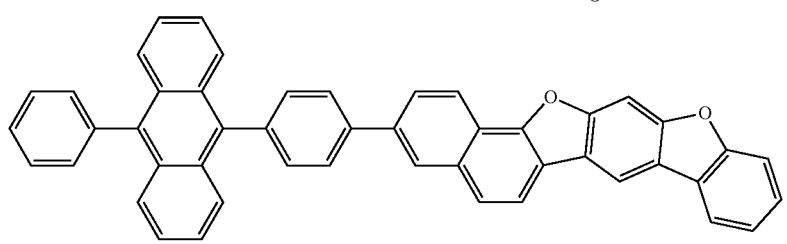

-continued
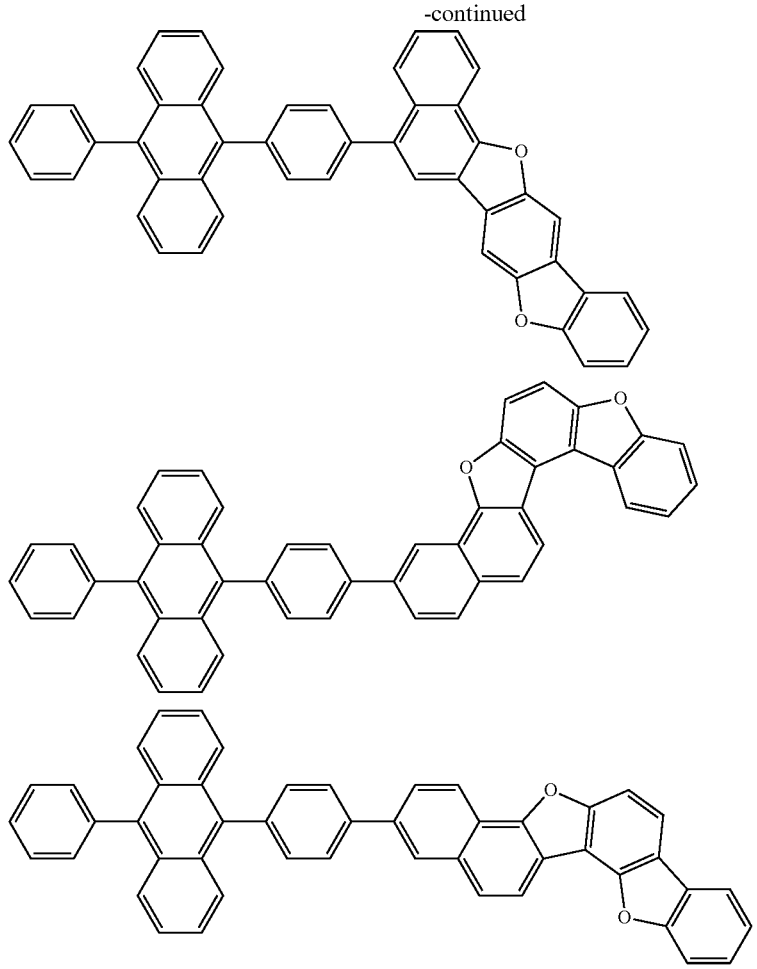
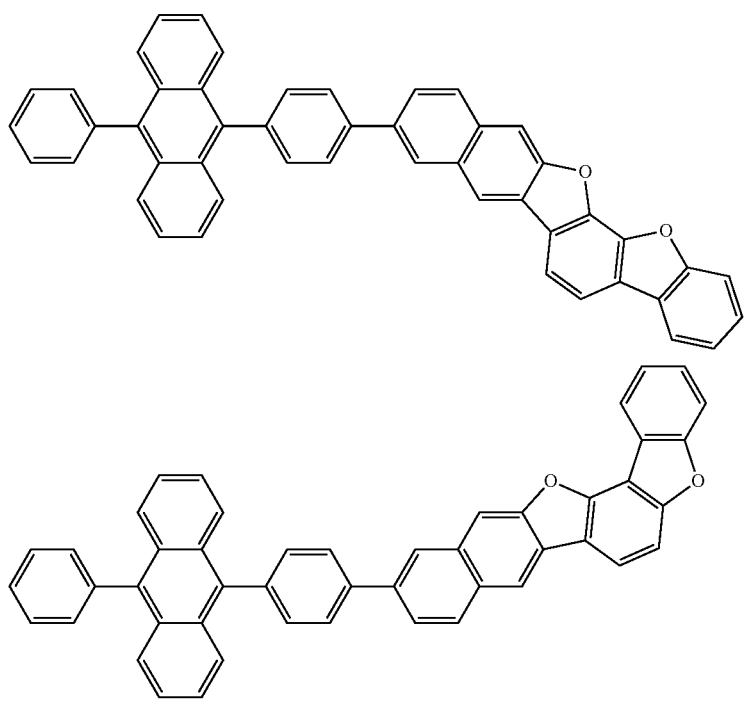

-continued
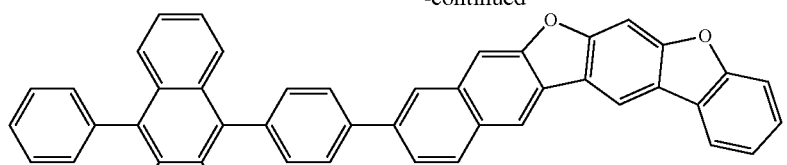
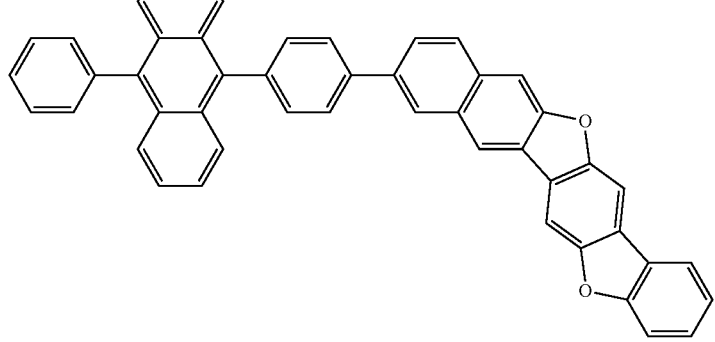
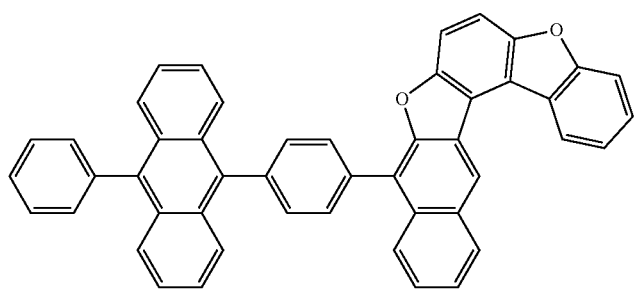
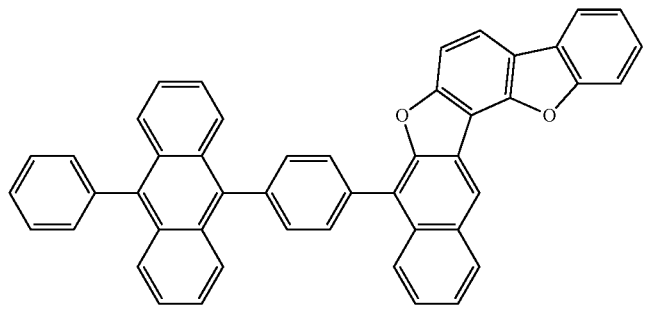
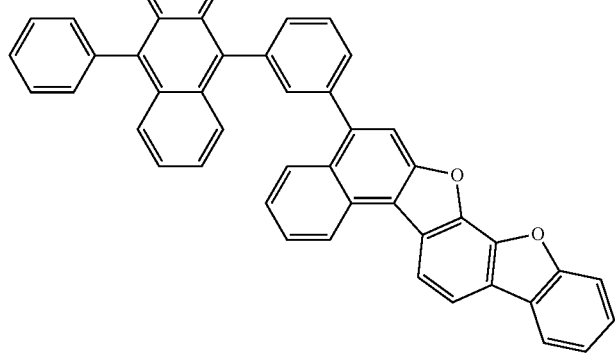

-continued
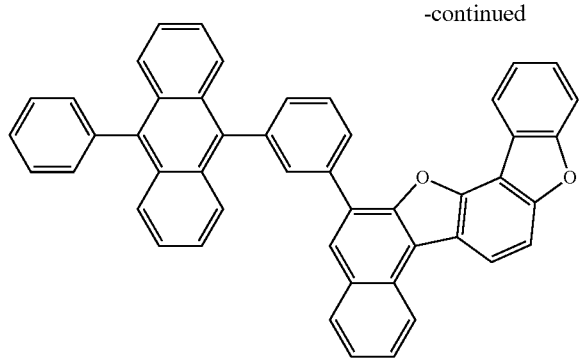
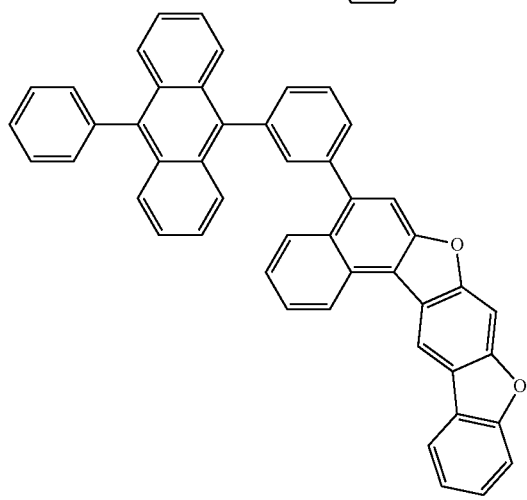
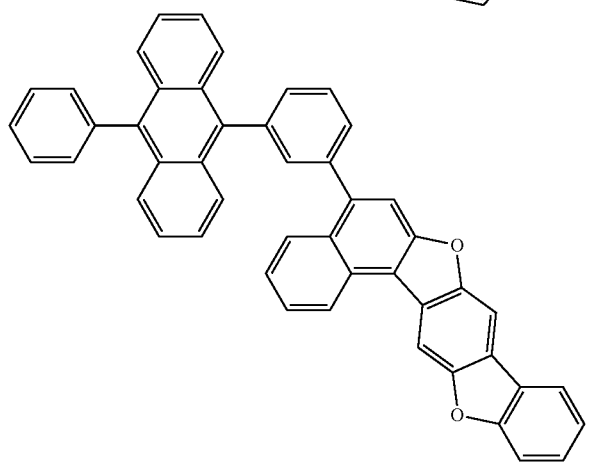
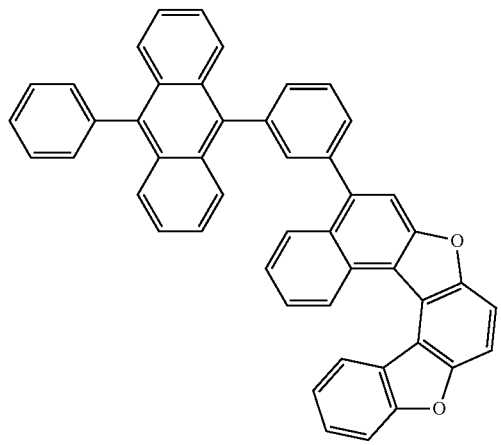

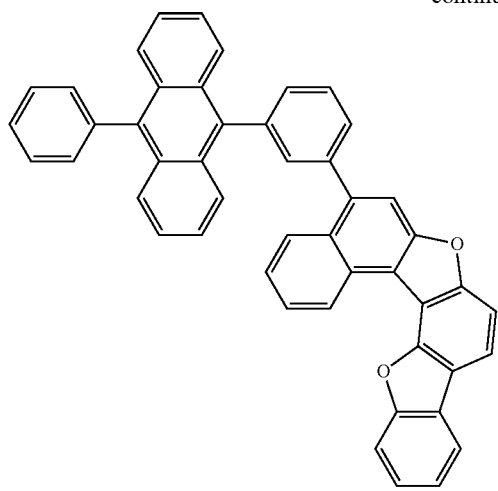
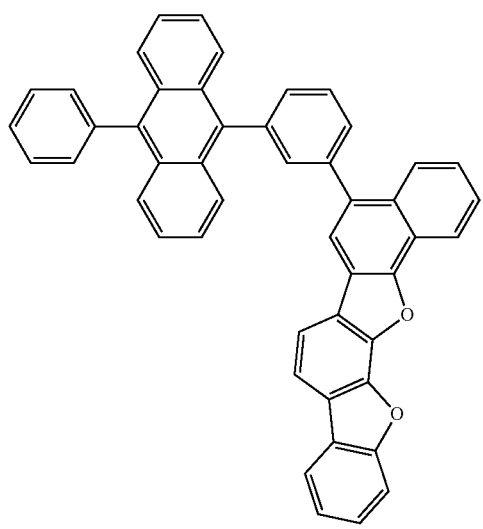
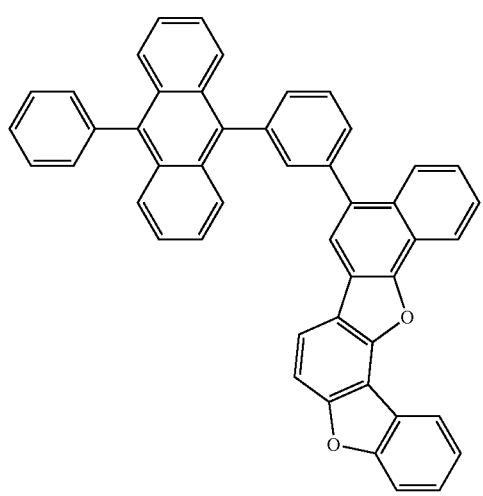

-continued
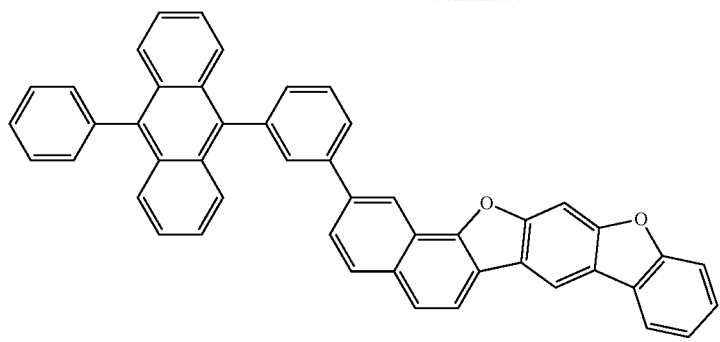
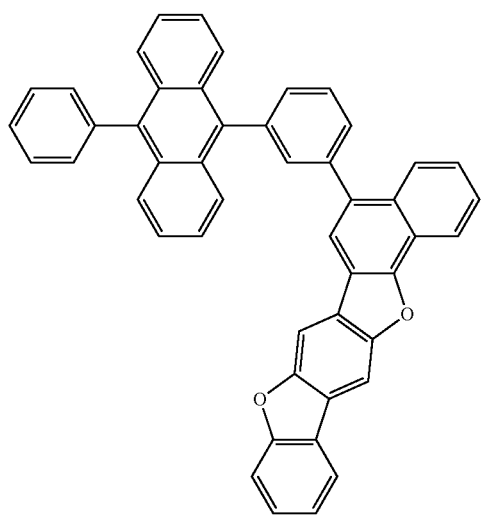
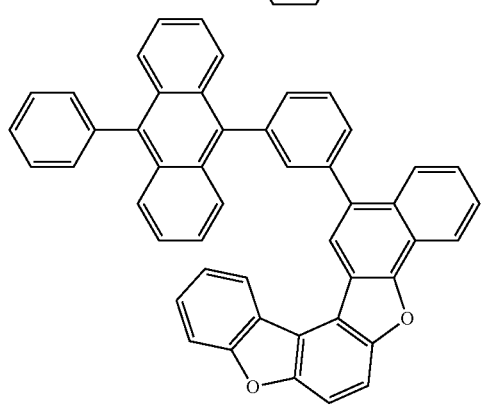
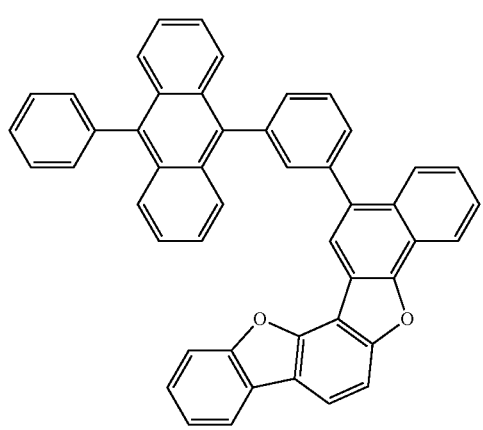

-continued
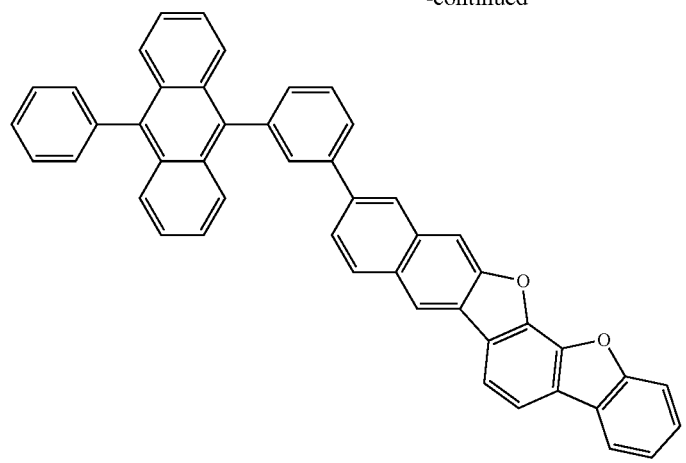
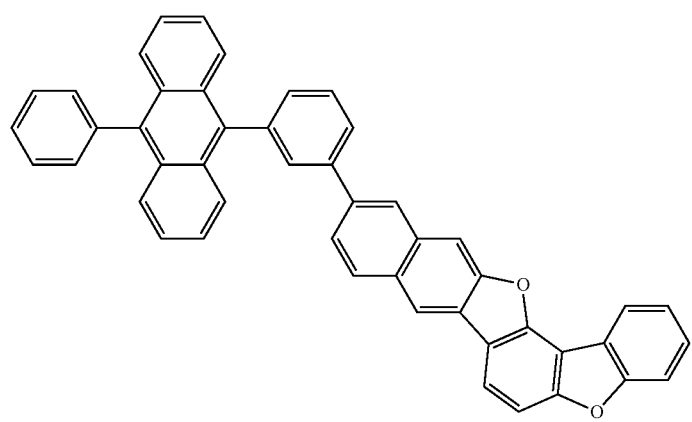
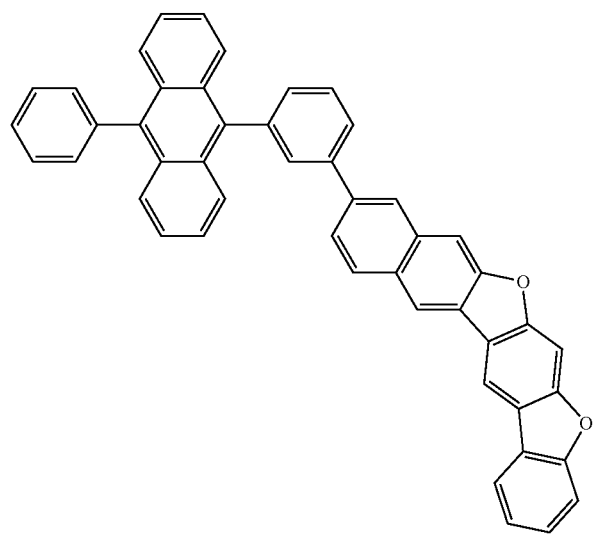

-continued
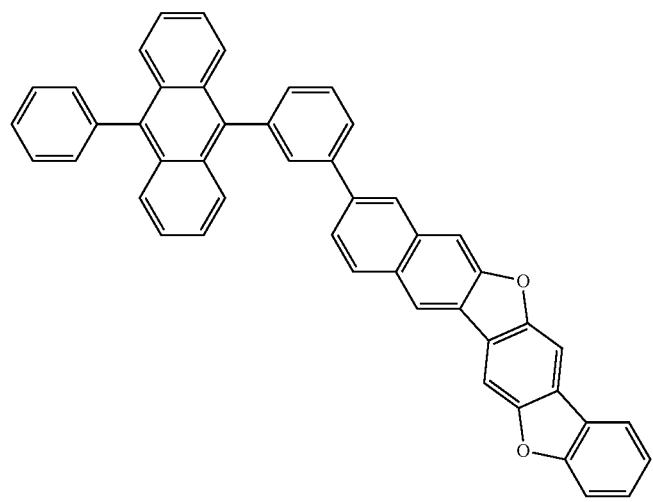
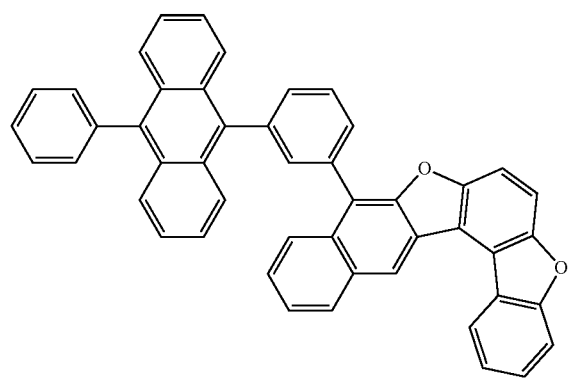
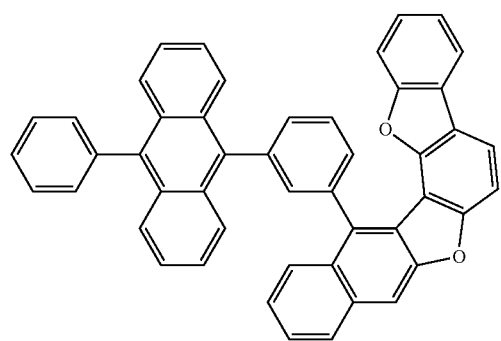
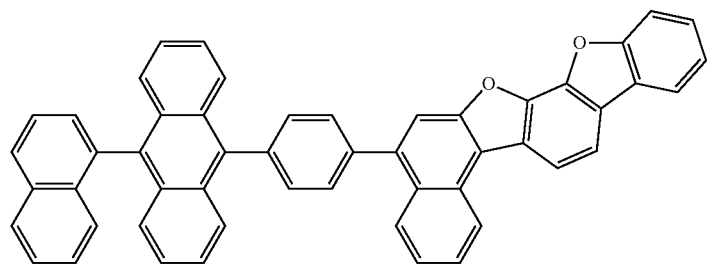

-continued
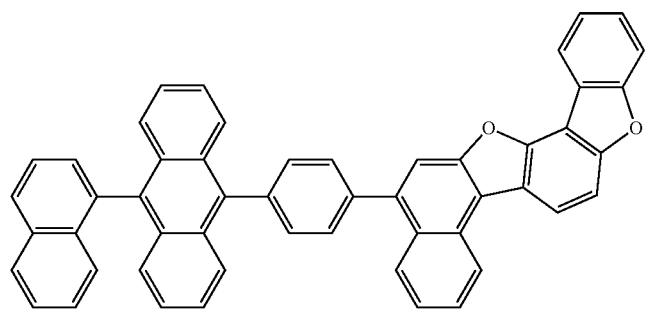
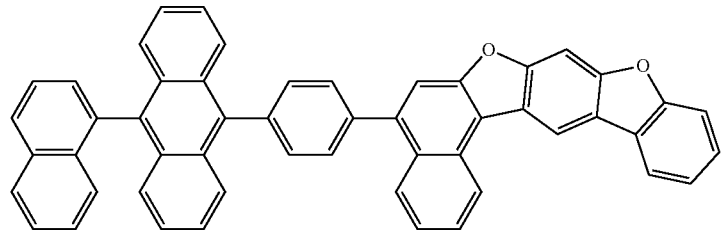
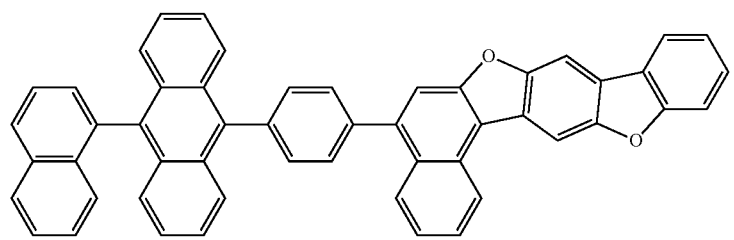
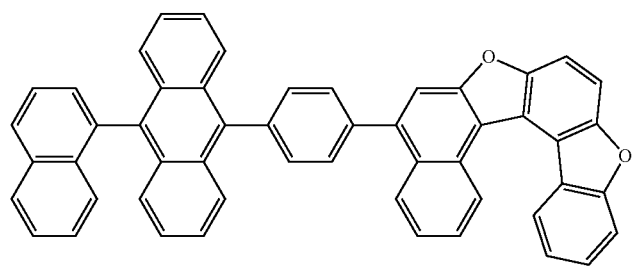
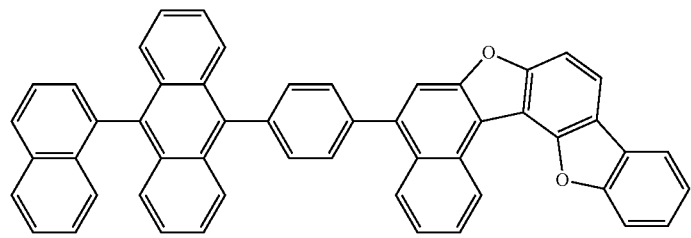
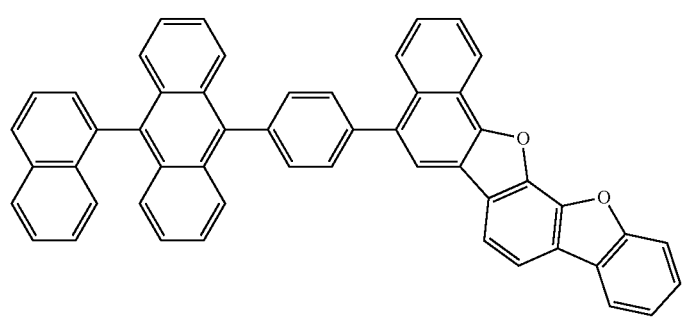

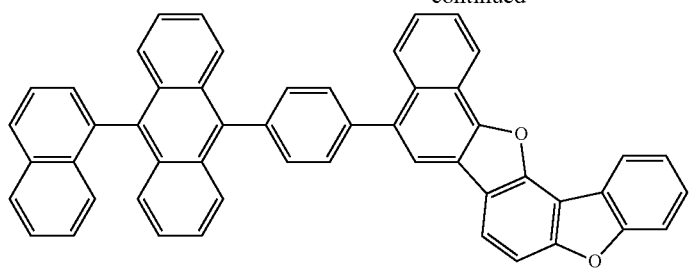
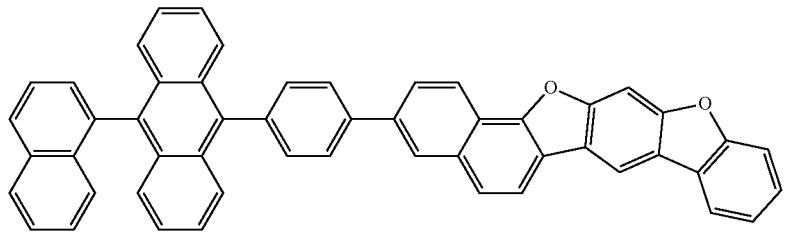
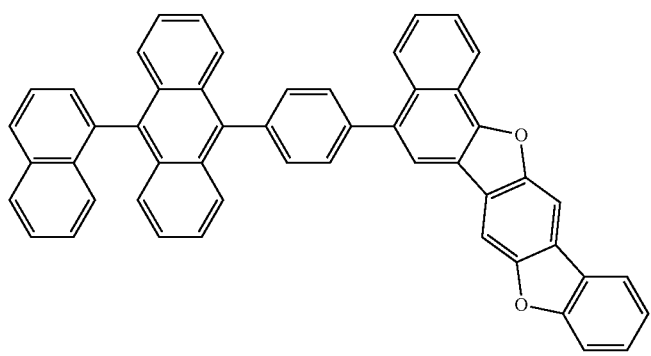
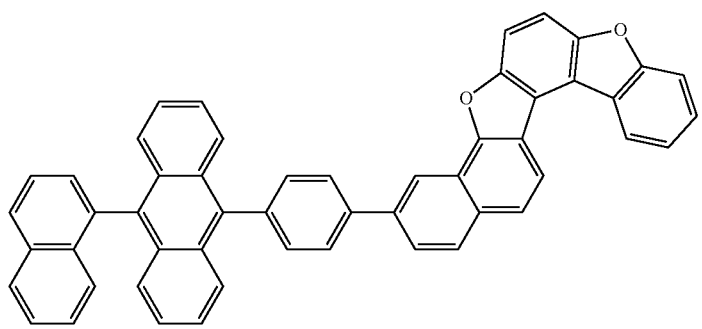
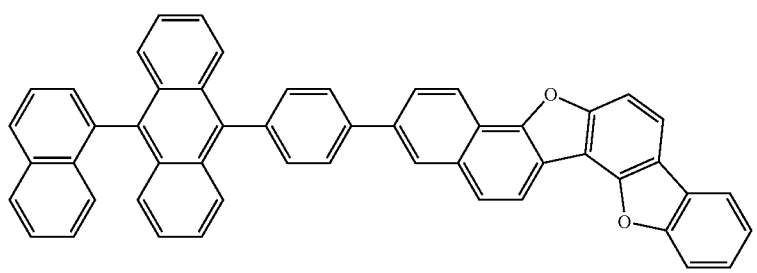

-continued
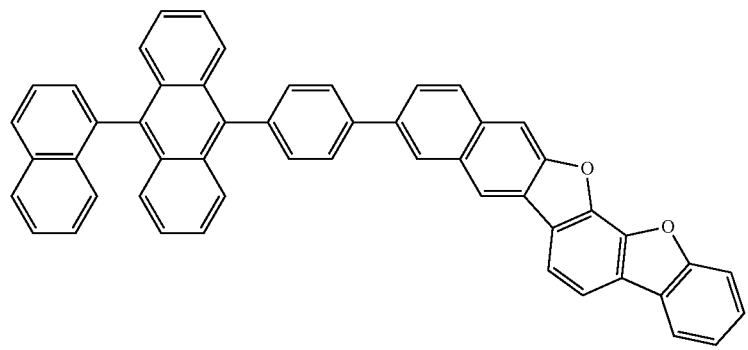
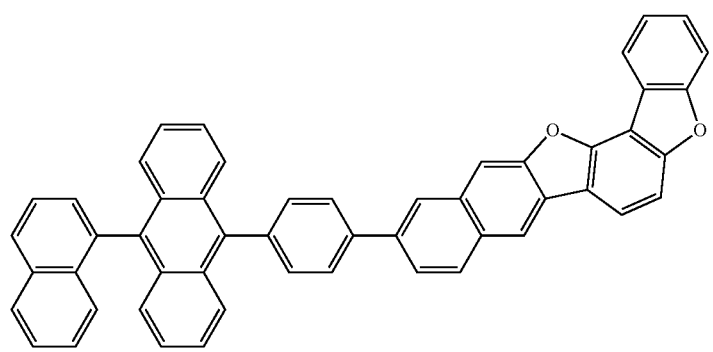
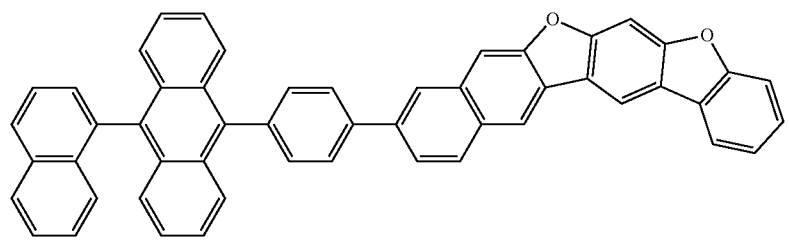
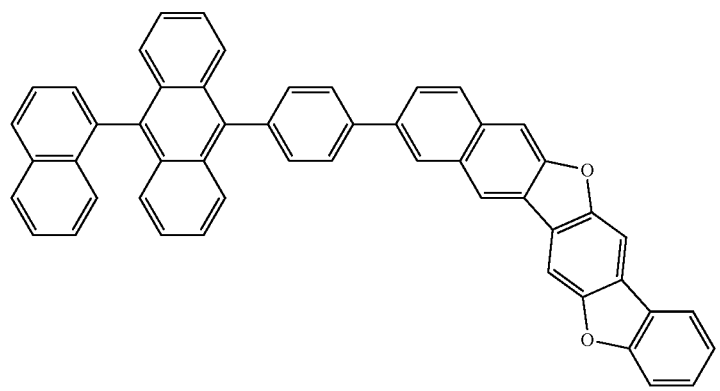
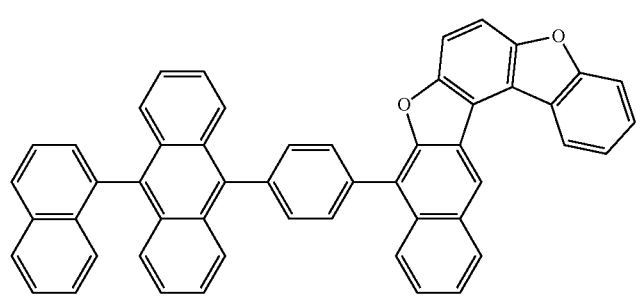

-continued
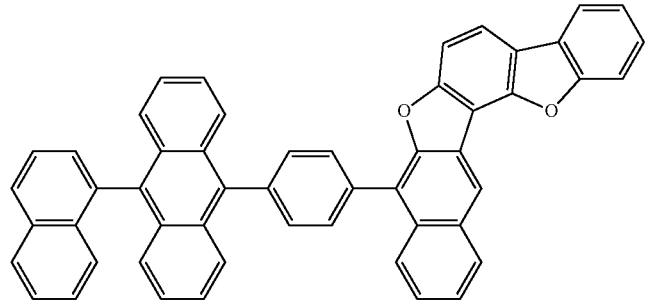
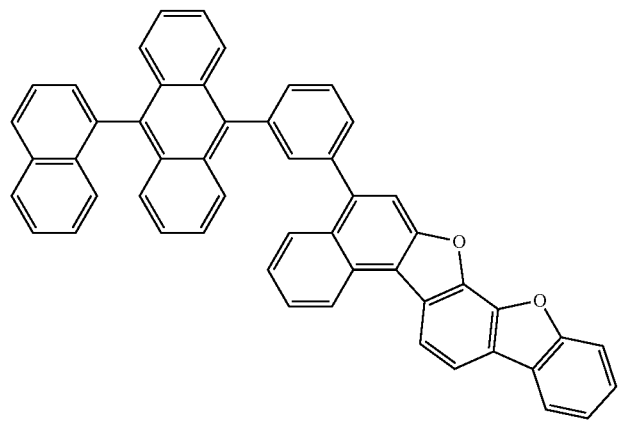
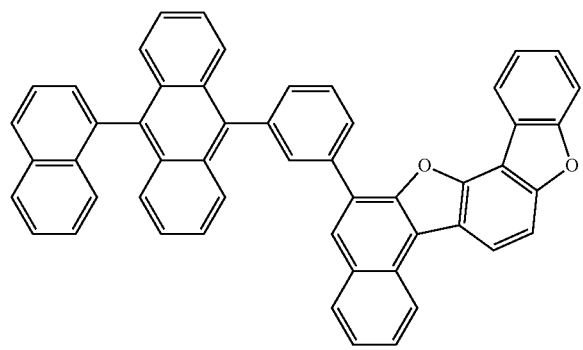
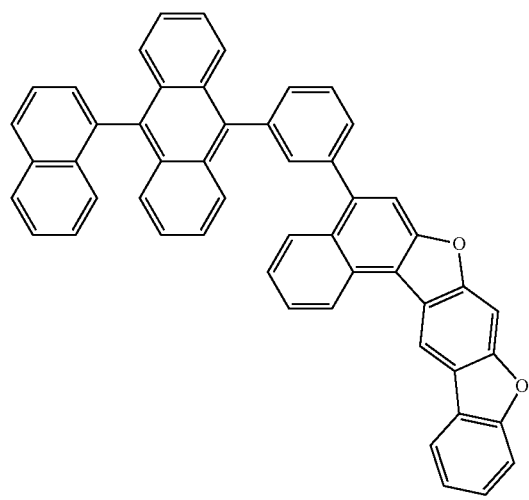

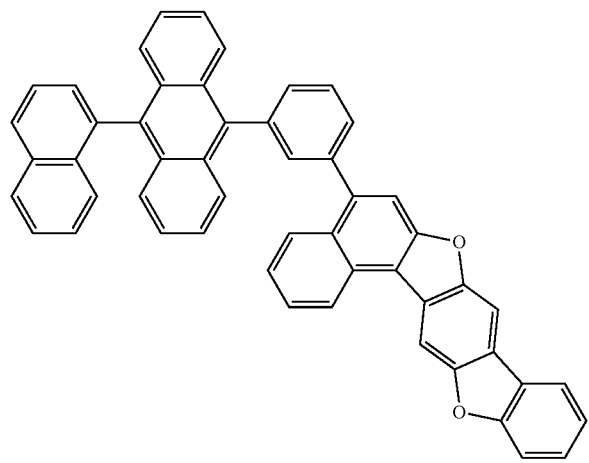

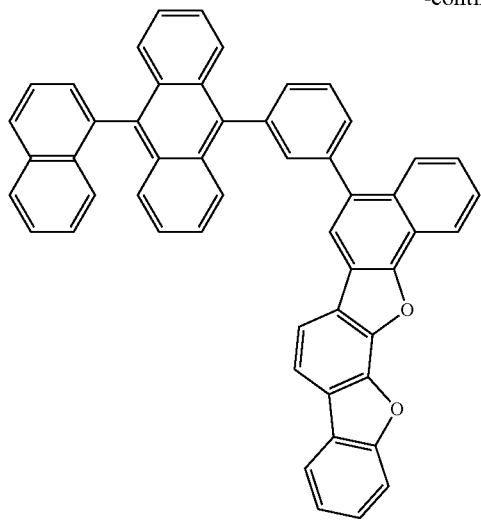
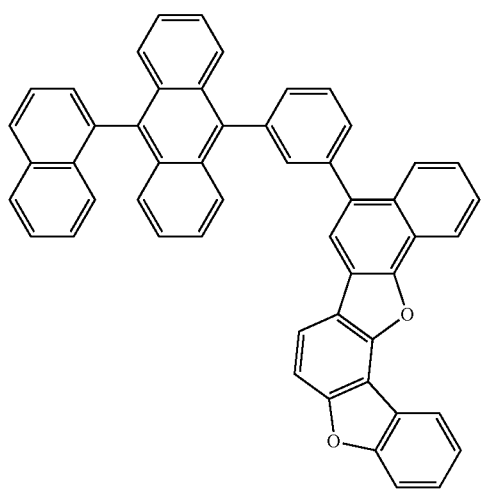
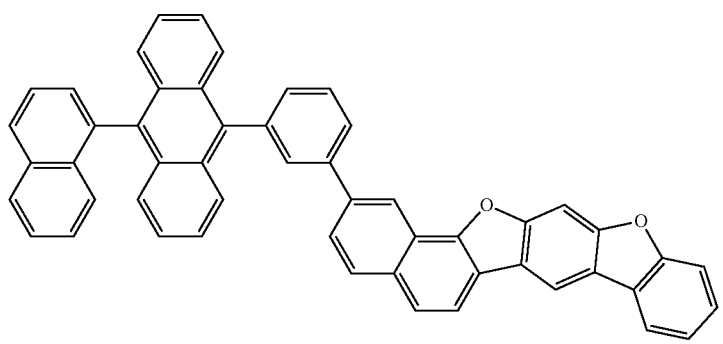

-continued
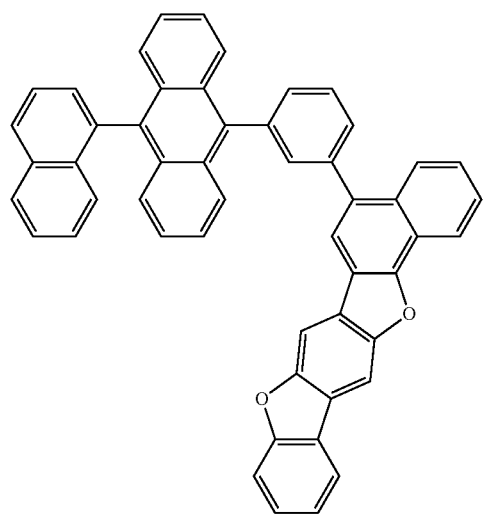

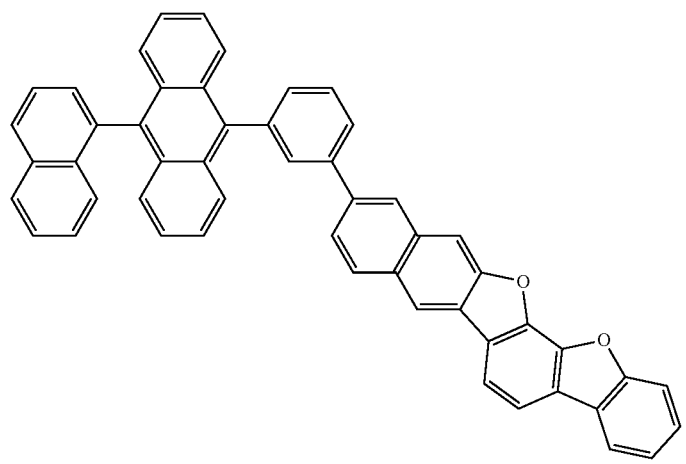
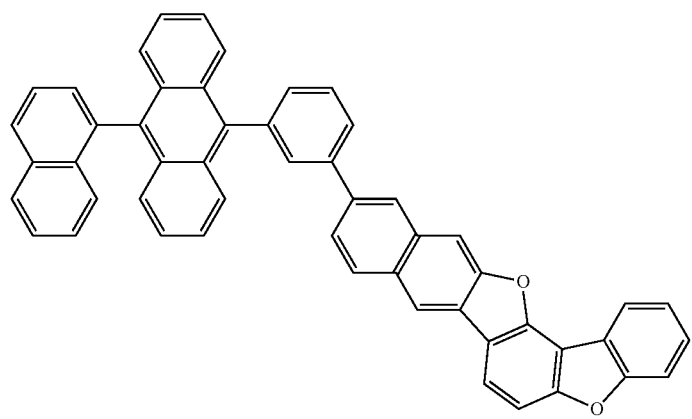
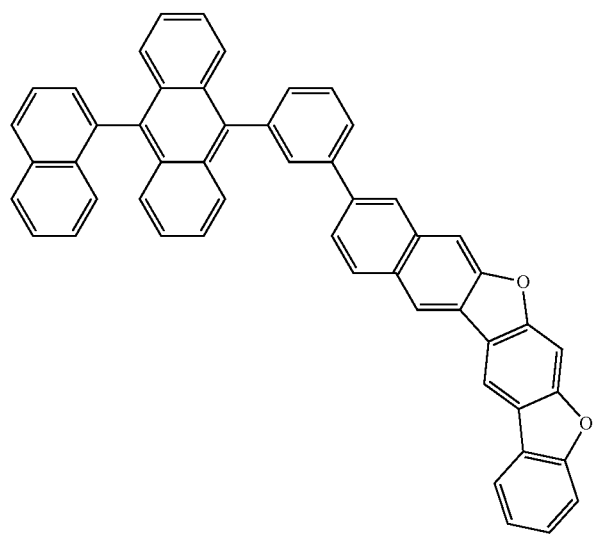

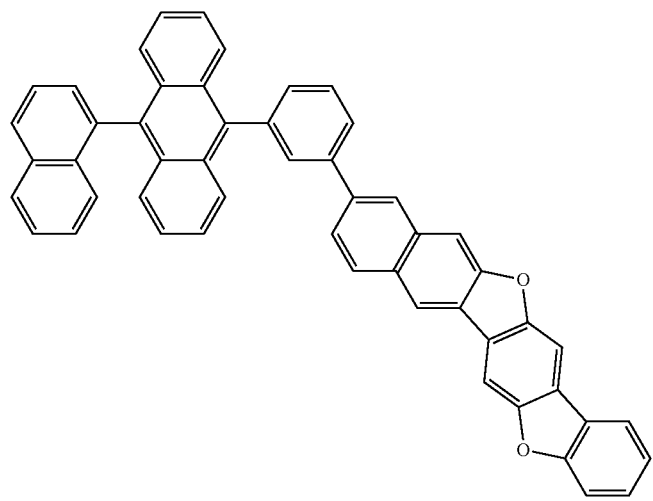
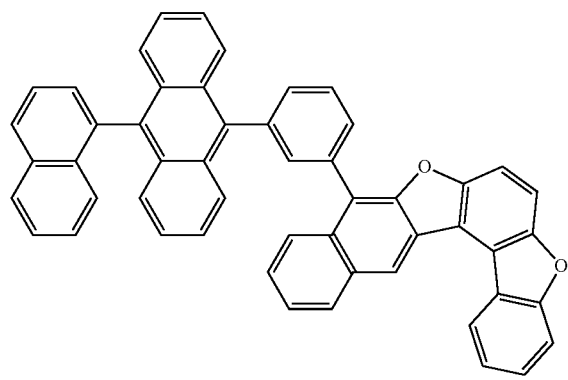
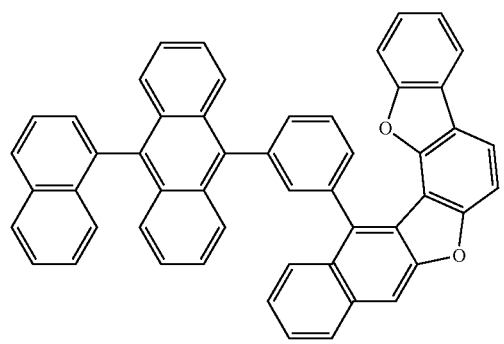
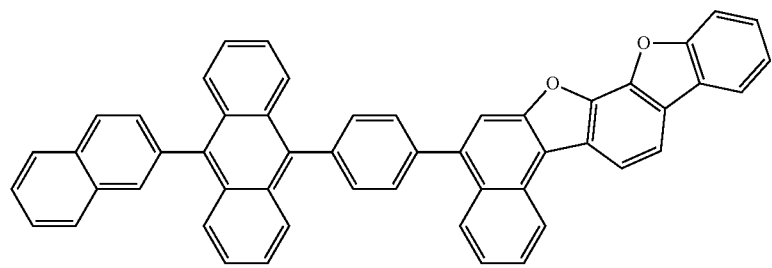

-continued
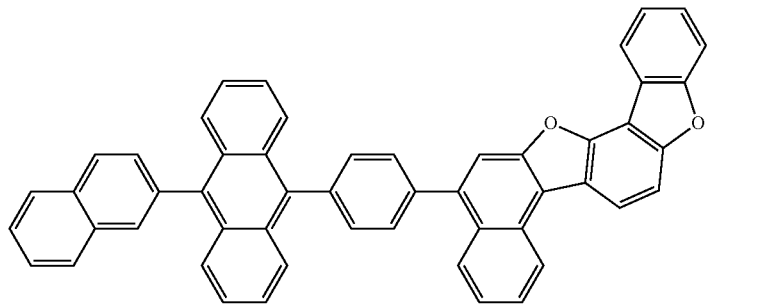
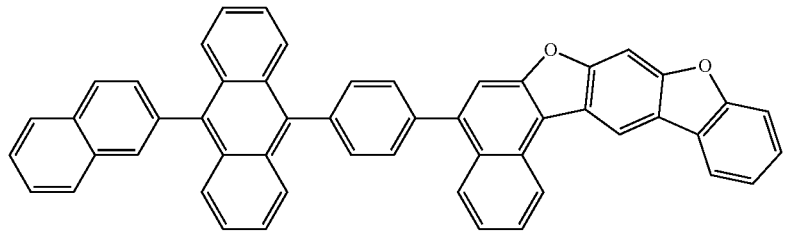
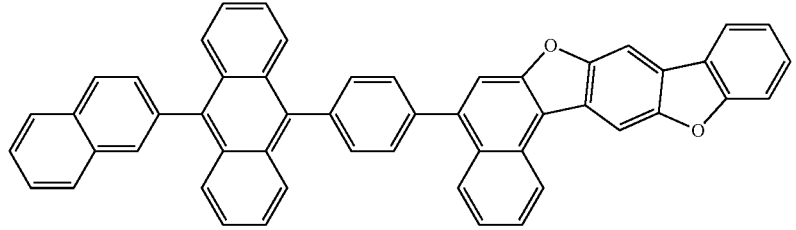
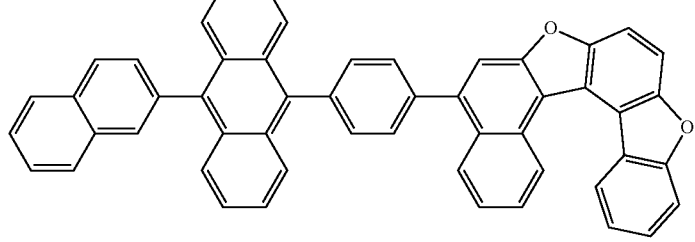
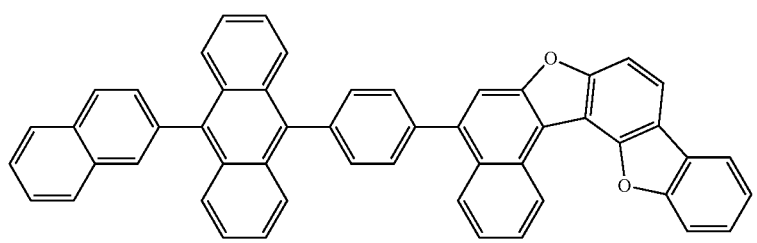
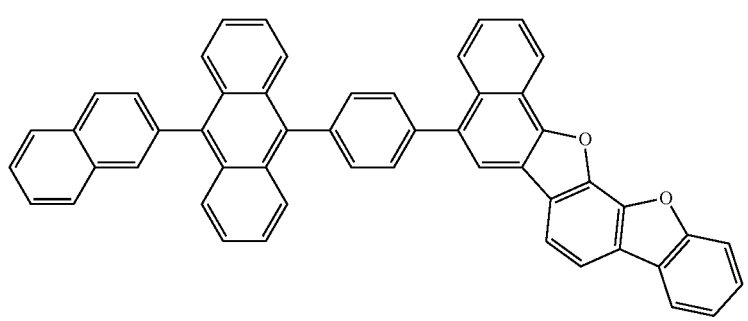

-continued
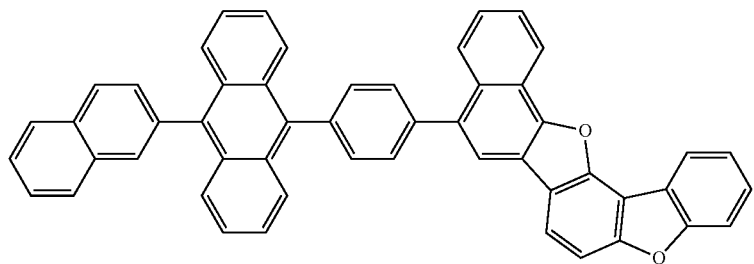
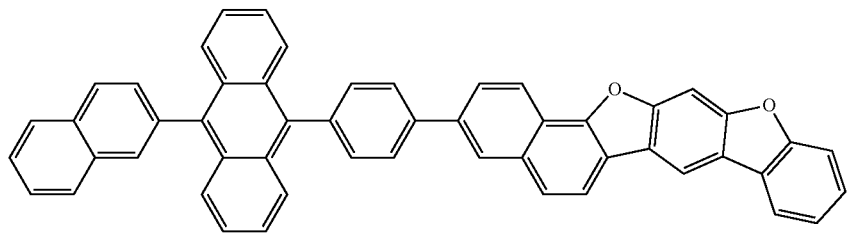
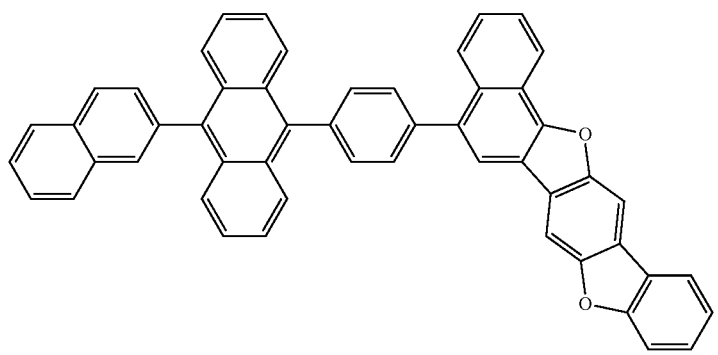
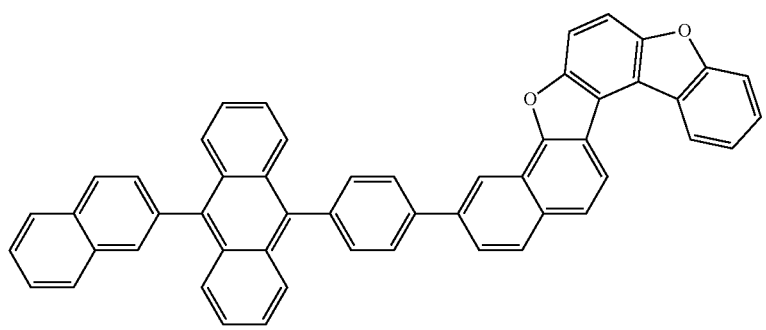
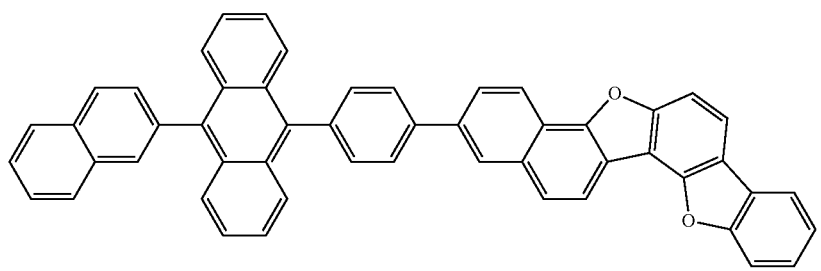

-continued
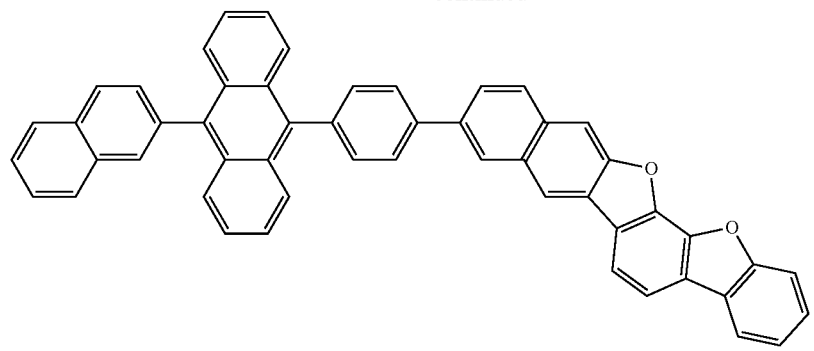
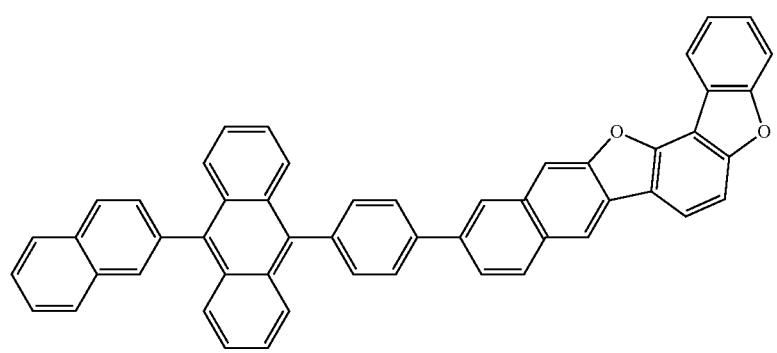
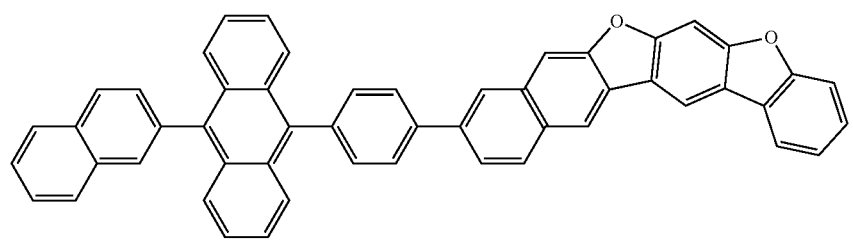
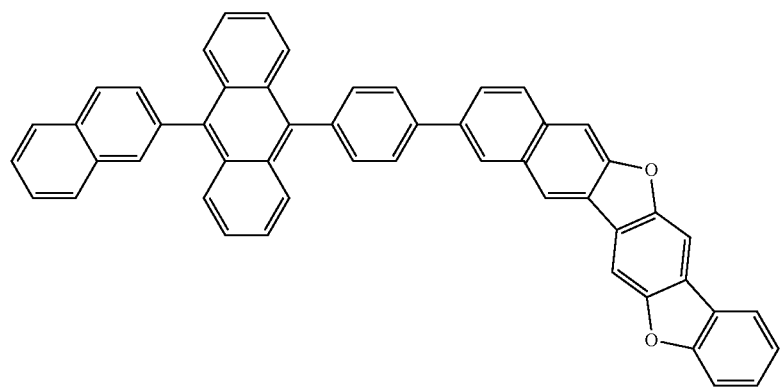
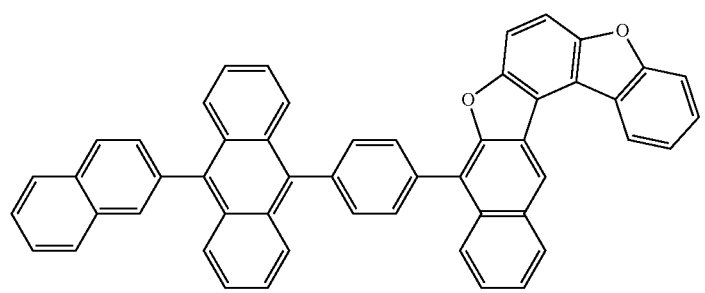

-continued
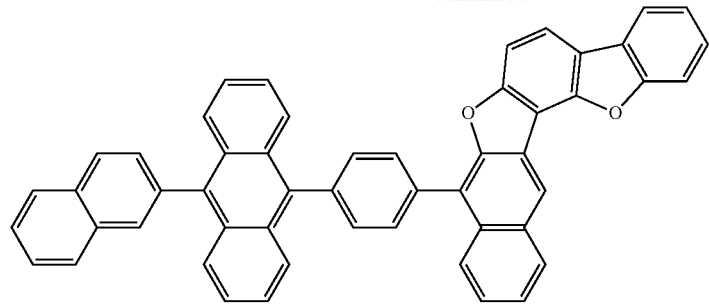

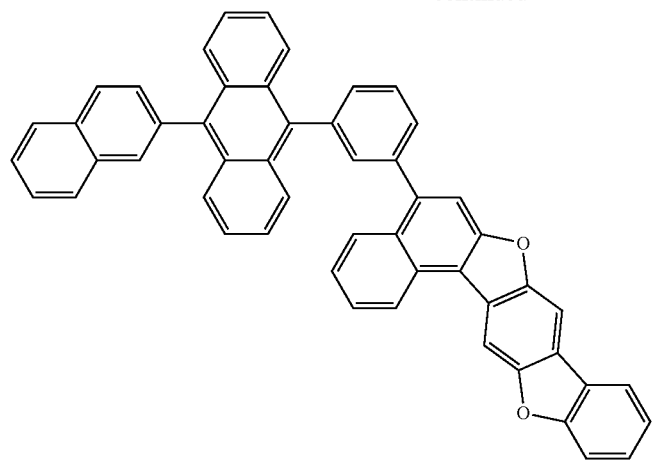
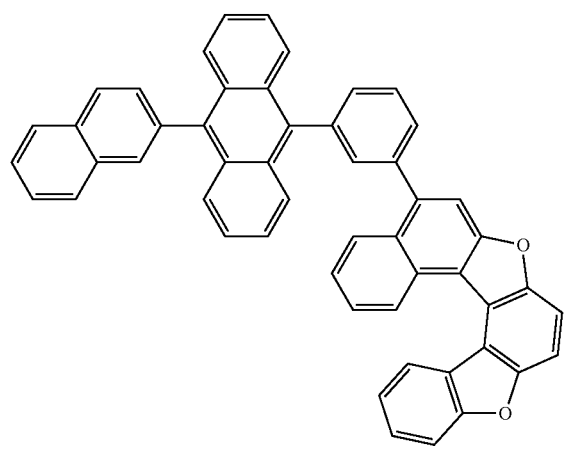
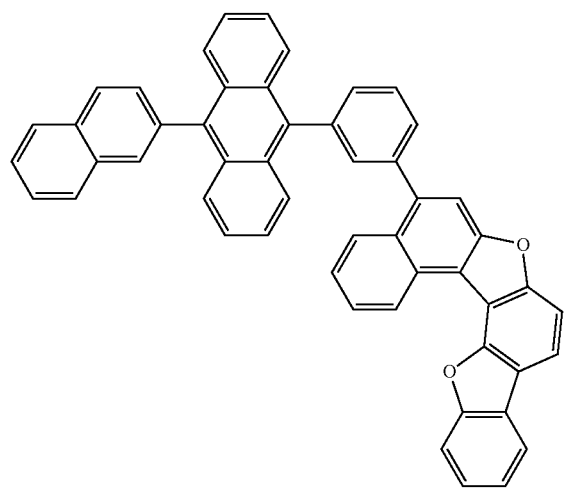

-continued
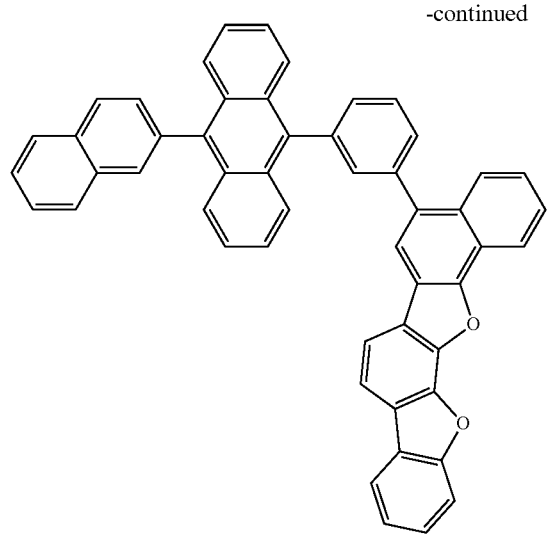
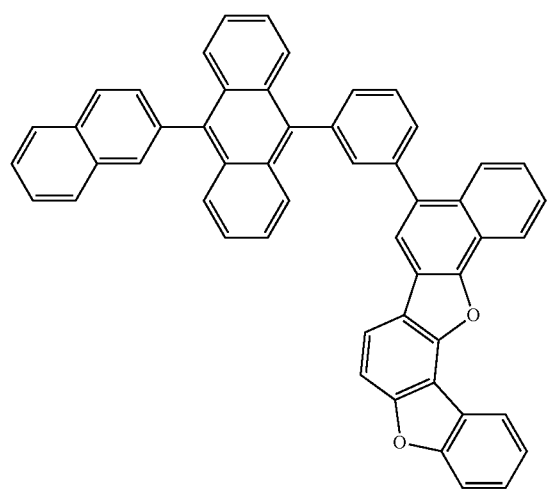
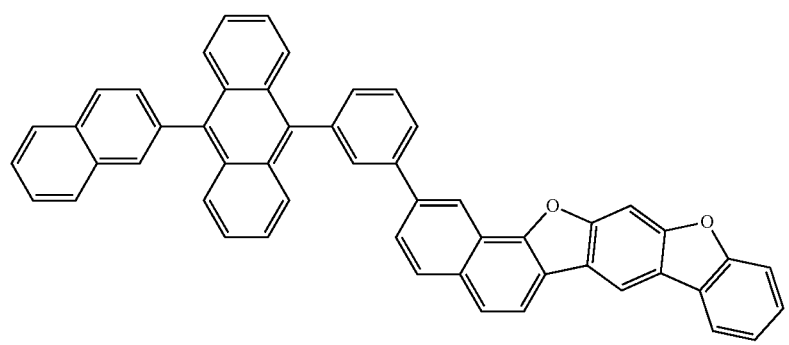

-continued
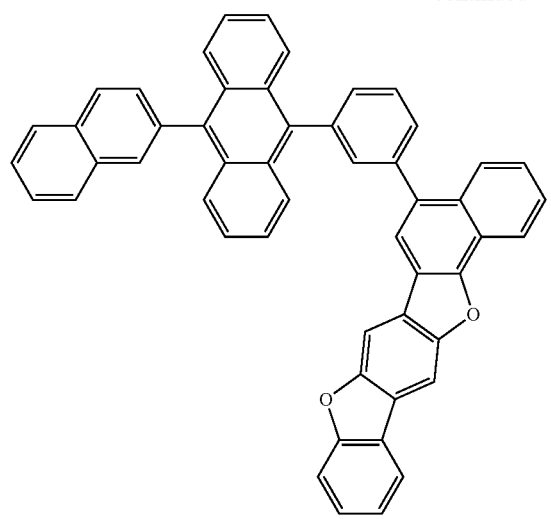
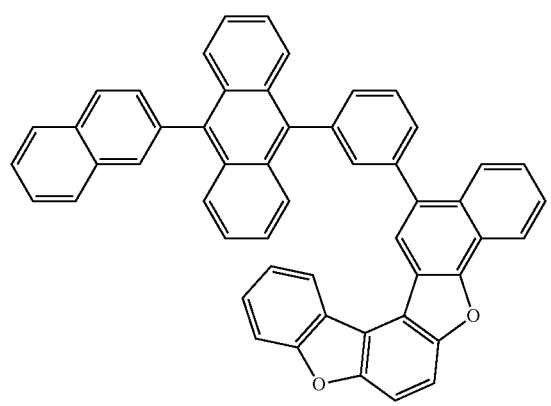
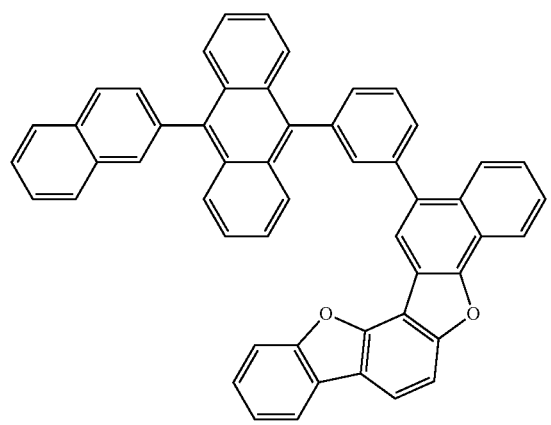

-continued
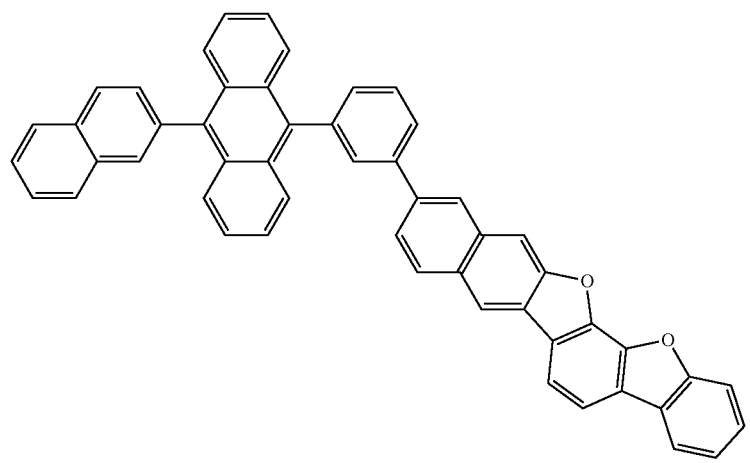
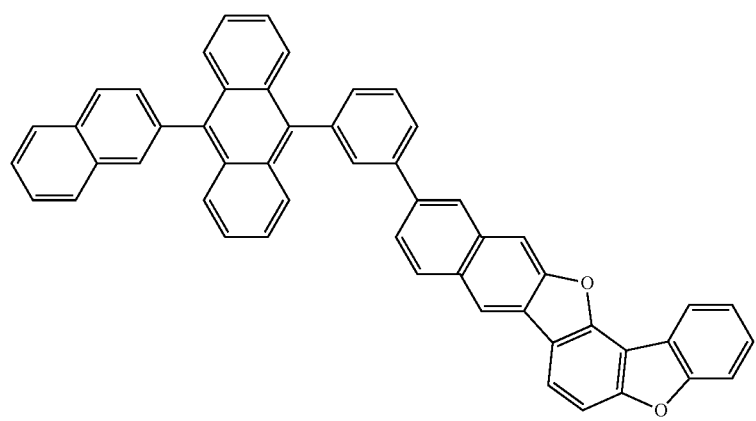
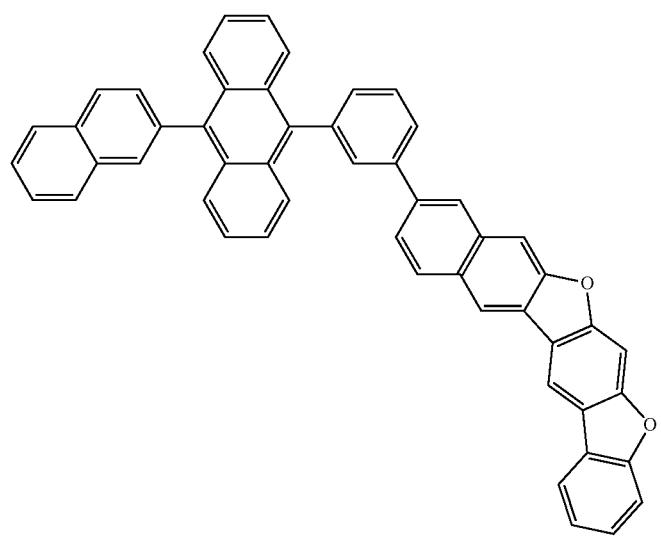

-continued
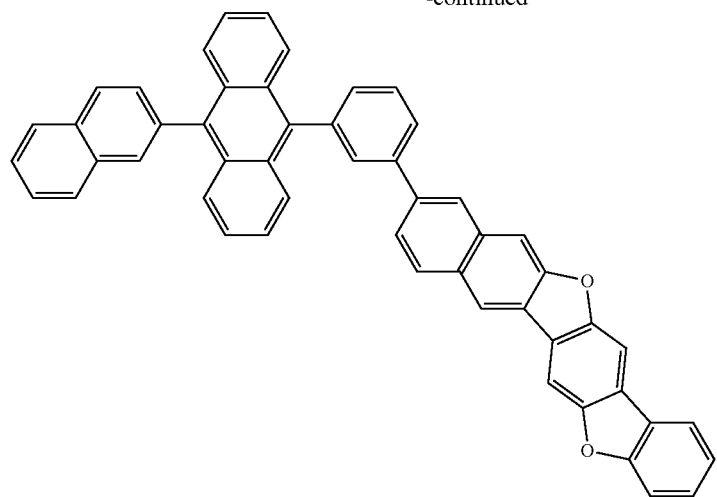
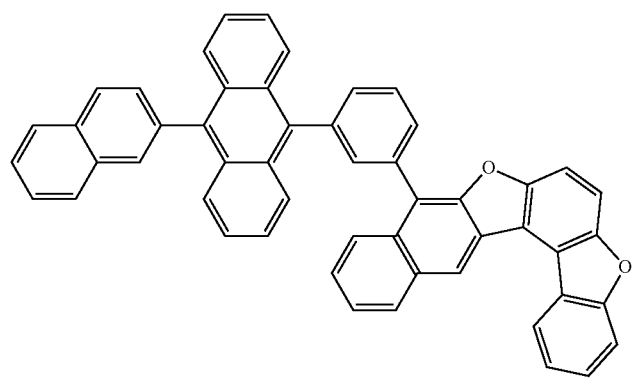
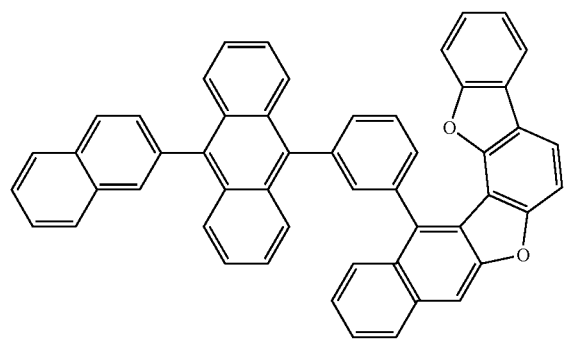
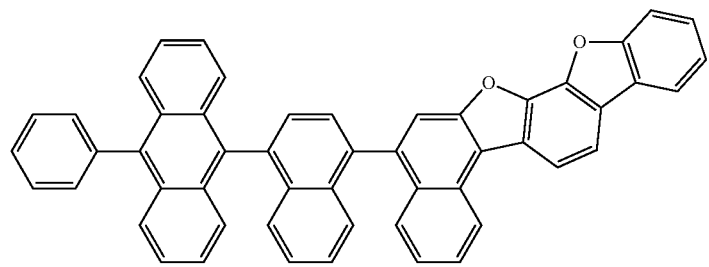

-continued
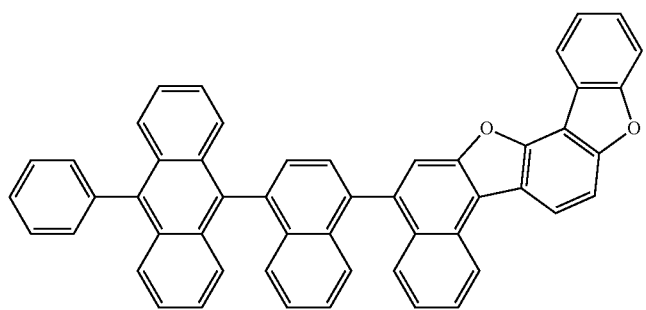
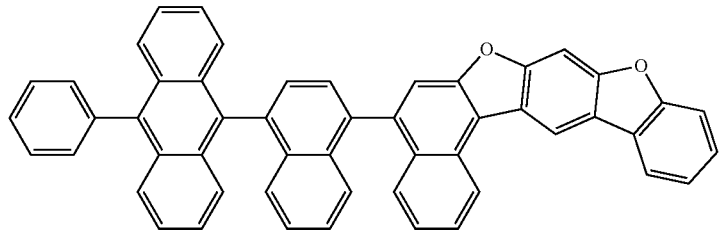
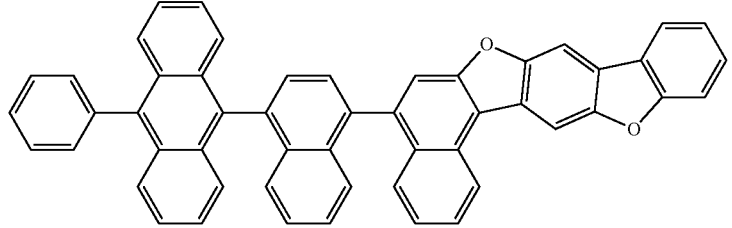
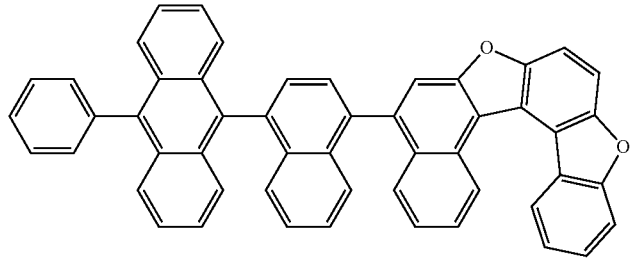
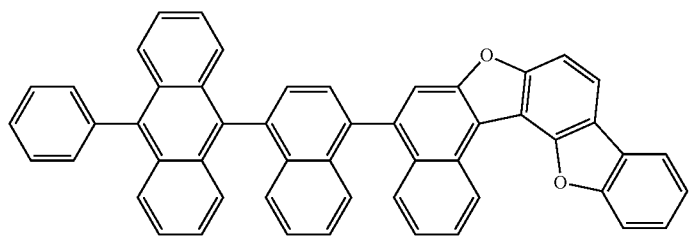
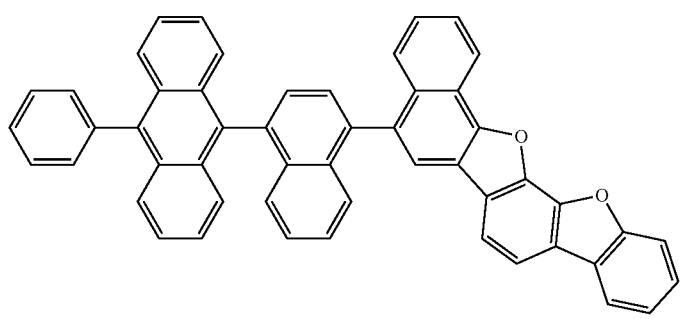

-continued
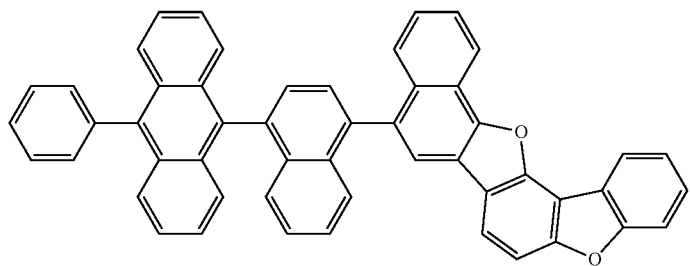
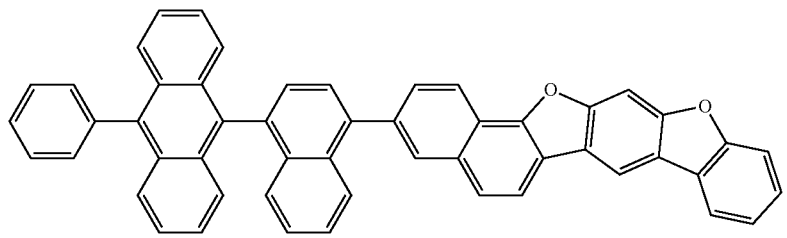
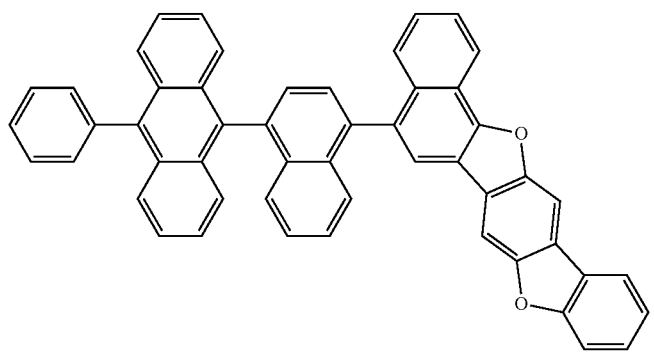
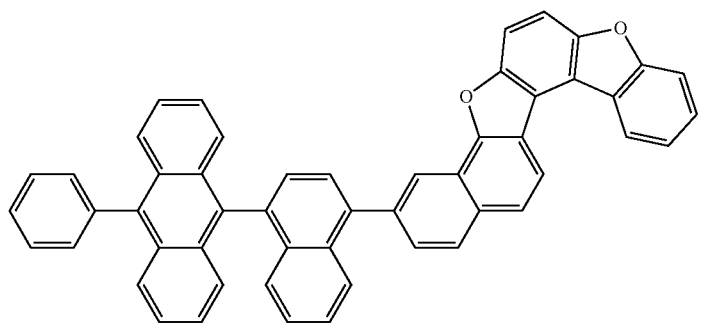
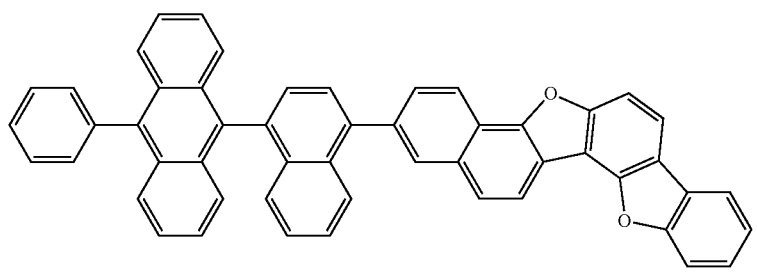

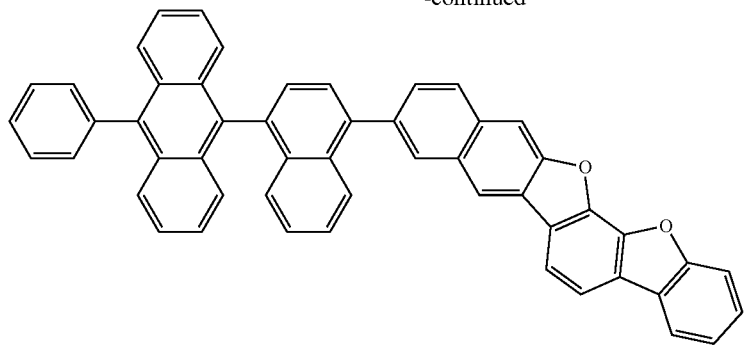
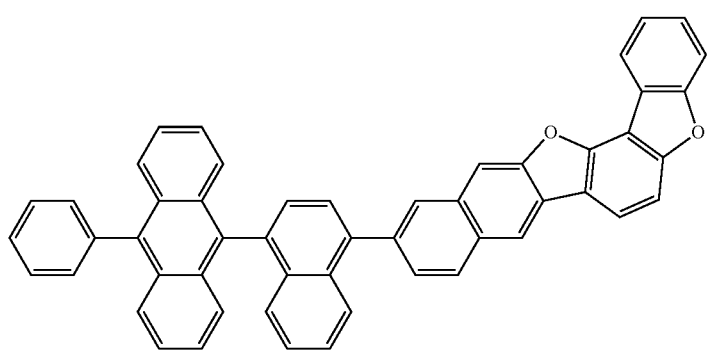
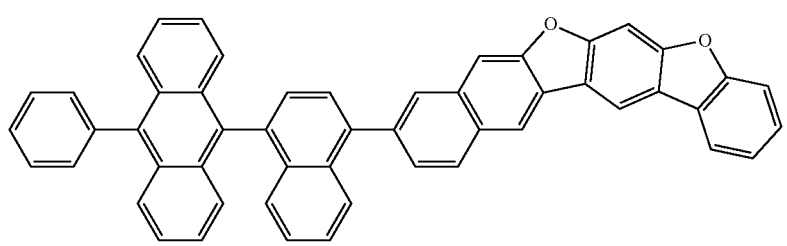
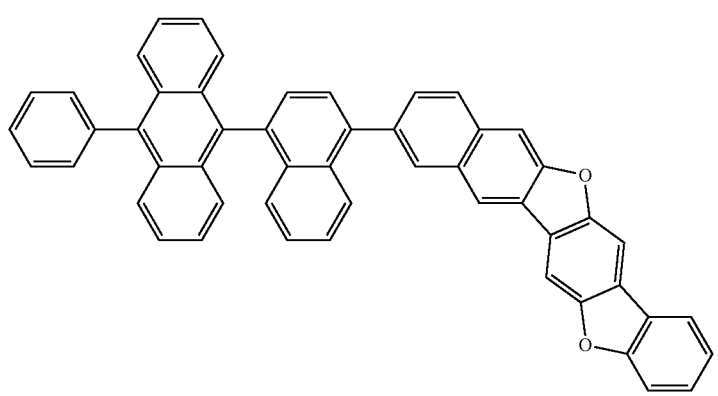
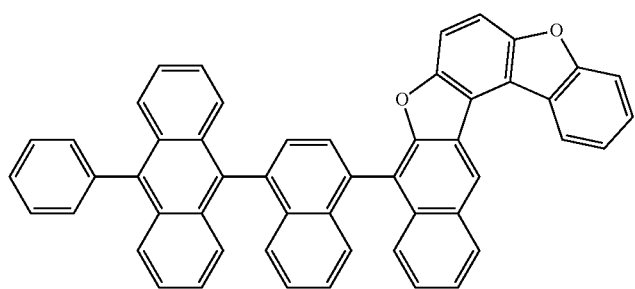

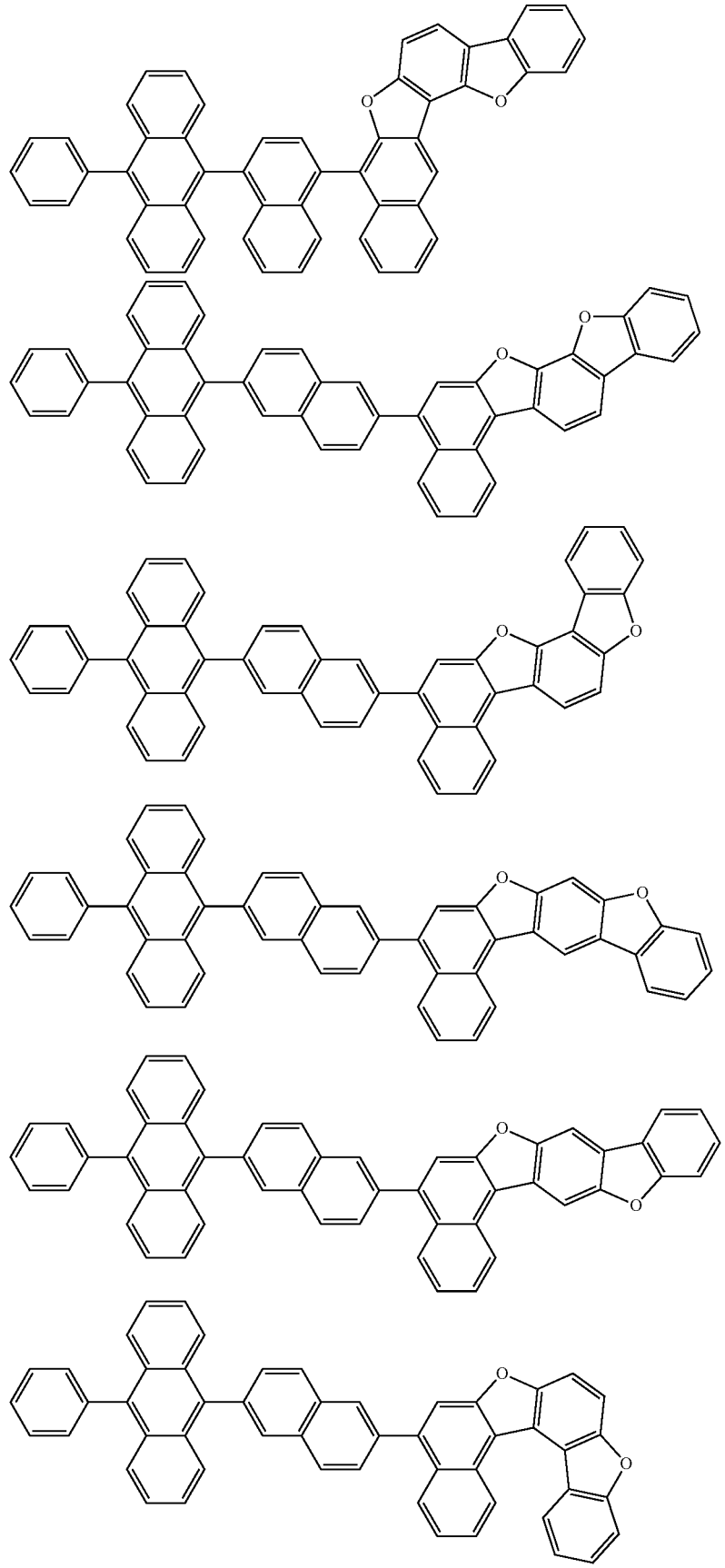

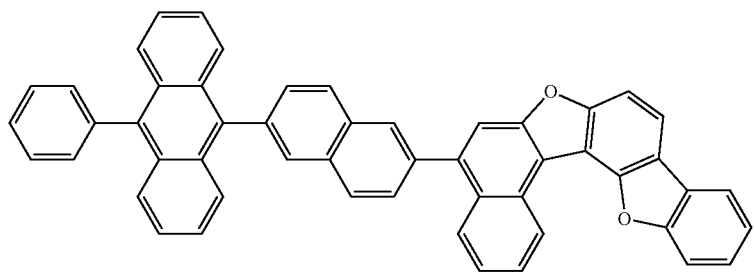
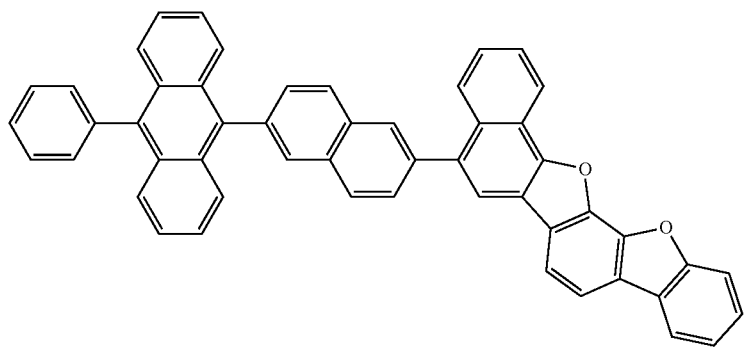
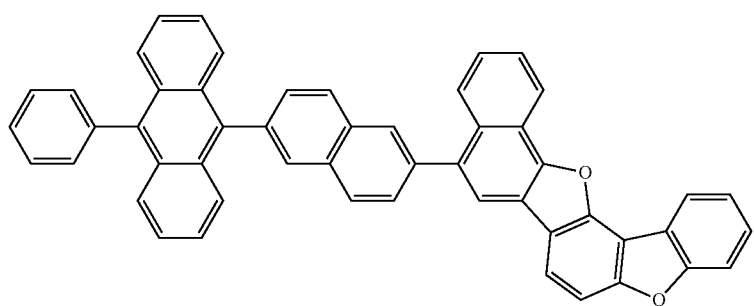
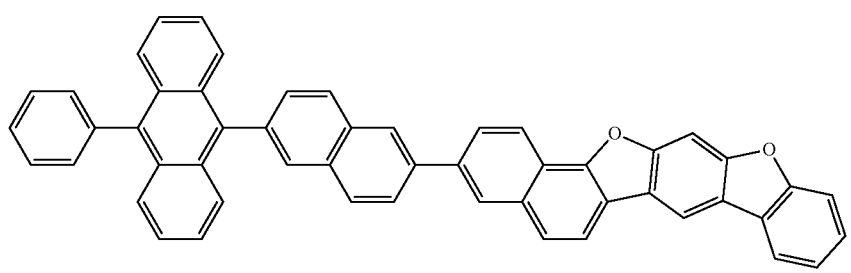
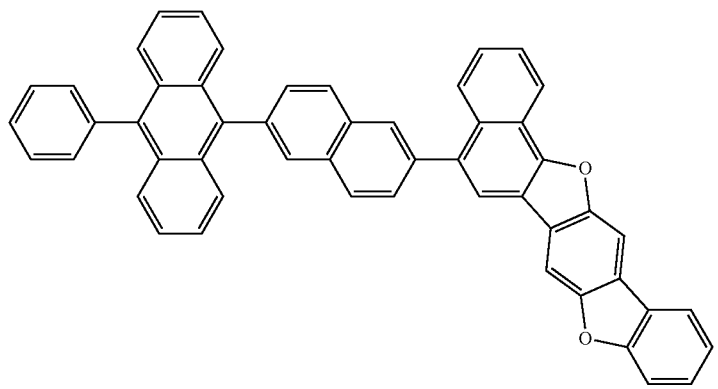

-continued
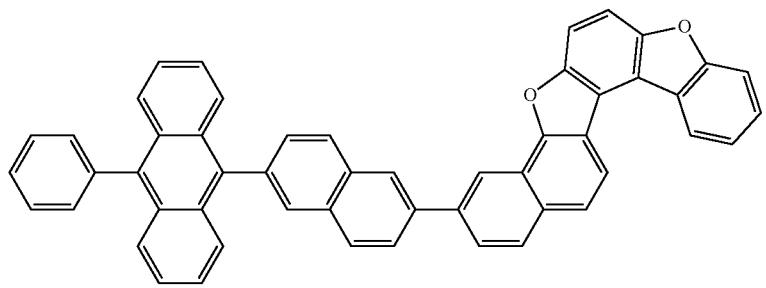
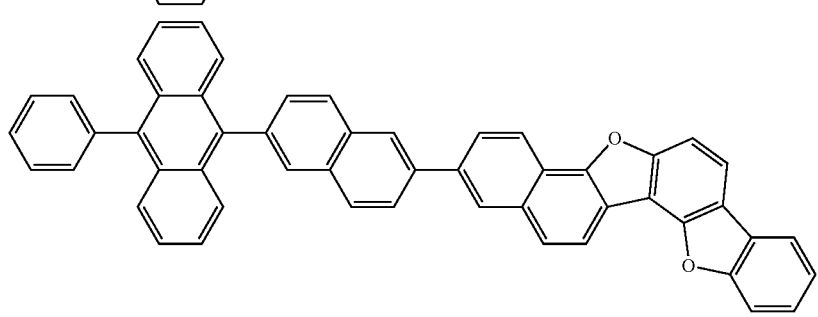
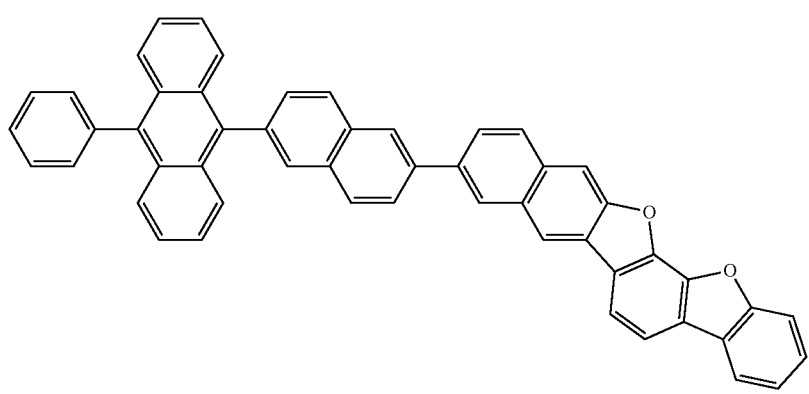
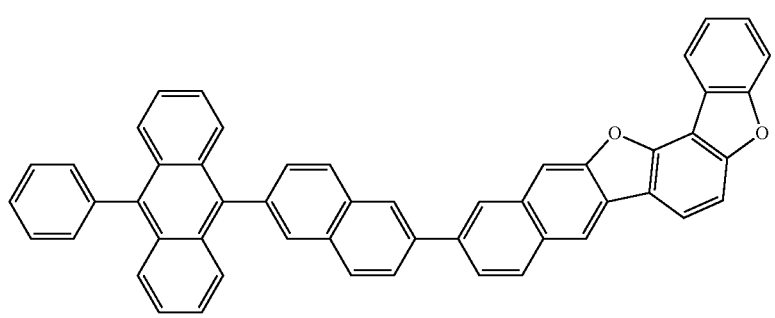
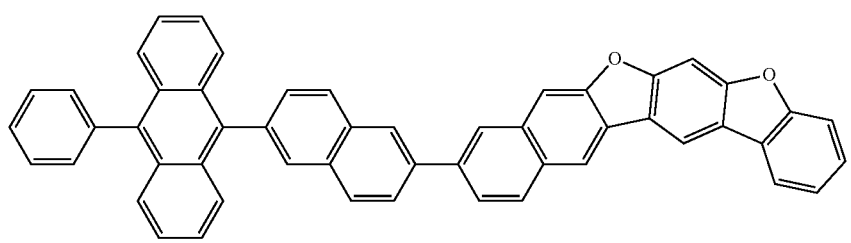

-continued
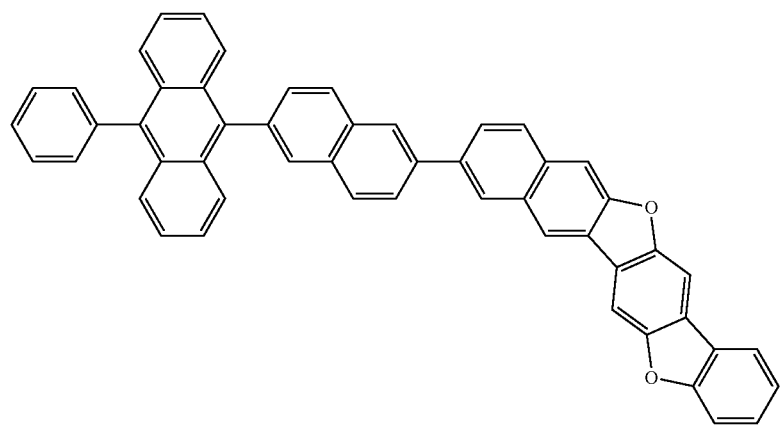
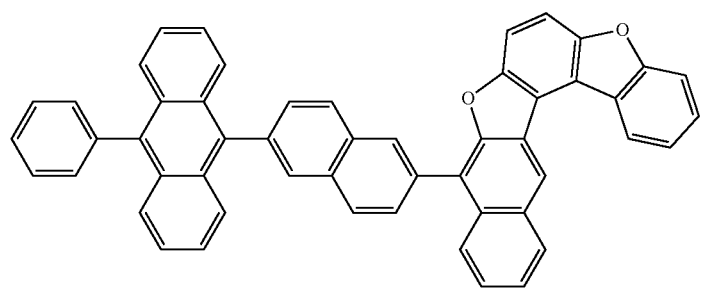
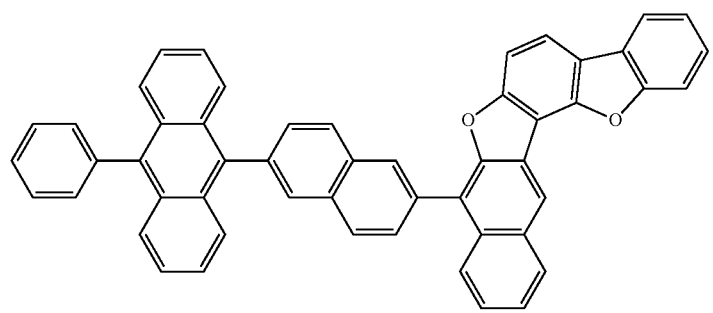
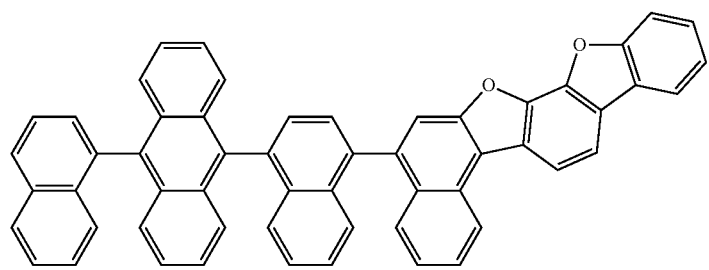
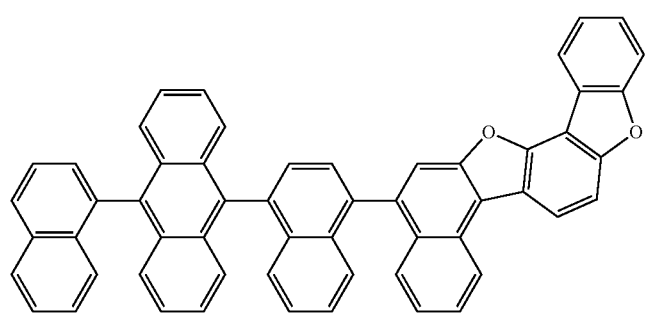

-continued
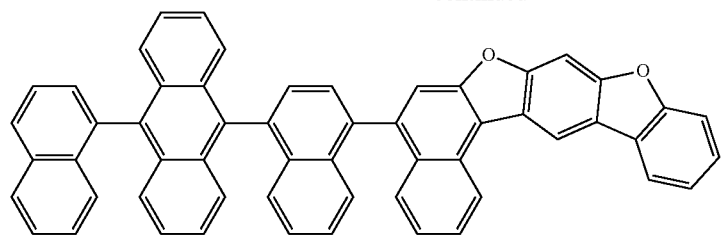

-continued
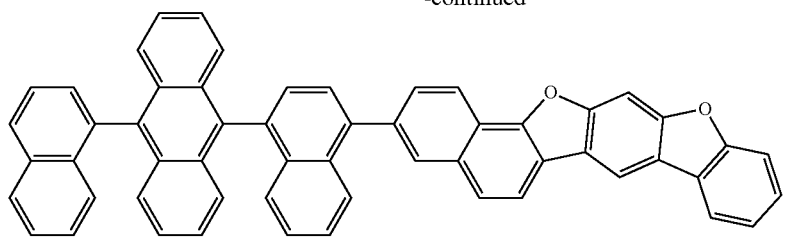
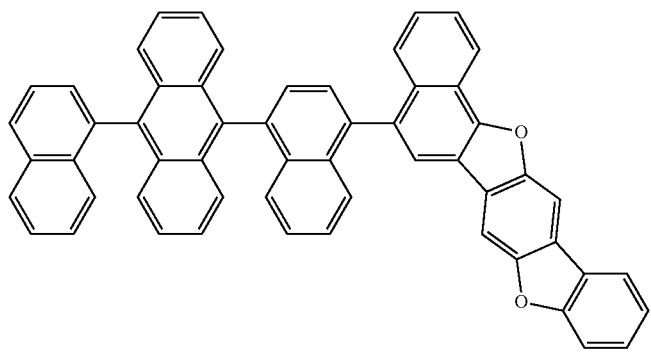
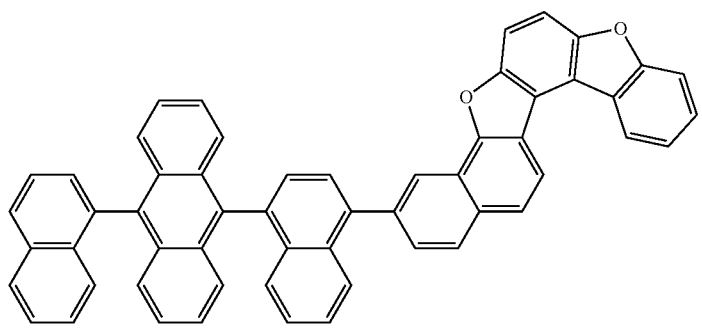
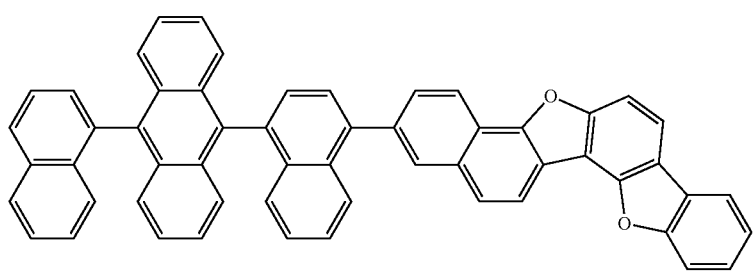
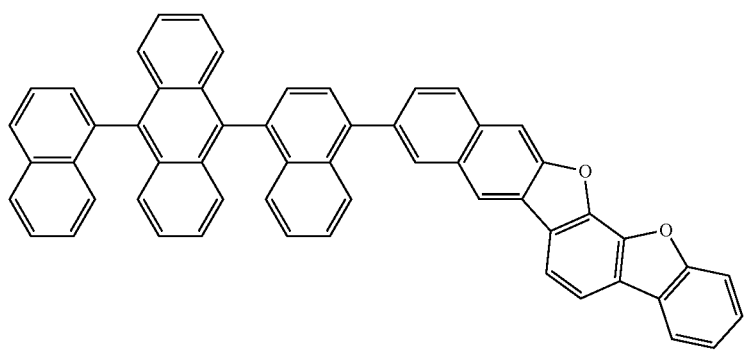

-continued
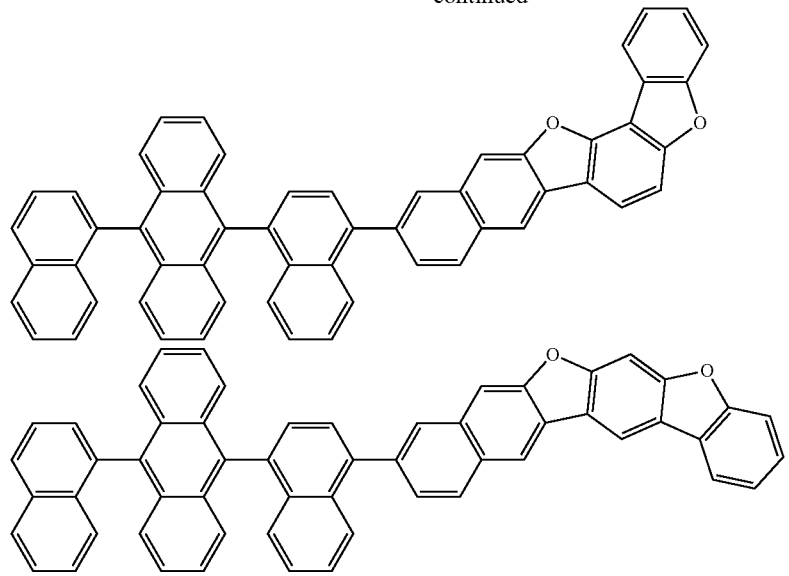
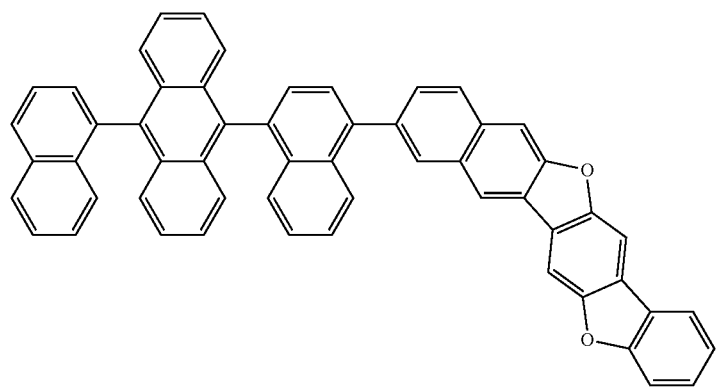
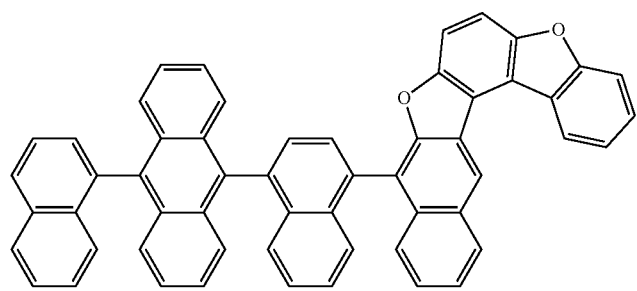
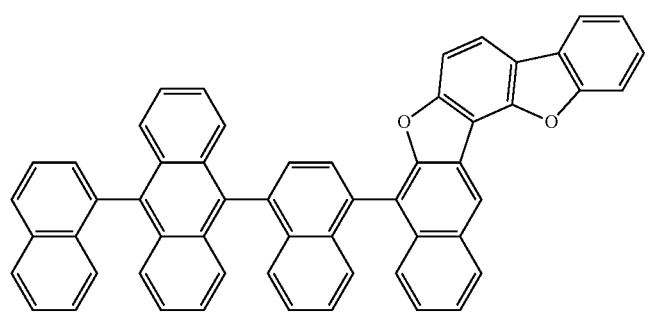

-continued
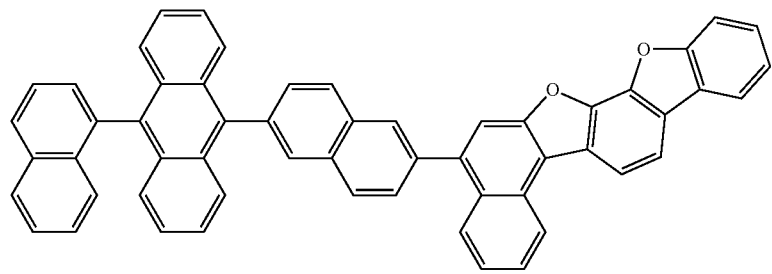
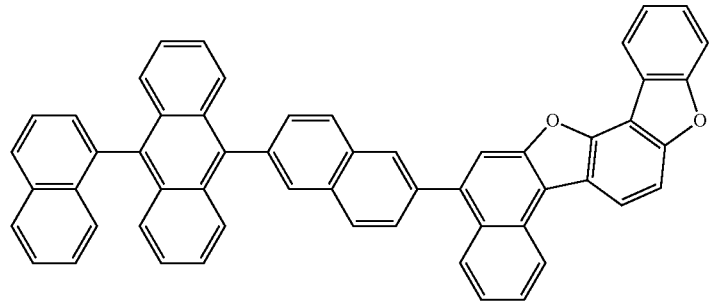
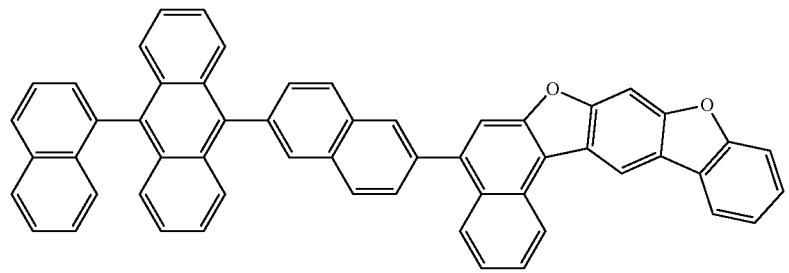
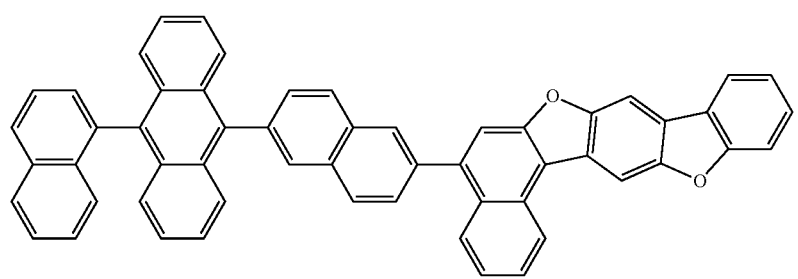
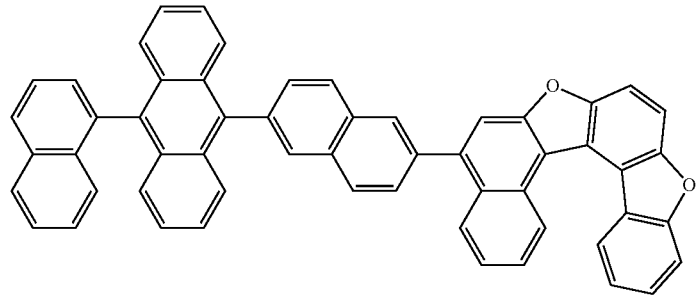
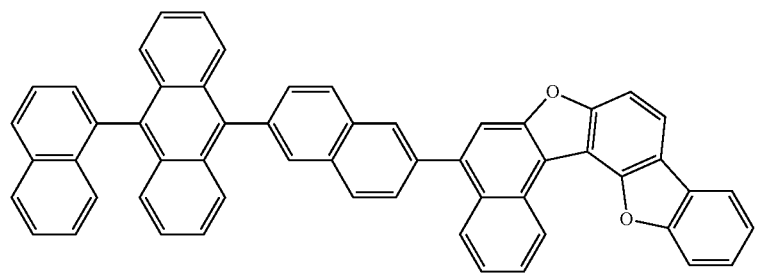

-continued
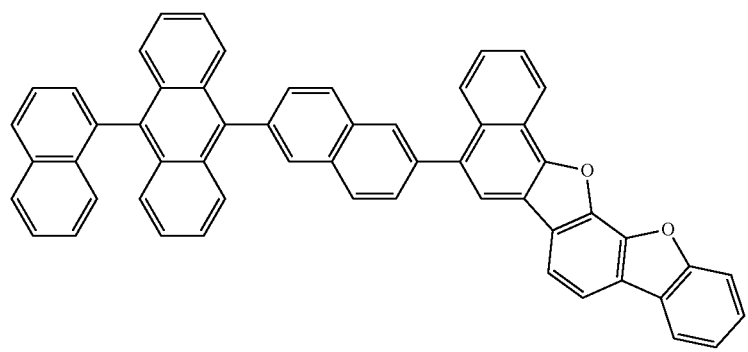
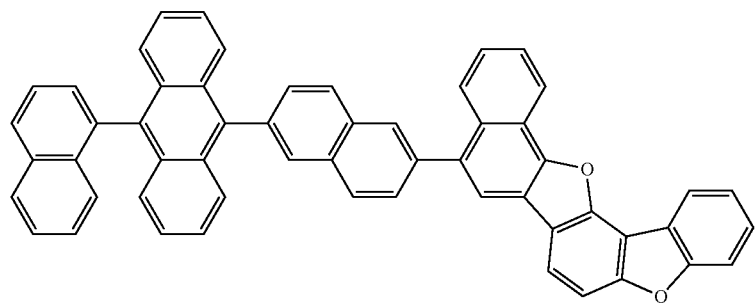
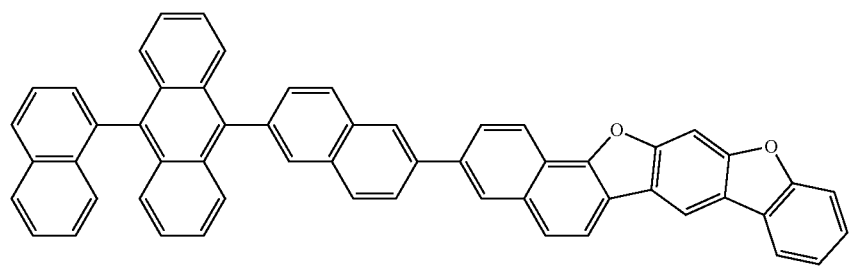
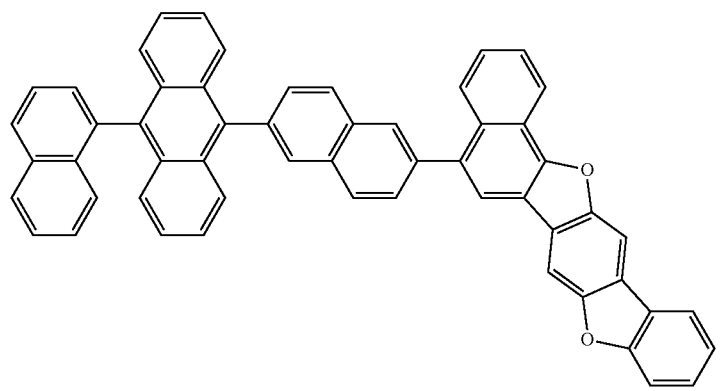
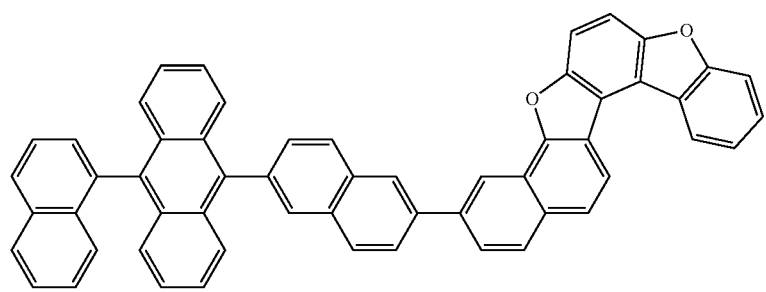

-continued
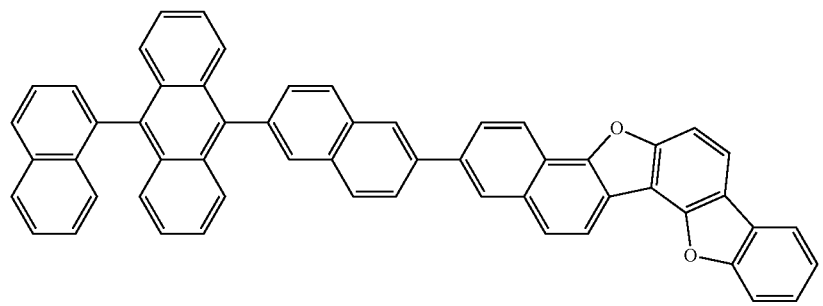
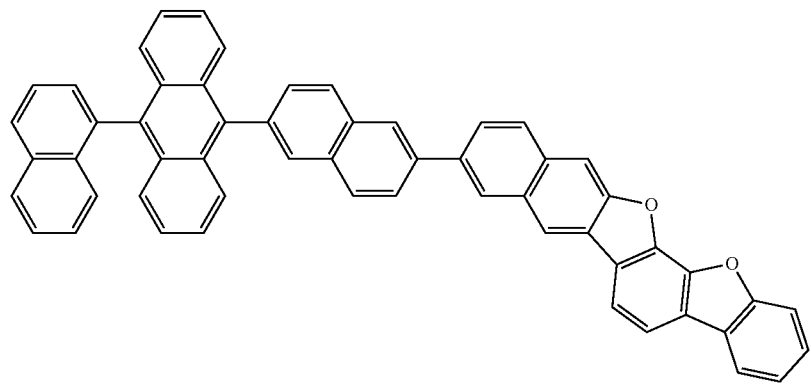
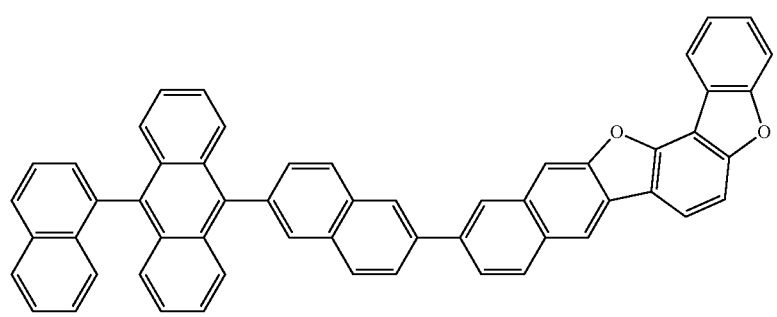
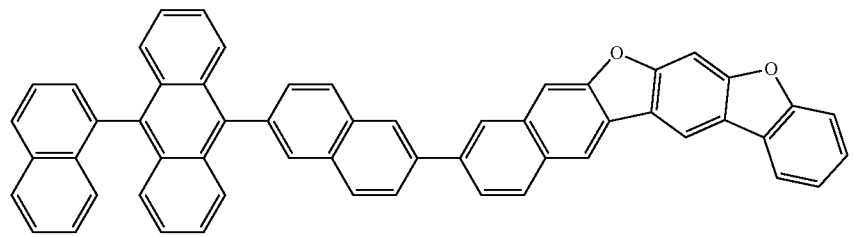
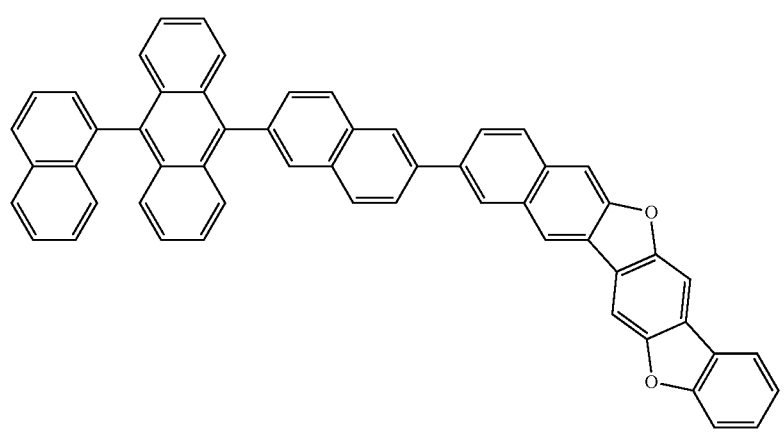

-continued
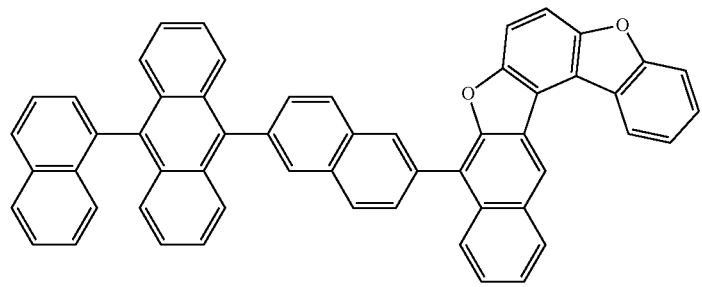
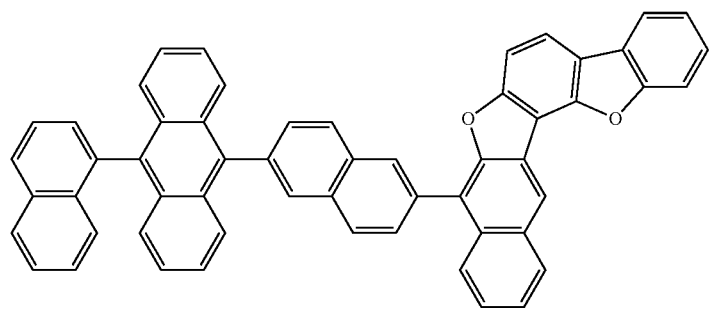
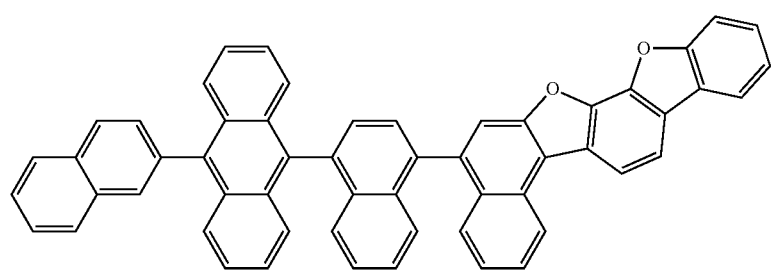
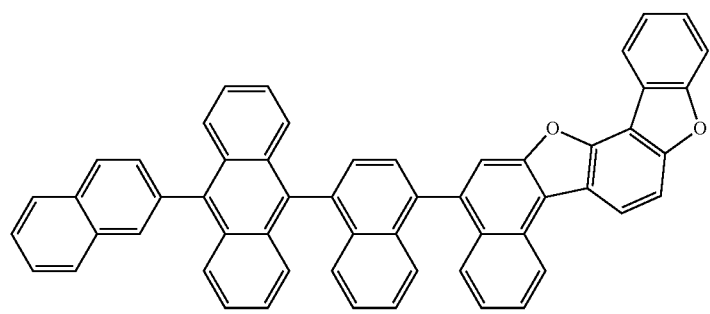
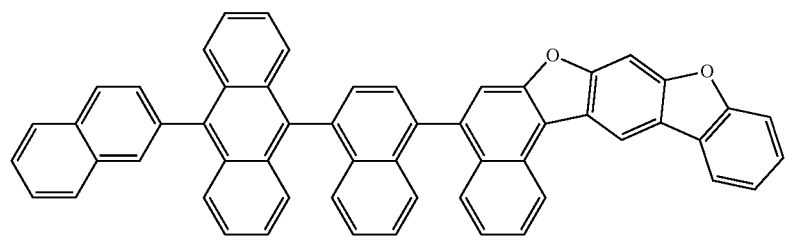
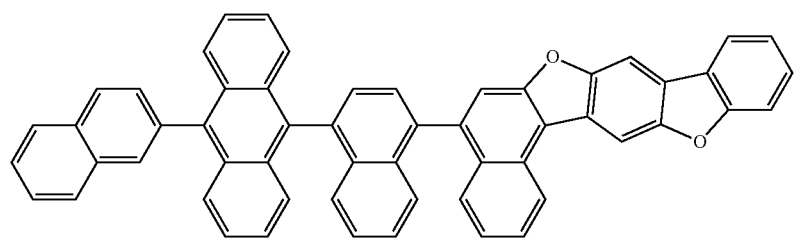

-continued
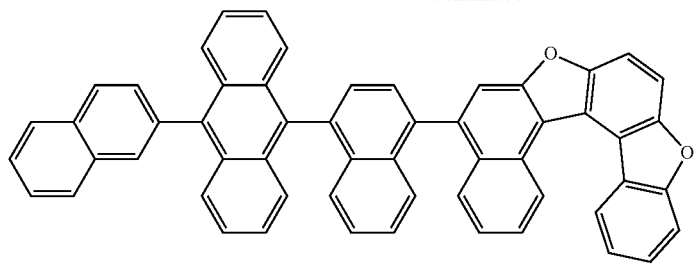
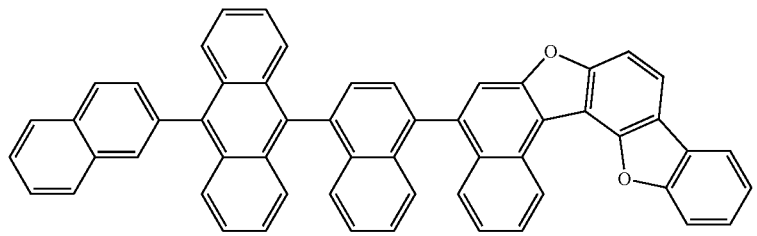
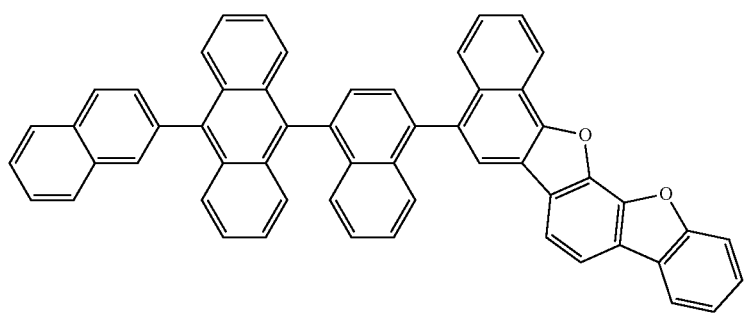
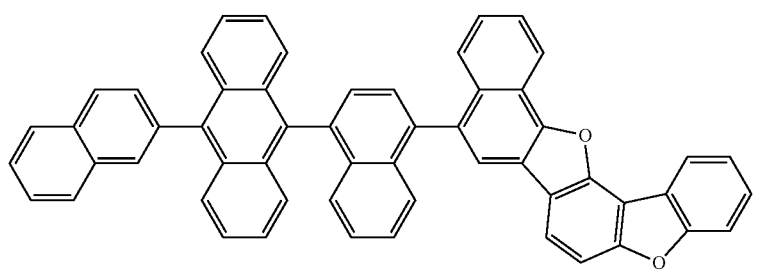
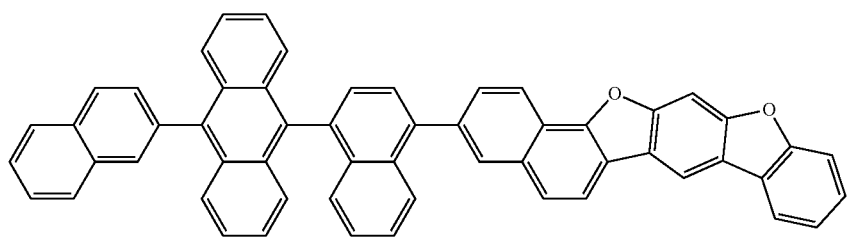
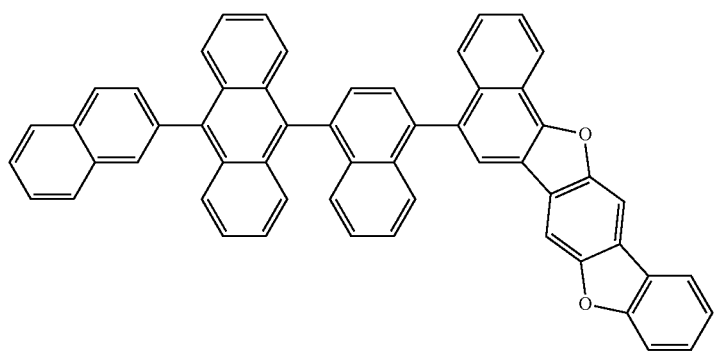

-continued
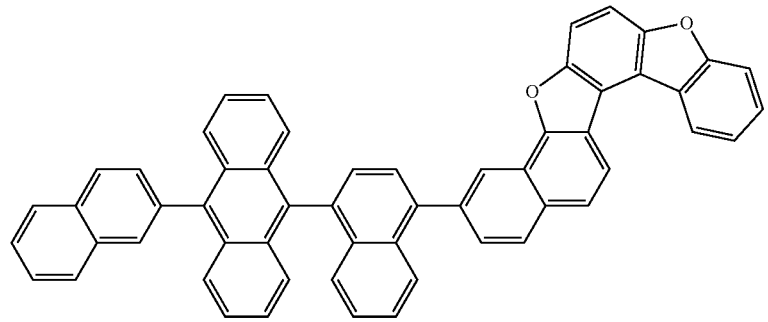
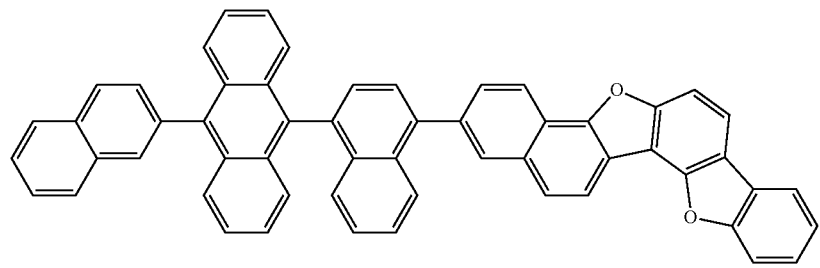
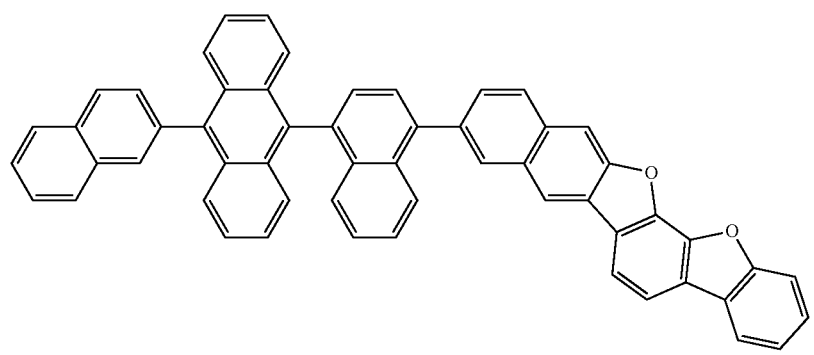
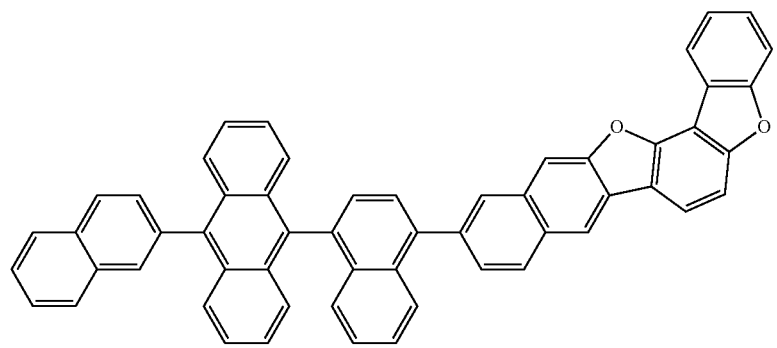
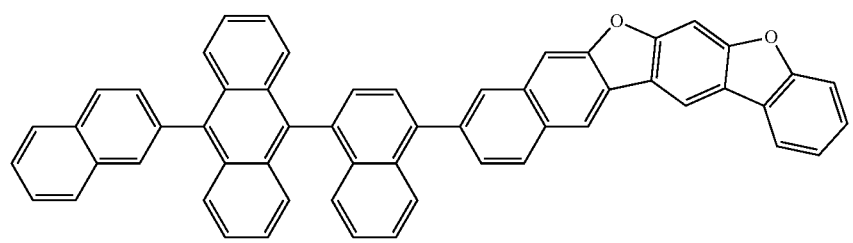

-continued
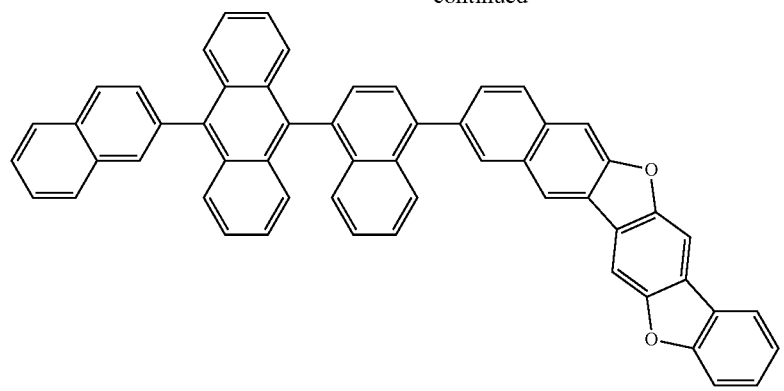
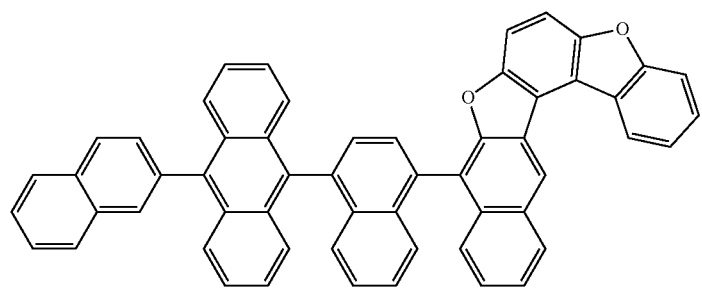
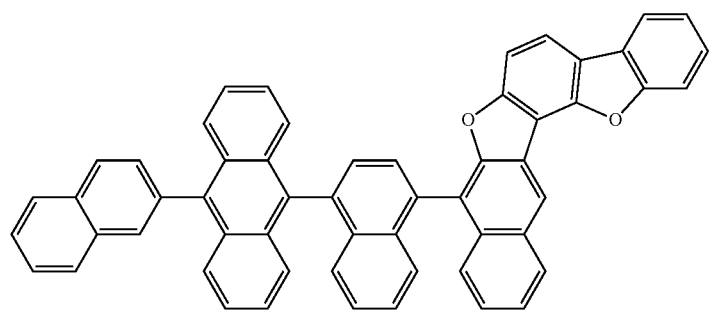
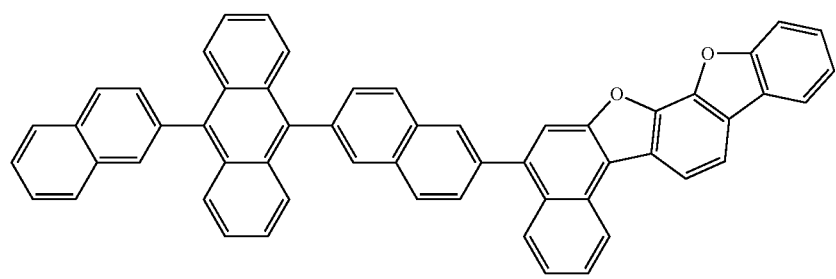
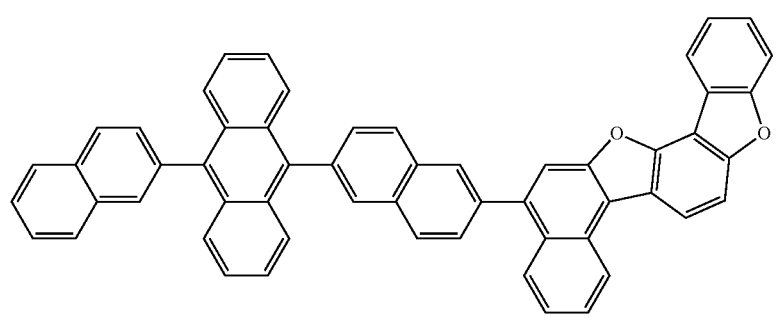

-continued
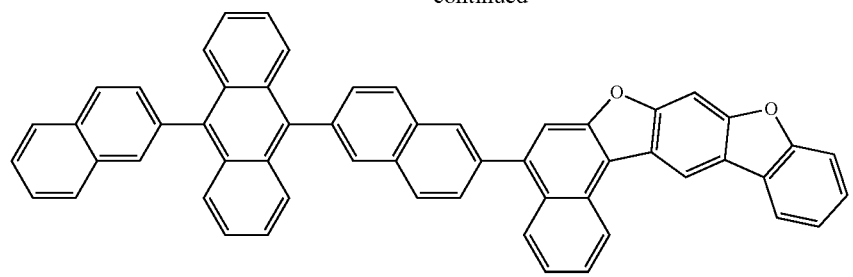
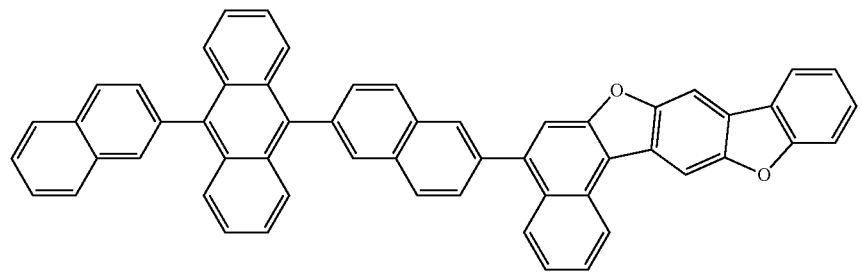
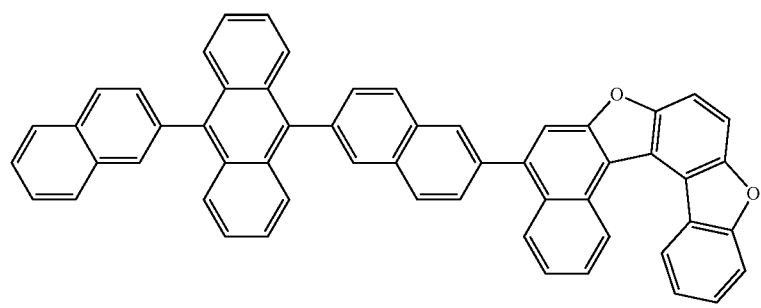
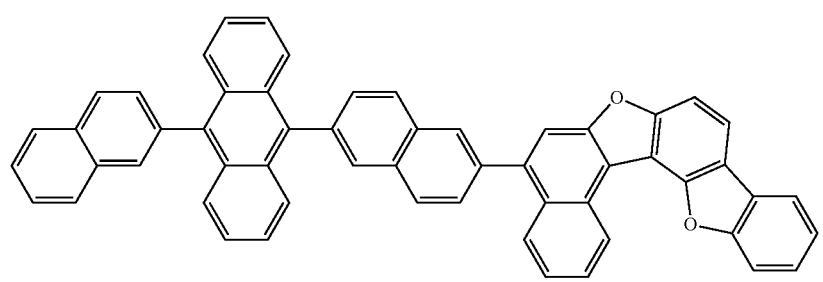
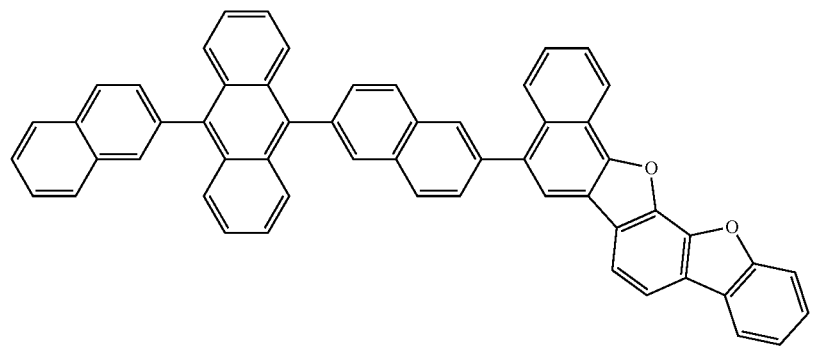

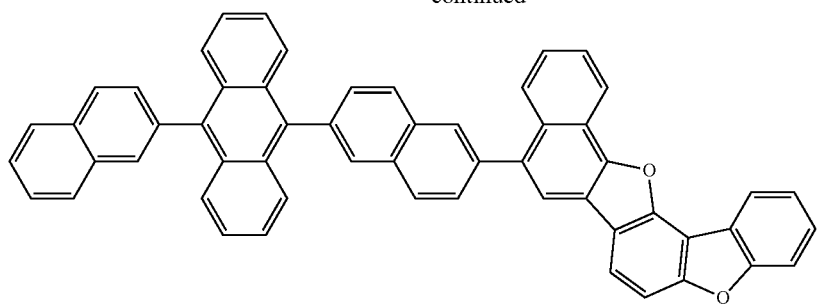
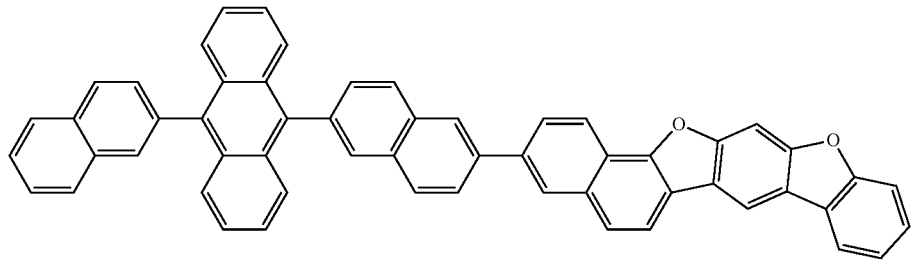
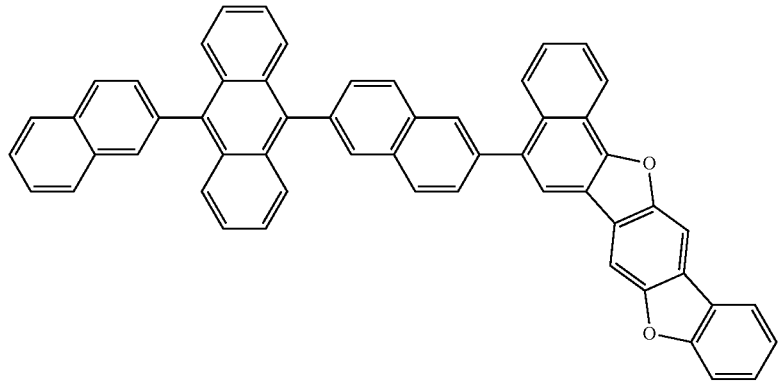
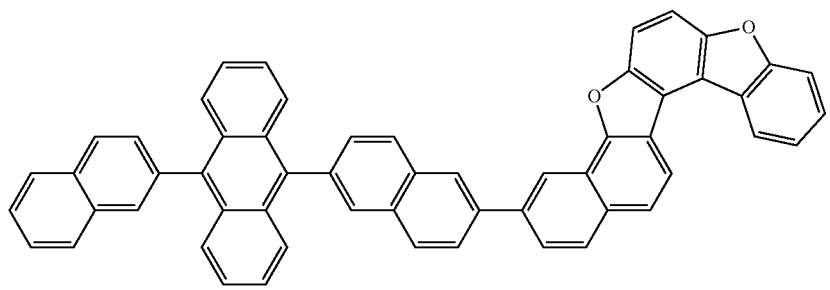
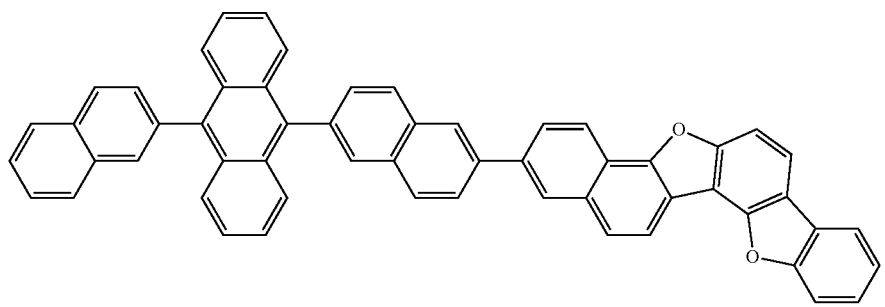

-continued
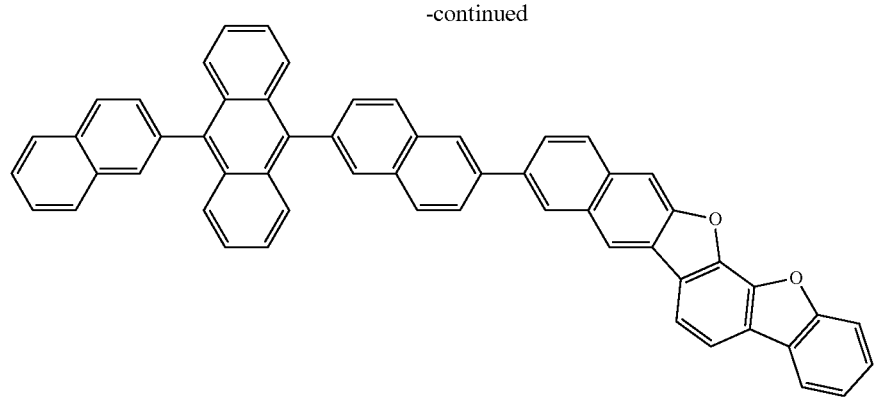
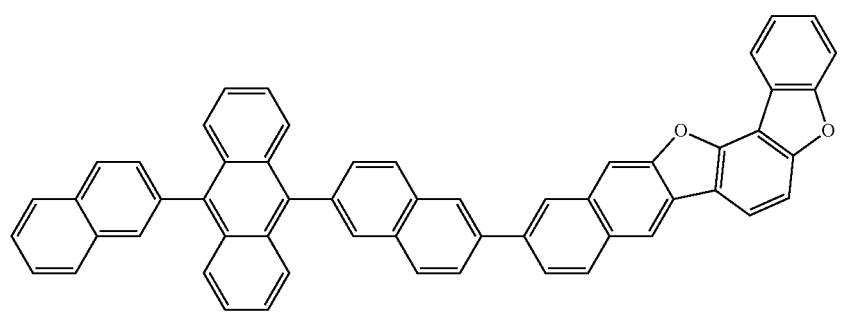
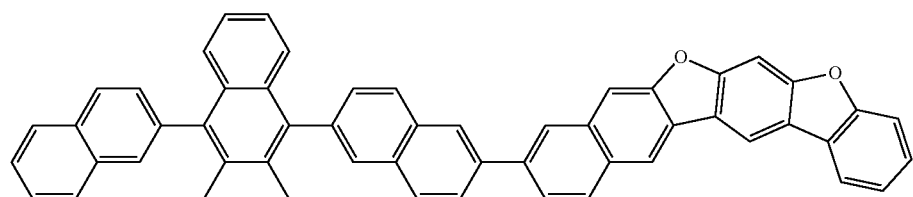
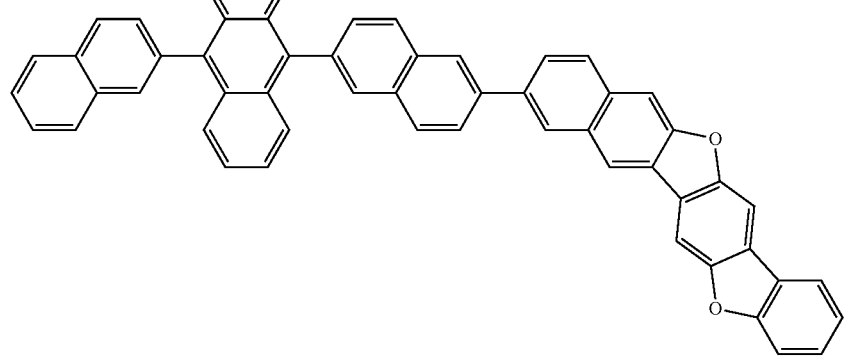
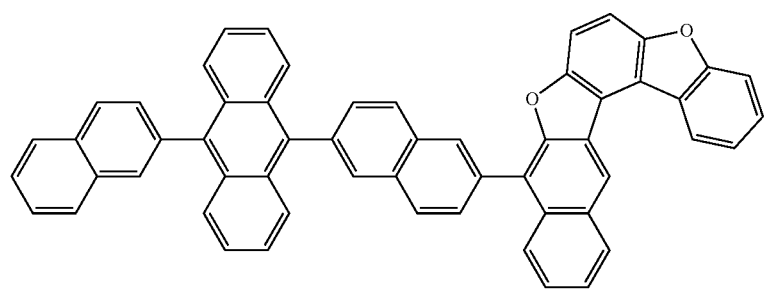

-continued
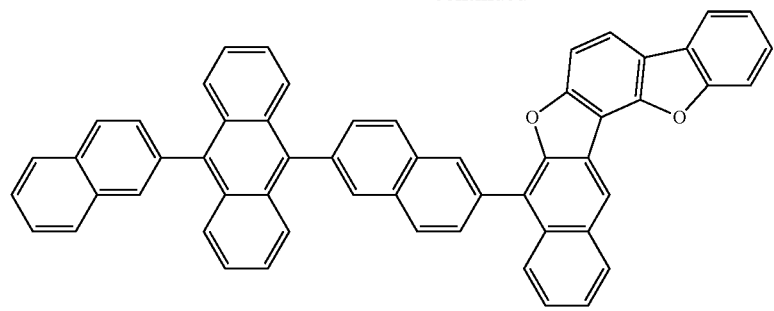
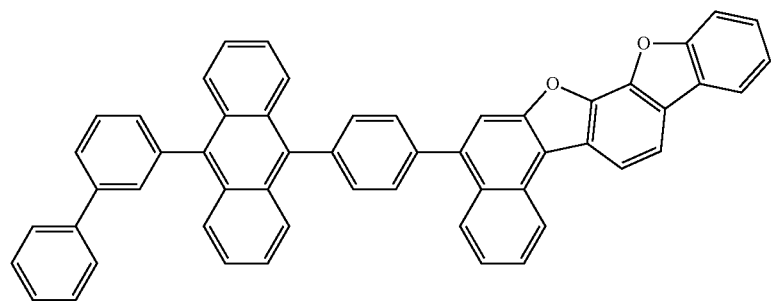
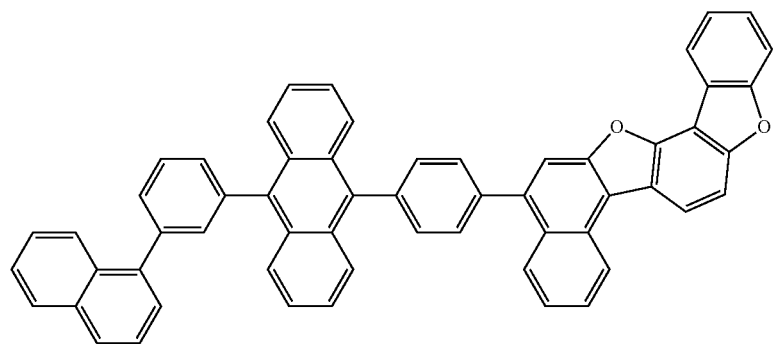
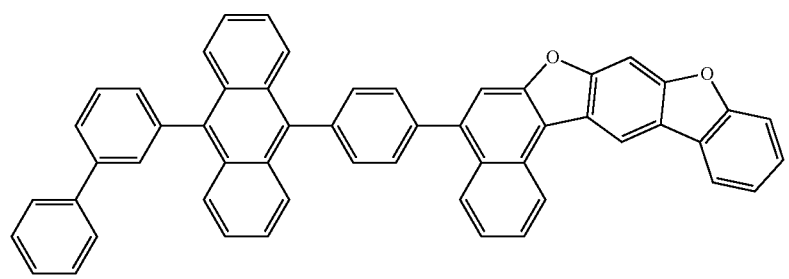
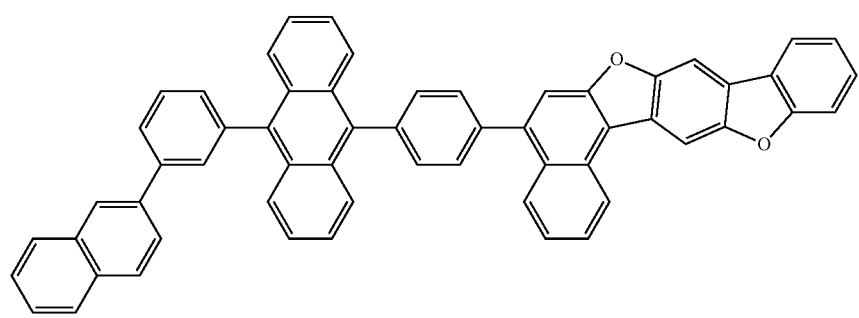

-continued
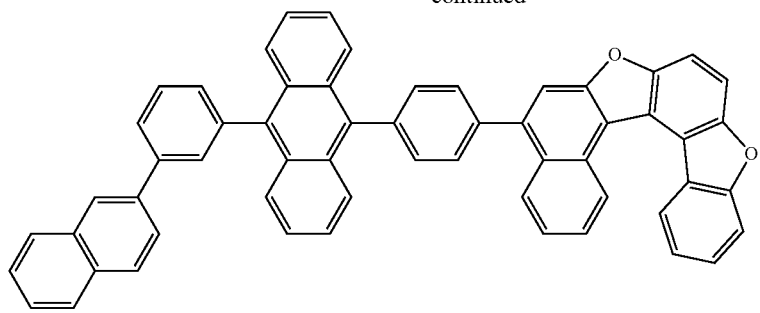
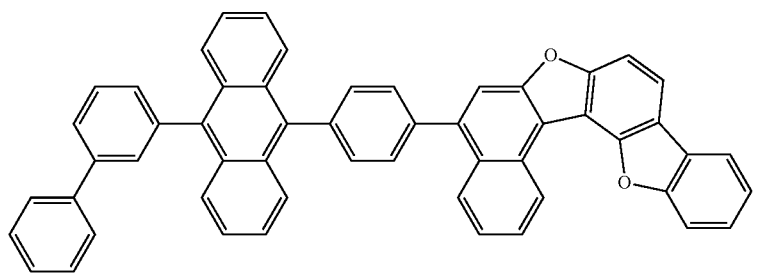
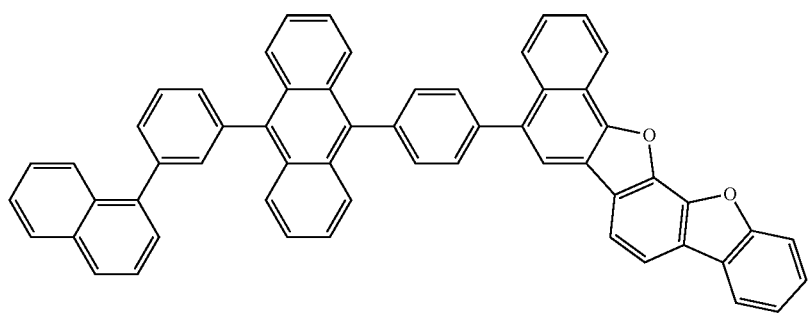
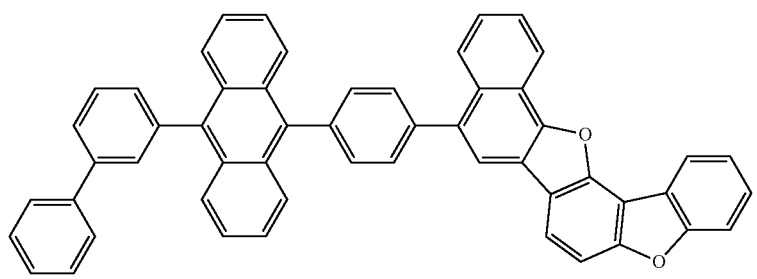
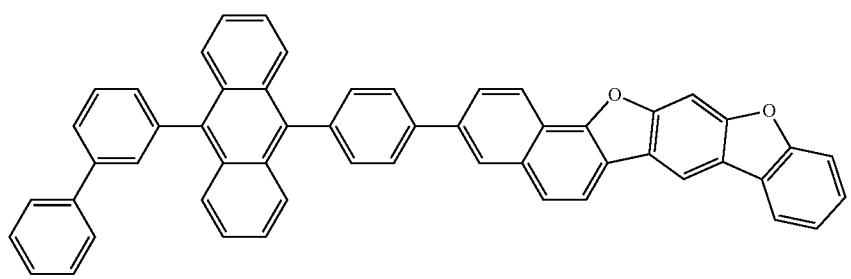

-continued
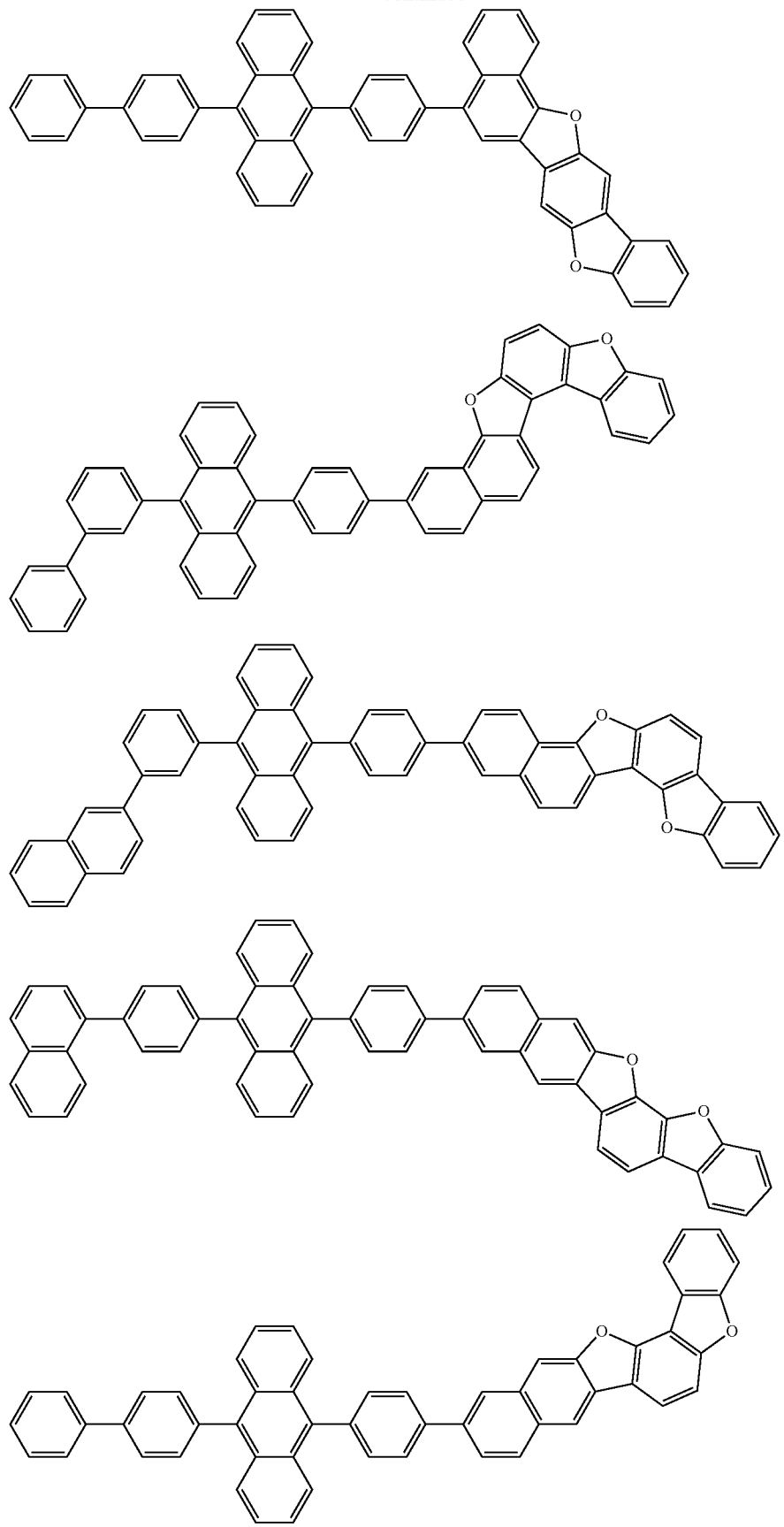

-continued
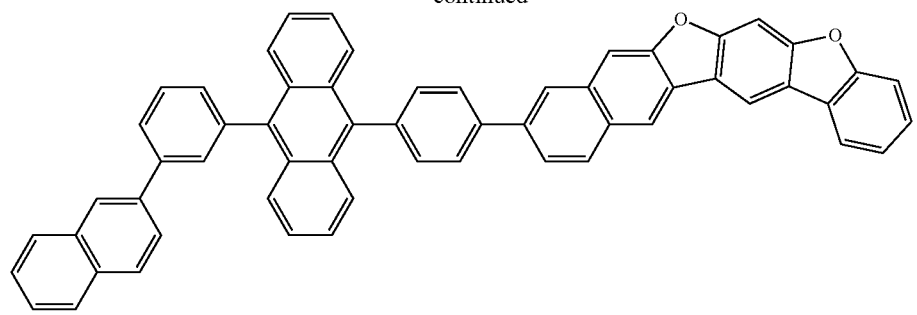
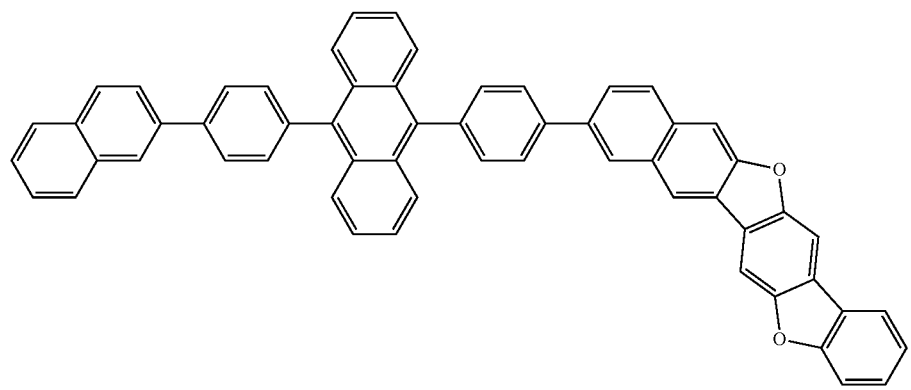
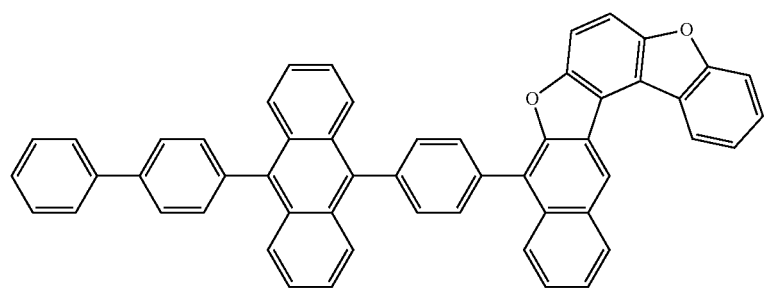
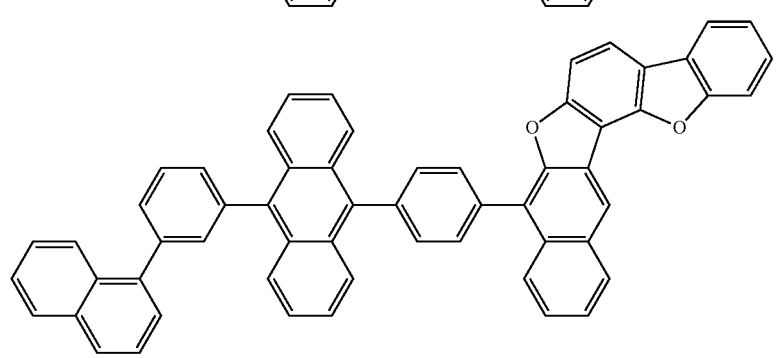
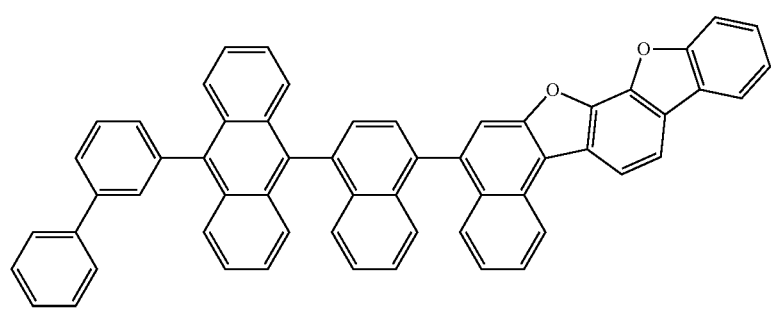

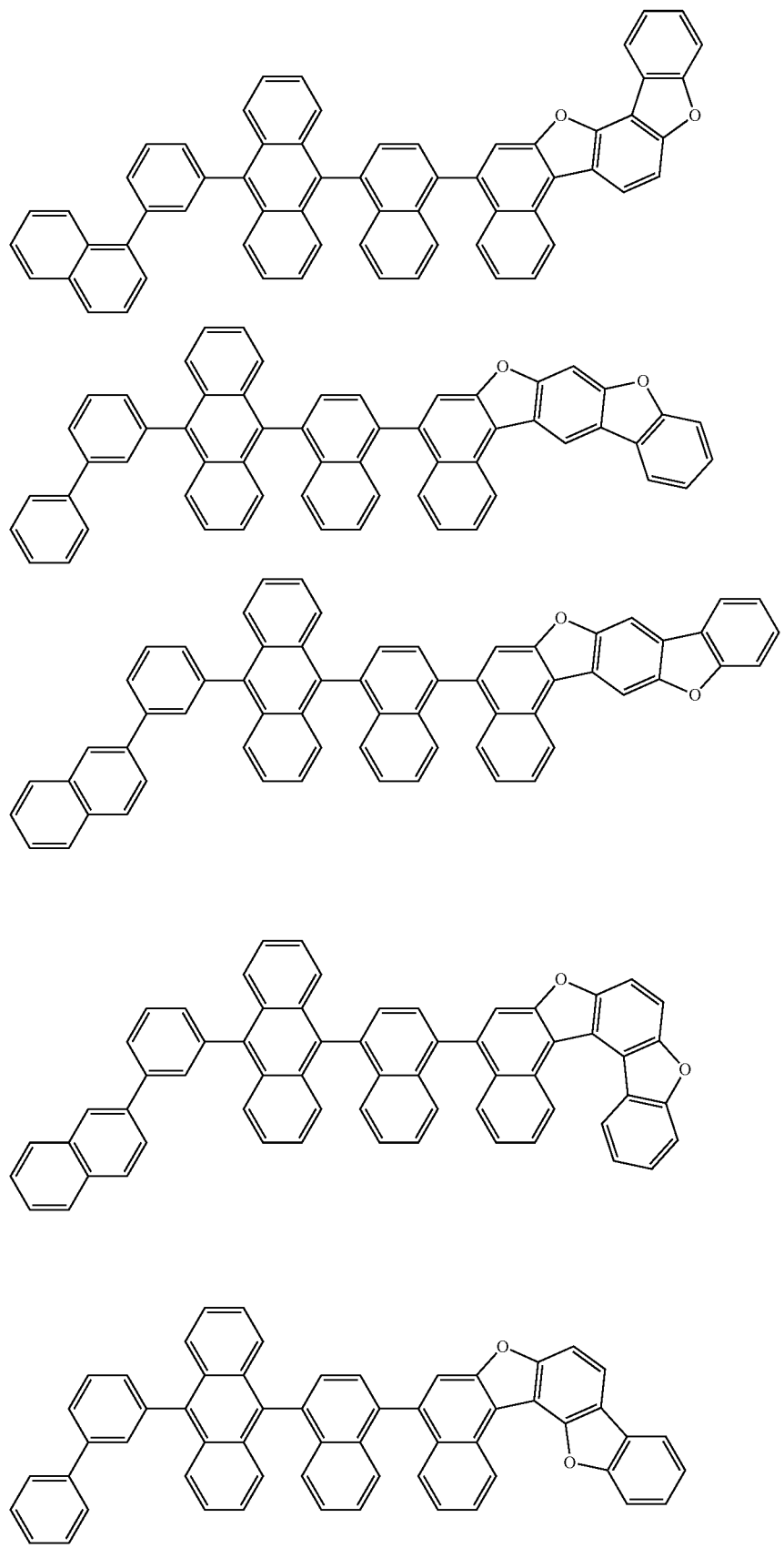

-continued
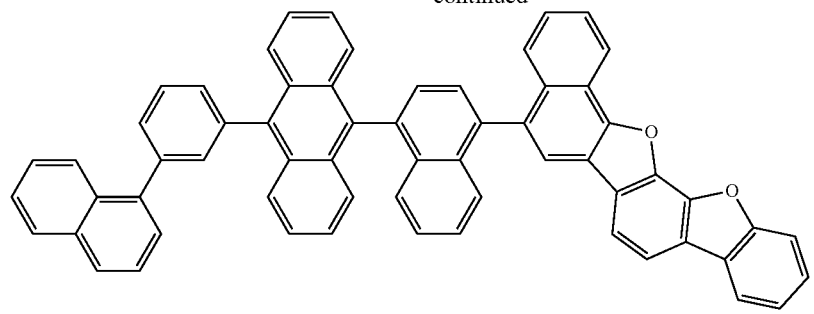
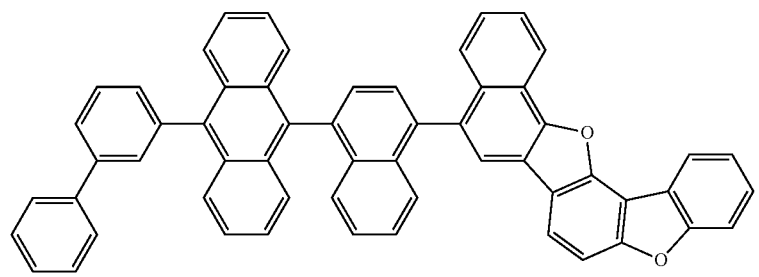
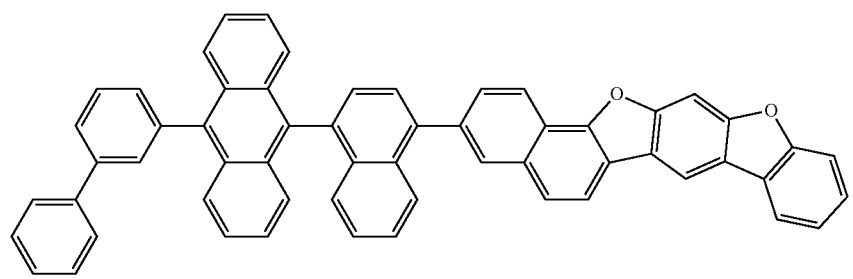
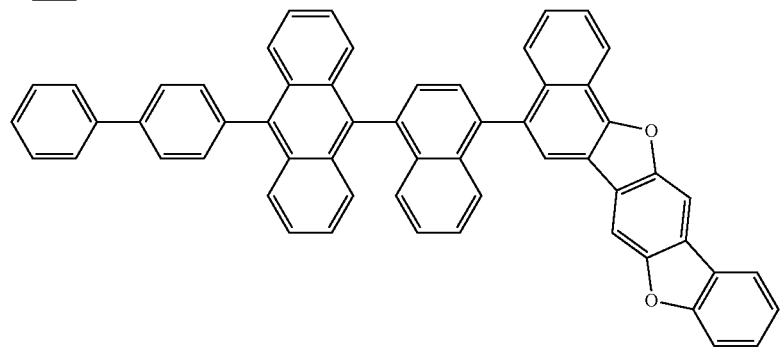
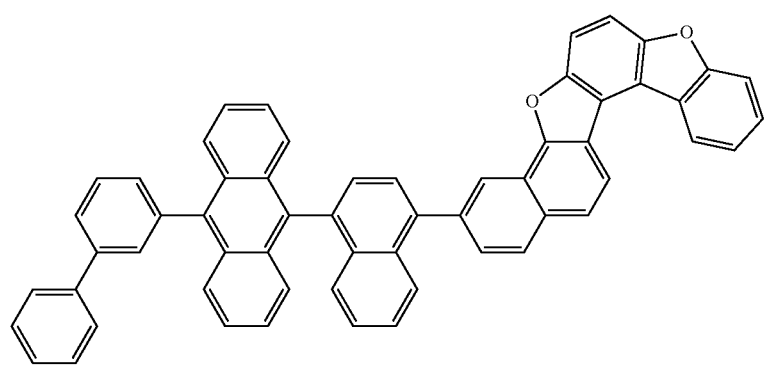

-continued
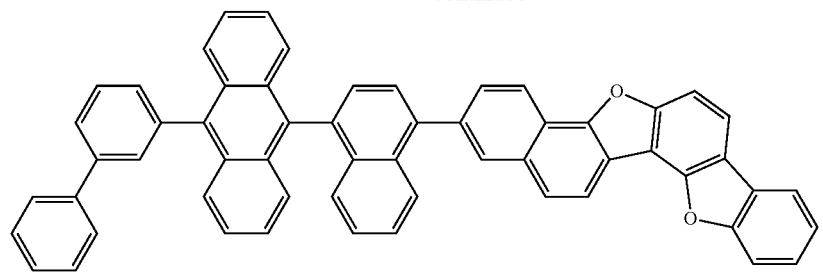
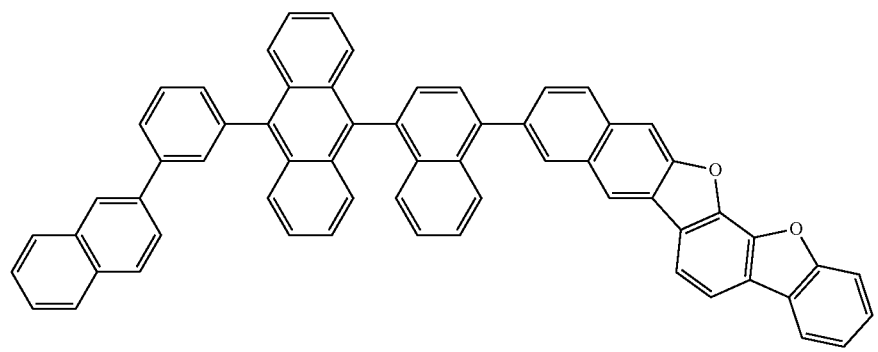
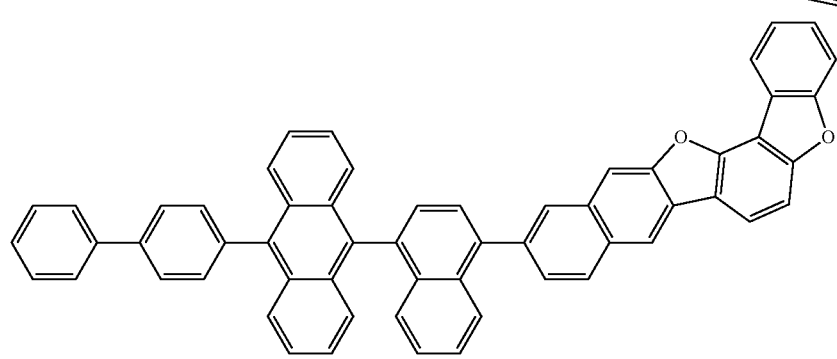
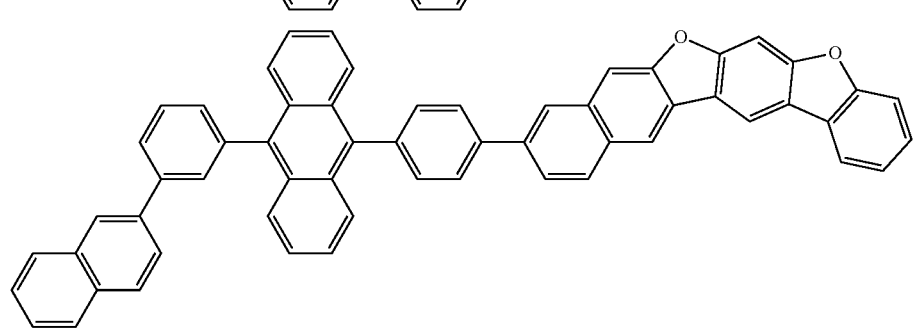
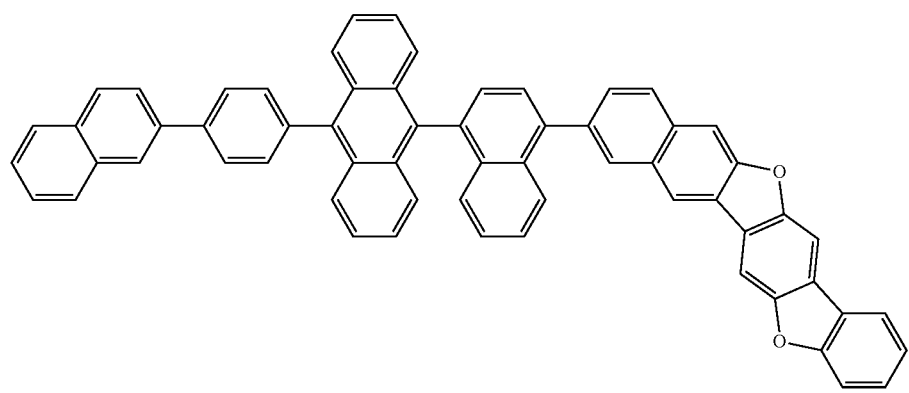

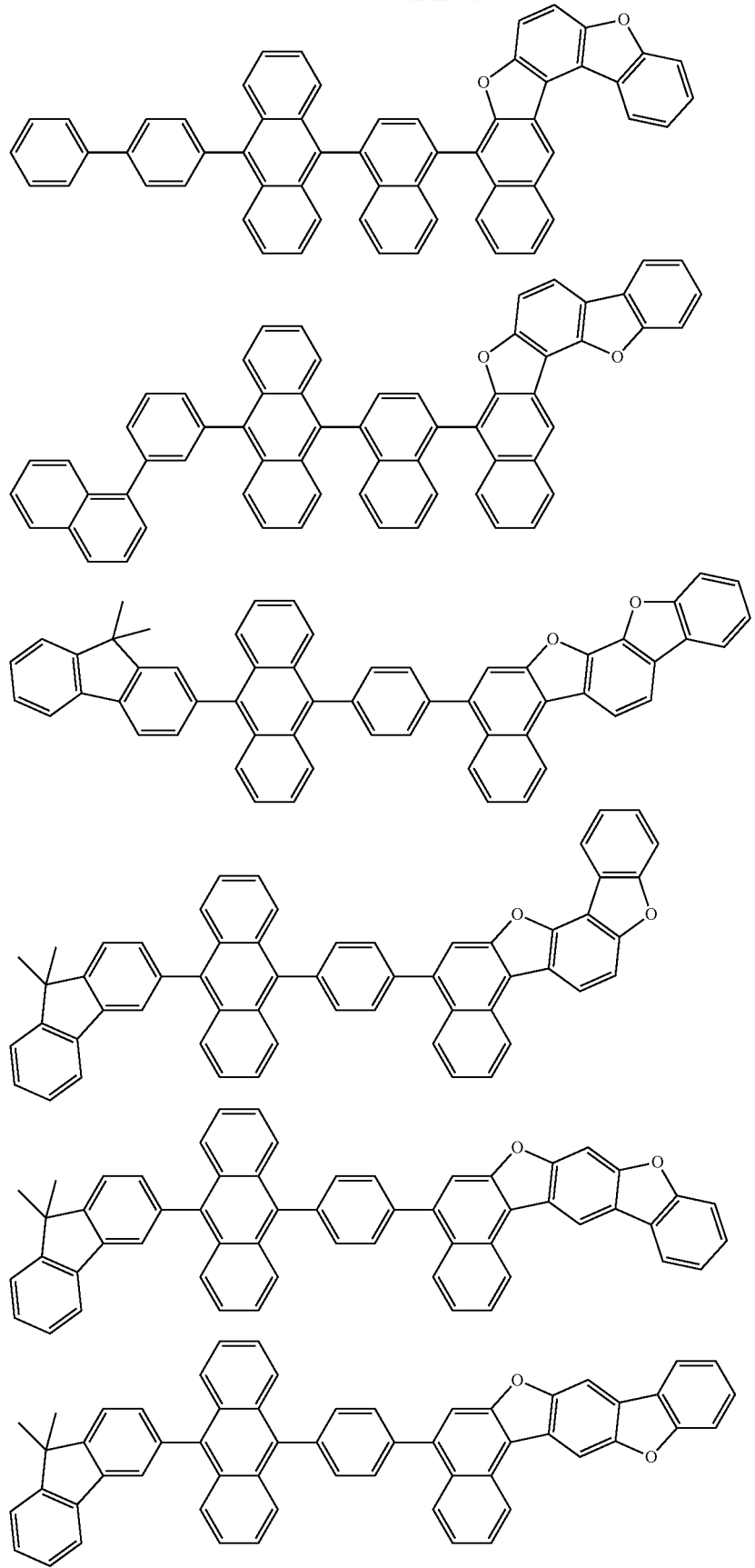

-continued
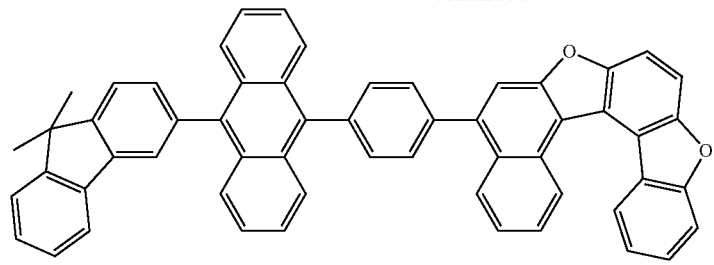
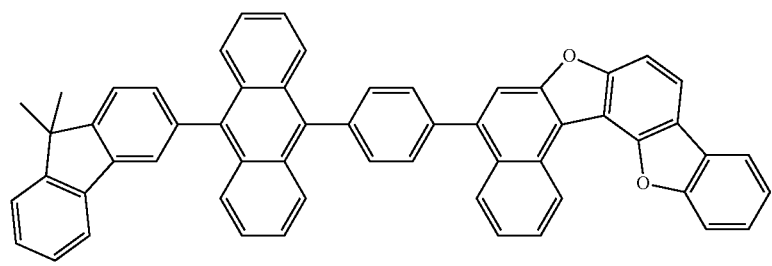
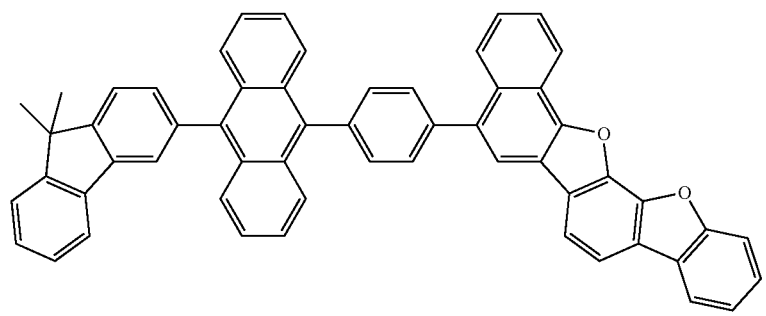
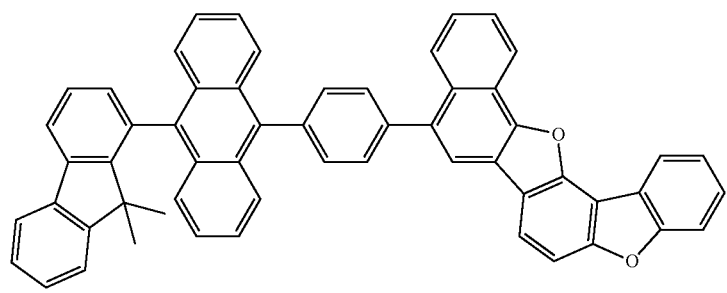
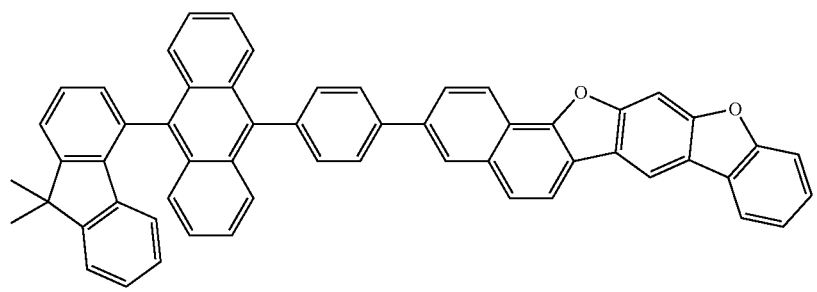

-continued
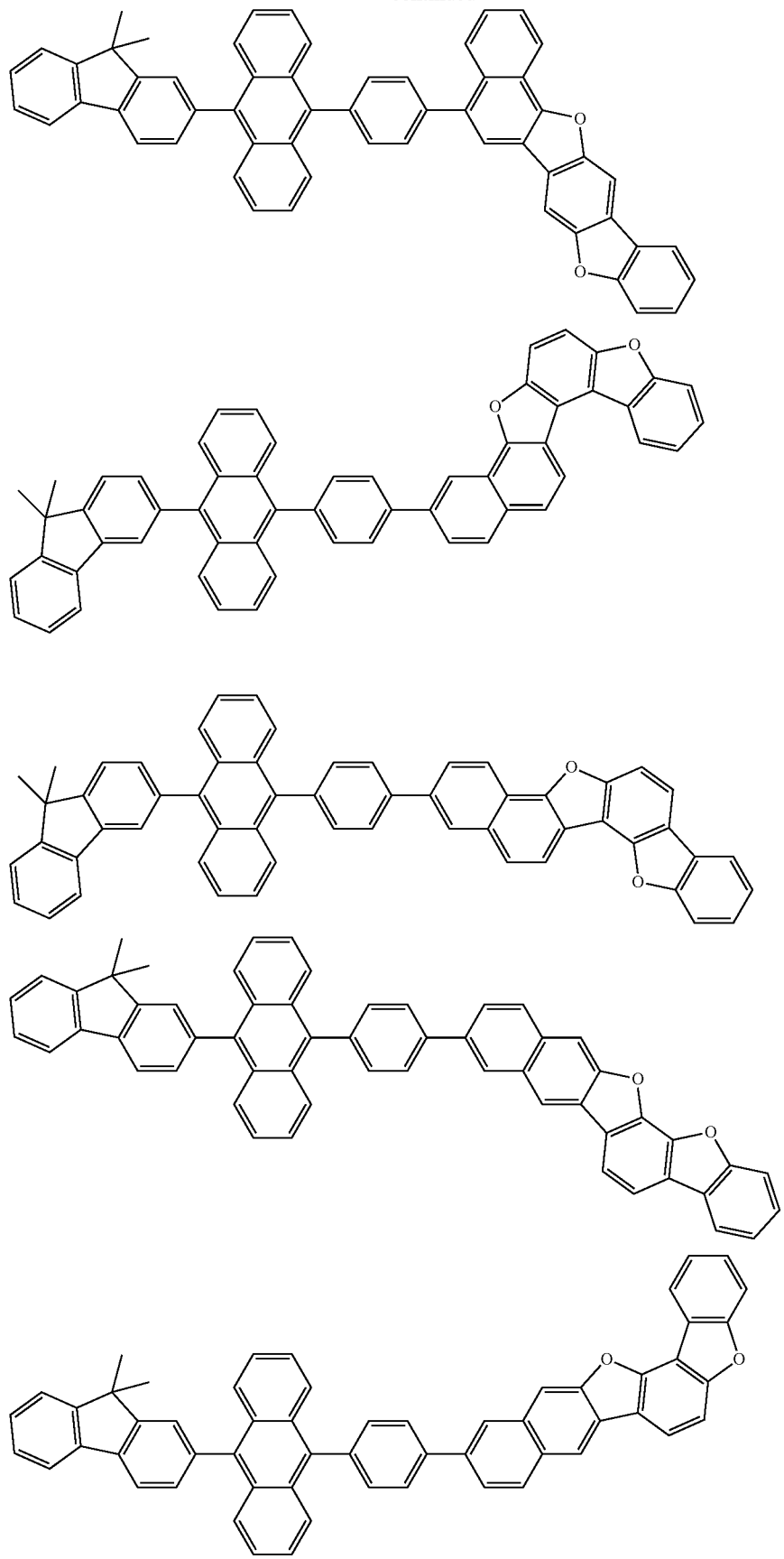

-continued
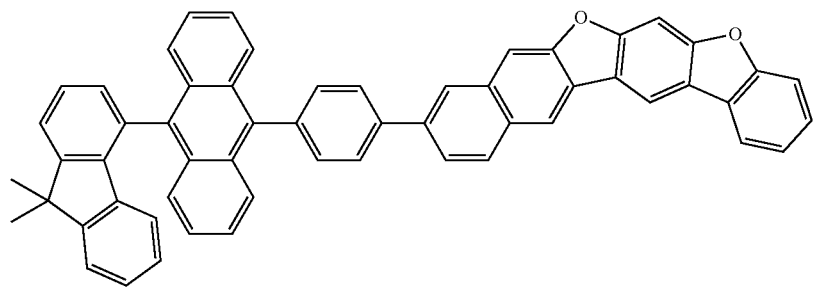
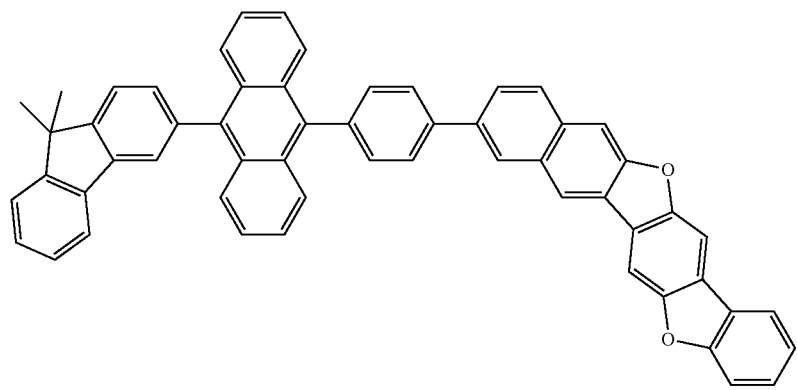
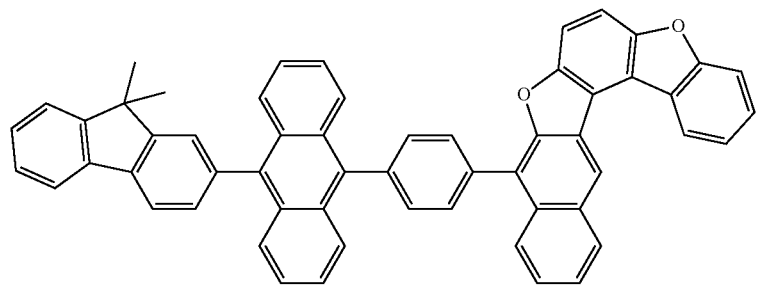
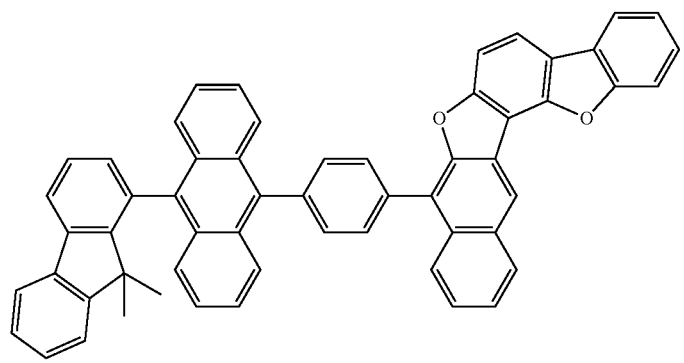
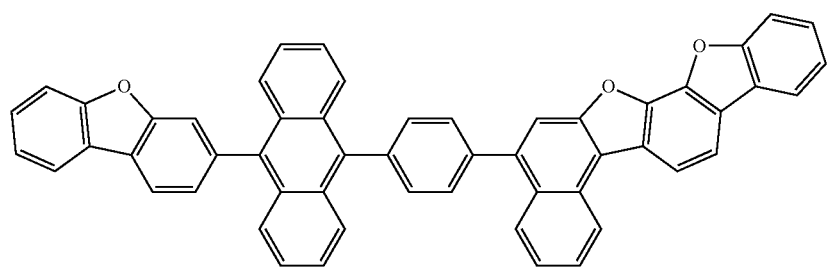

-continued
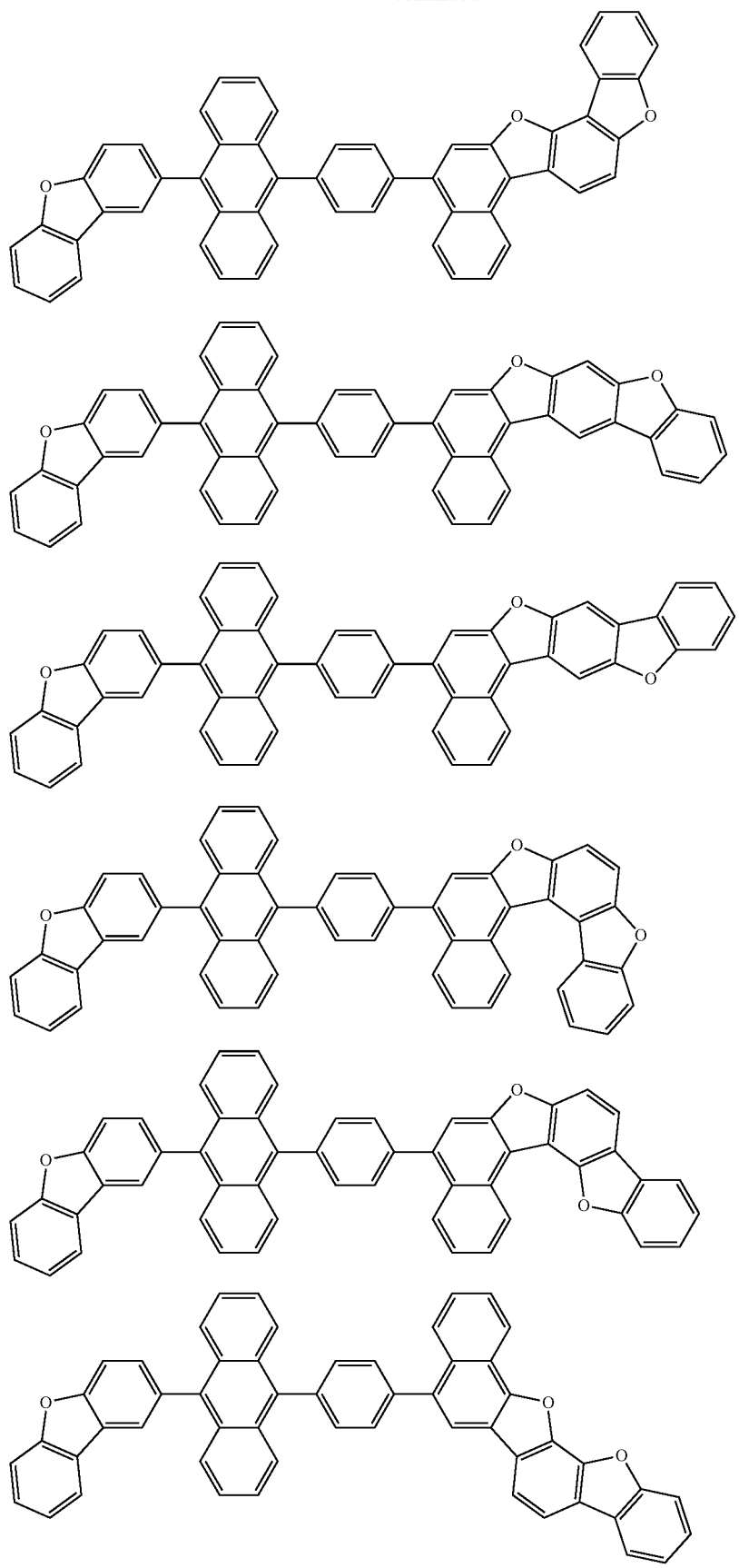

-continued
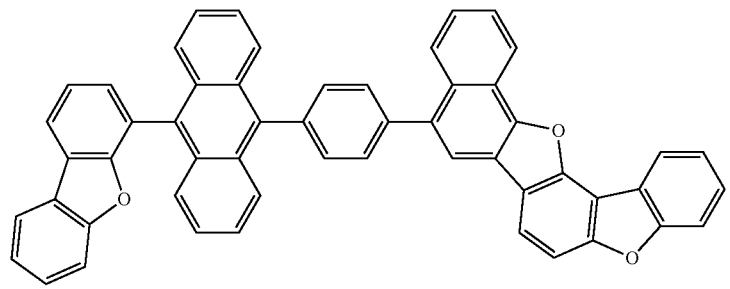
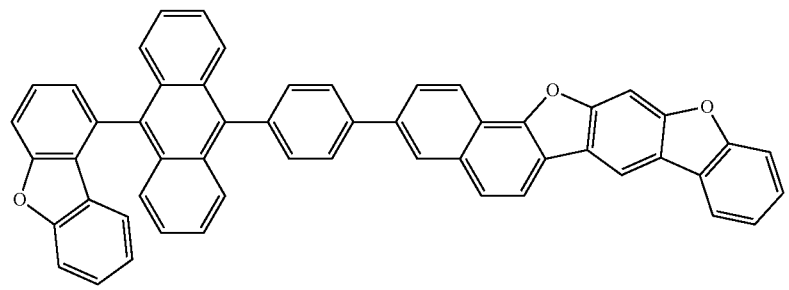
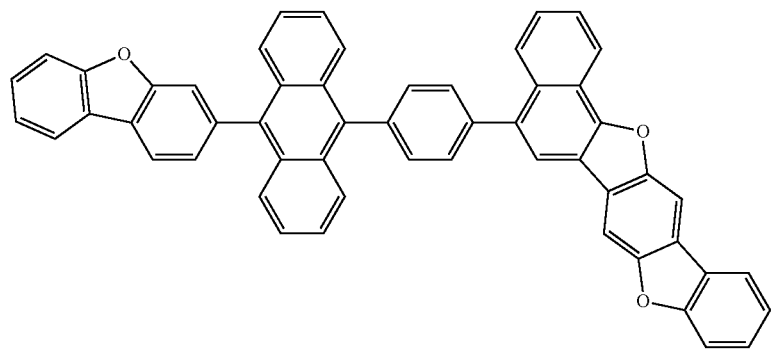
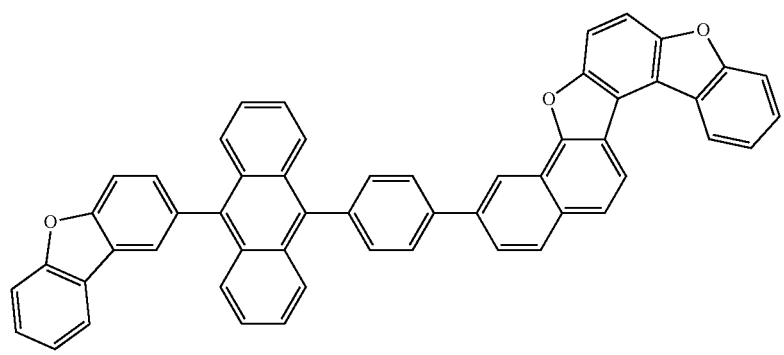
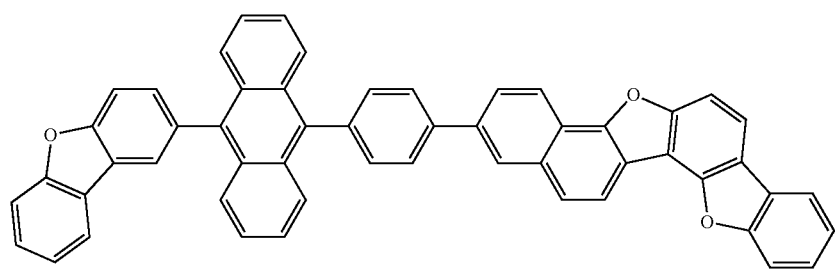

-continued
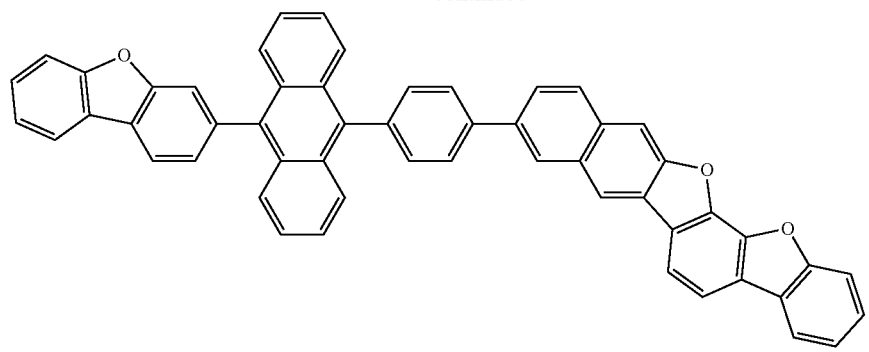
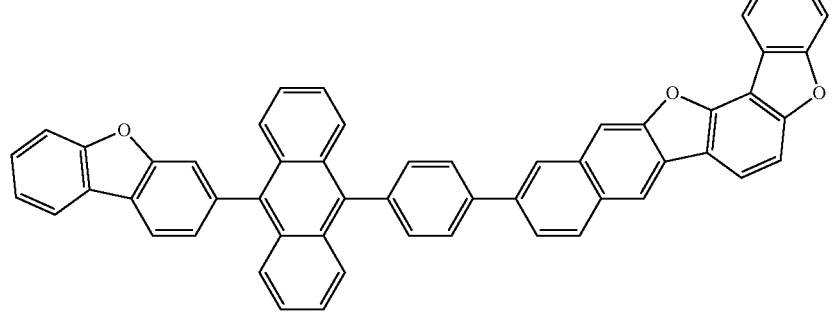
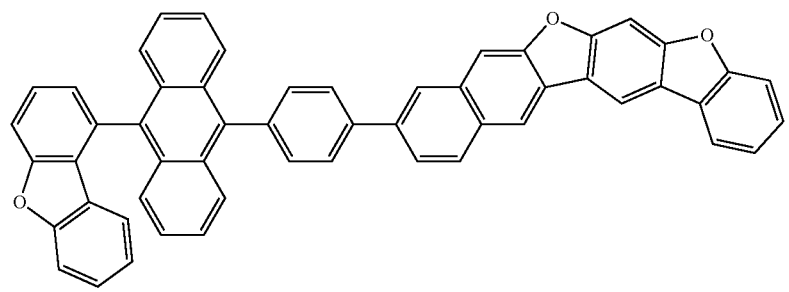
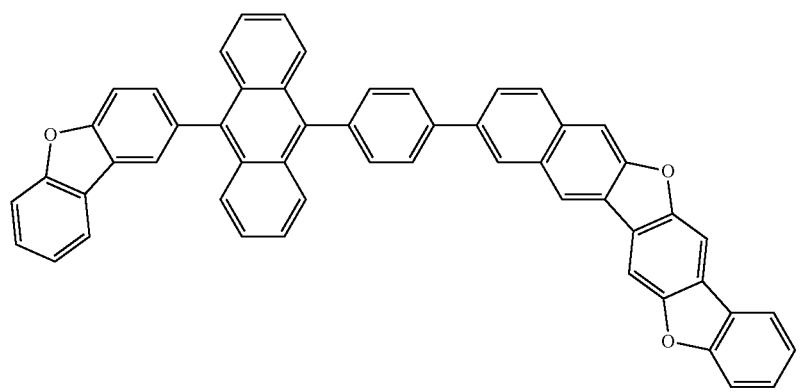
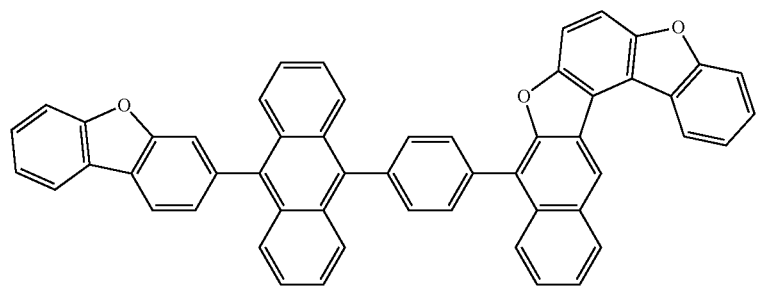

-continued
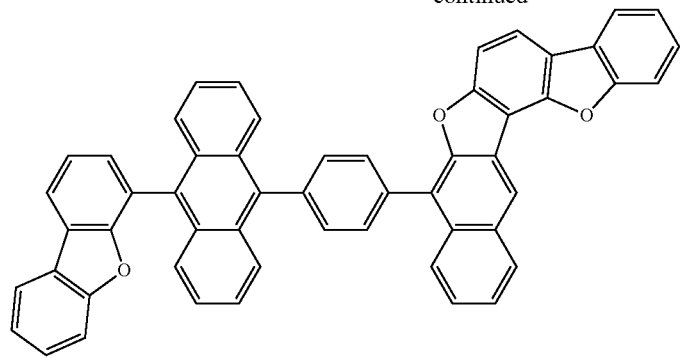
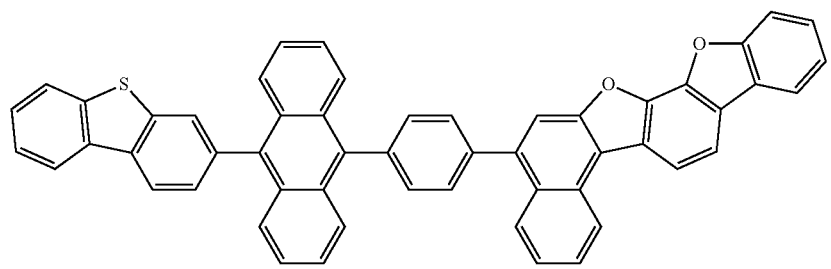
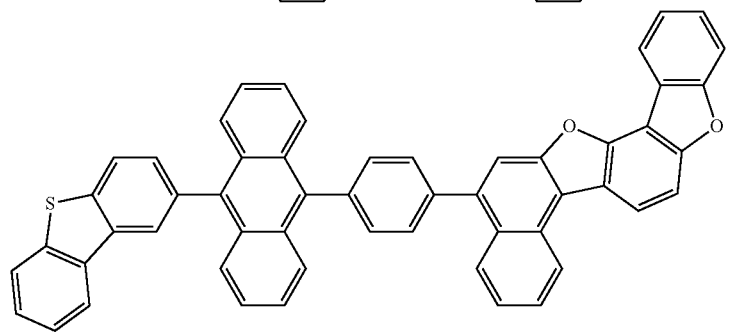
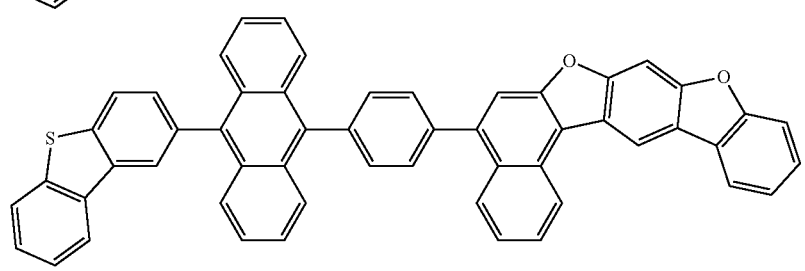
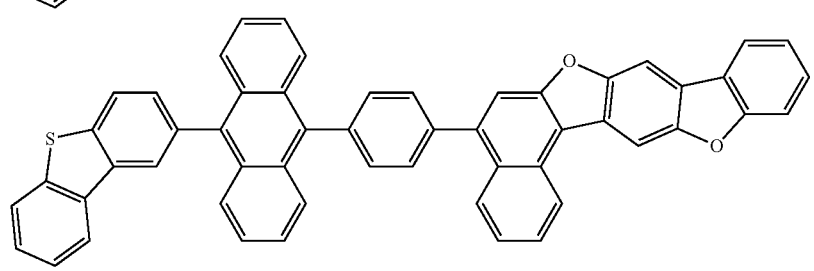
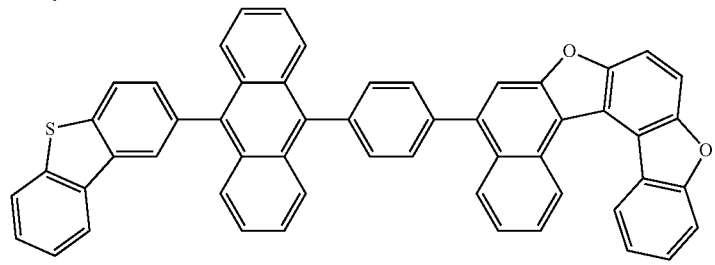

-continued
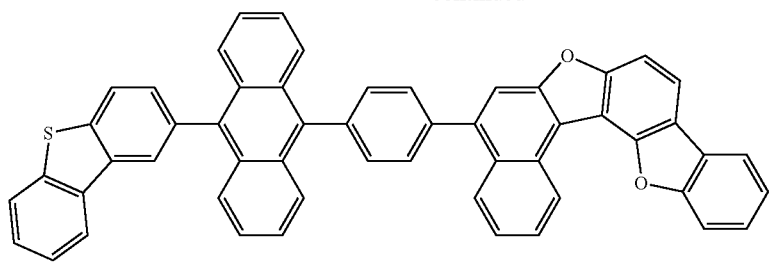
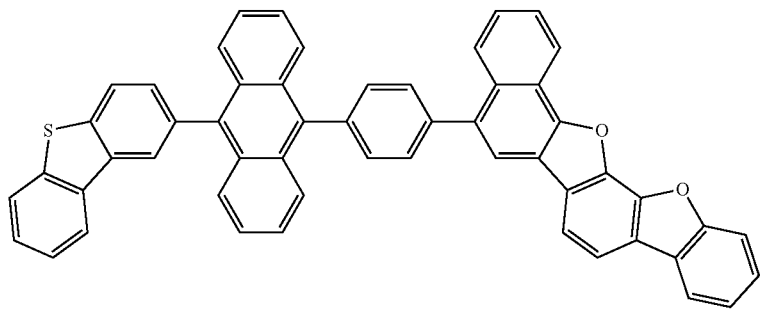
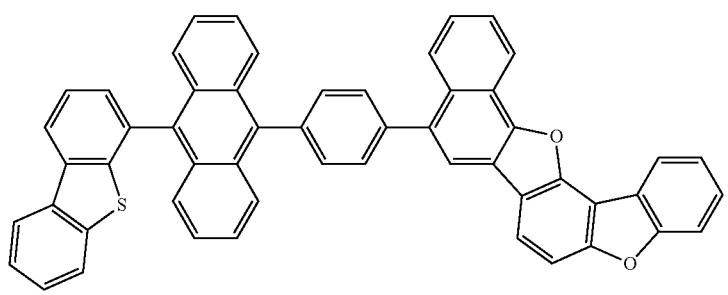
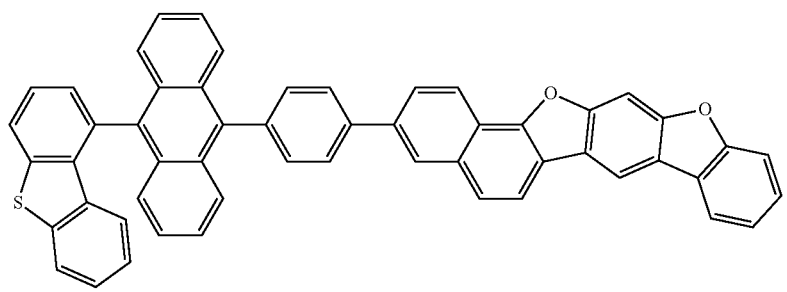
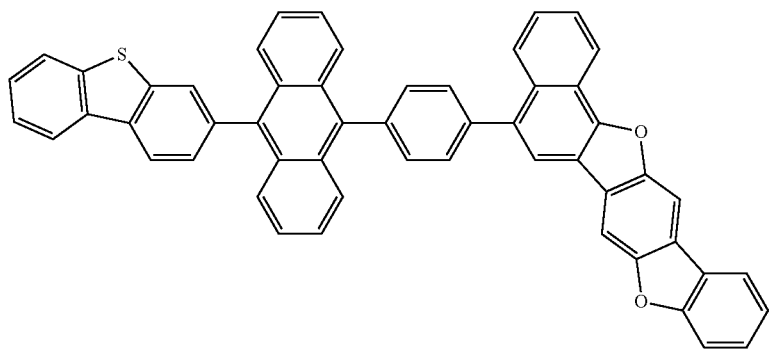

-continued
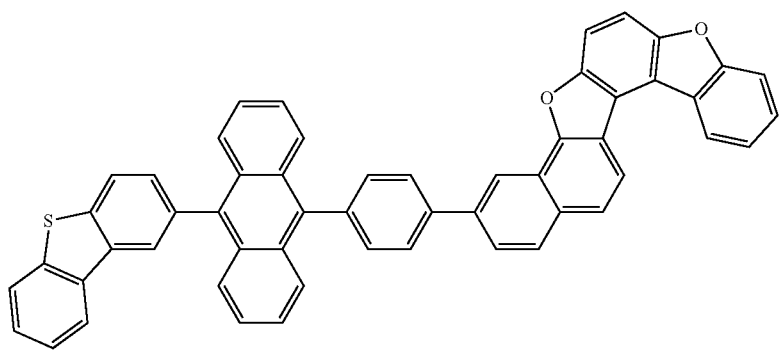
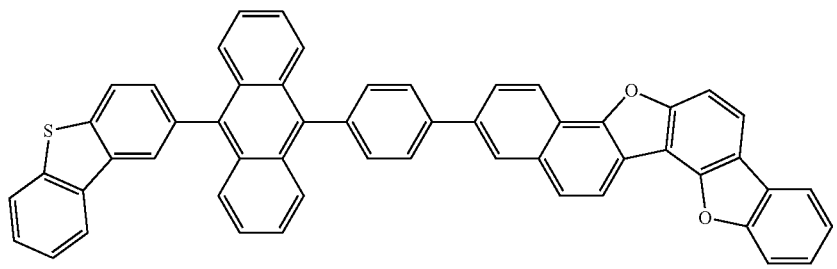
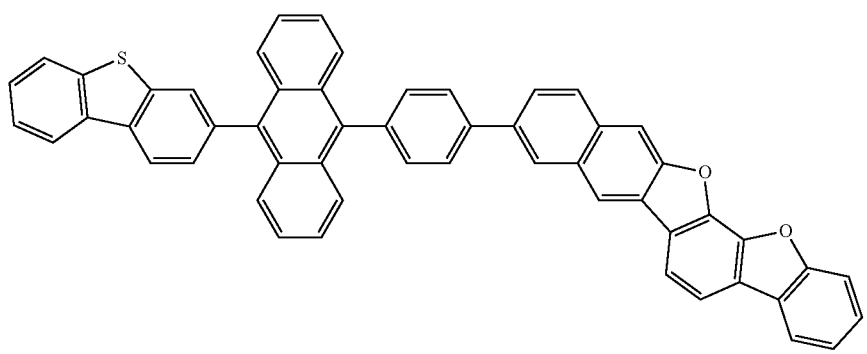
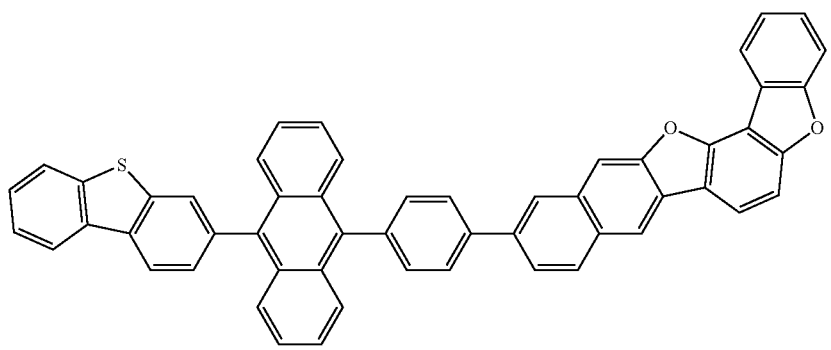
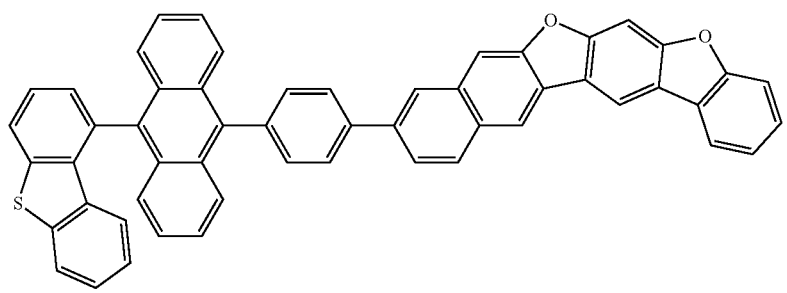

-continued
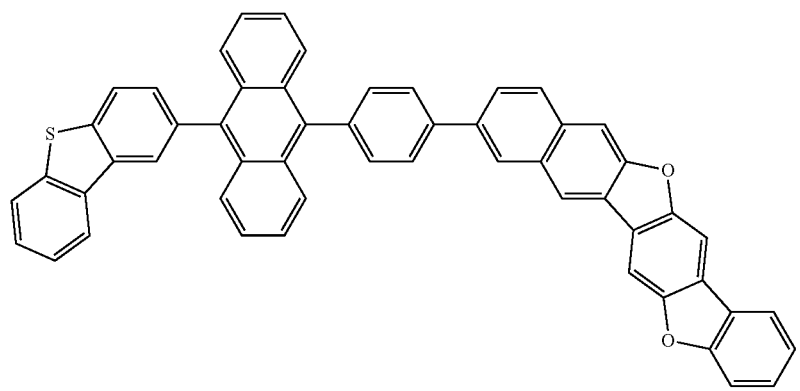
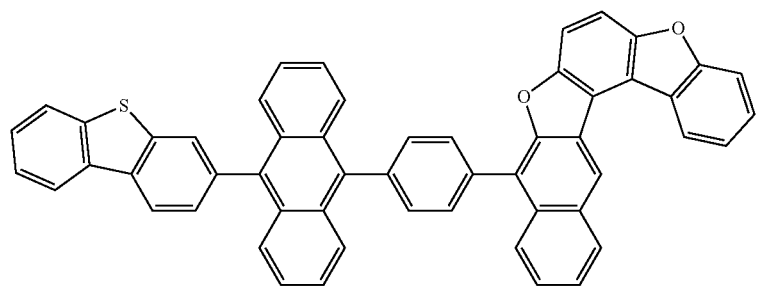
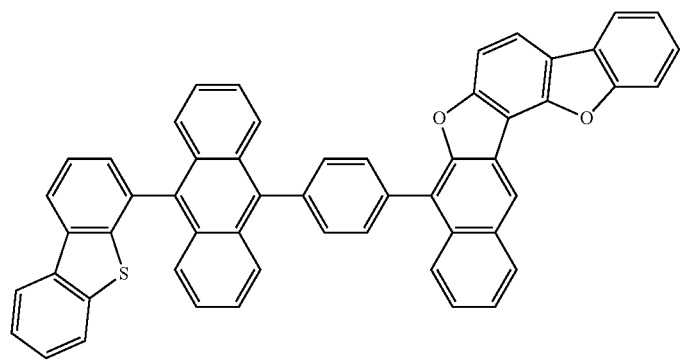
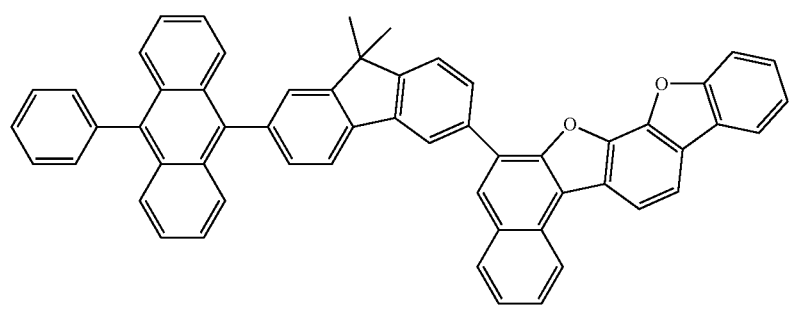
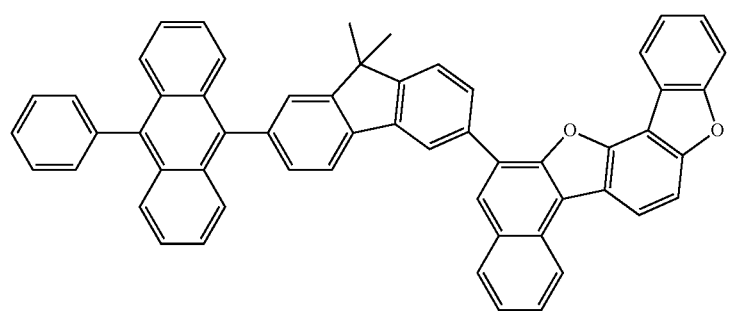

-continued
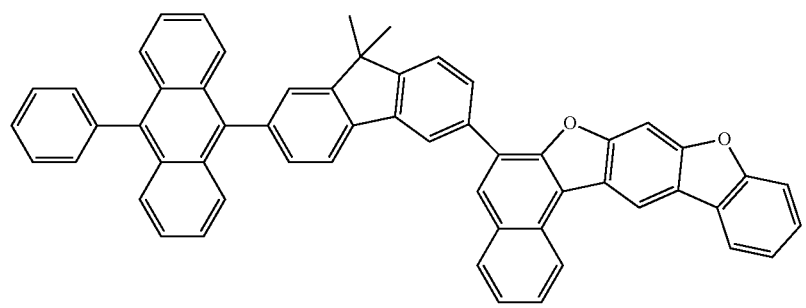
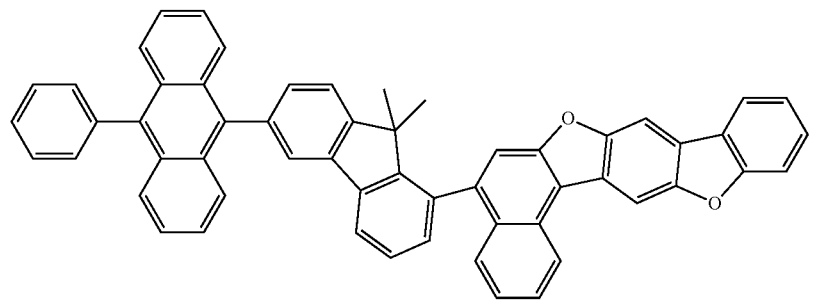
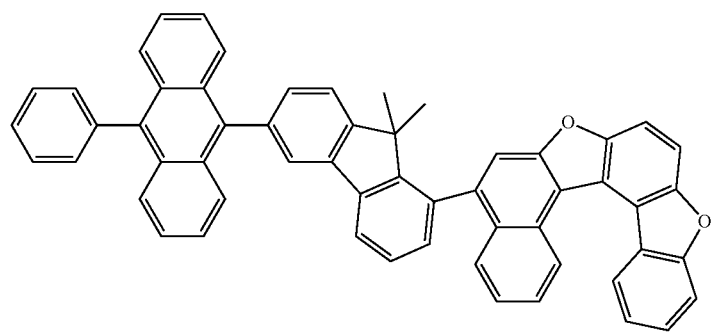
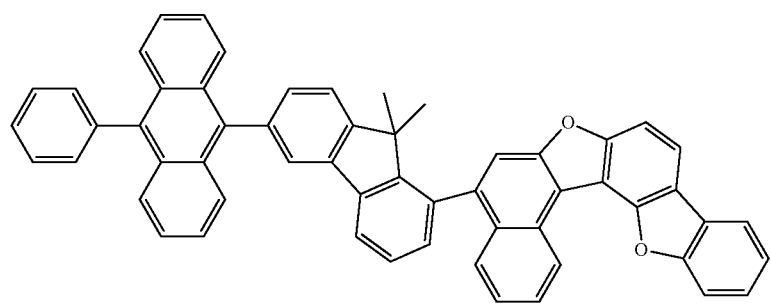
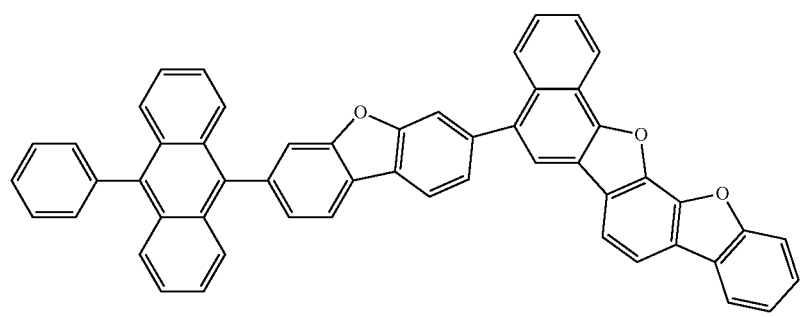

-continued
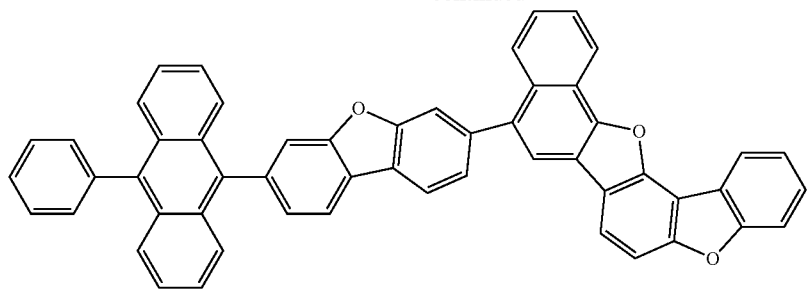
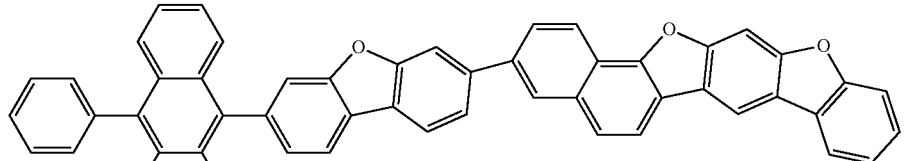
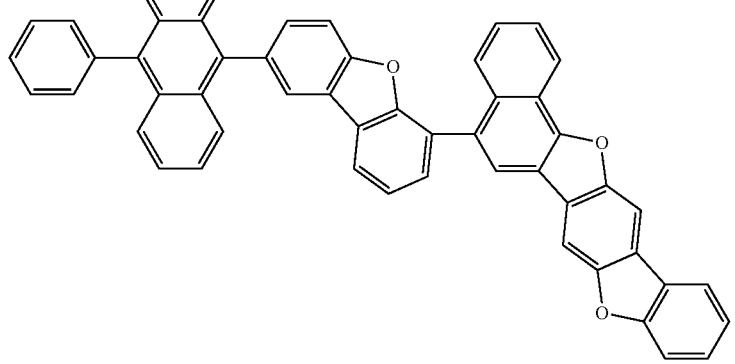
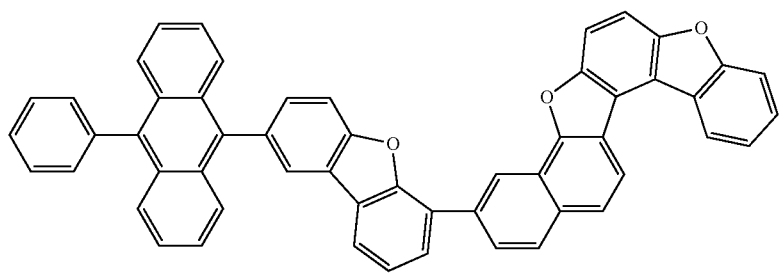
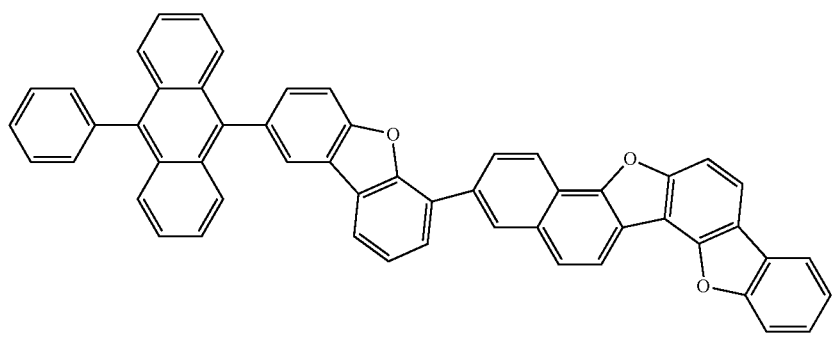

-continued
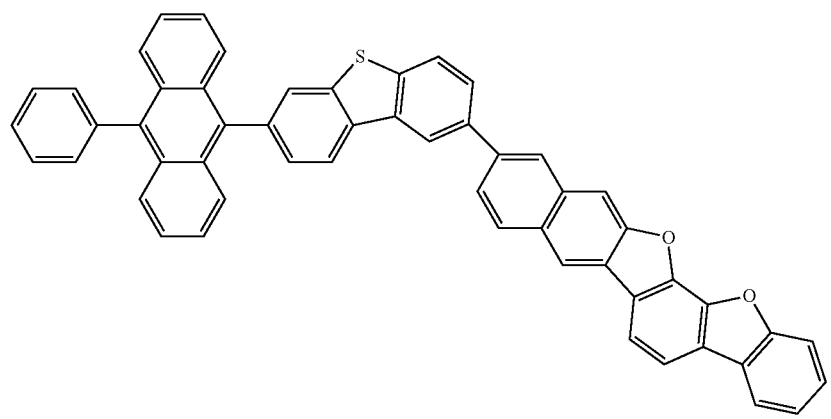
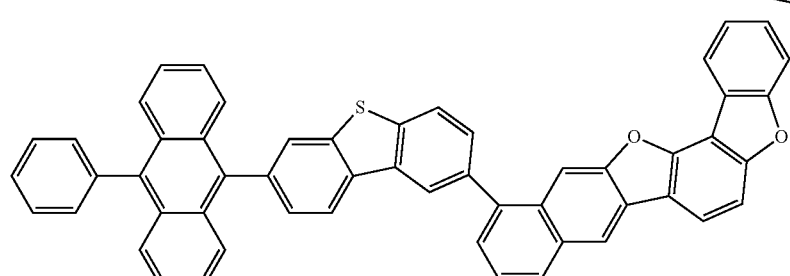
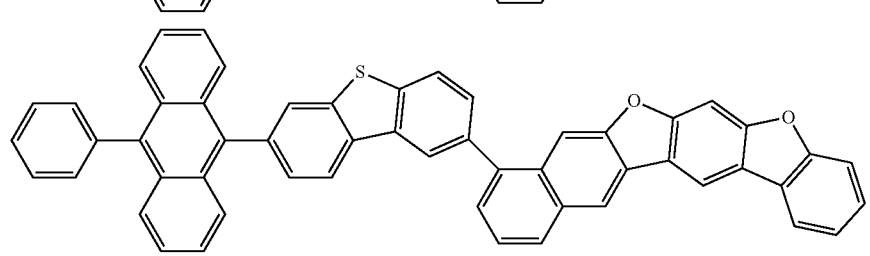
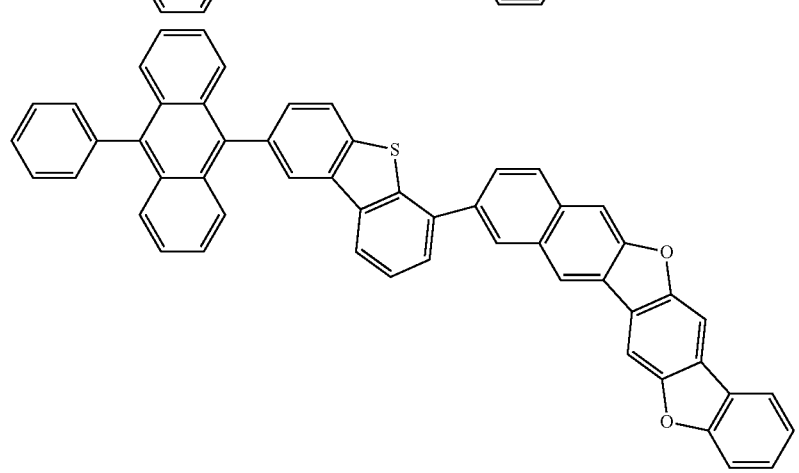
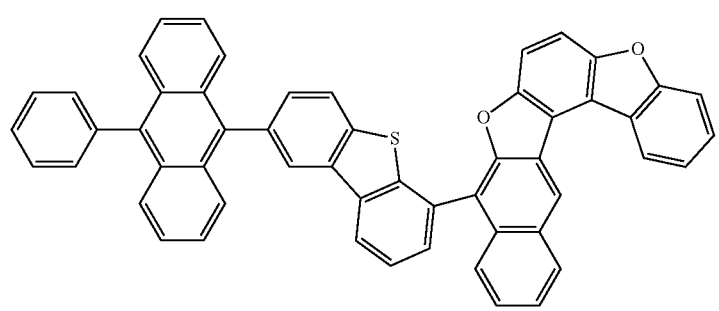

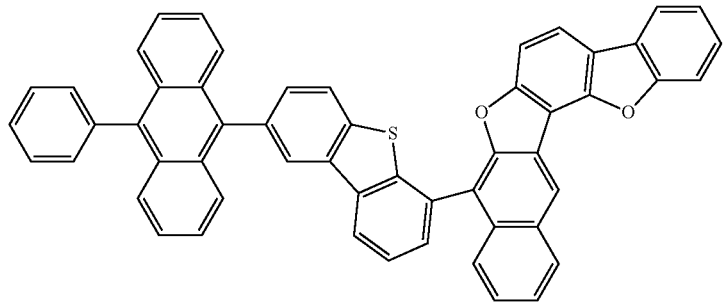
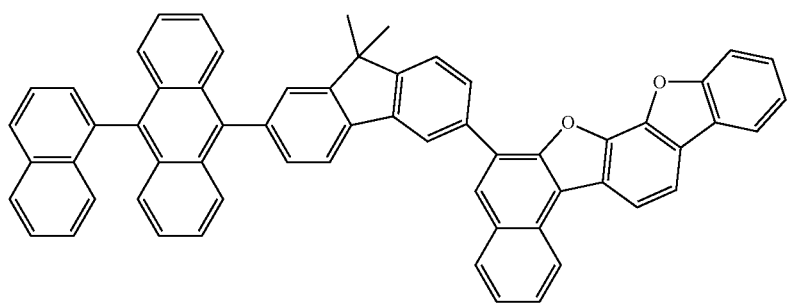
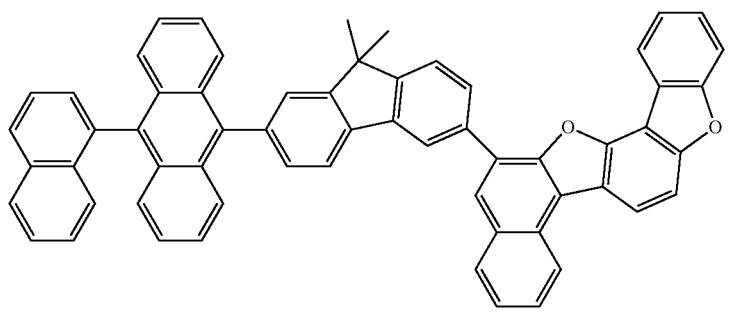
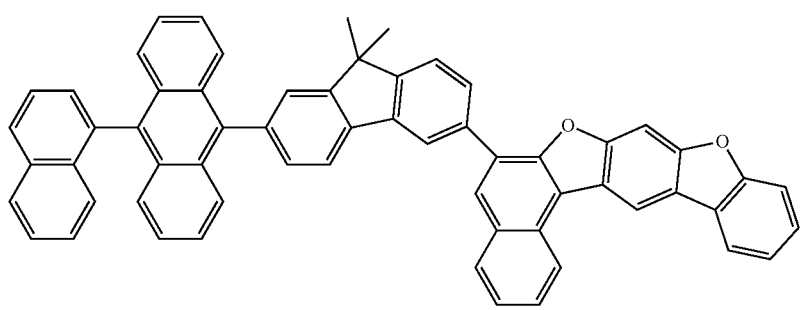
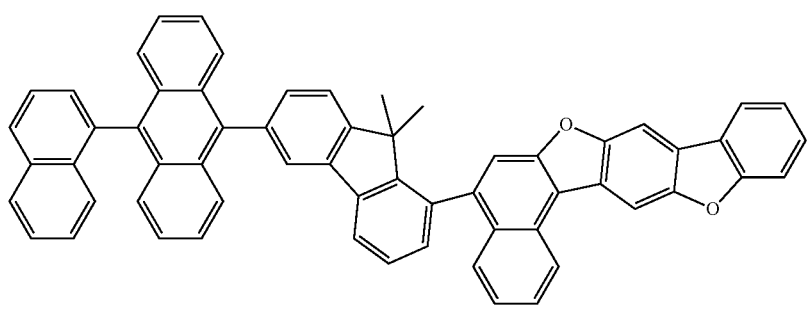

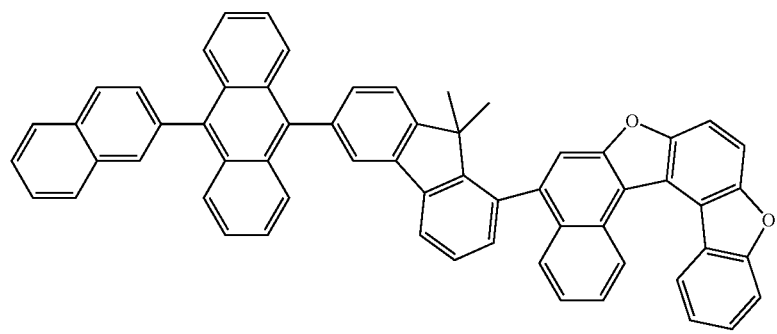
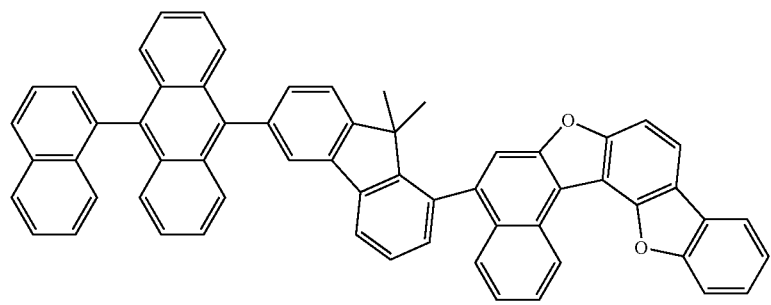
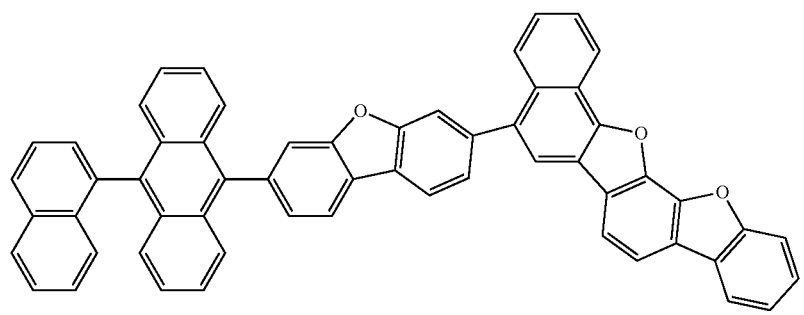
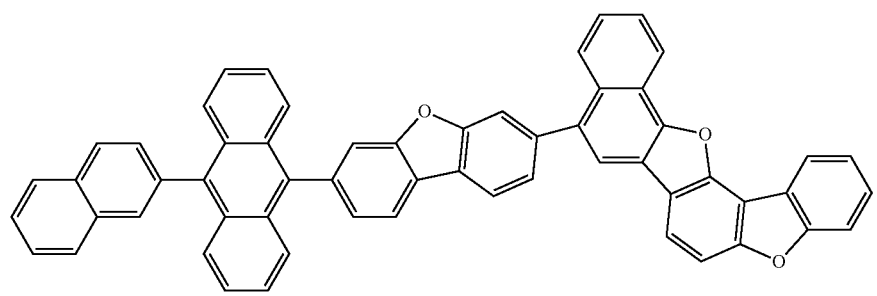
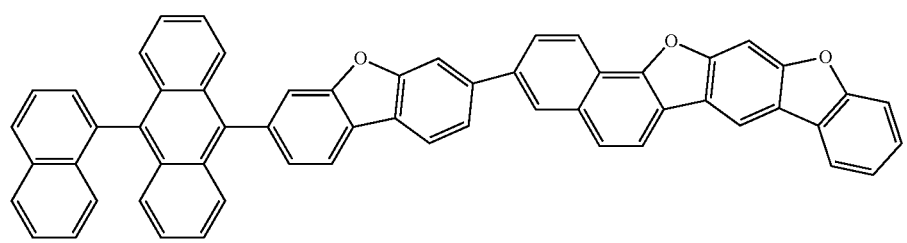

-continued
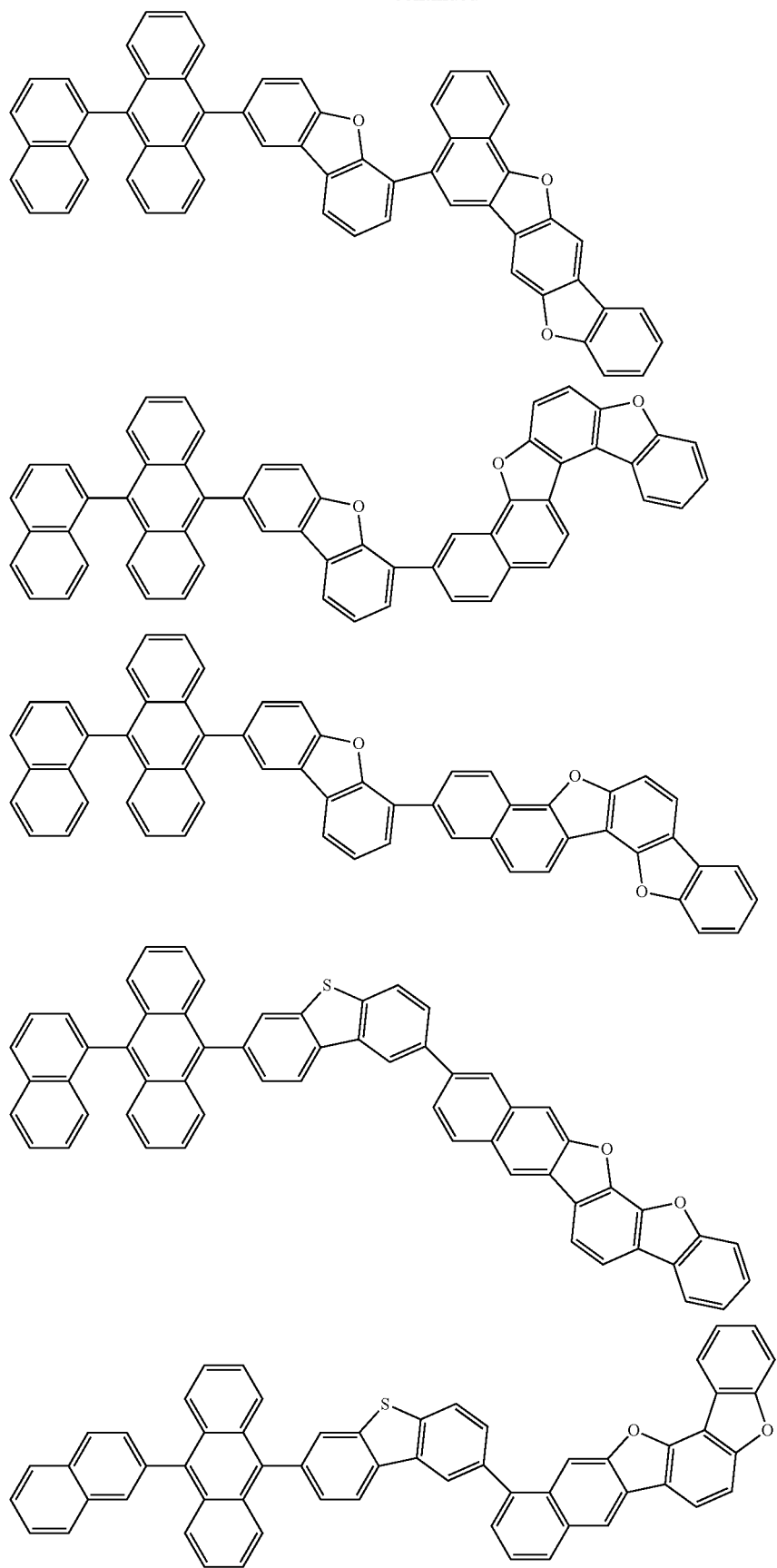

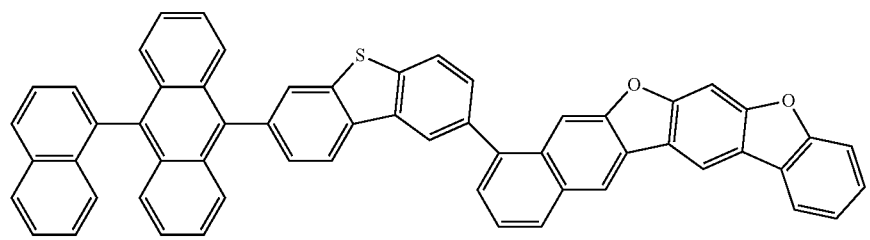
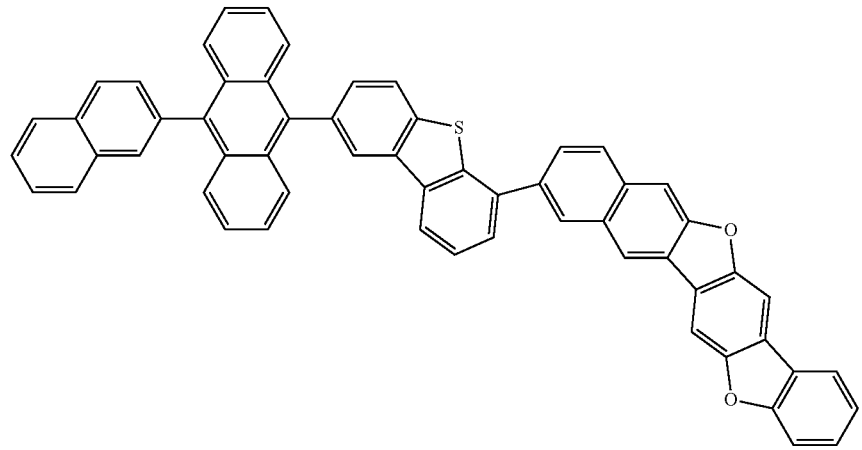
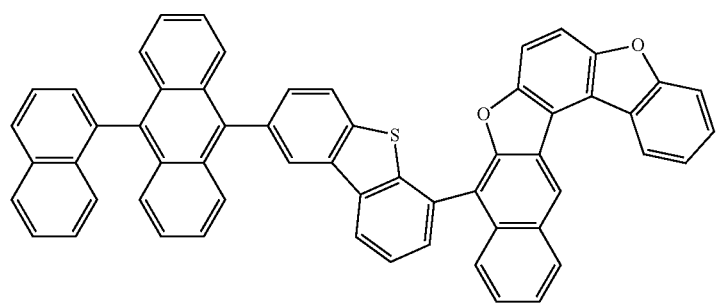
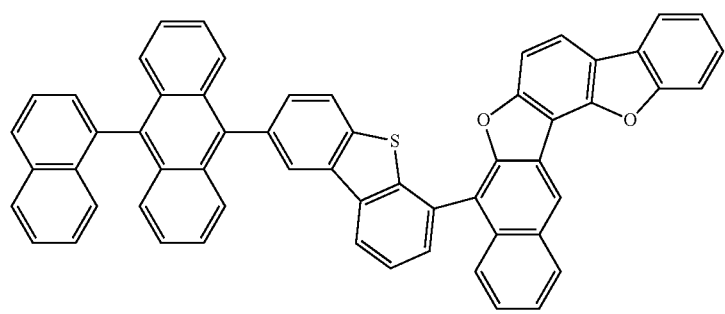
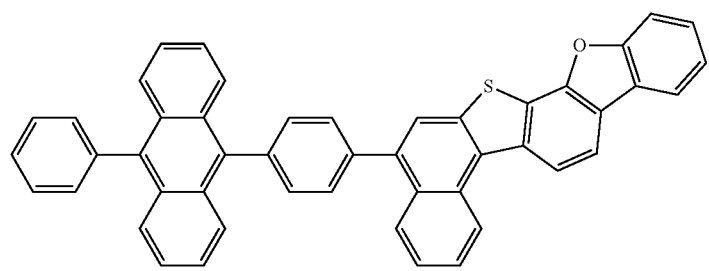

-continued
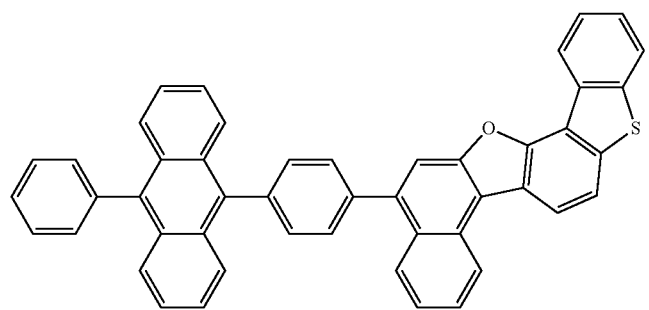
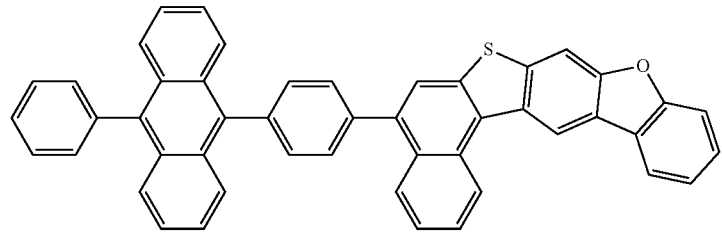
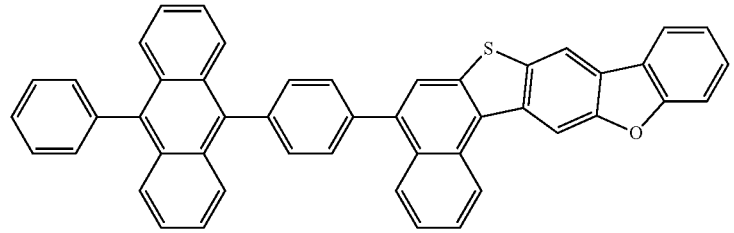
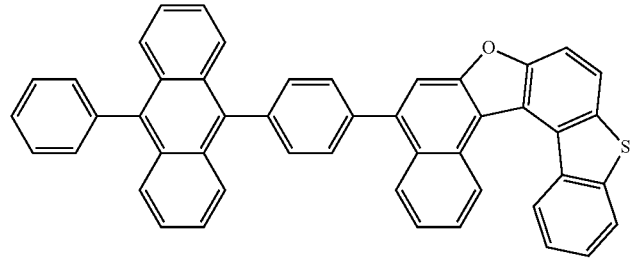
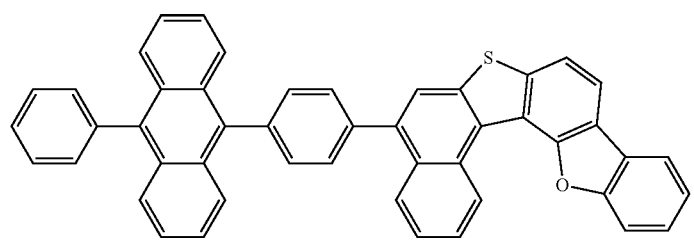
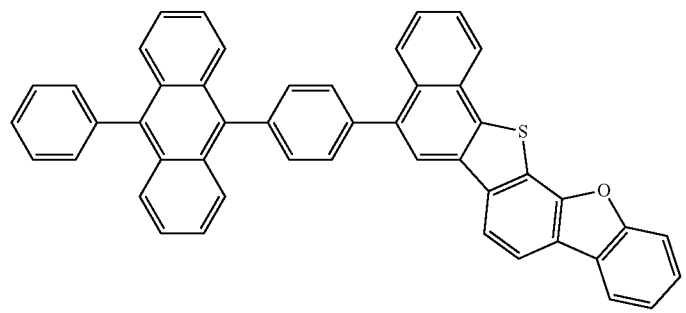

-continued
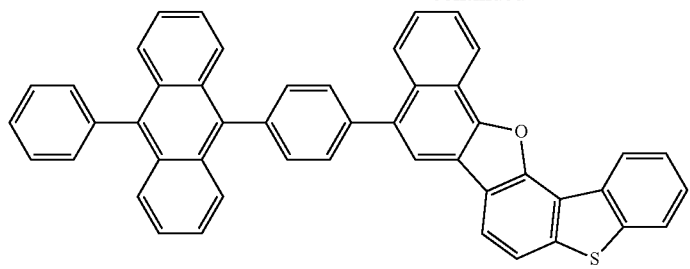
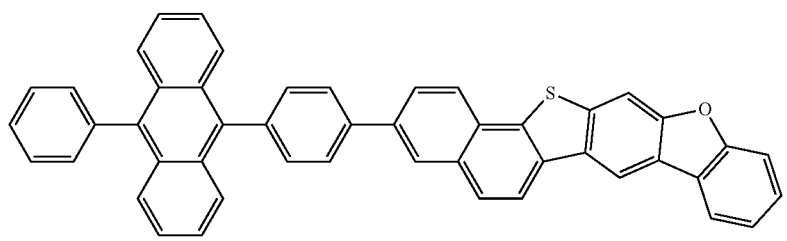
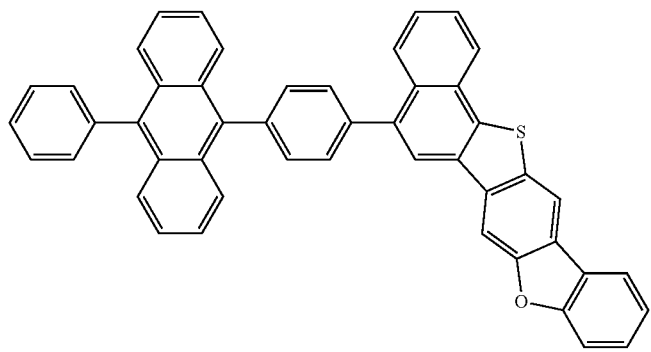
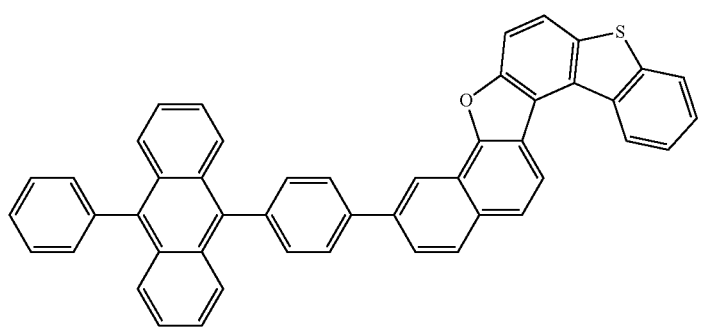
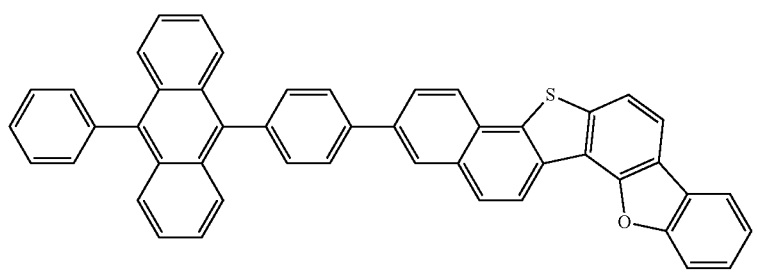

-continued
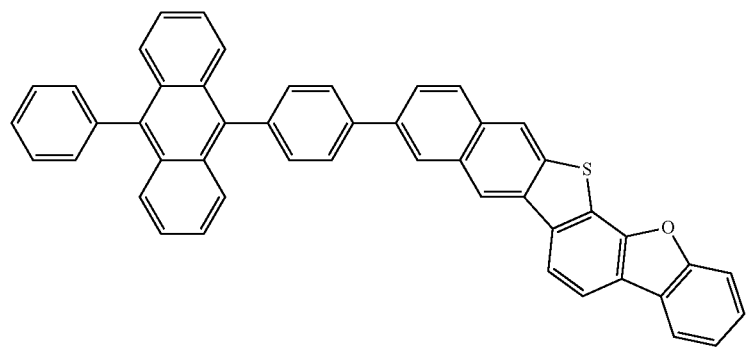
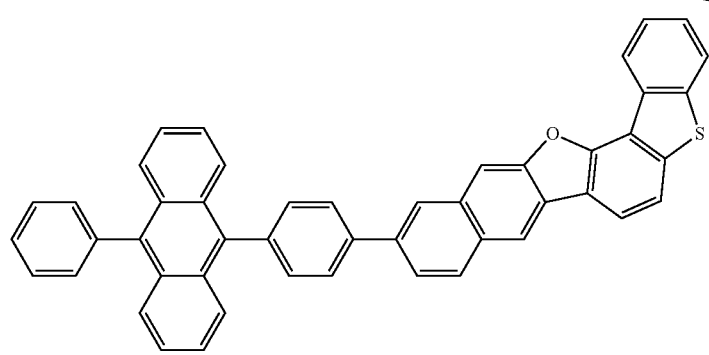
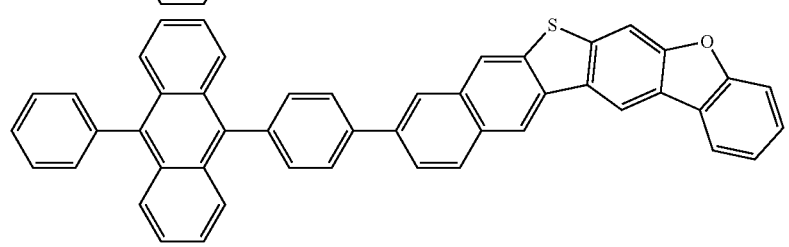
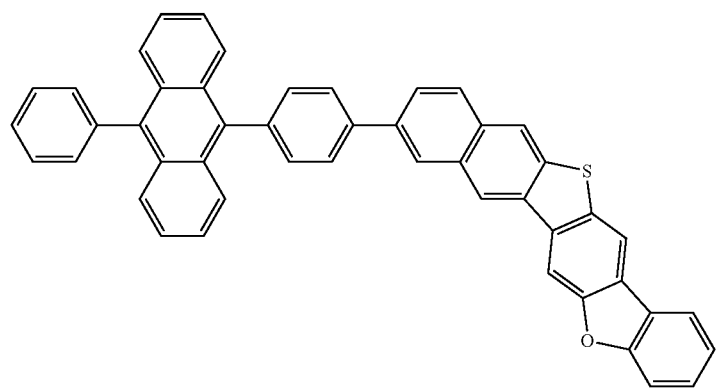
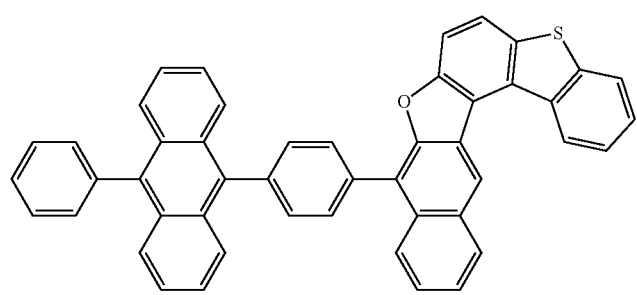

-continued
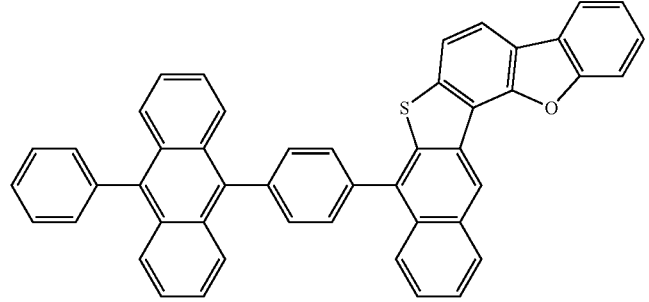
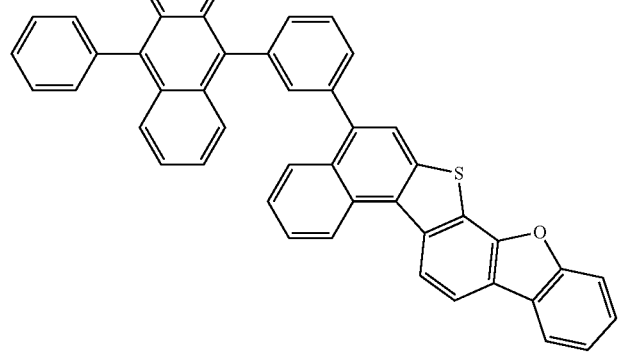
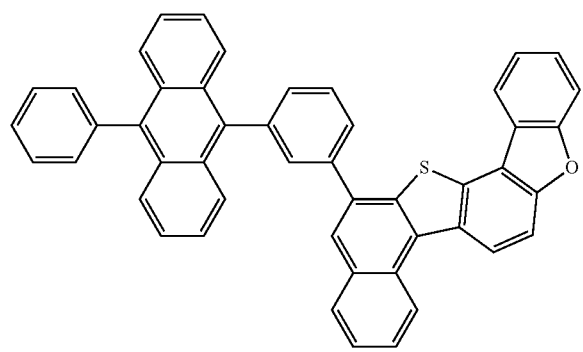
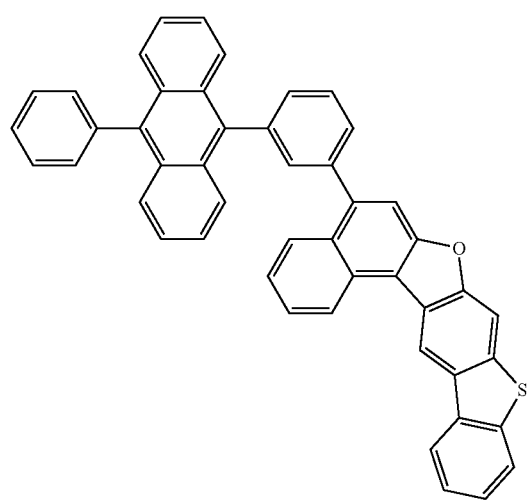

-continued
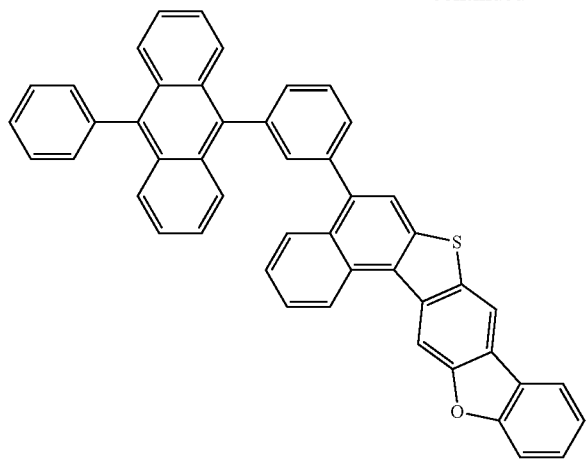
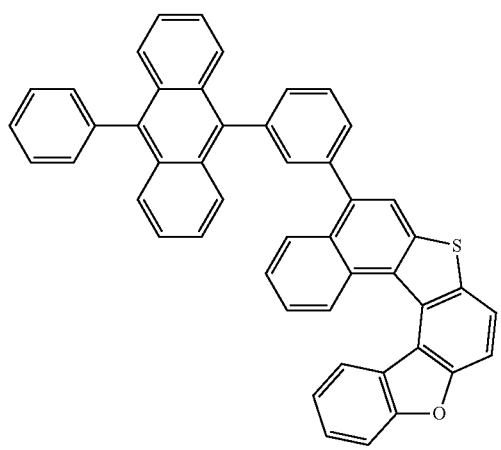
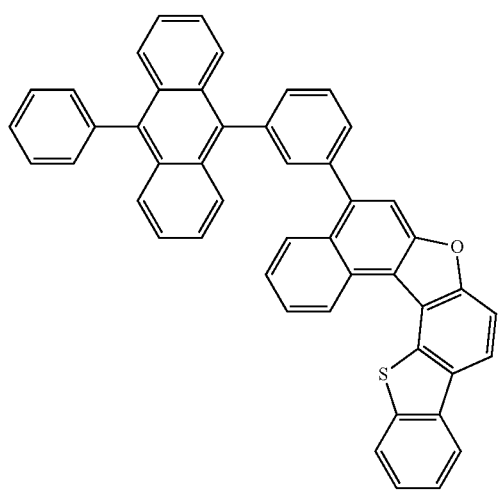

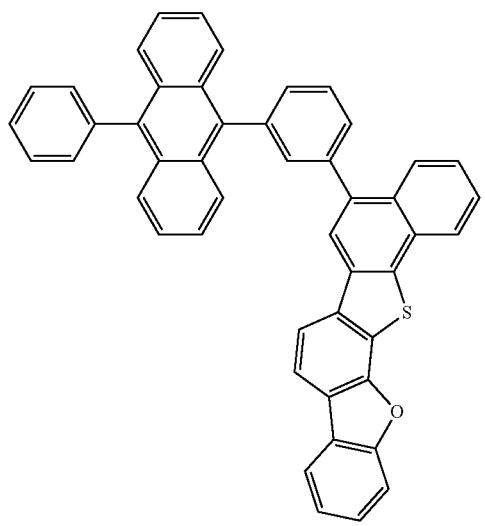
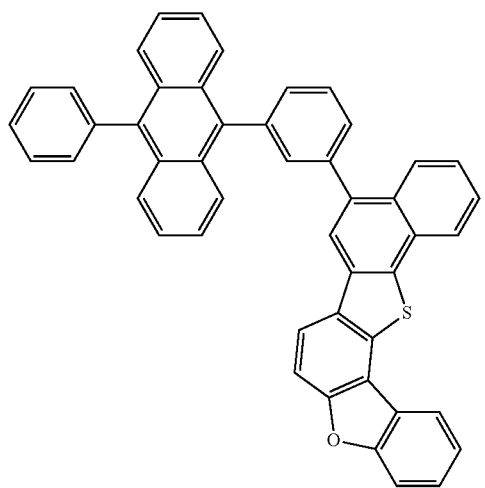
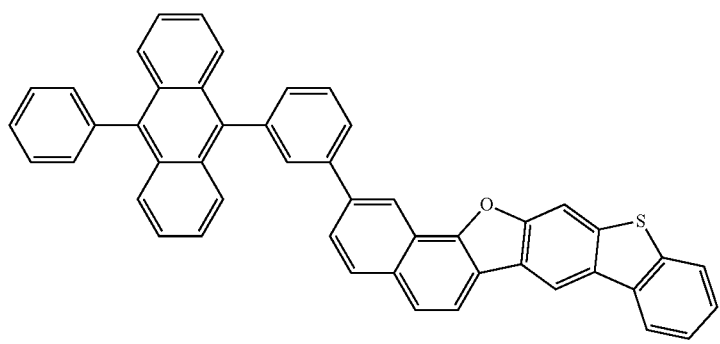

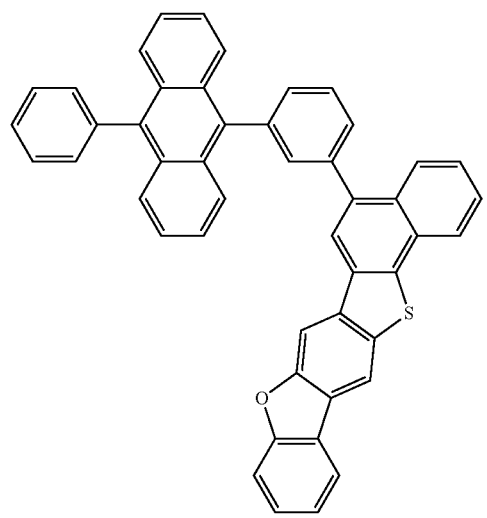
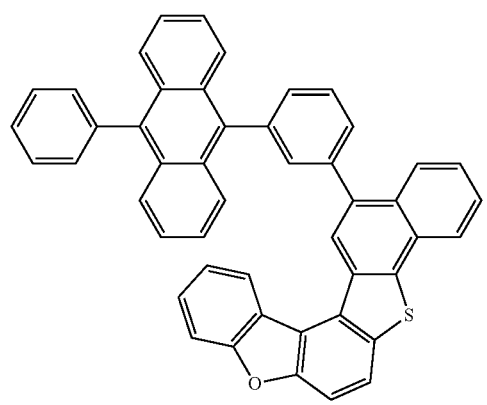
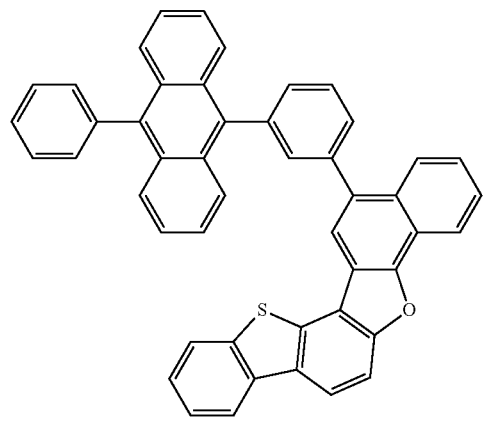

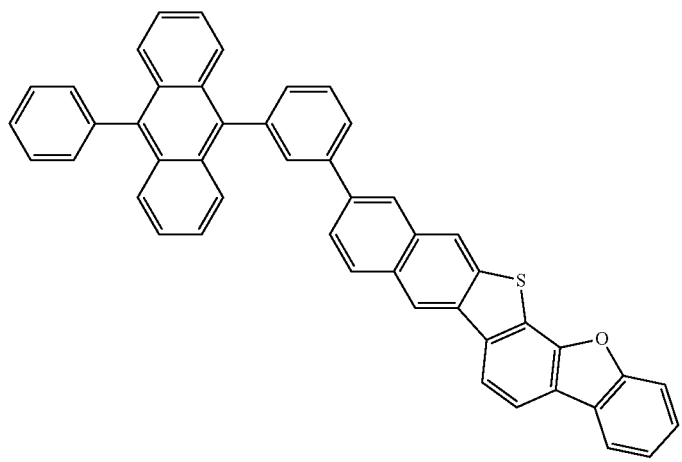
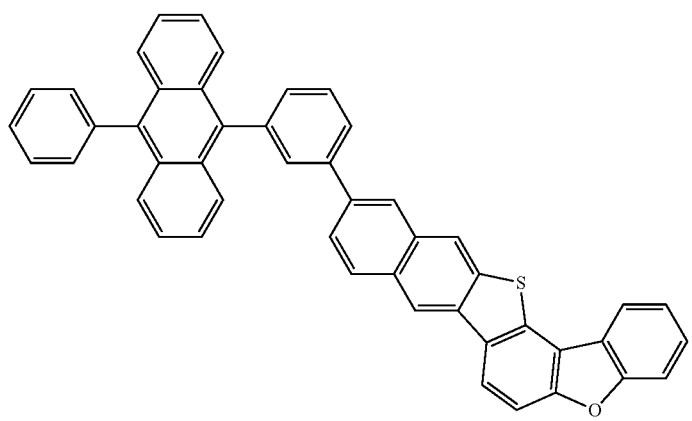
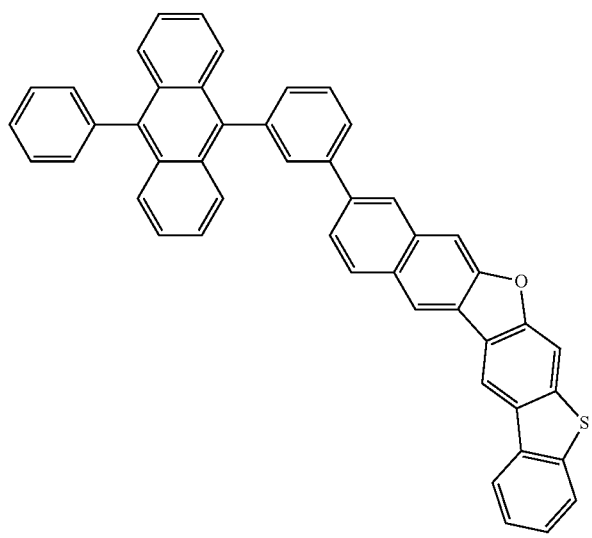

-continued
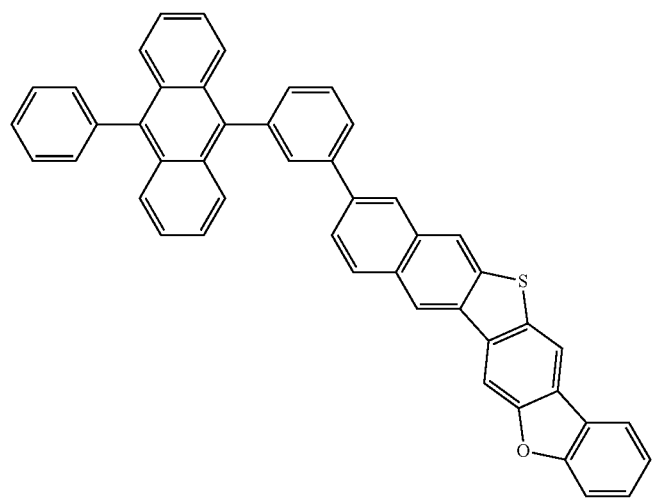
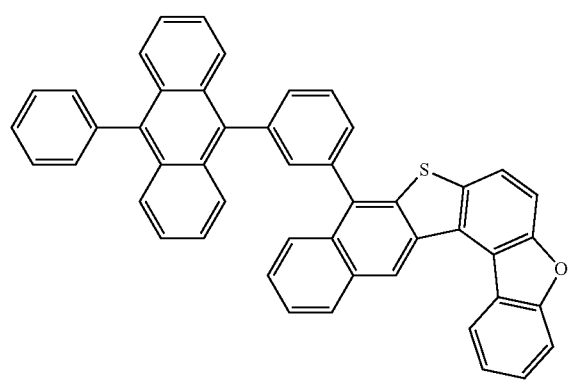
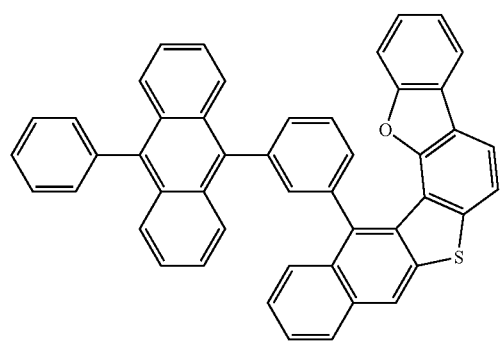
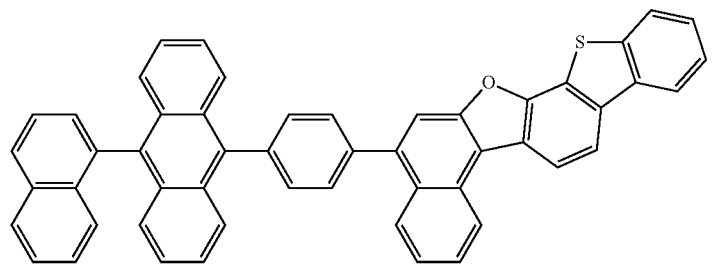

-continued
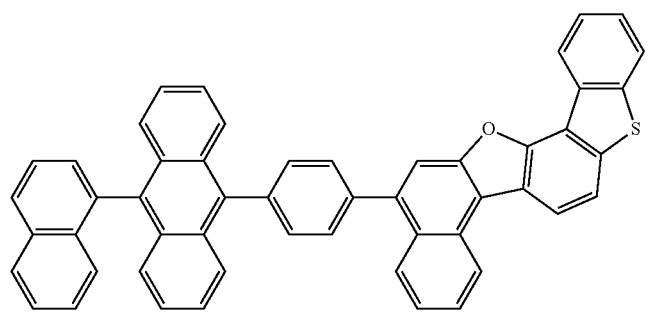
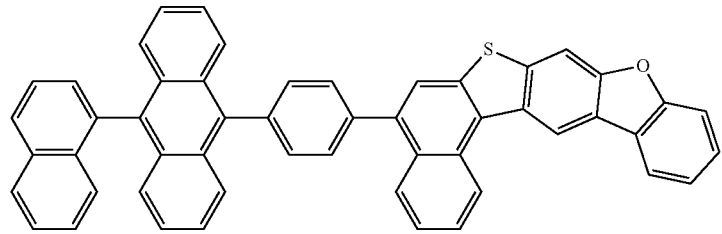
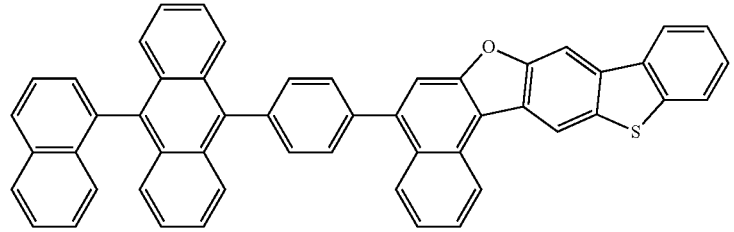
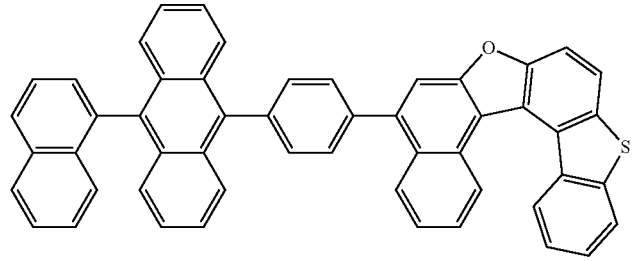
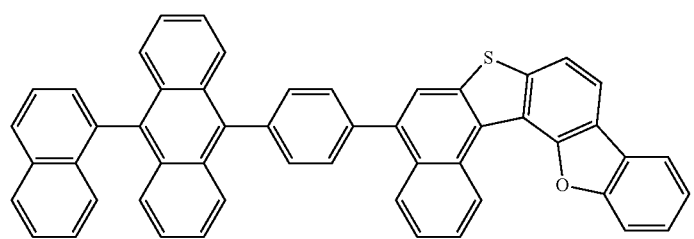
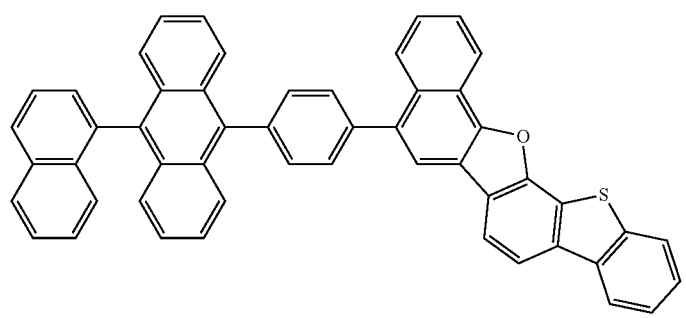

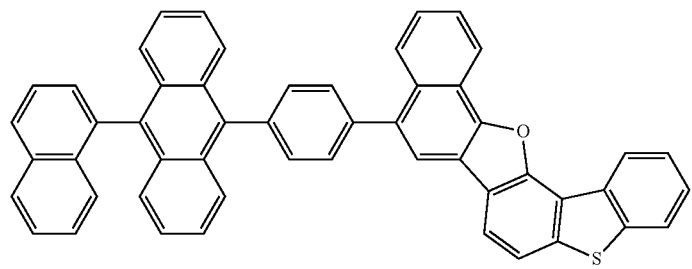
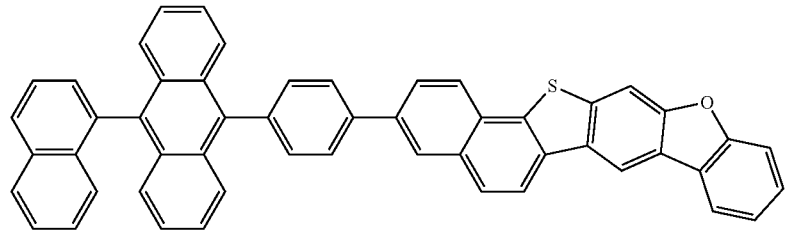
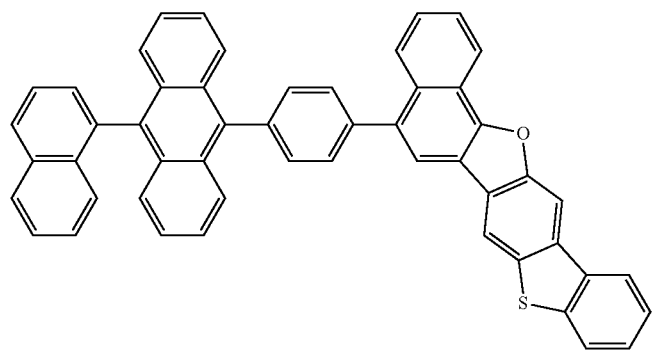
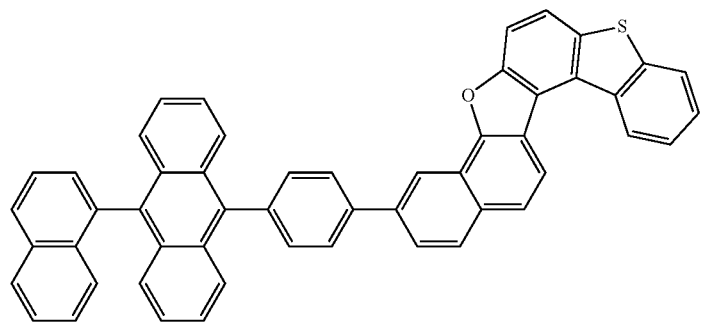
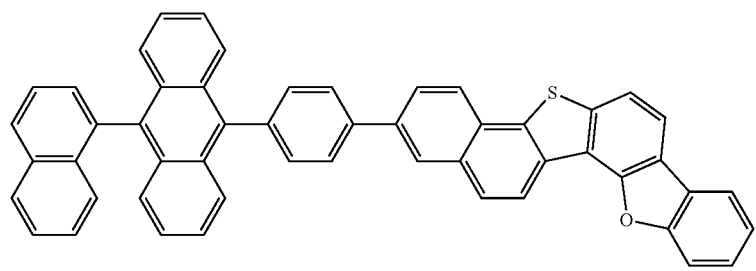

-continued
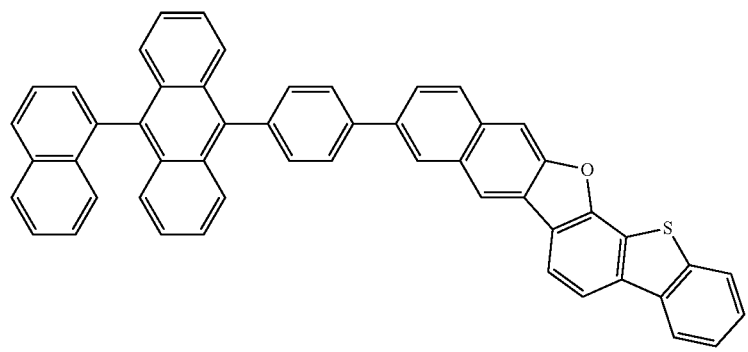

-continued
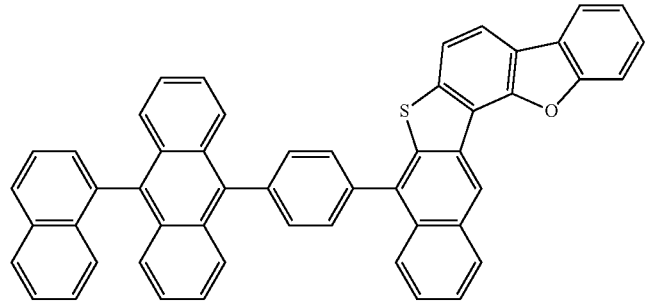
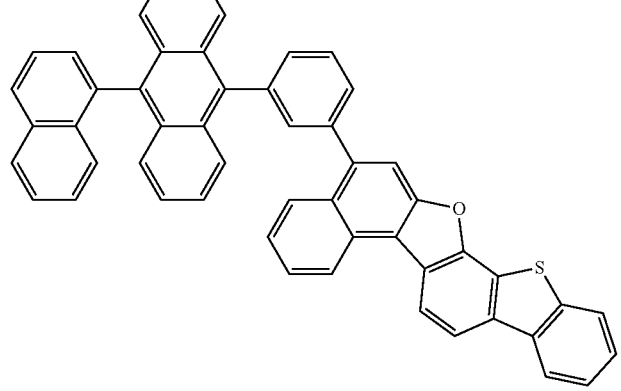
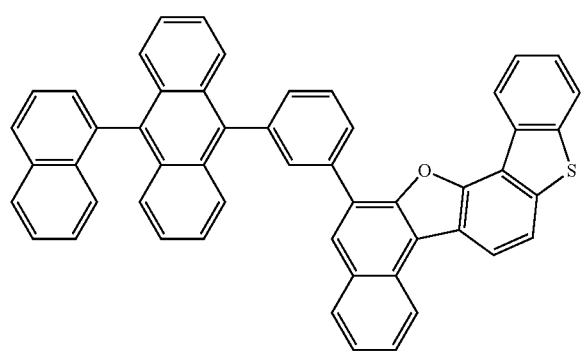
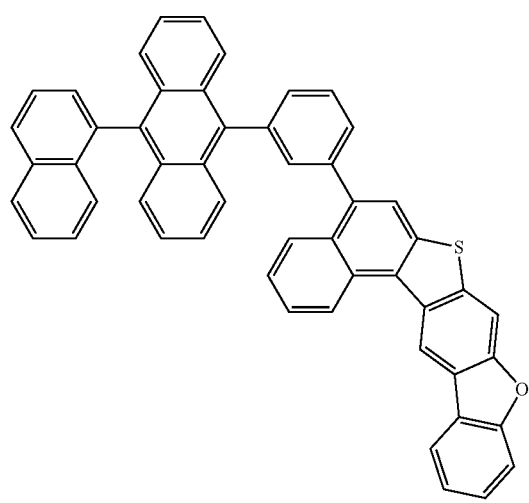

-continued
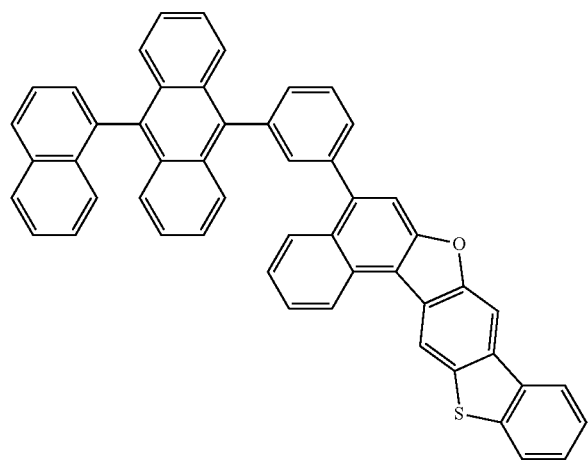
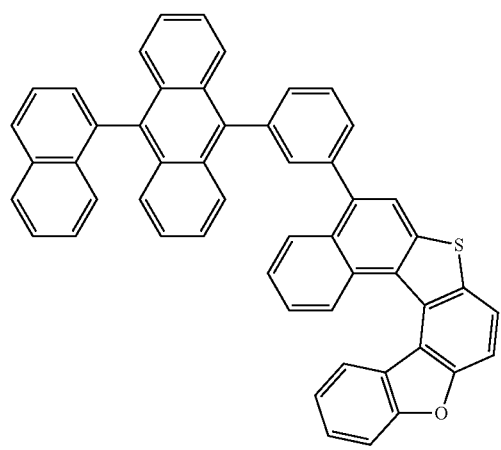
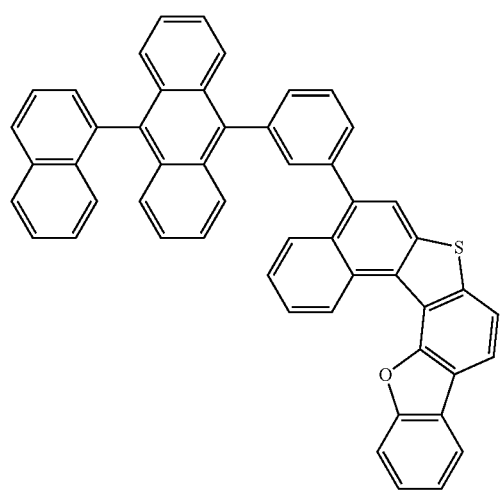

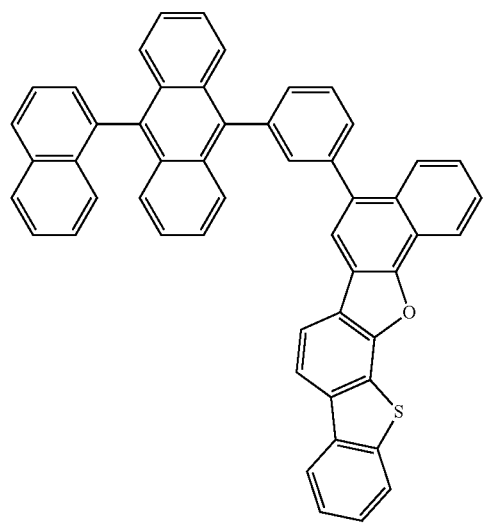
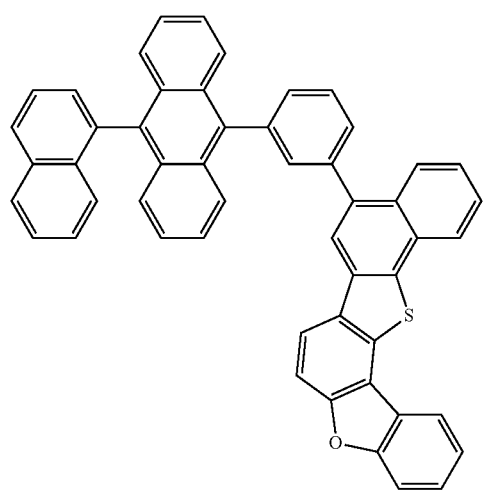
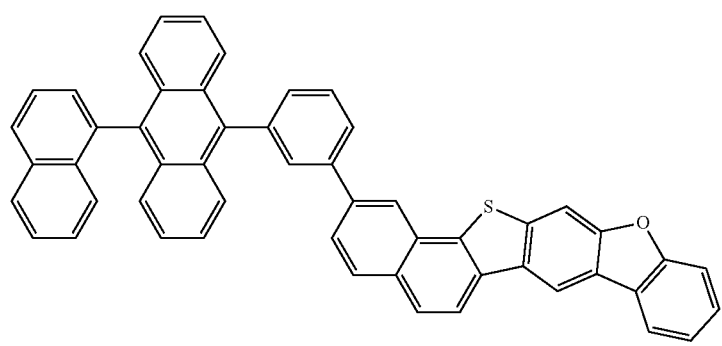

-continued
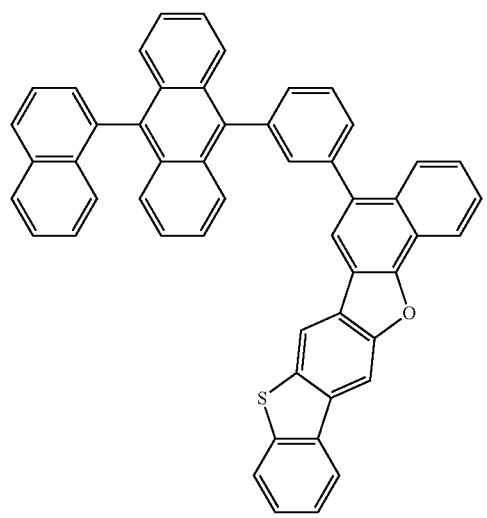
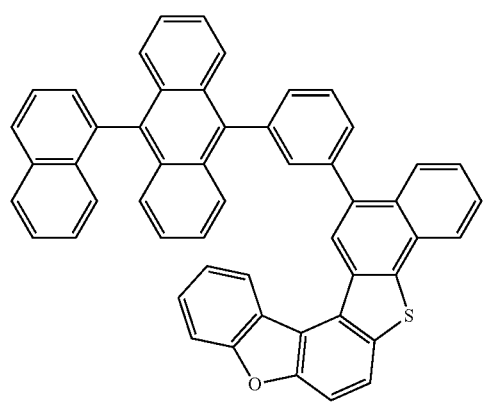
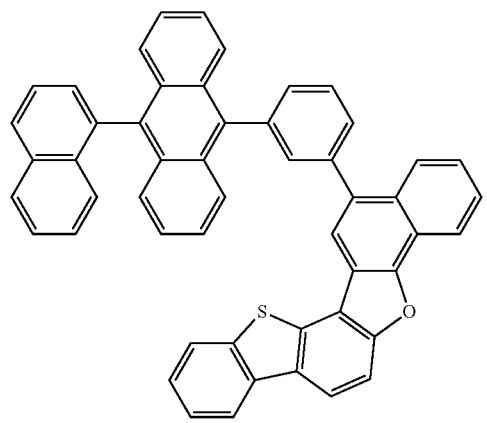

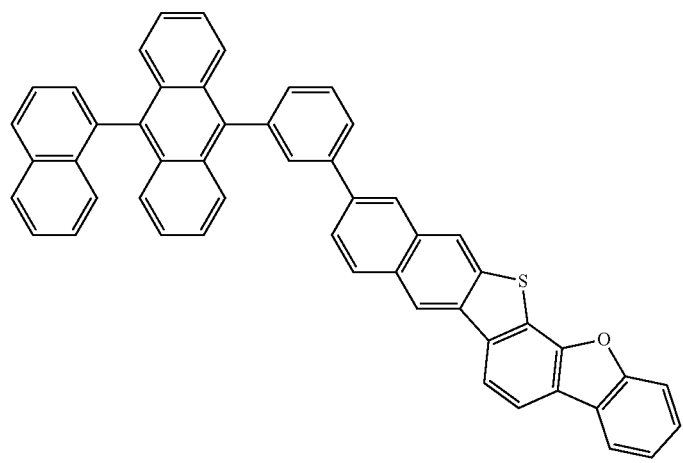
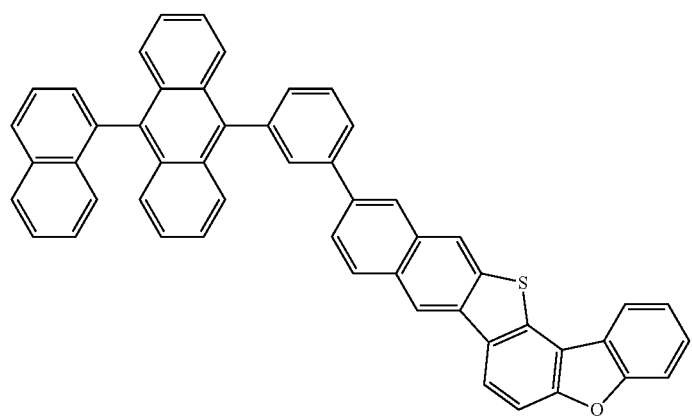
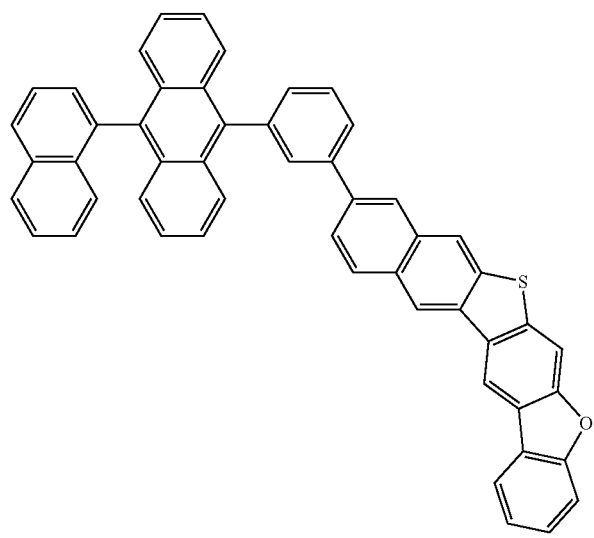

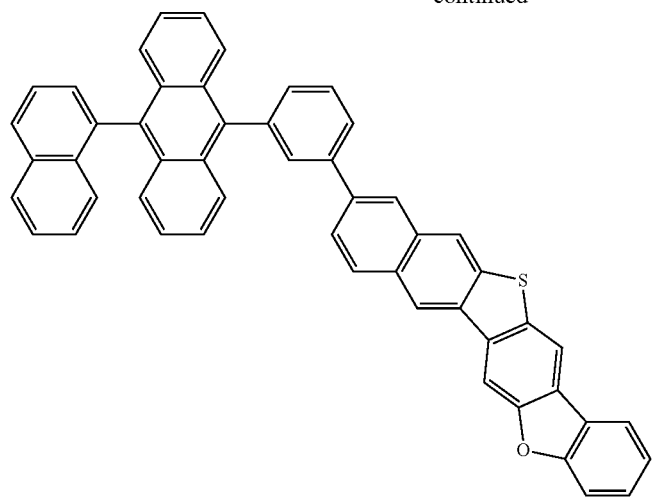
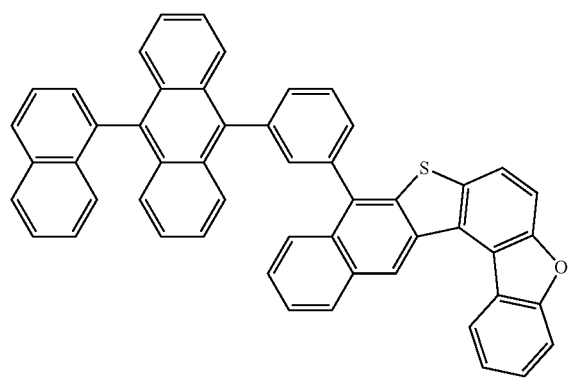
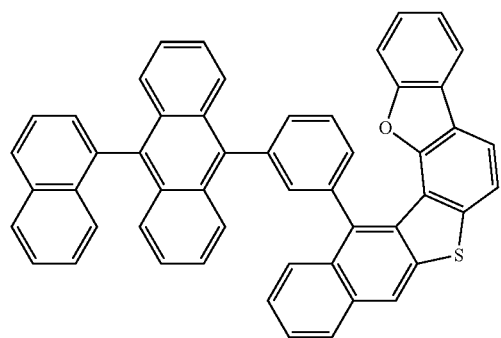
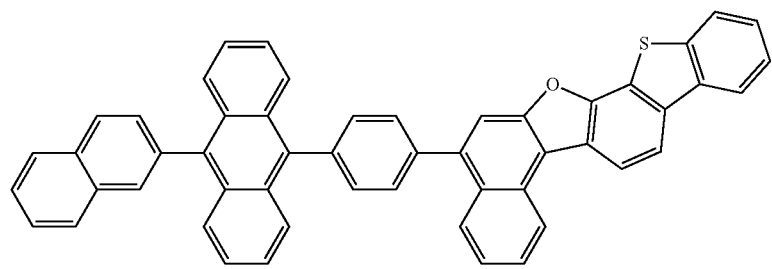

-continued
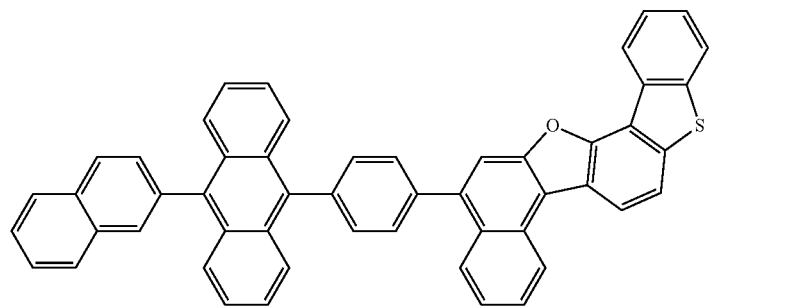
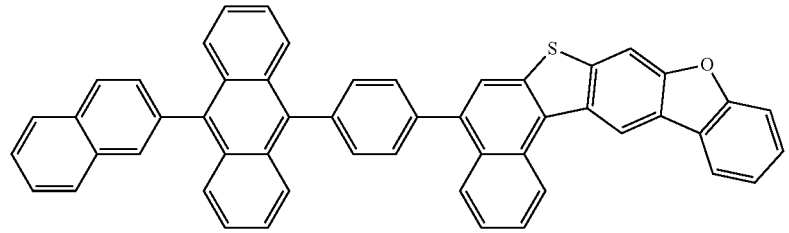
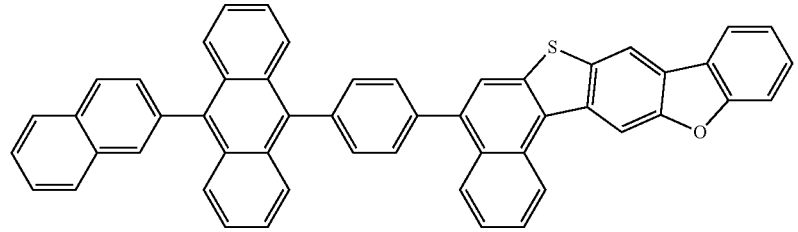
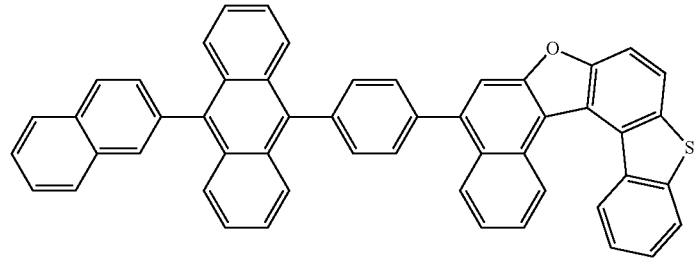
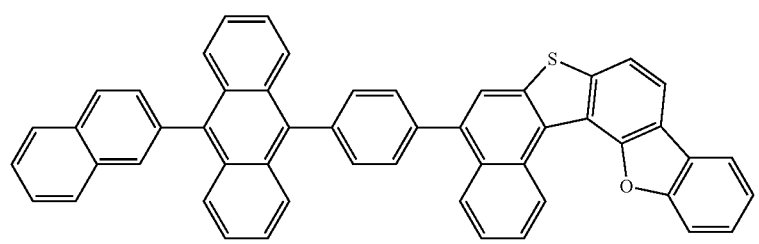
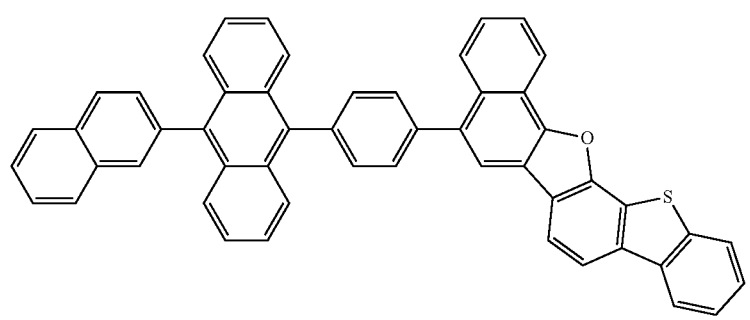

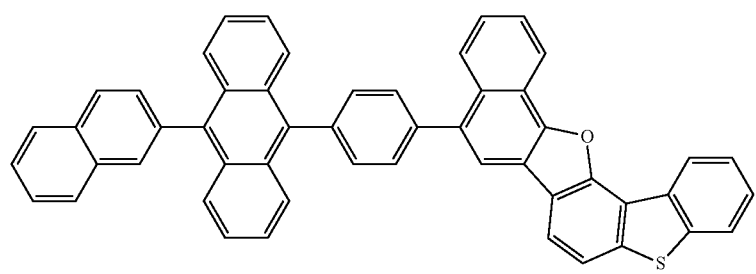
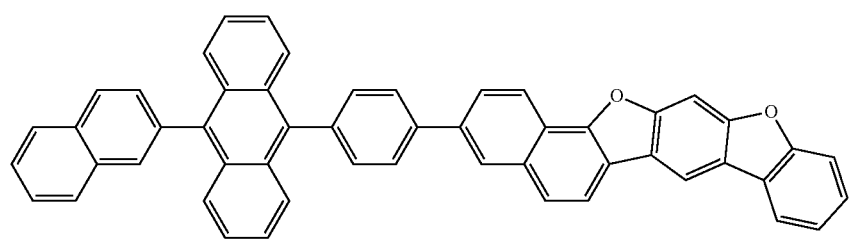
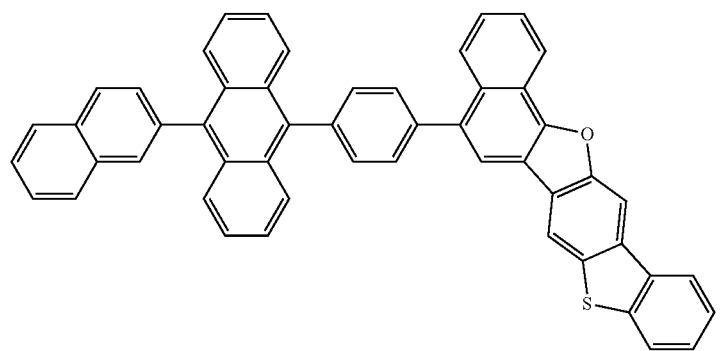
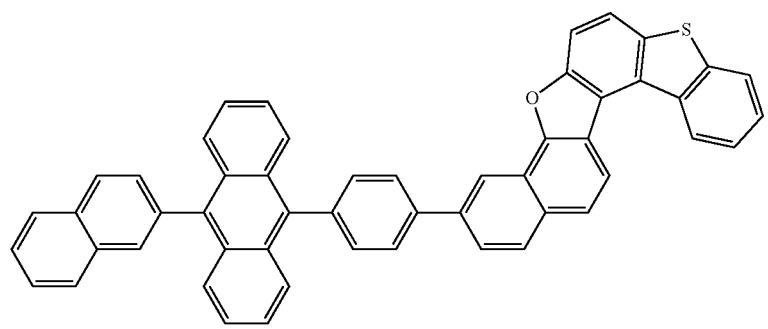
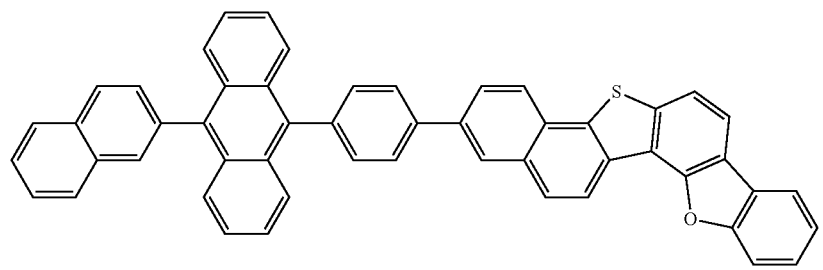

-continued
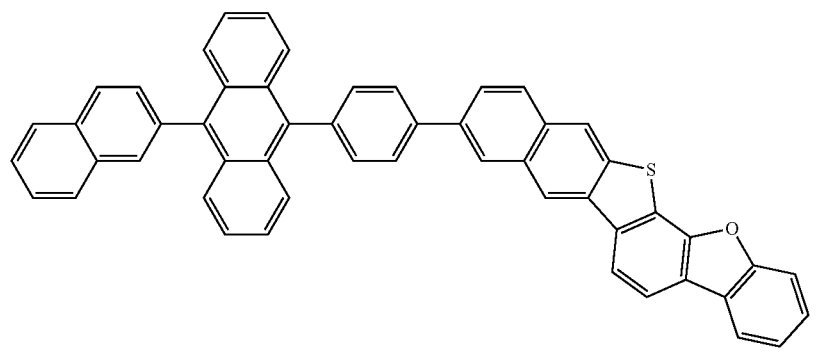
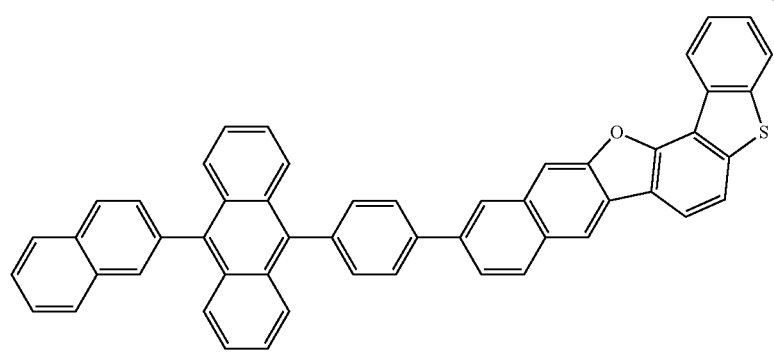
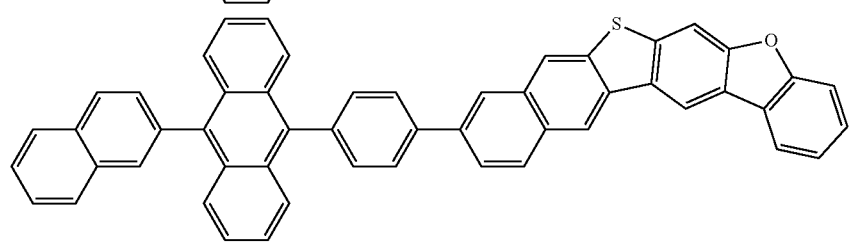
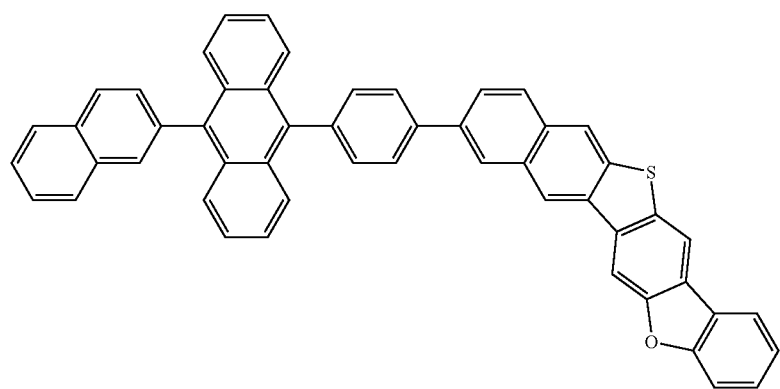
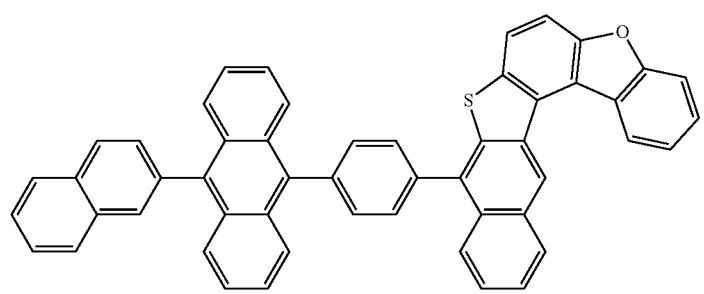

-continued
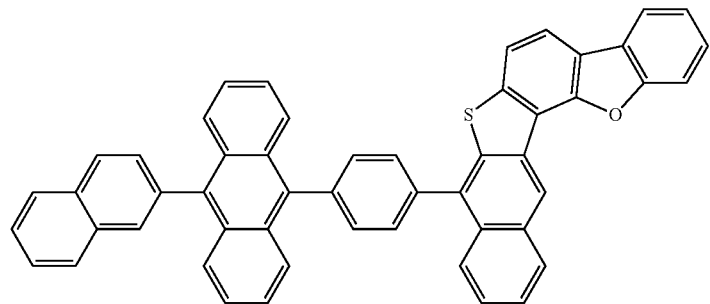
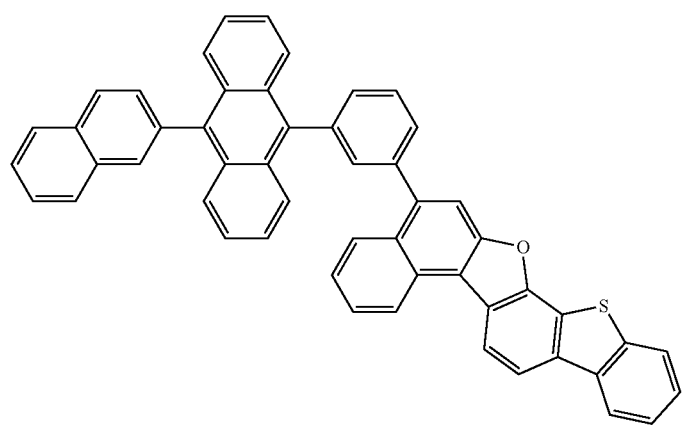
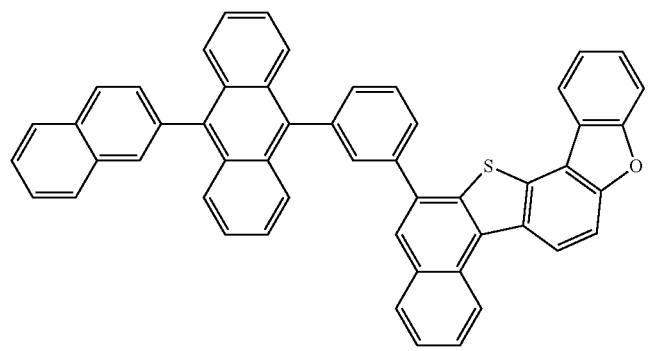
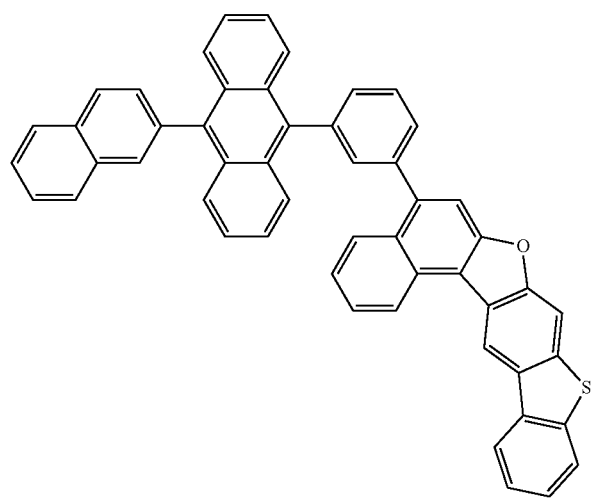

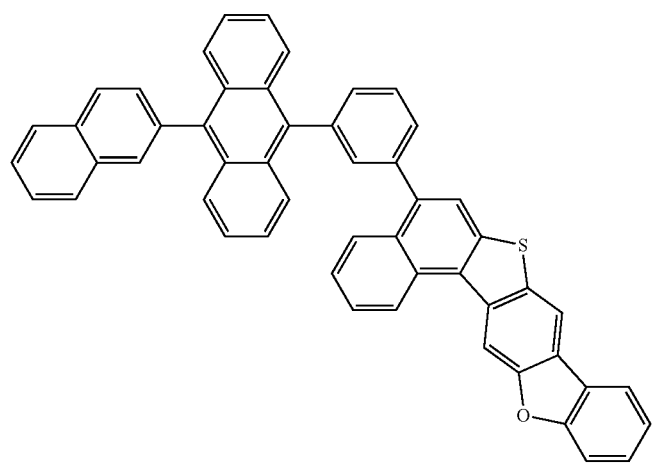
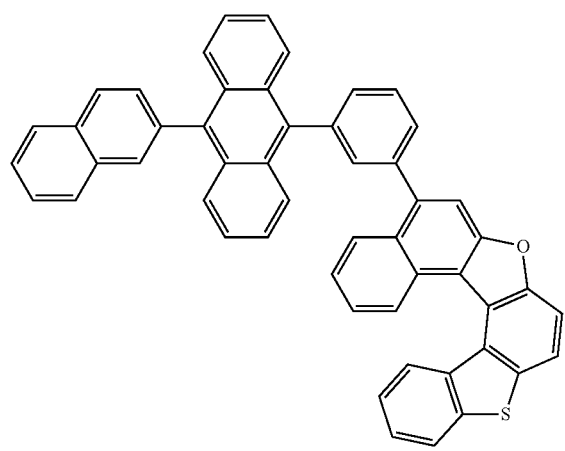
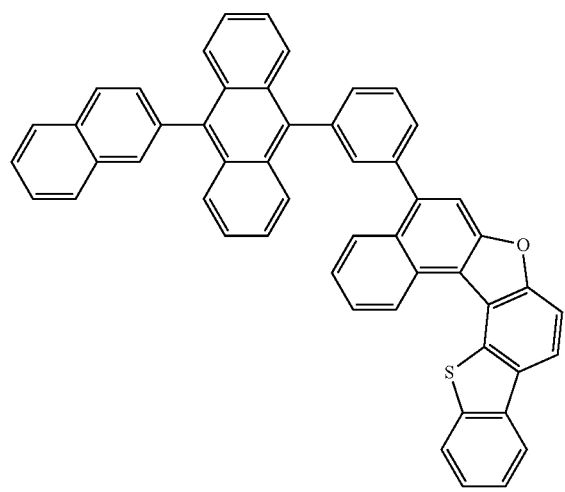

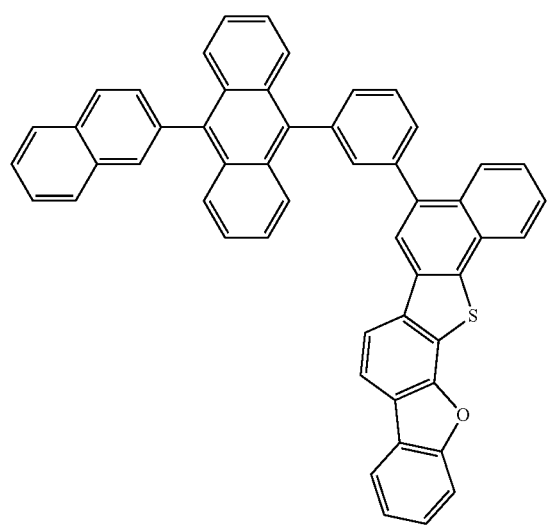
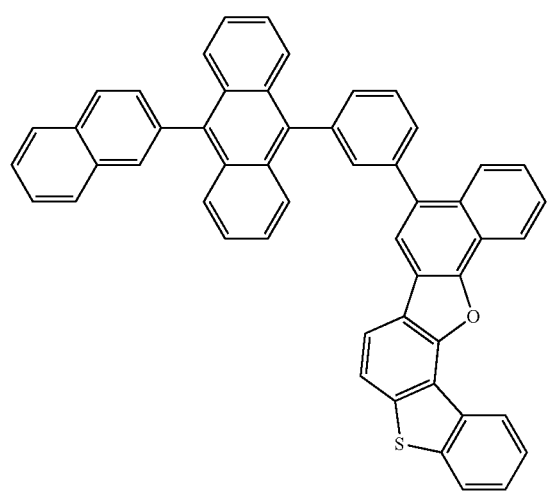
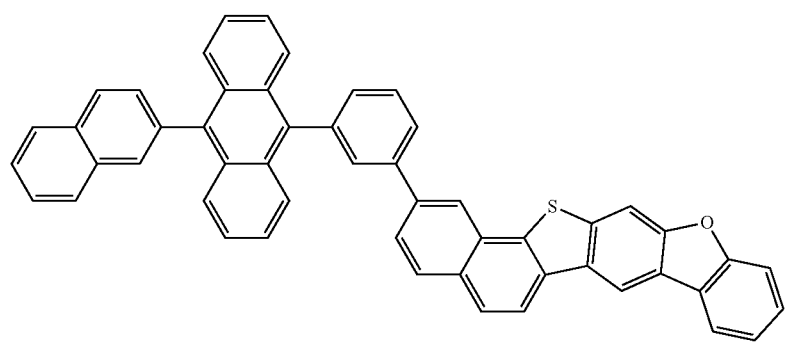

-continued
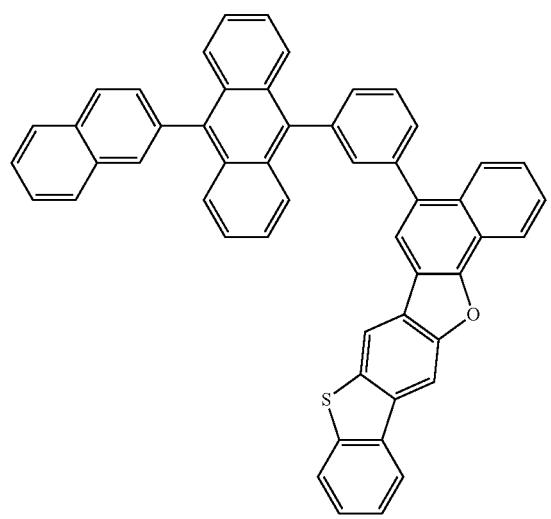
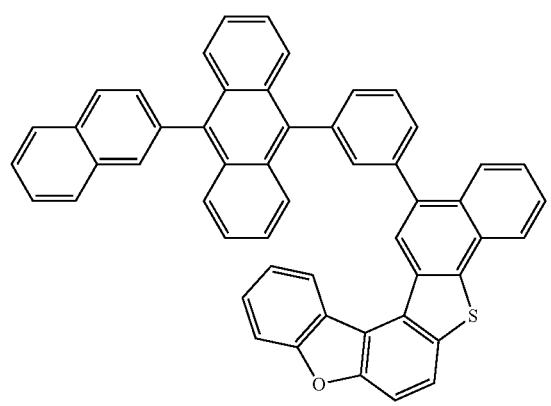
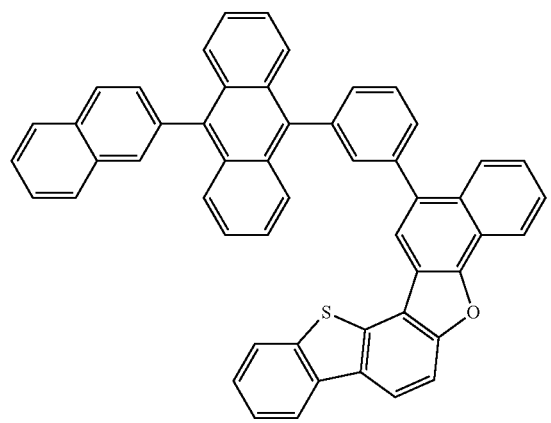

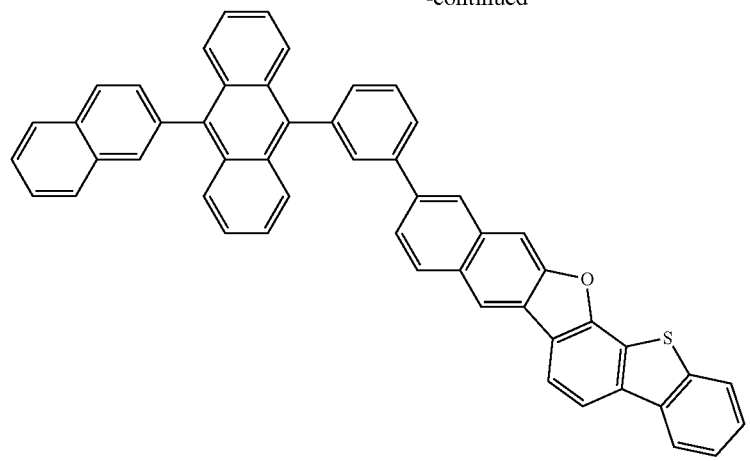

231
232
-continued
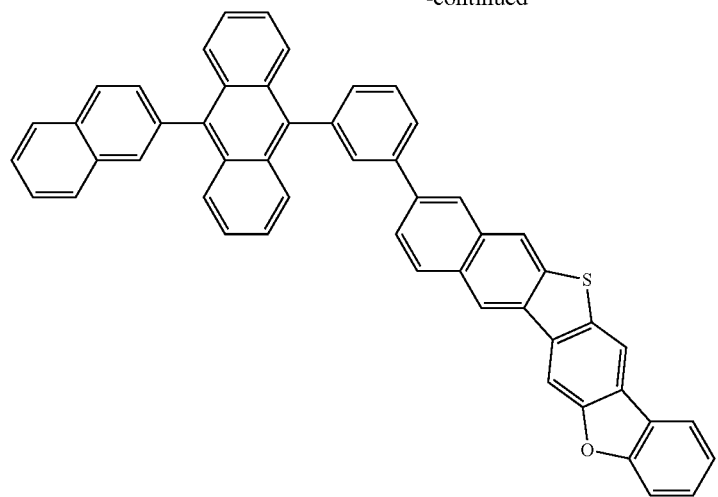
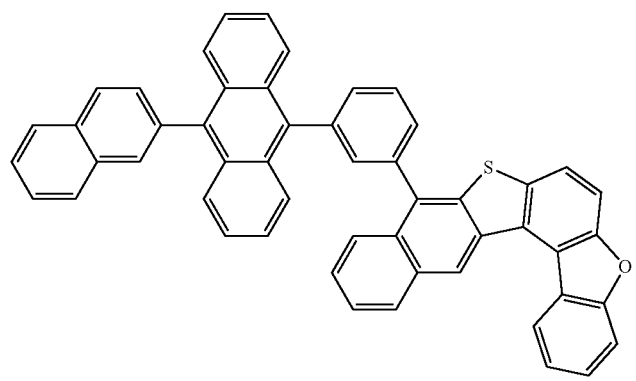
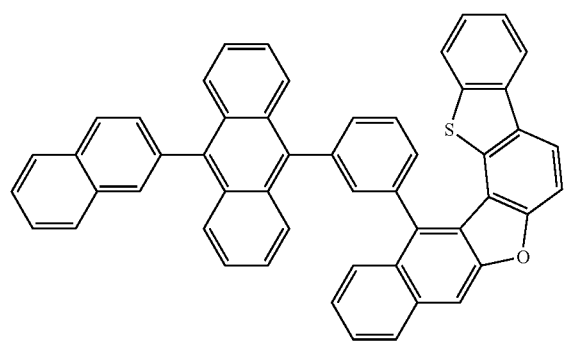
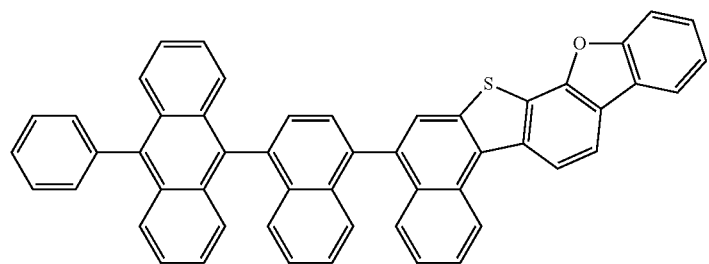

-continued
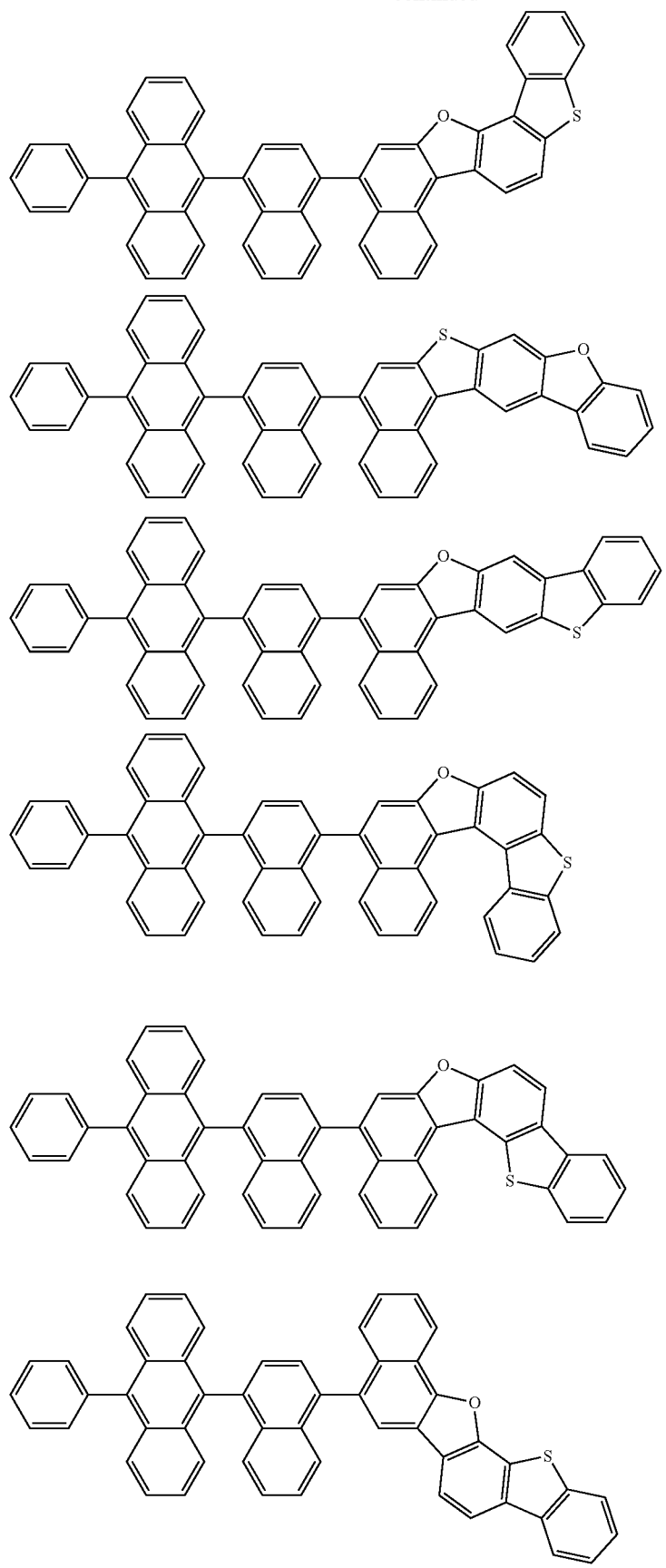

-continued
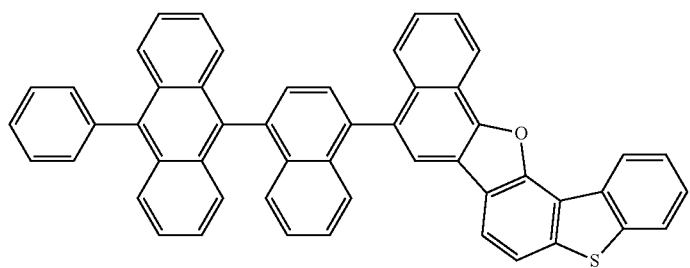
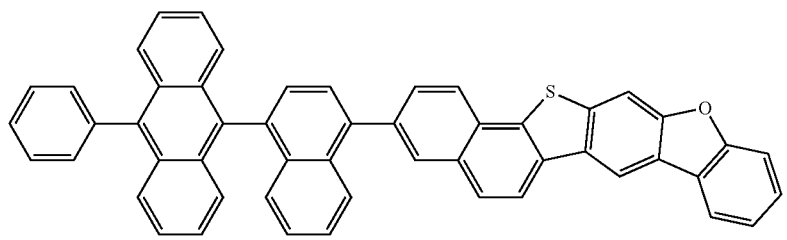
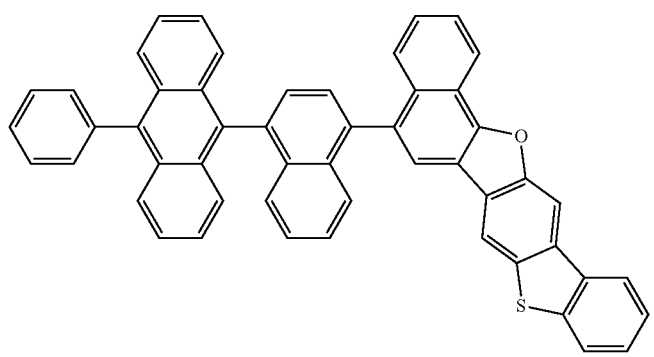
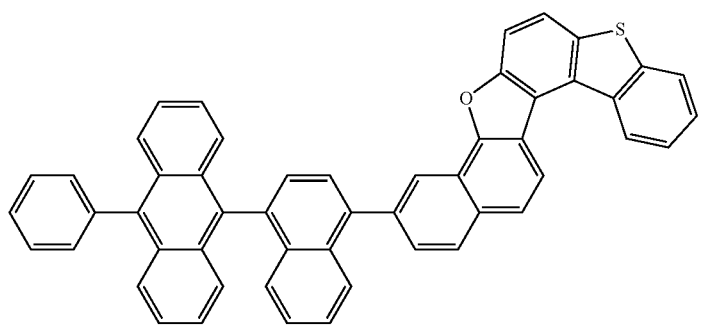
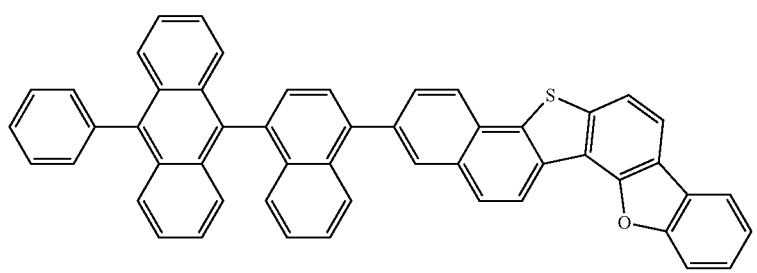

-continued
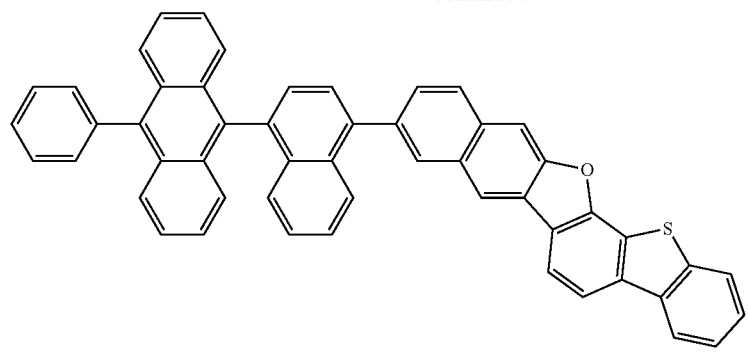
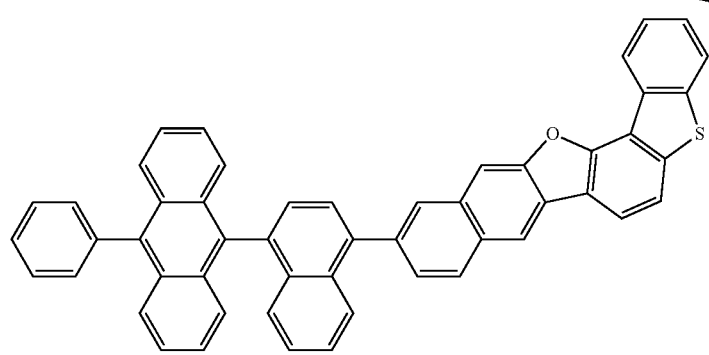
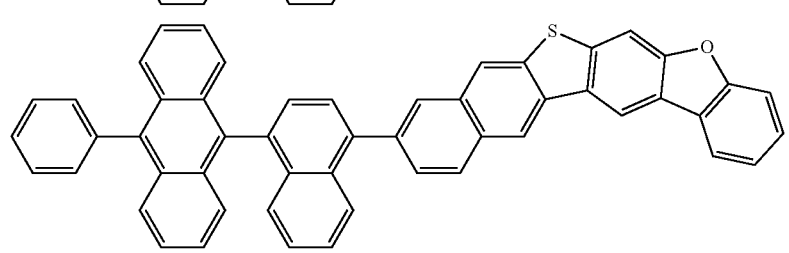
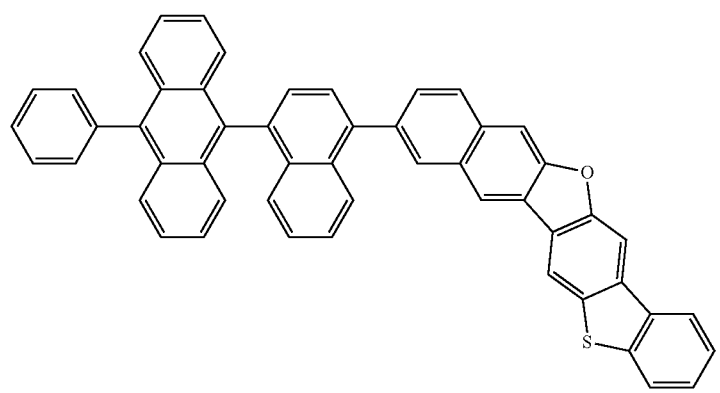
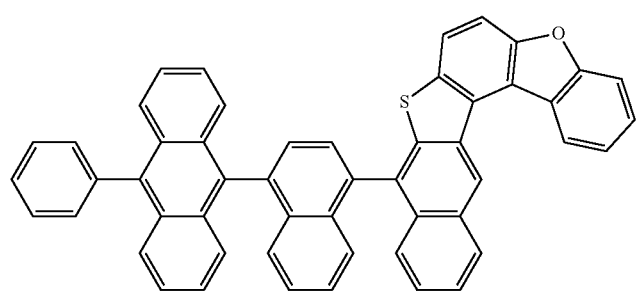

-continued
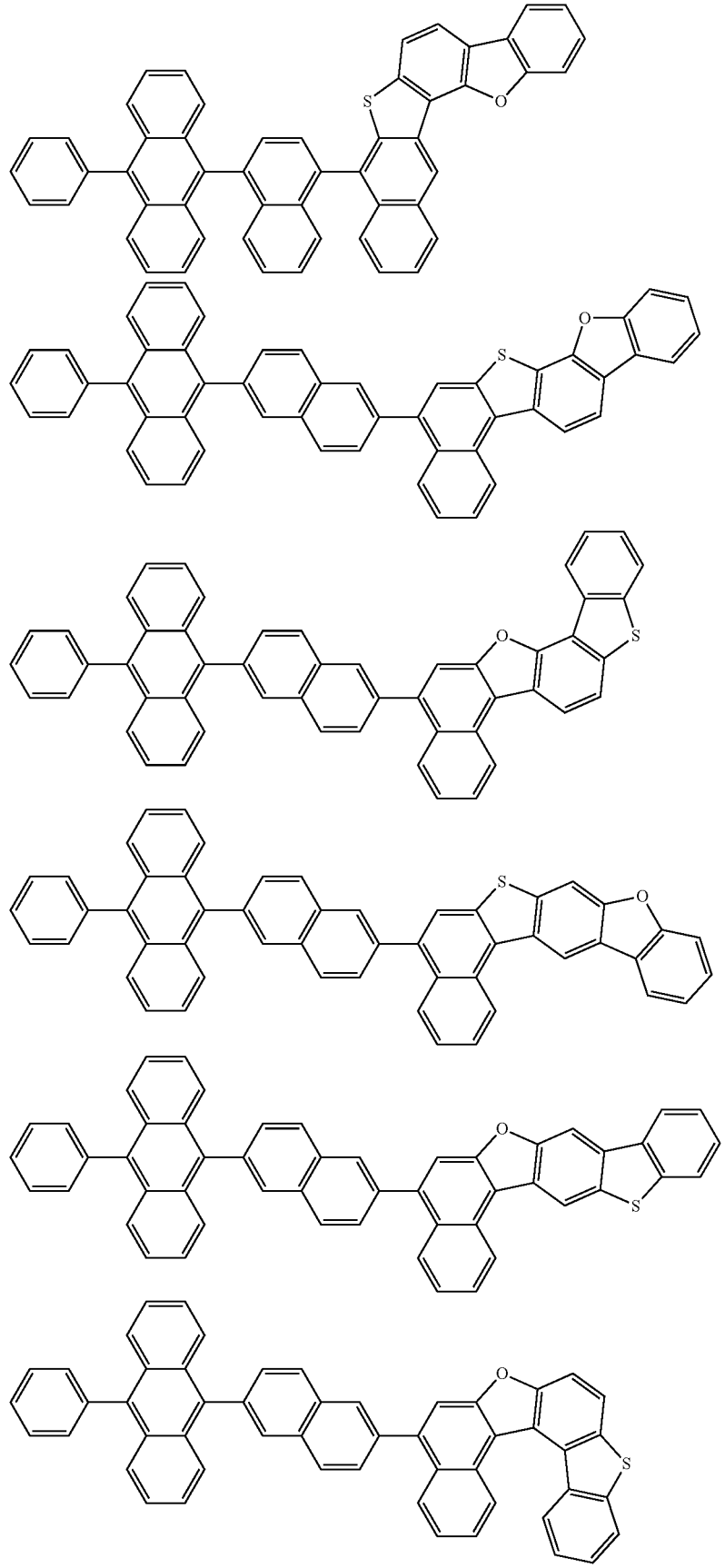

-continued
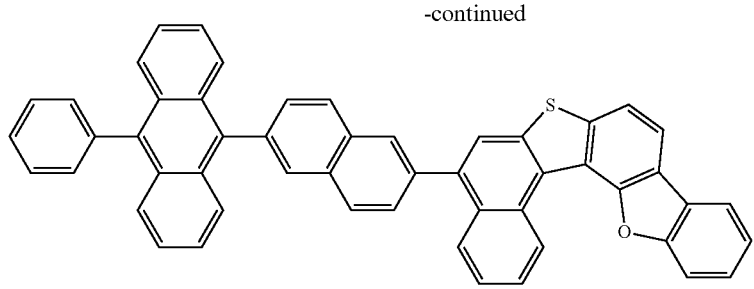
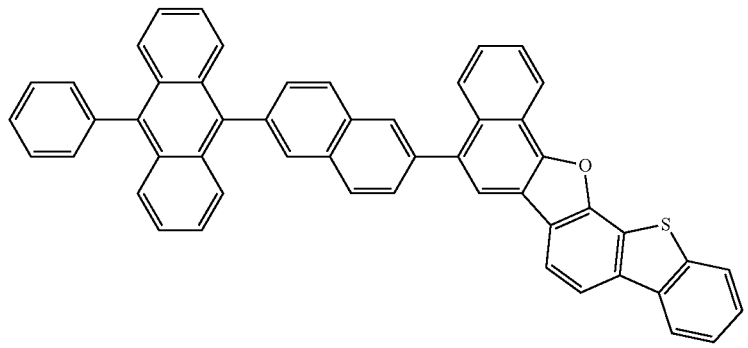
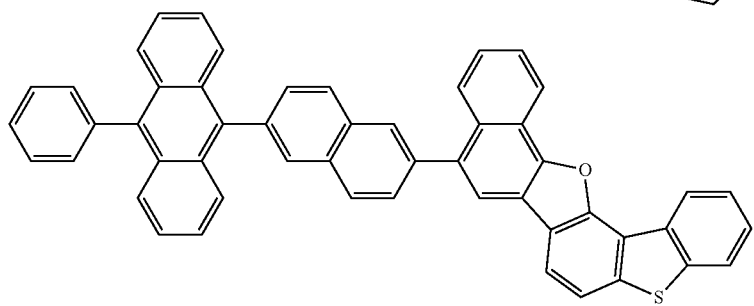
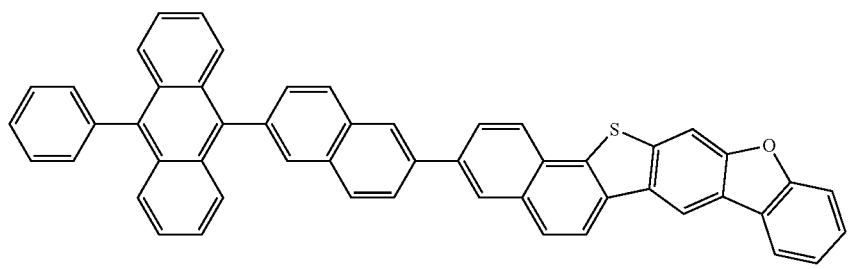
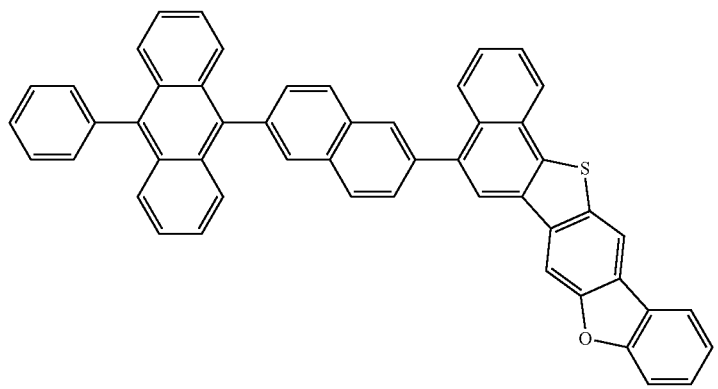

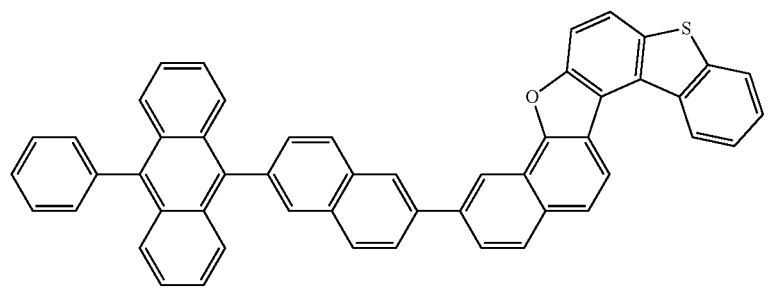
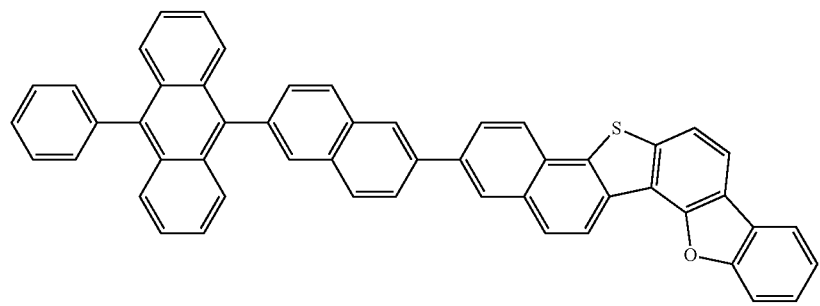
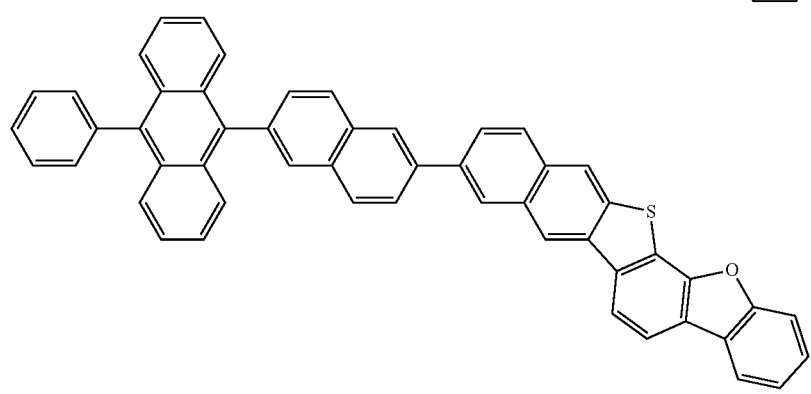
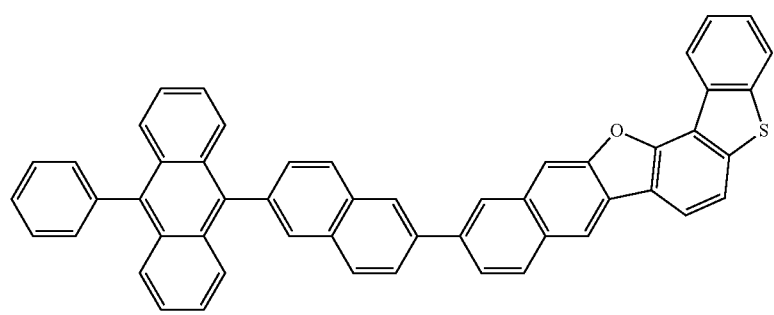
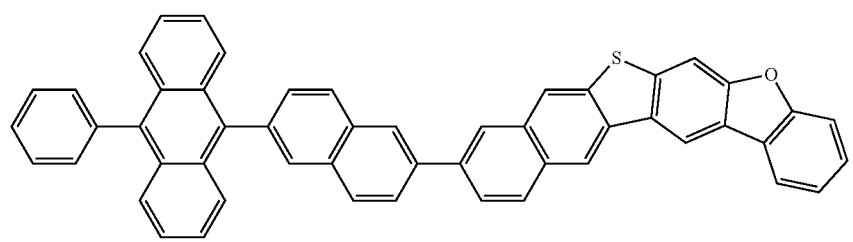

-continued
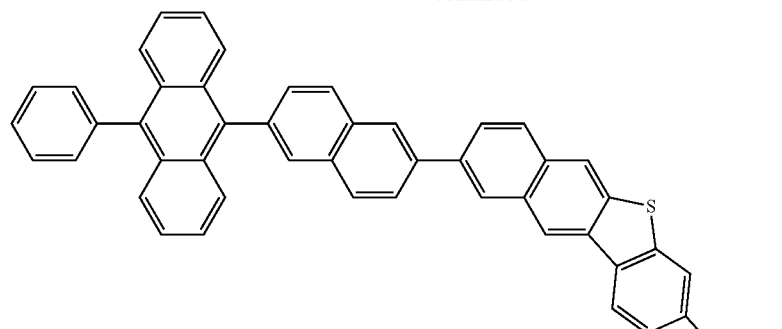
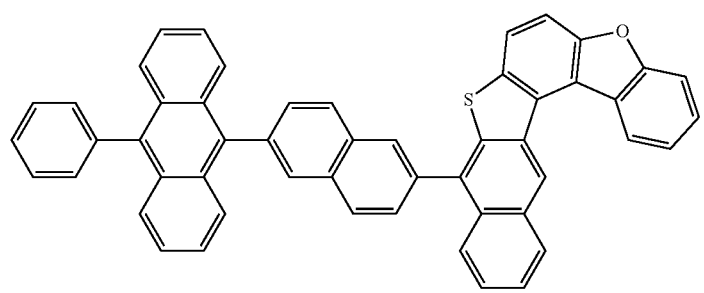
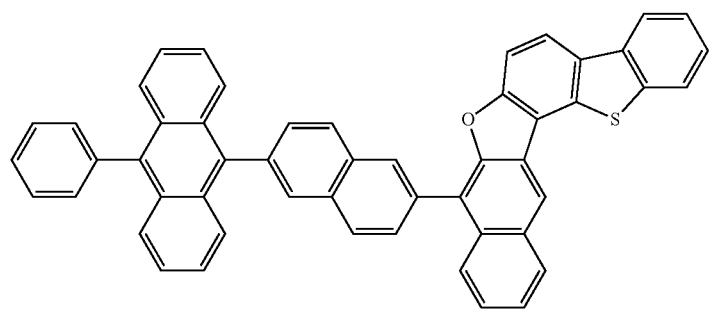
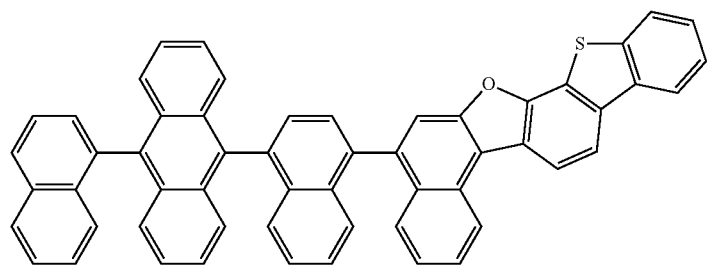
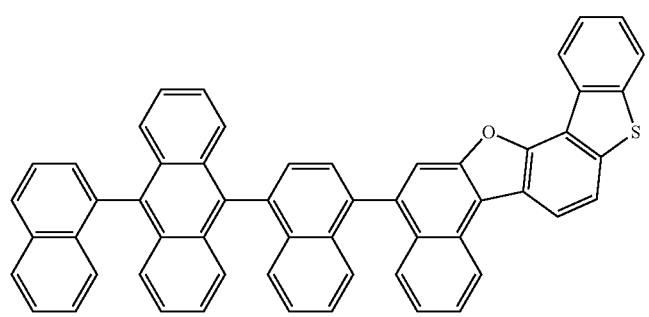

-continued
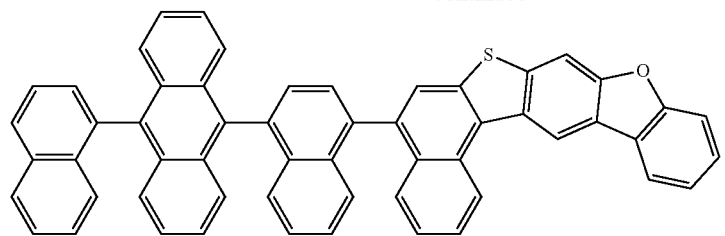
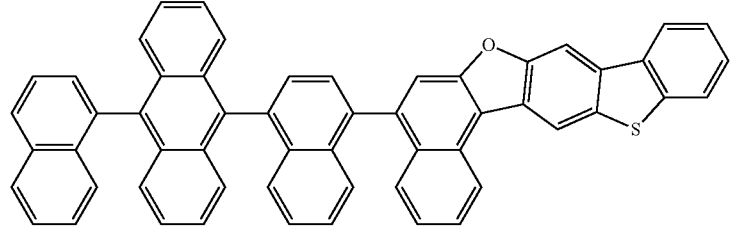
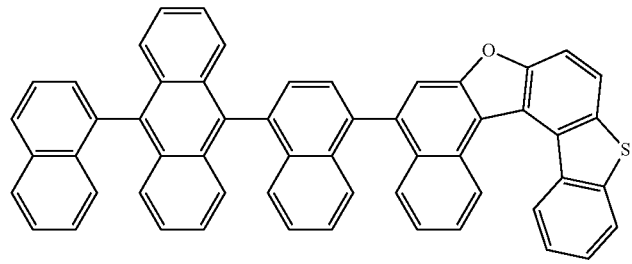
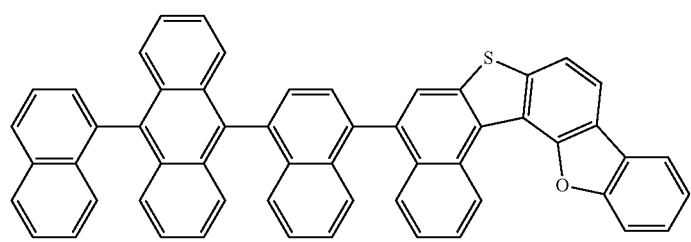
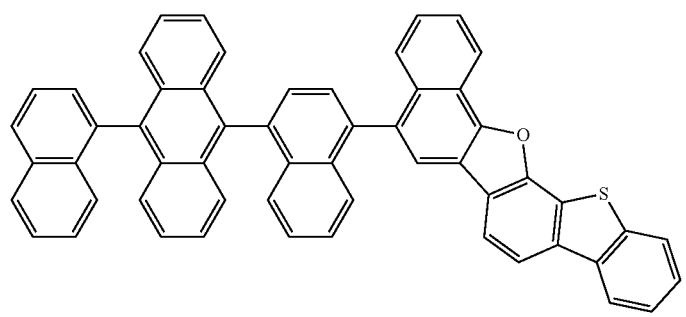
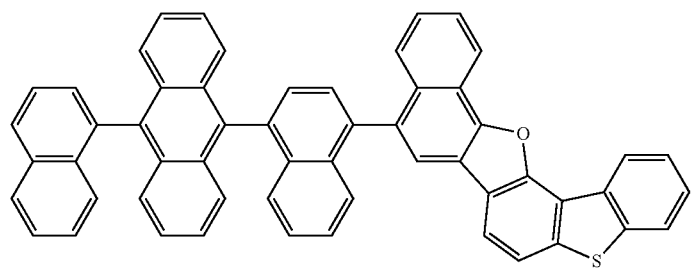

-continued
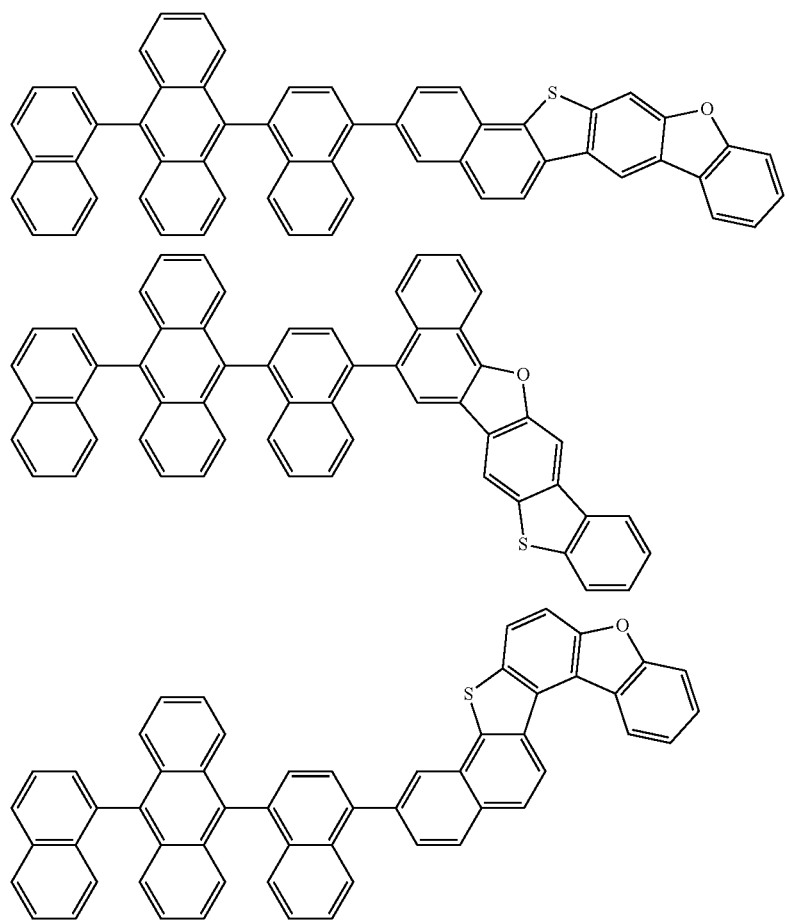
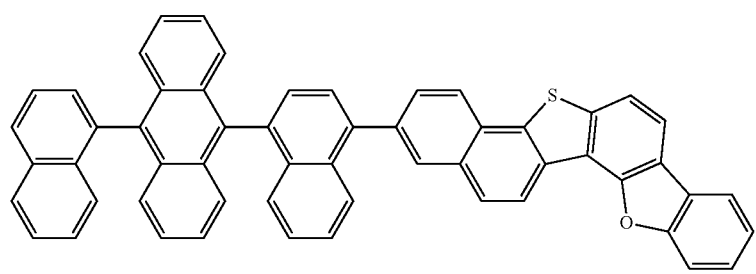
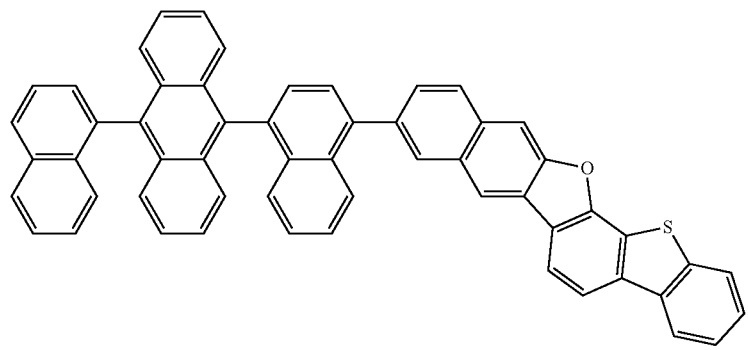

-continued
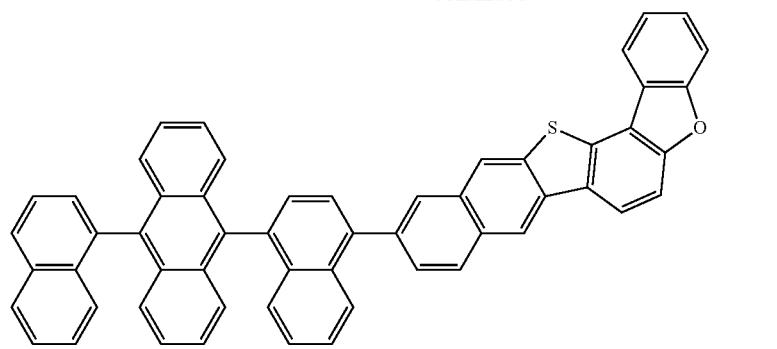
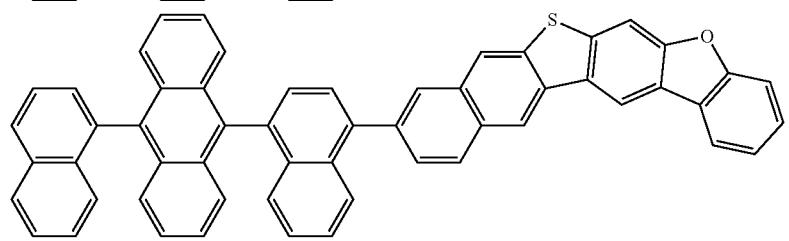
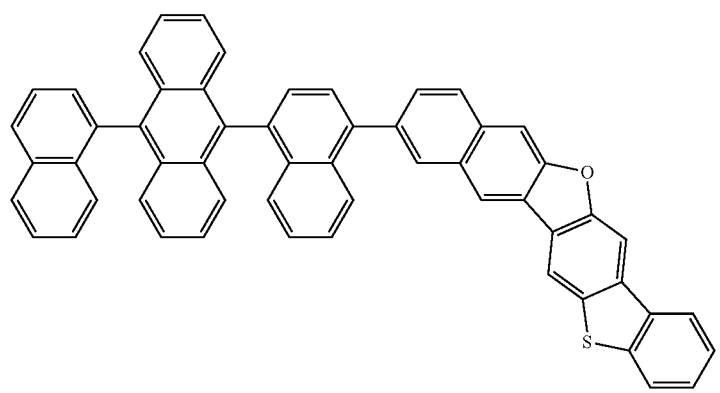
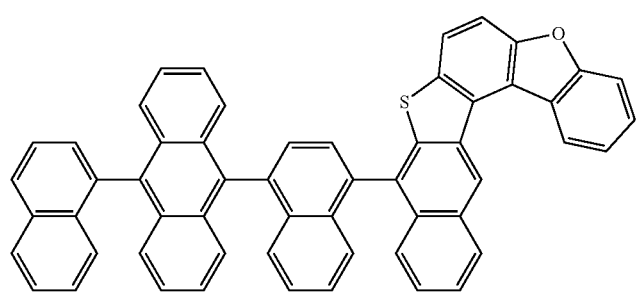
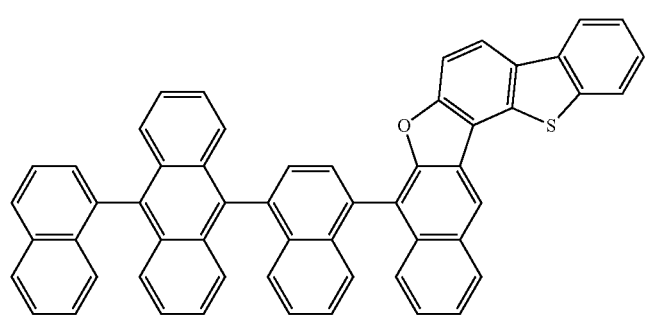

-continued
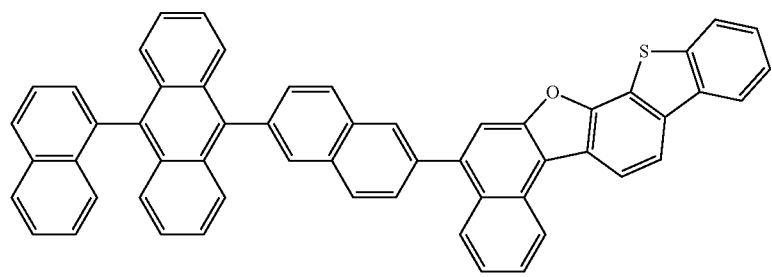
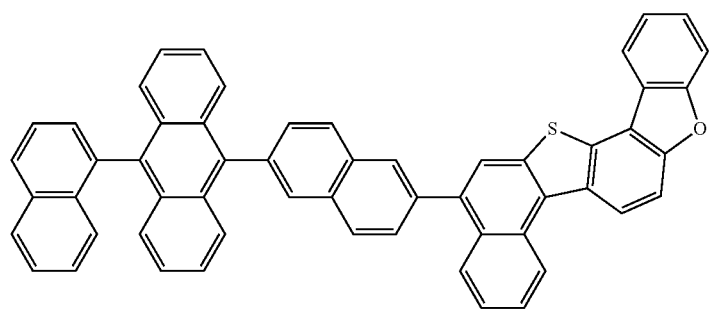
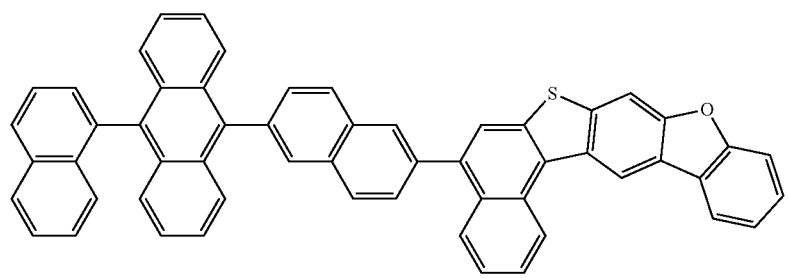
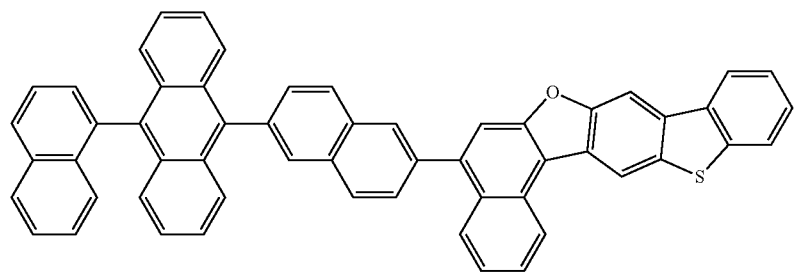
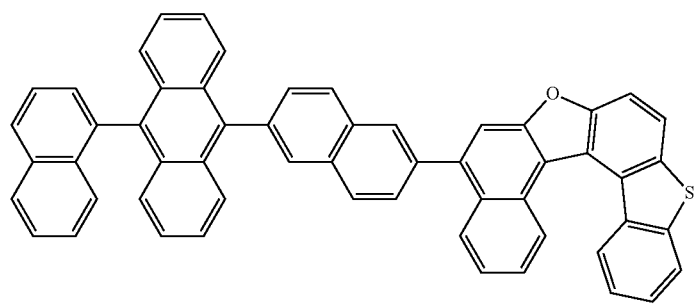
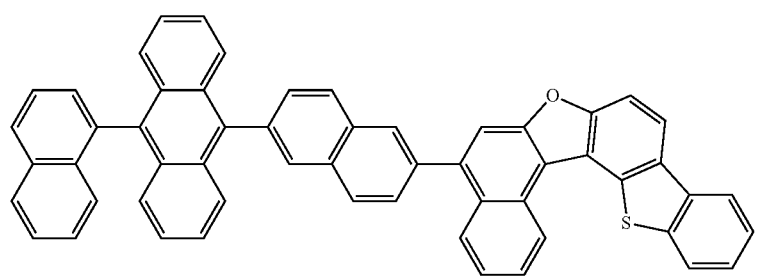

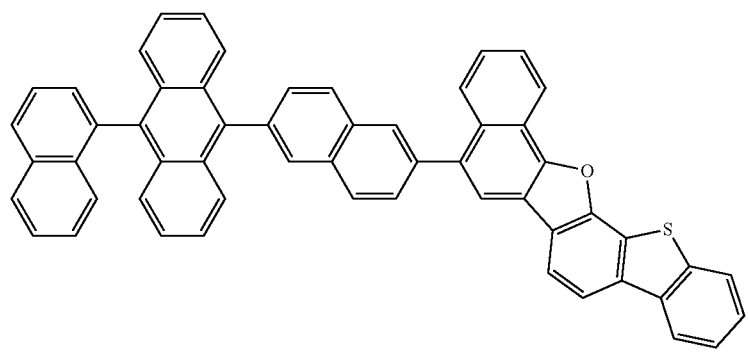
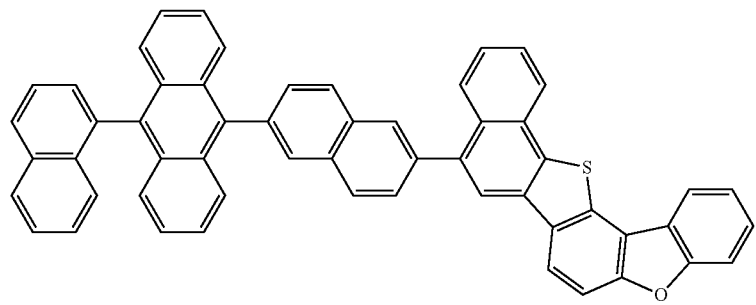
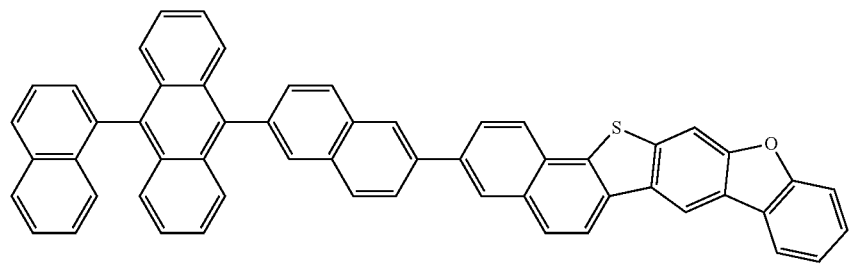
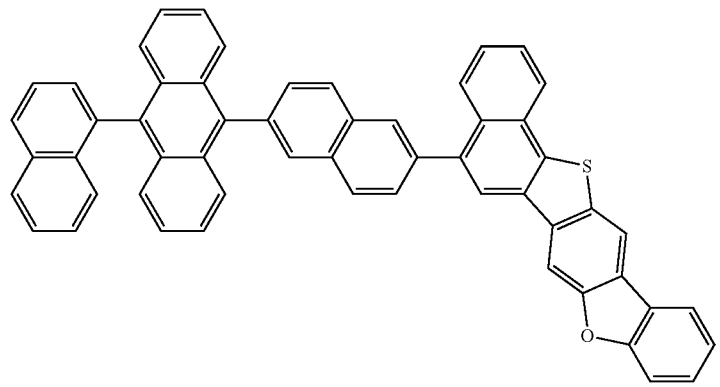
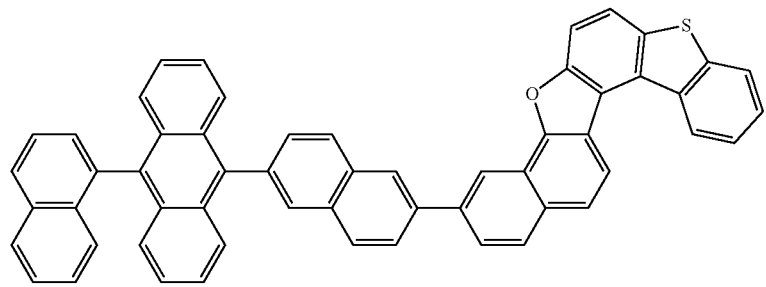

-continued
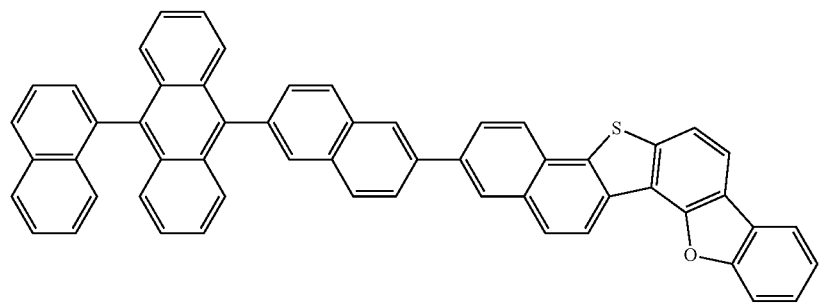
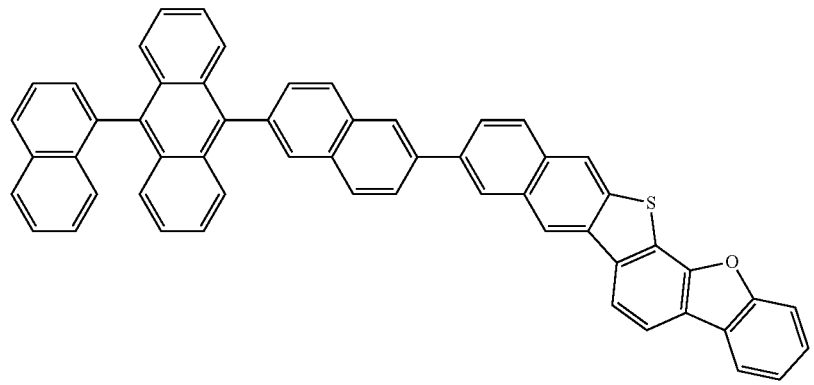
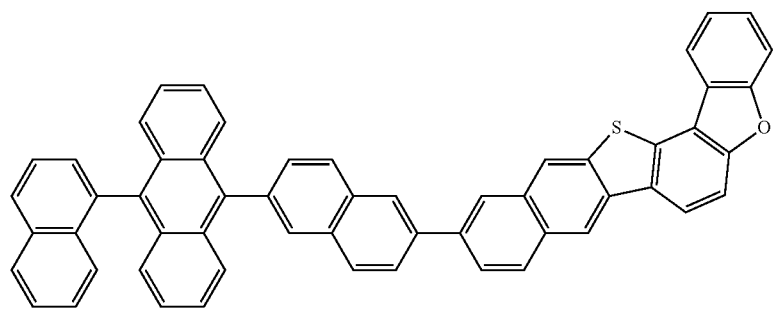
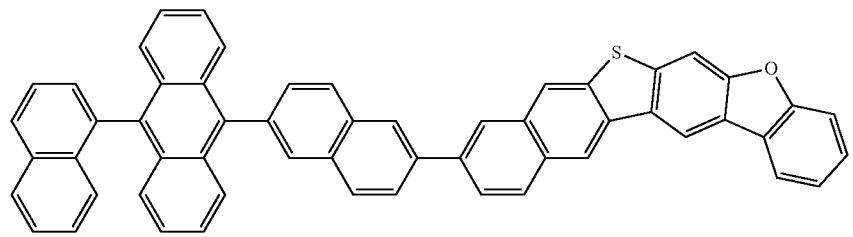
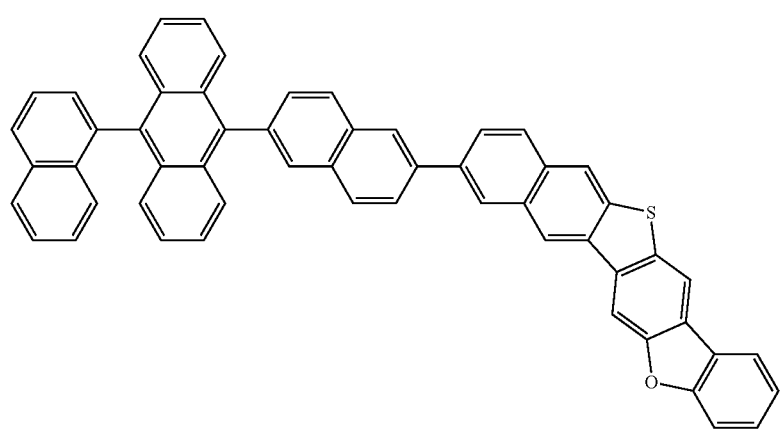

-continued
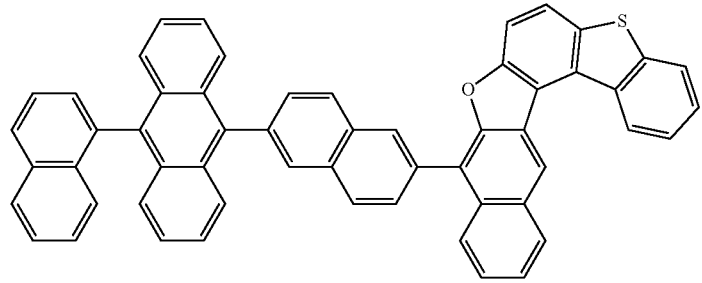

-continued
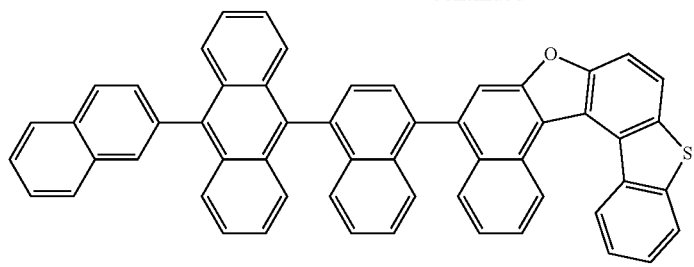
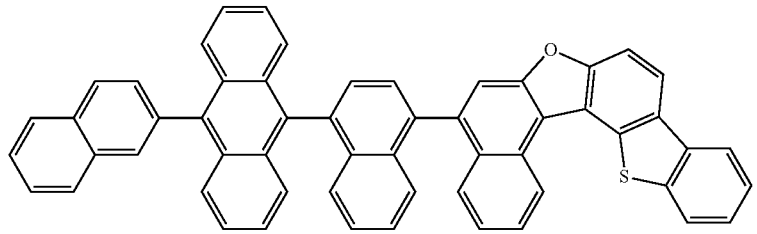
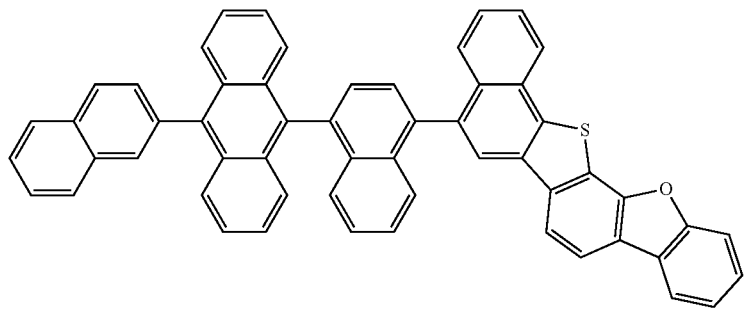
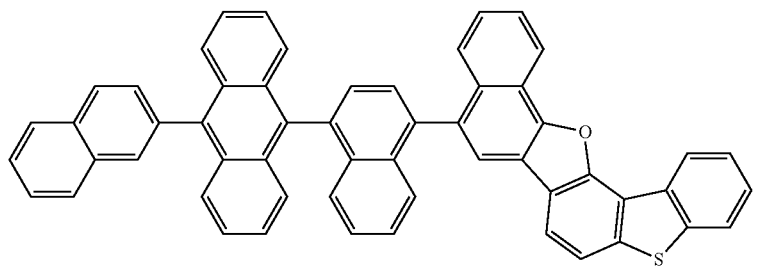
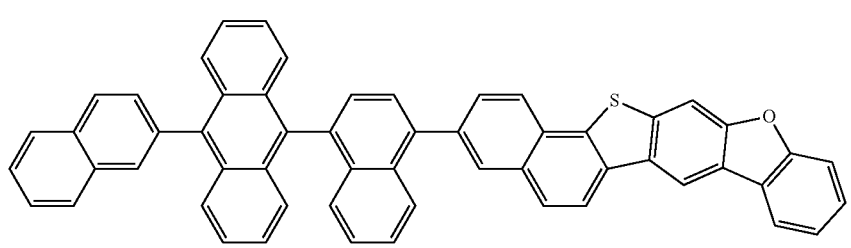
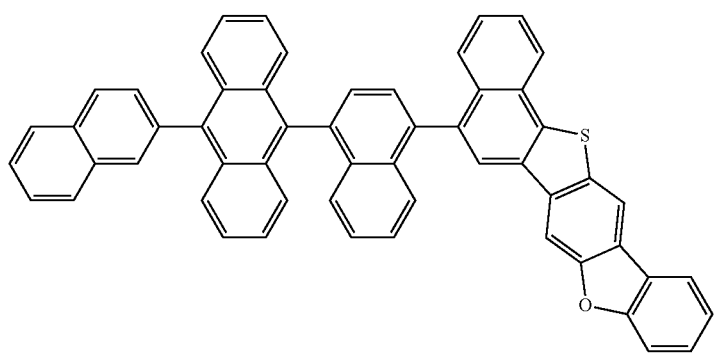

-continued
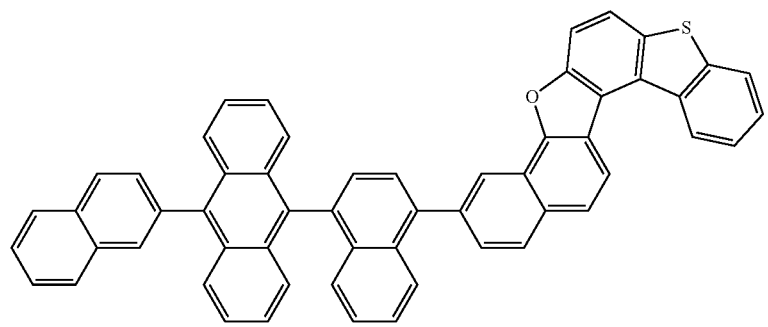
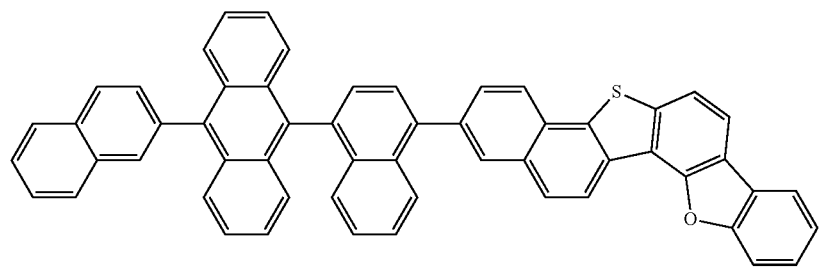
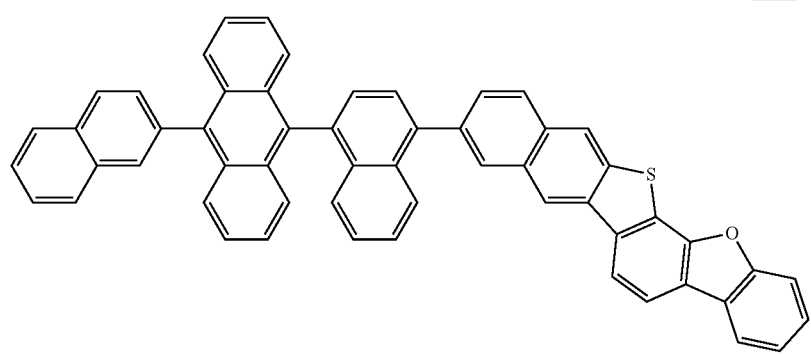
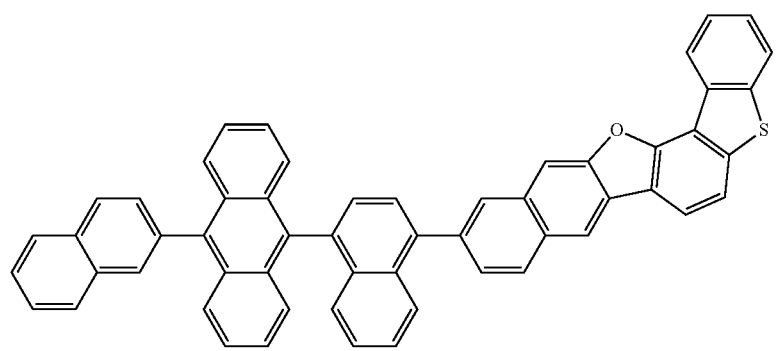
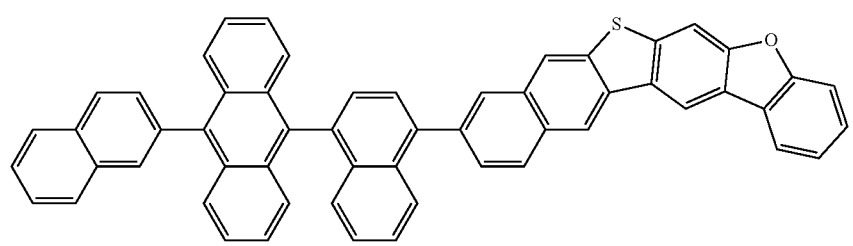

-continued
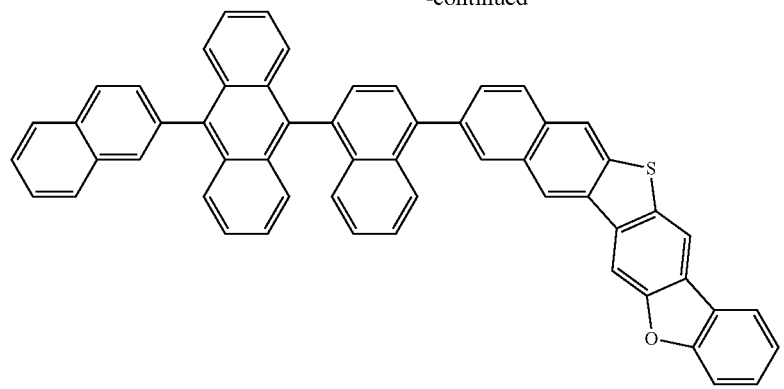
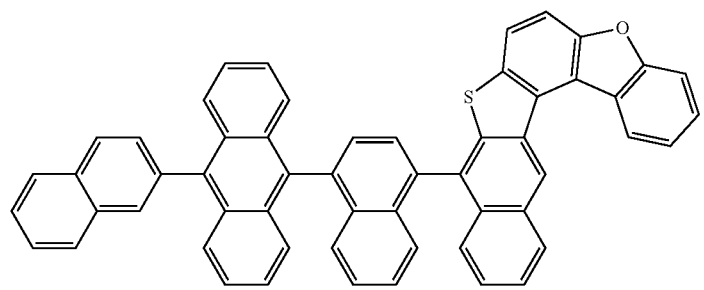
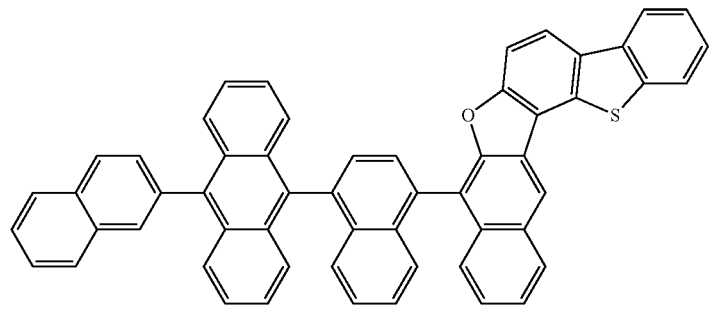
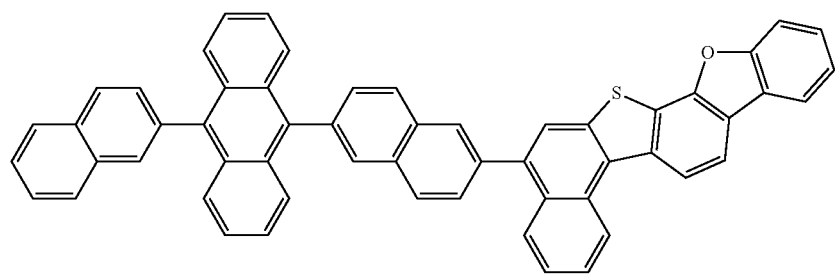
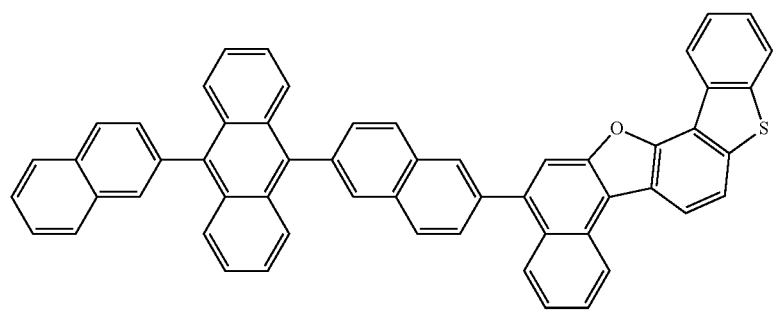

-continued
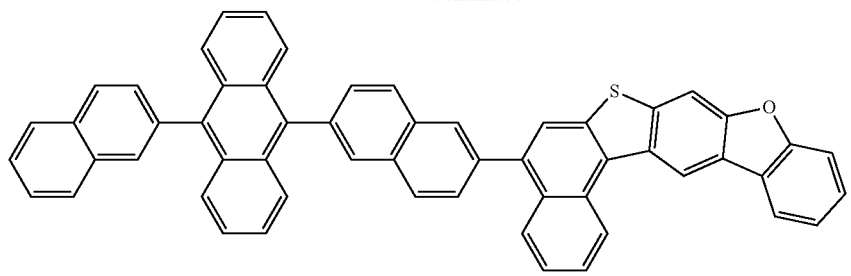
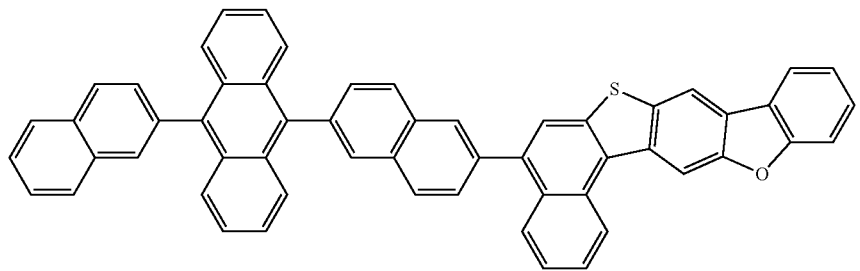
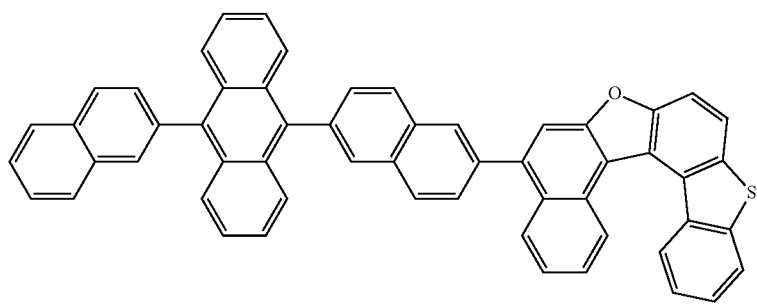
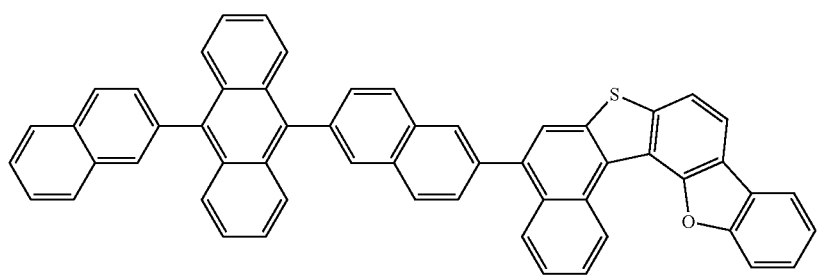
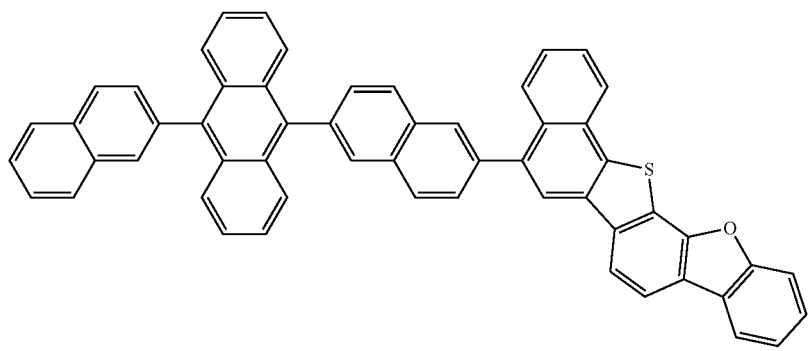

-continued
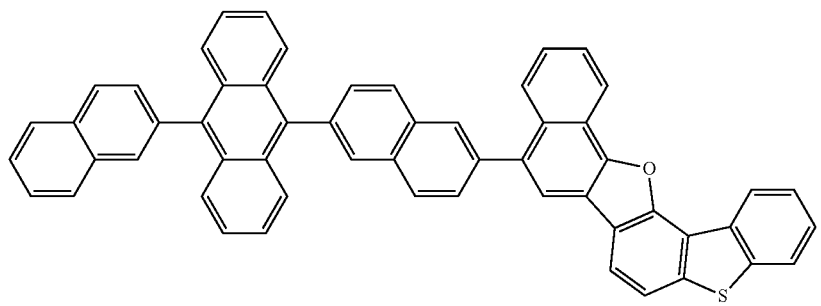
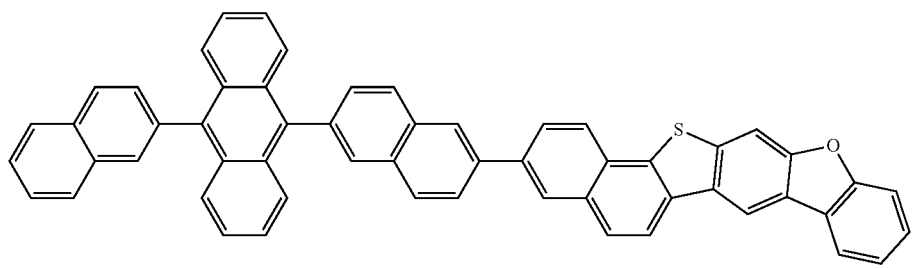
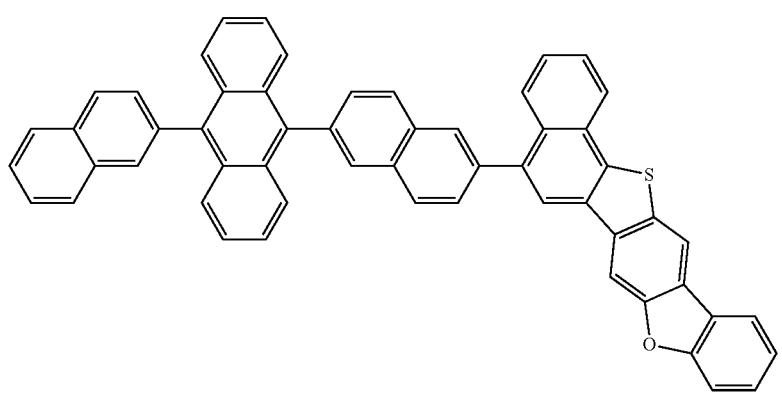
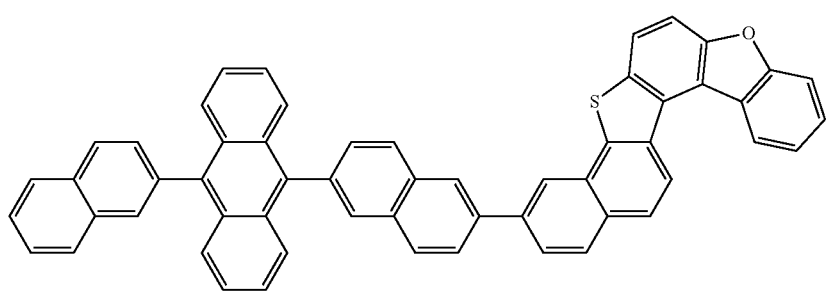
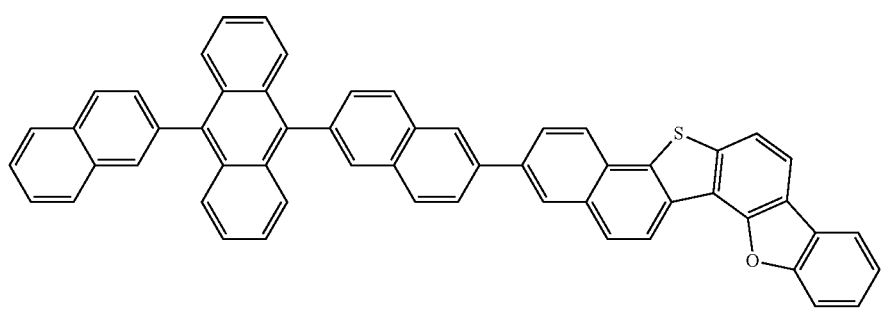

-continued
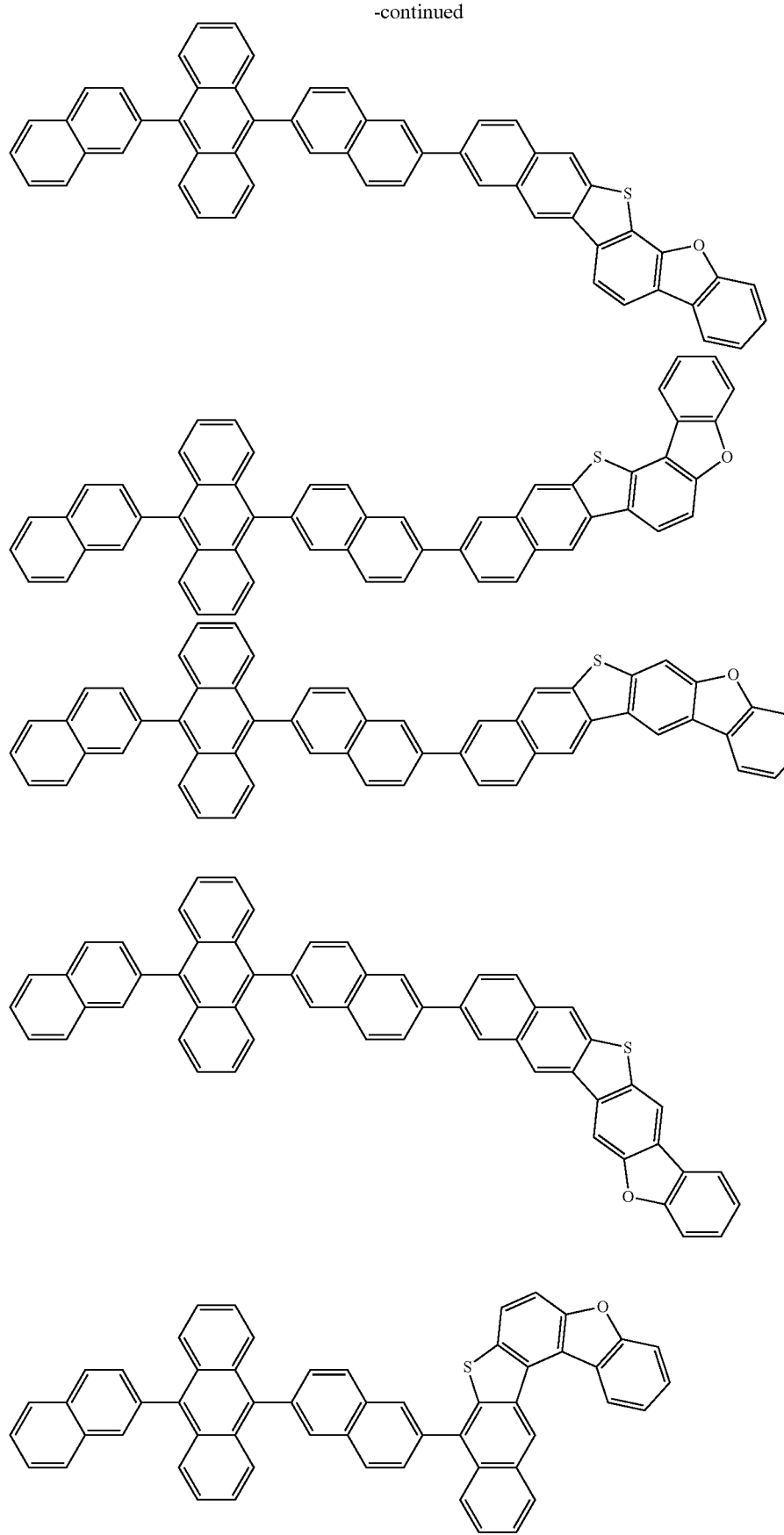

-continued
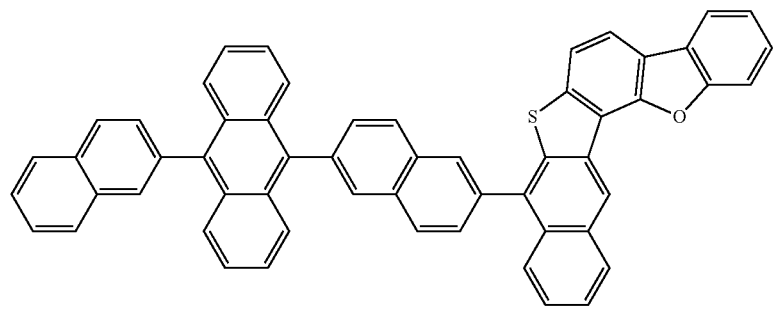
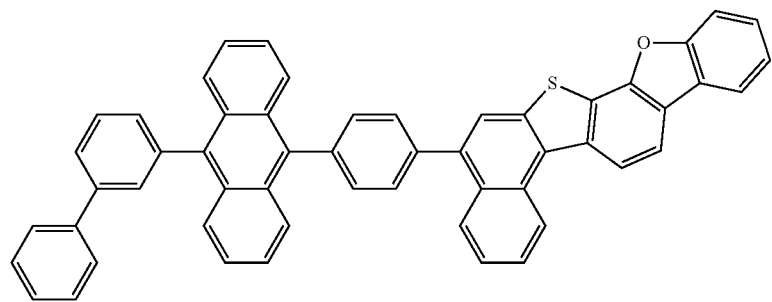
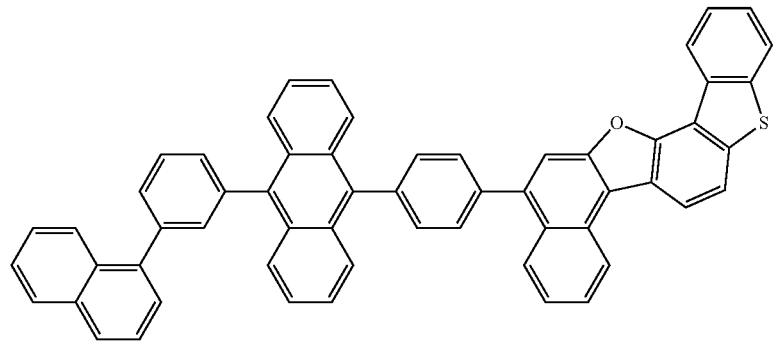
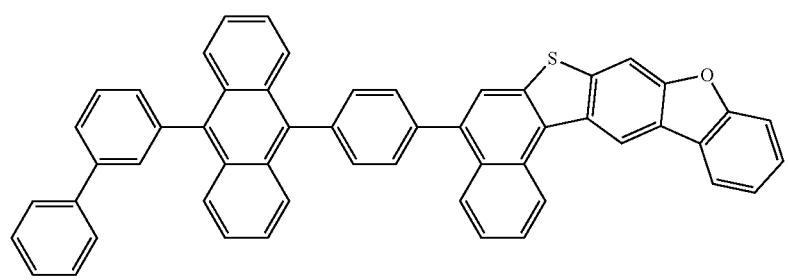
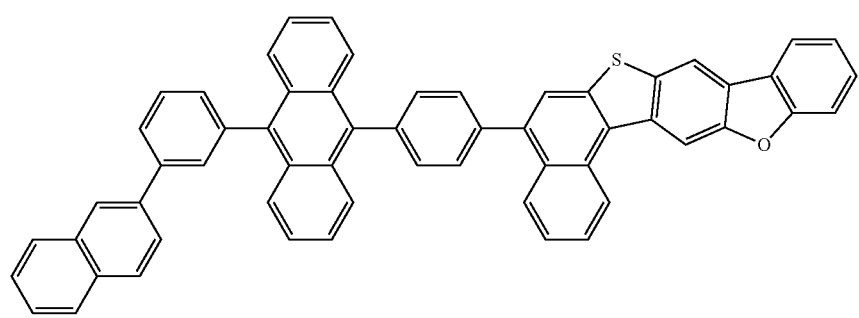

-continued
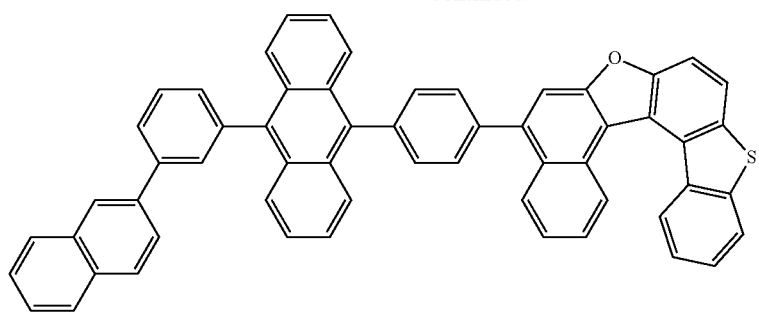
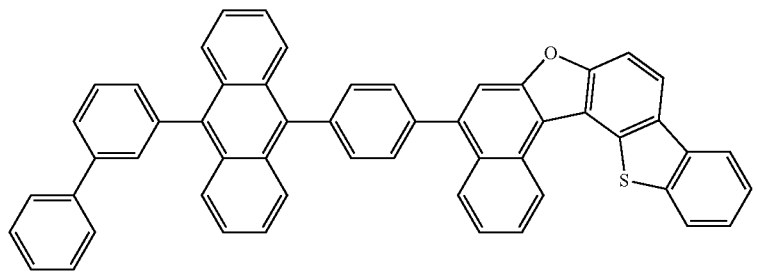
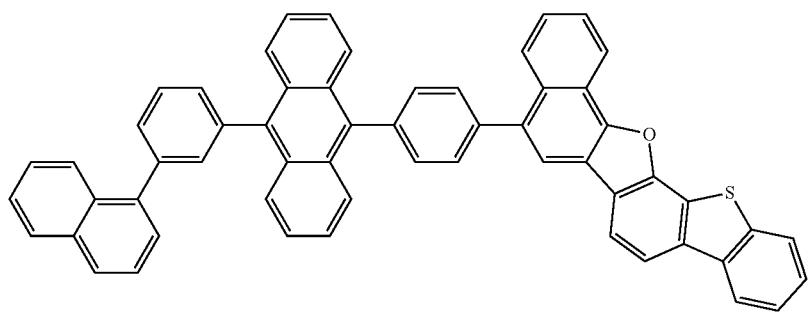
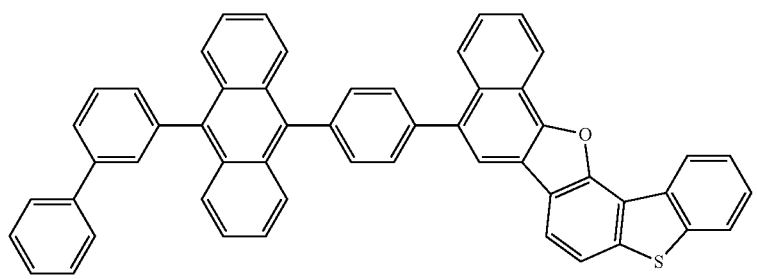
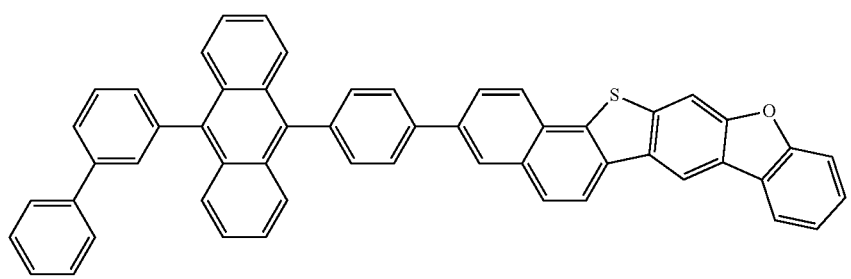

-continued
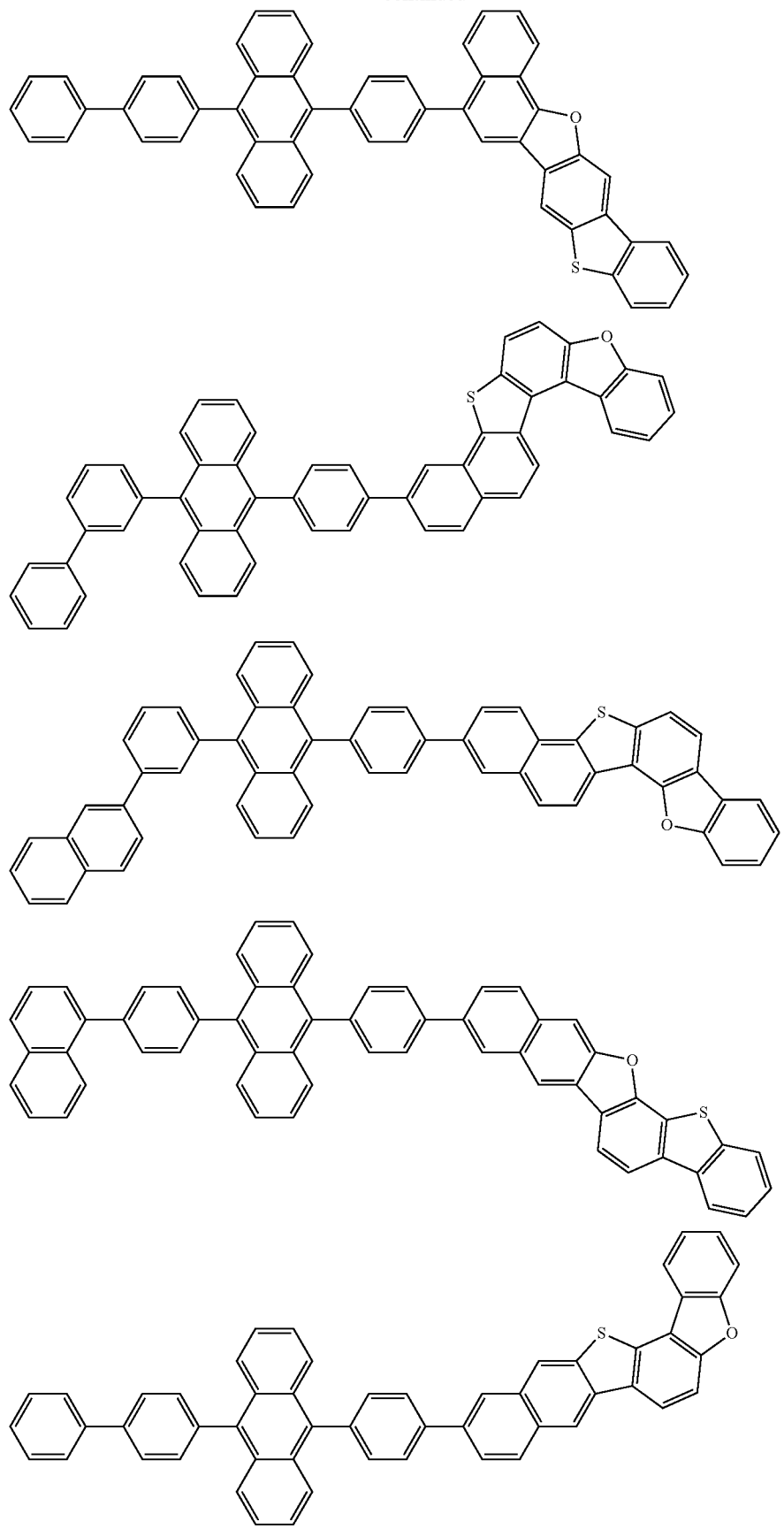

-continued
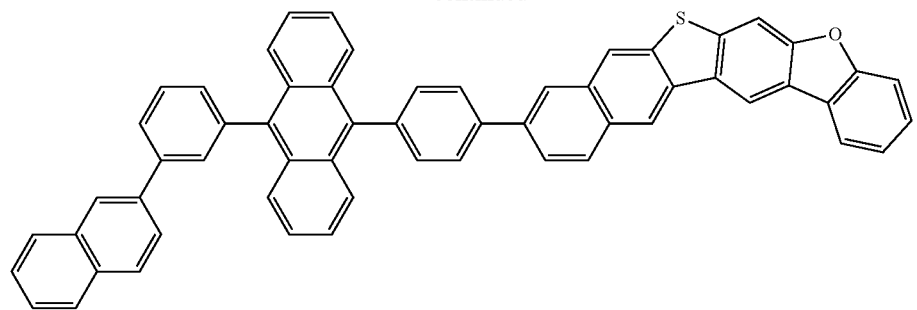
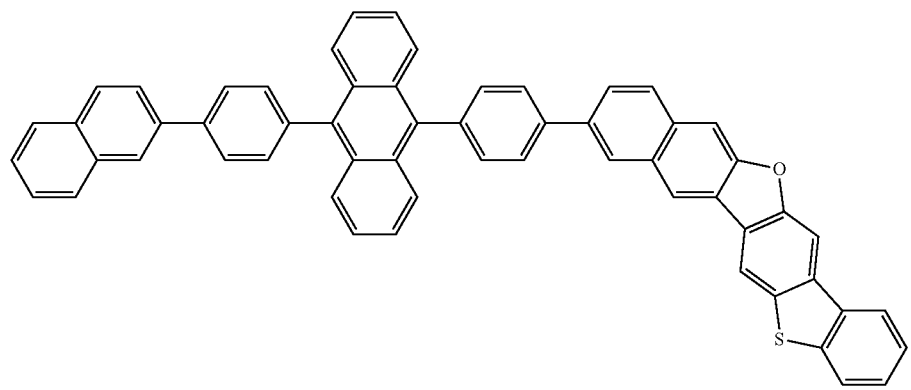
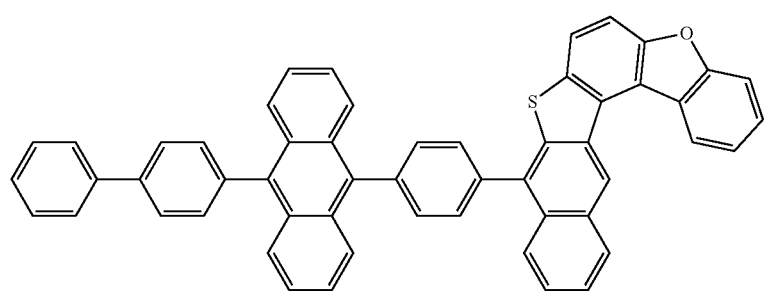
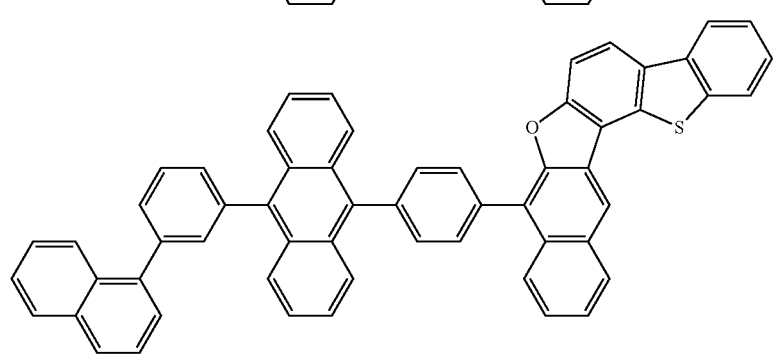
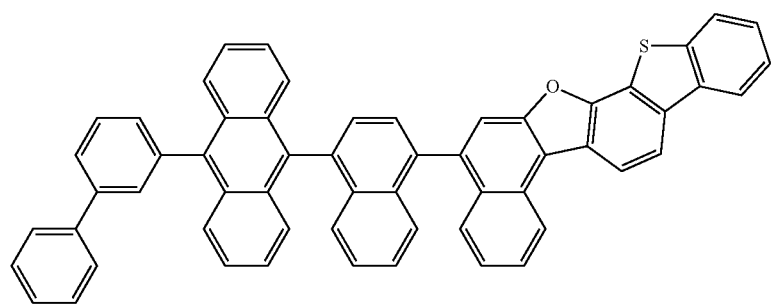

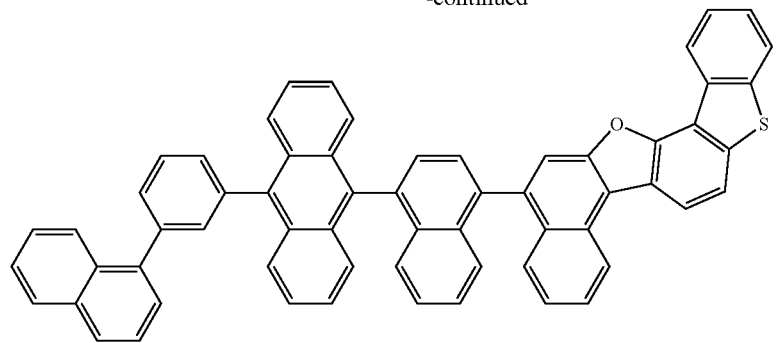
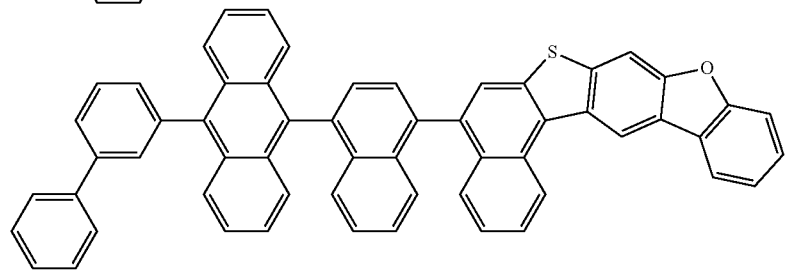
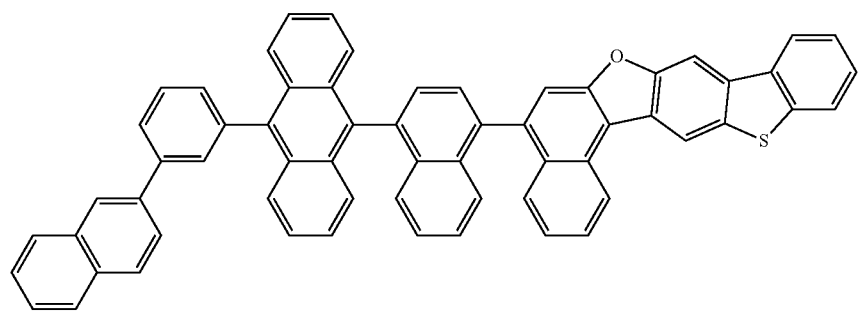
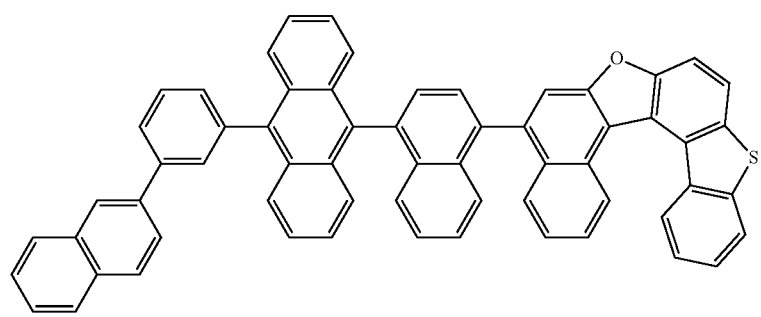
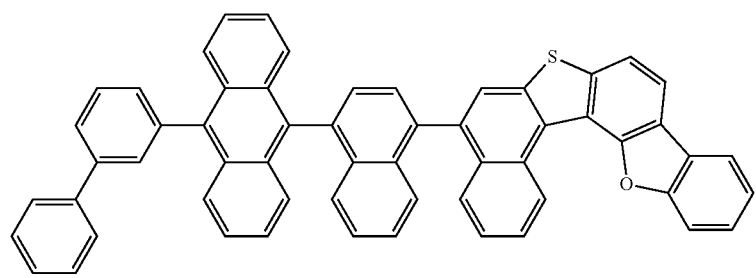

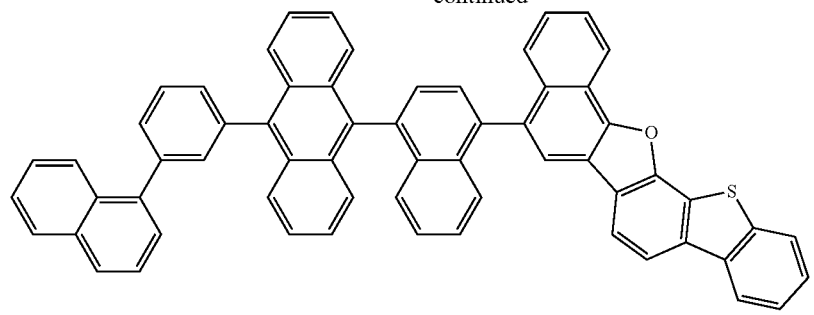
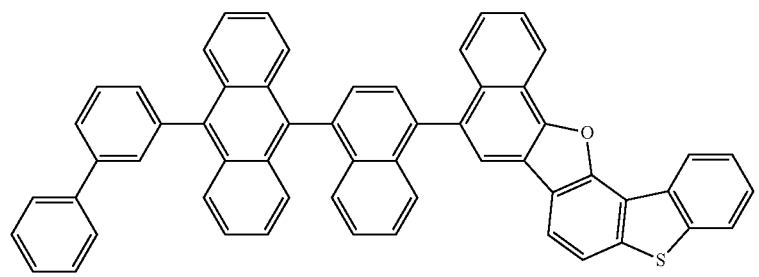
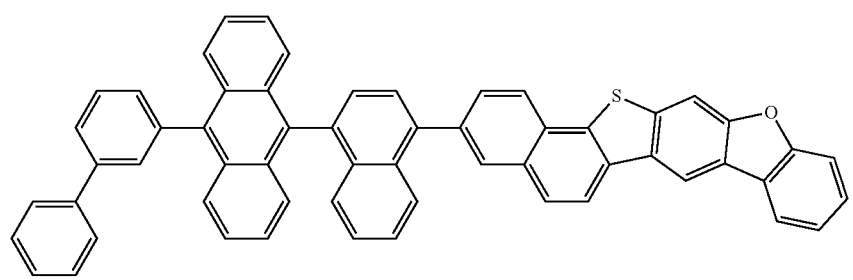
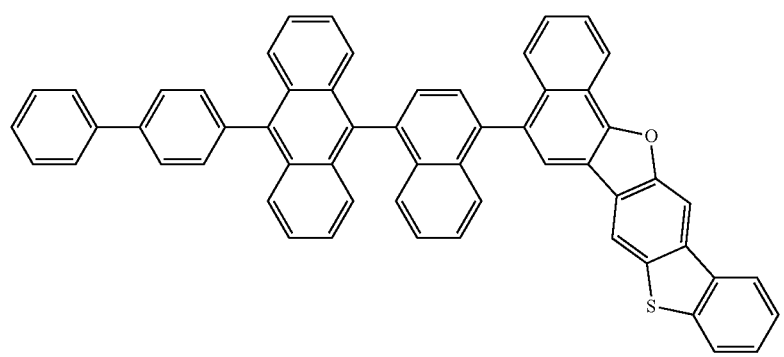
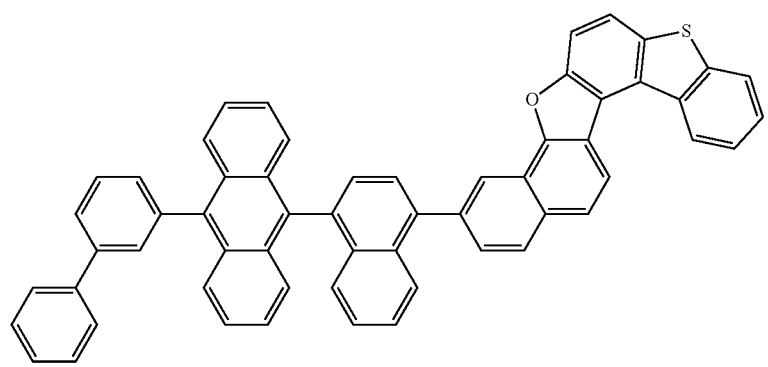

-continued
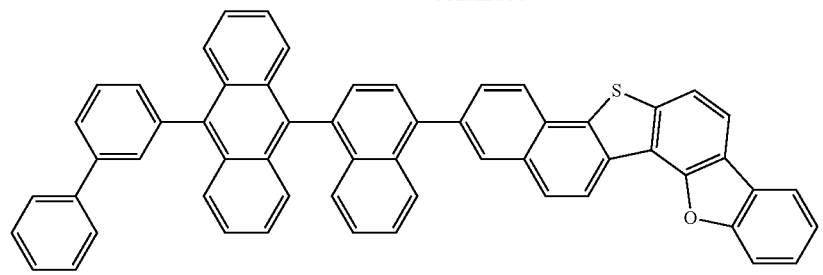
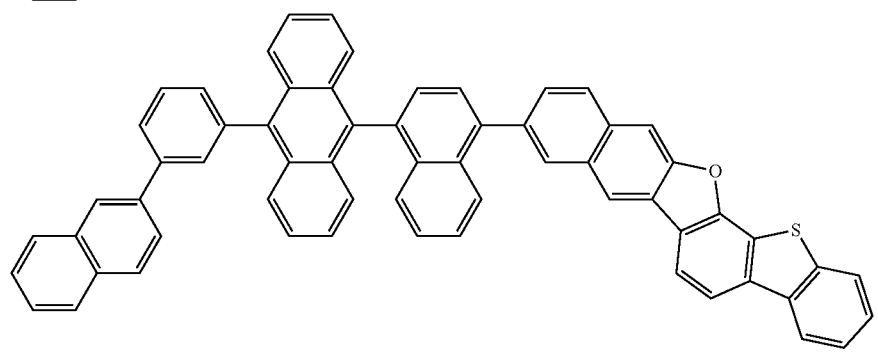
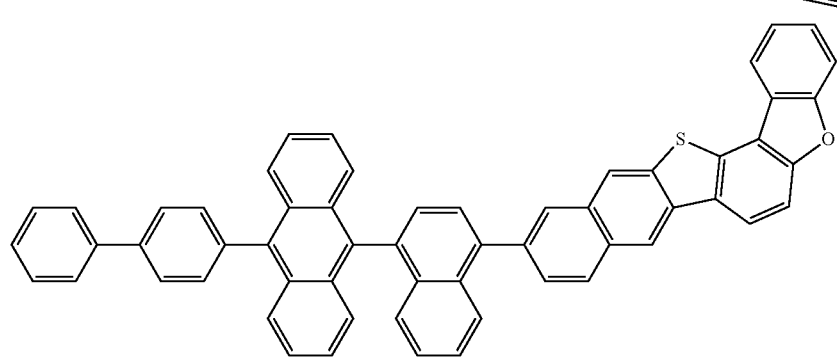
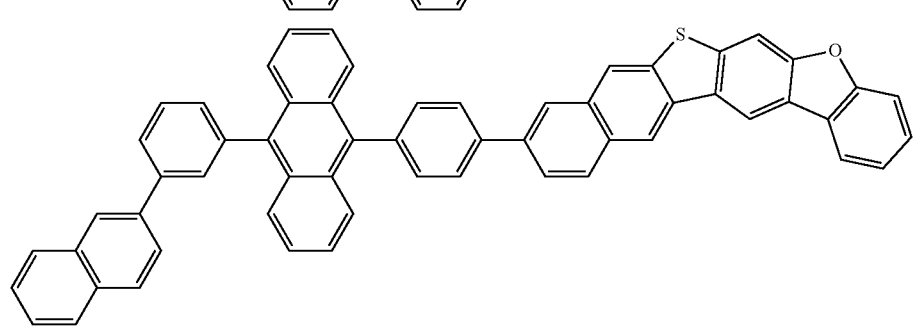
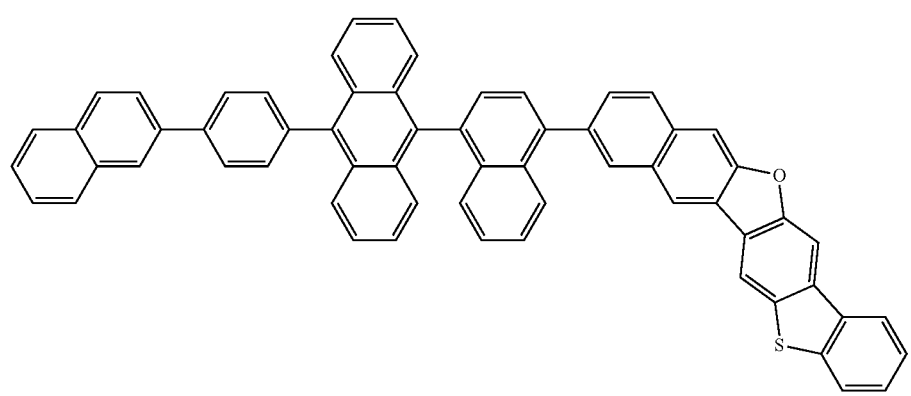

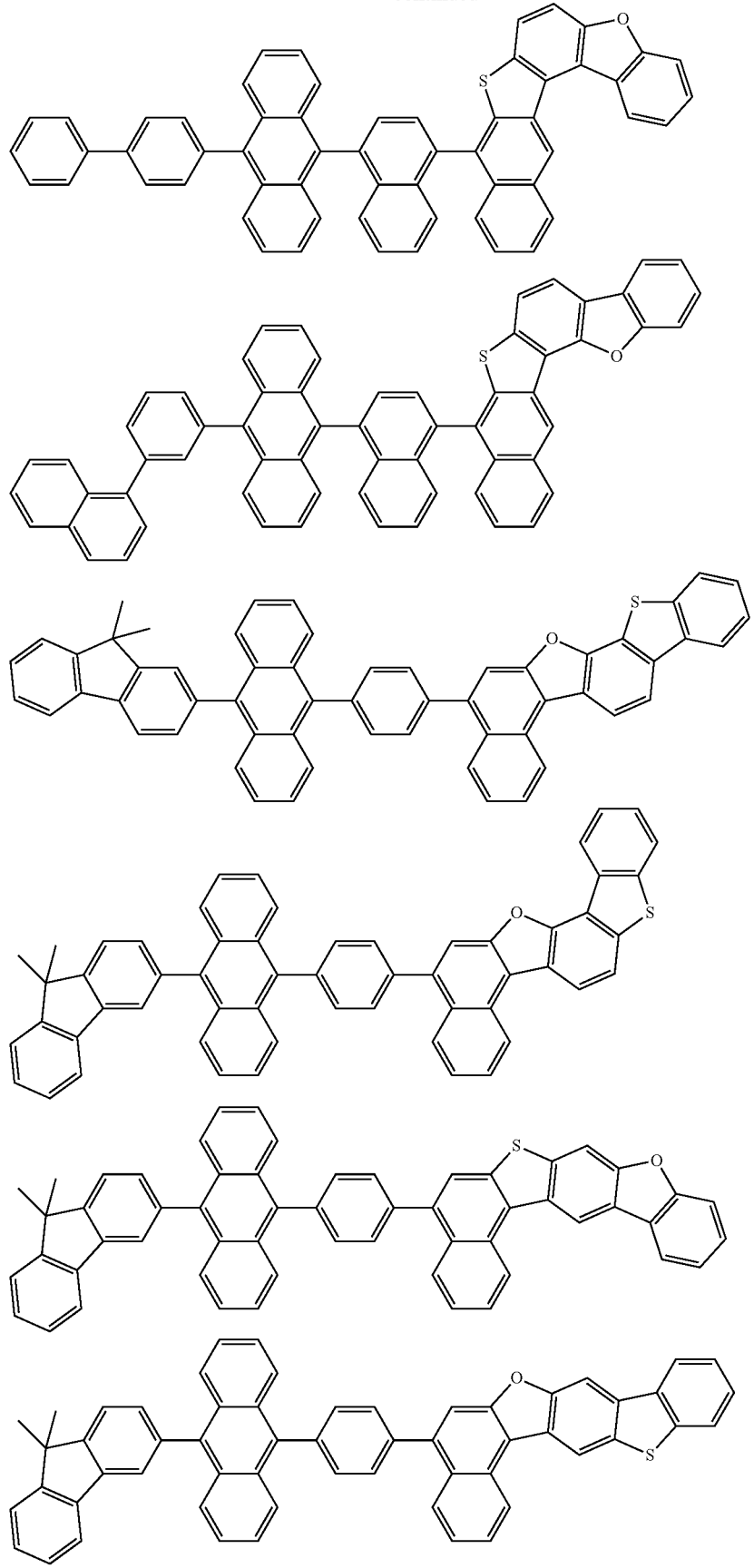

-continued
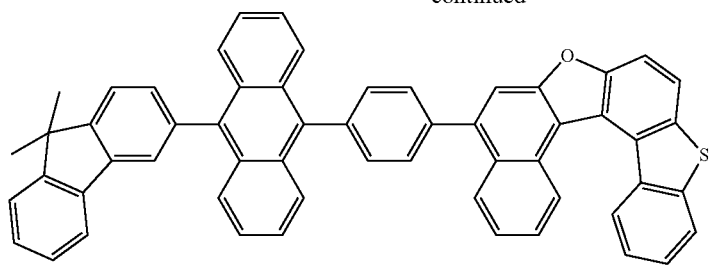
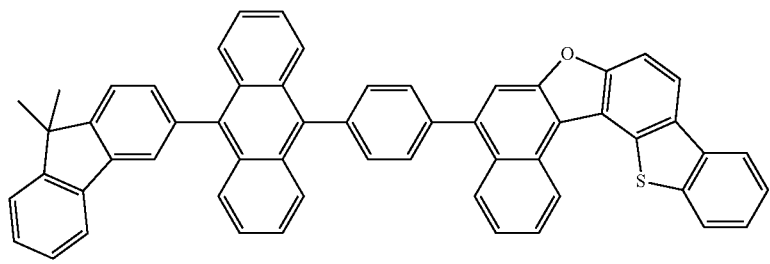
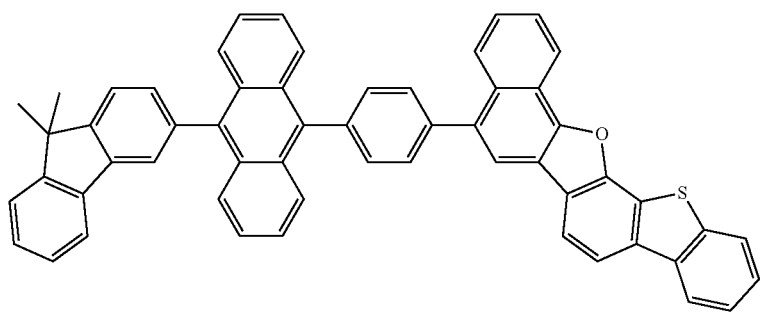
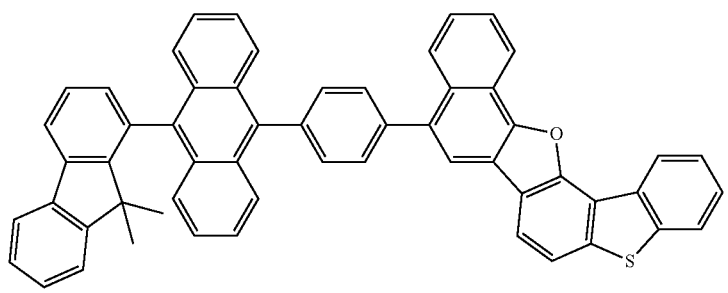
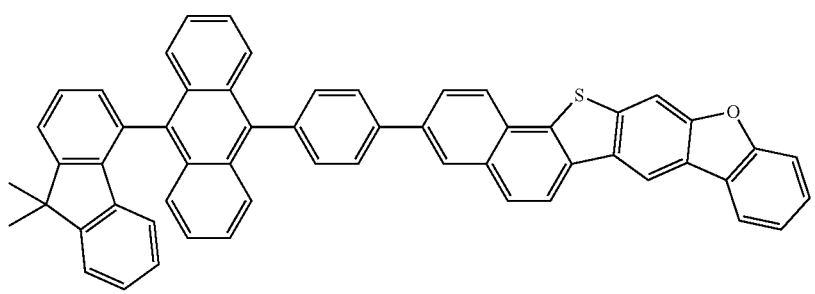

-continued
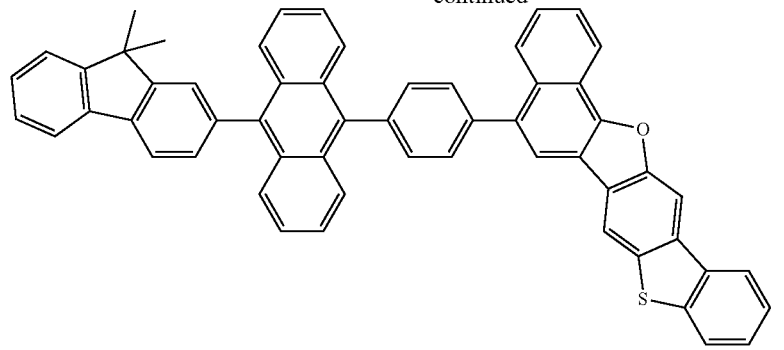
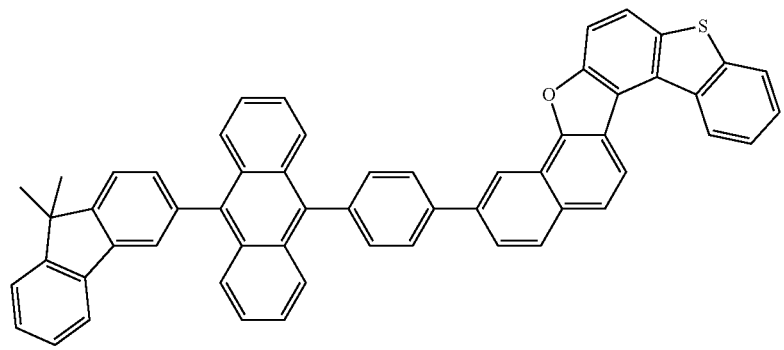
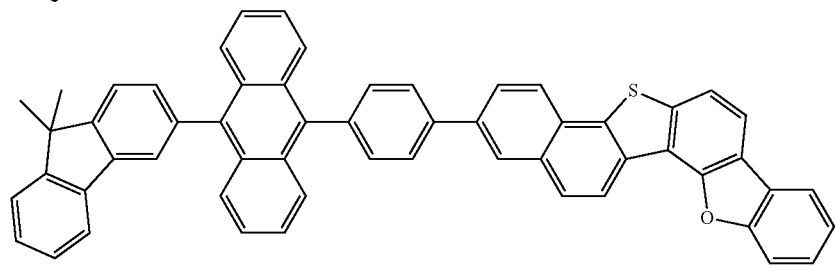
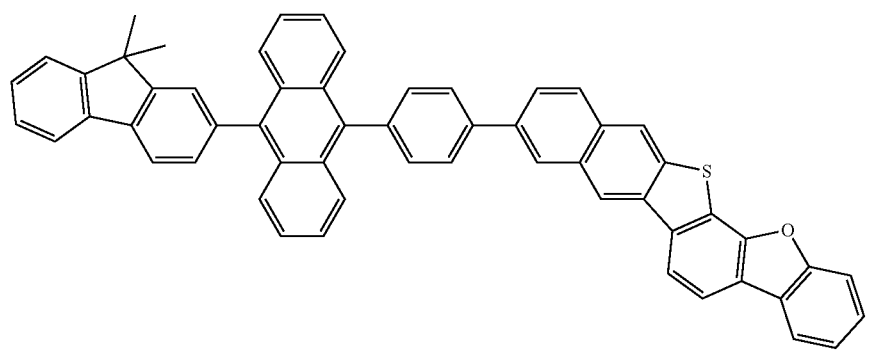
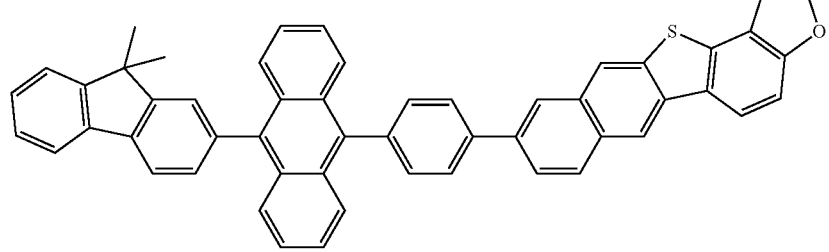

-continued
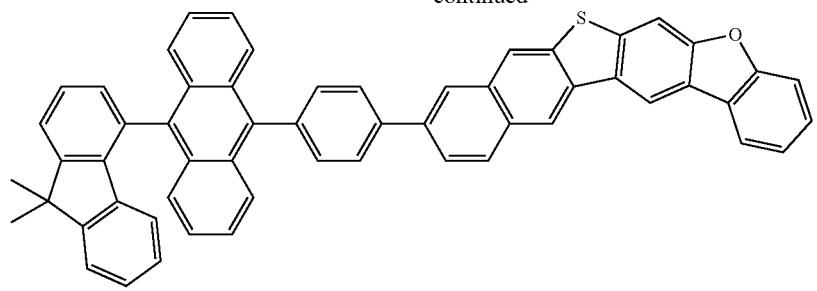
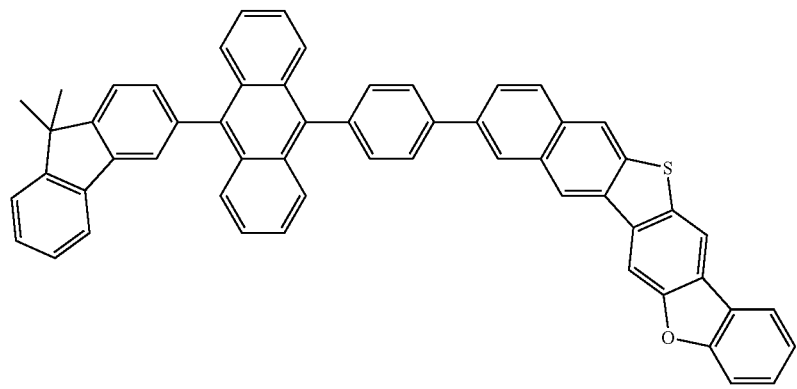
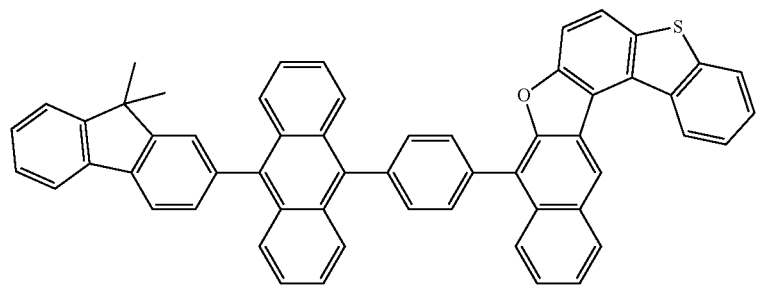
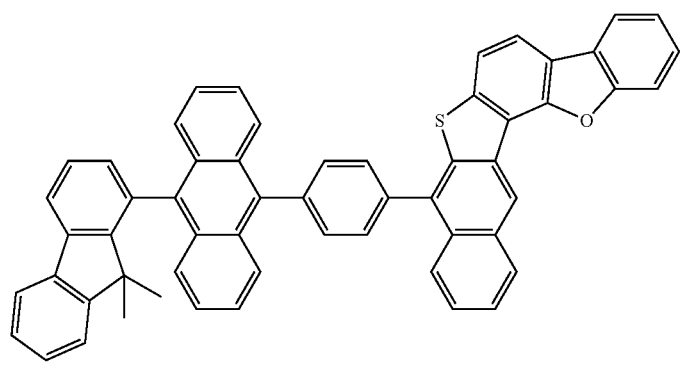
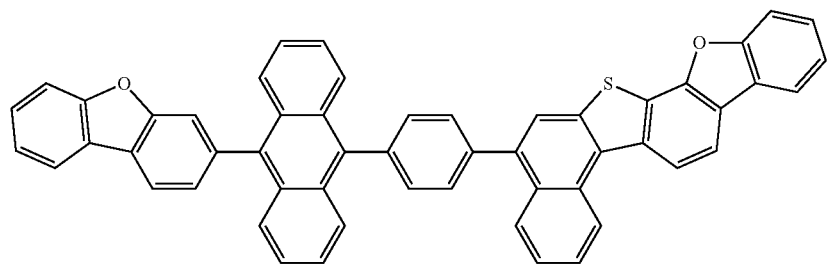

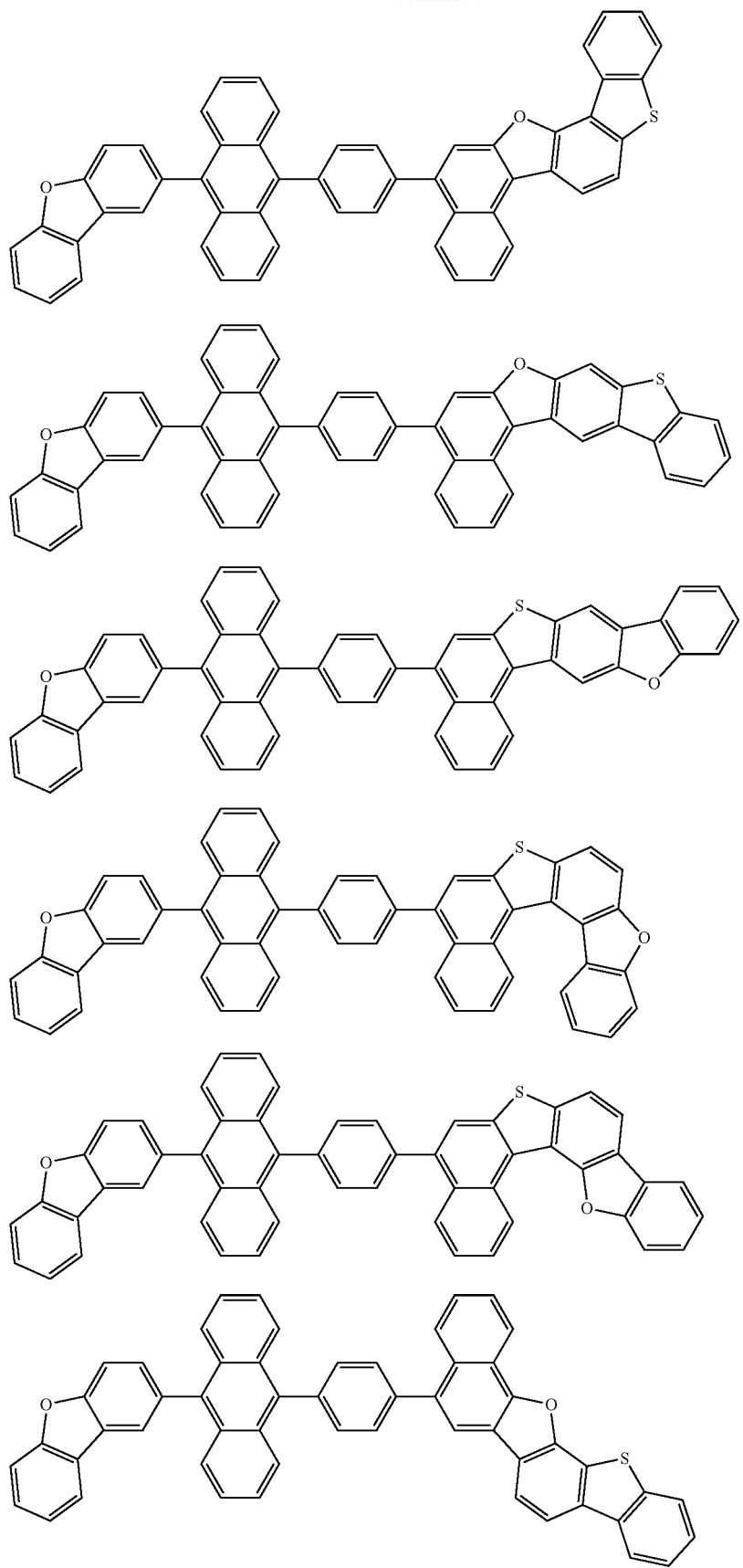

-continued
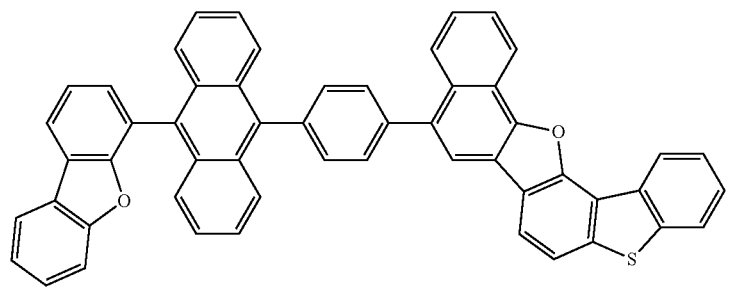
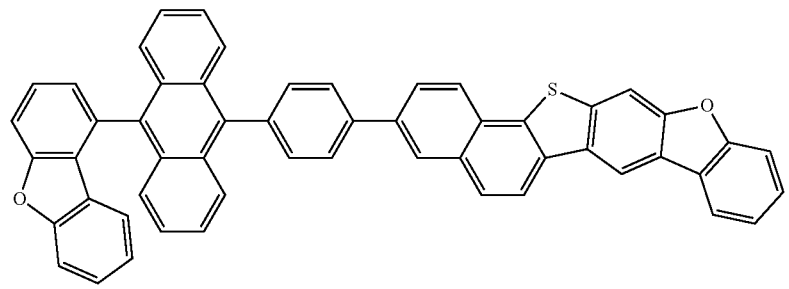
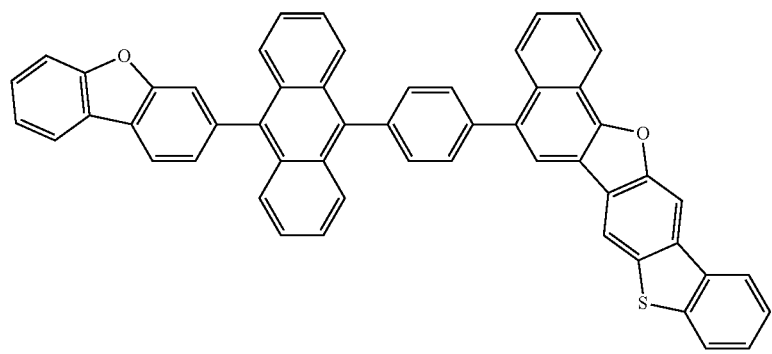
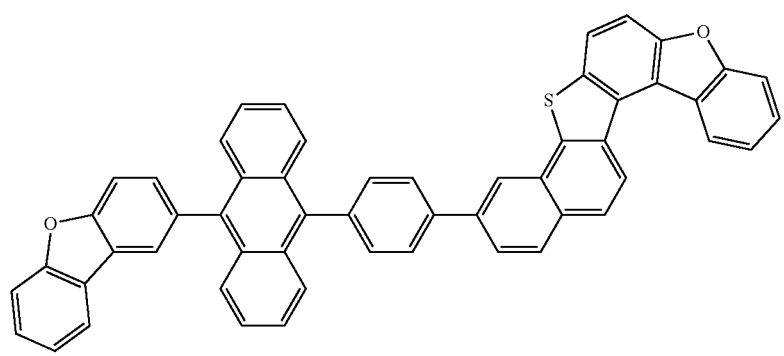
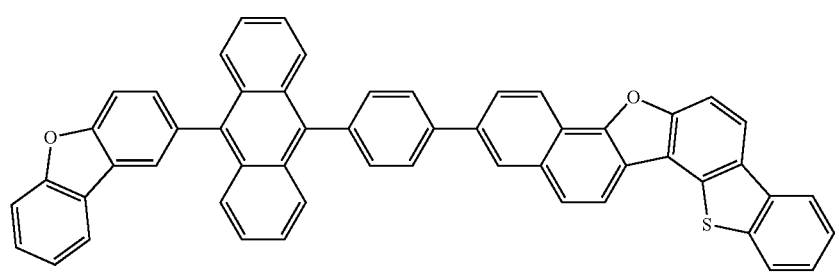

-continued
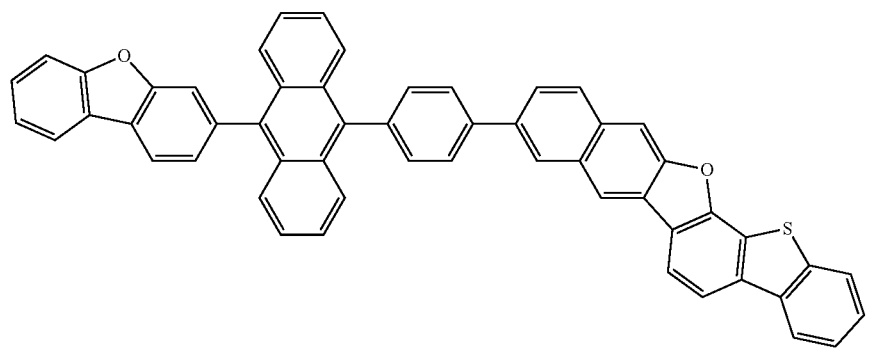
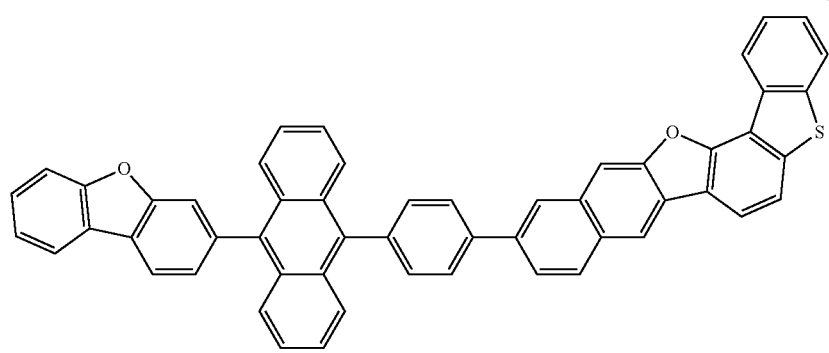
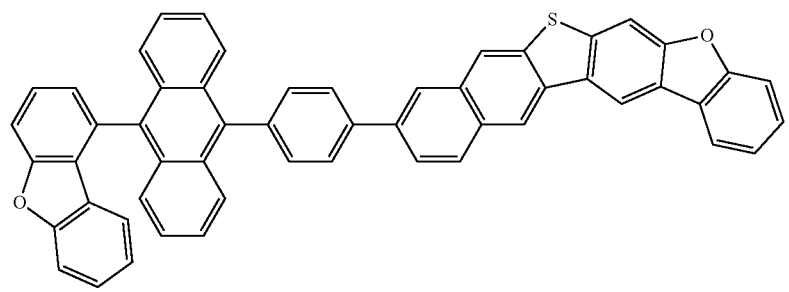
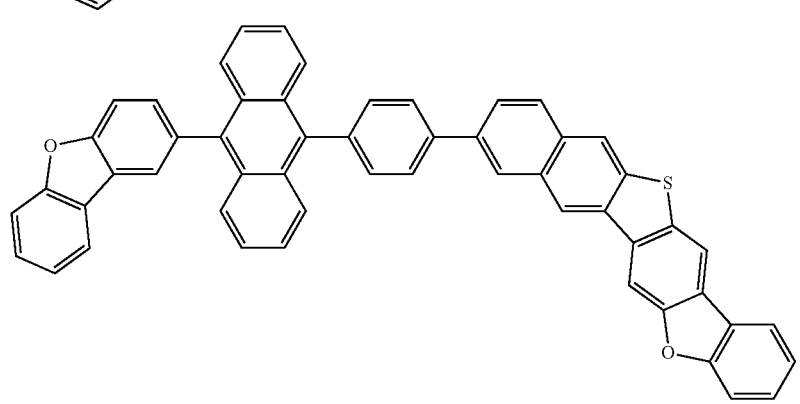
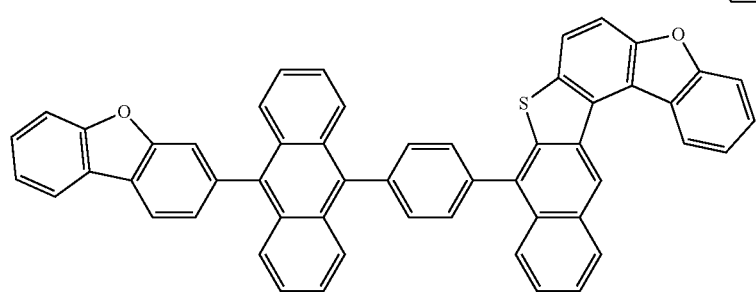

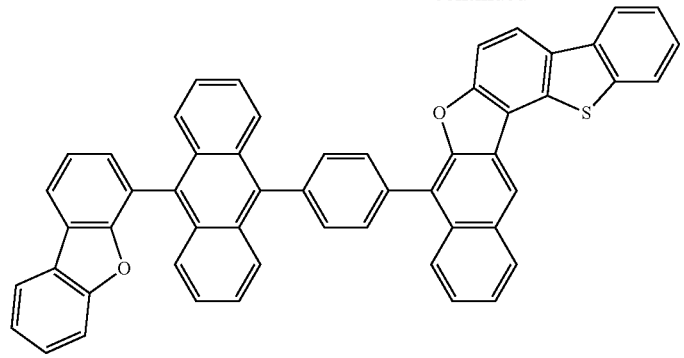

-continued
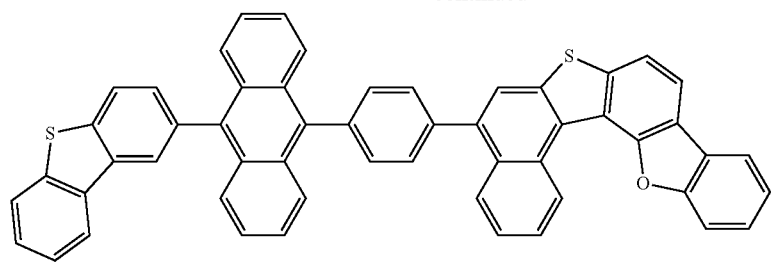
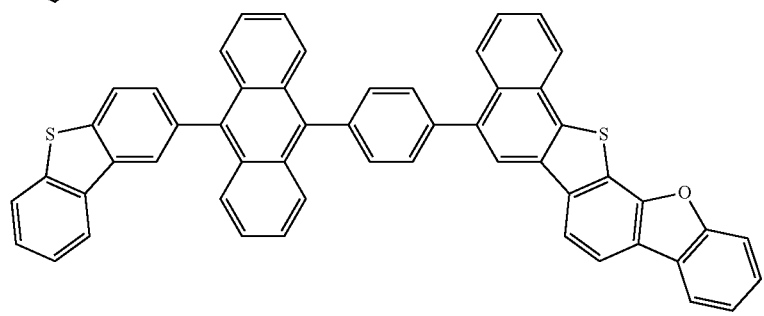
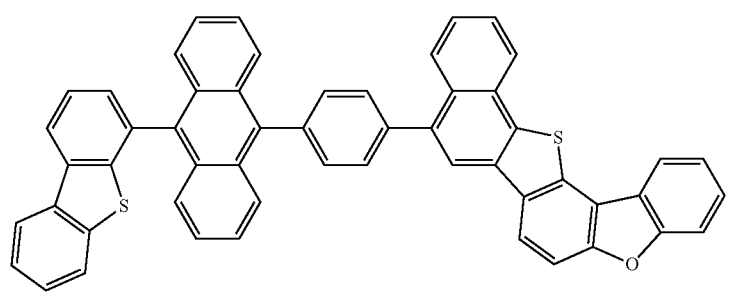
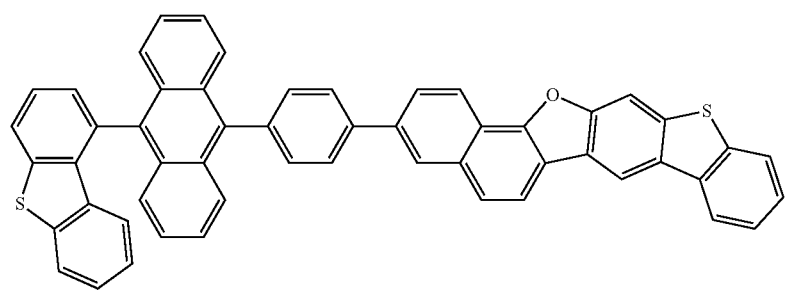
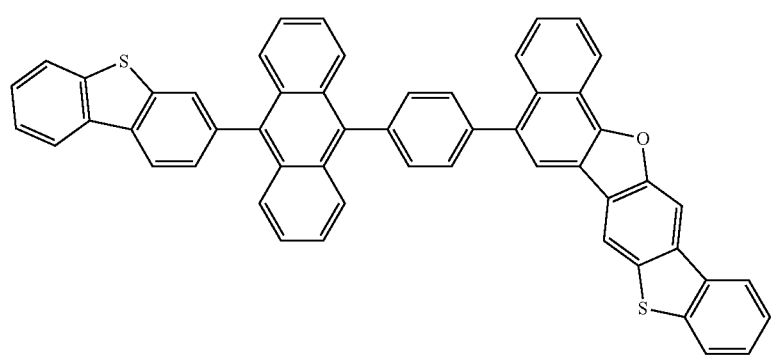

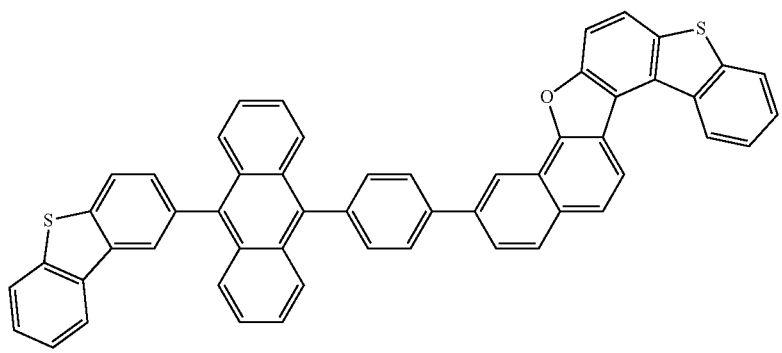
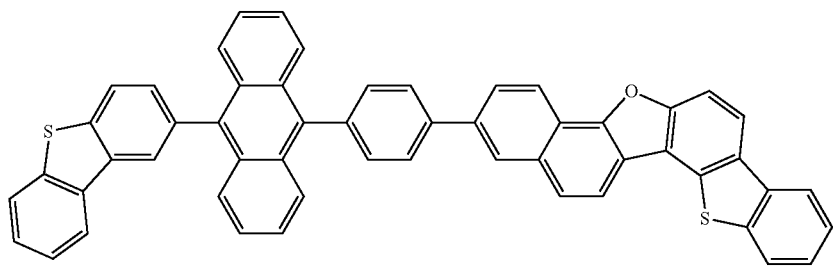
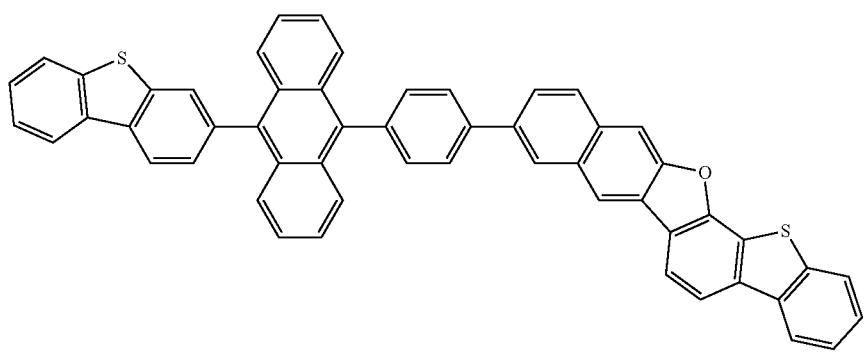
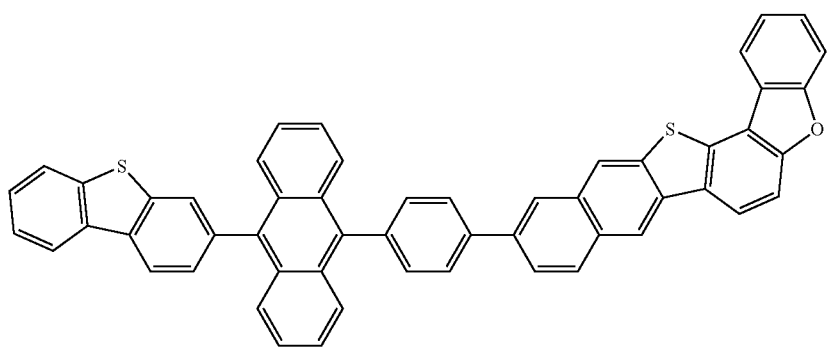
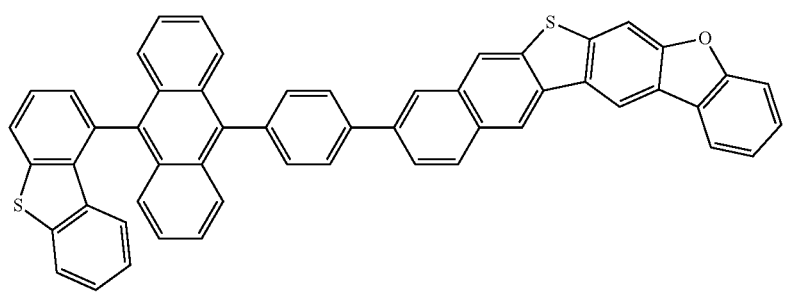

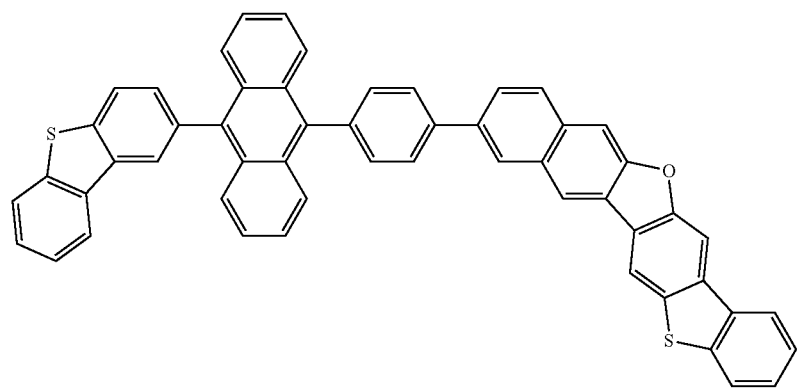
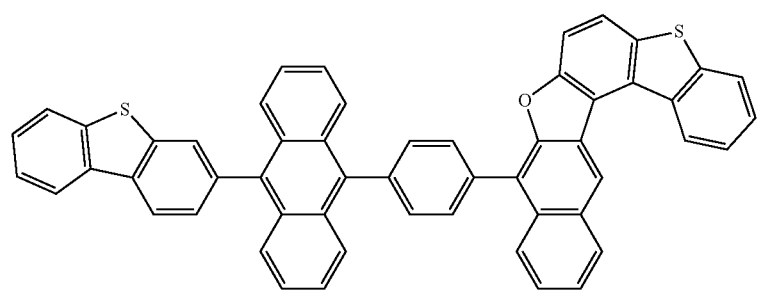
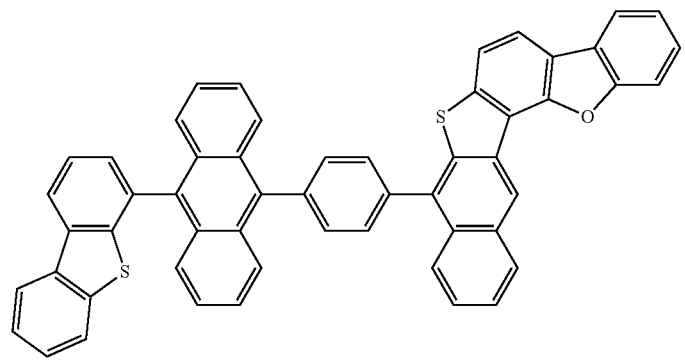
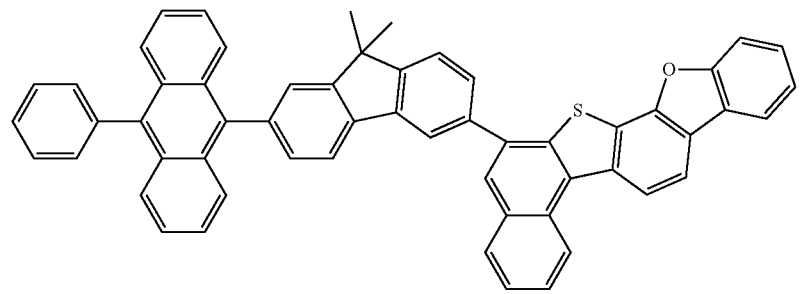
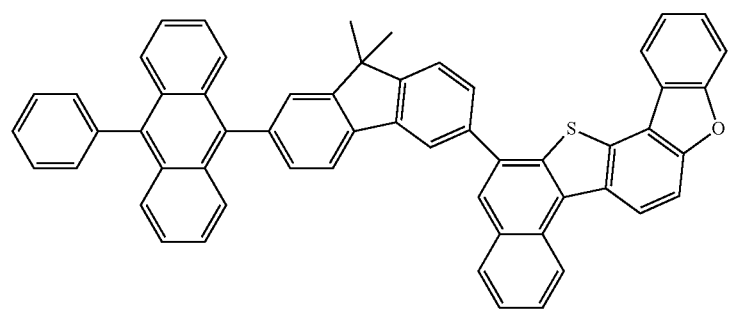

-continued
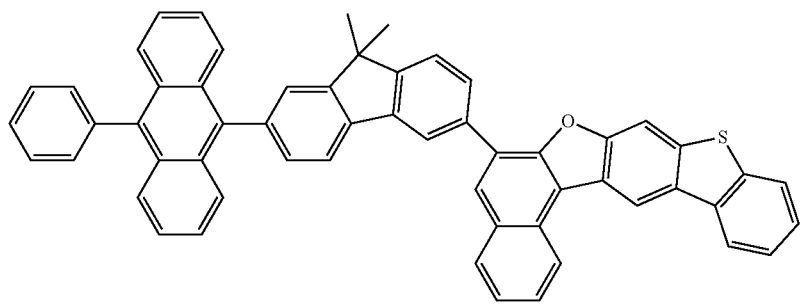
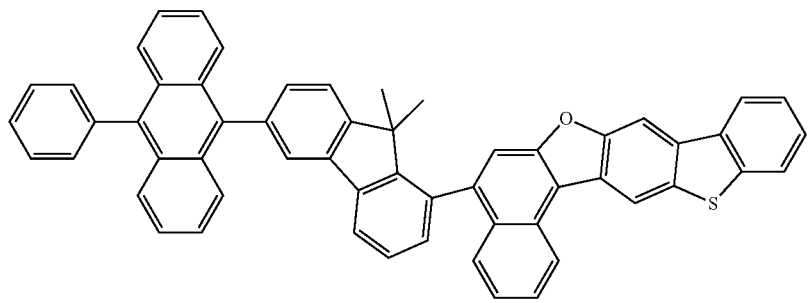
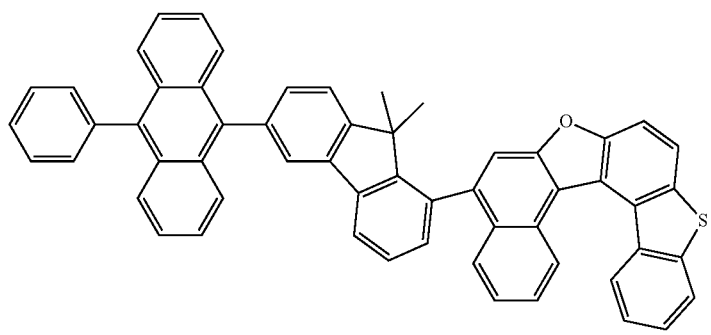
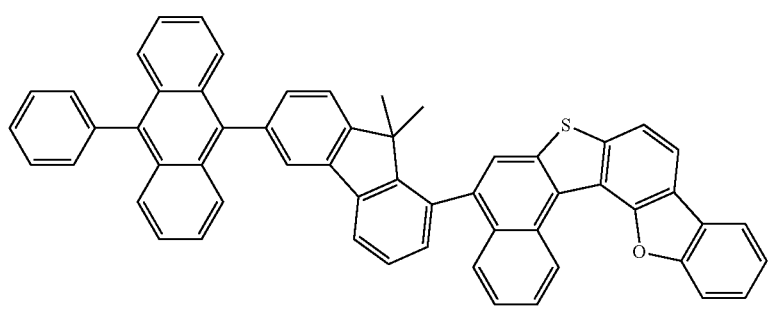
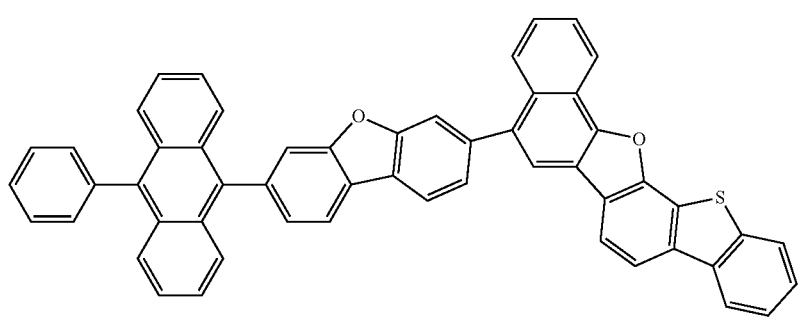

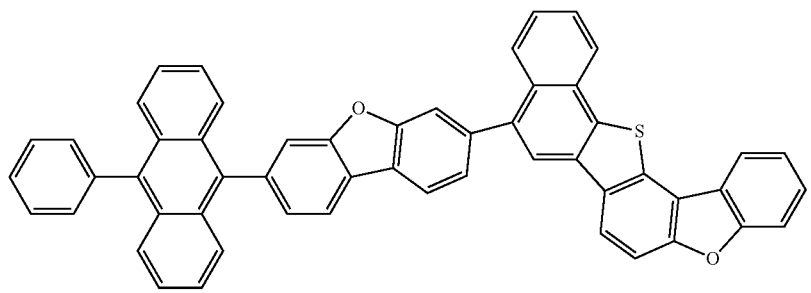
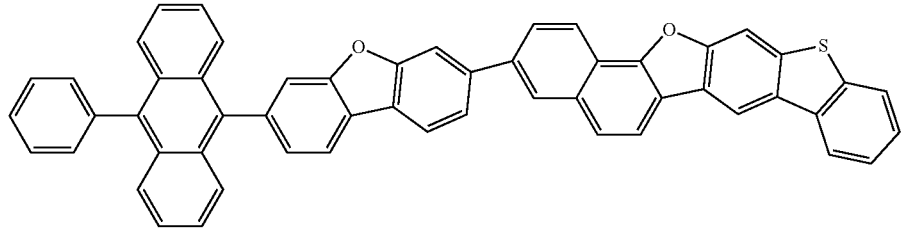
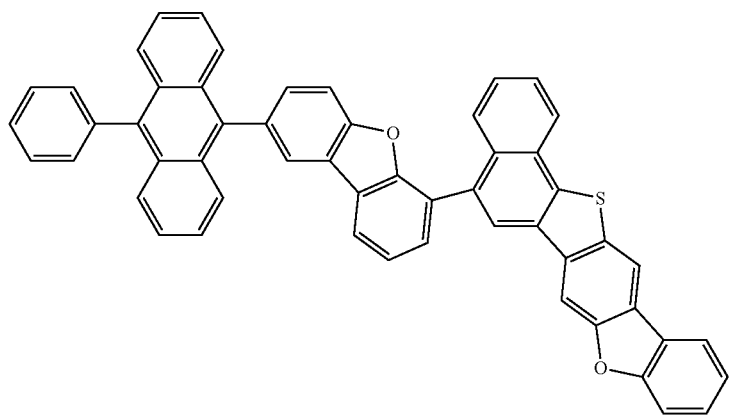
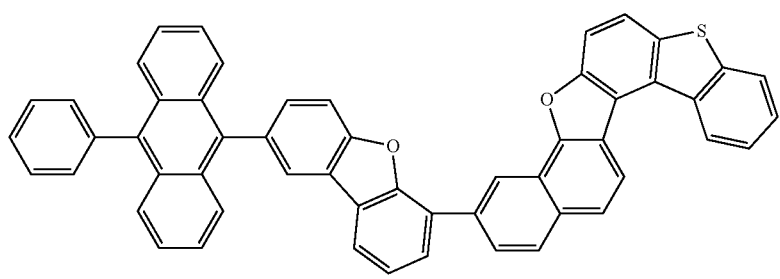
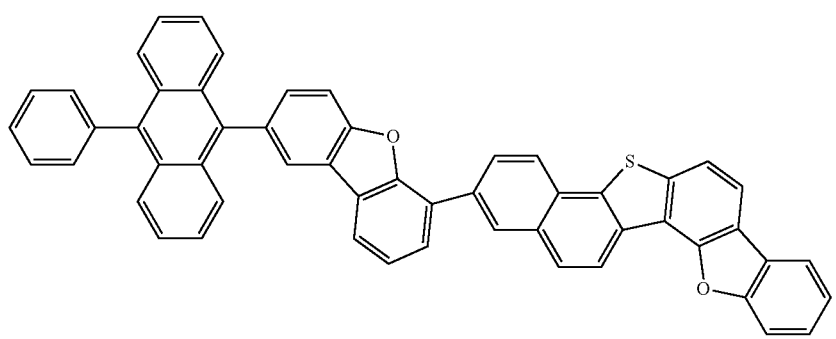

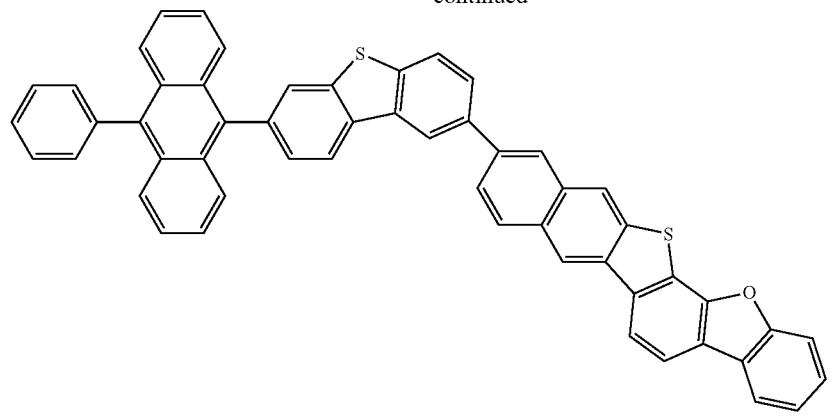
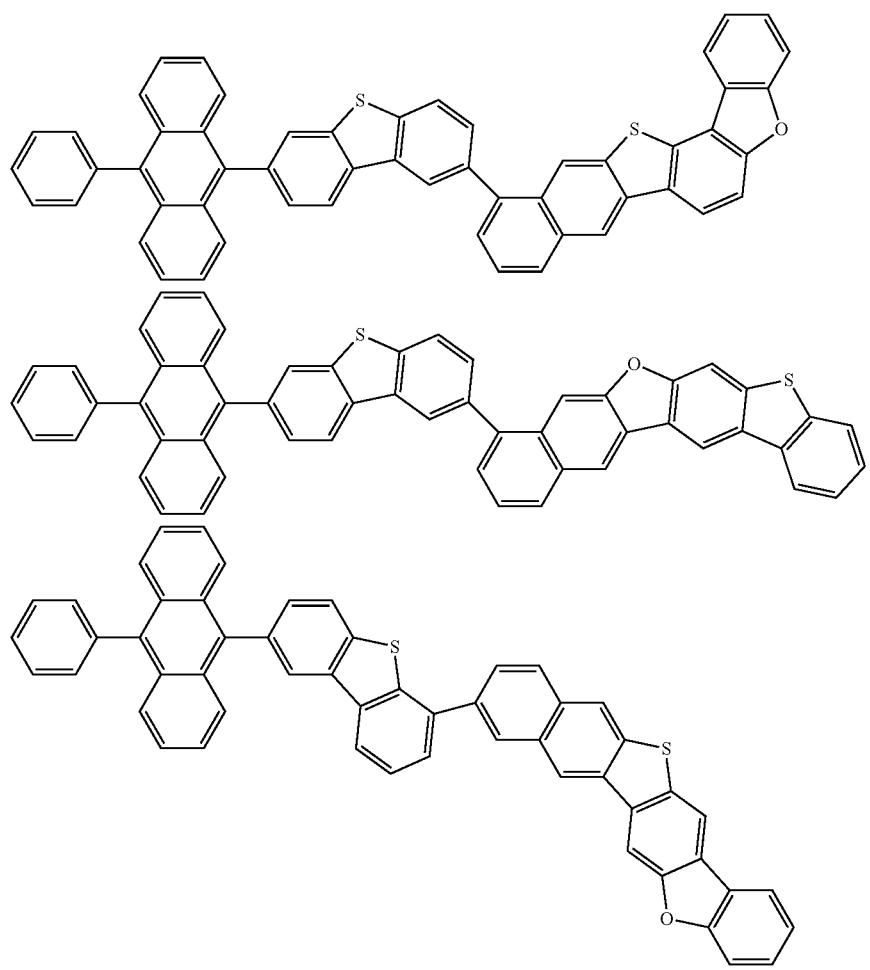
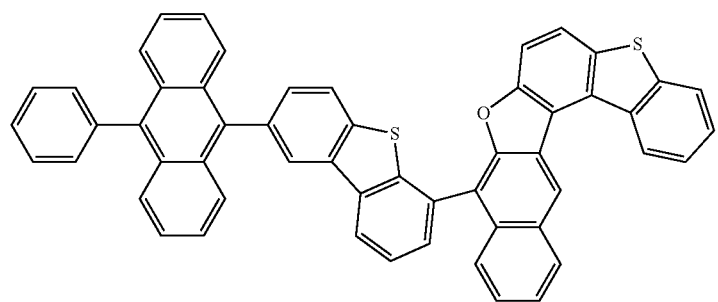

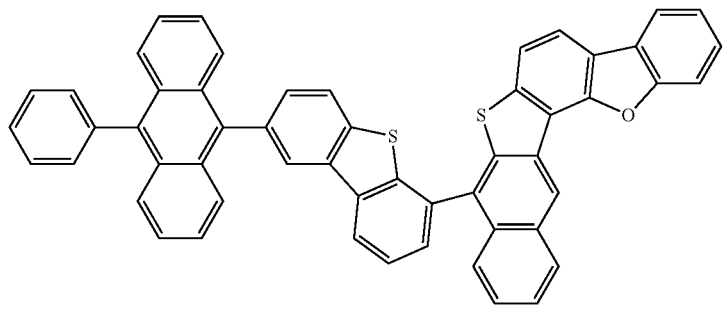
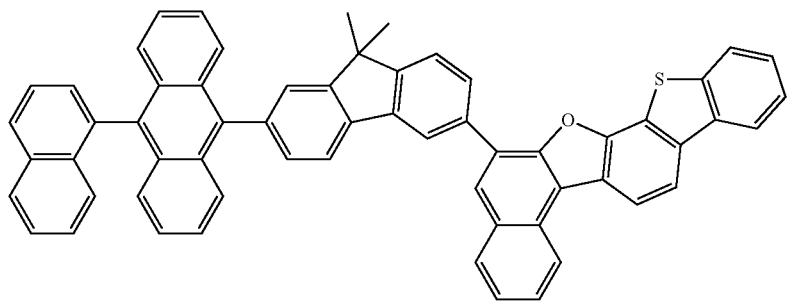
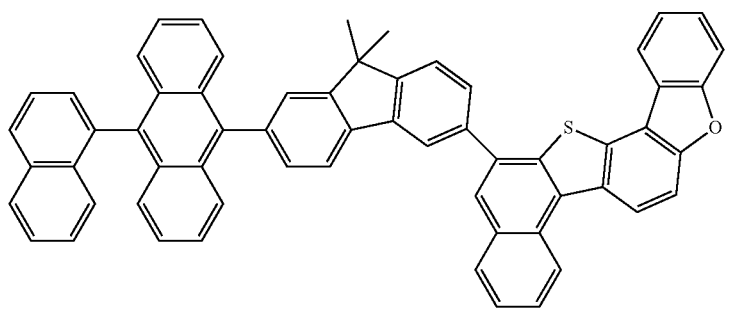
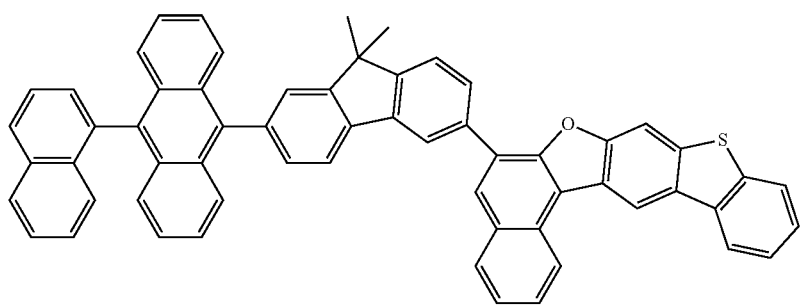
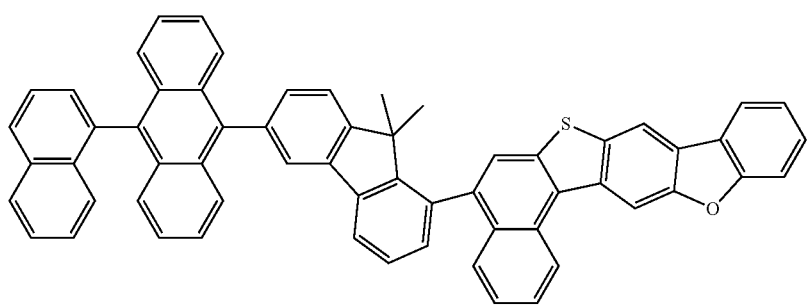

-continued
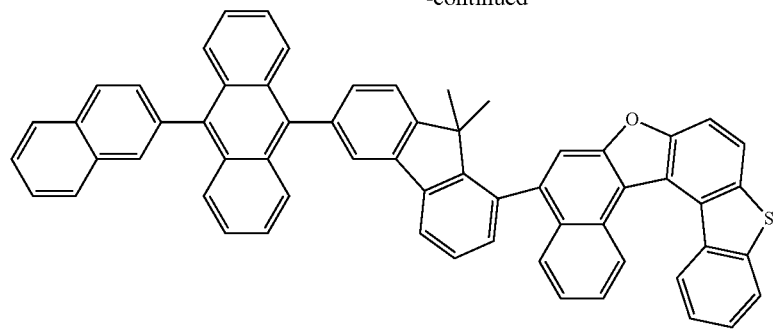
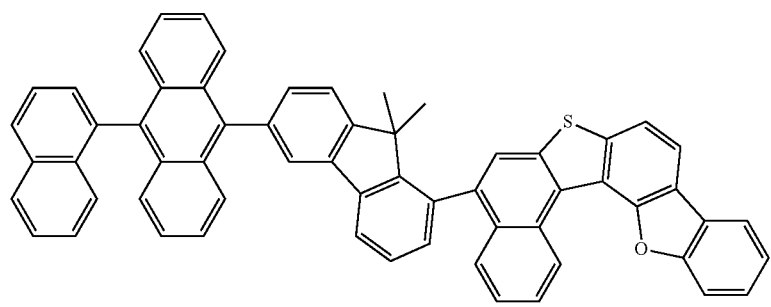
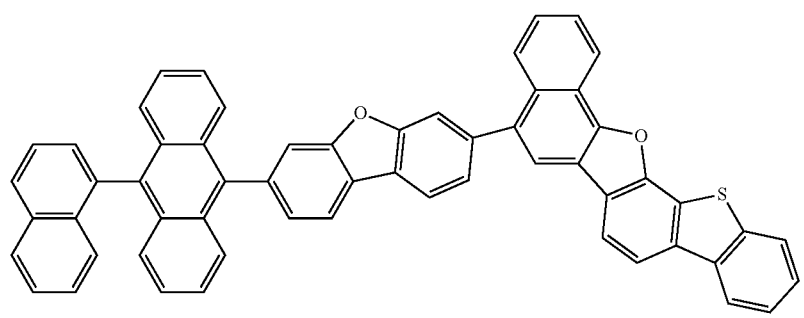
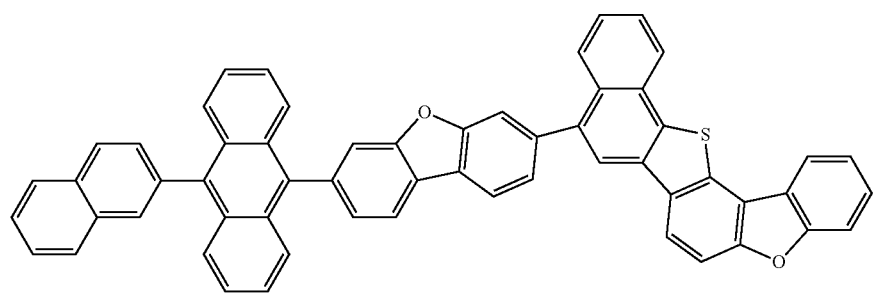
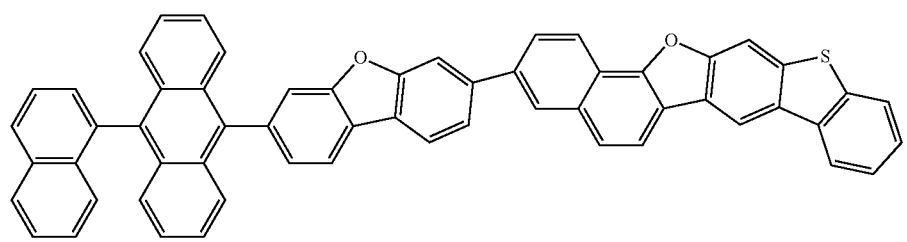

-continued
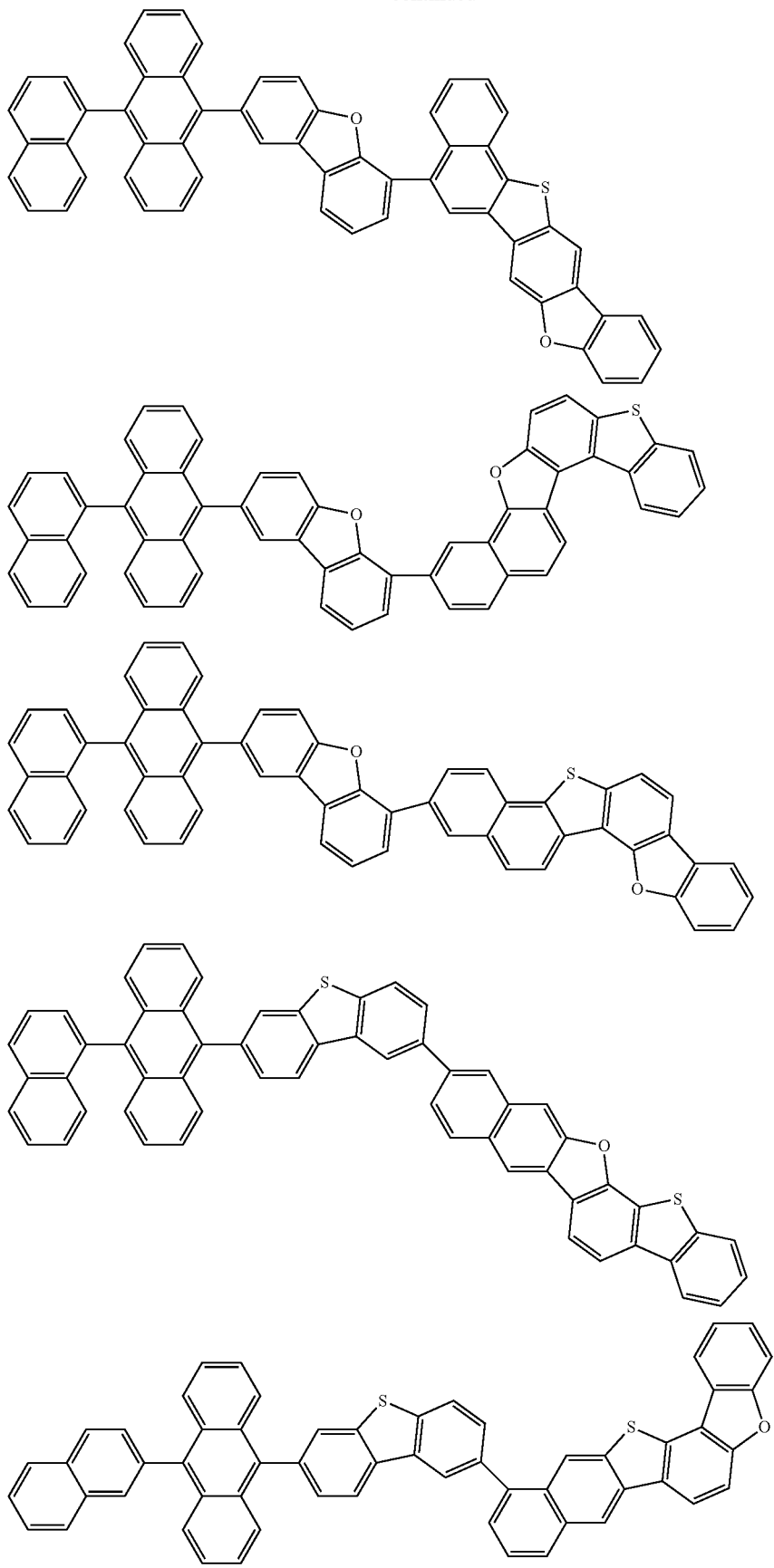

-continued
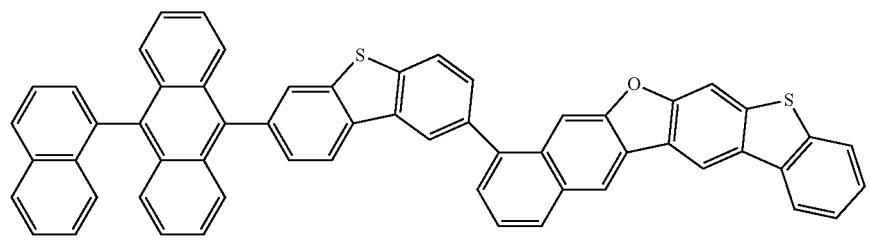
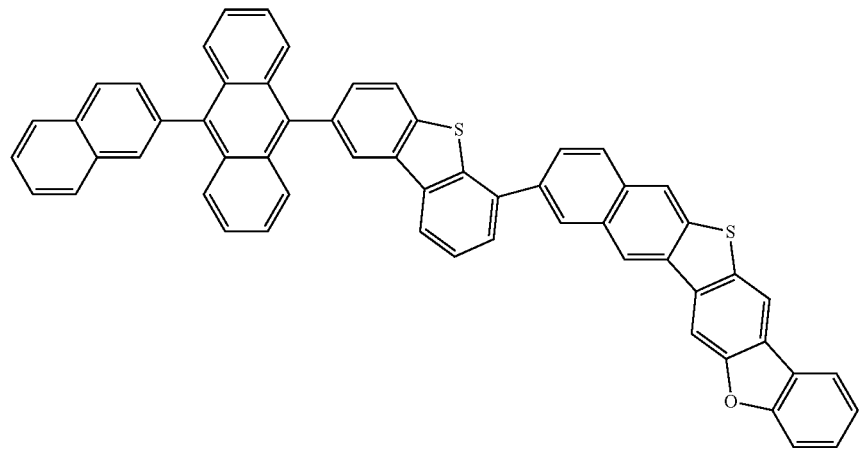
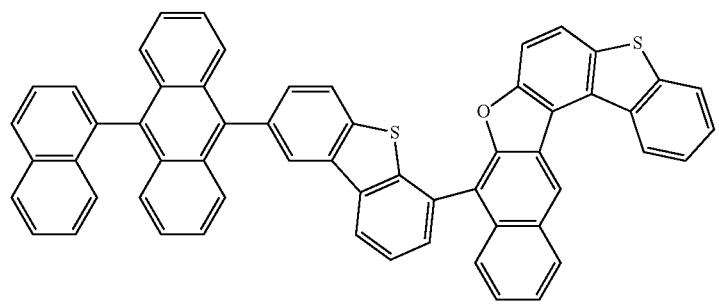
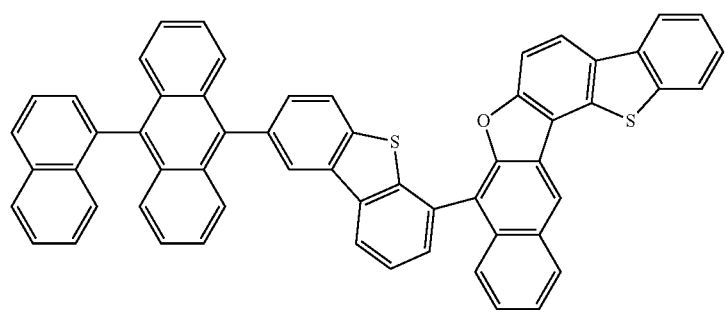
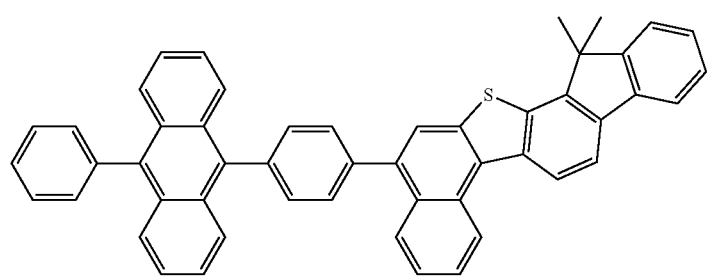

-continued
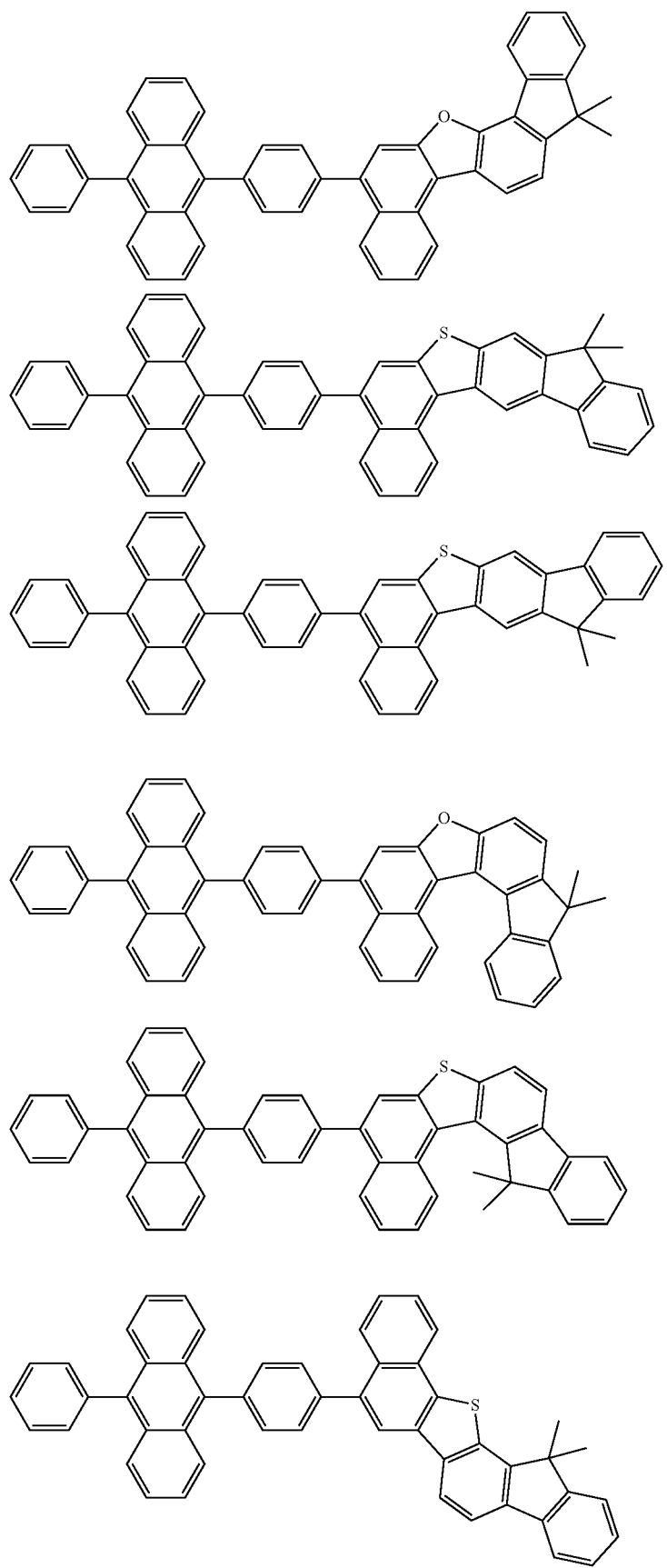

-continued
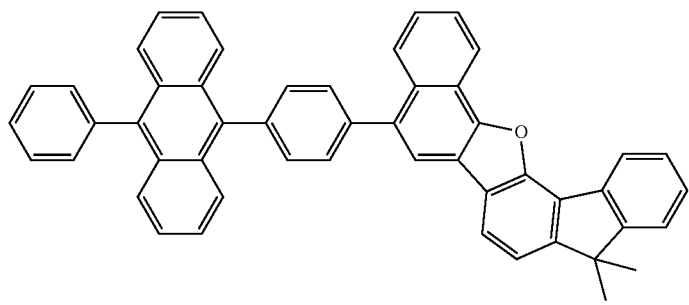
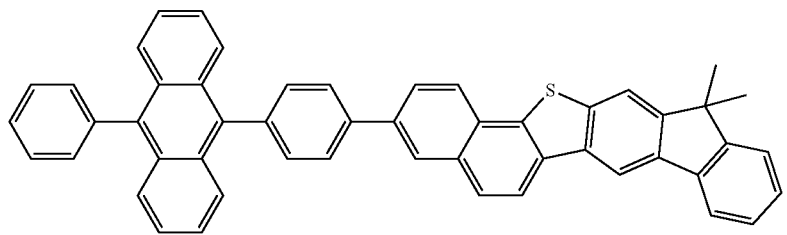
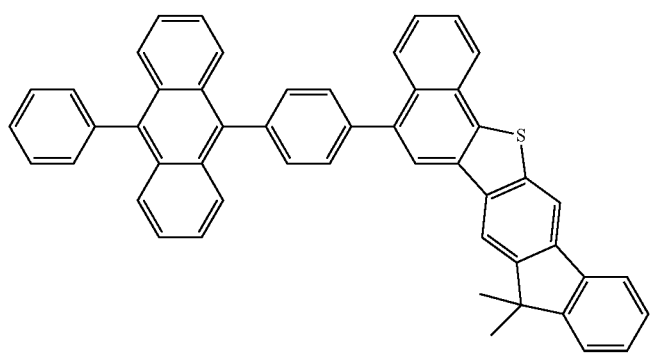
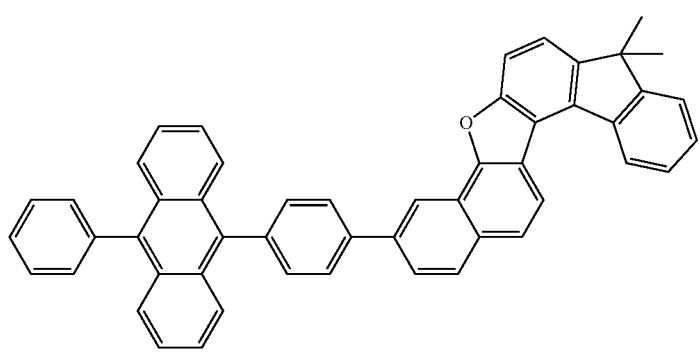
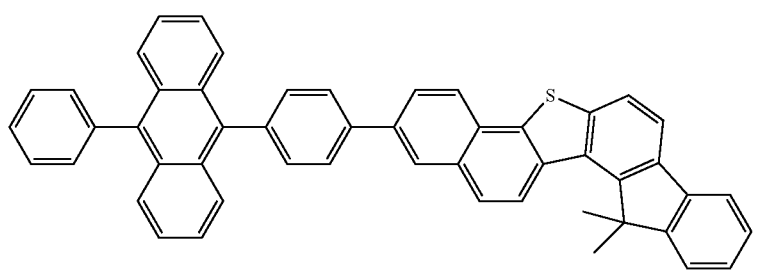

-continued
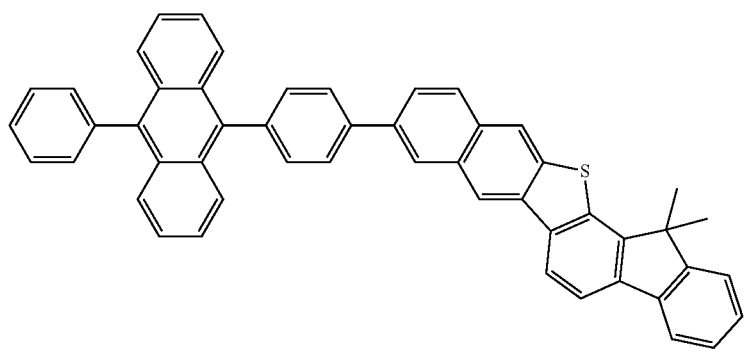
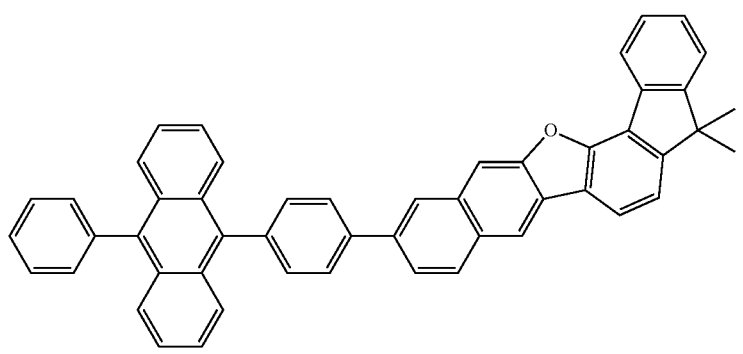
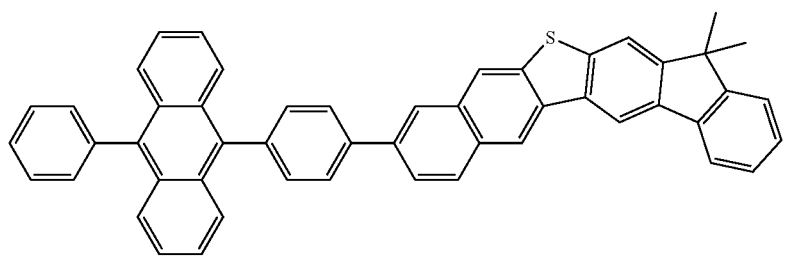
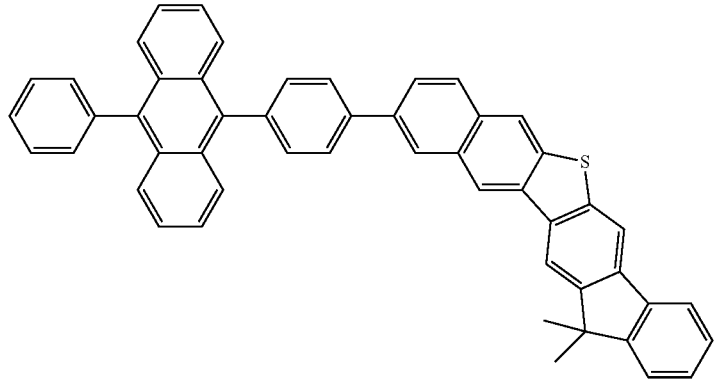
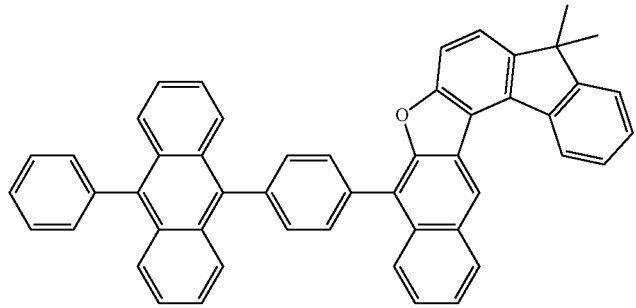

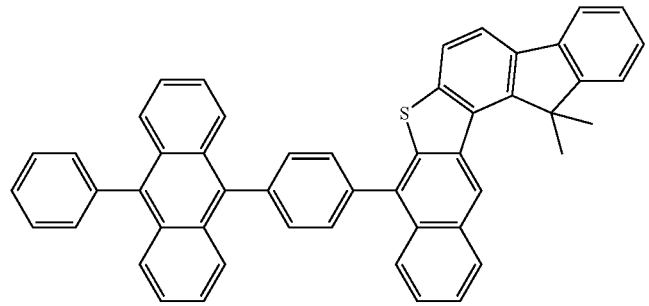
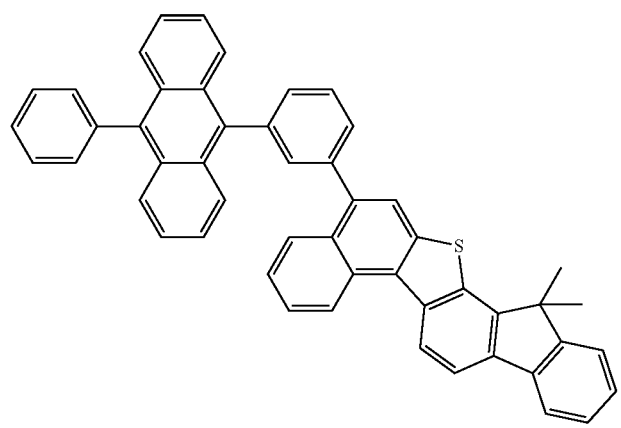
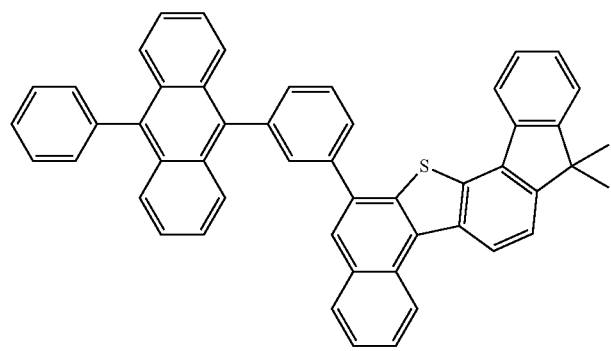
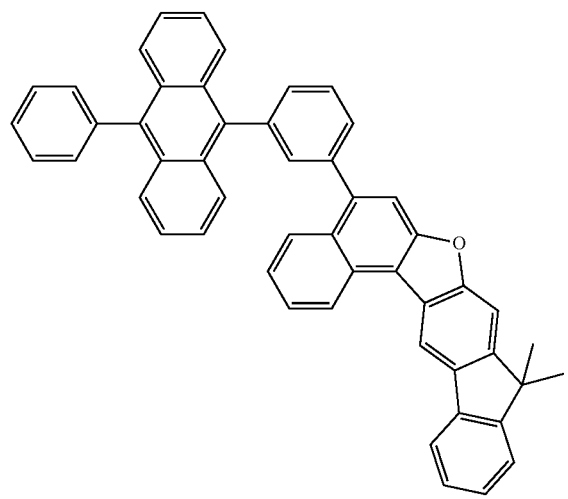

-continued
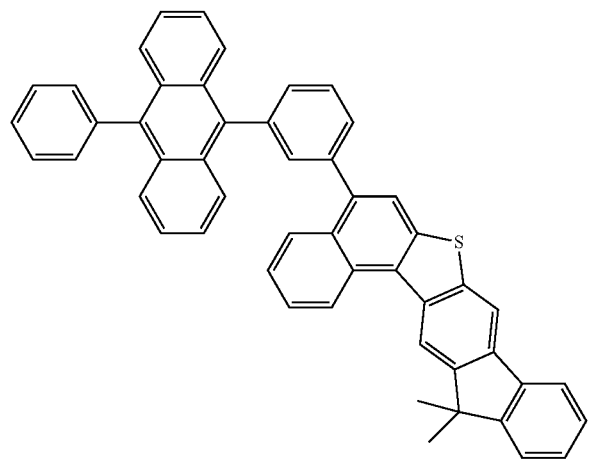

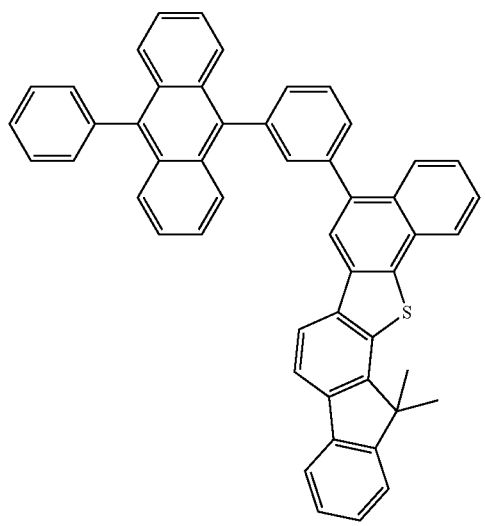
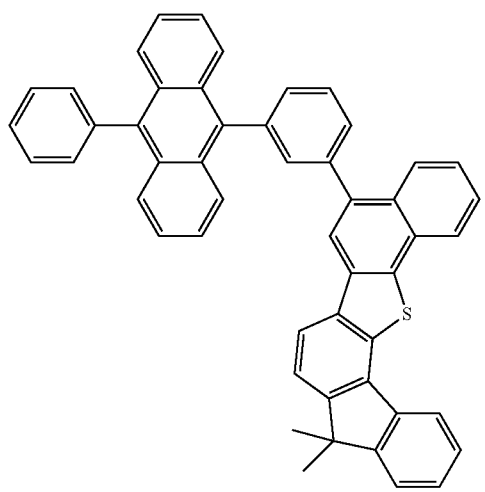
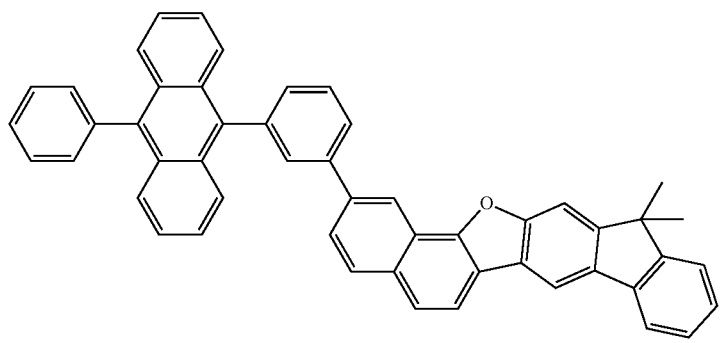

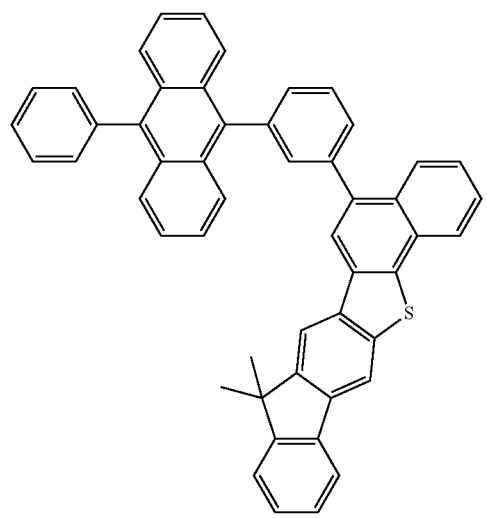
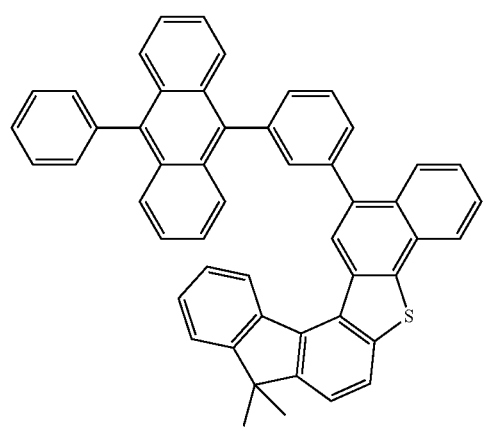
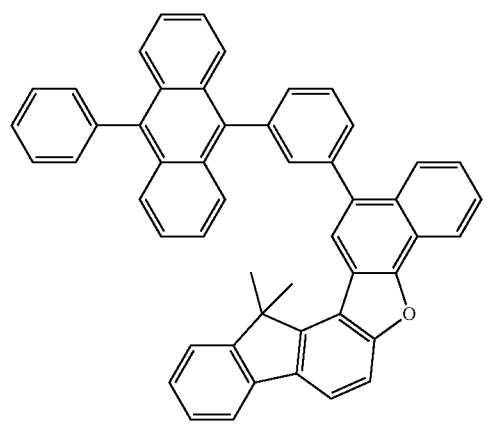

-continued
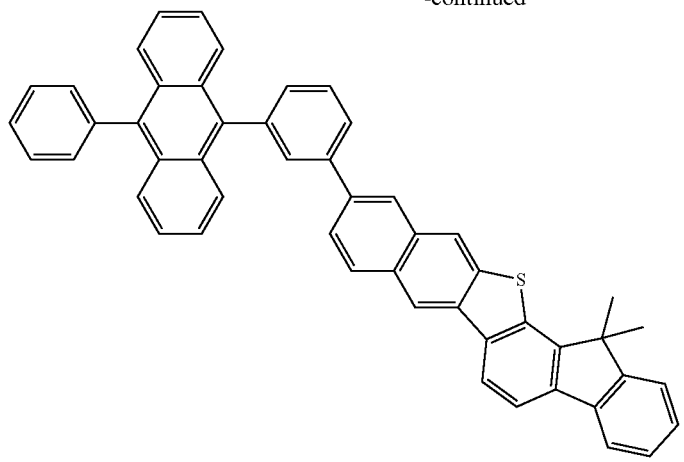
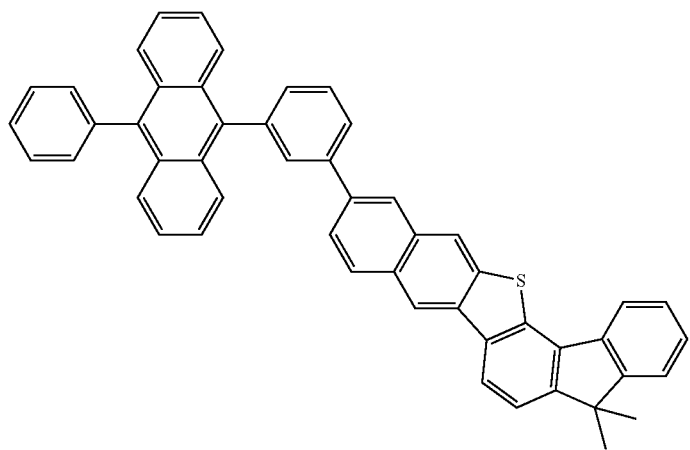
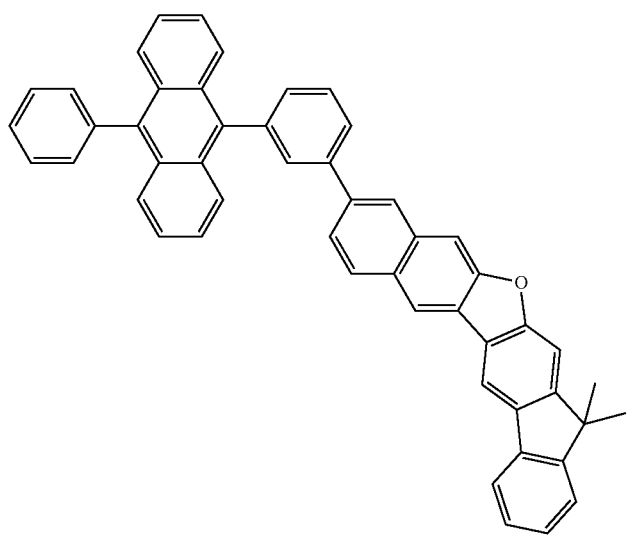

-continued
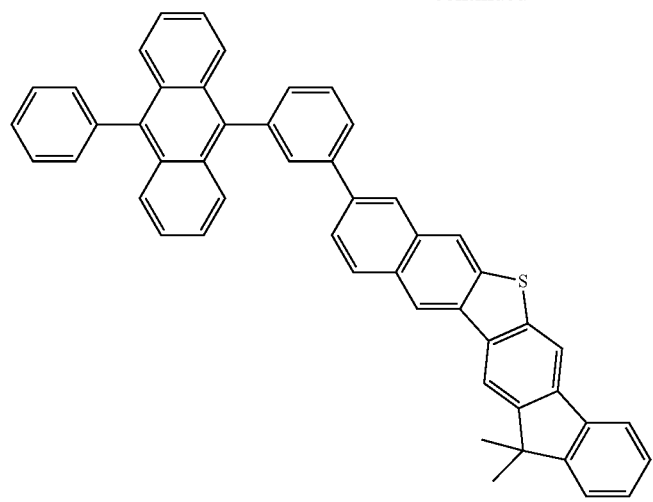
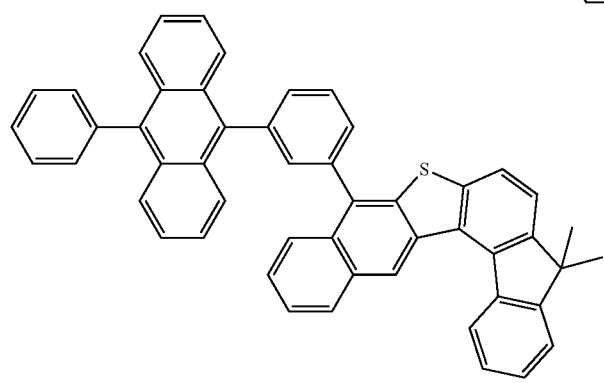
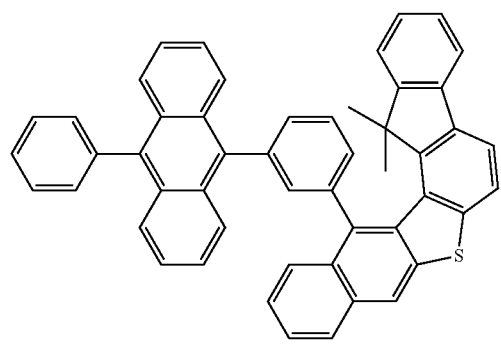
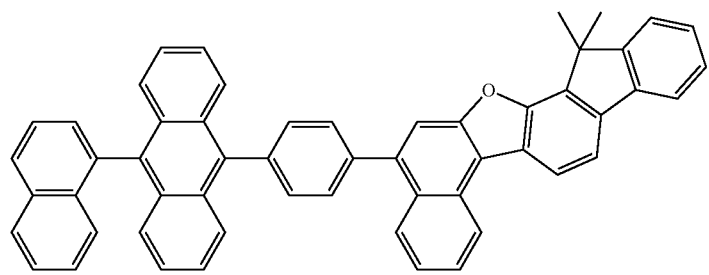

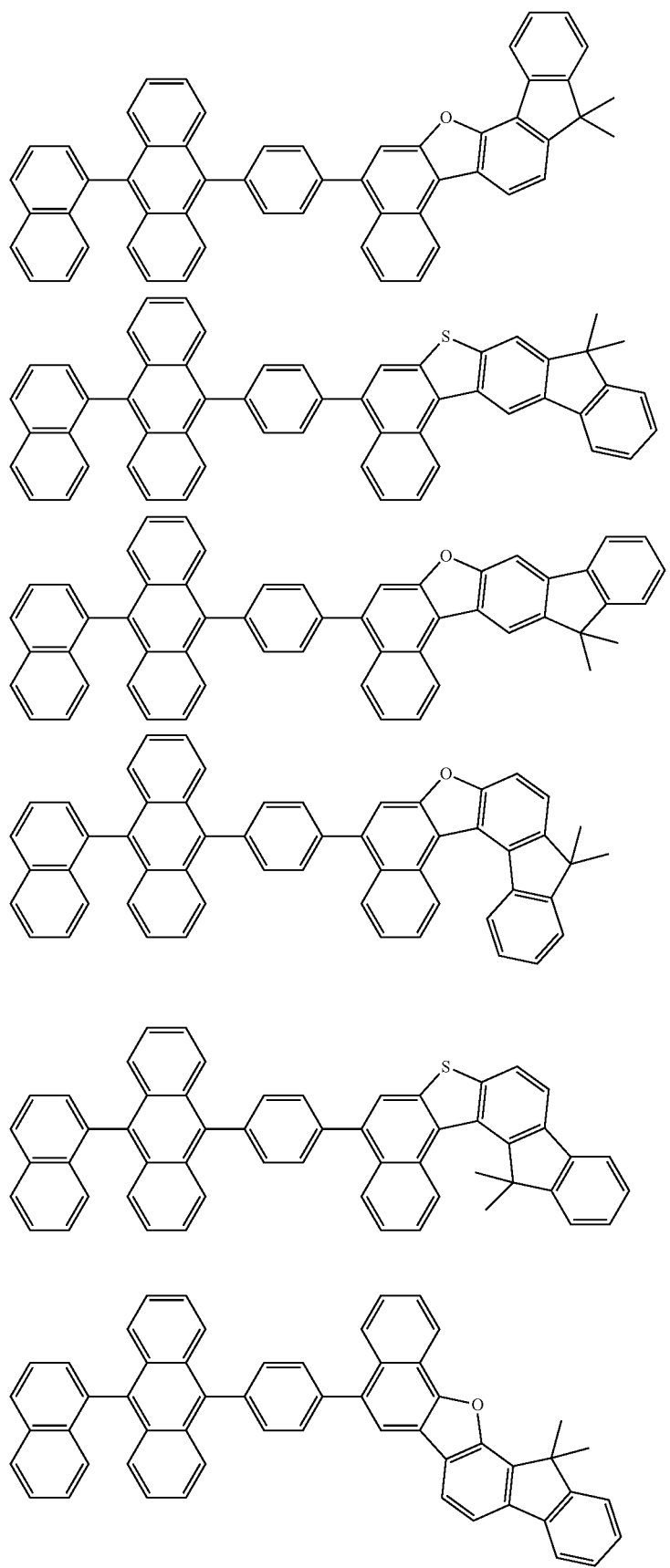

-continued
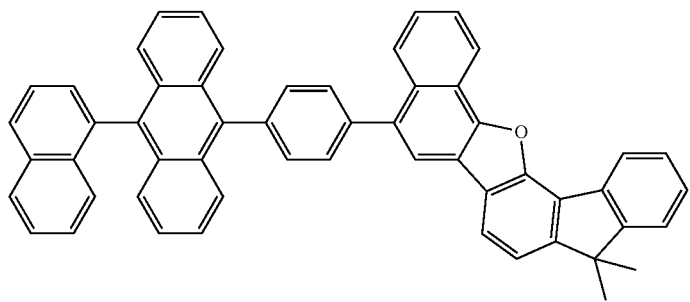
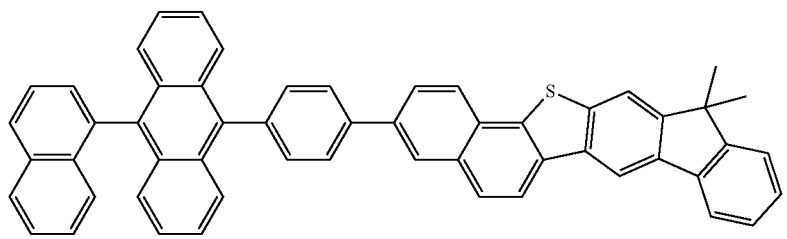
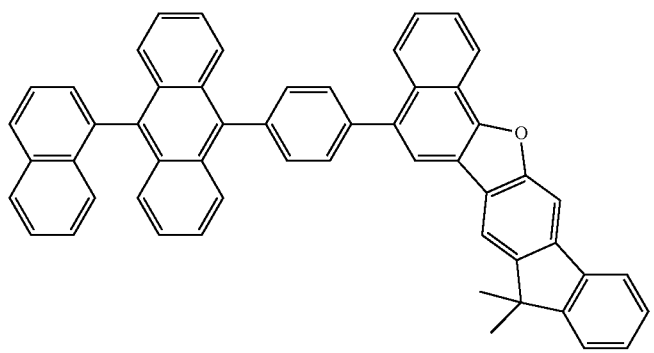
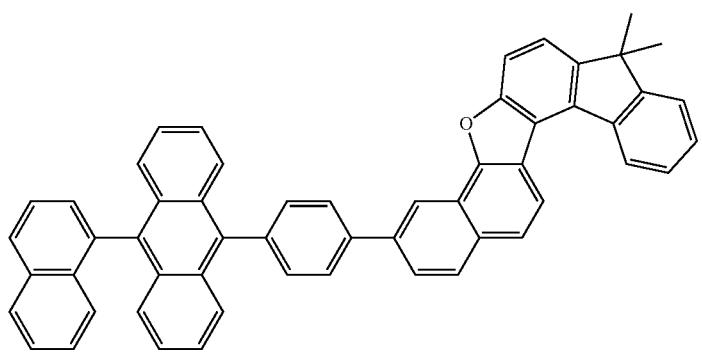
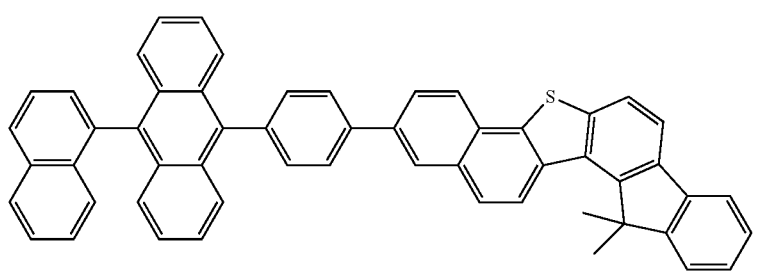

-continued
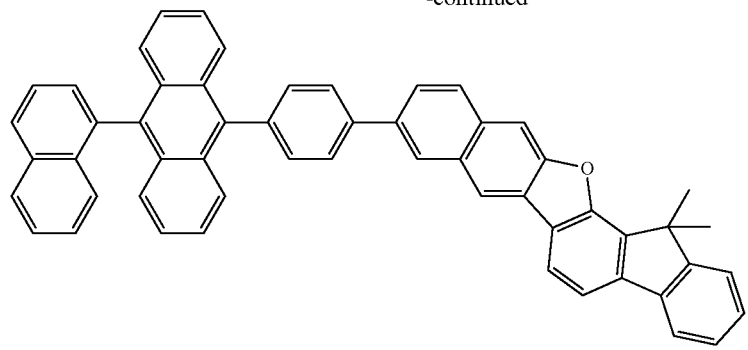
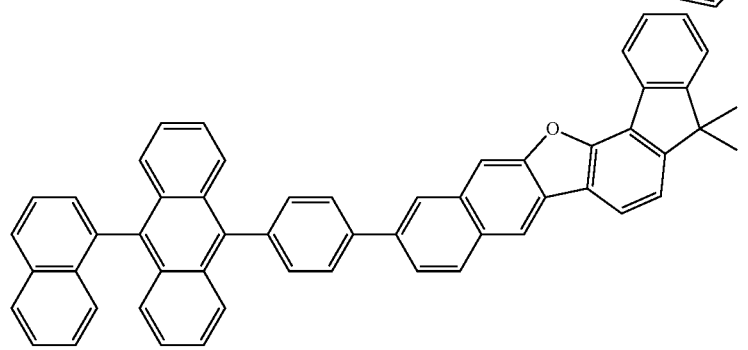
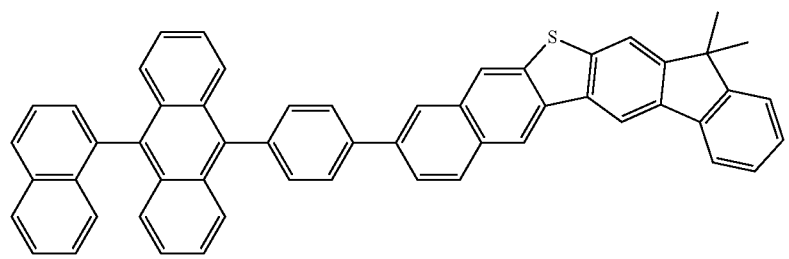
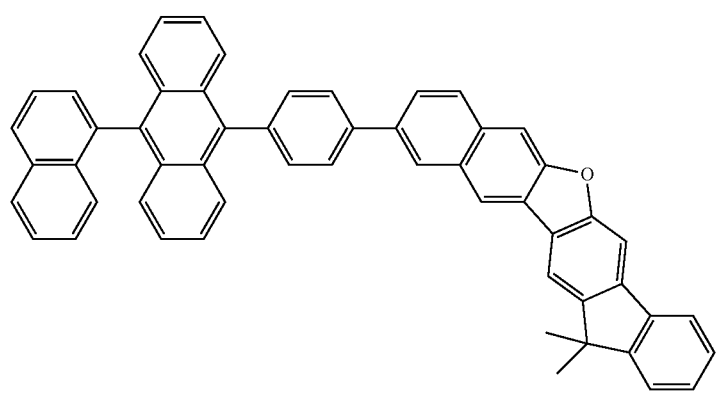
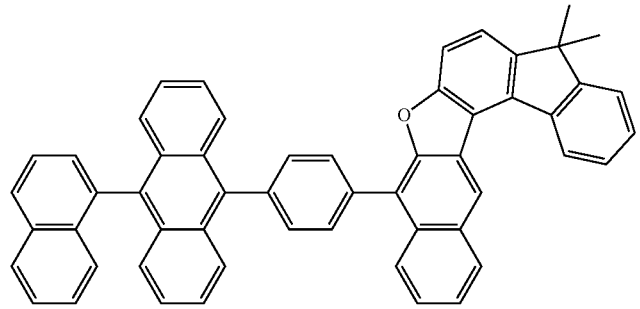

-continued
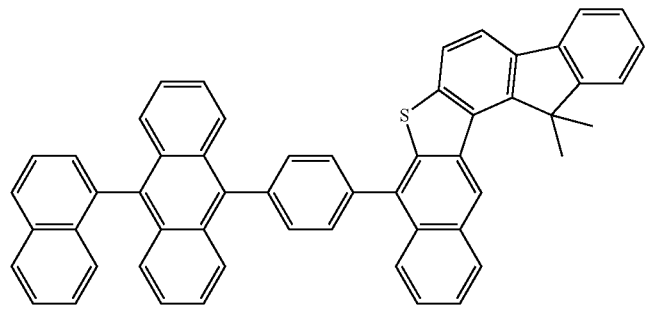
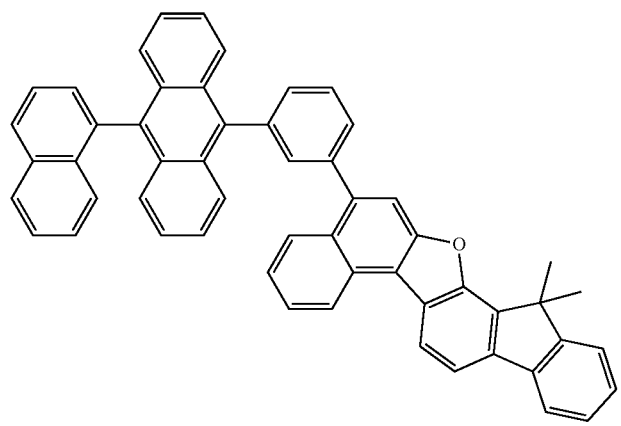
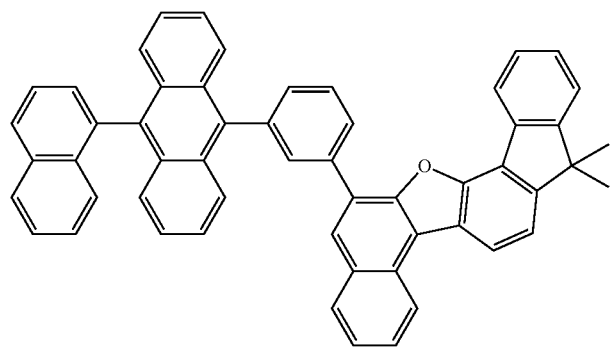
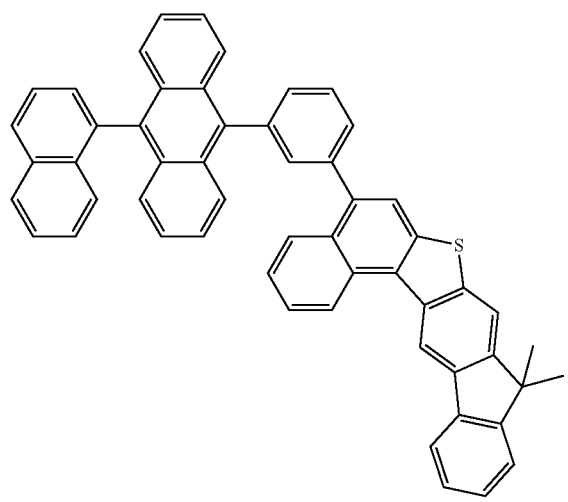

-continued
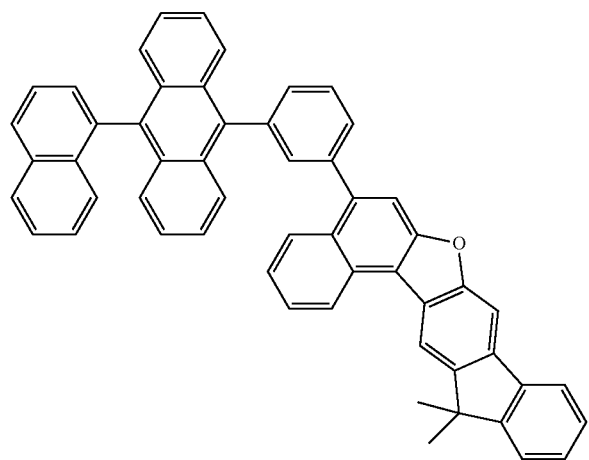
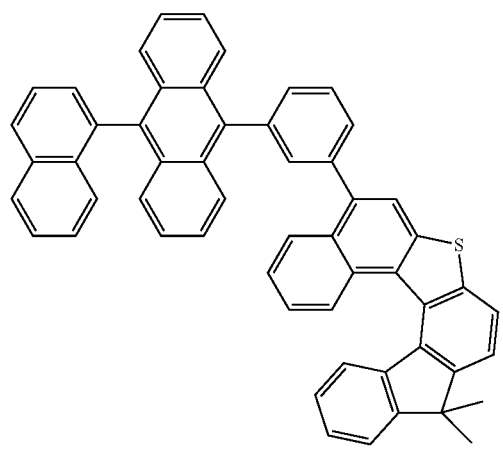
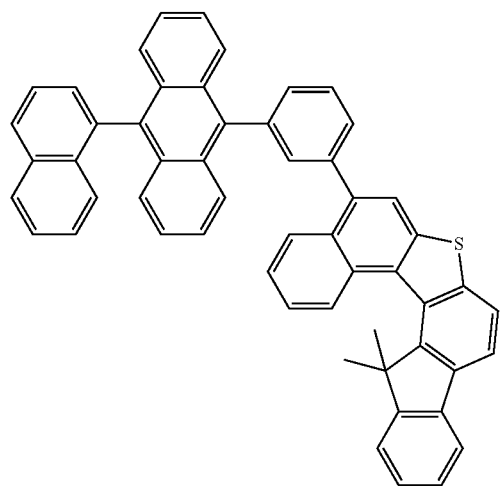

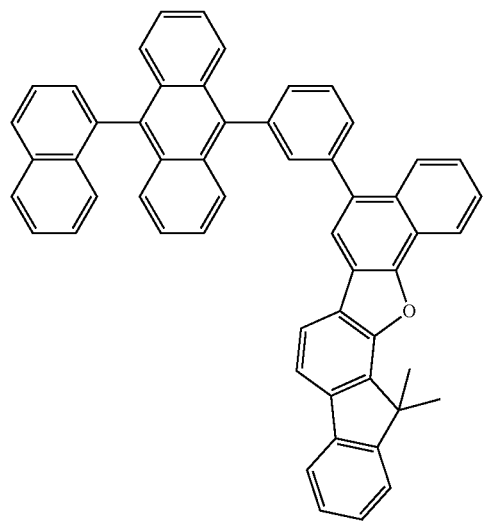
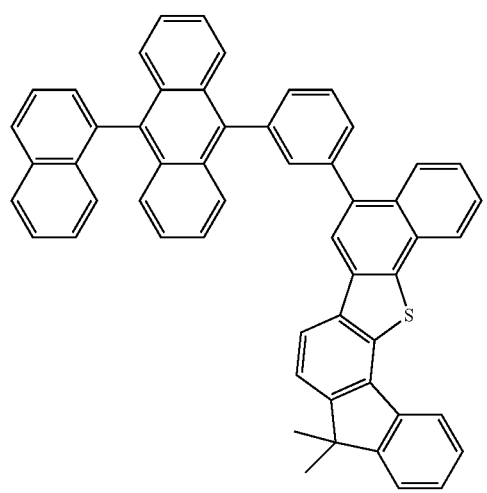
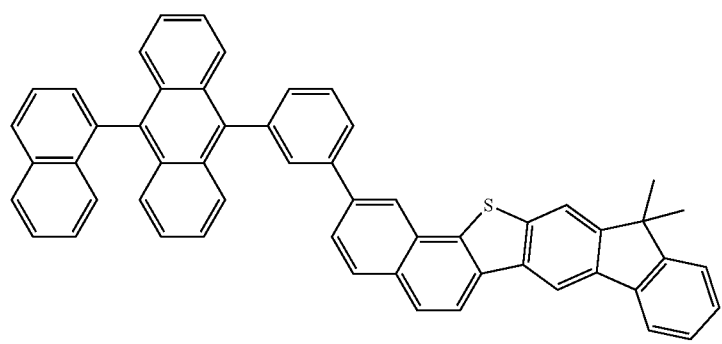

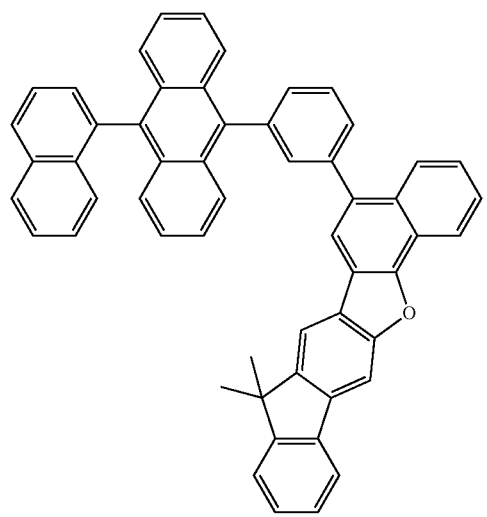
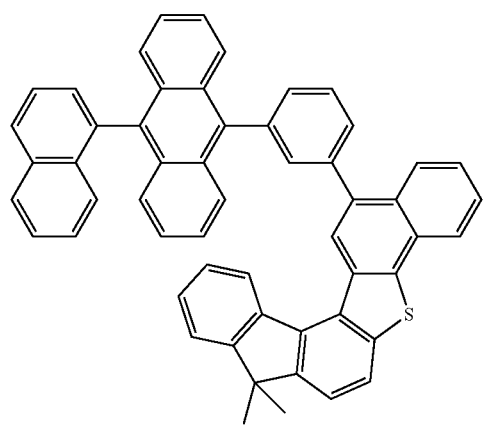
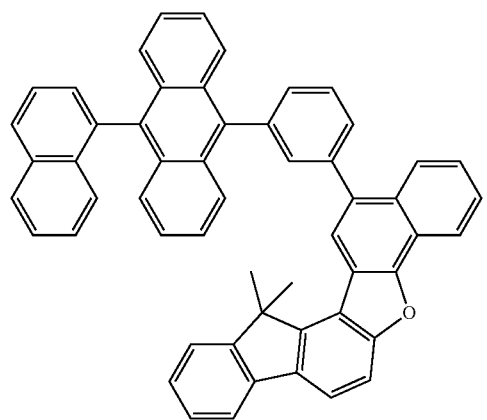

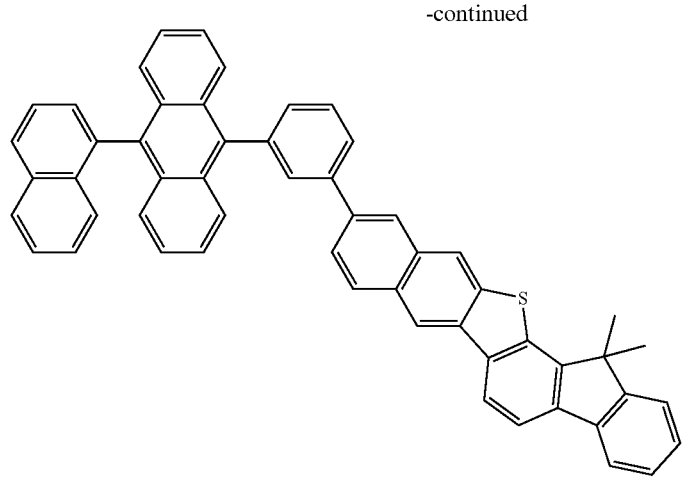
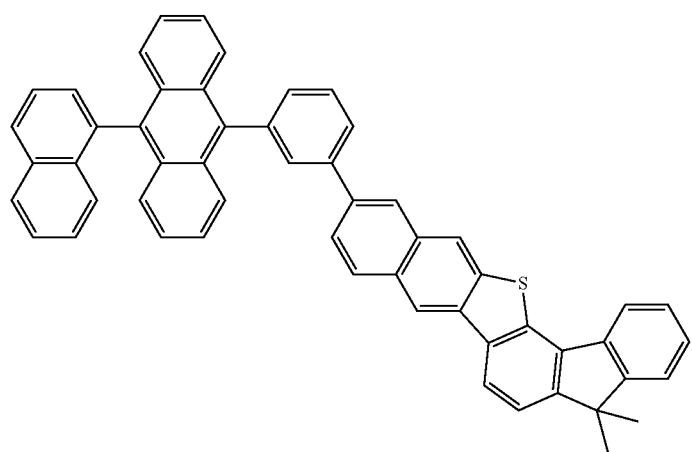
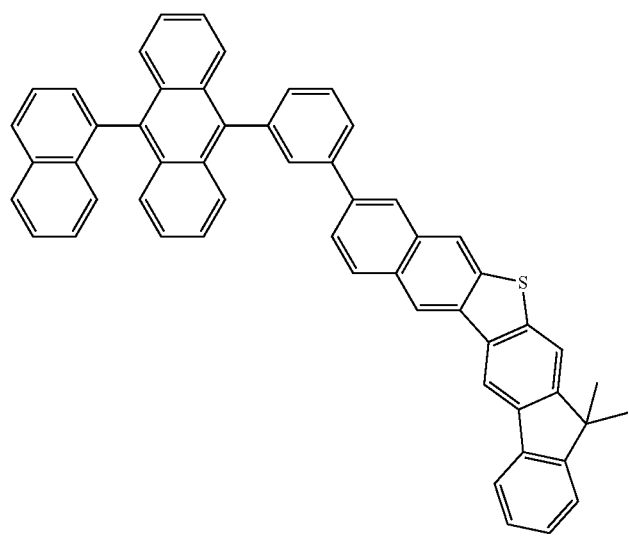

-continued
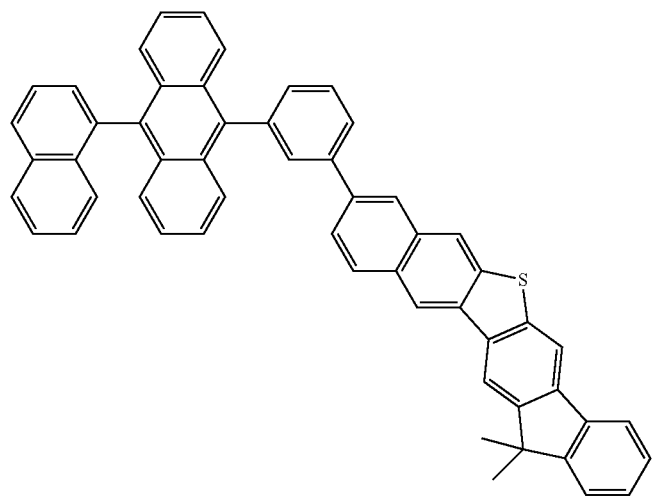
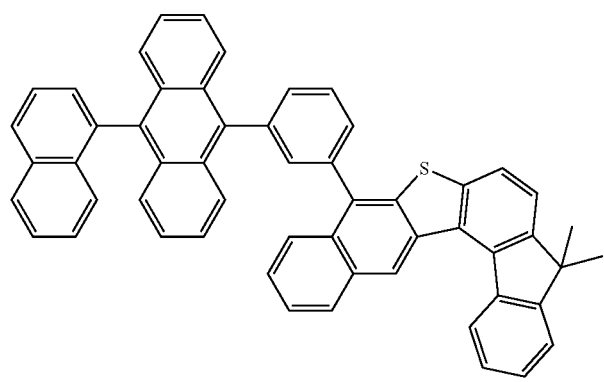
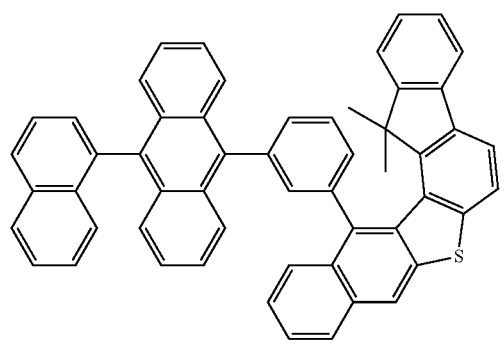
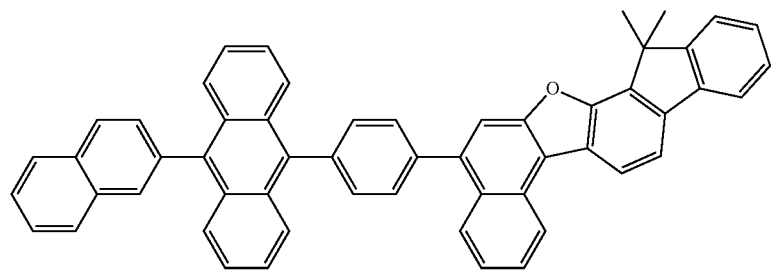

-continued
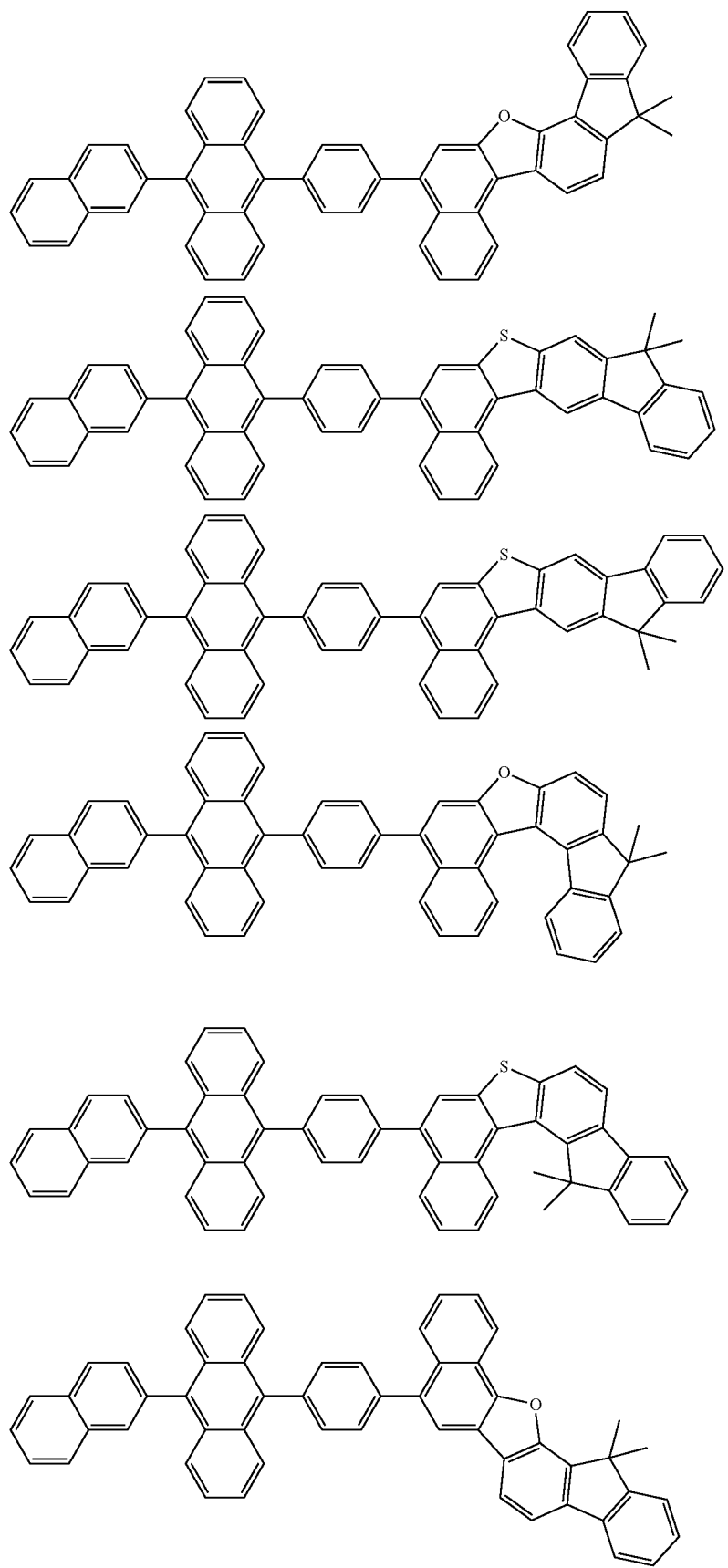

-continued
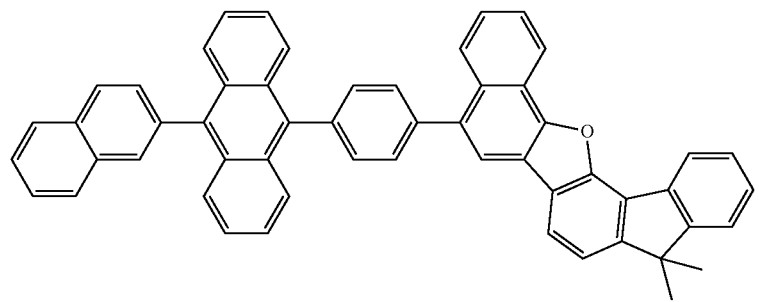
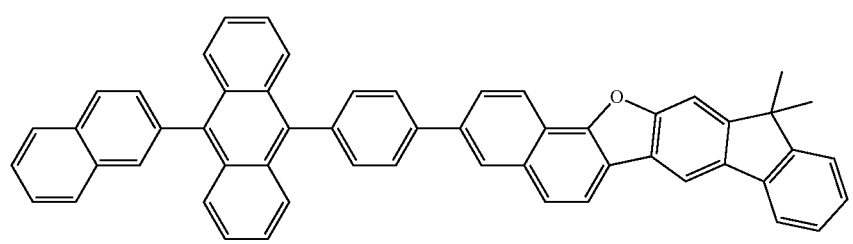
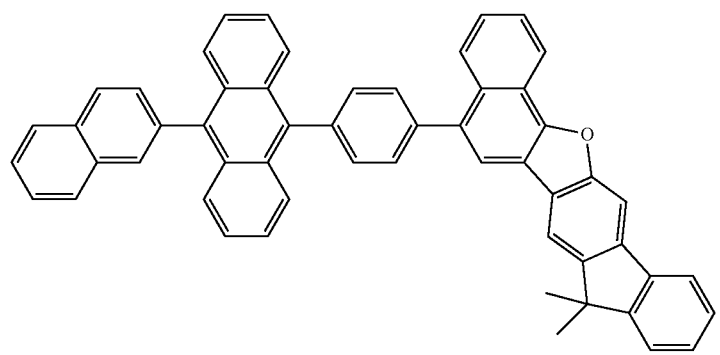
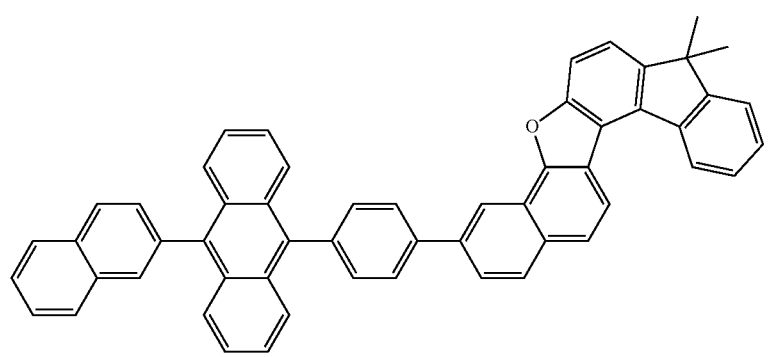
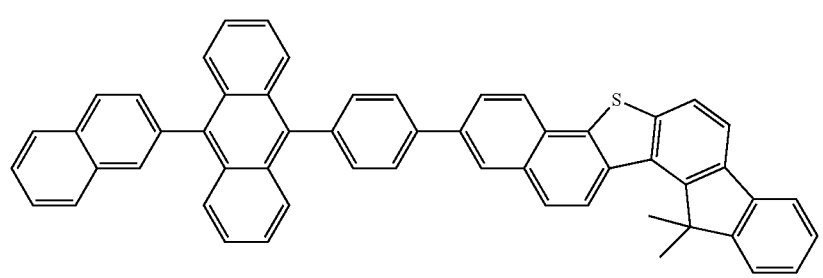

-continued
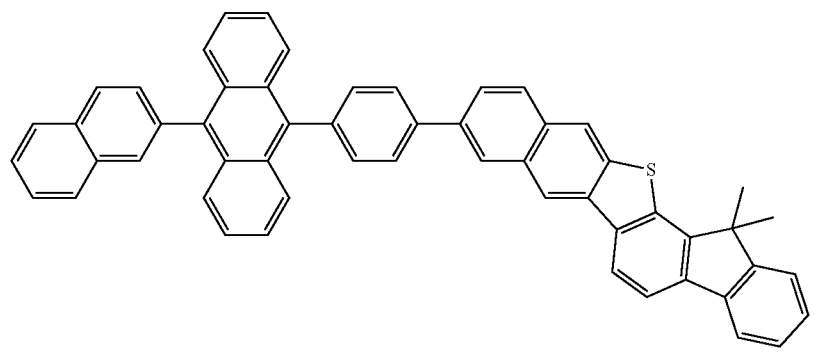
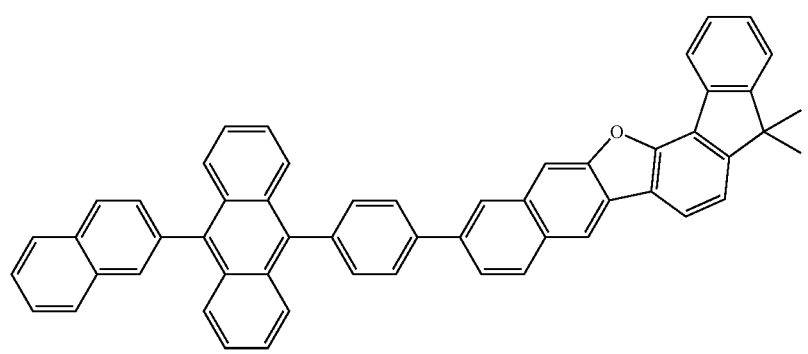
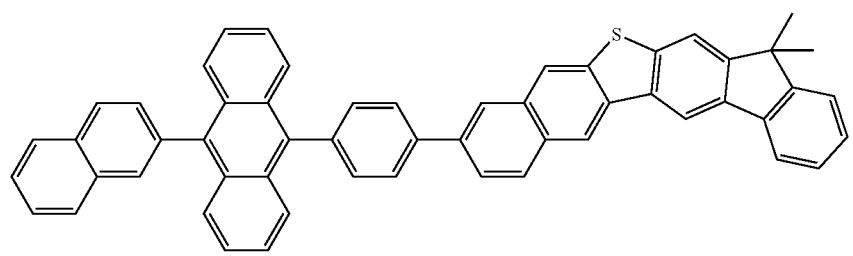
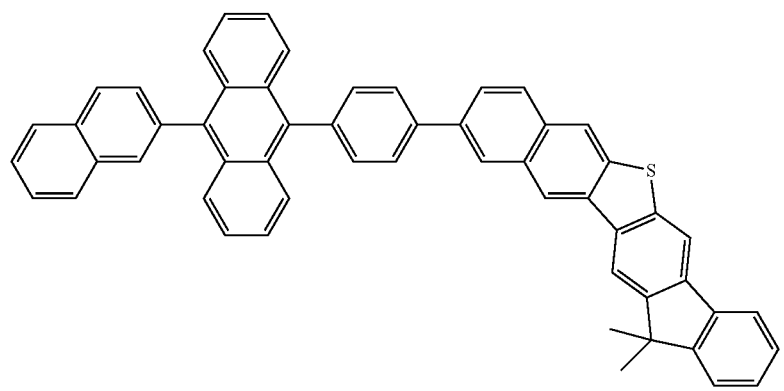
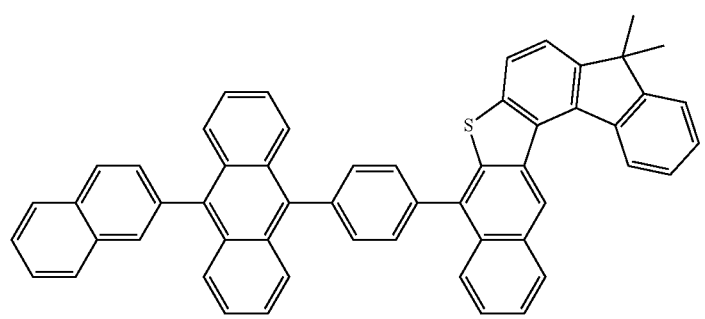

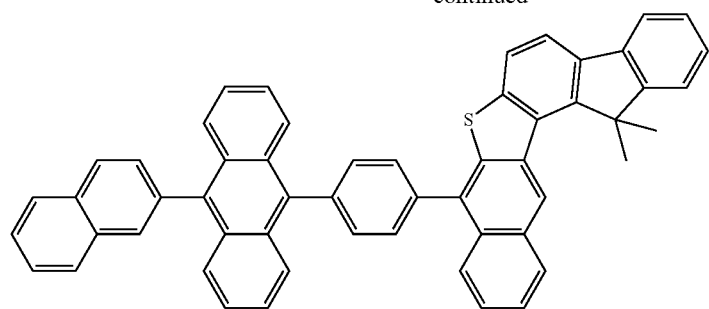
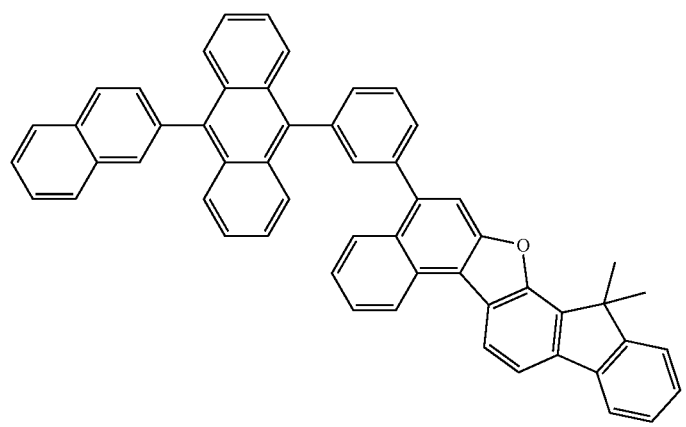
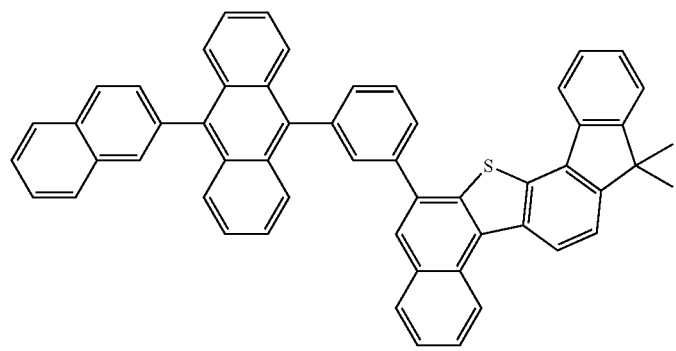
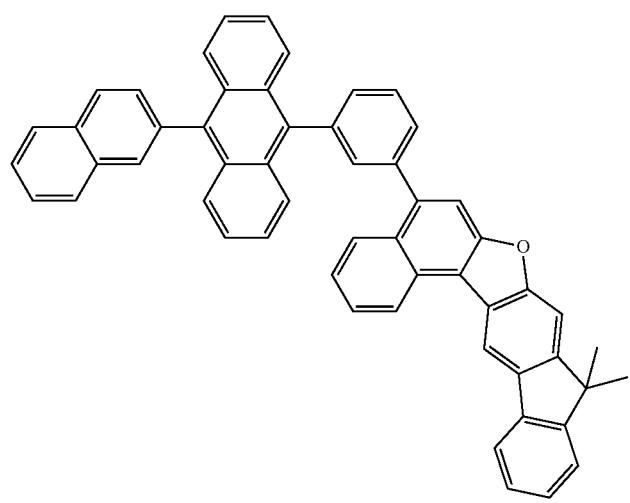

-continued
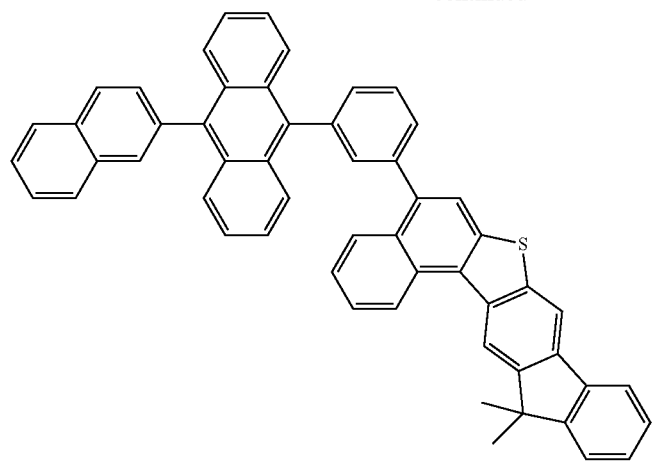
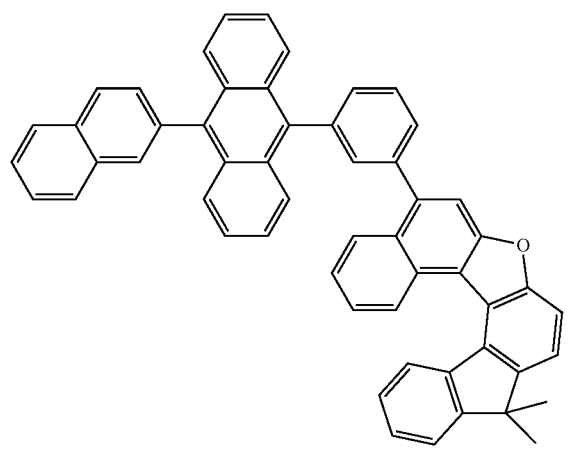
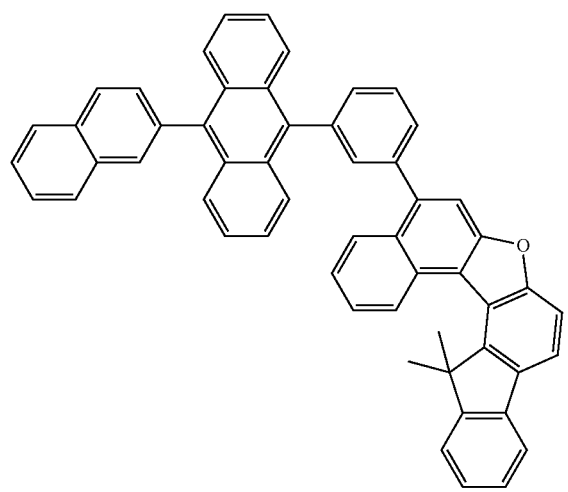

-continued
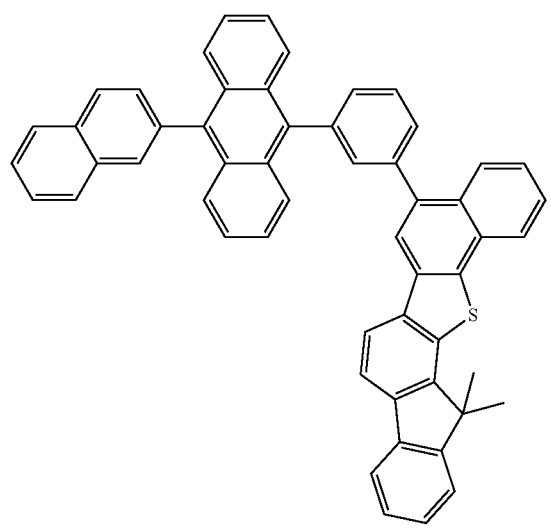
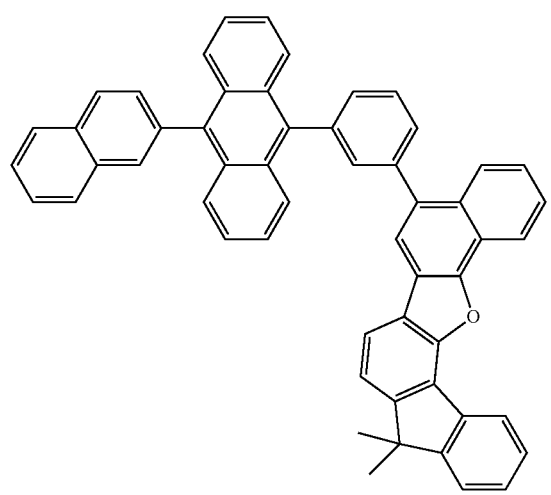
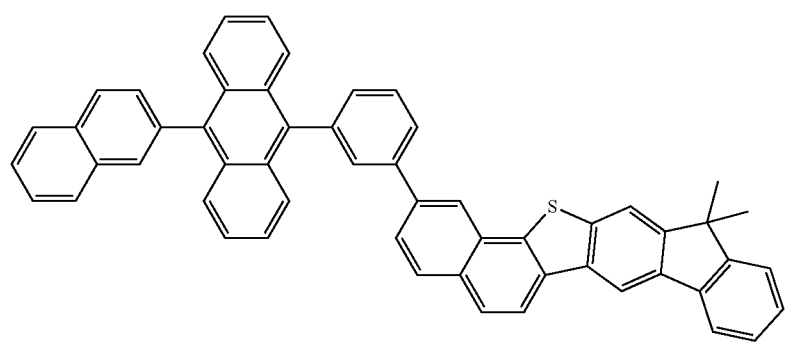

-continued
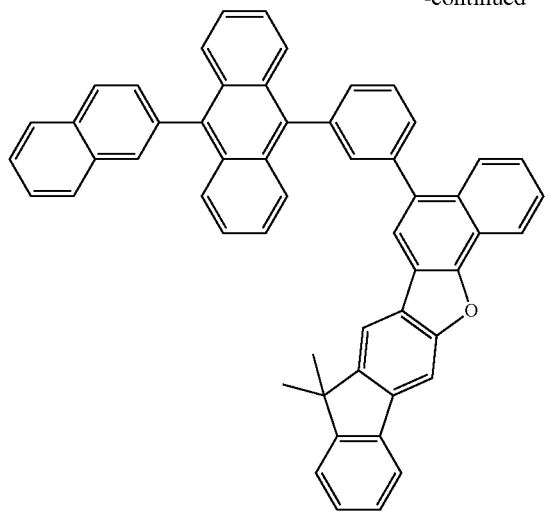
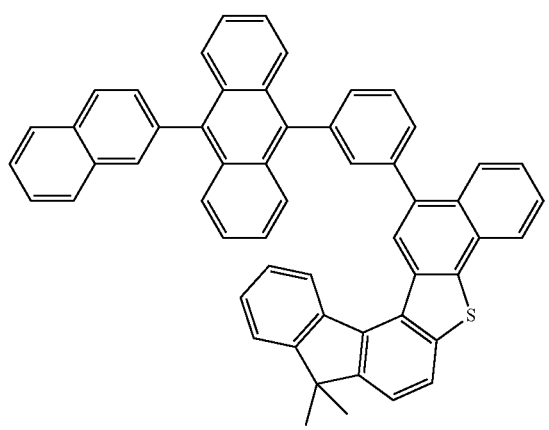
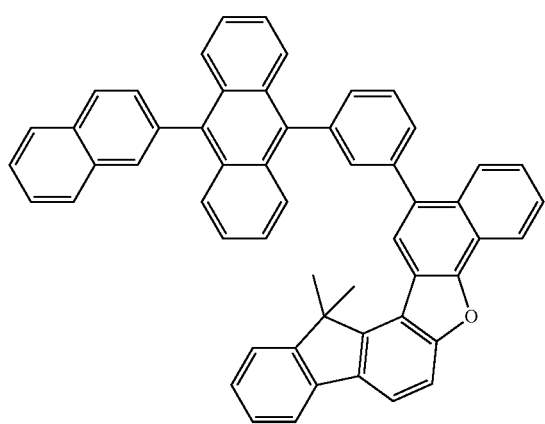

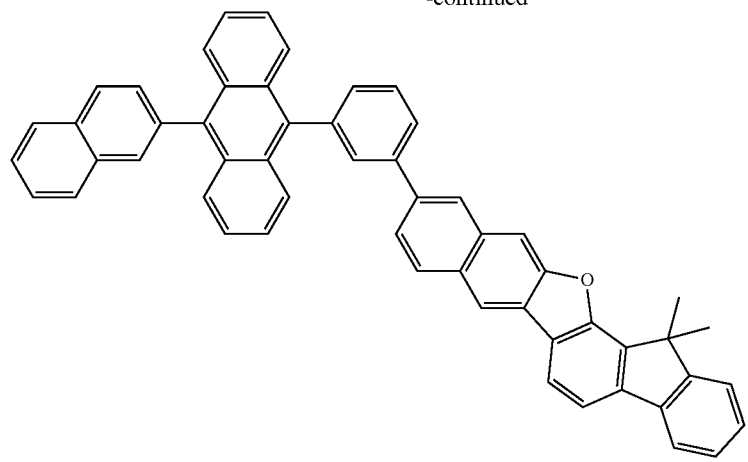
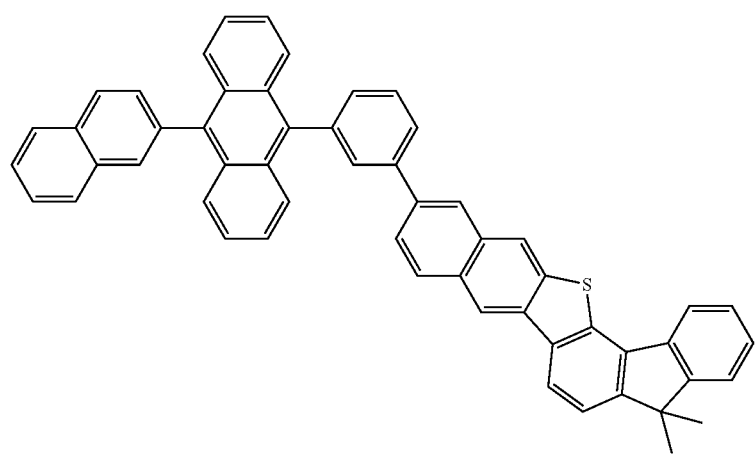
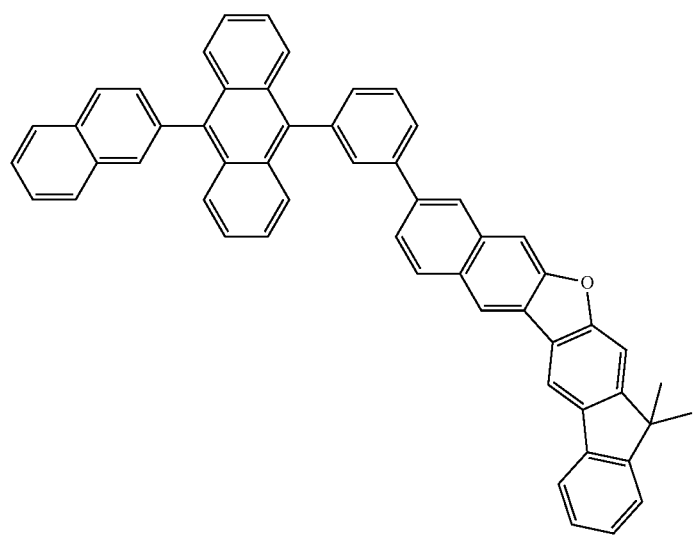

-continued
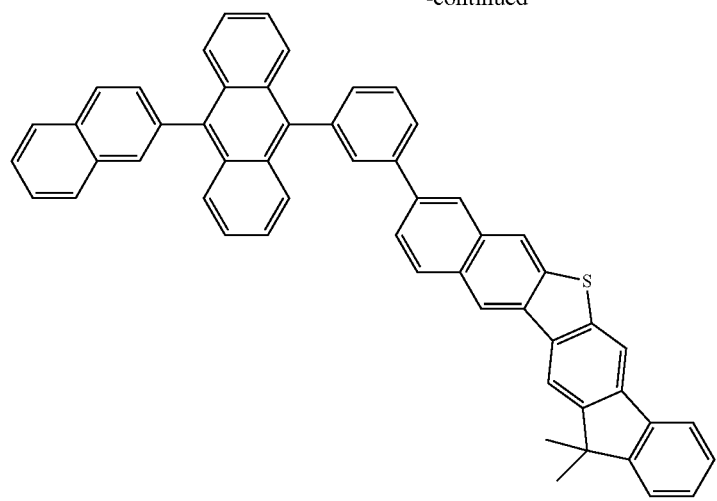
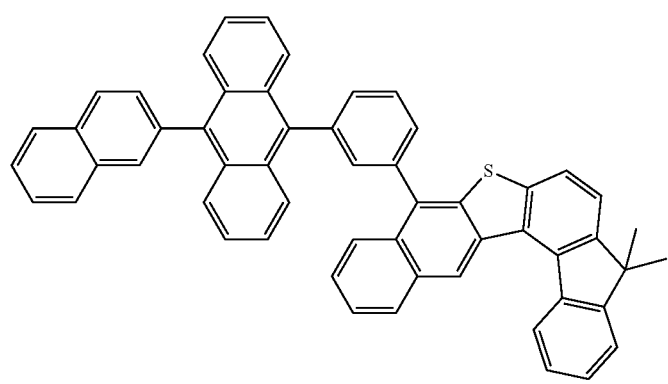
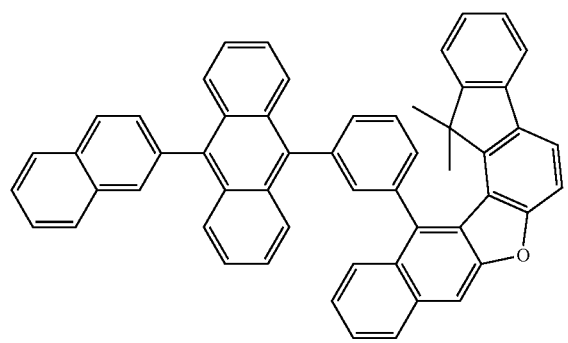
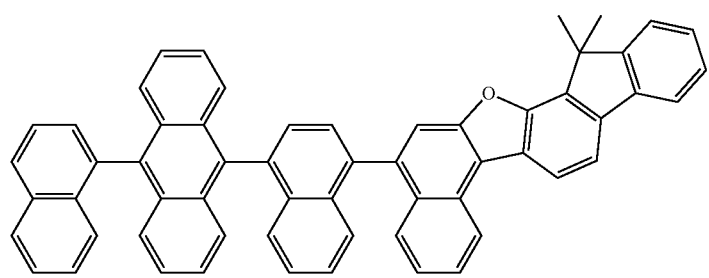

-continued
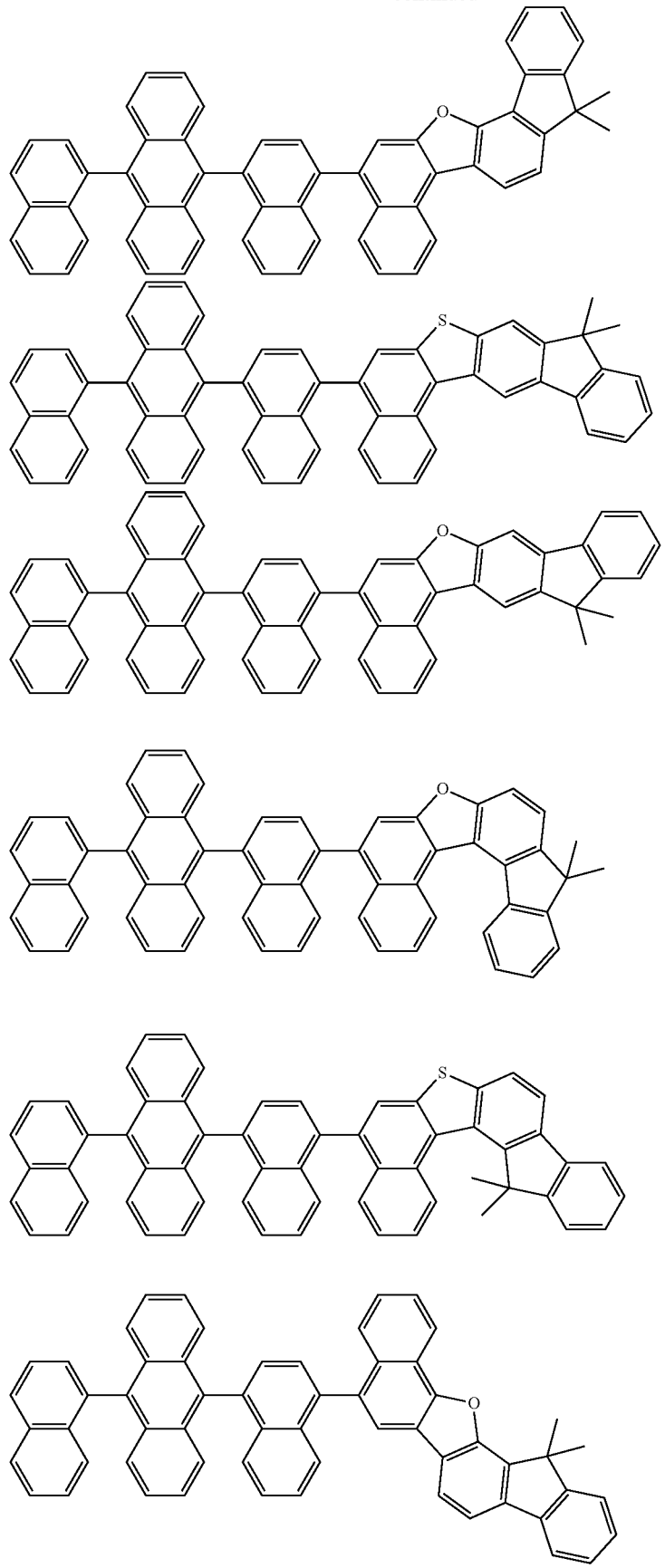

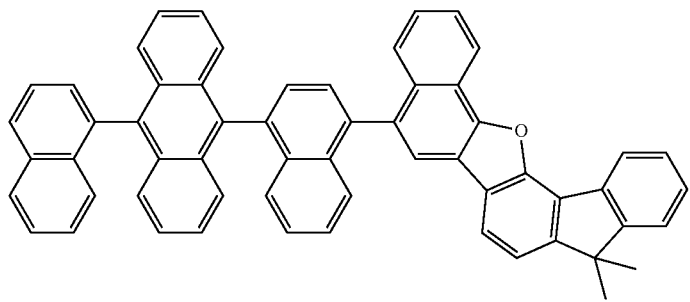

-continued
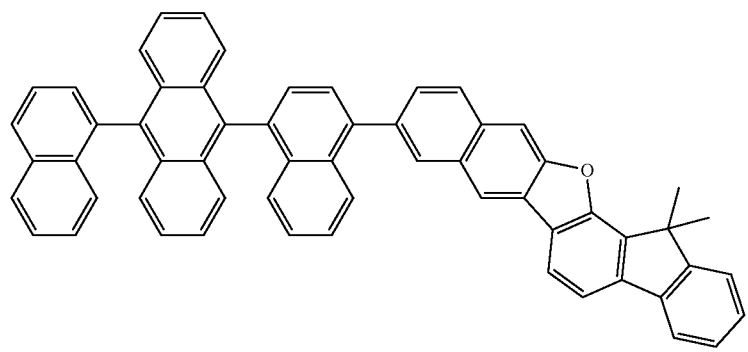
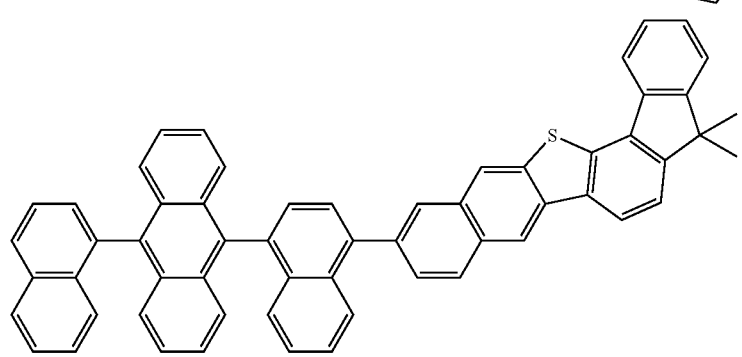
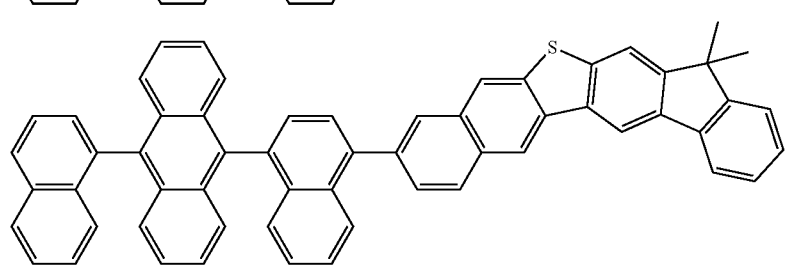
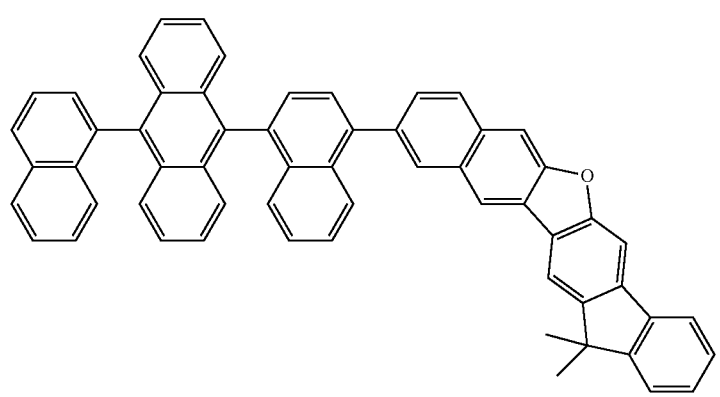
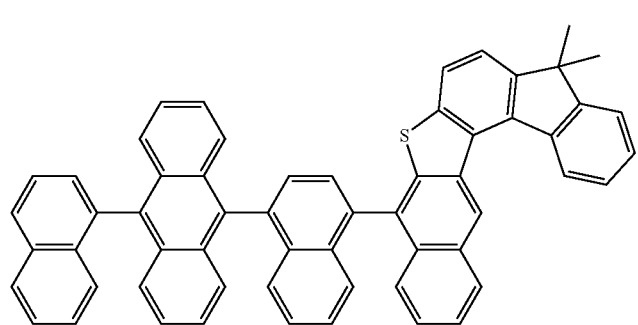

-continued
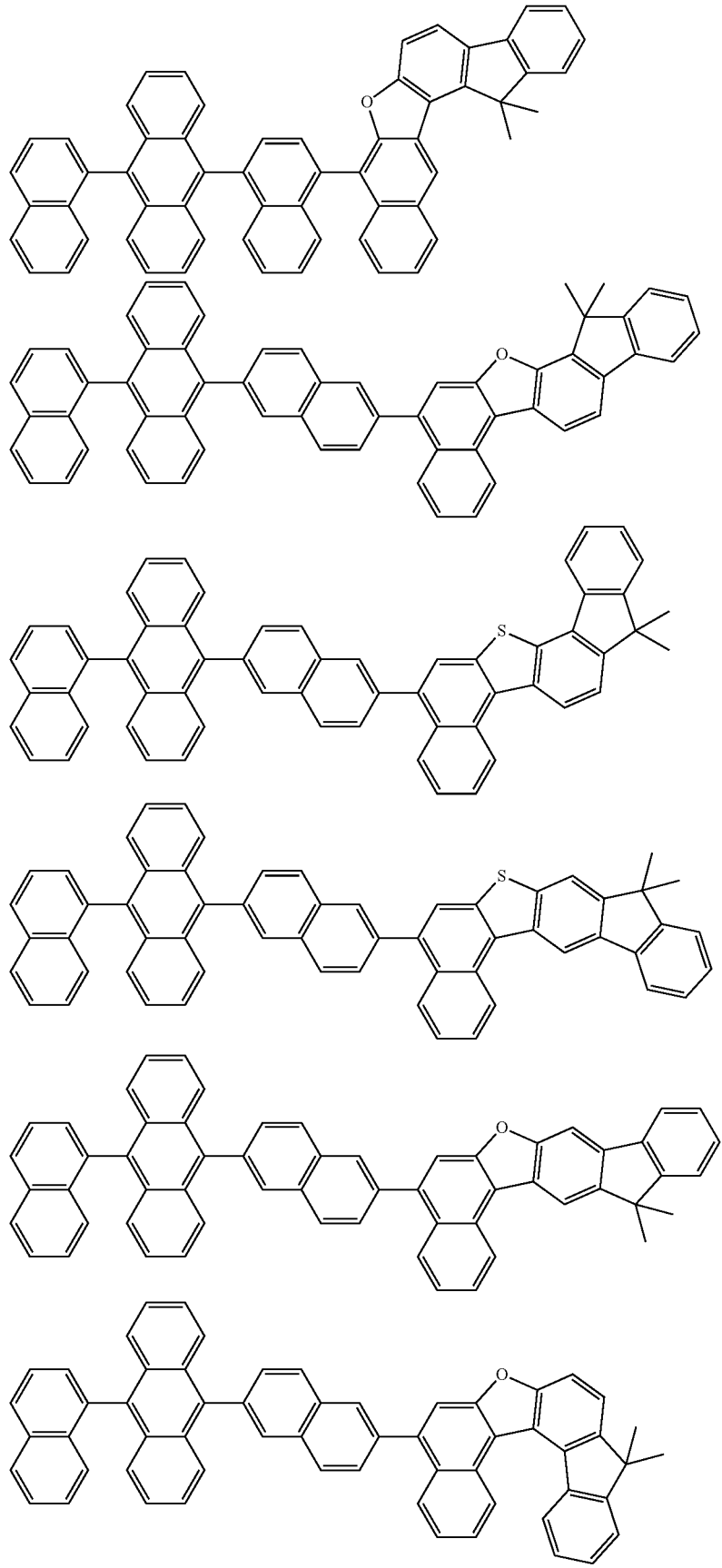

-continued
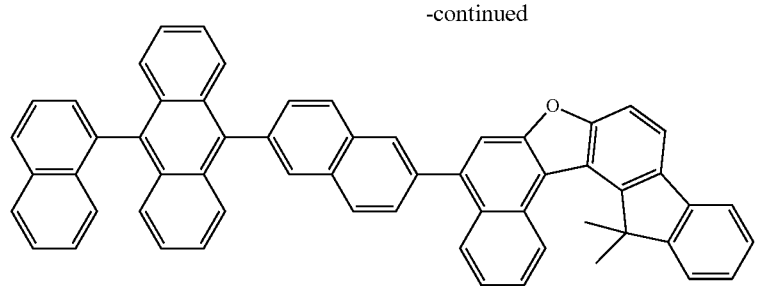
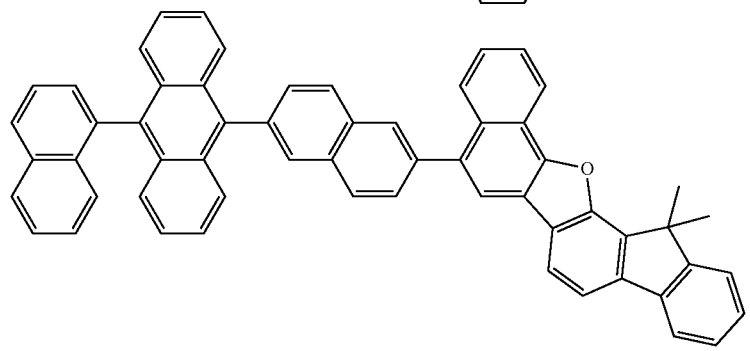
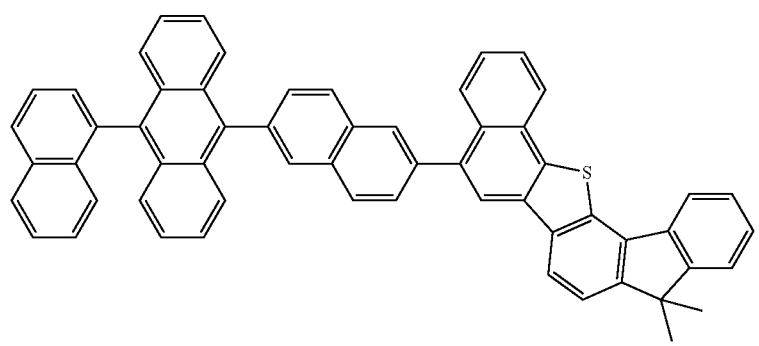
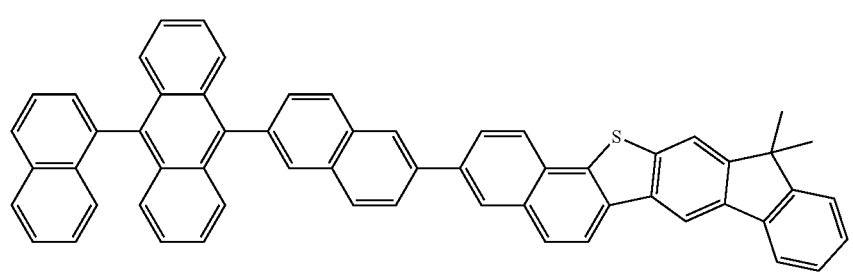
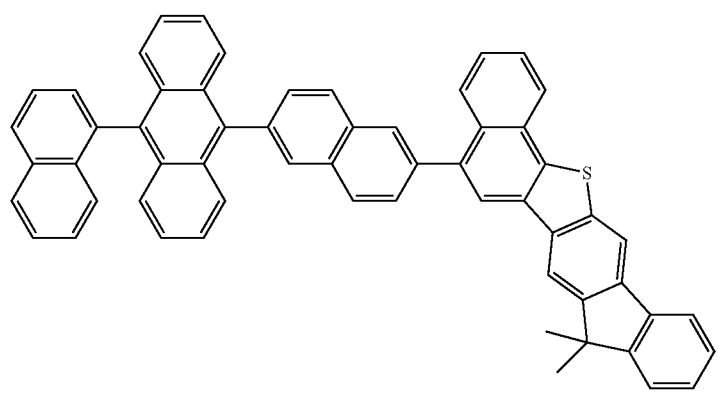

-continued
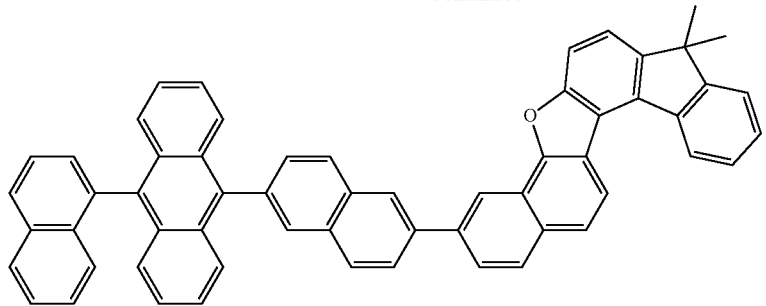

-continued
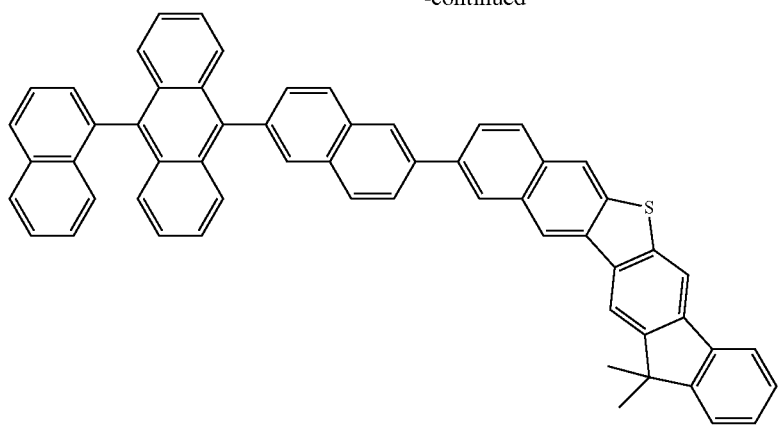
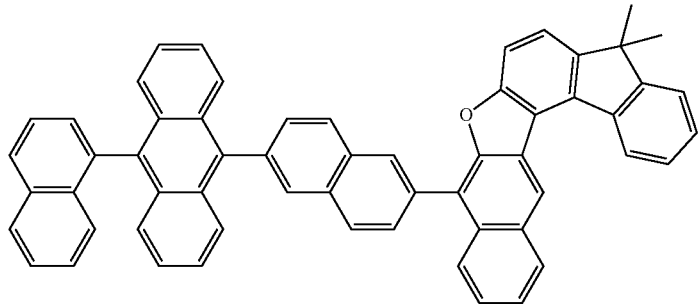
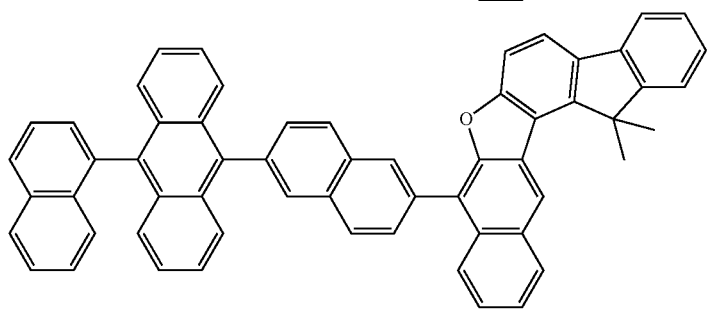
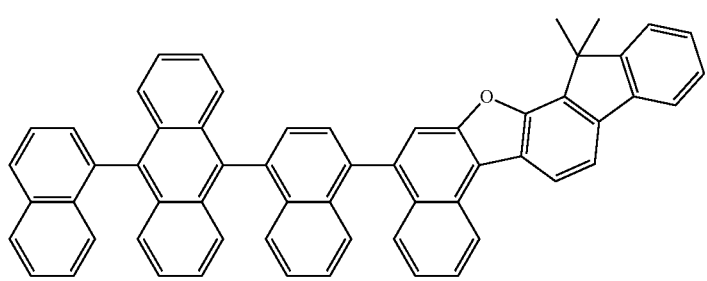
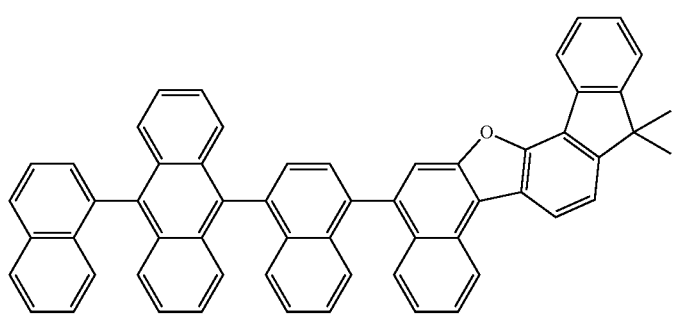

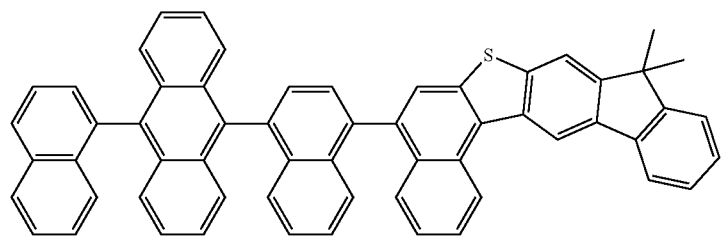

-continued
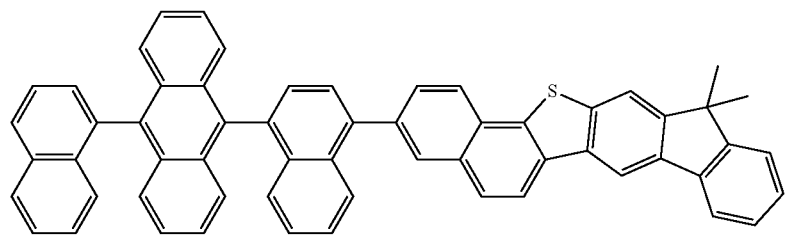
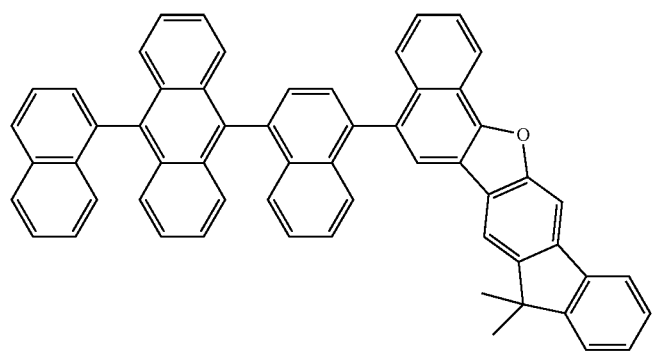
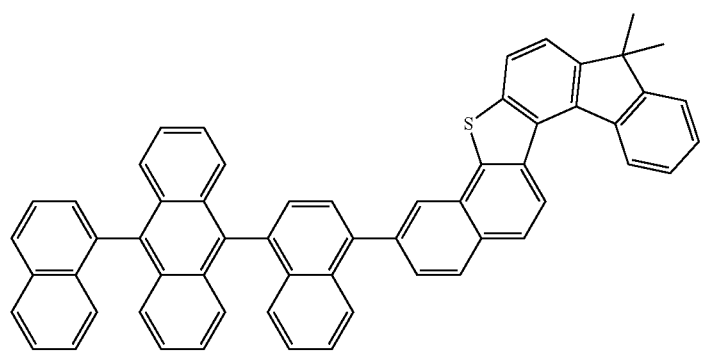
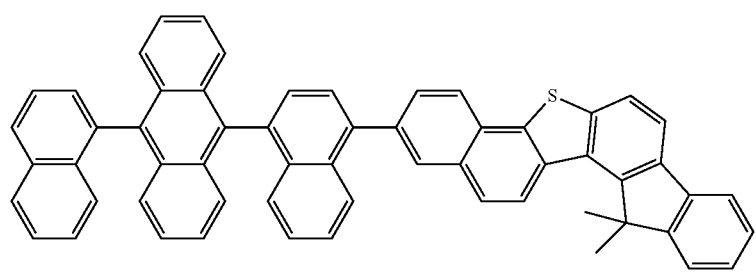
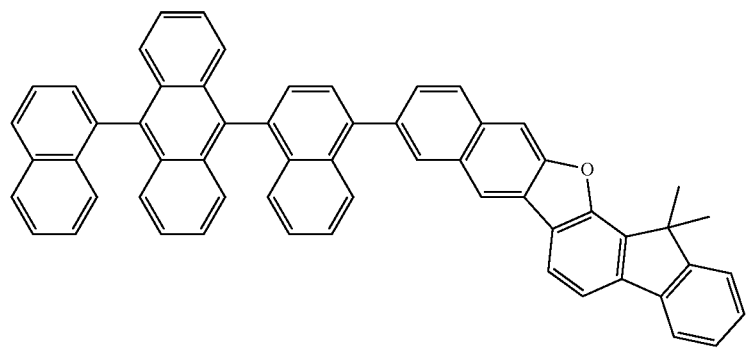

-continued
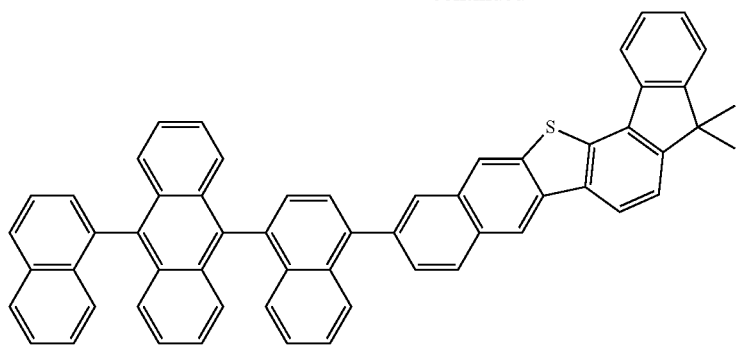
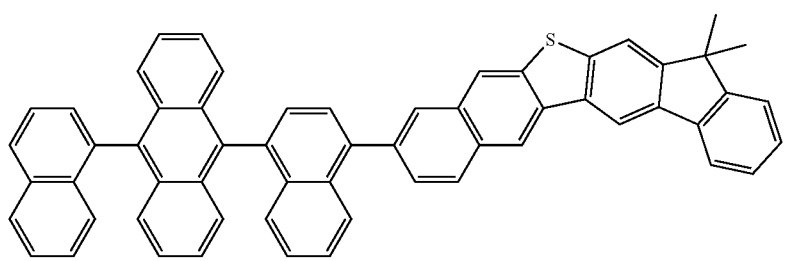
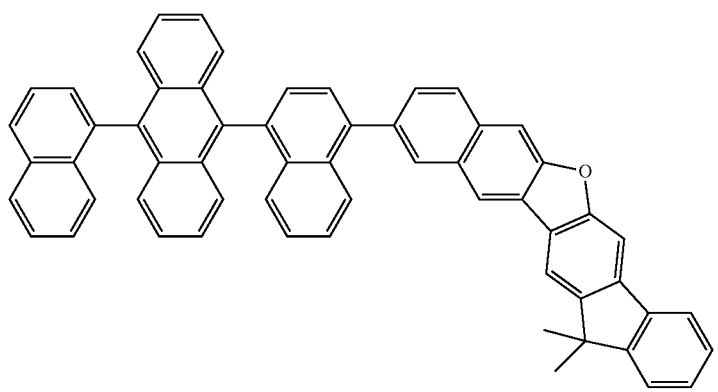
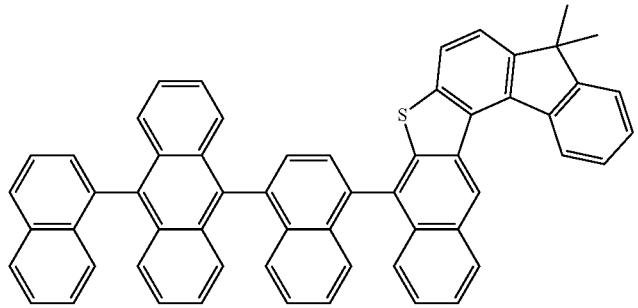
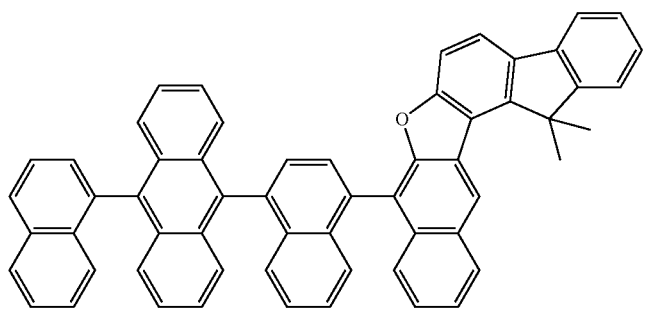

-continued
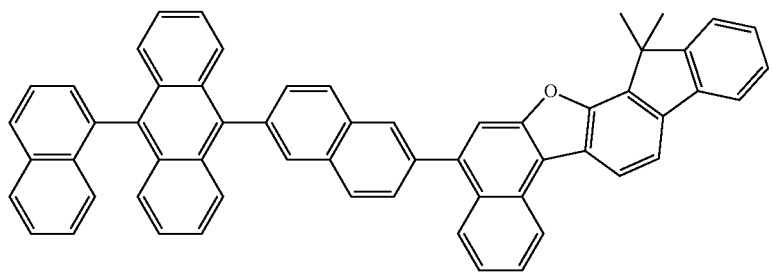
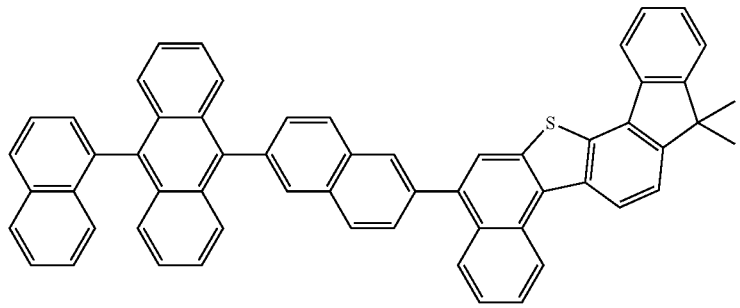
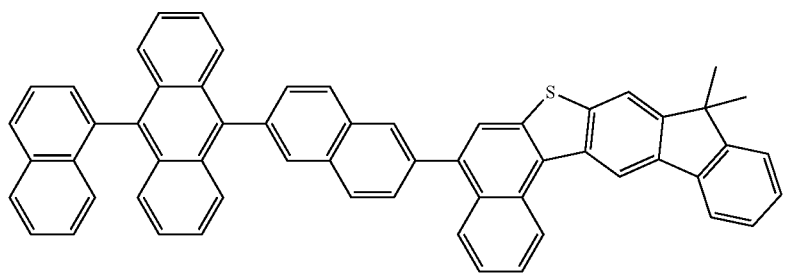
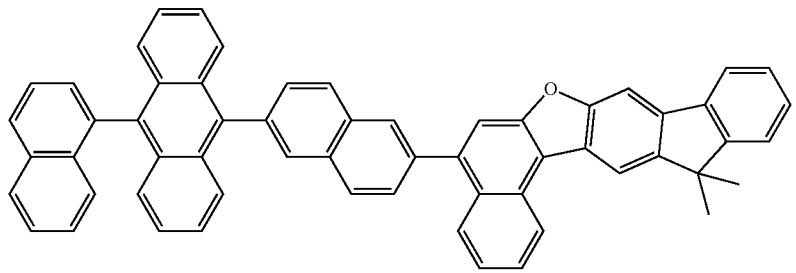
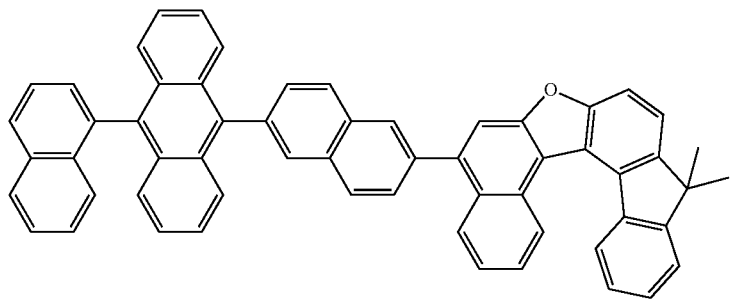
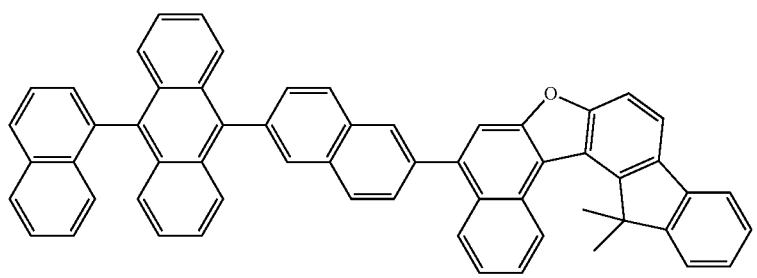

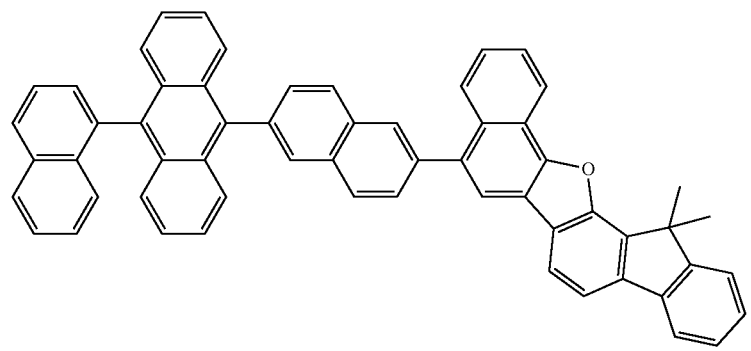
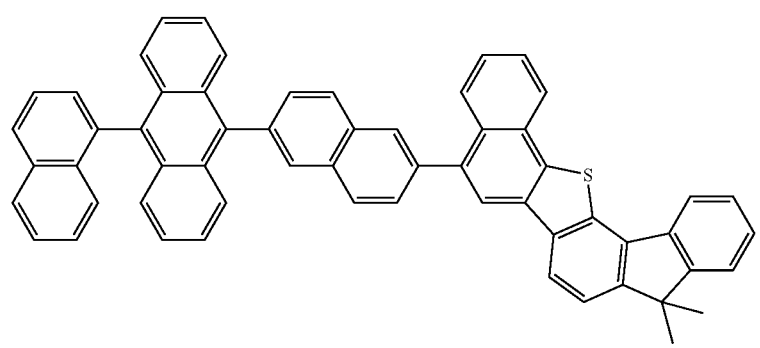
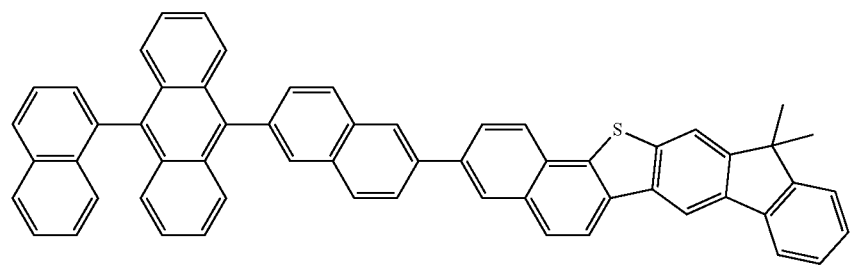
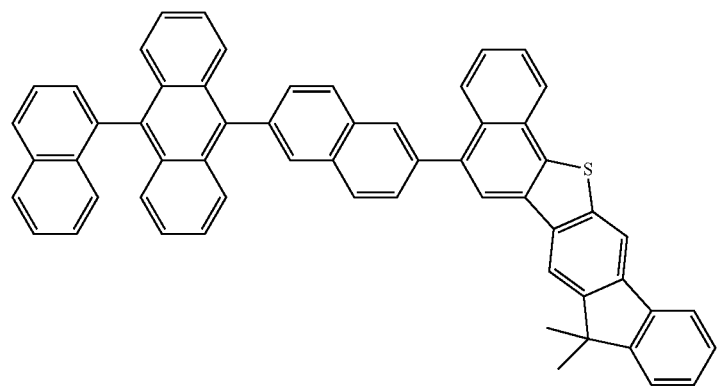
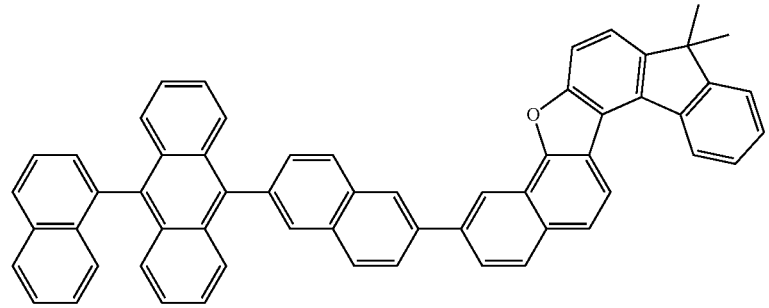

-continued
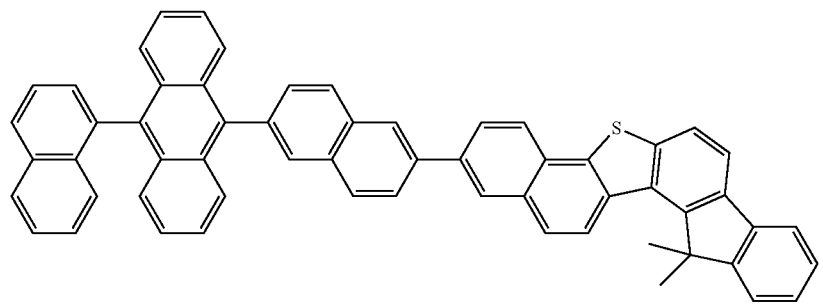
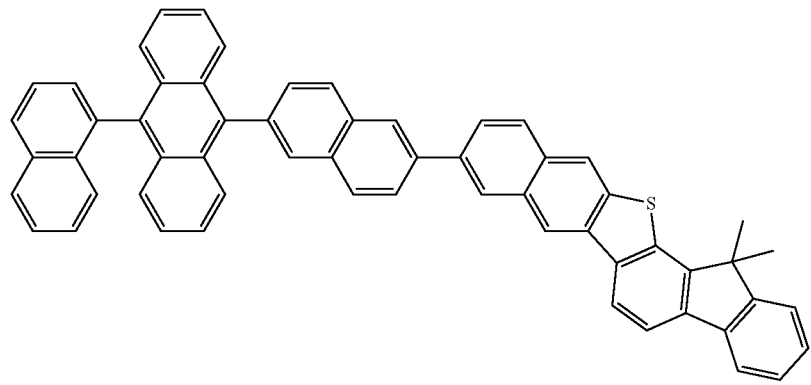
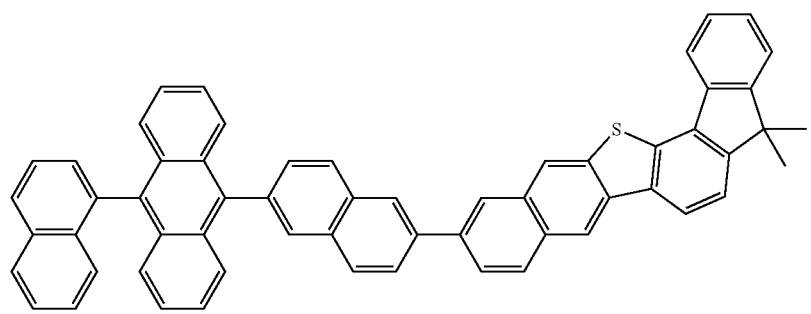
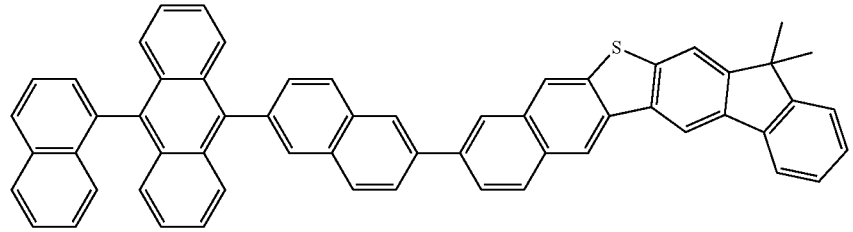
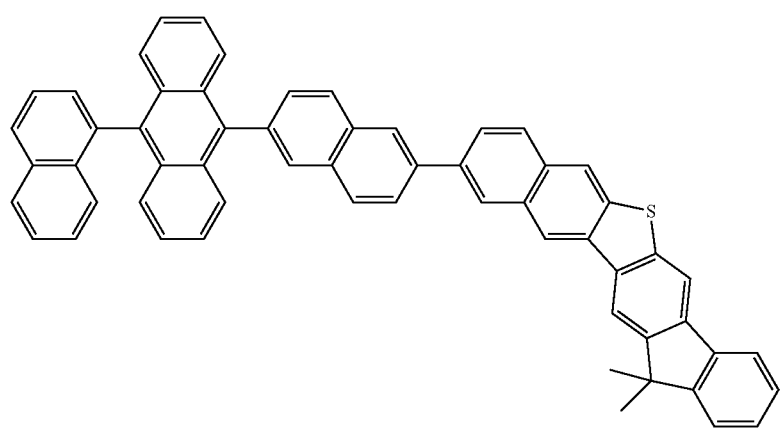

-continued
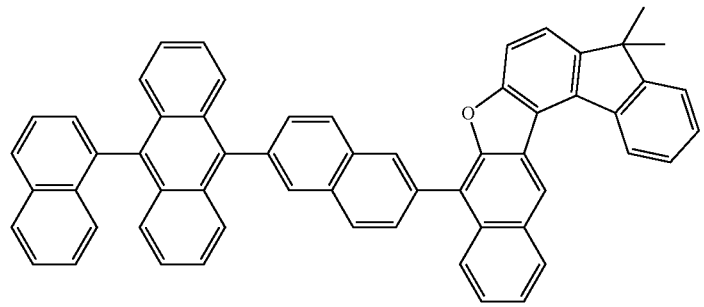
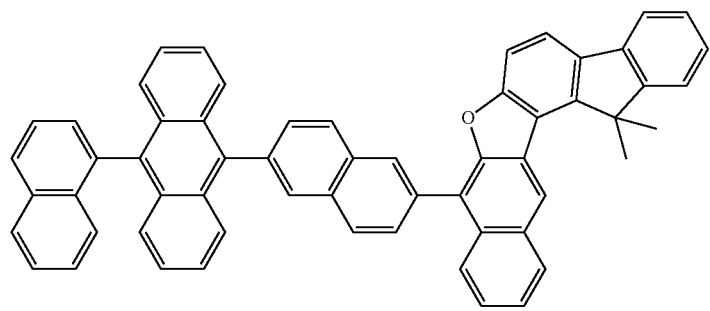
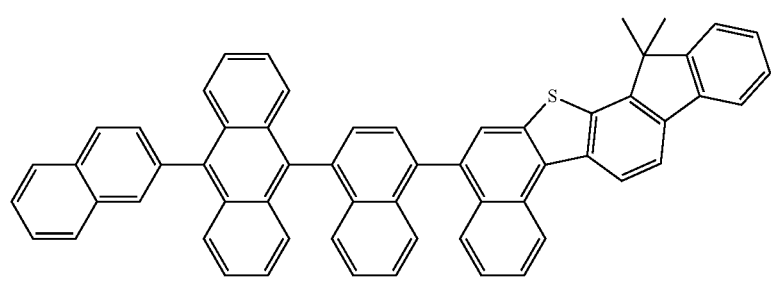
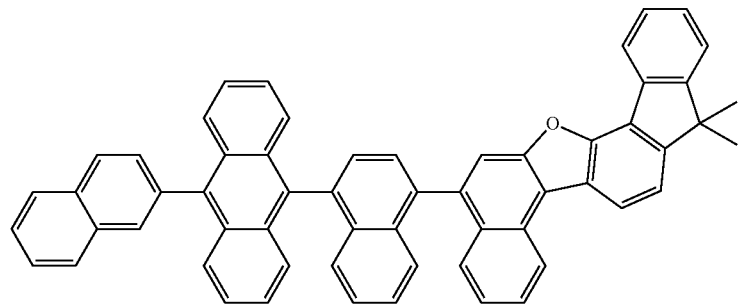
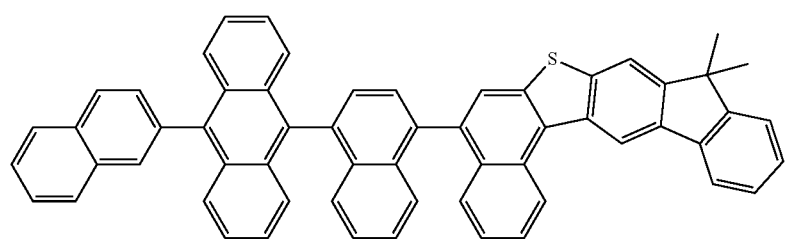
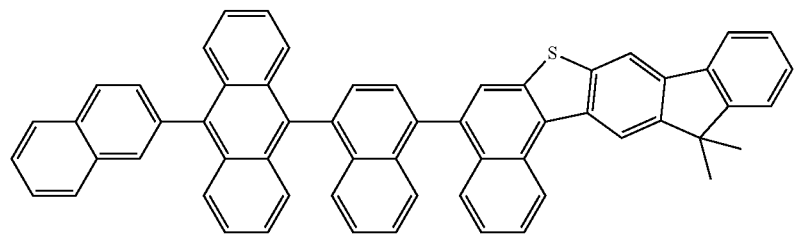

-continued
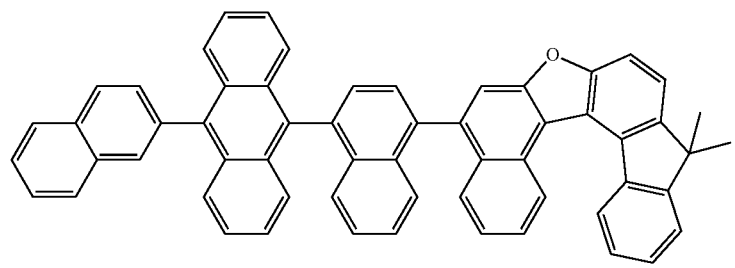
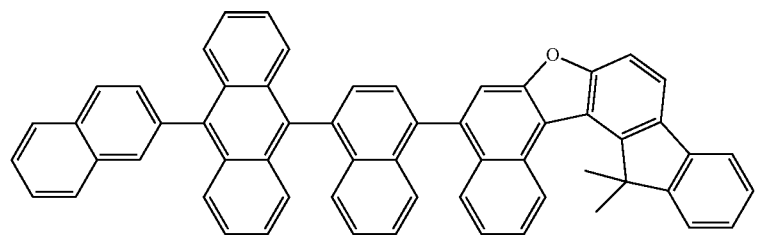
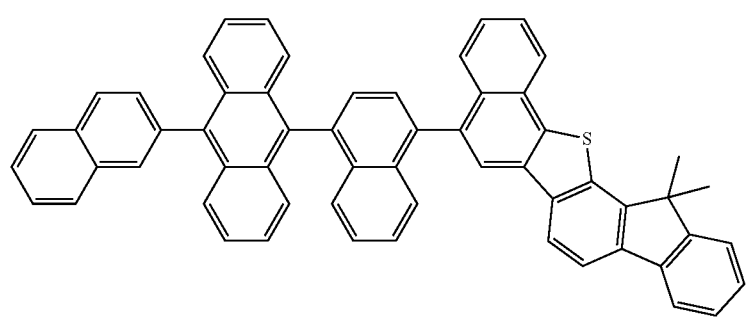
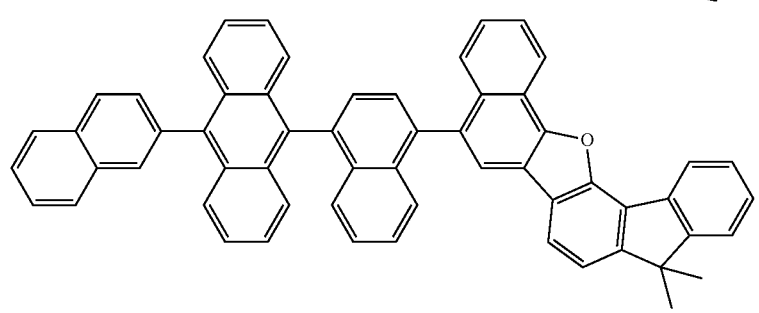
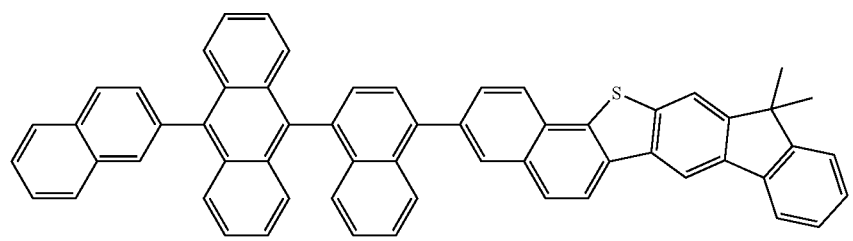
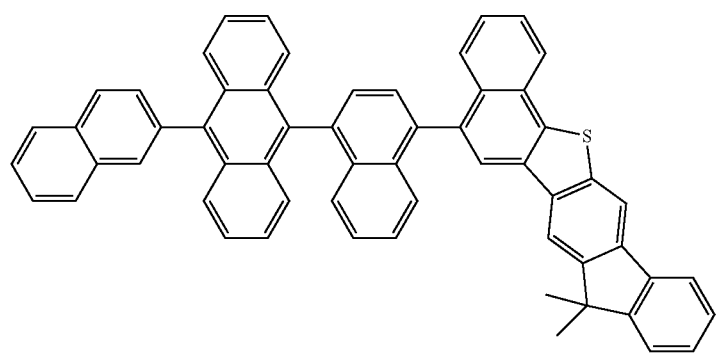

-continued
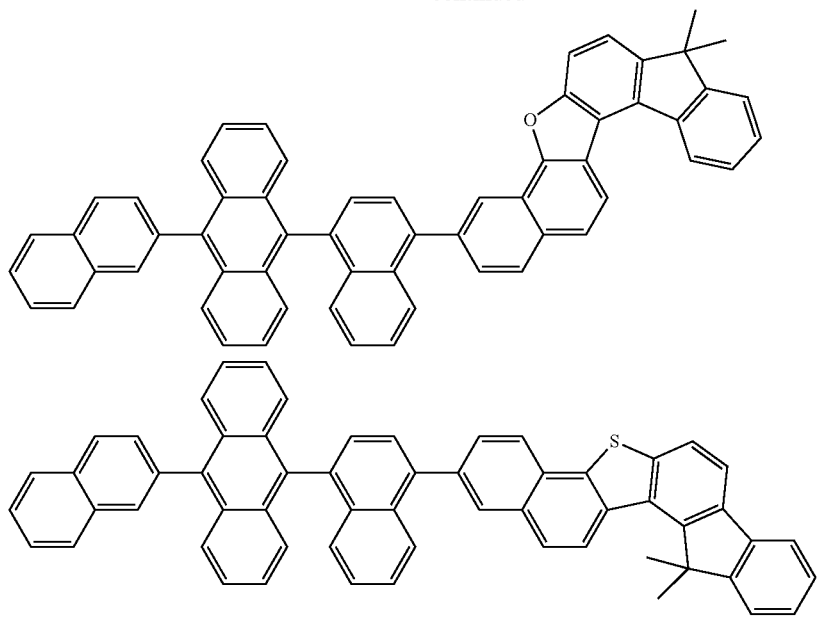
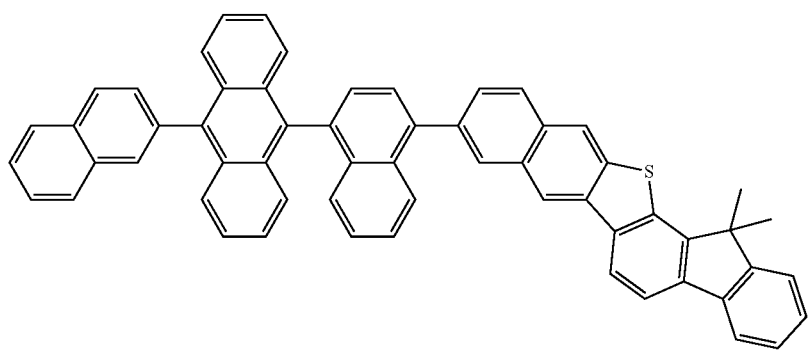
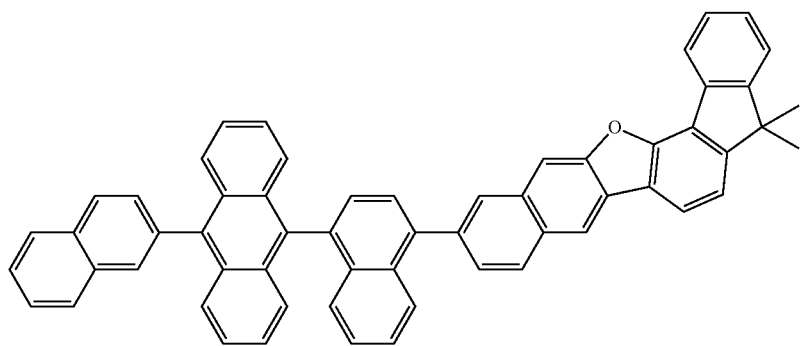
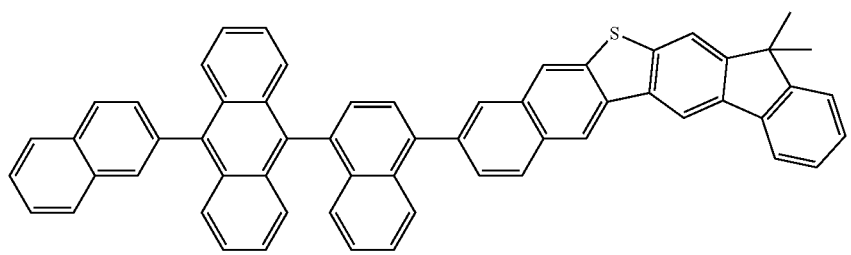

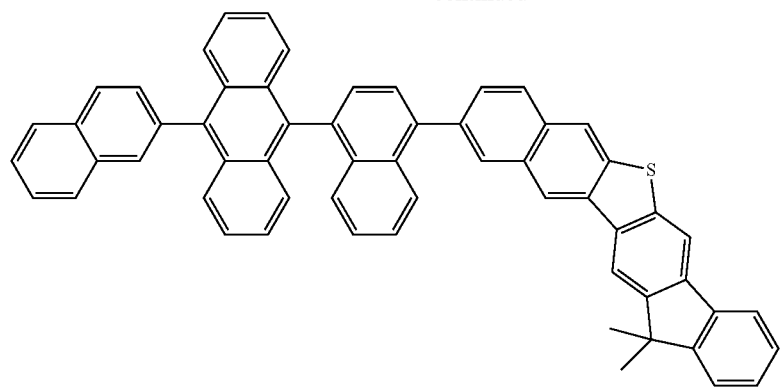

-continued
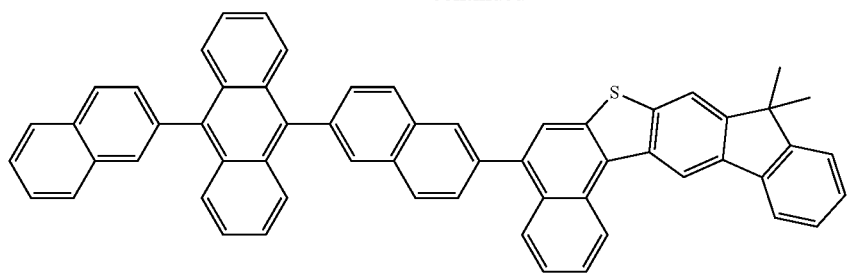
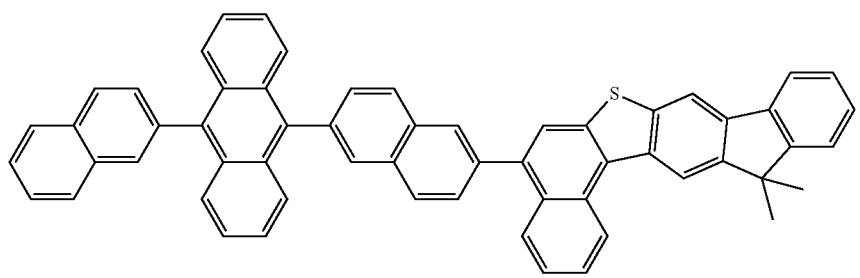
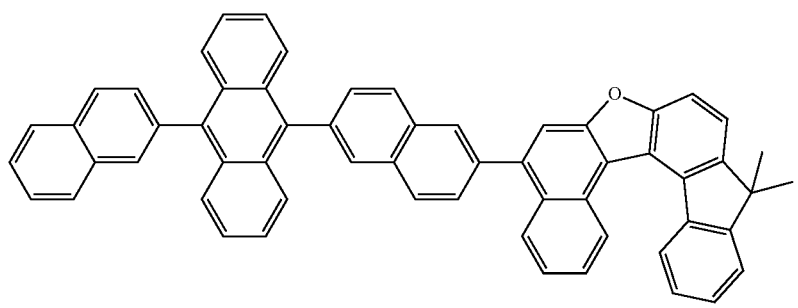
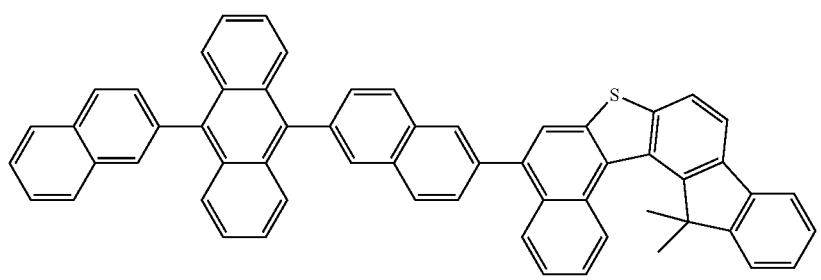
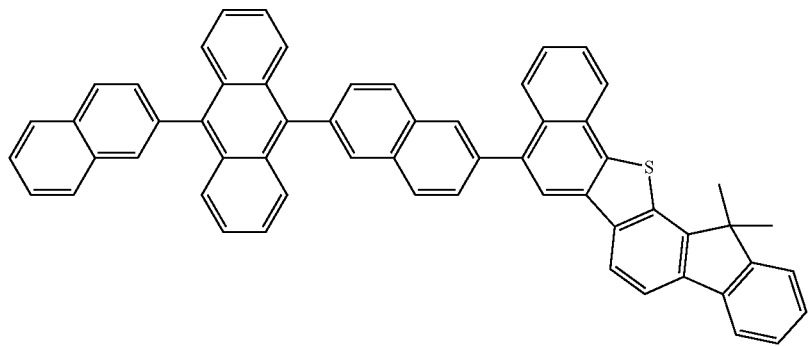

-continued
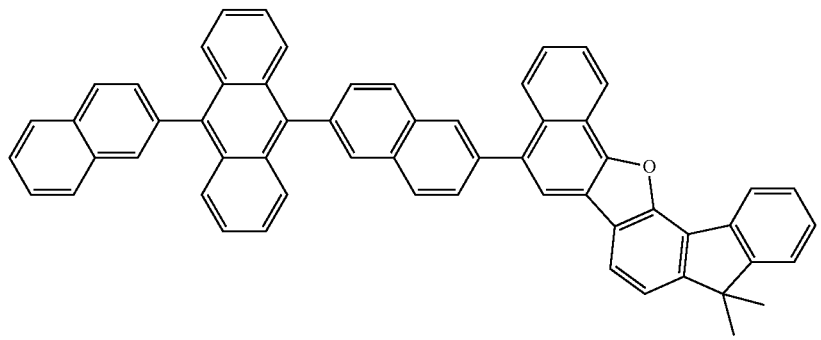
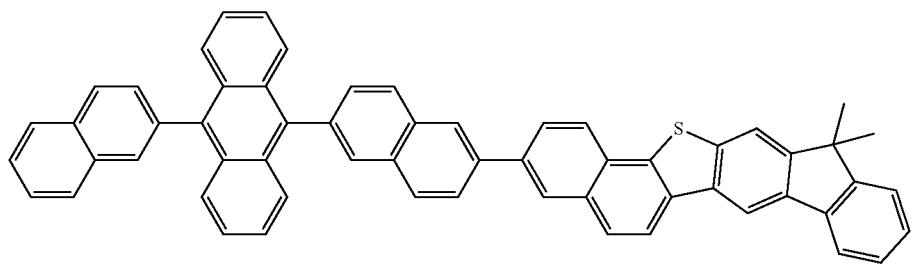
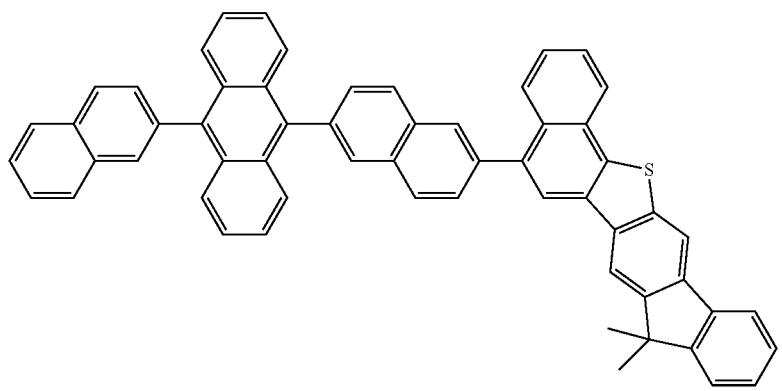
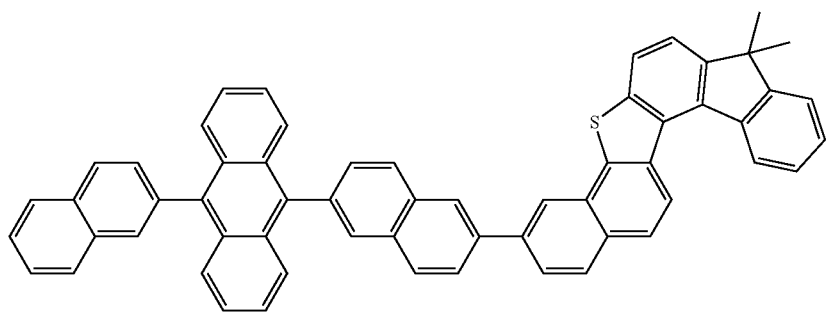
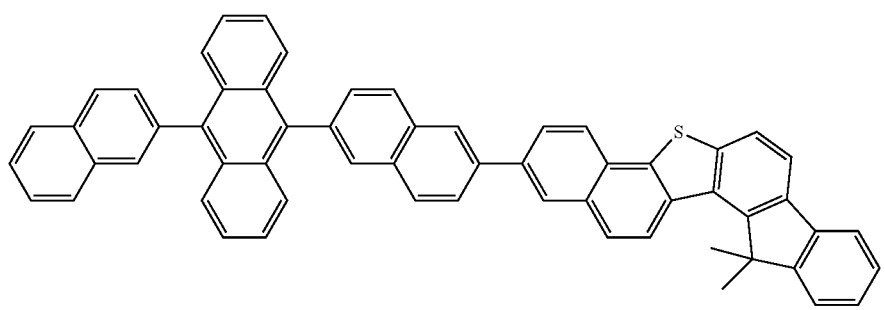

-continued
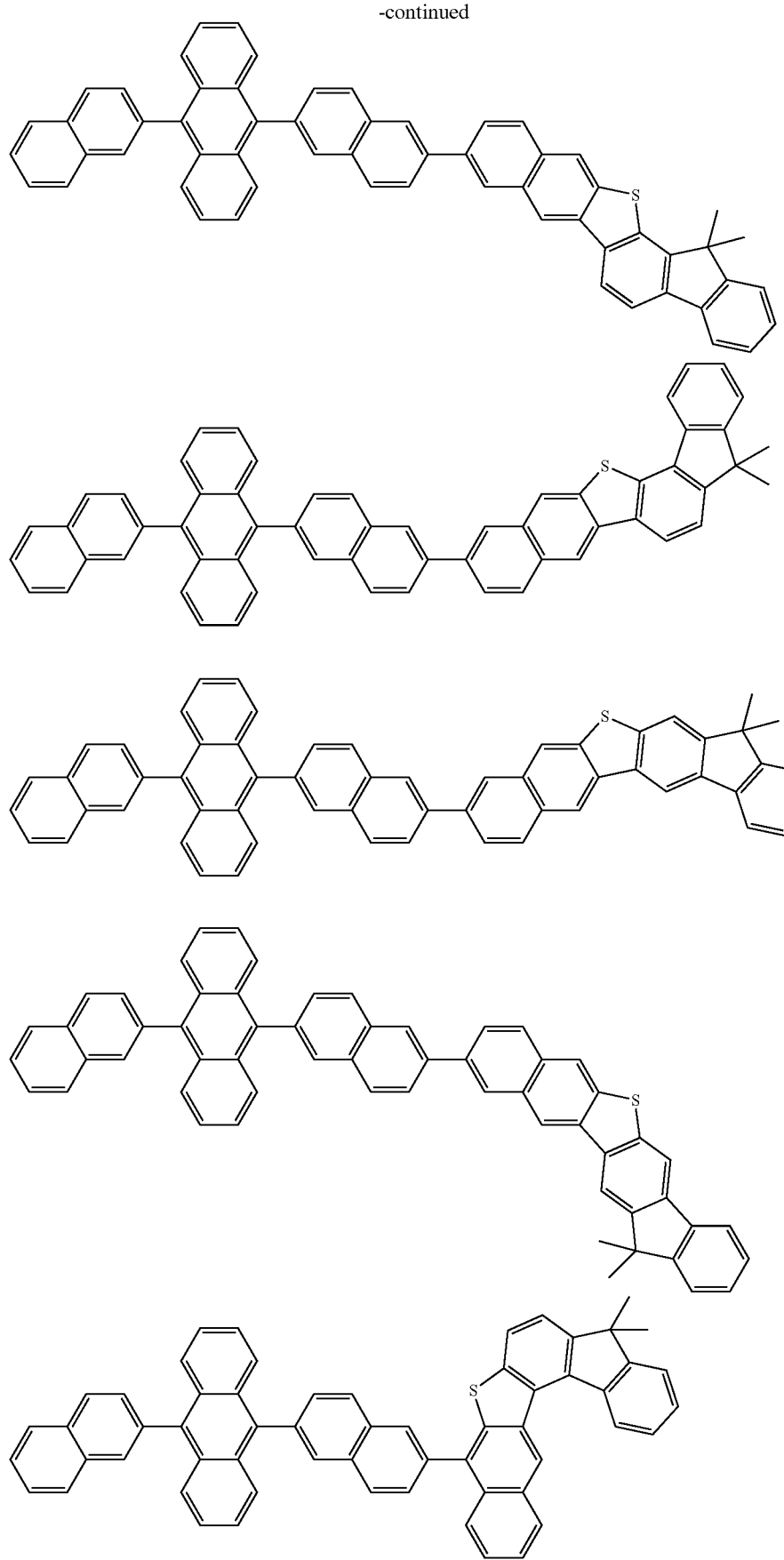

-continued
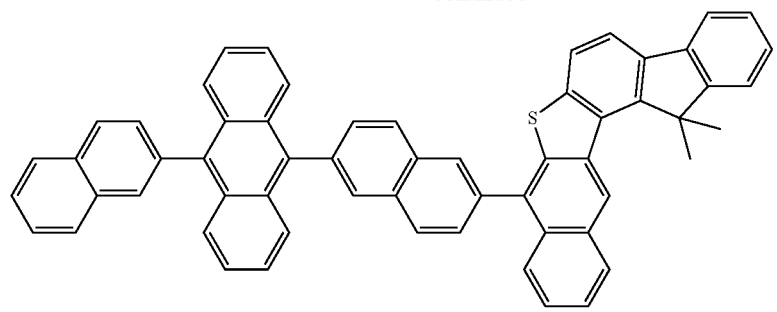
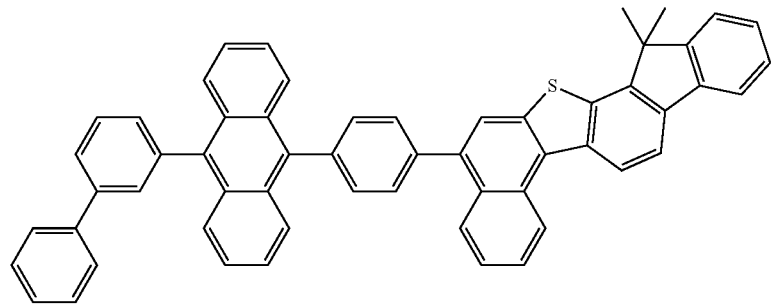
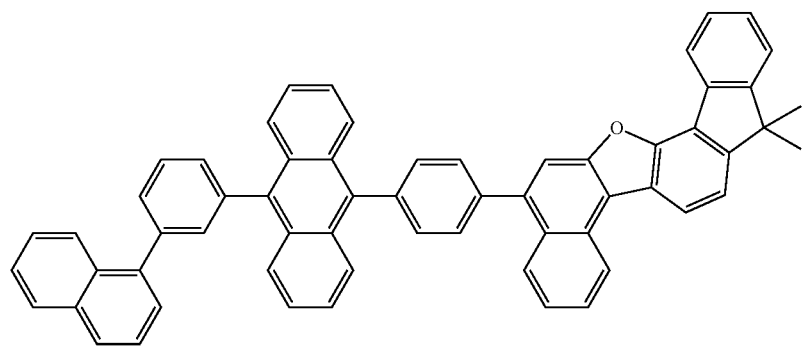
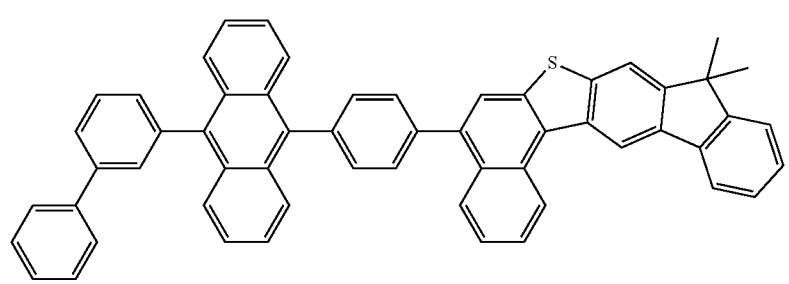
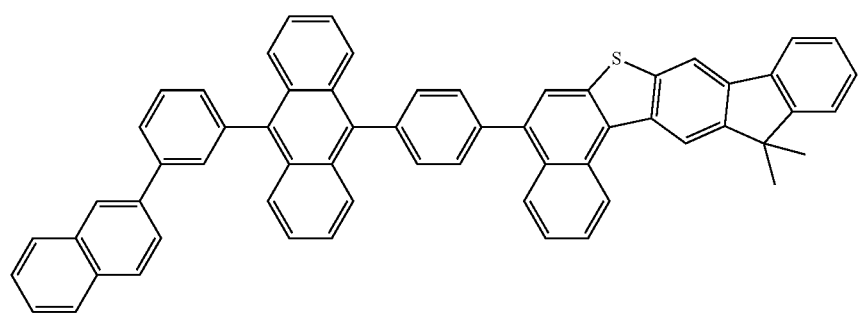

-continued
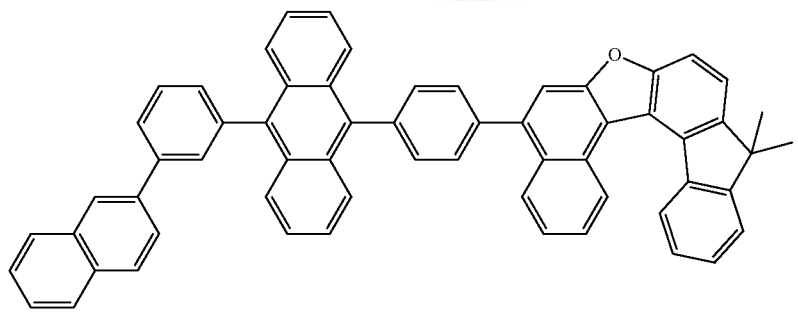
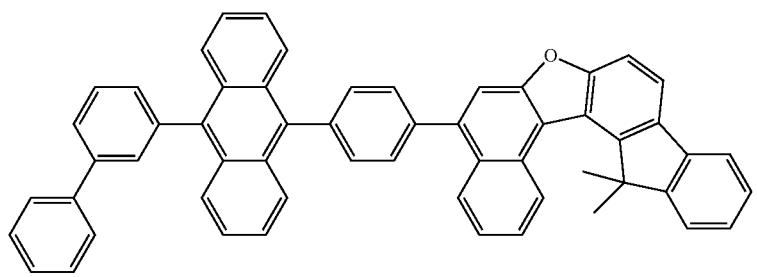
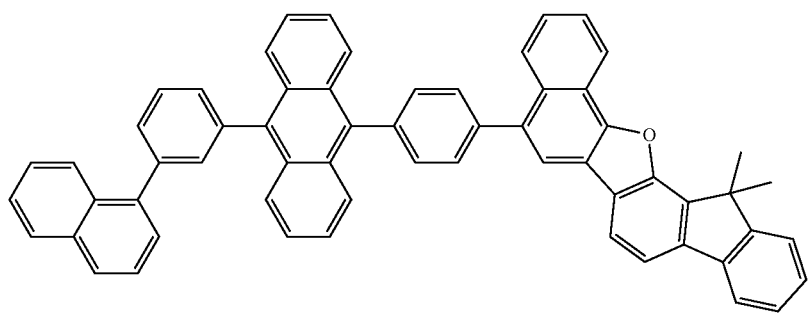
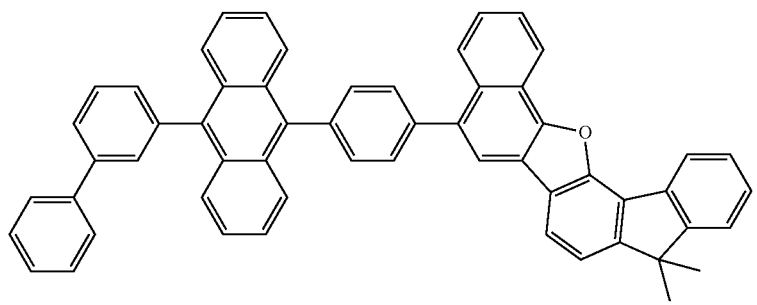
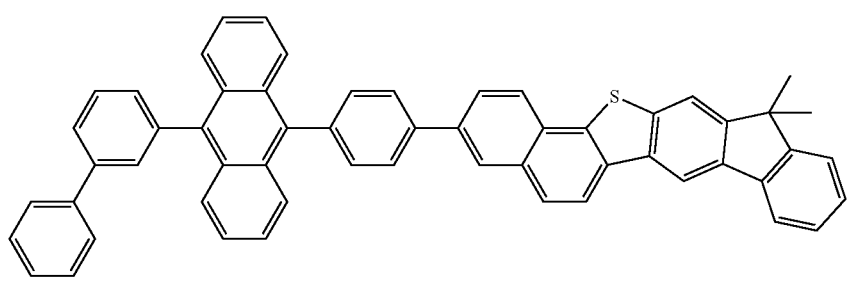

-continued
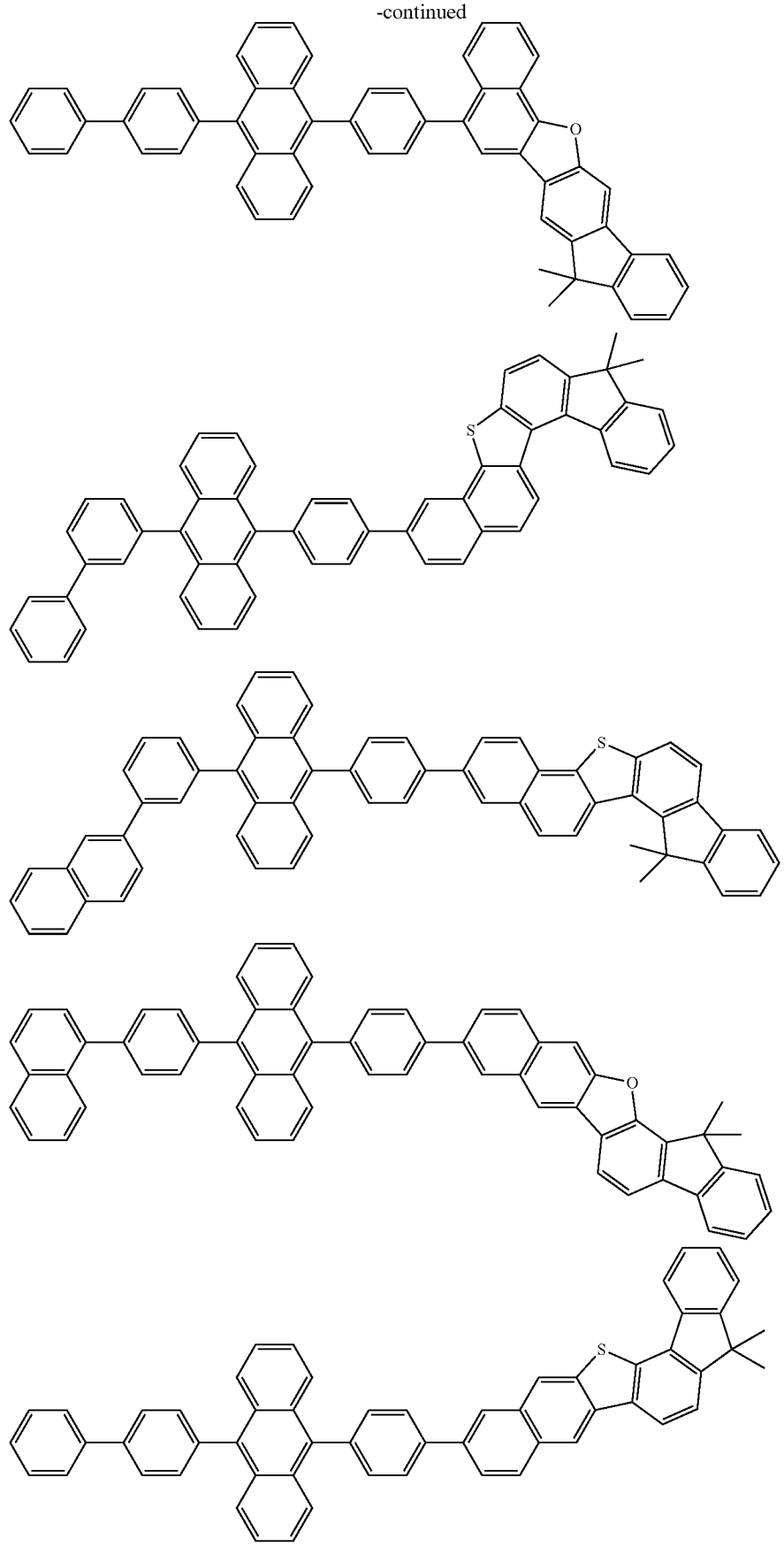

-continued
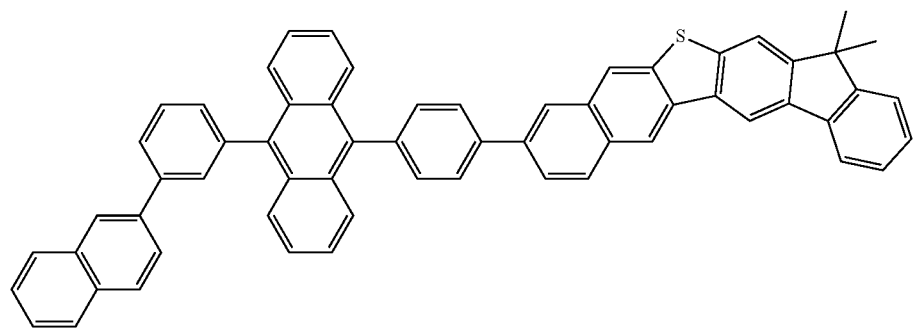
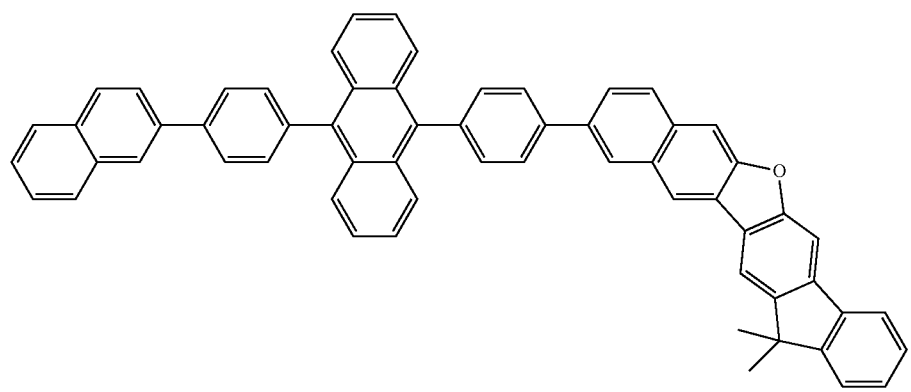
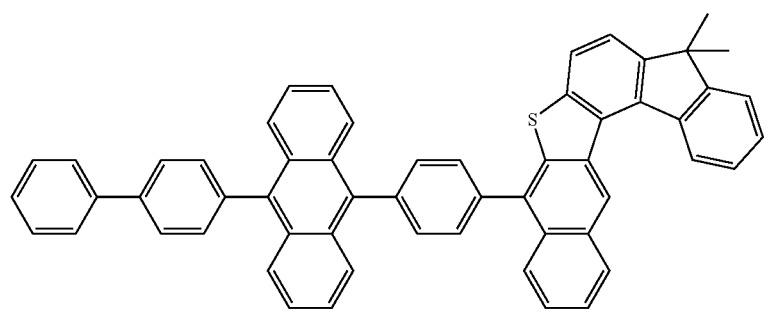
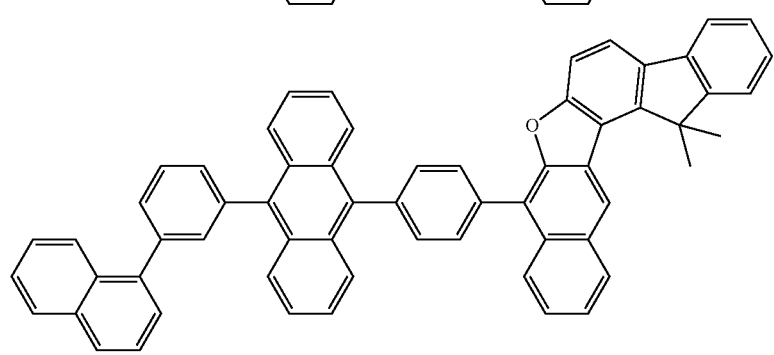
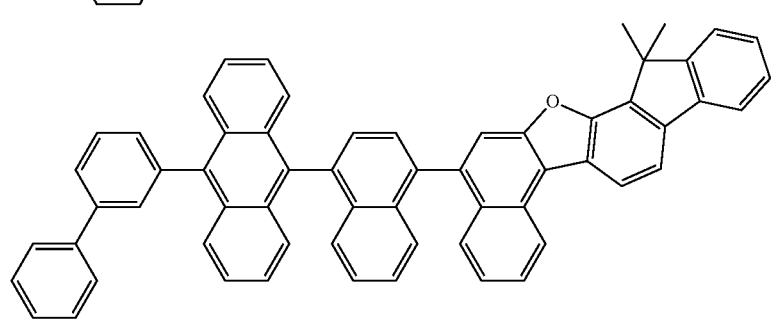

-continued
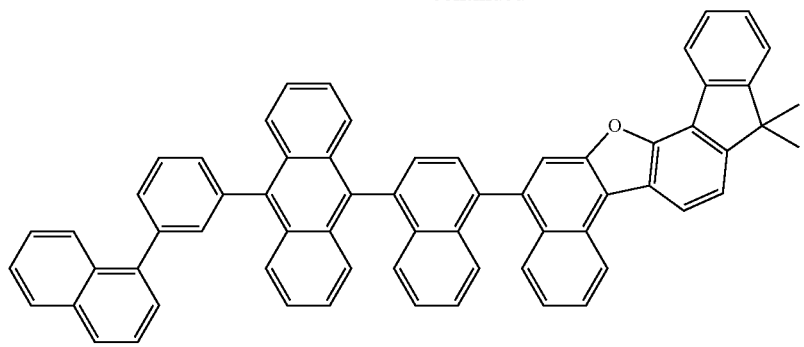
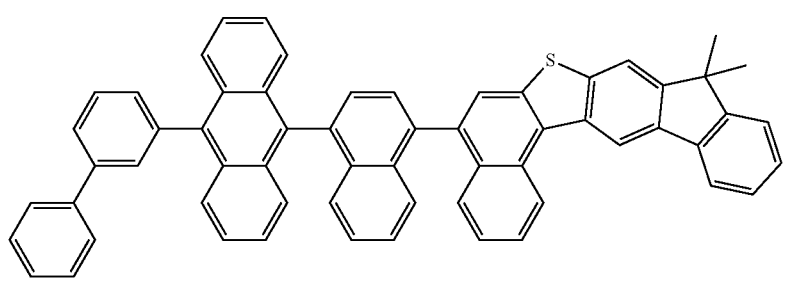
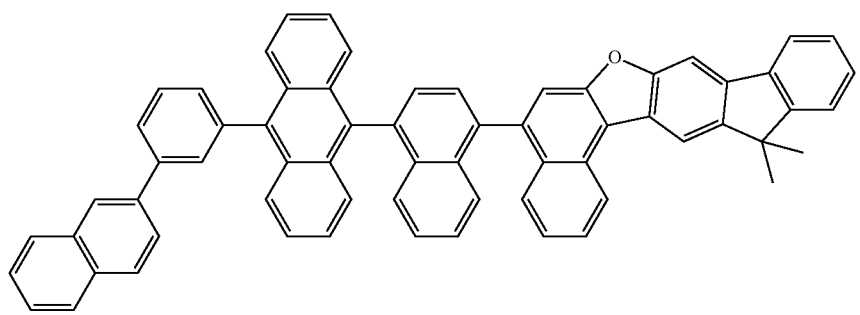
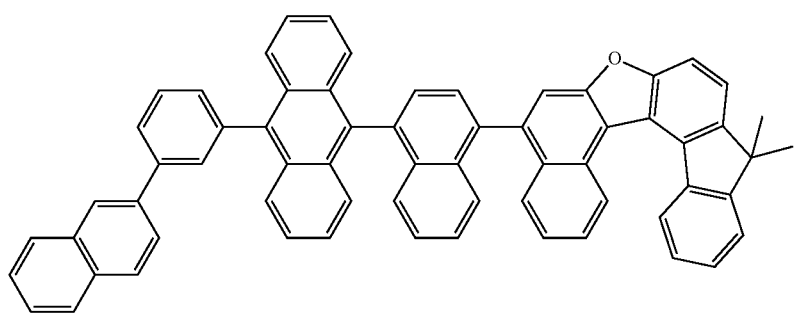
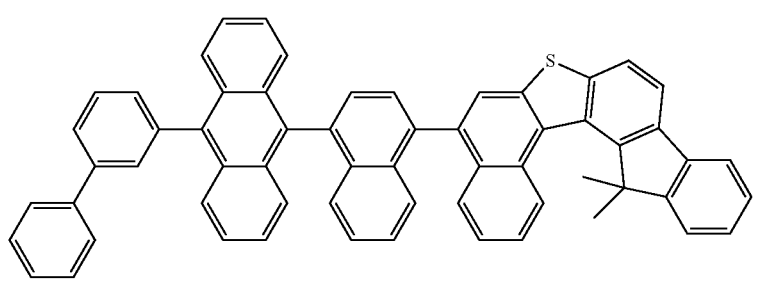

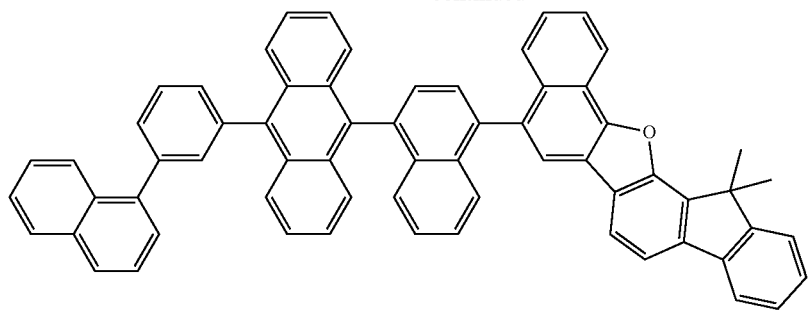
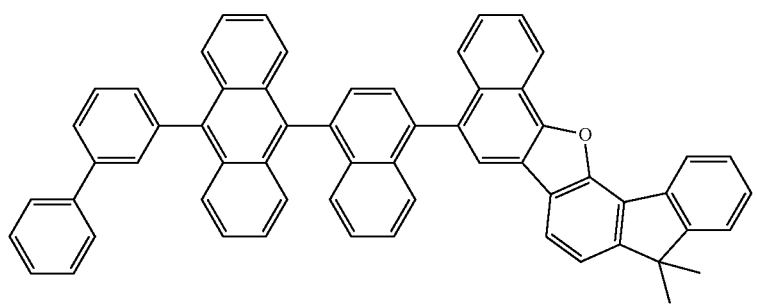
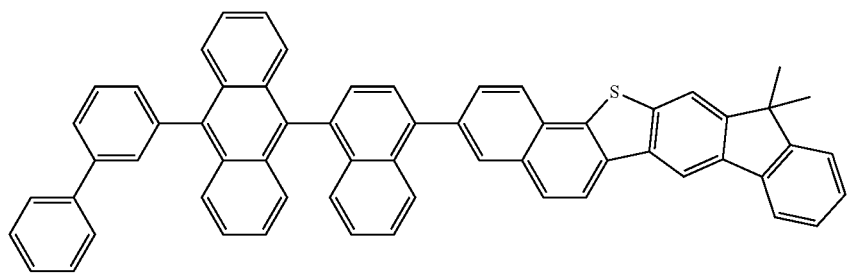
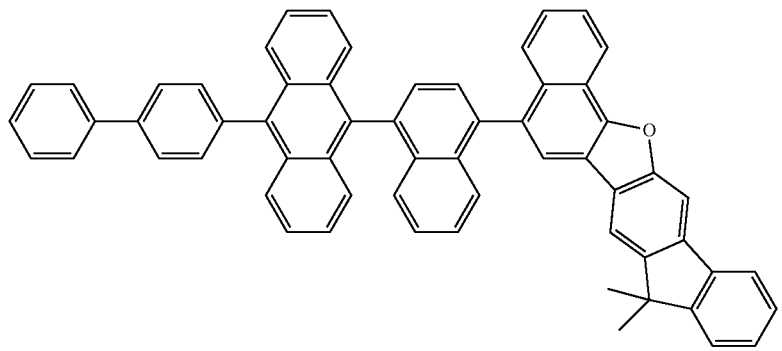
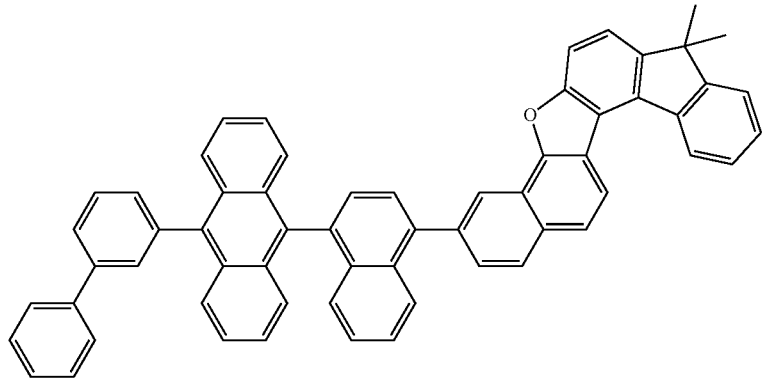

-continued
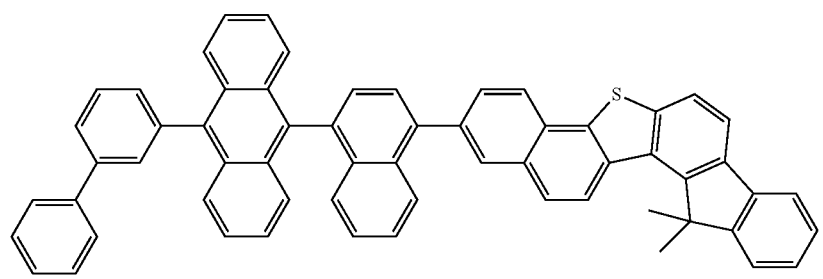
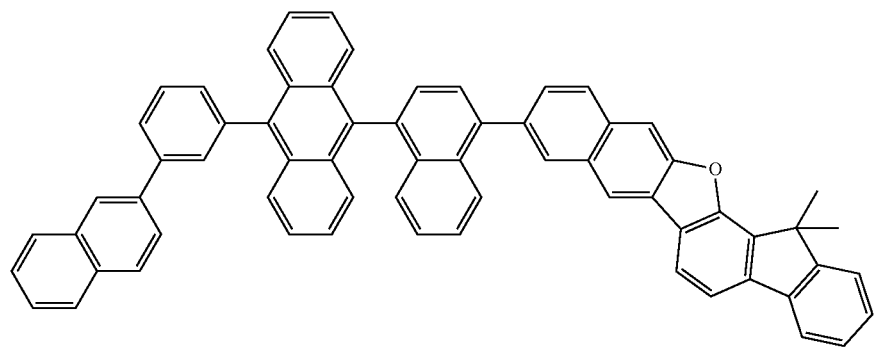
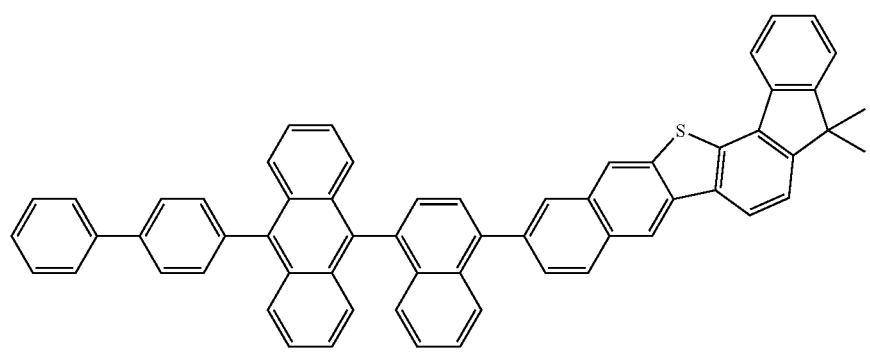
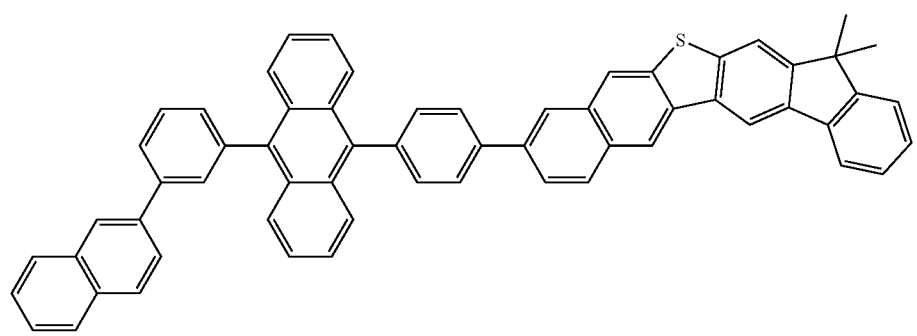
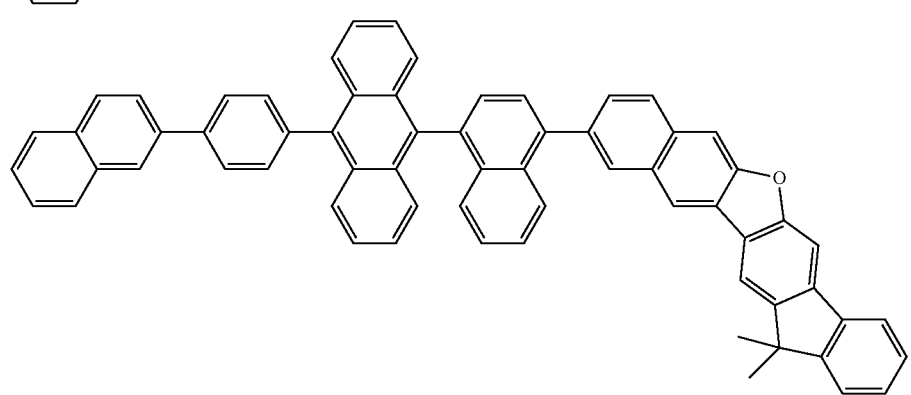

-continued
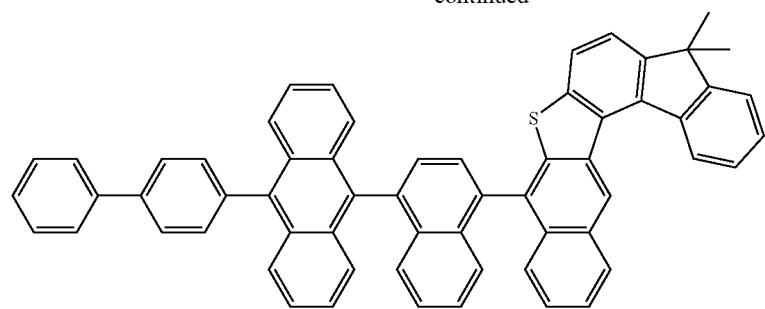
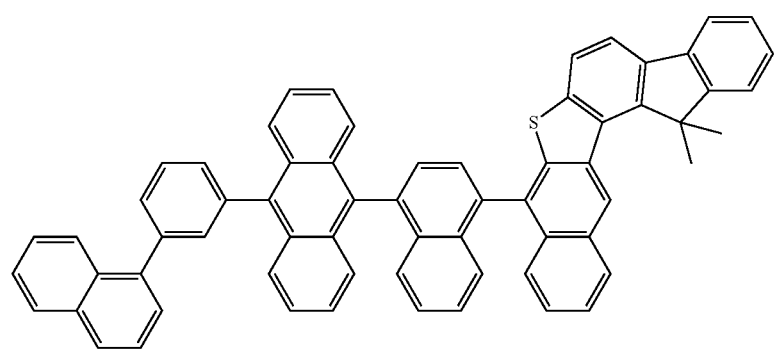
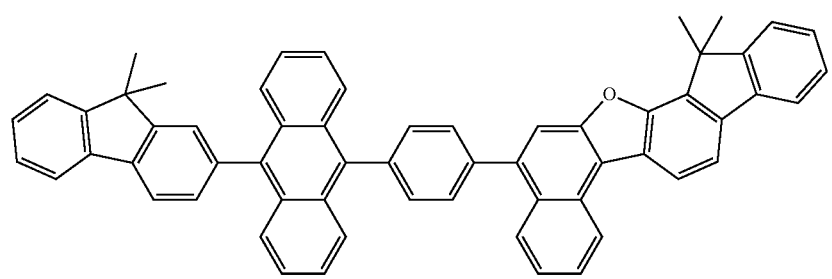
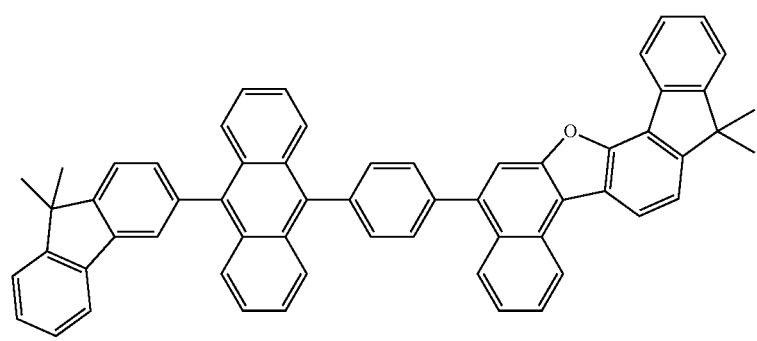
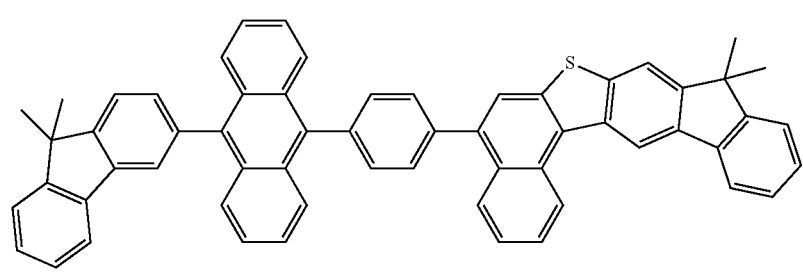

-continued
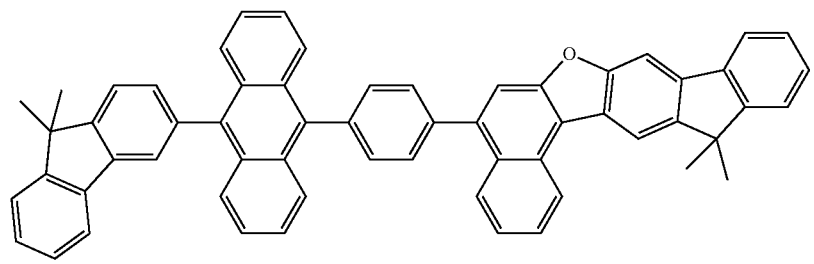
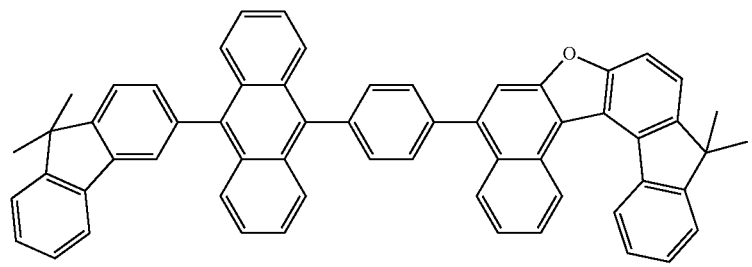
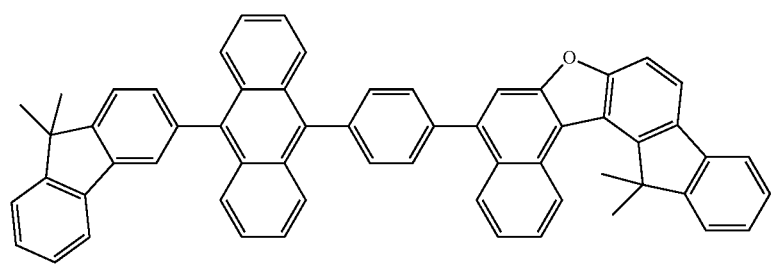
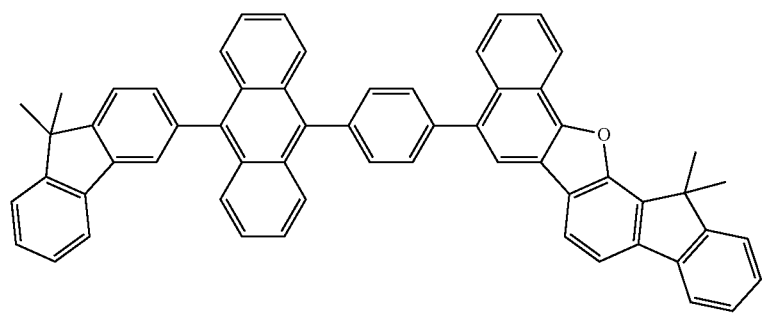
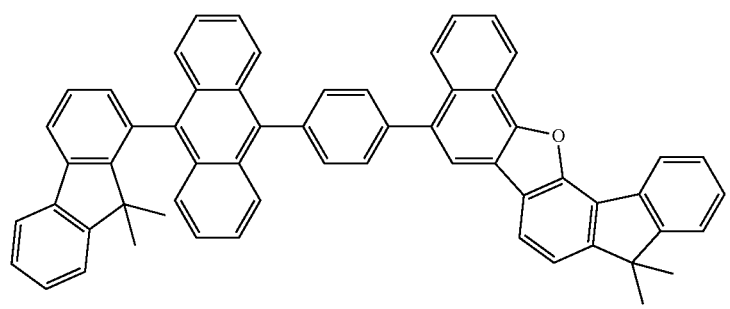
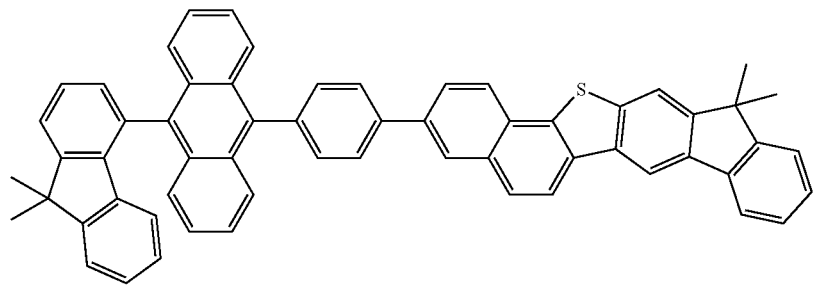

-continued
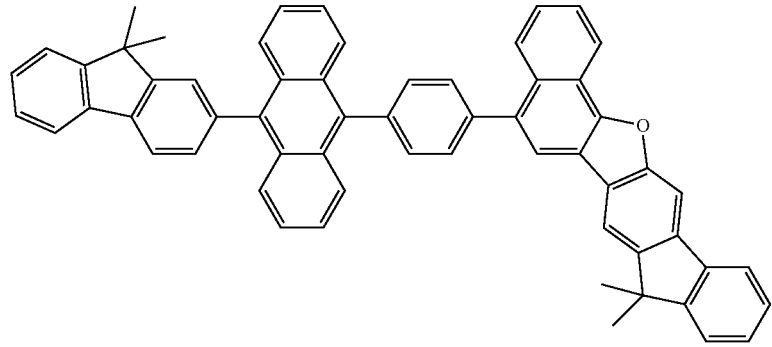
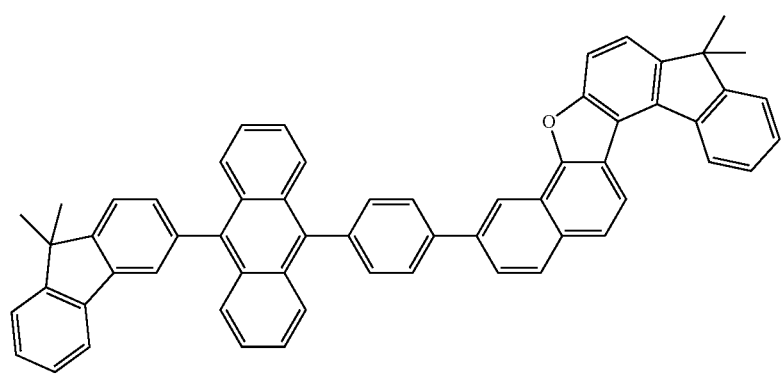
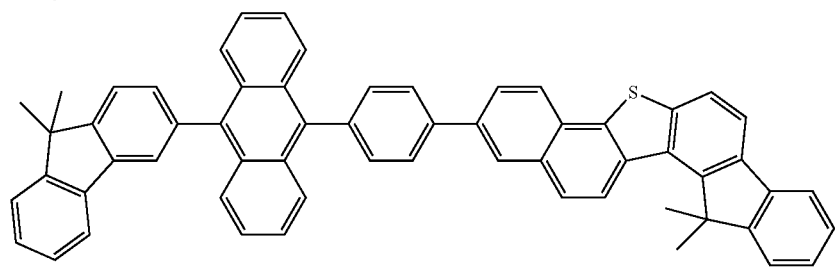
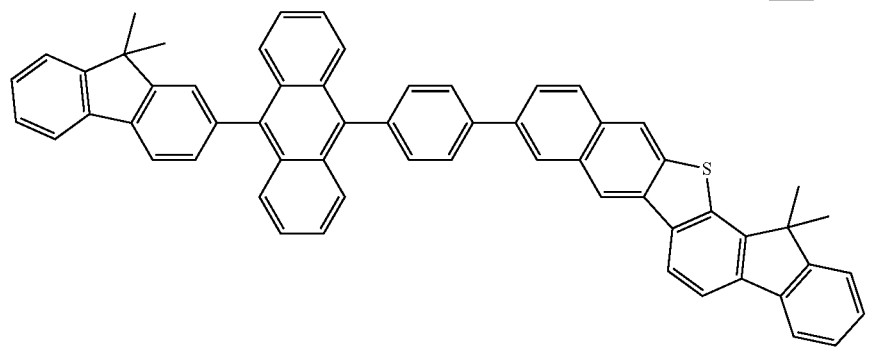
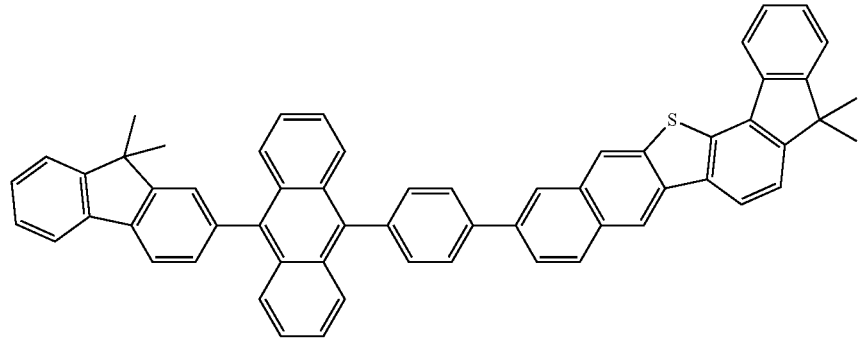

-continued
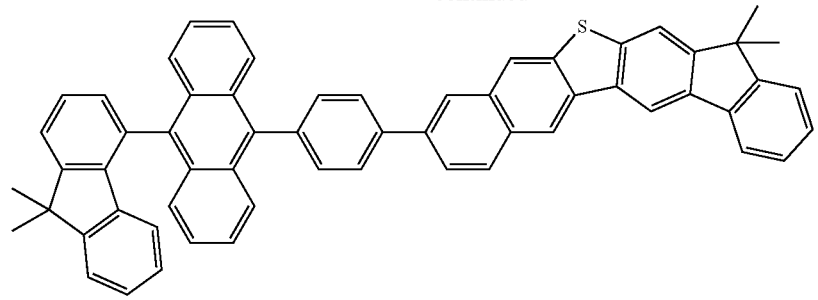
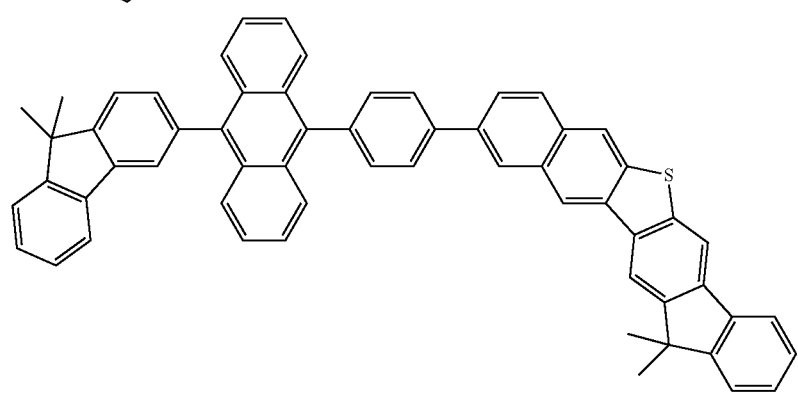
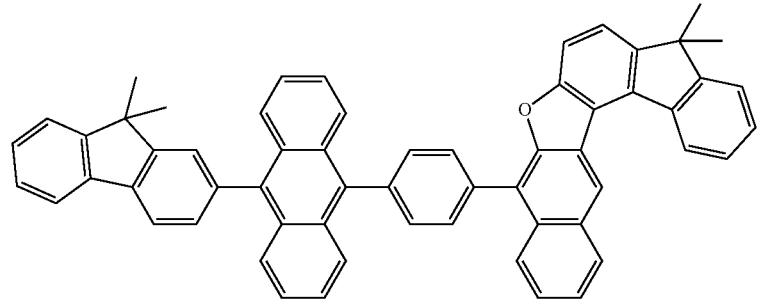
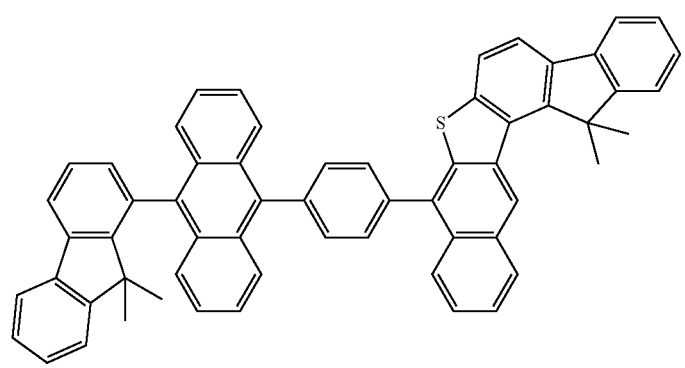
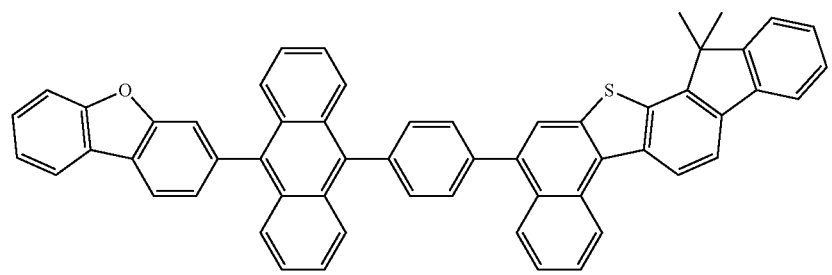

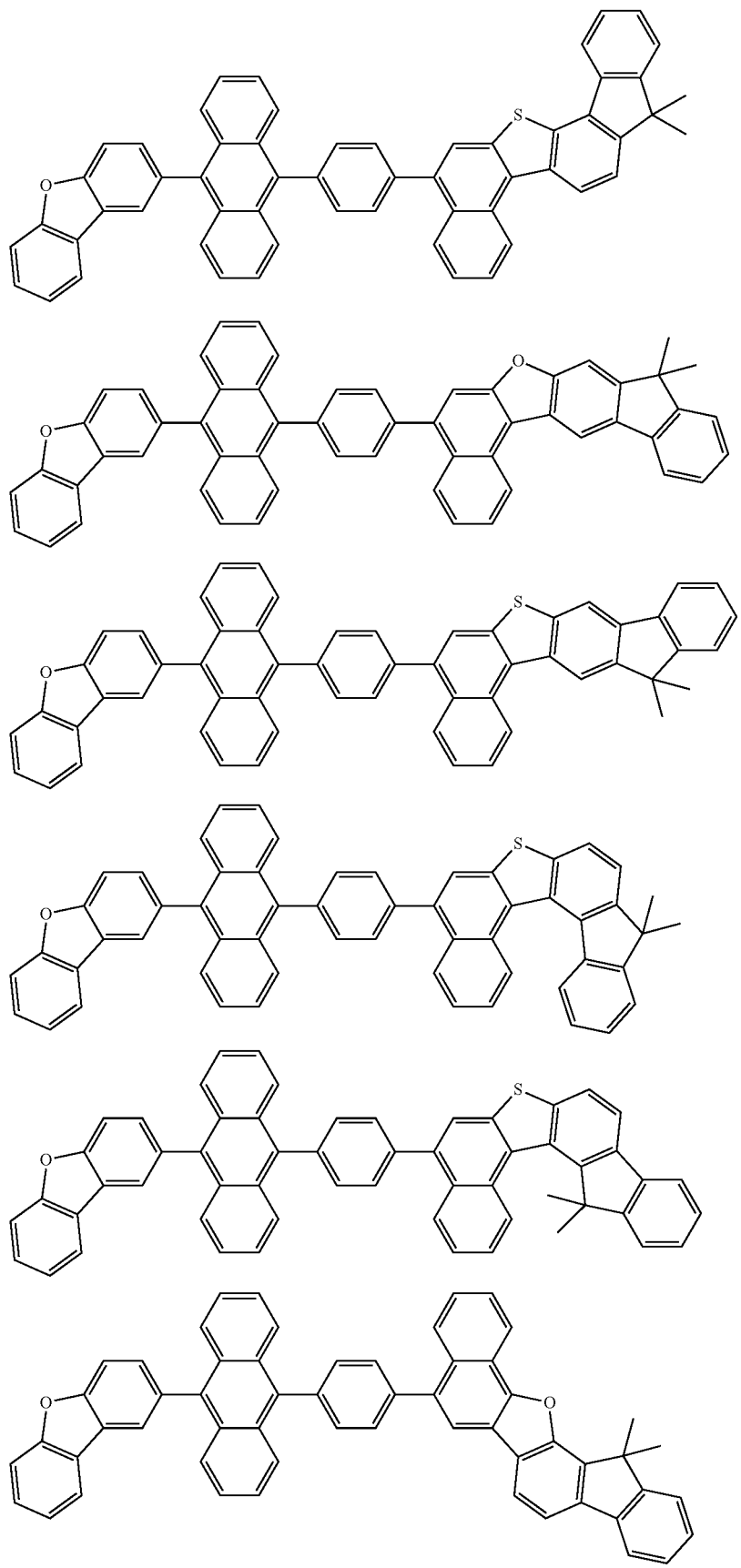

-continued
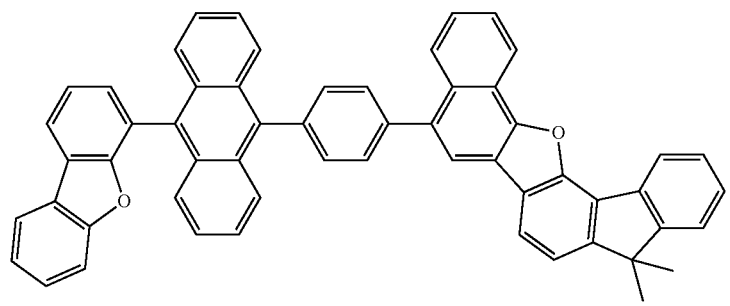
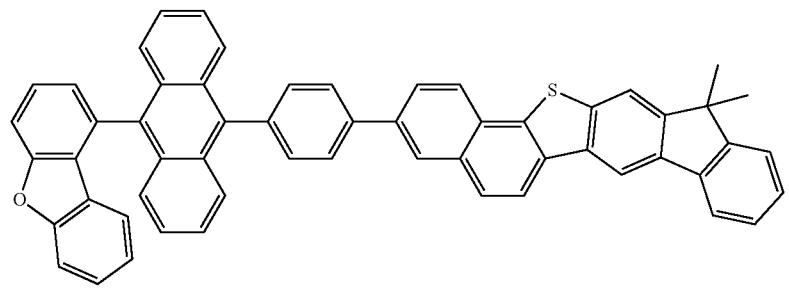
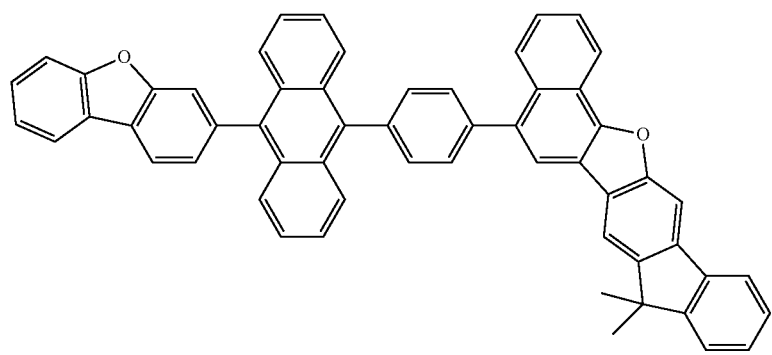
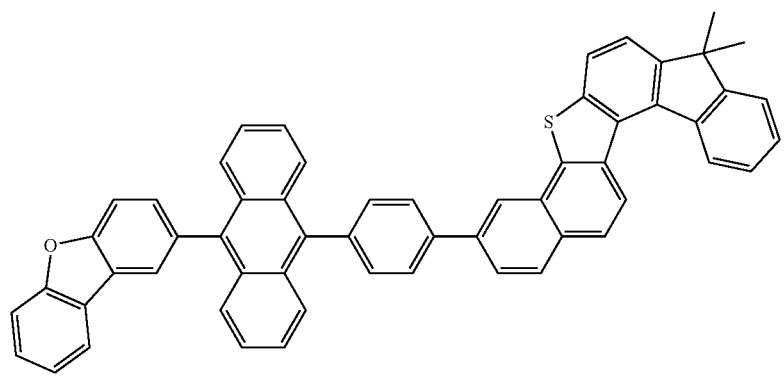
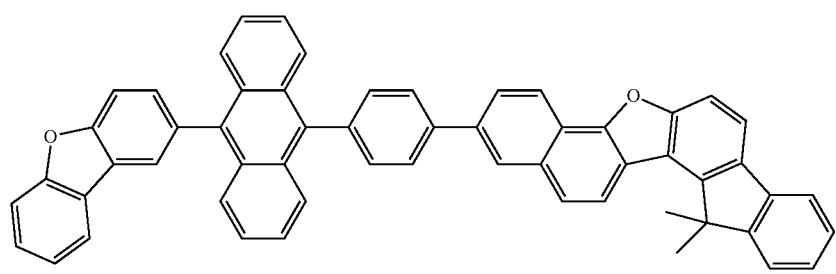

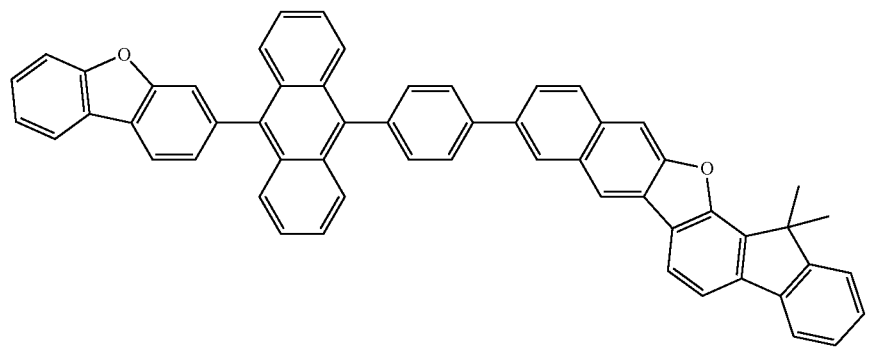
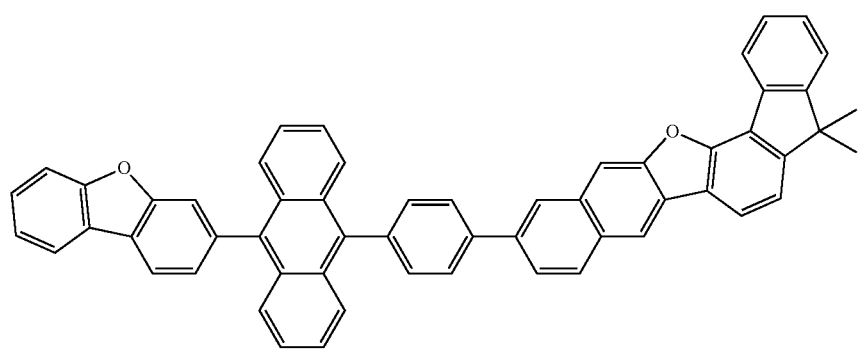
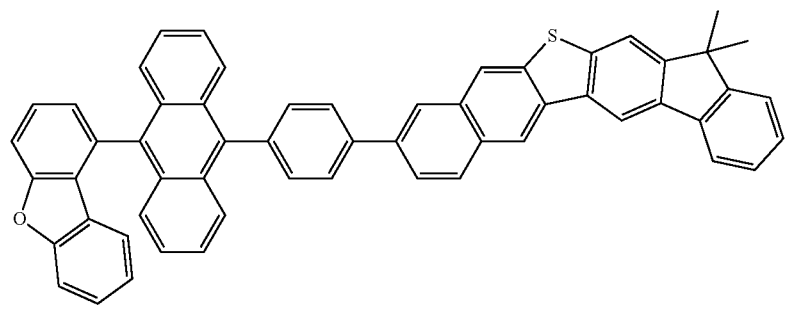
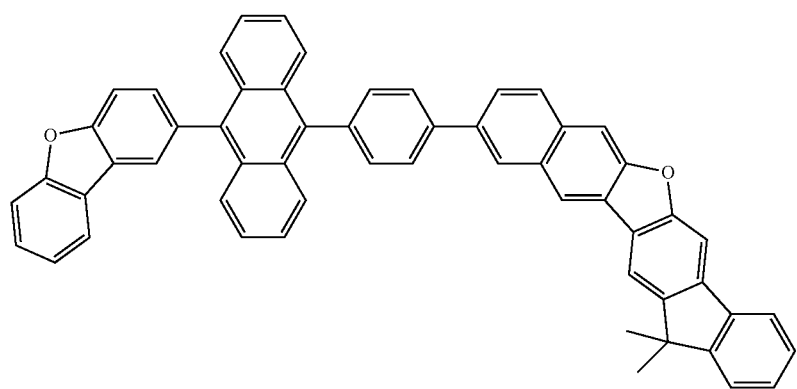
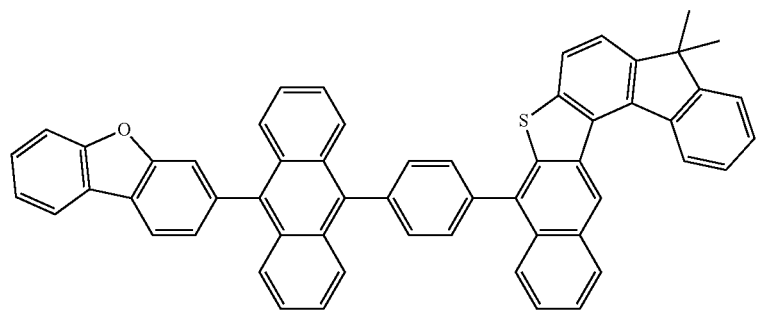

-continued
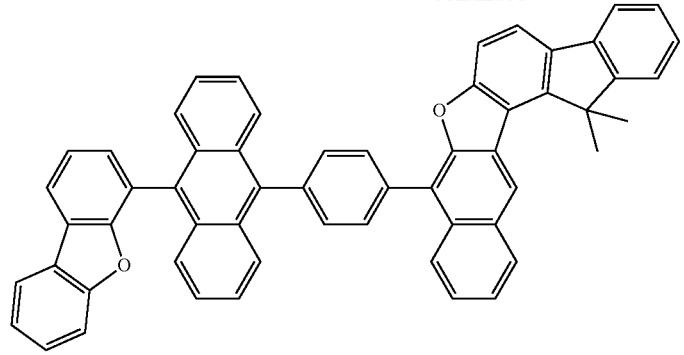
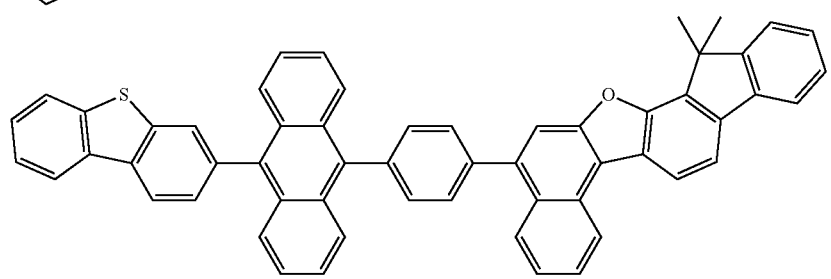
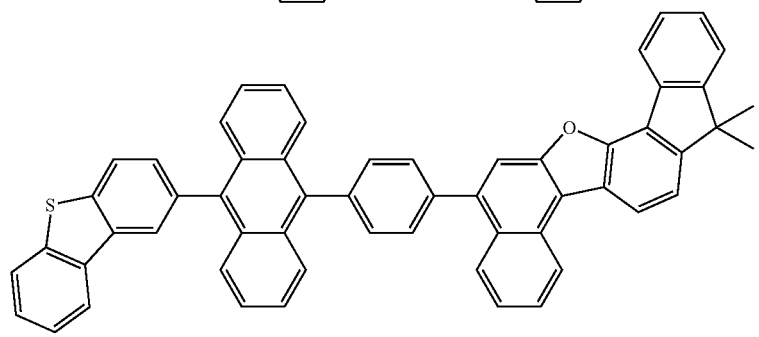
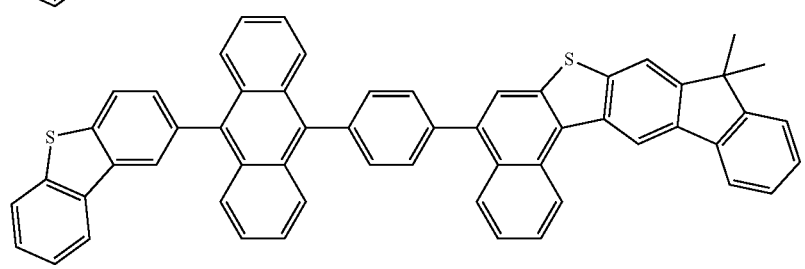
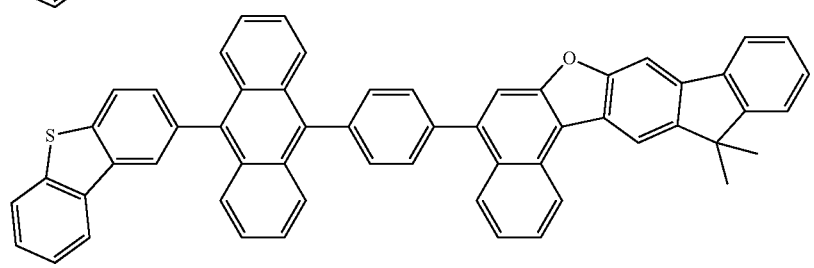
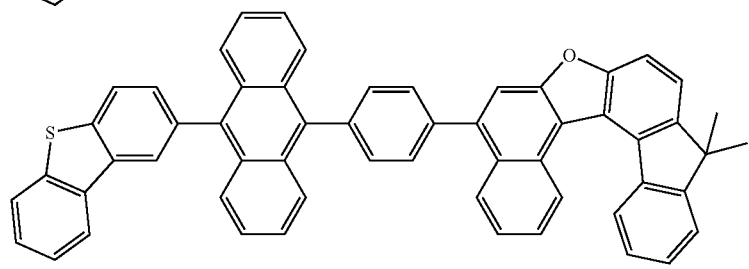

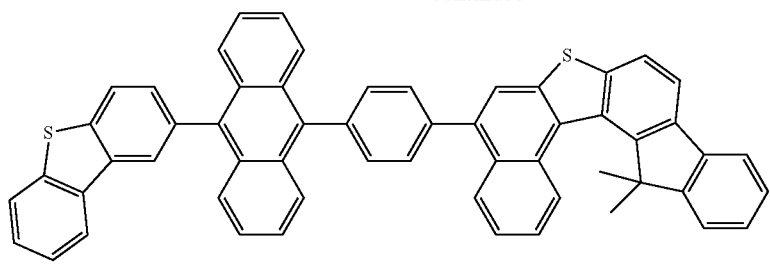
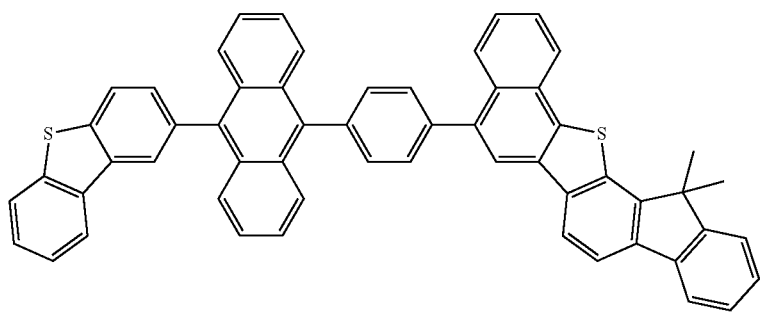
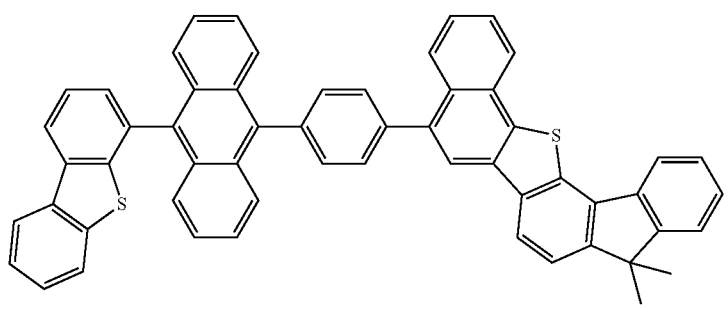
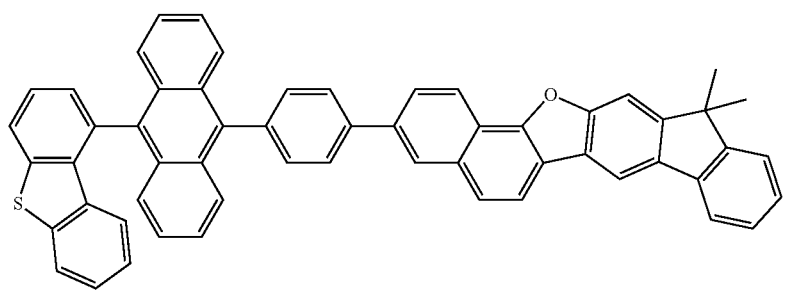
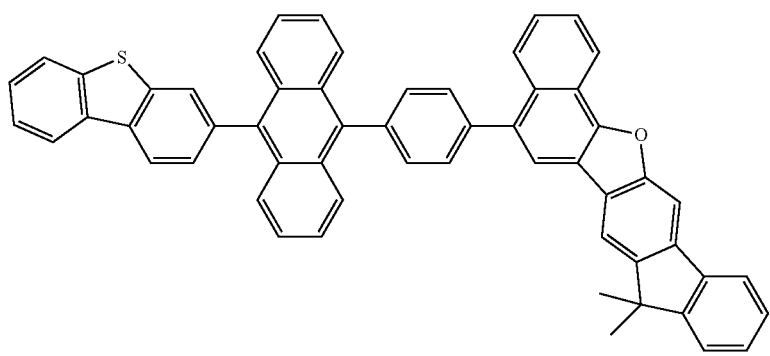

-continued
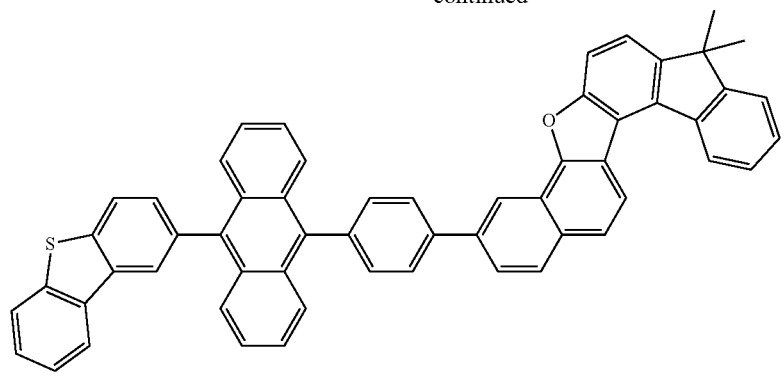
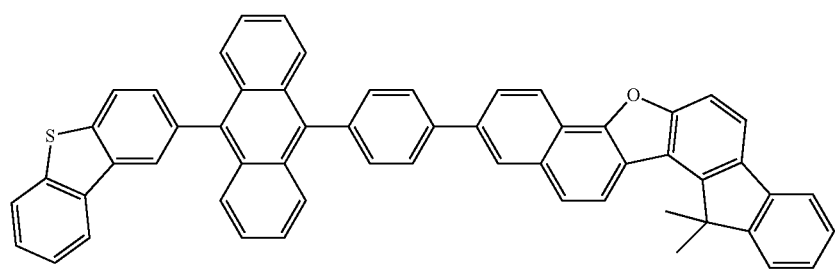
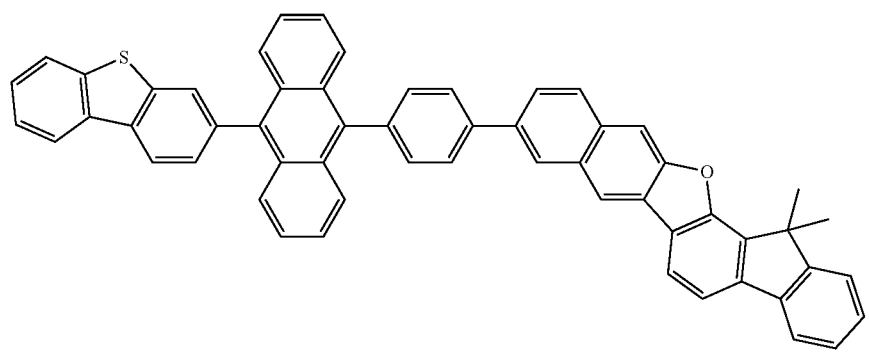
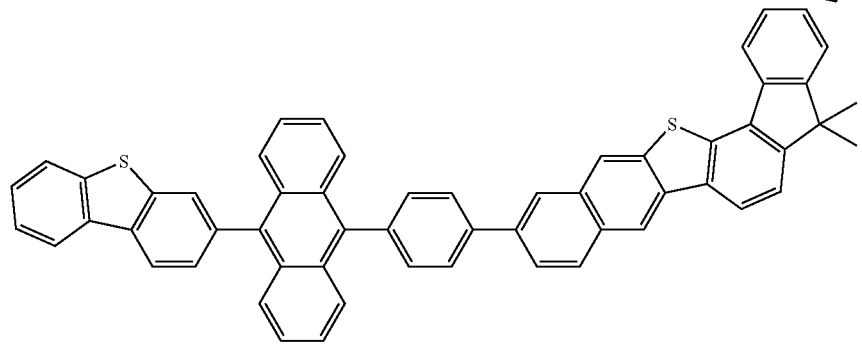
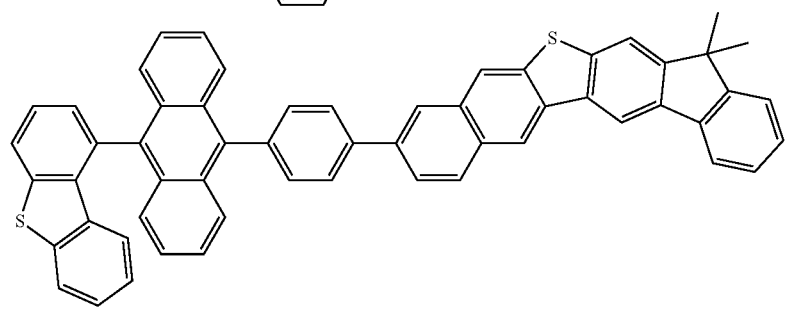

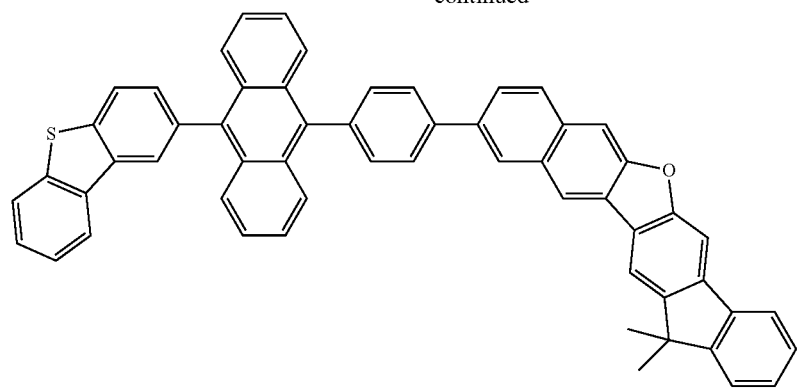
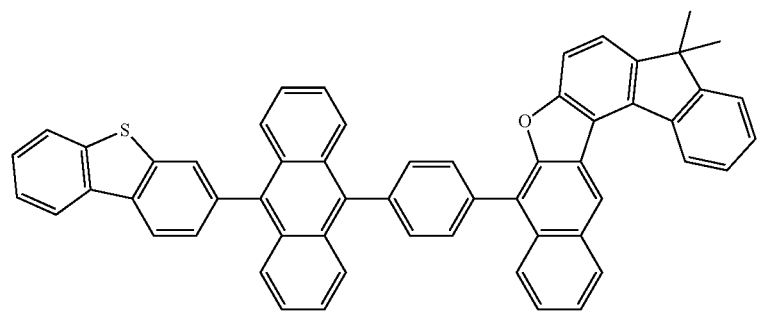
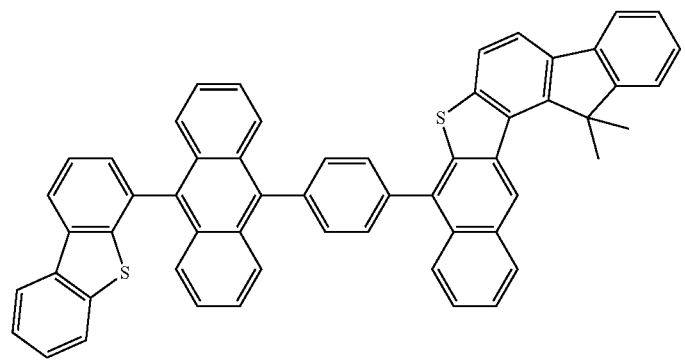
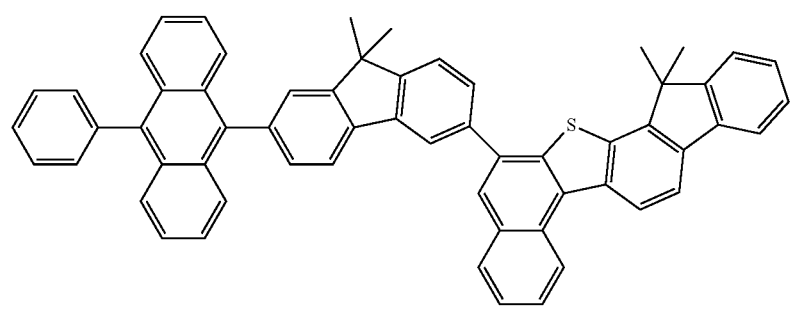
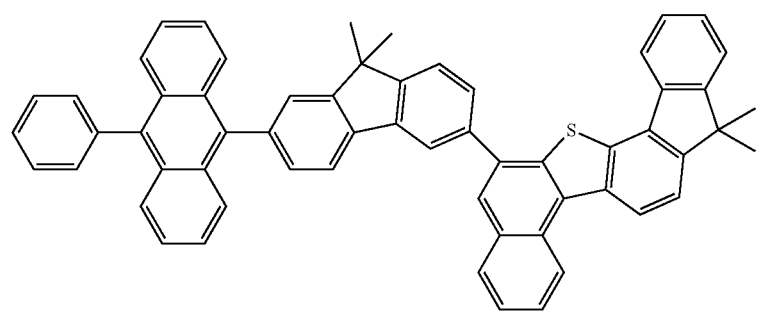

-continued
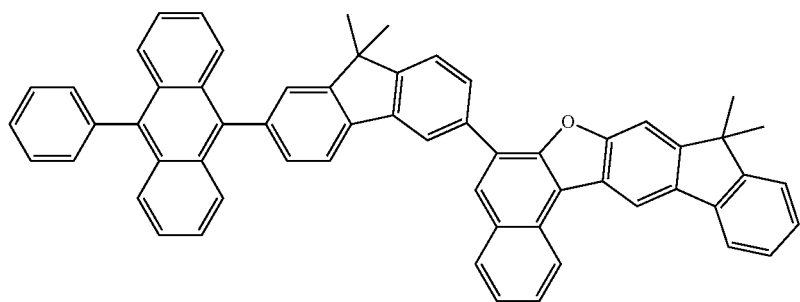
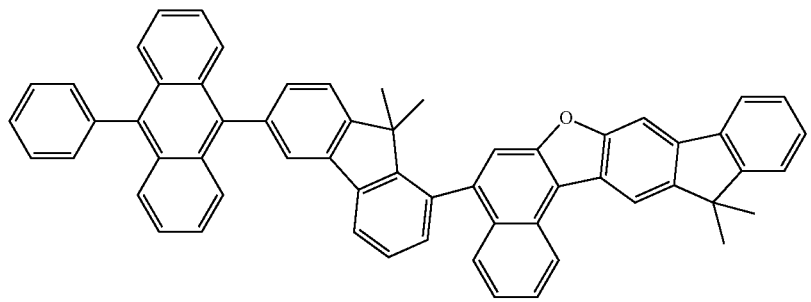
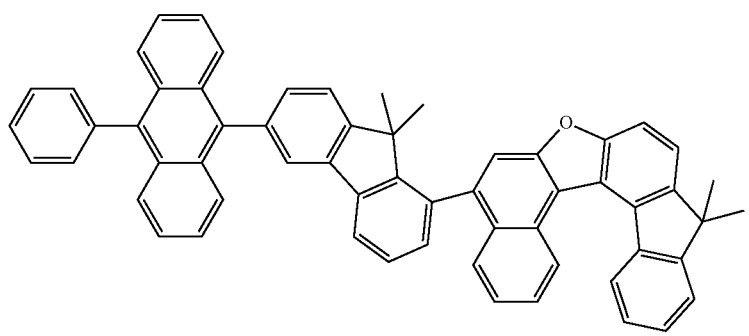
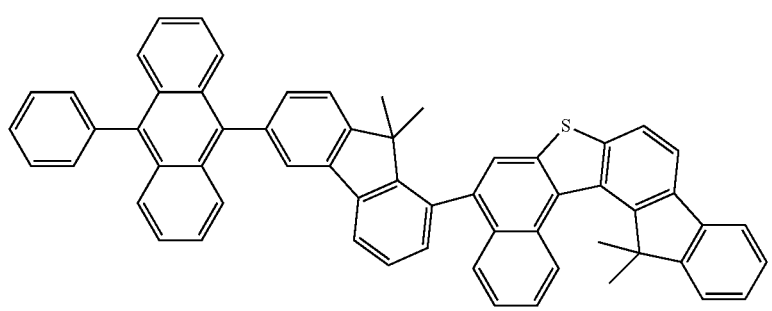
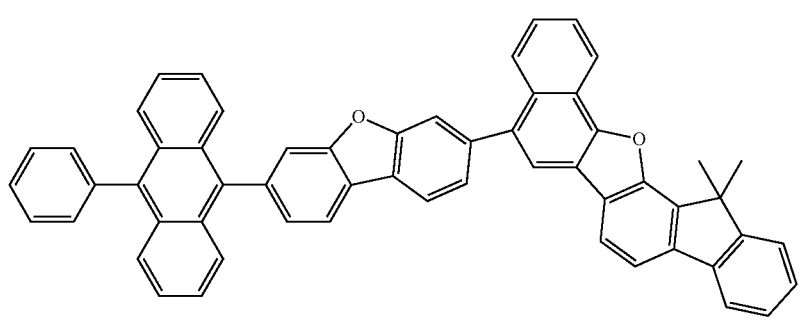

-continued
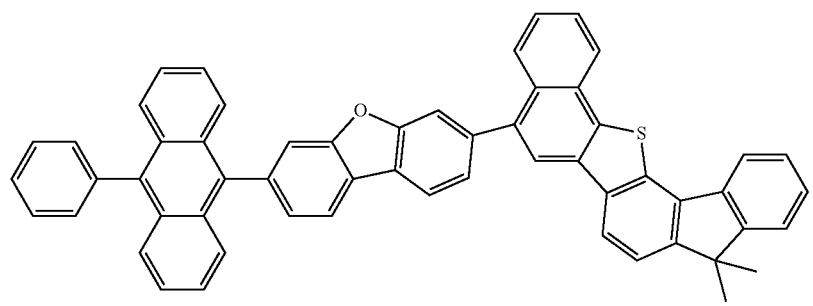
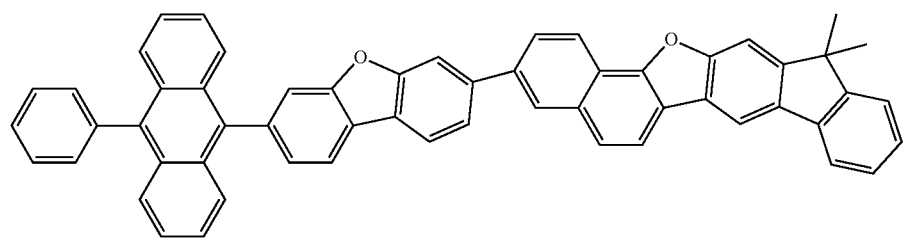
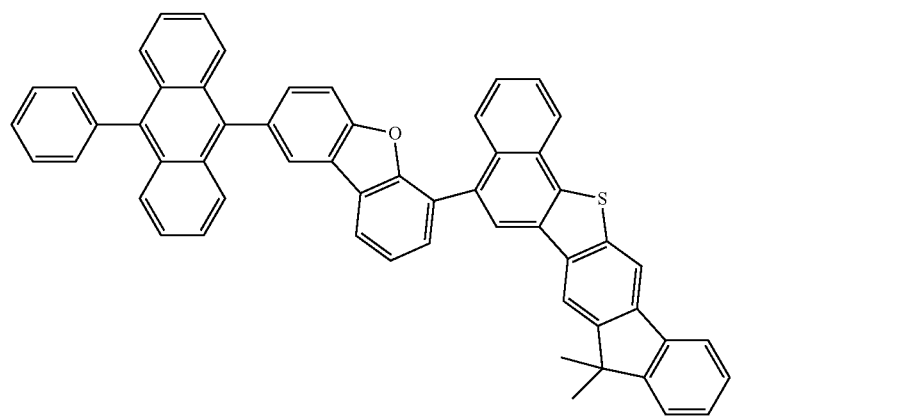
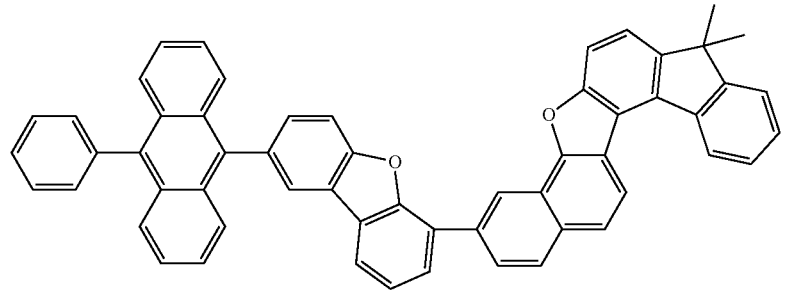
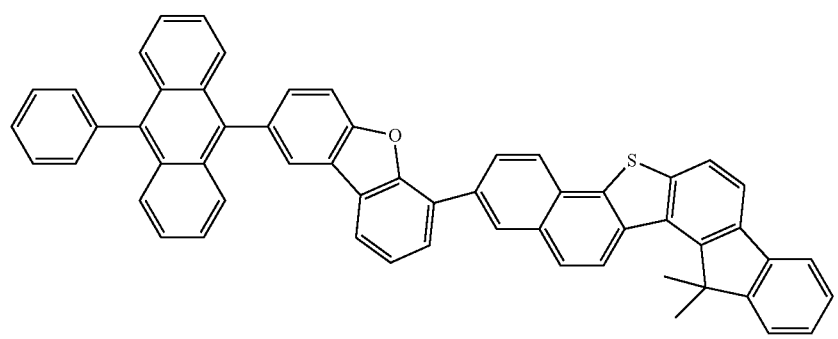

-continued
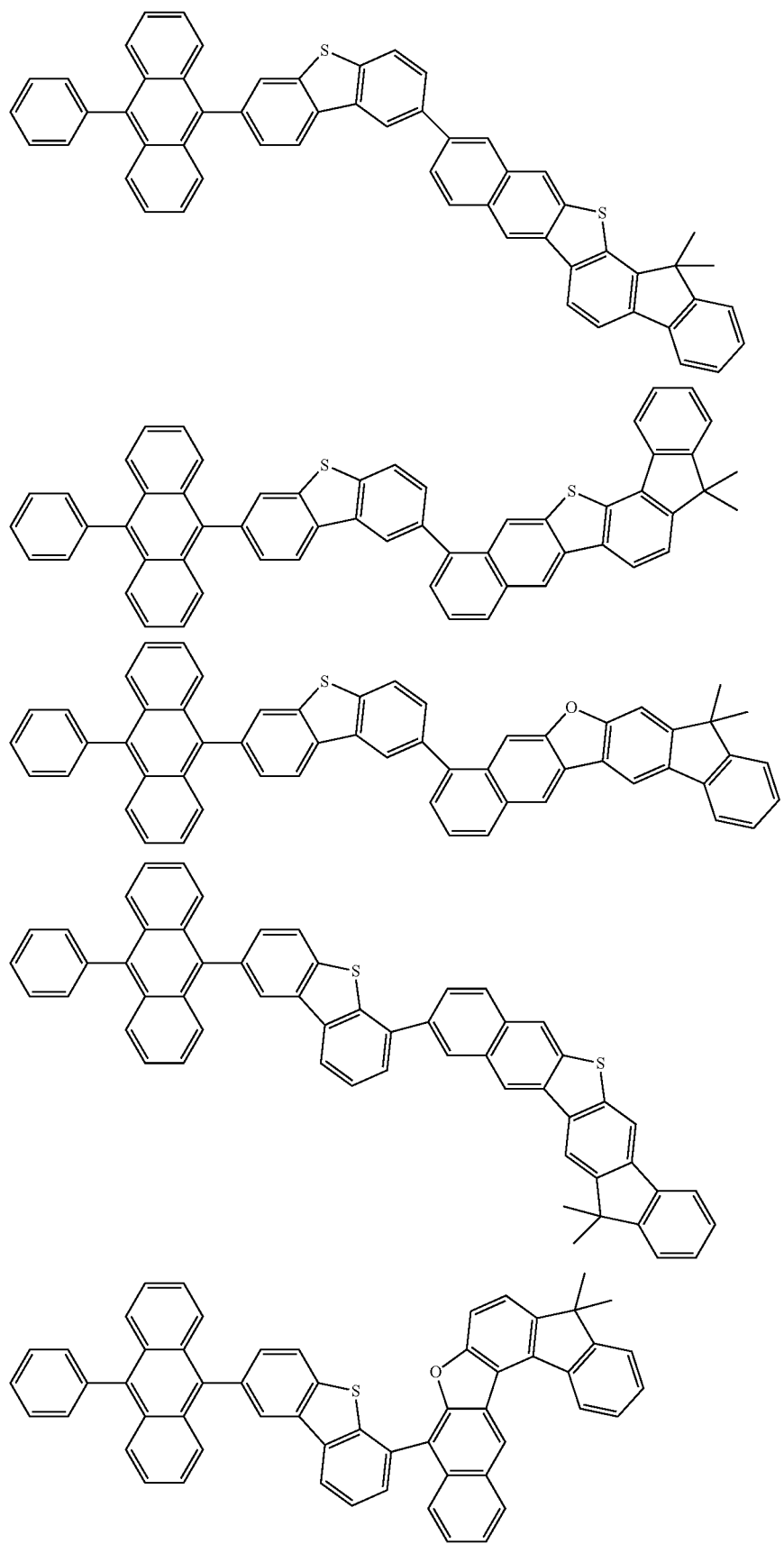

-continued
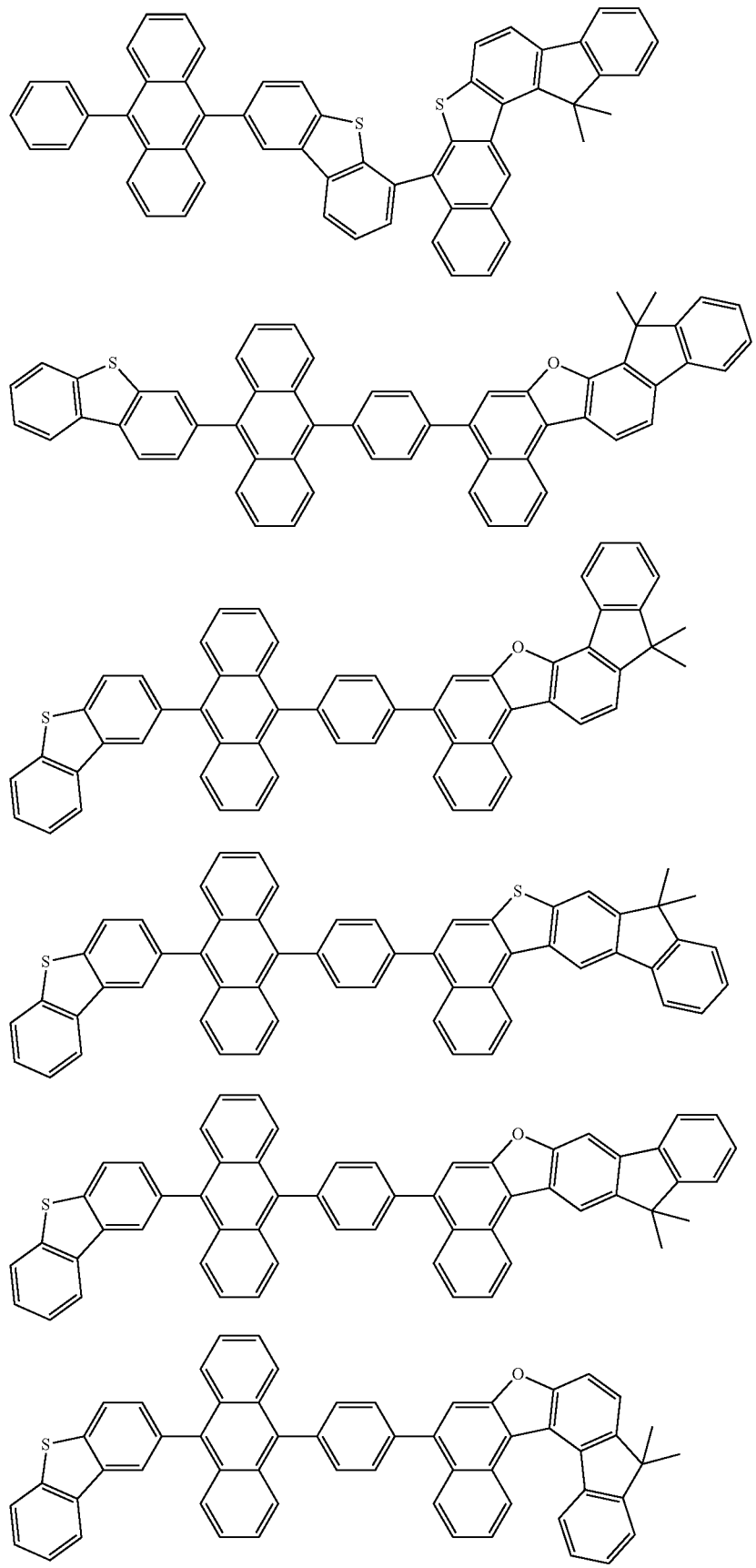

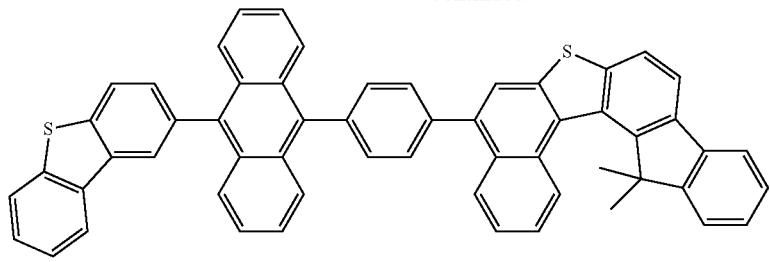
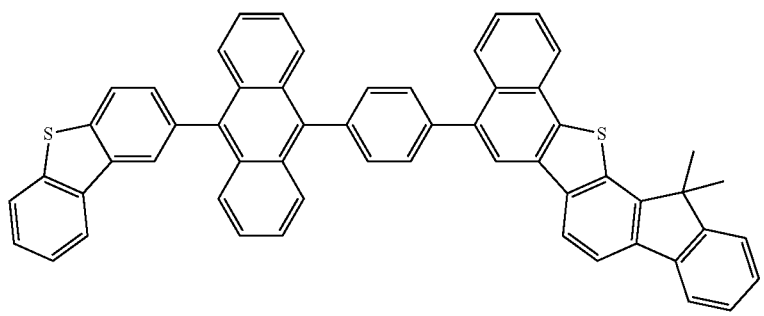
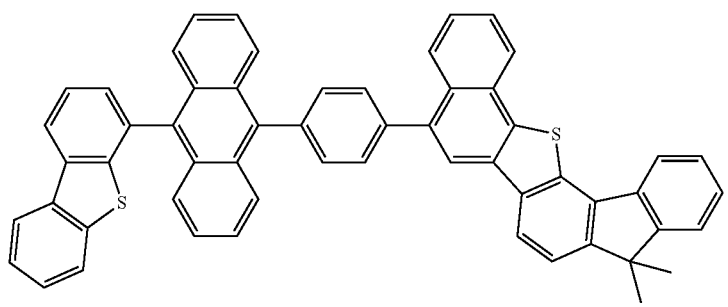
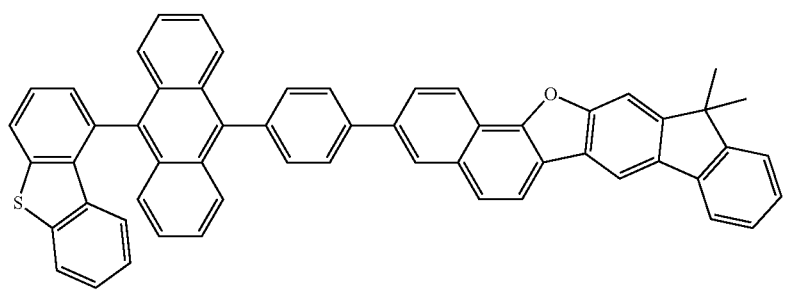
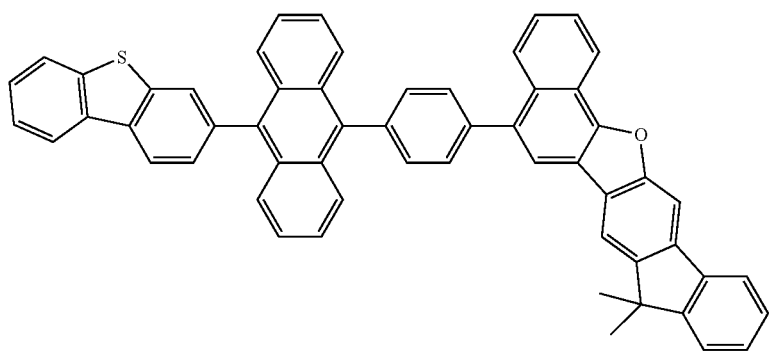

-continued
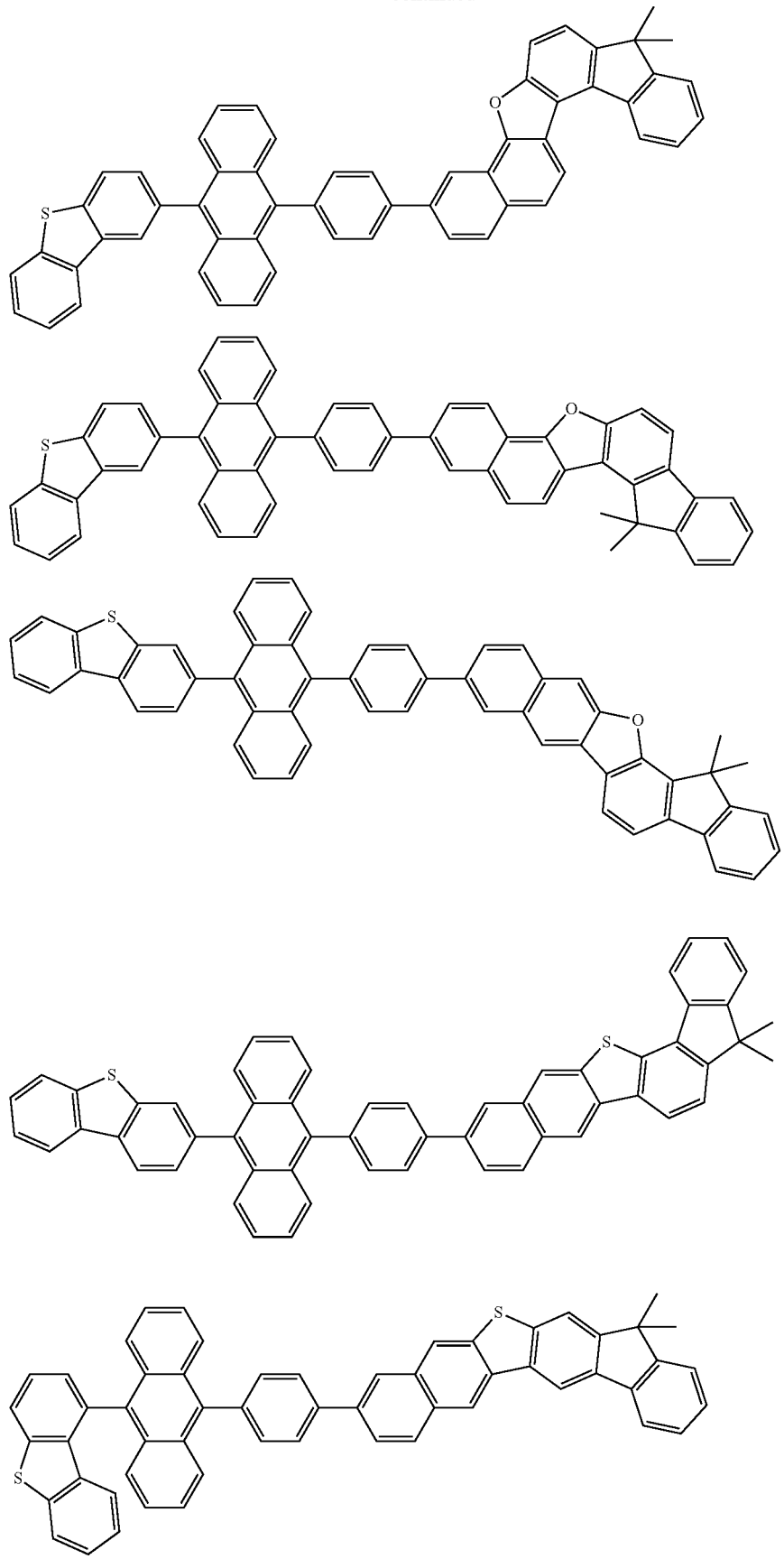

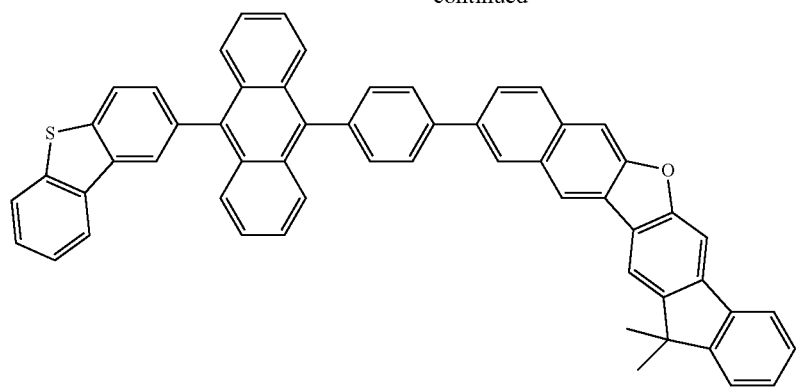
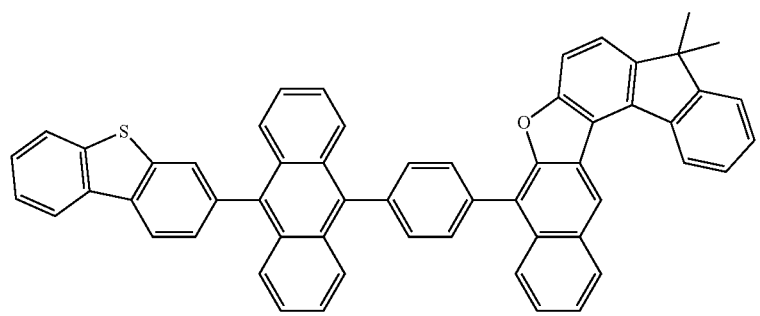
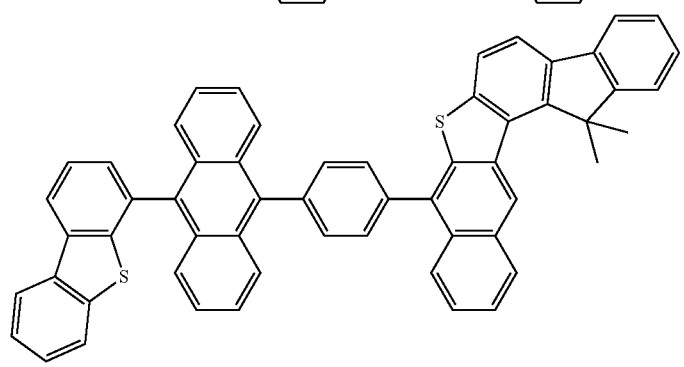
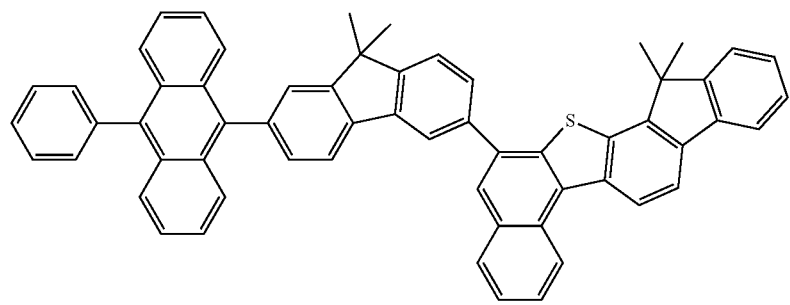
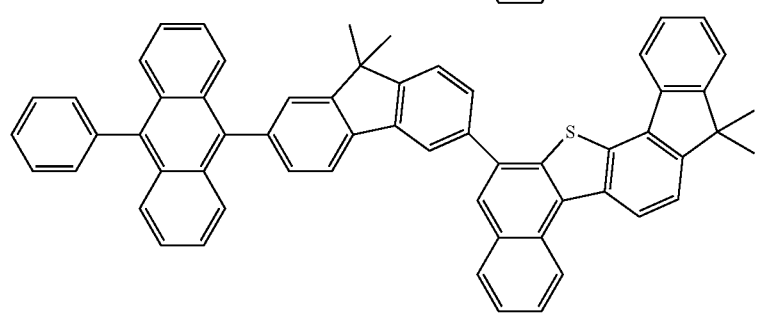

-continued
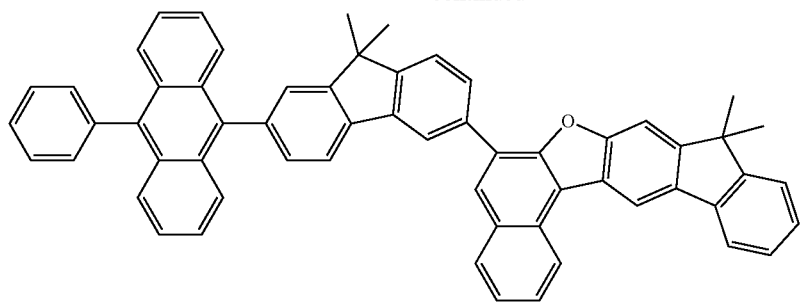
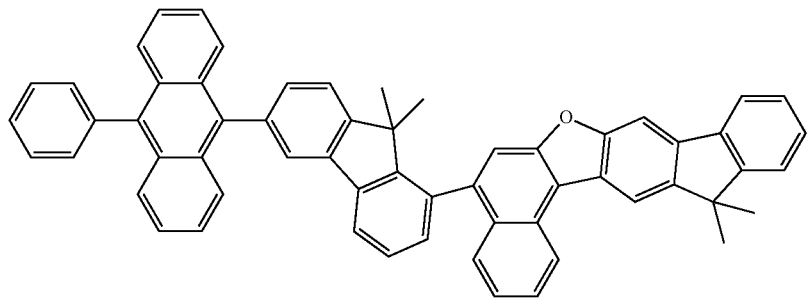
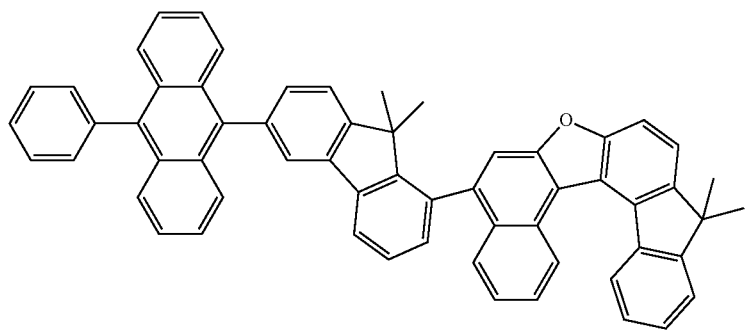
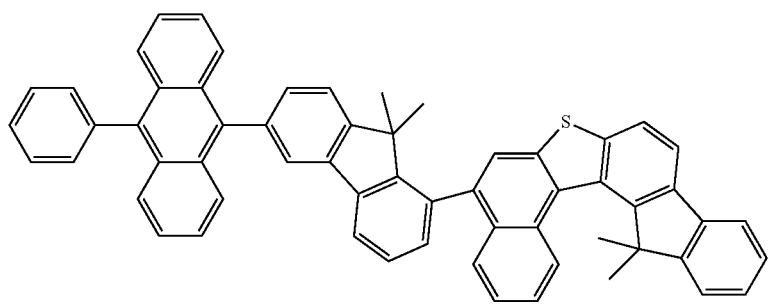
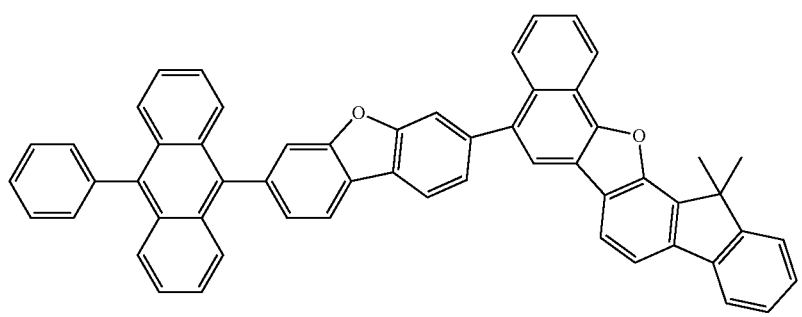

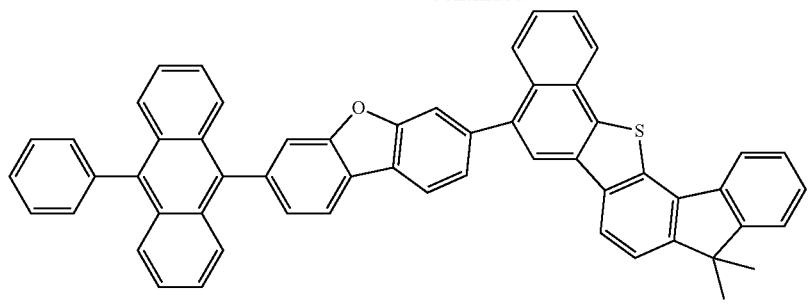
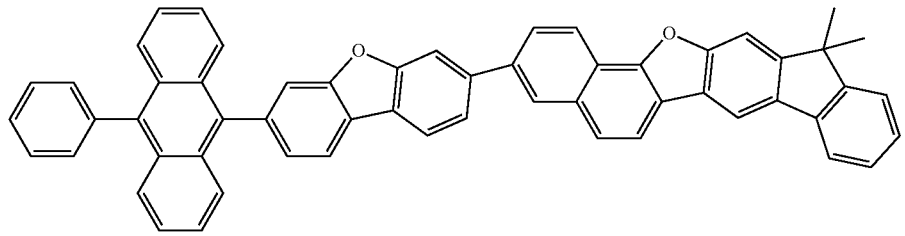
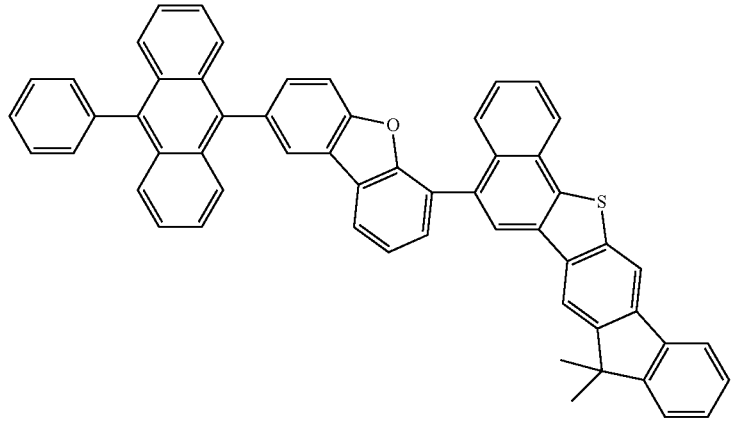
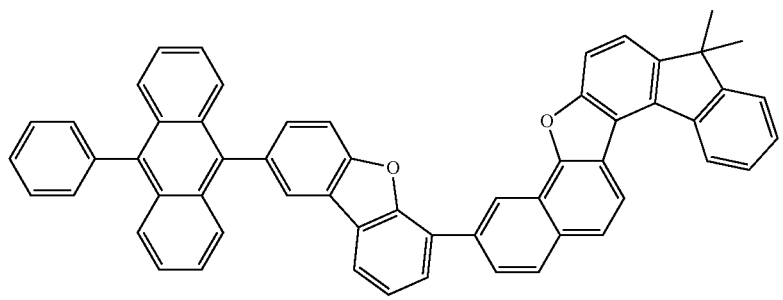
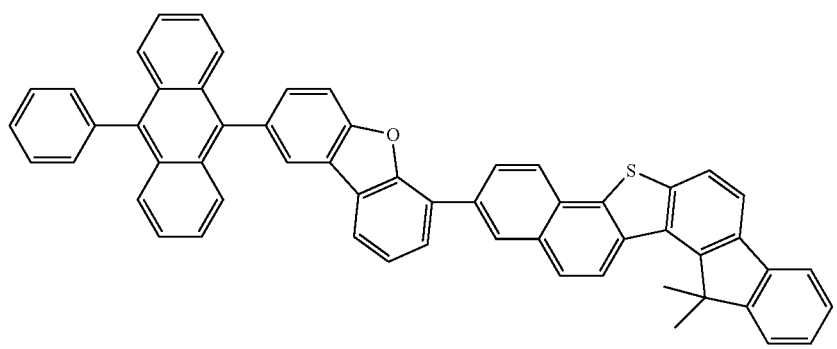

-continued
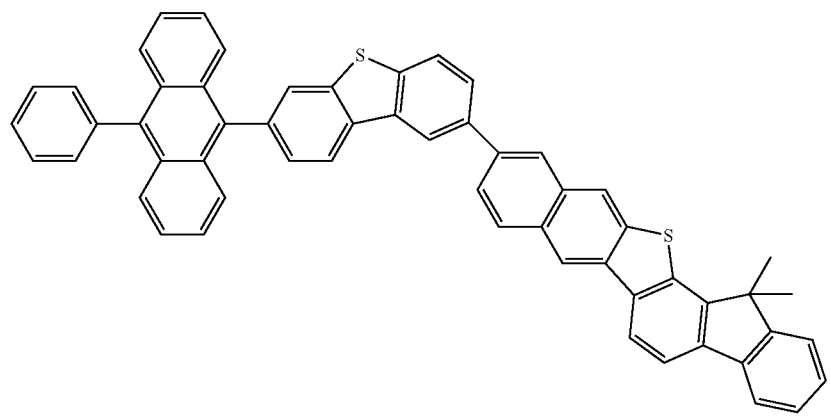
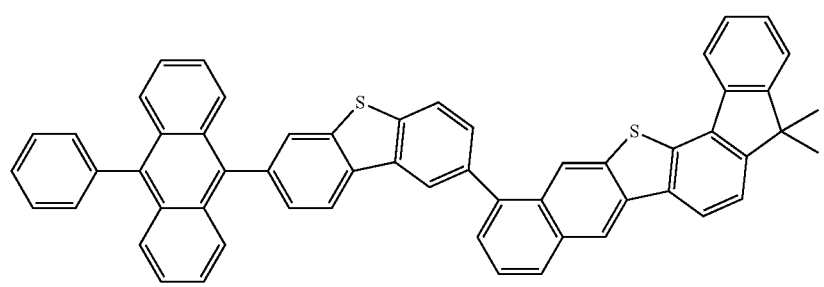
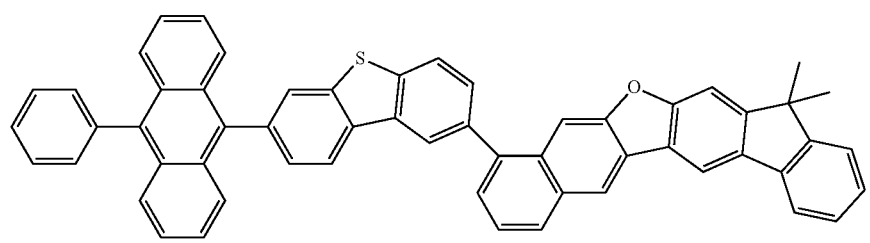
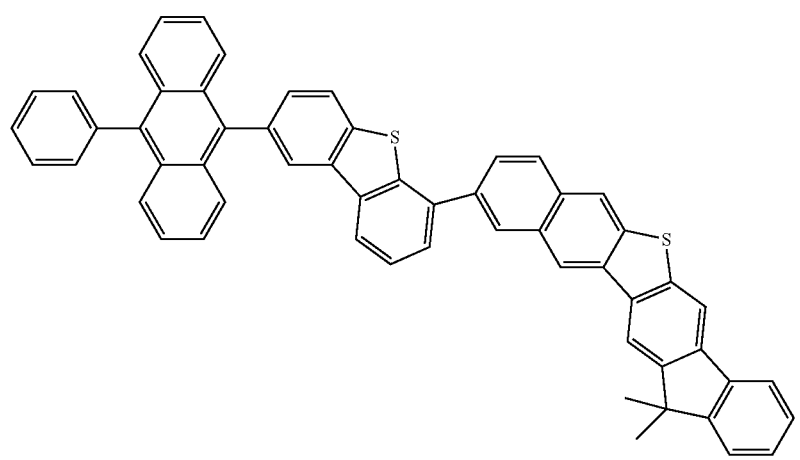
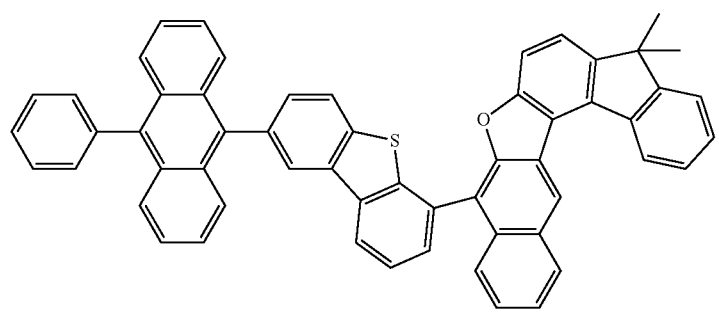

-continued
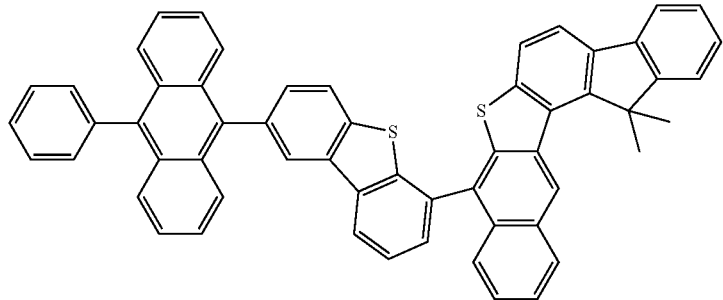

-continued
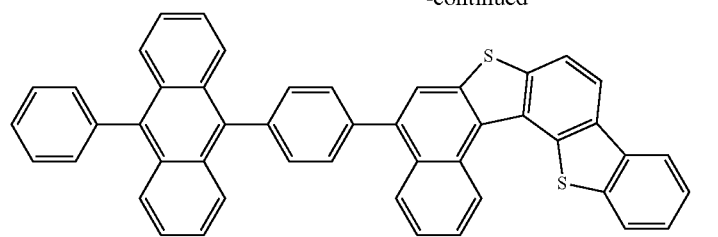
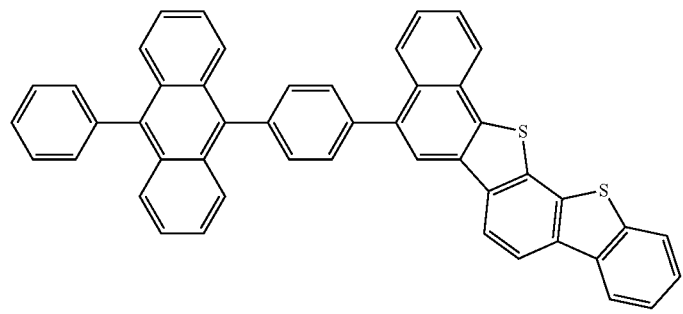
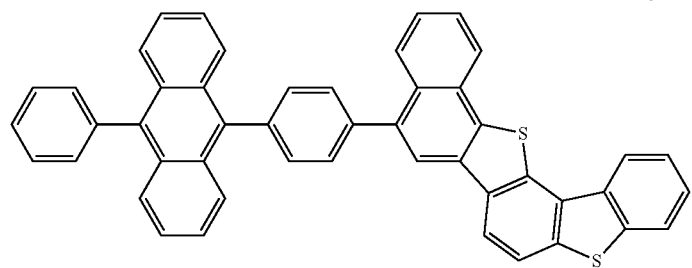
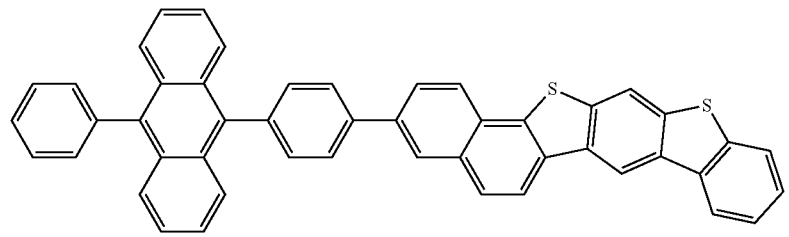
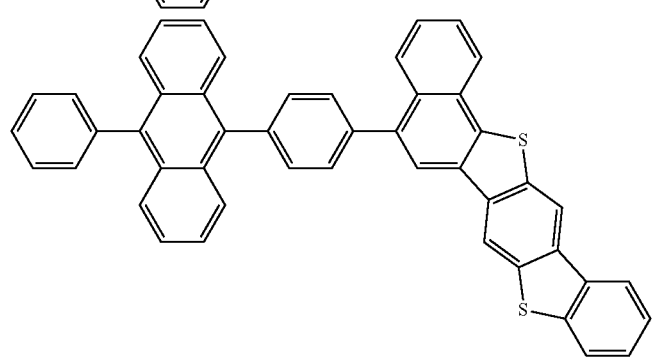
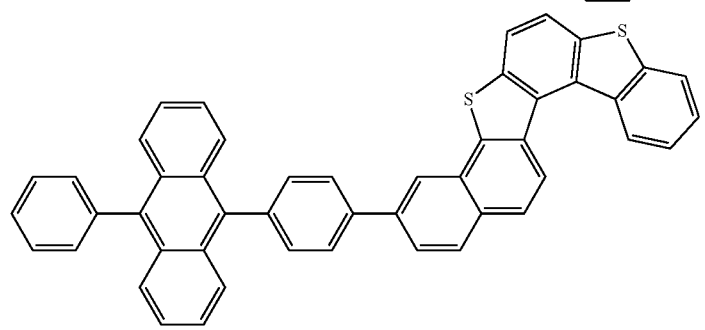

-continued
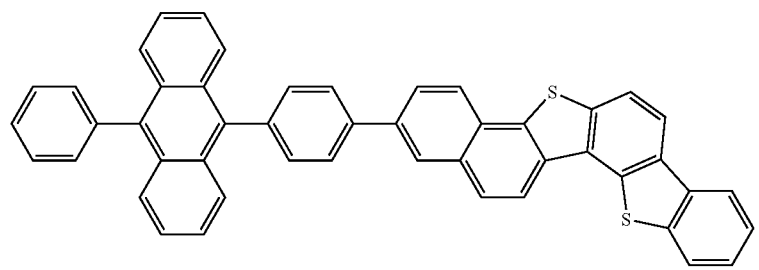
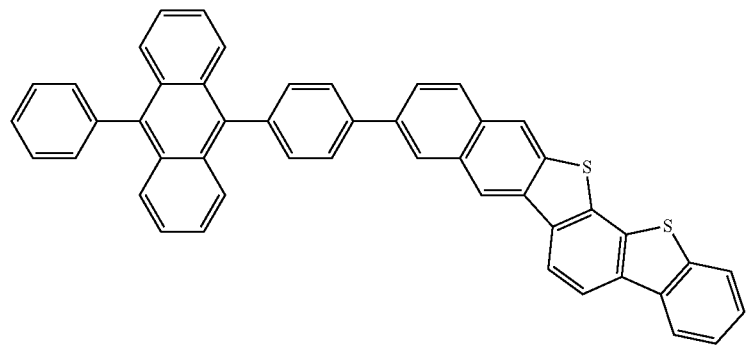
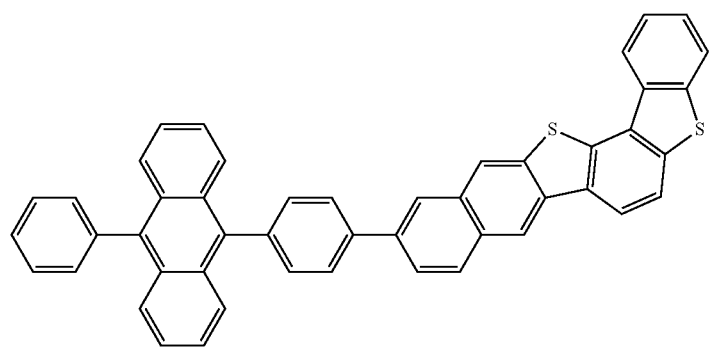
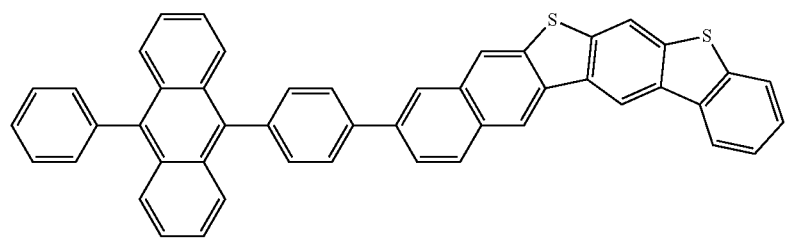
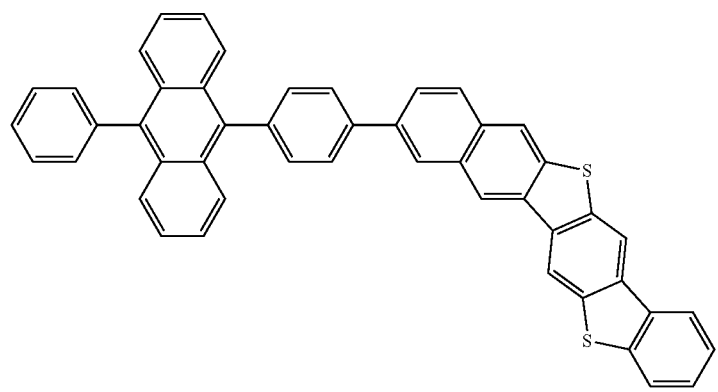

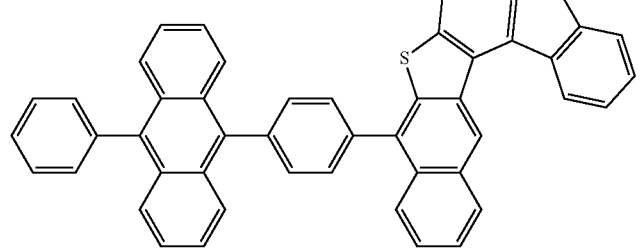
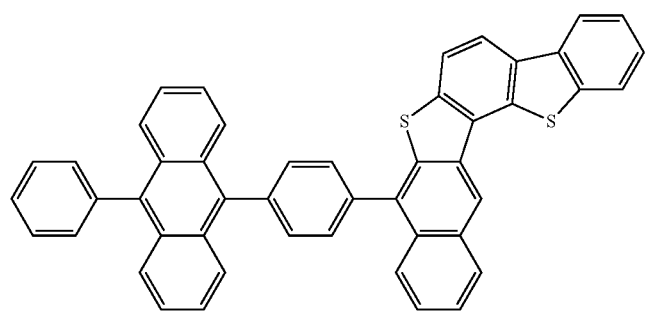
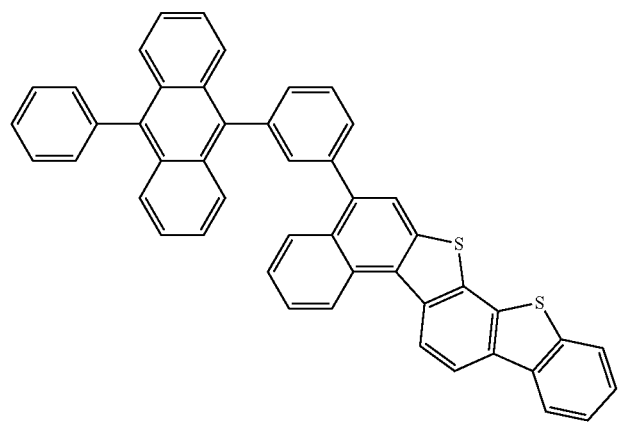
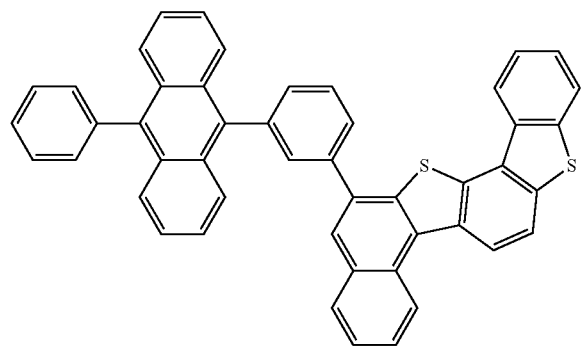

-continued
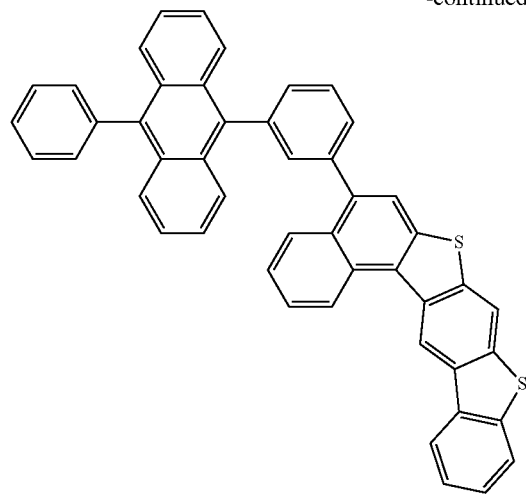
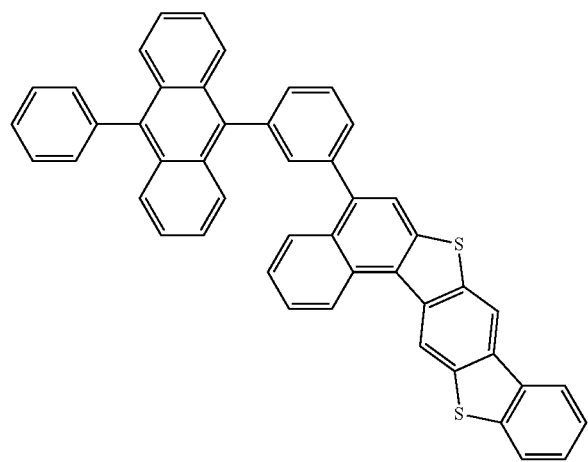
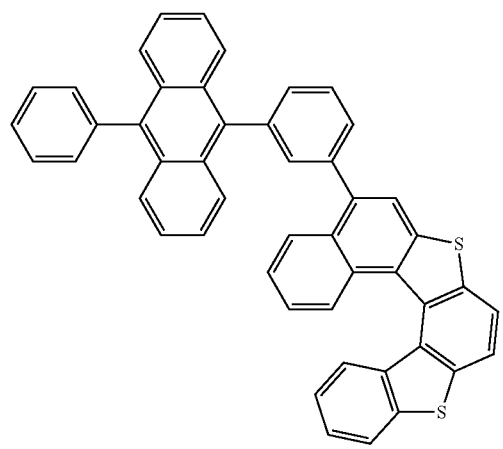

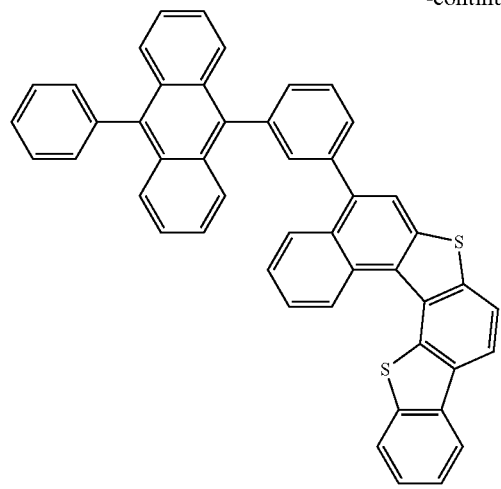
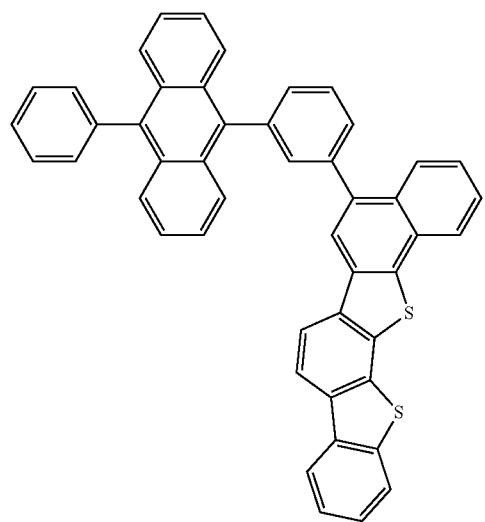
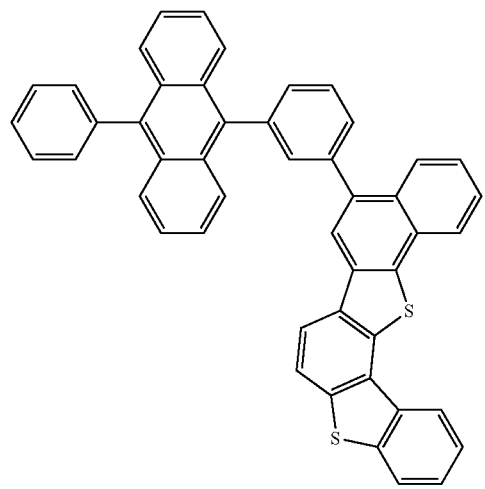

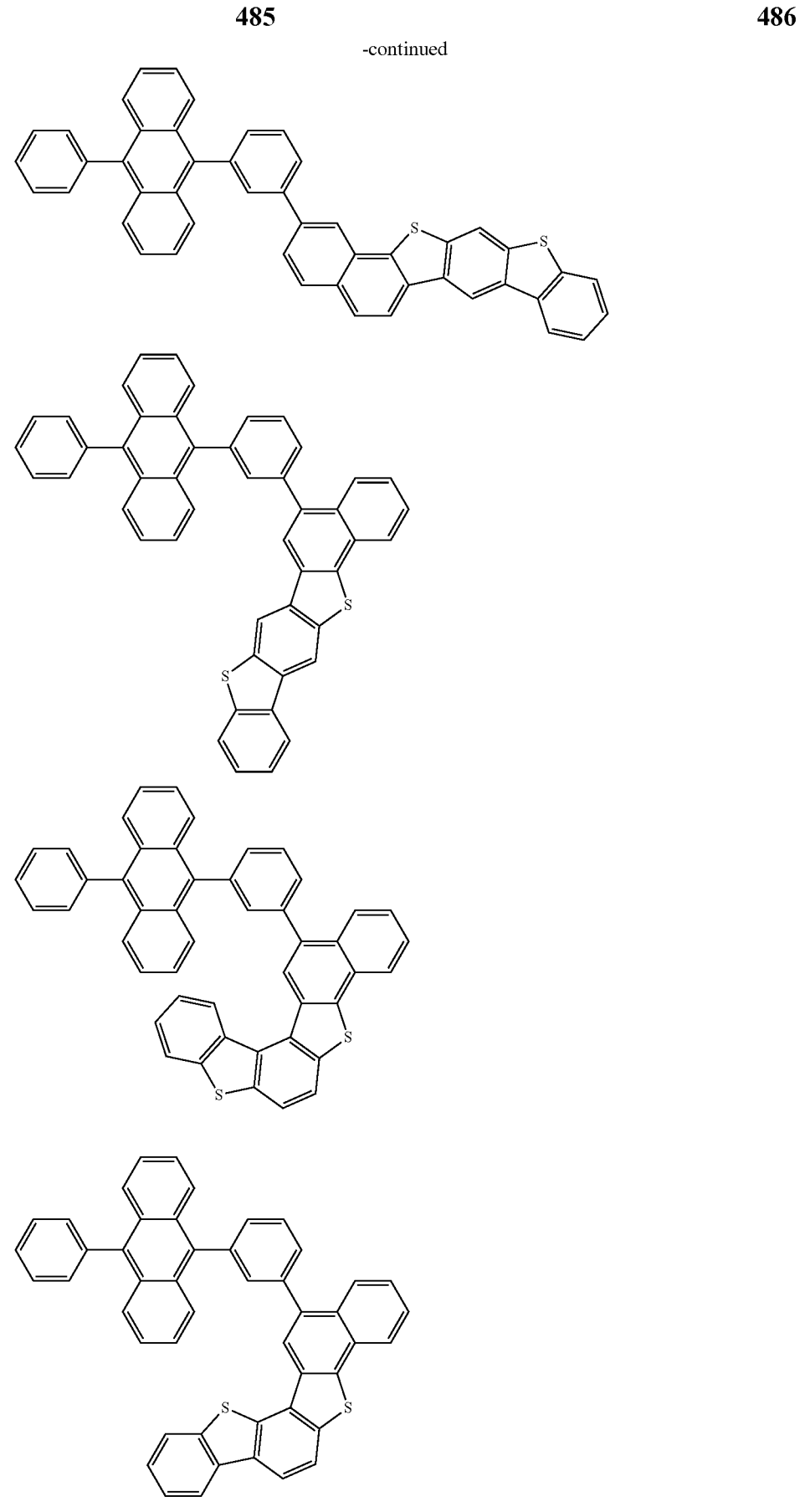

-continued

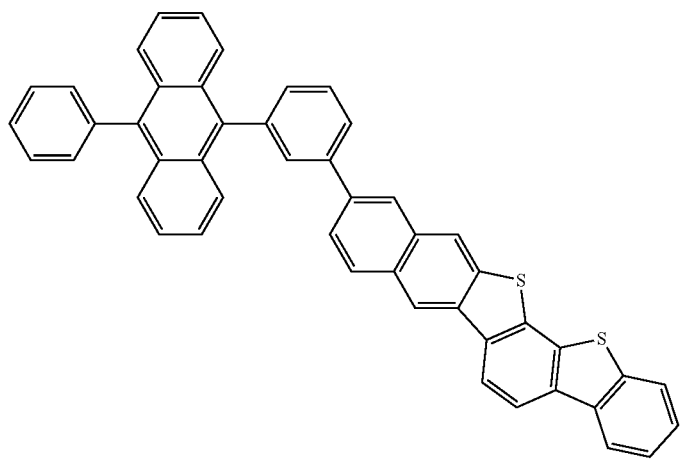
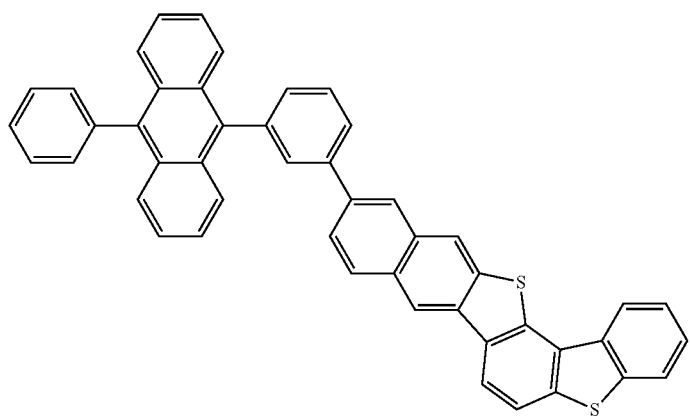
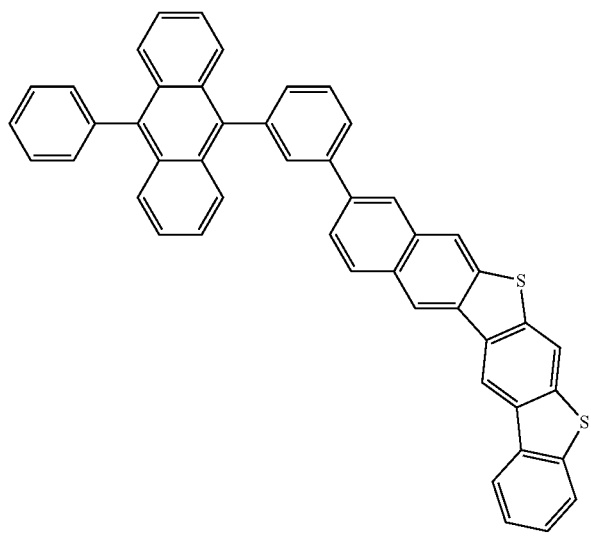

-continued
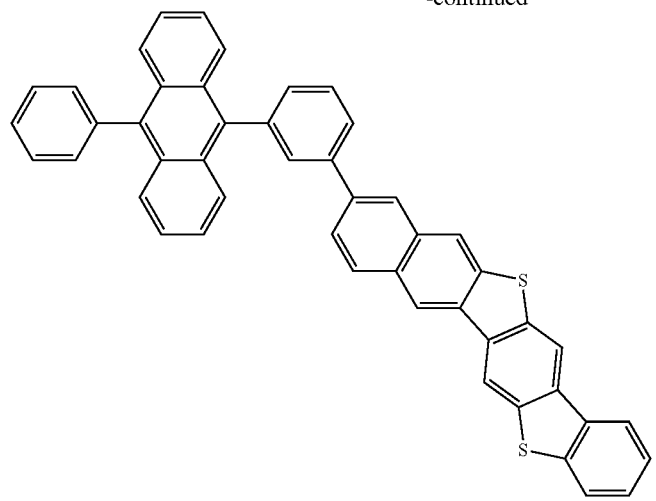
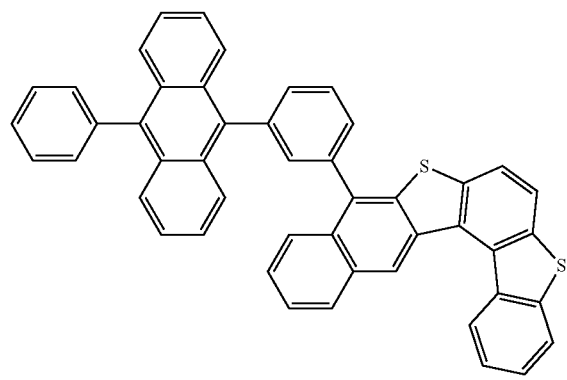
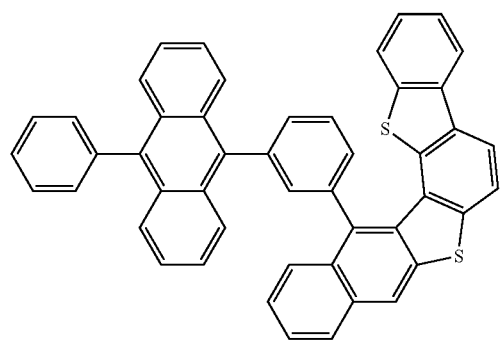
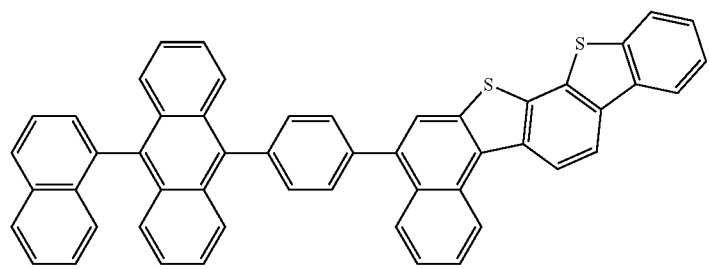

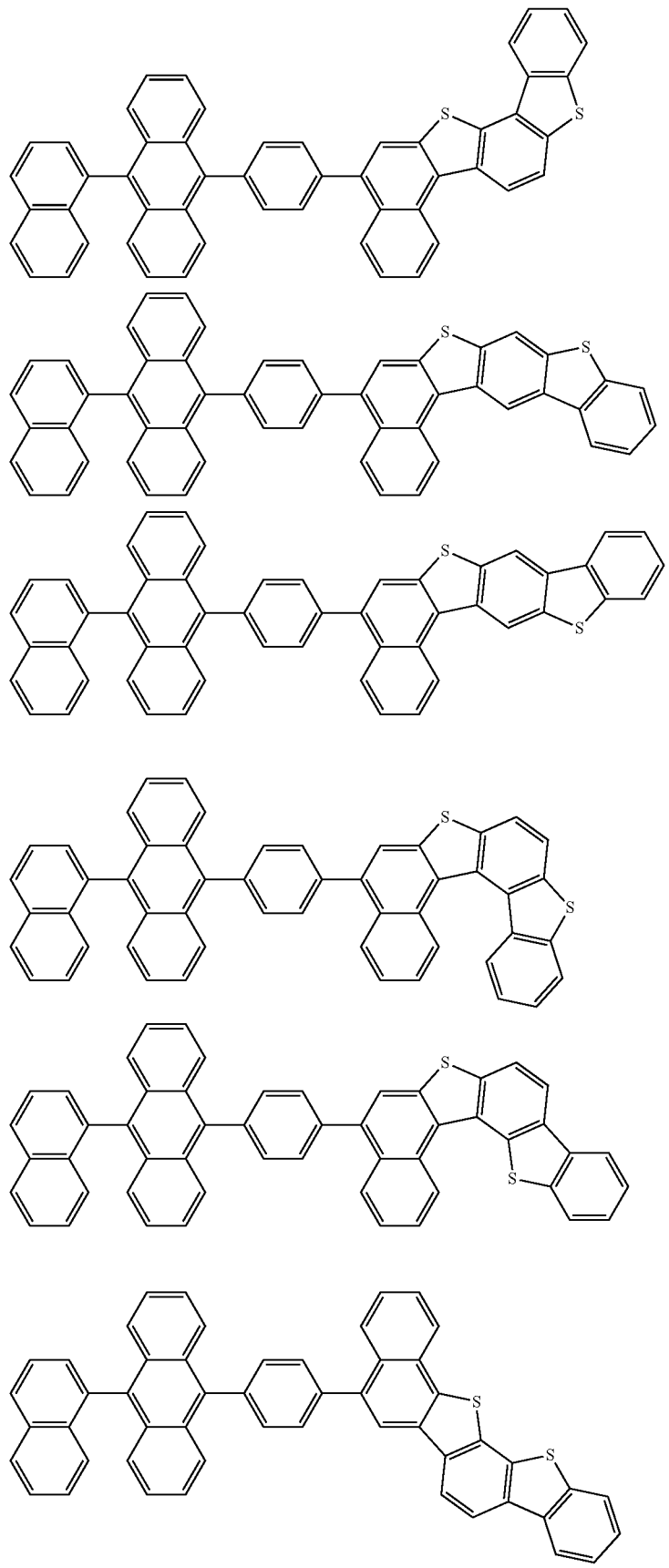

-continued
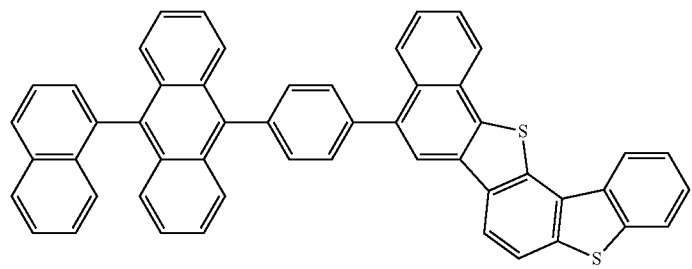
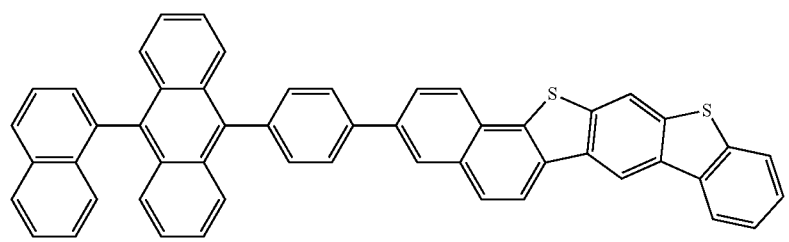
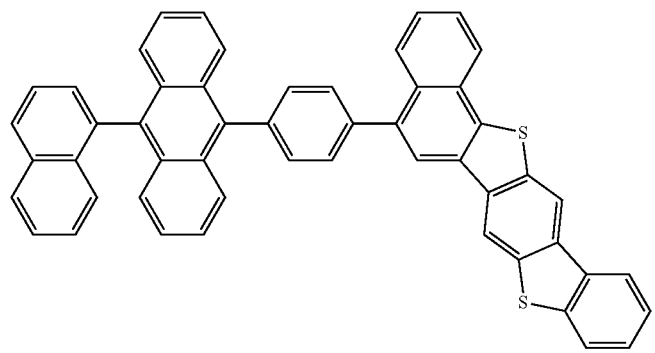
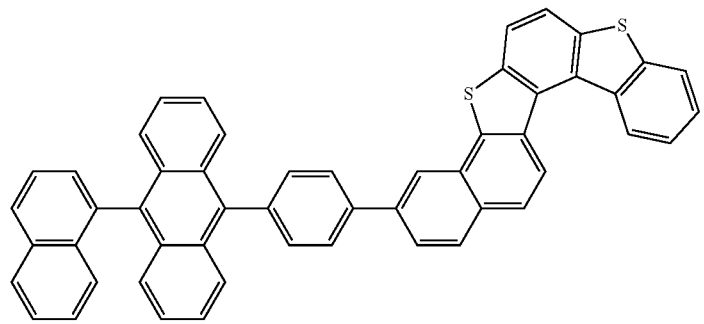
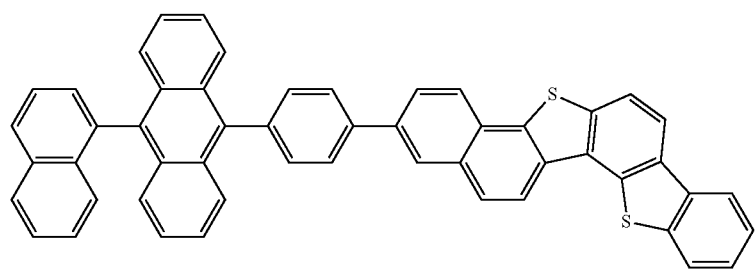

-continued
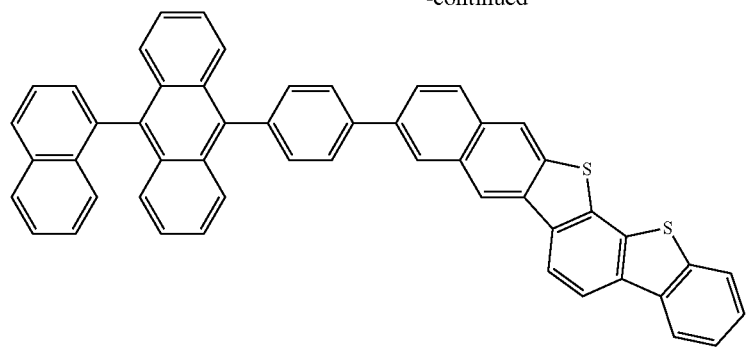
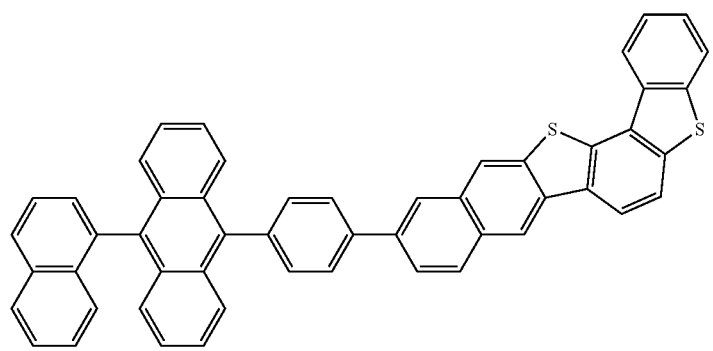
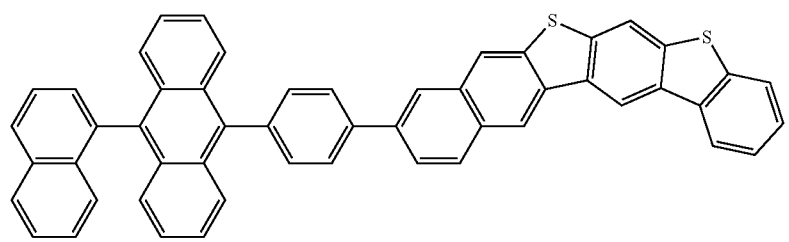
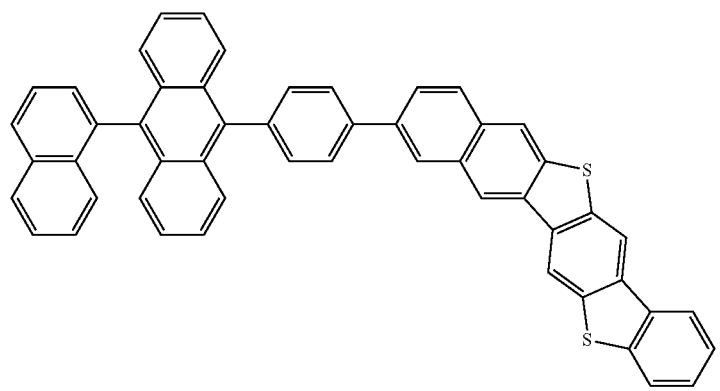
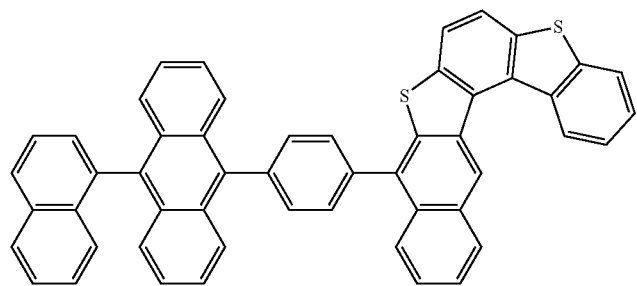

-continued
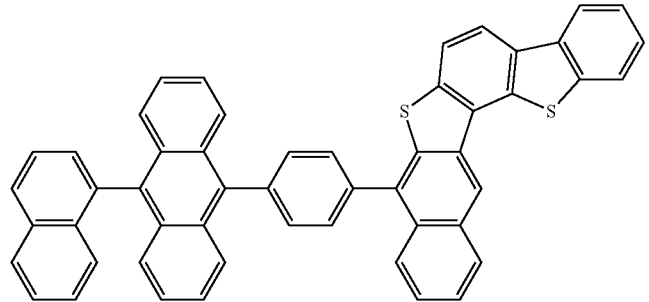
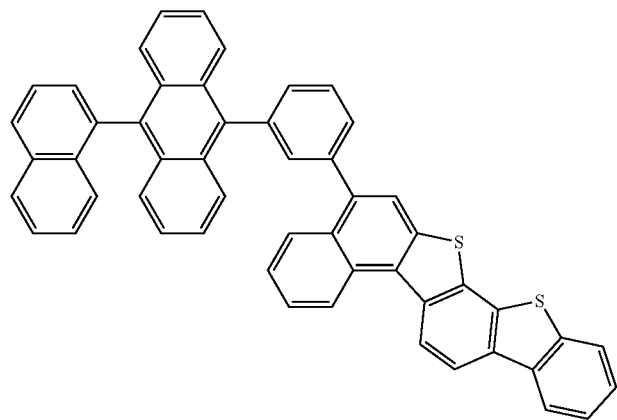
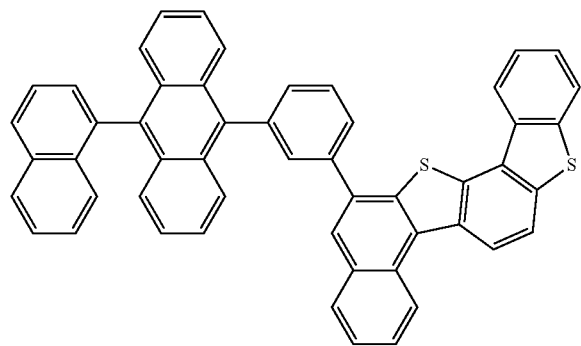
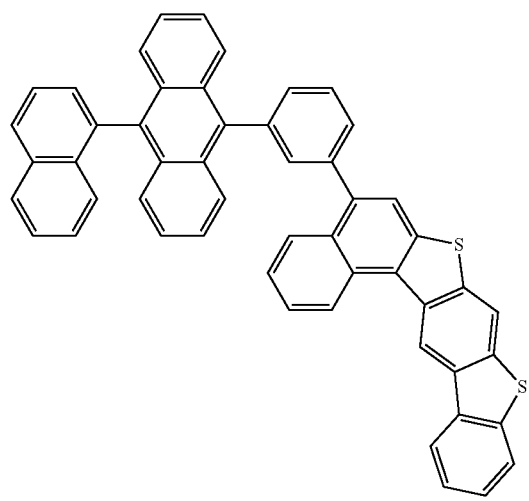

-continued
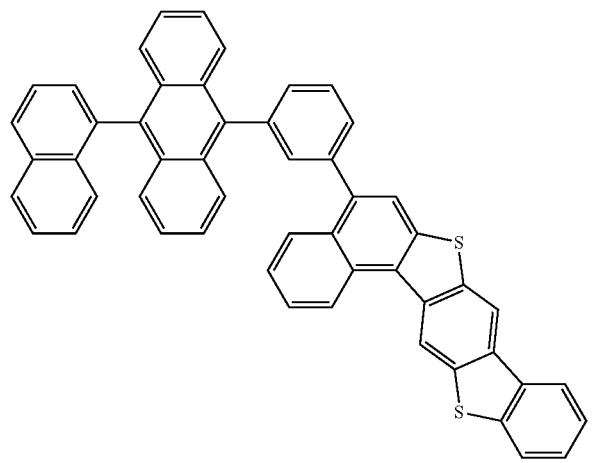
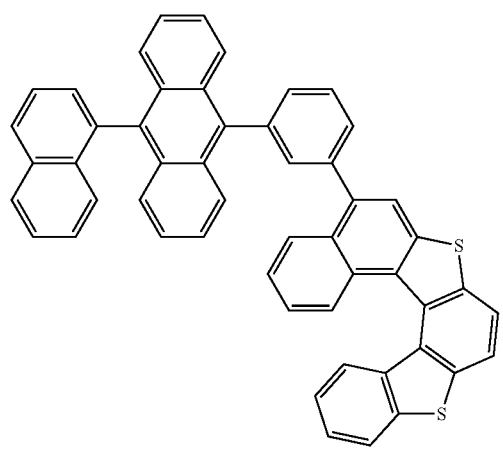
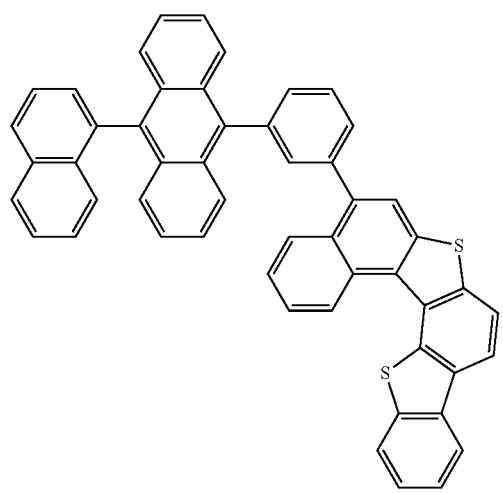

-continued
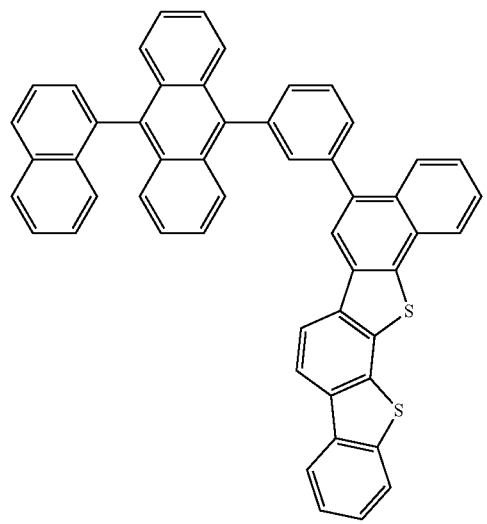
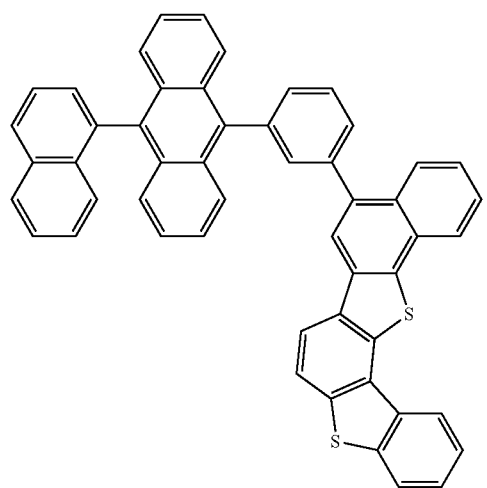
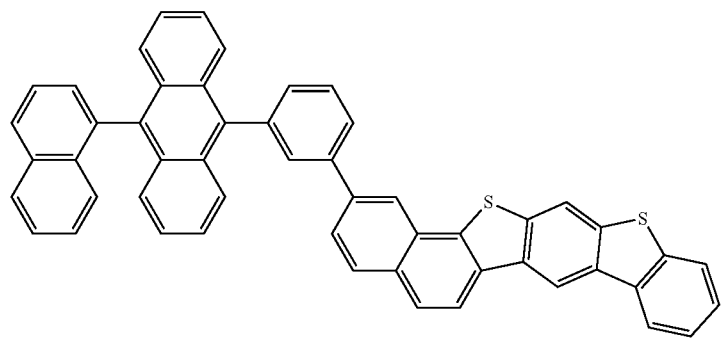

-continued
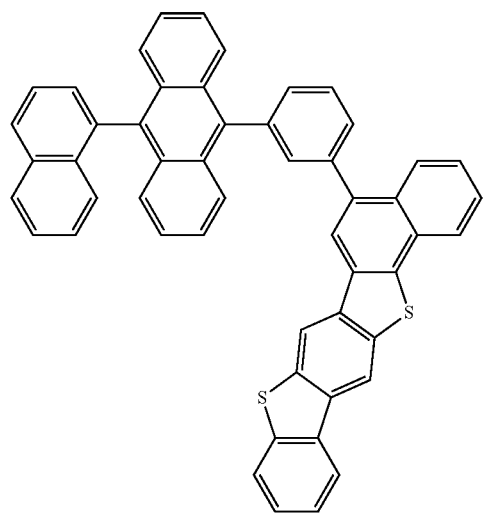
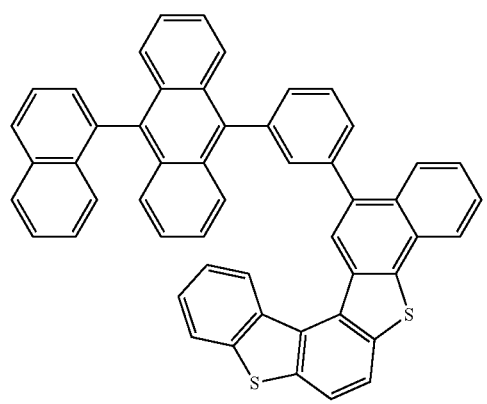
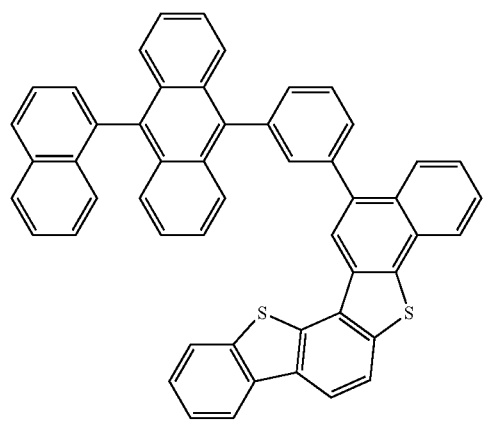

-continued
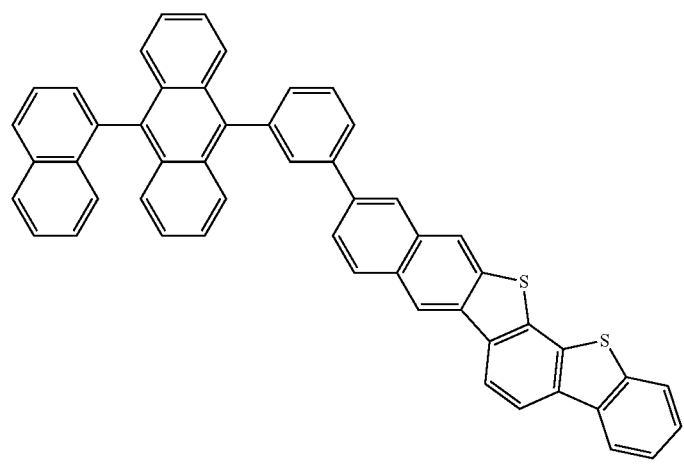
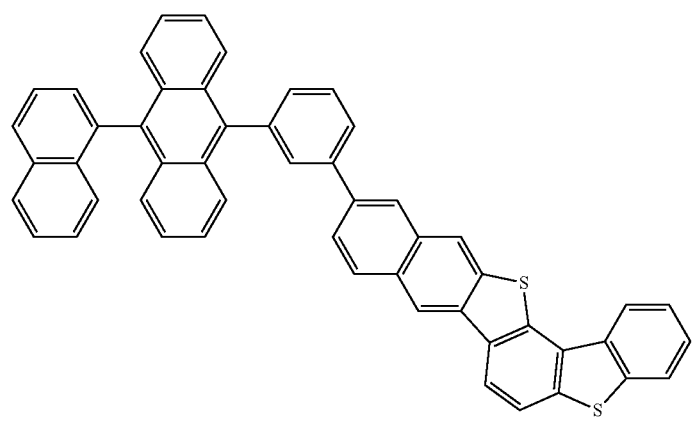
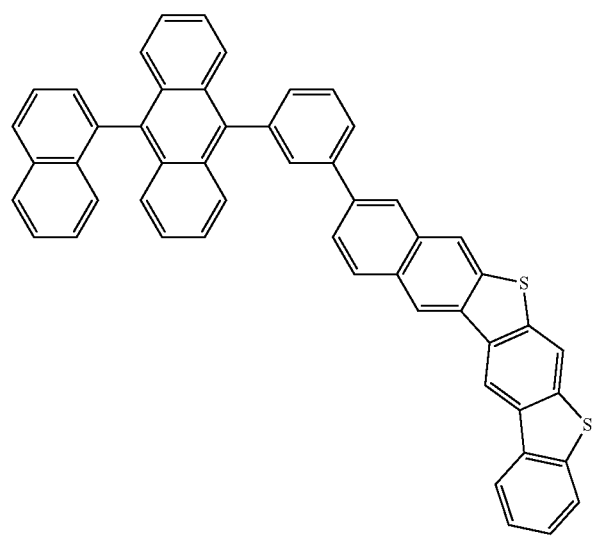

-continued
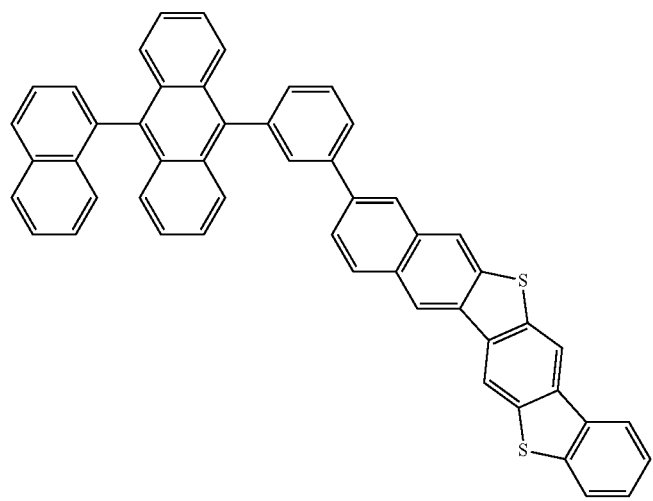
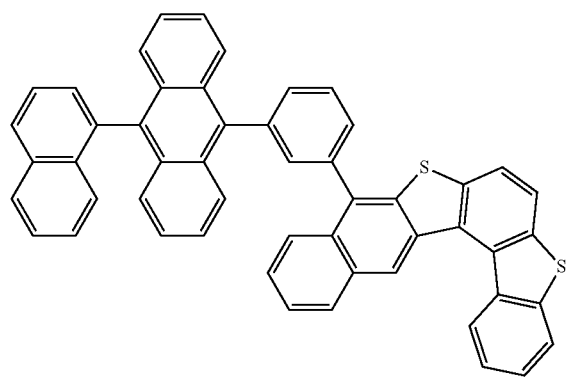
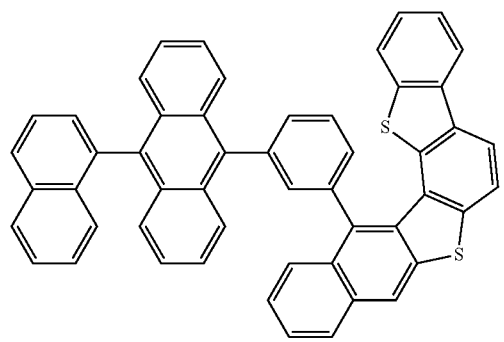
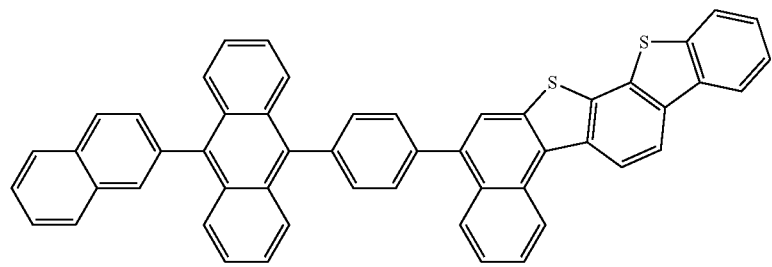

-continued
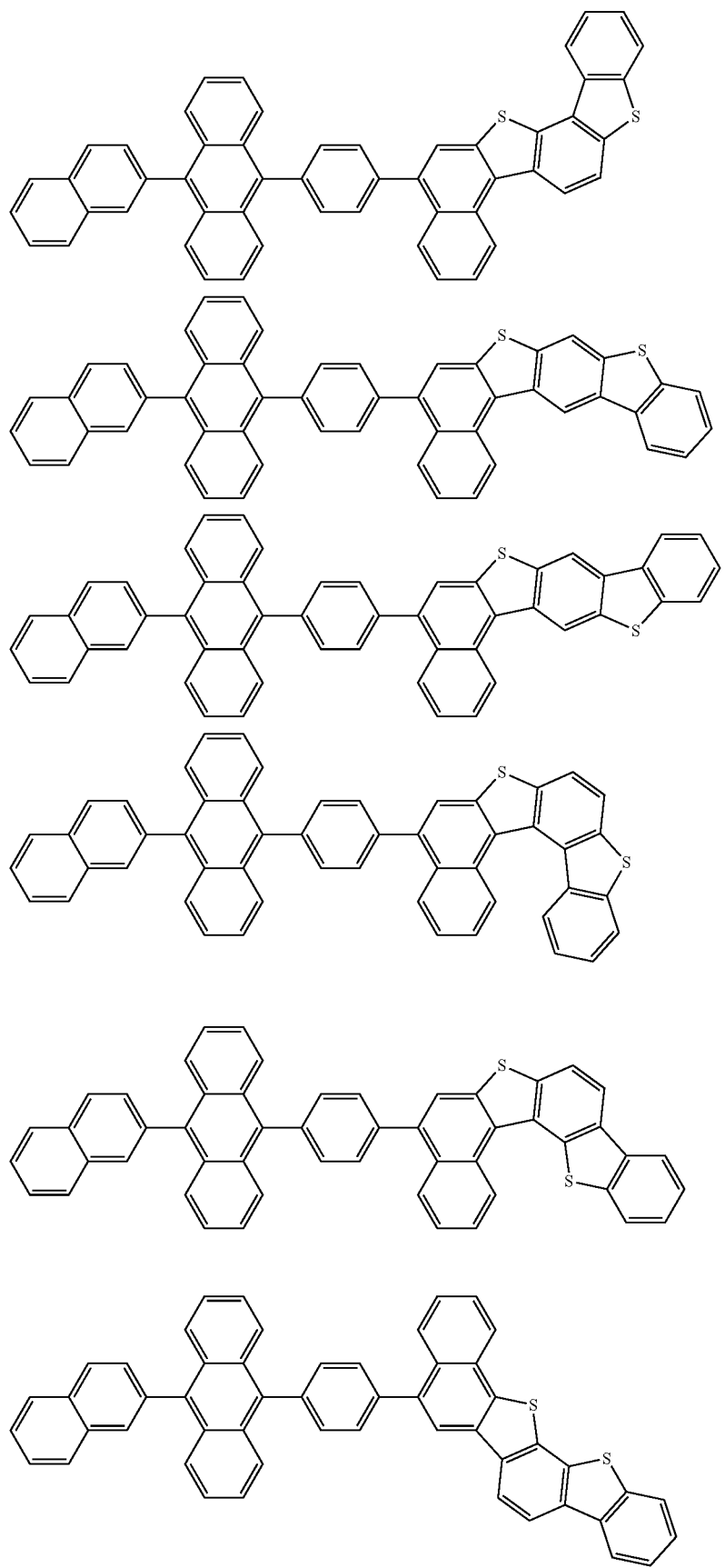

-continued
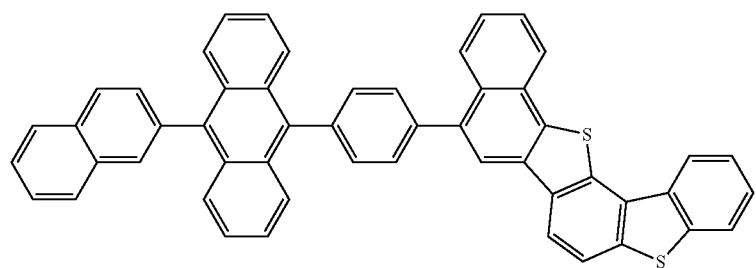
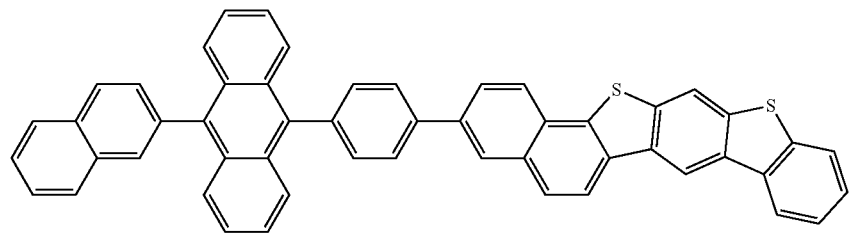
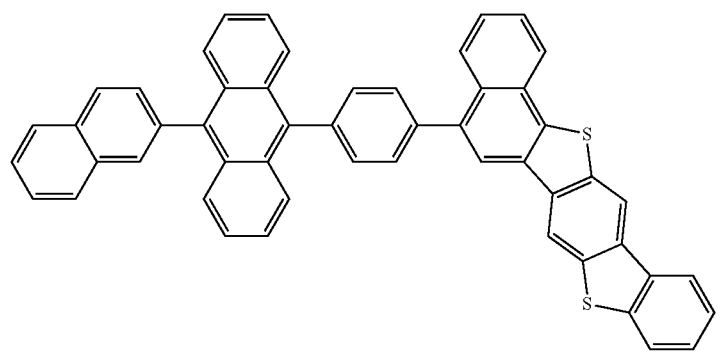
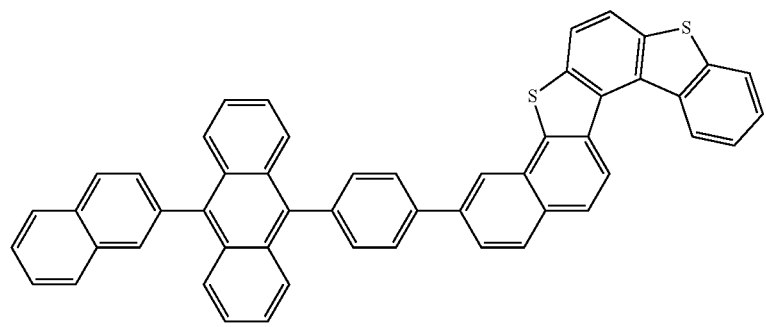
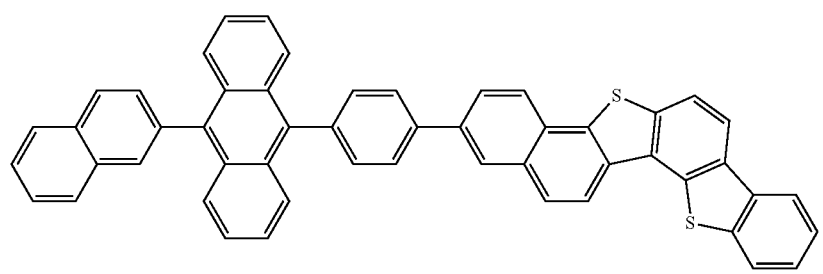

-continued
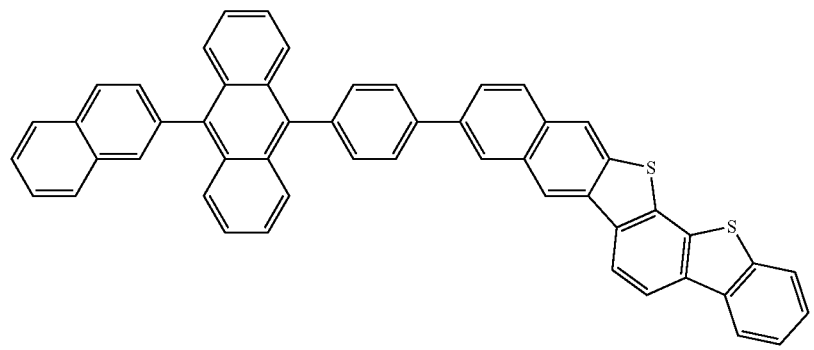
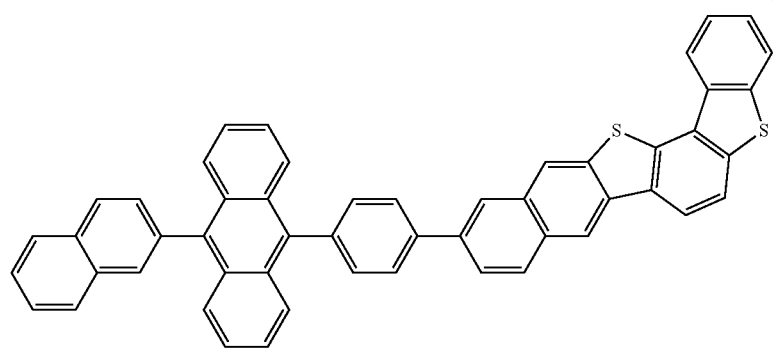
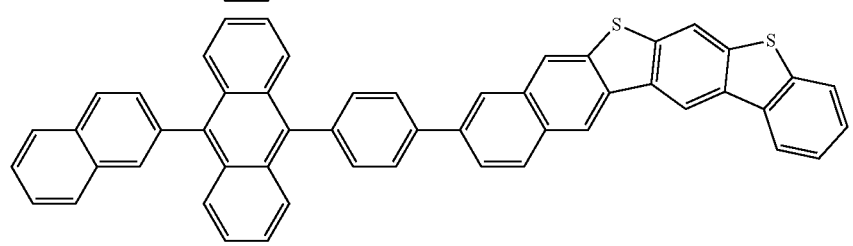
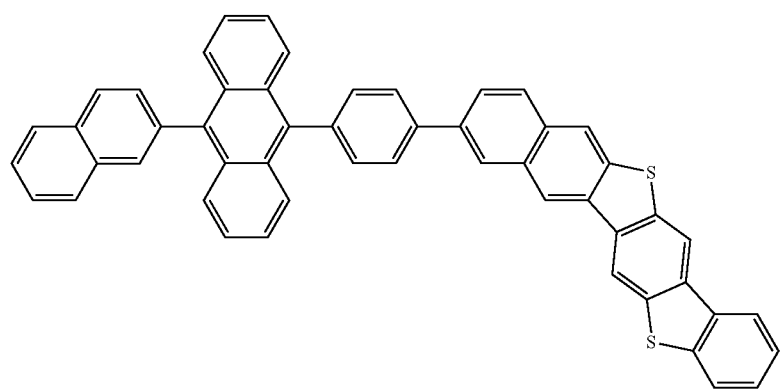
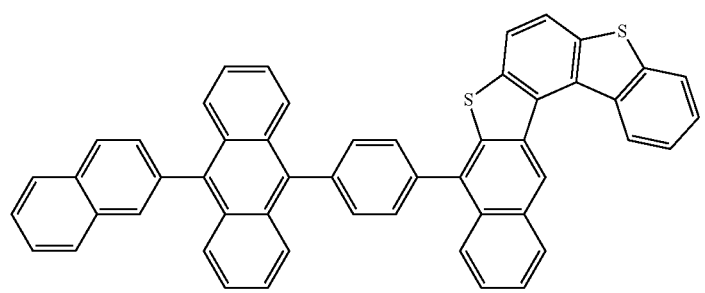

-continued
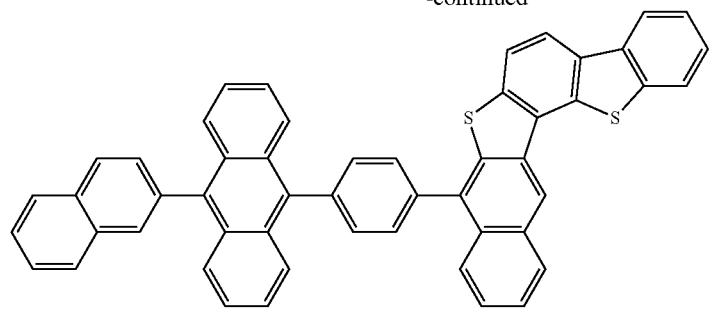
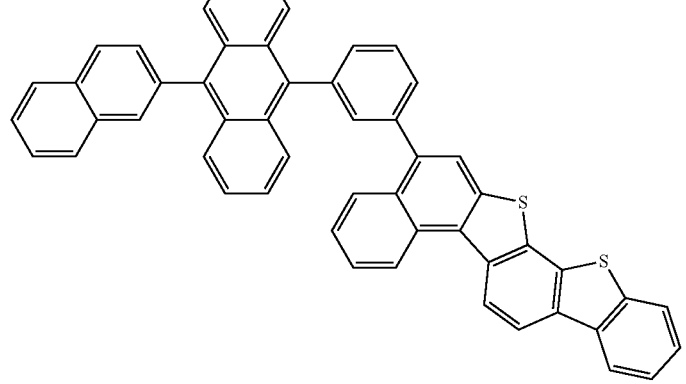
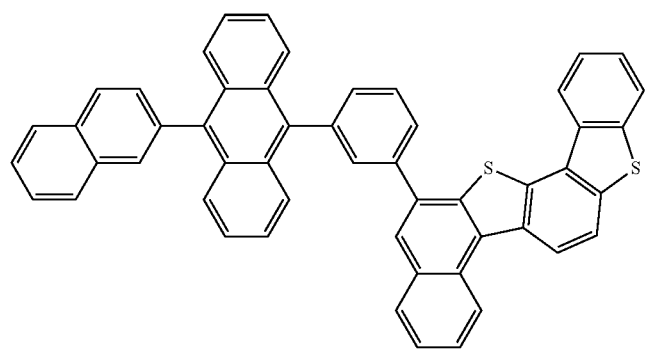
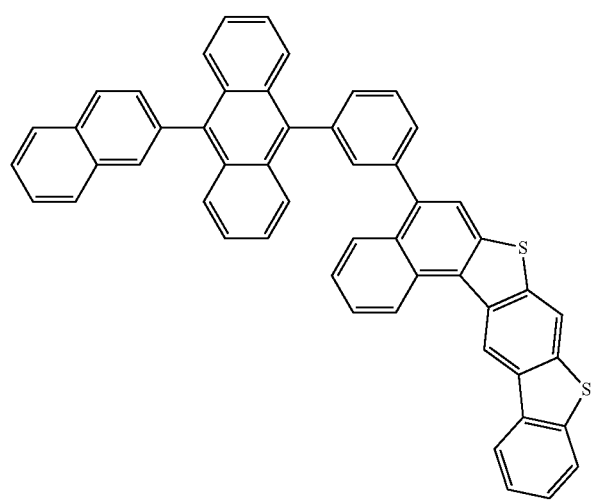

517
-continued
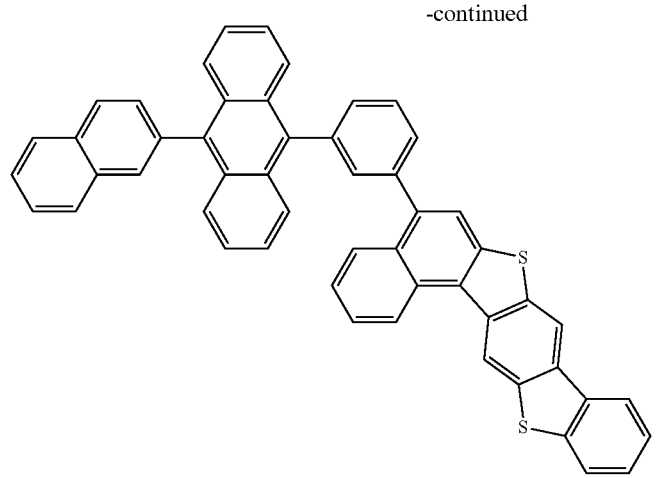
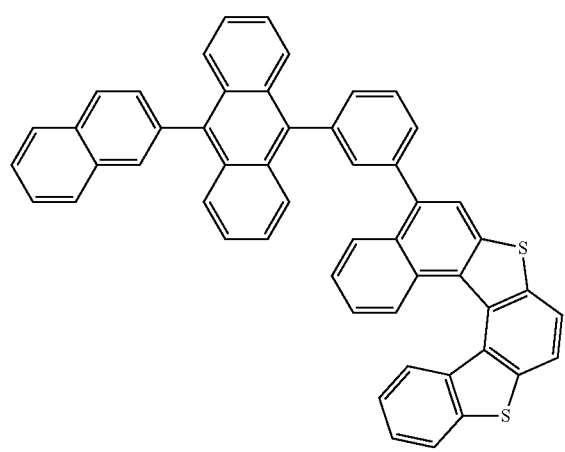
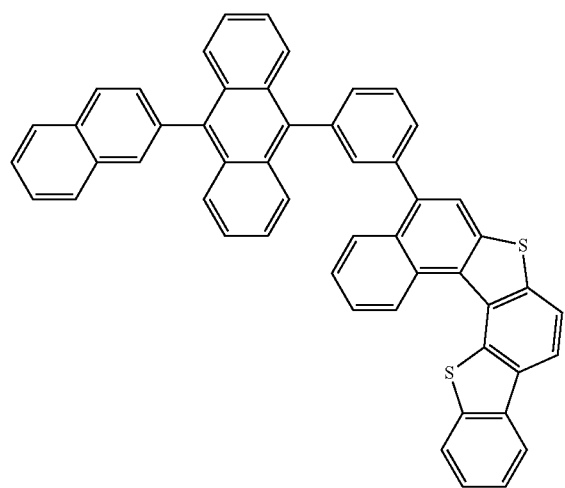
518

-continued
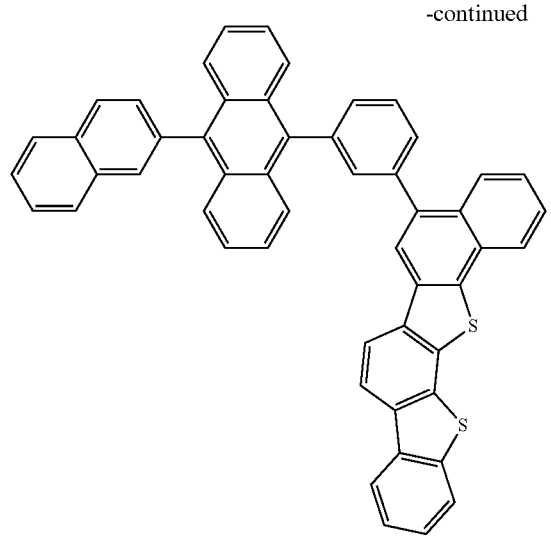
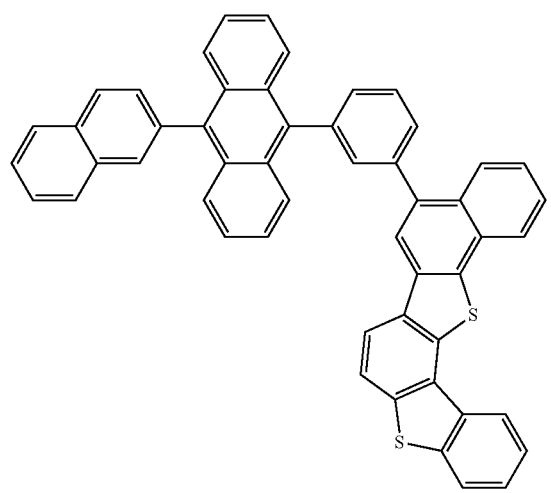
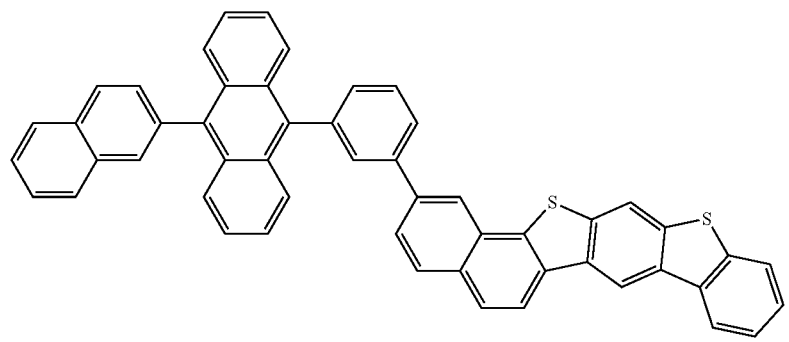

-continued
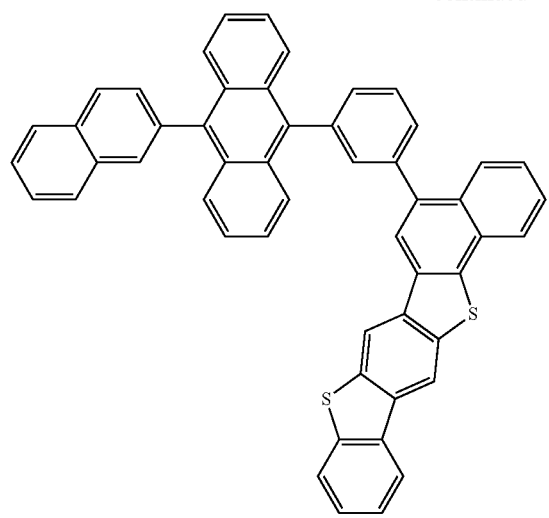
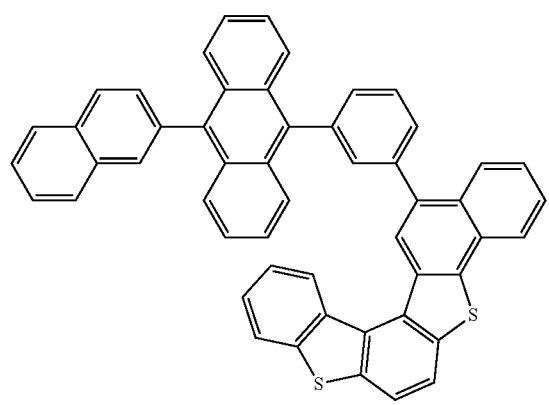
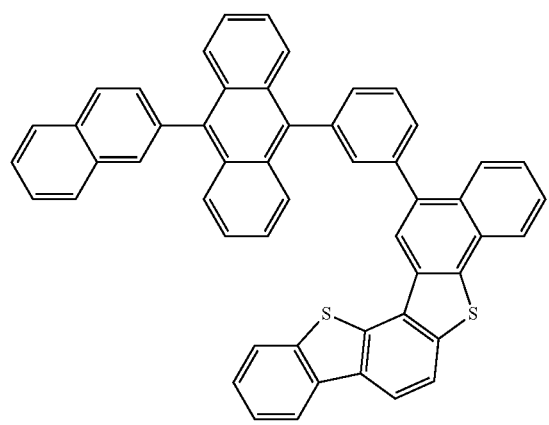

-continued
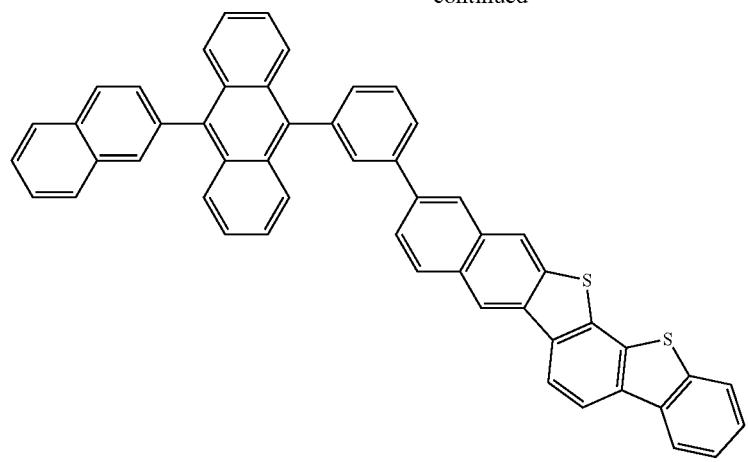
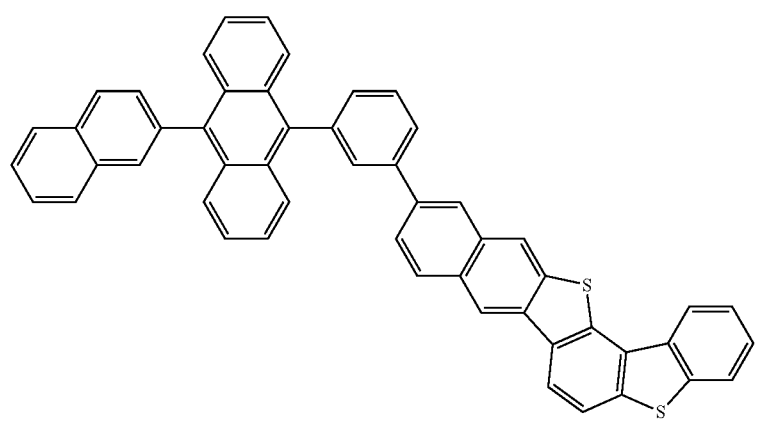
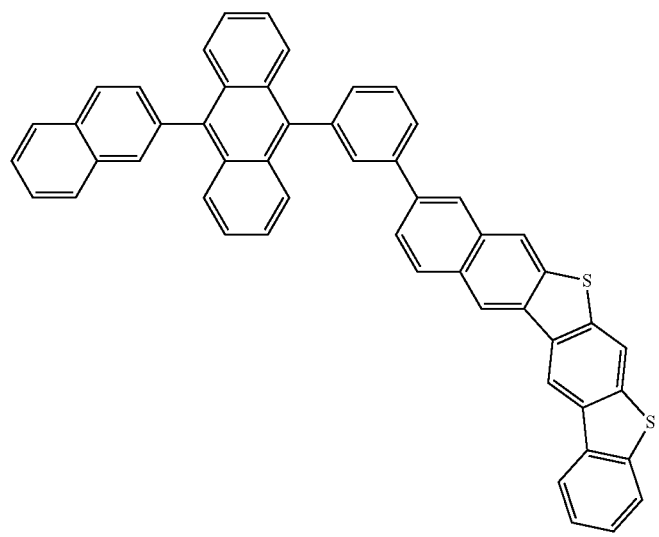

-continued
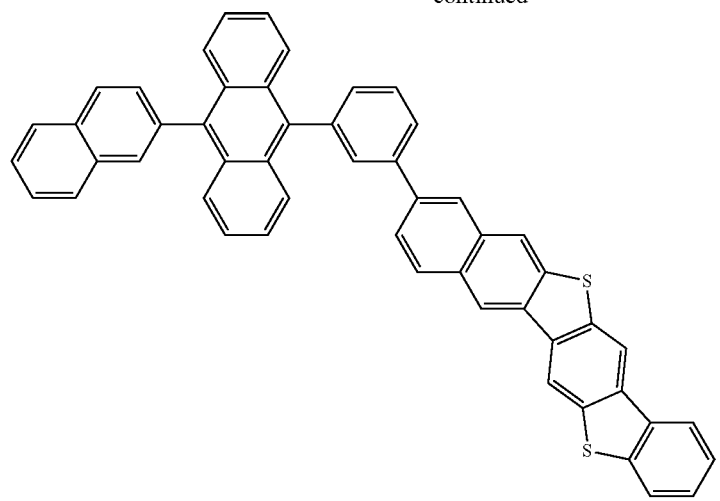
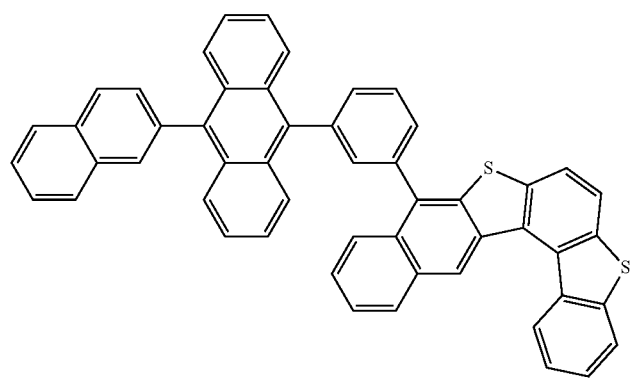
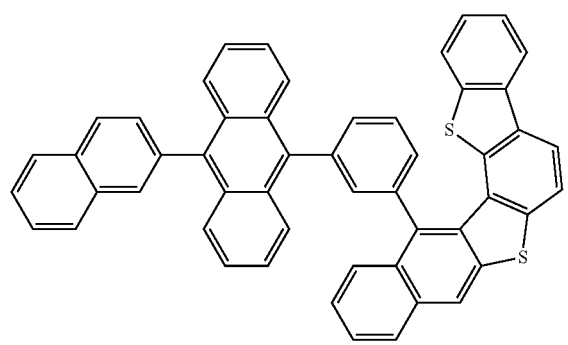
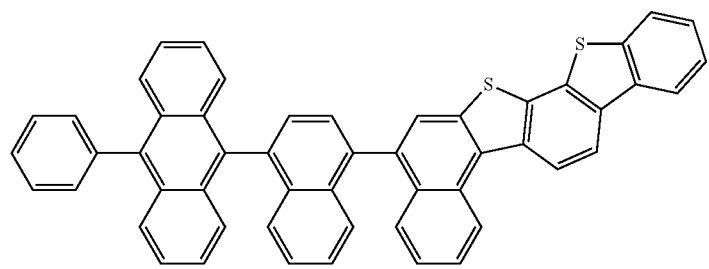

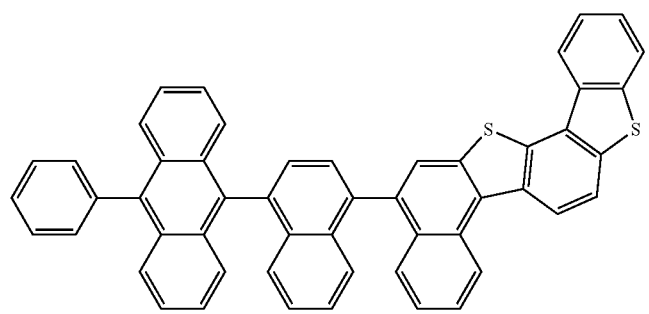
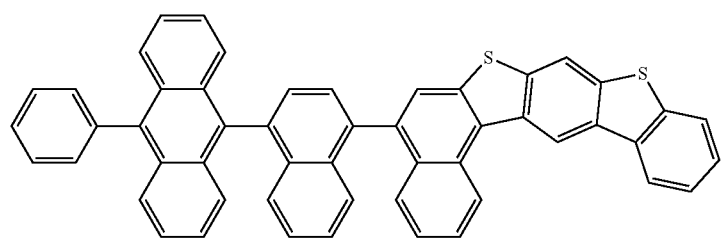
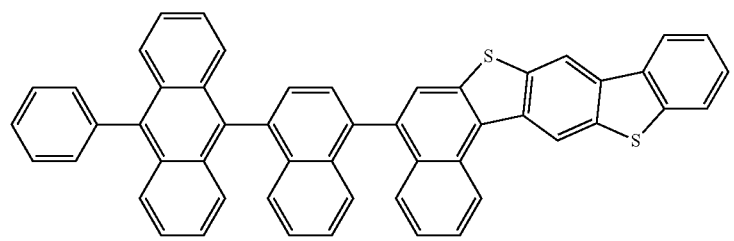
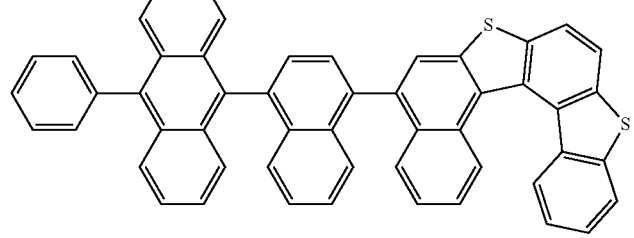
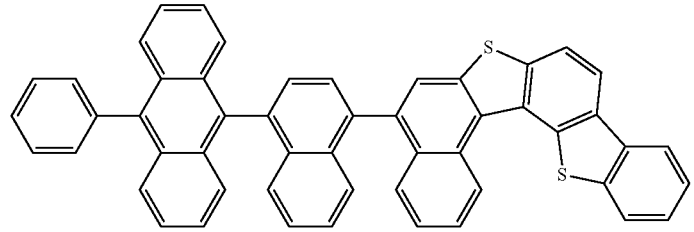
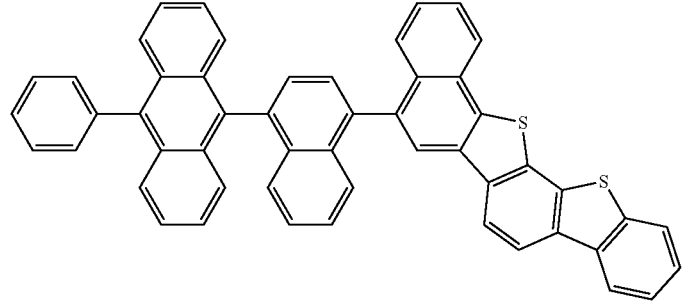

-continued
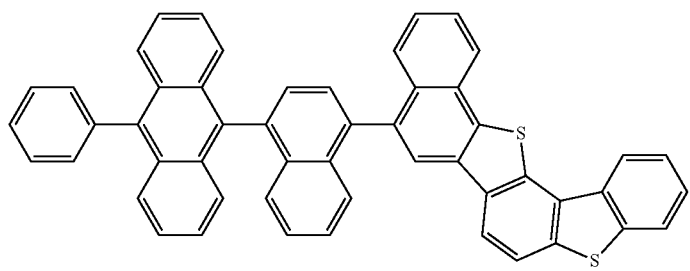
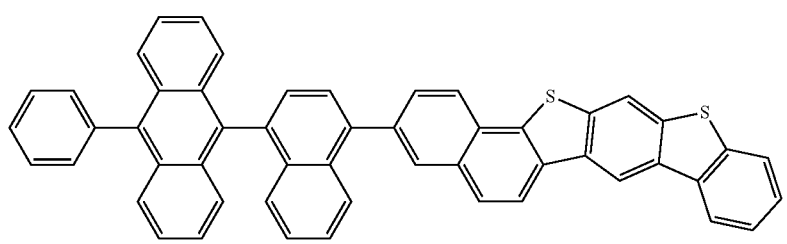
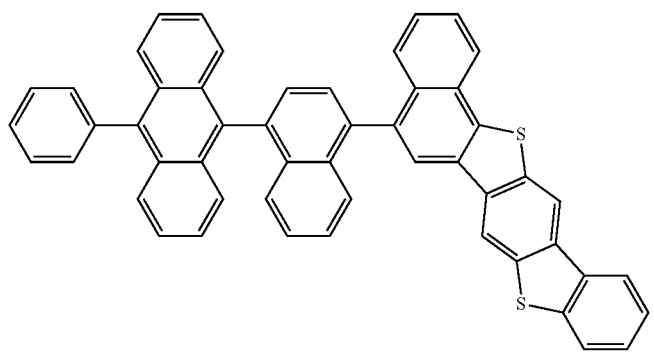
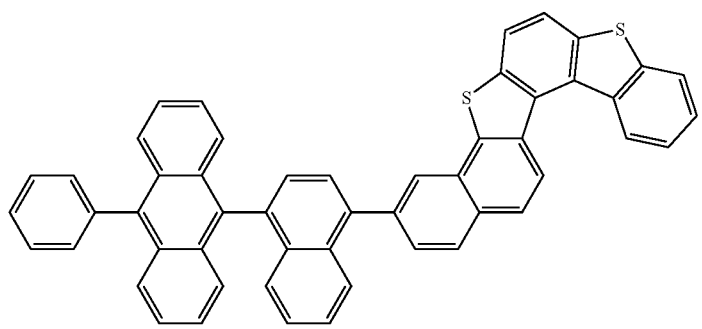
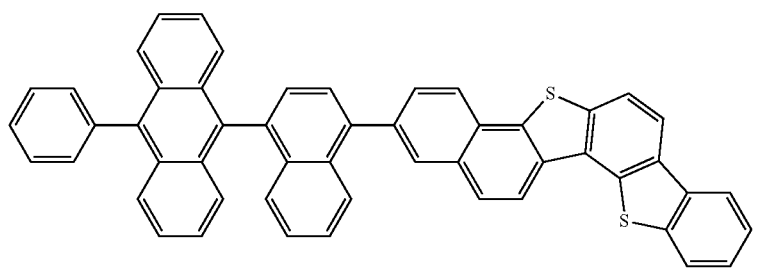

-continued
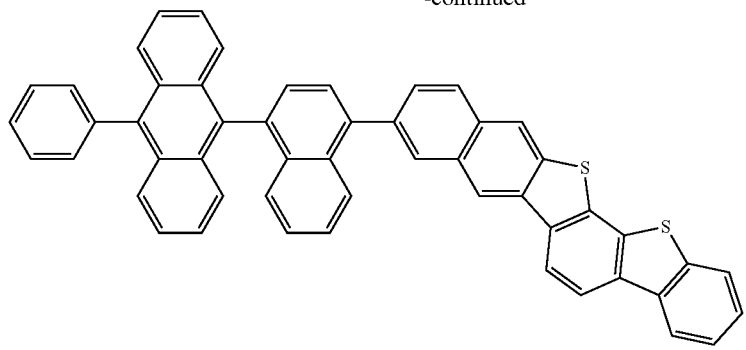
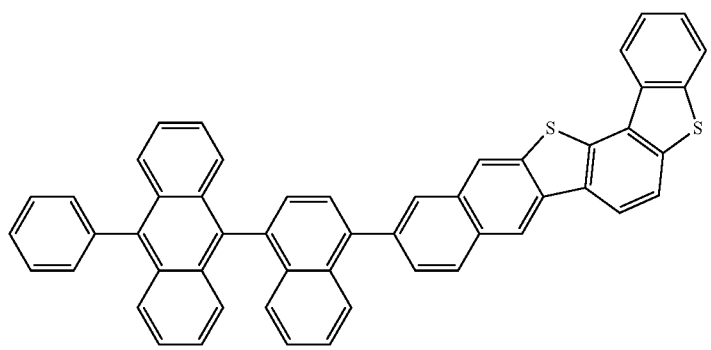
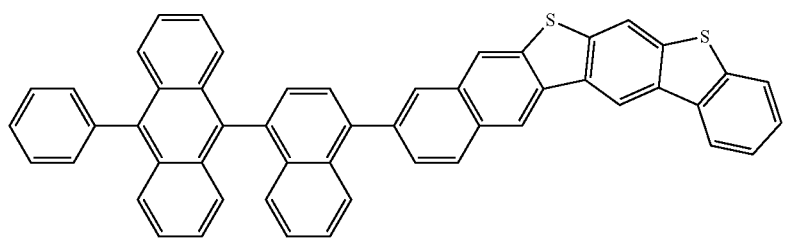
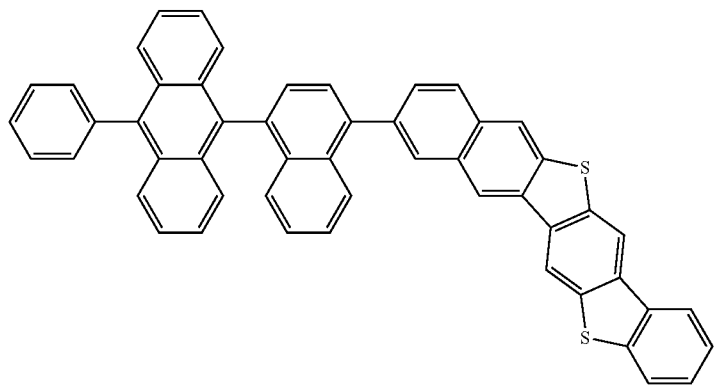
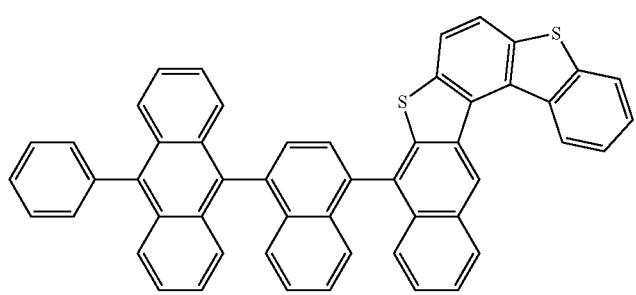

-continued
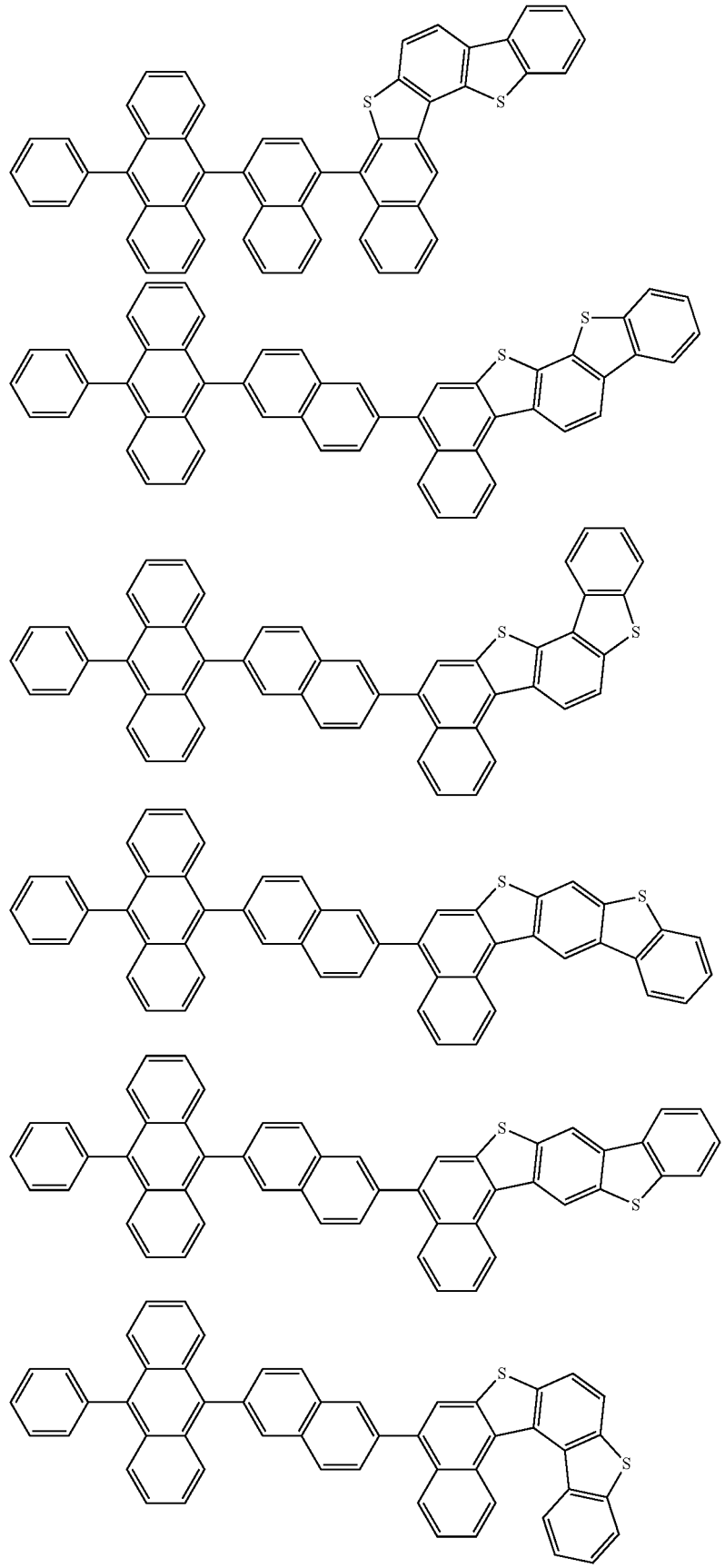

-continued
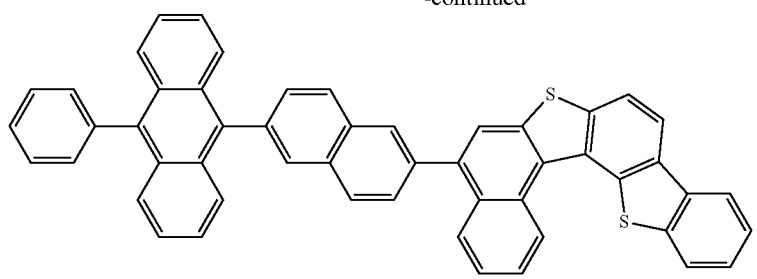
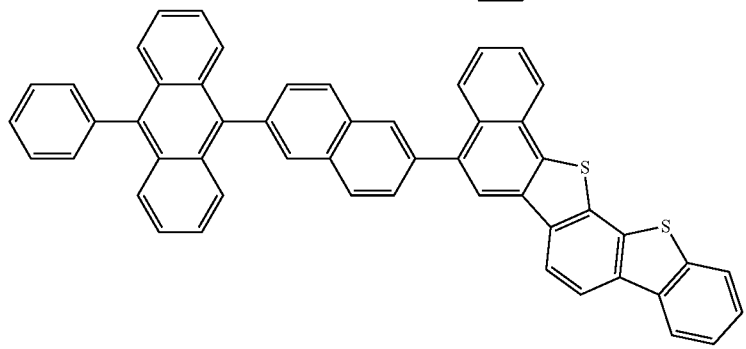
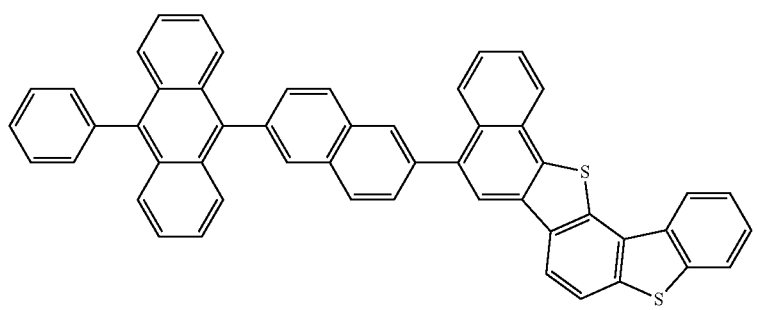
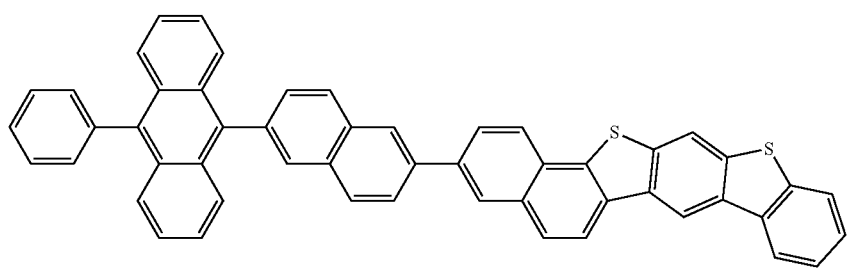
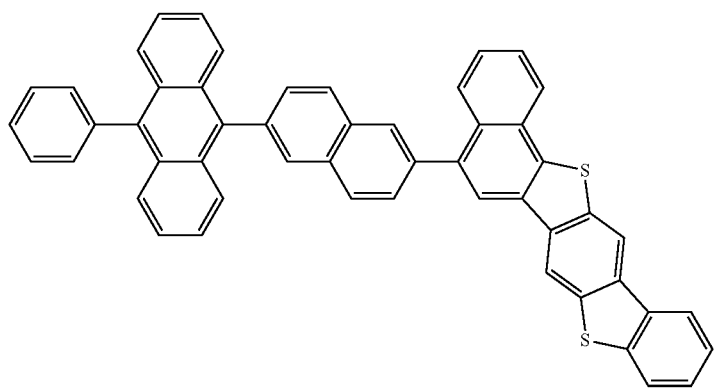

-continued
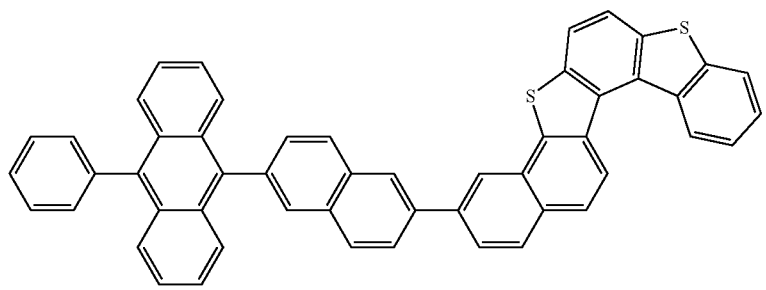
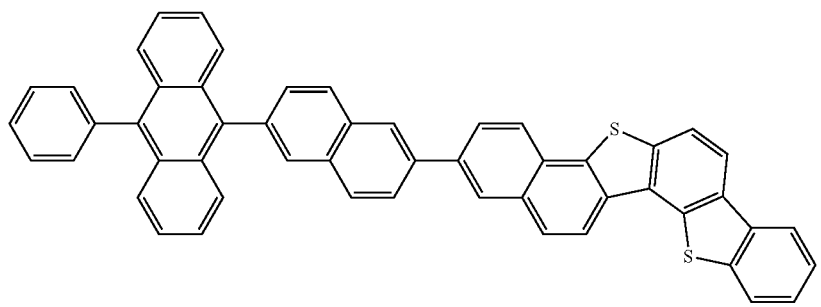
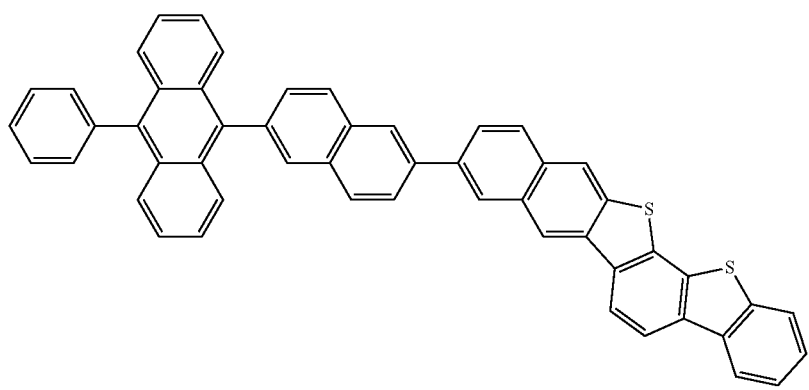
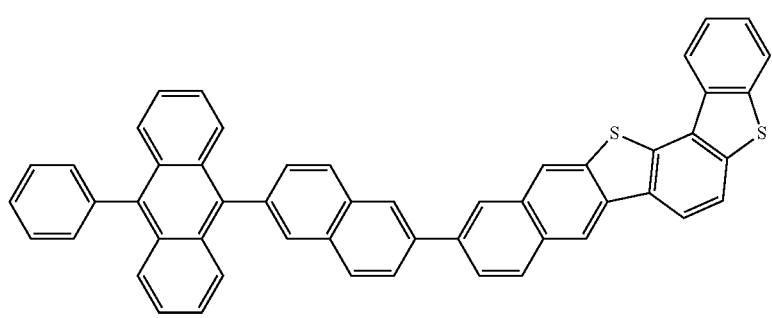
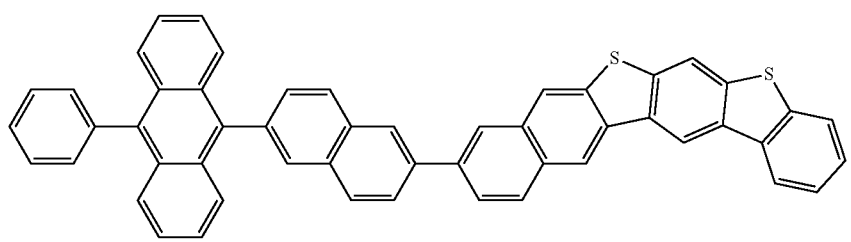

-continued
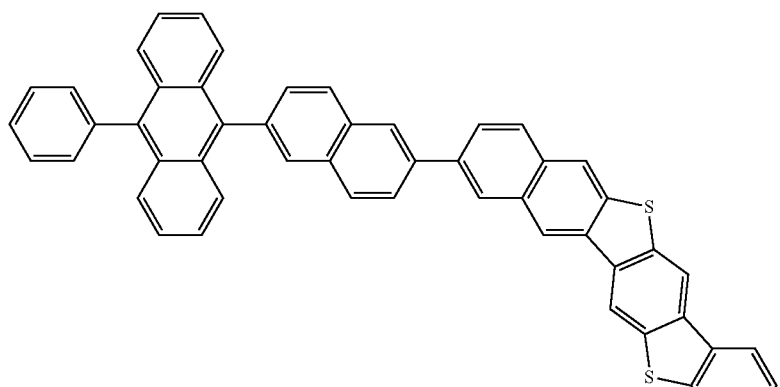
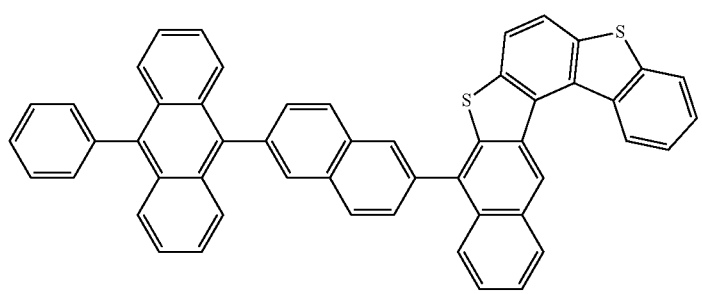
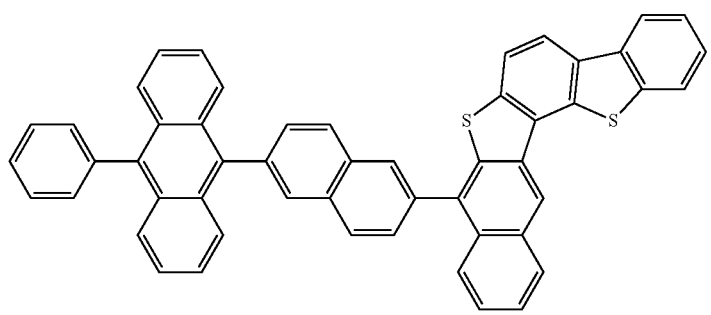
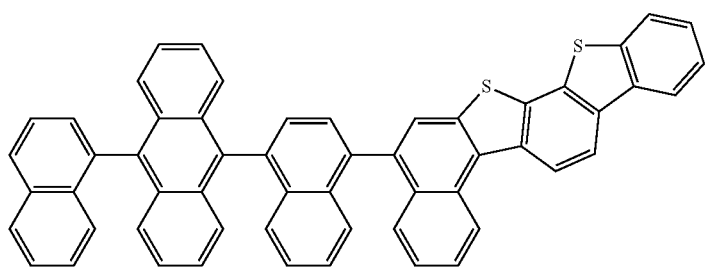
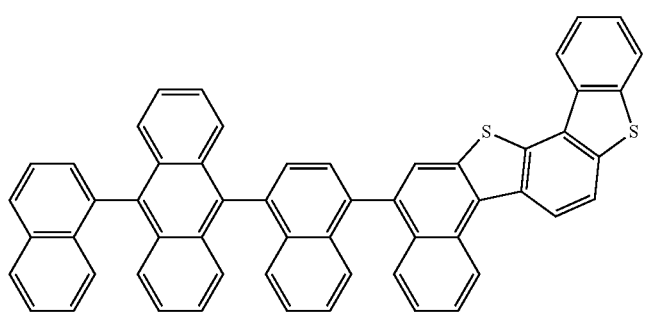

-continued
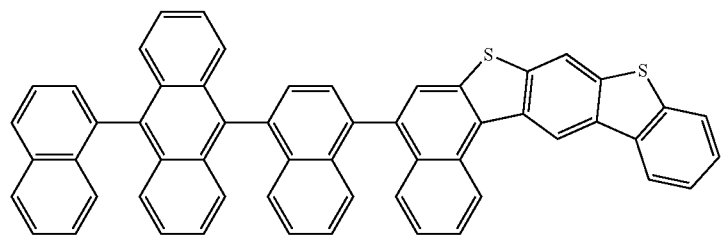
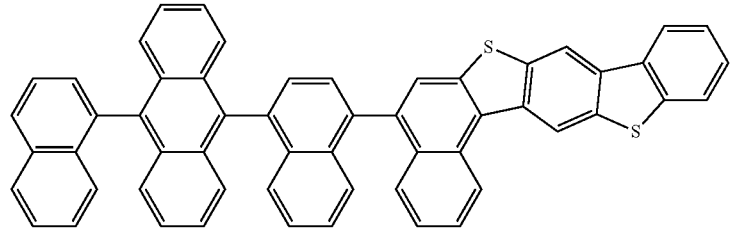
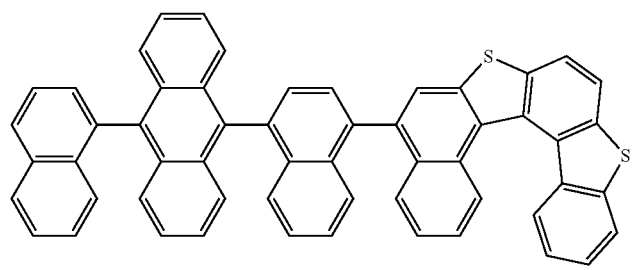
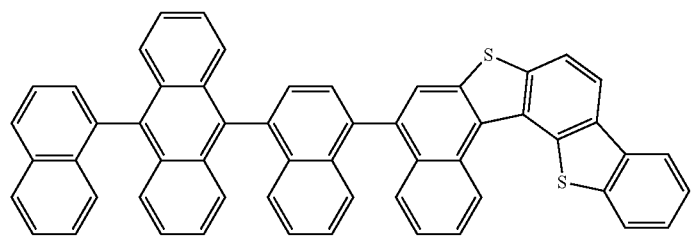
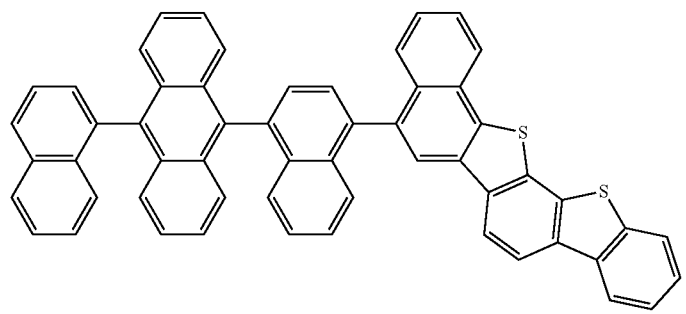
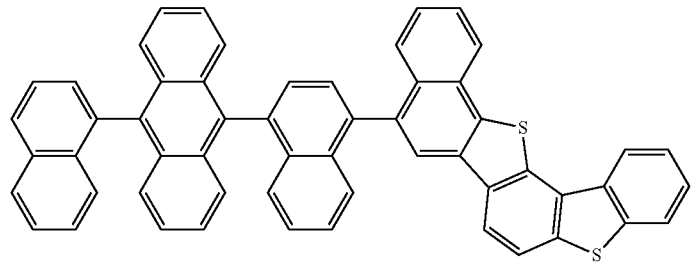

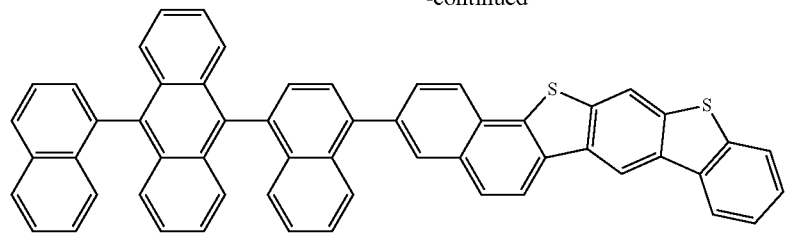
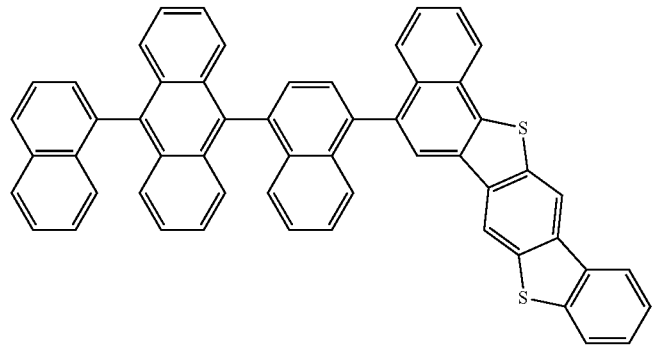
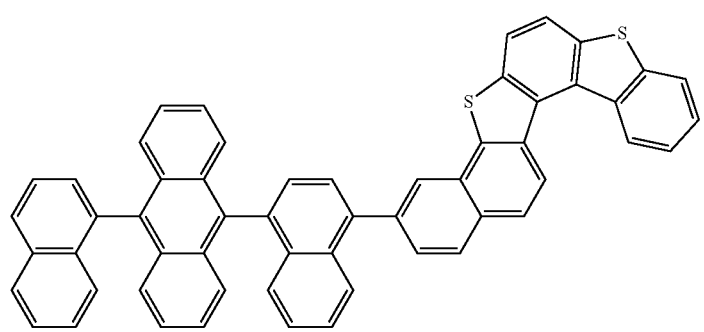
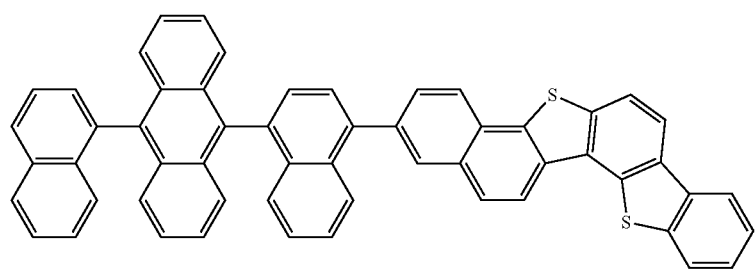
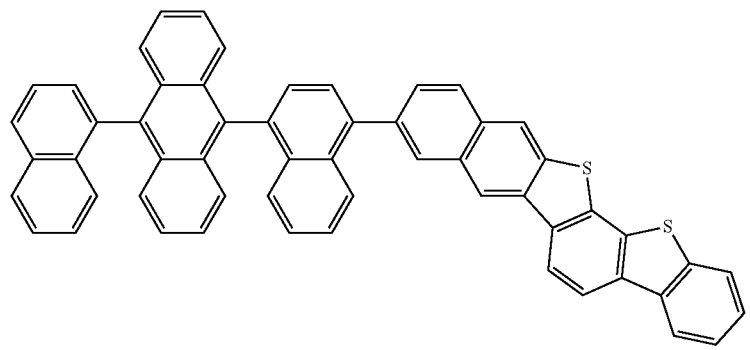

-continued
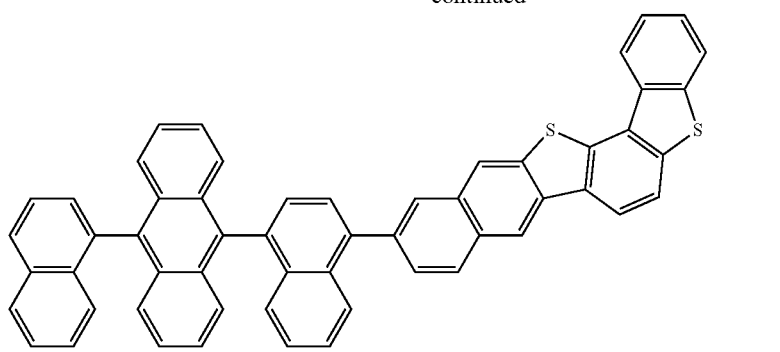
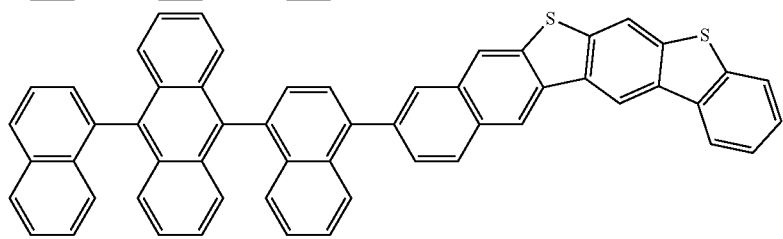
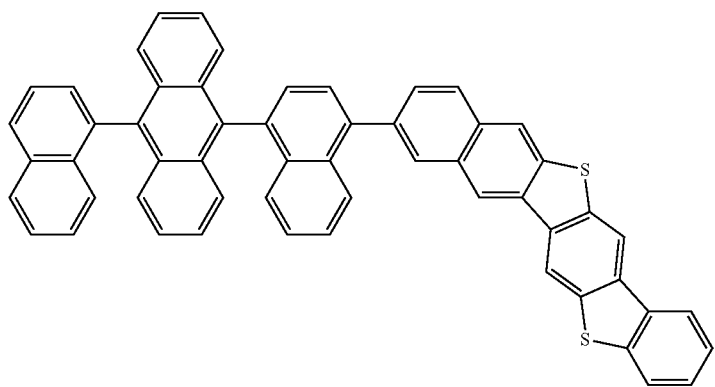
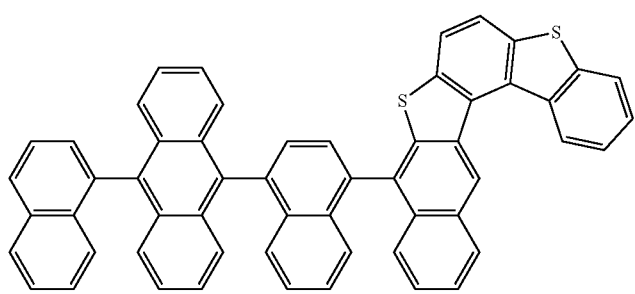
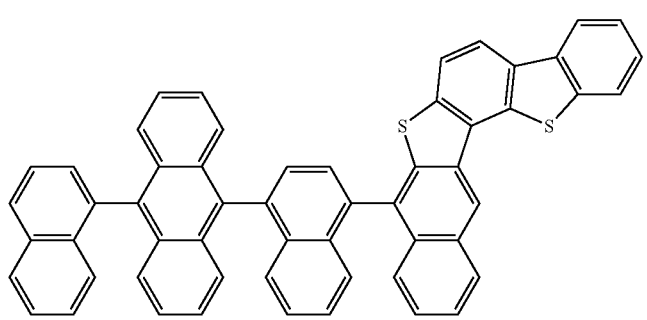

-continued
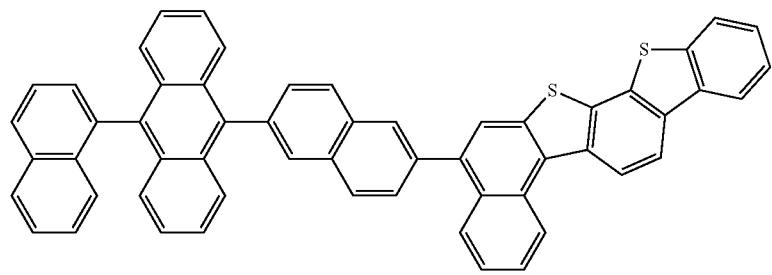
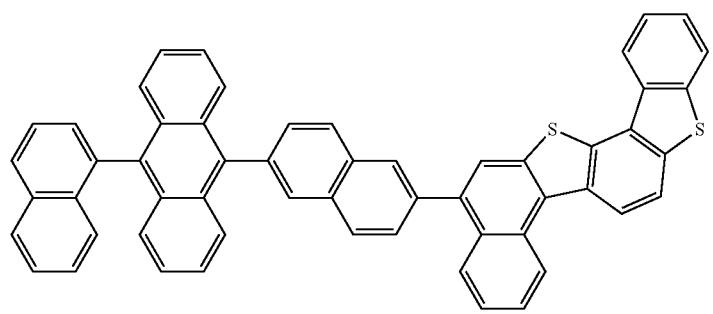
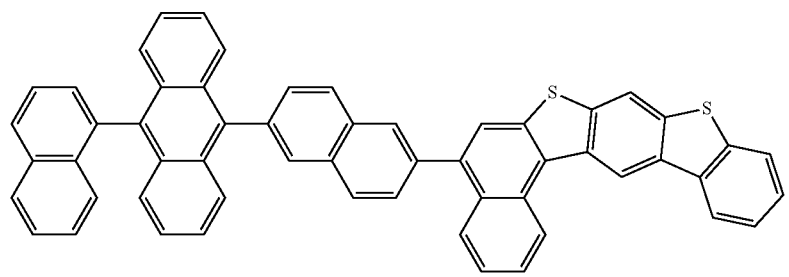
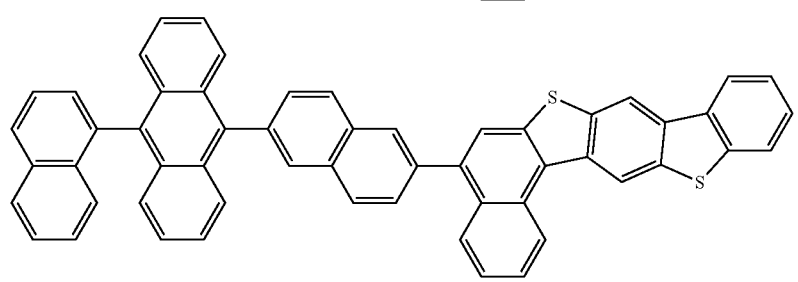
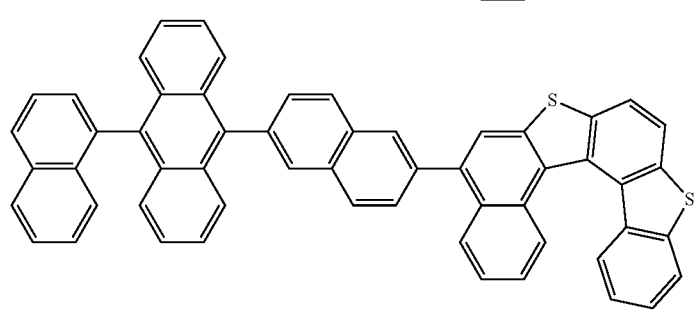
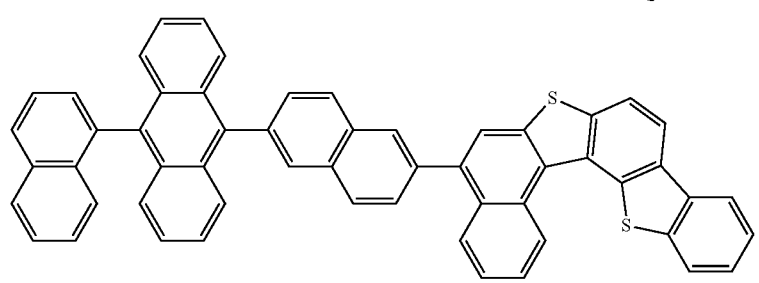

-continued
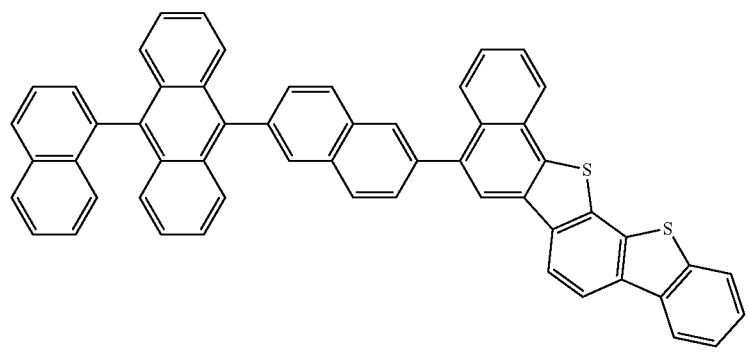
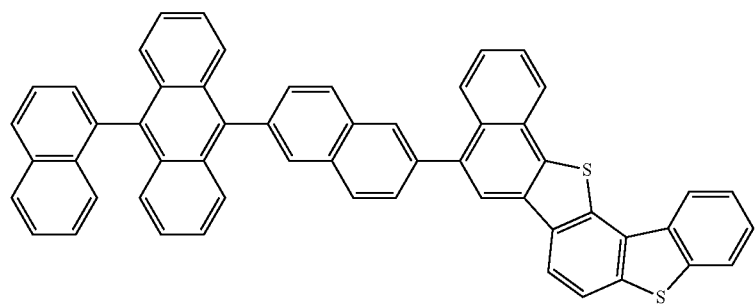
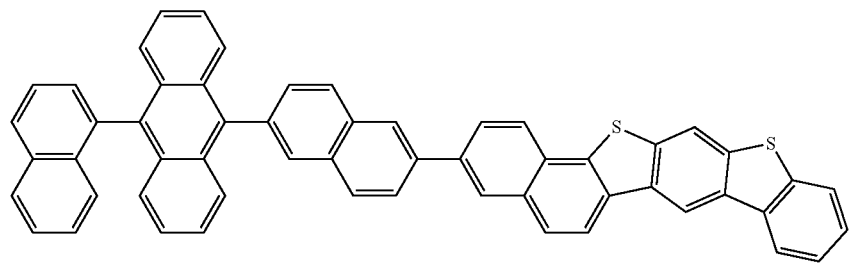
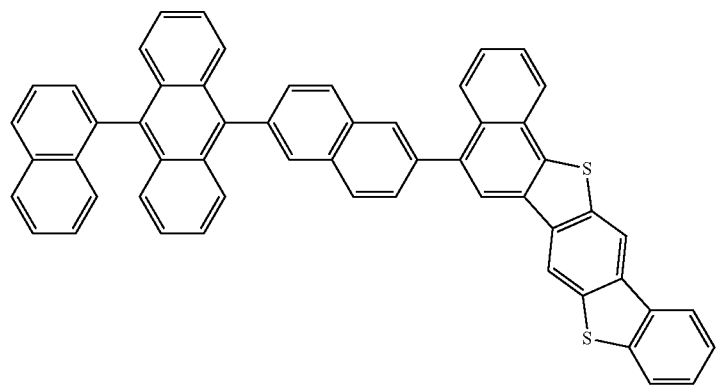
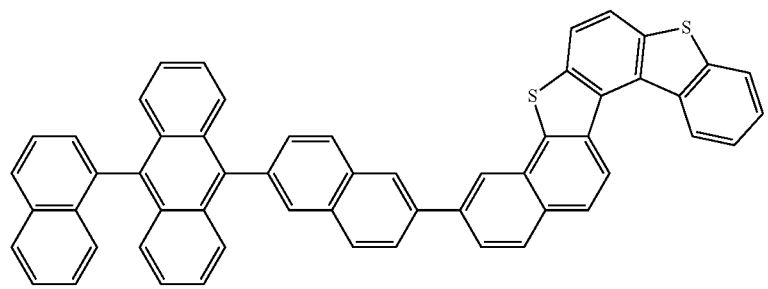

-continued
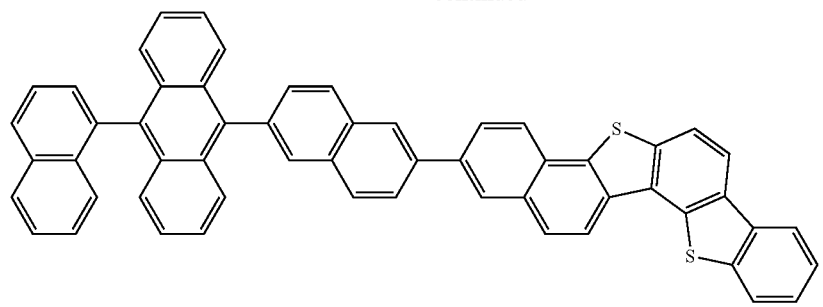
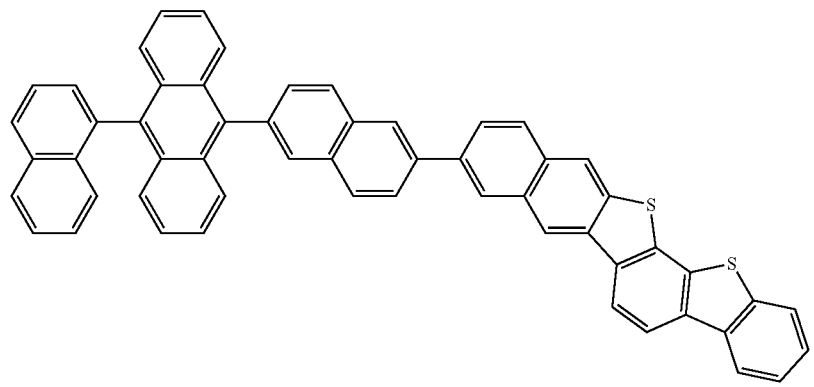
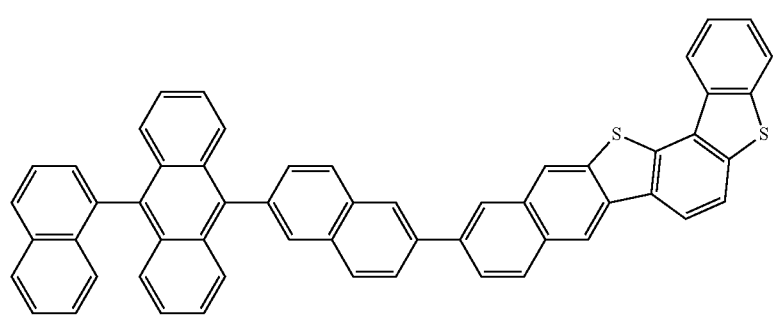
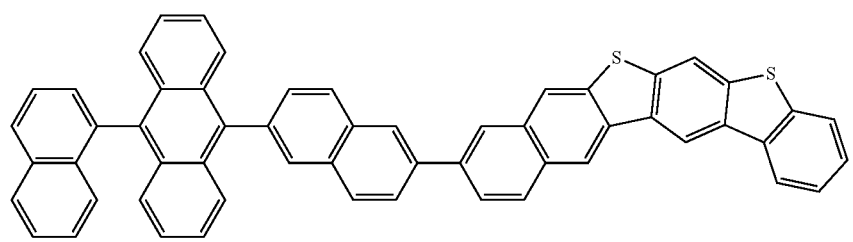
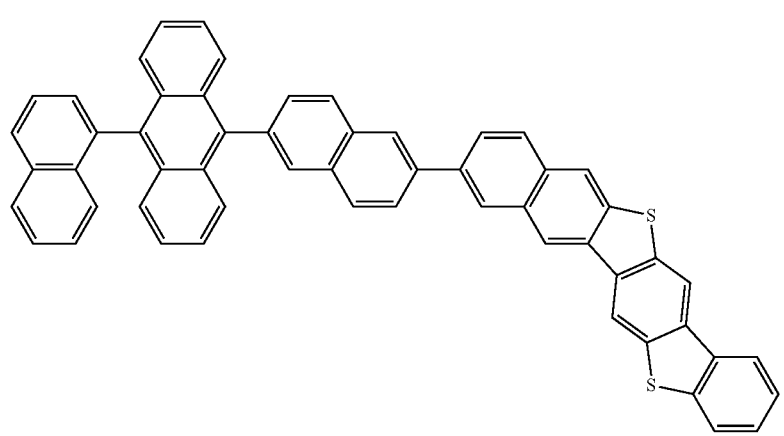

-continued
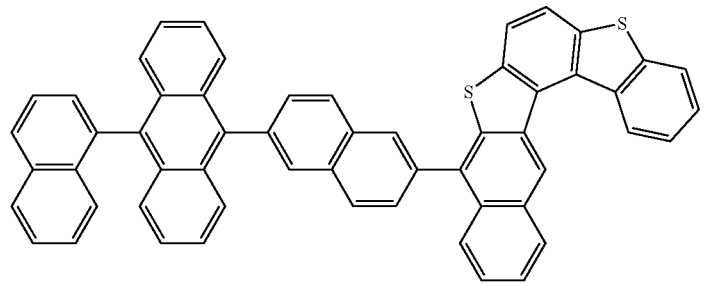
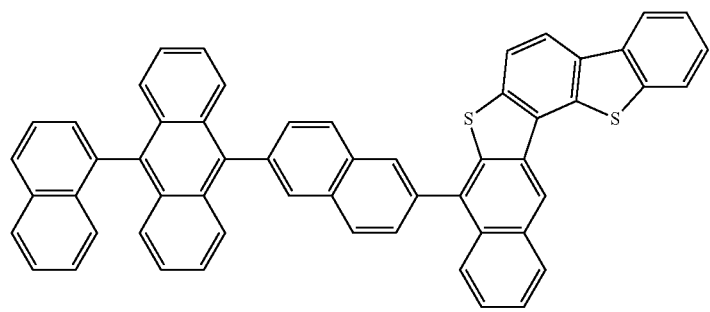
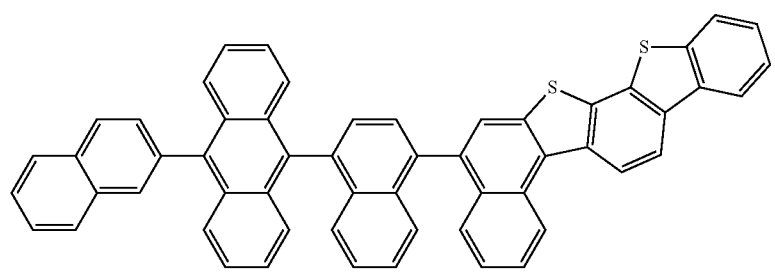
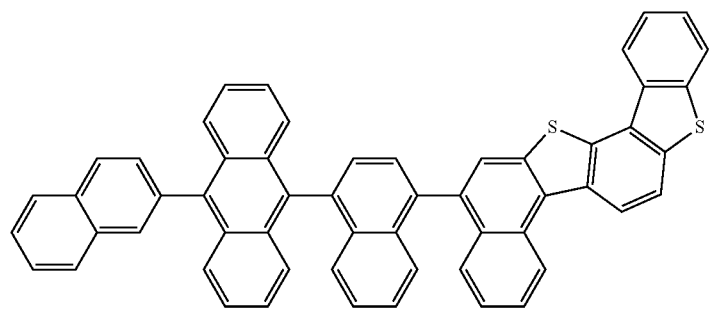
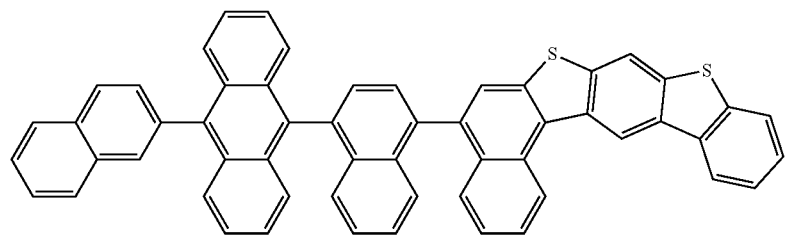
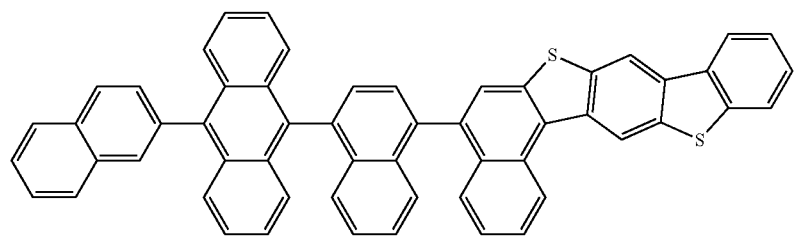

-continued
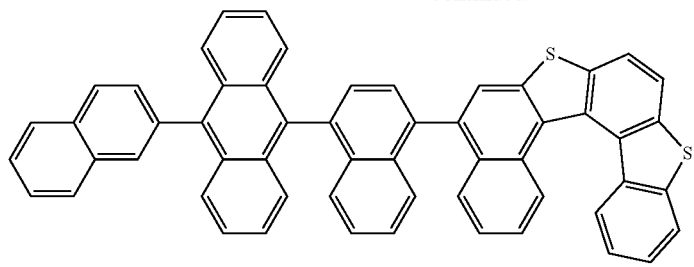
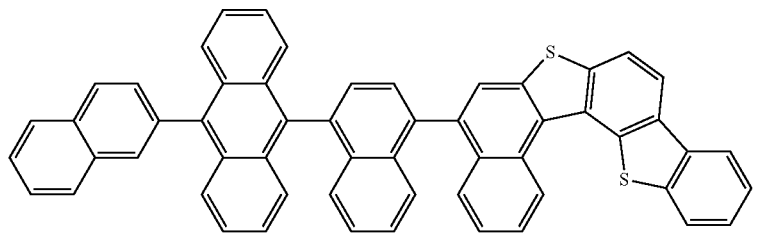
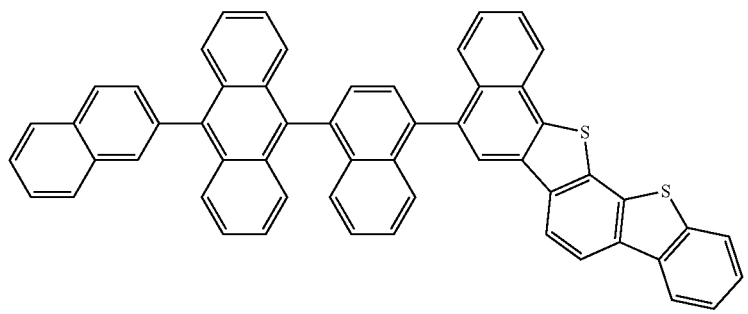
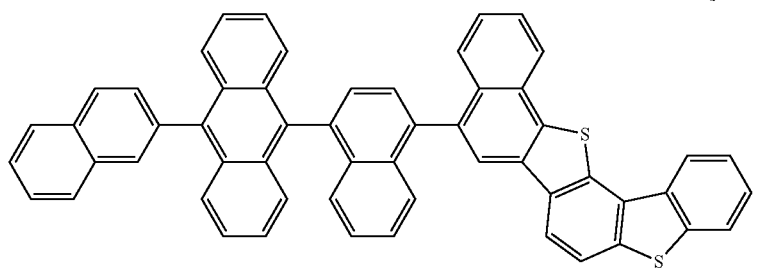
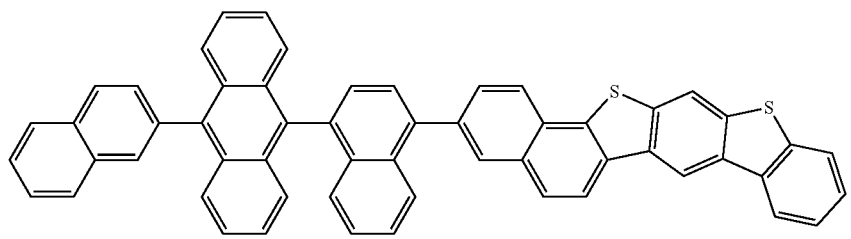
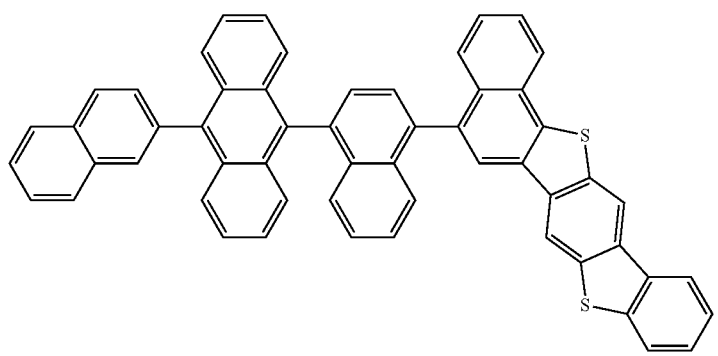

-continued
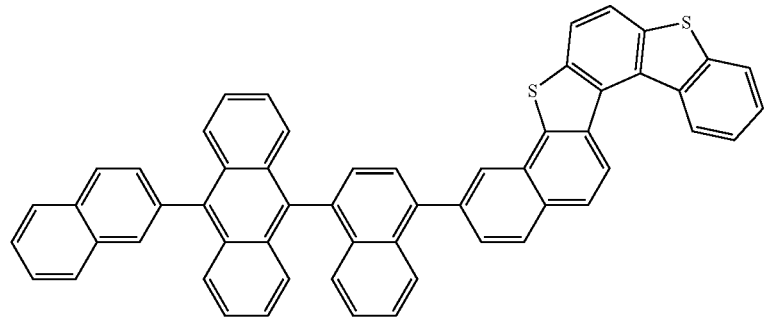
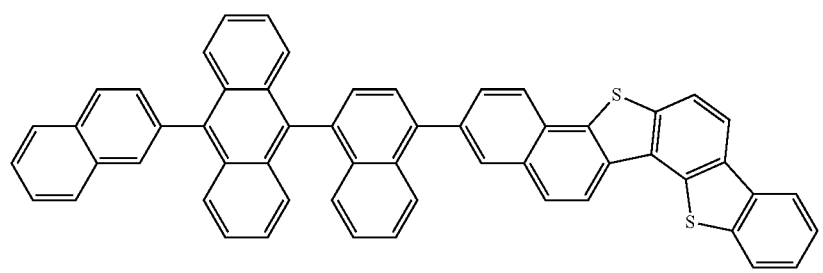
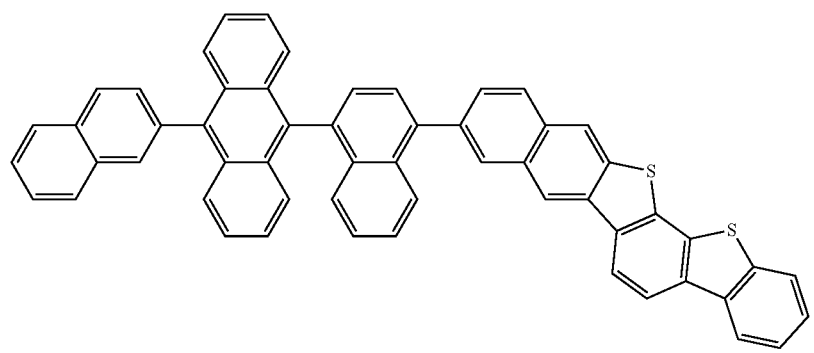
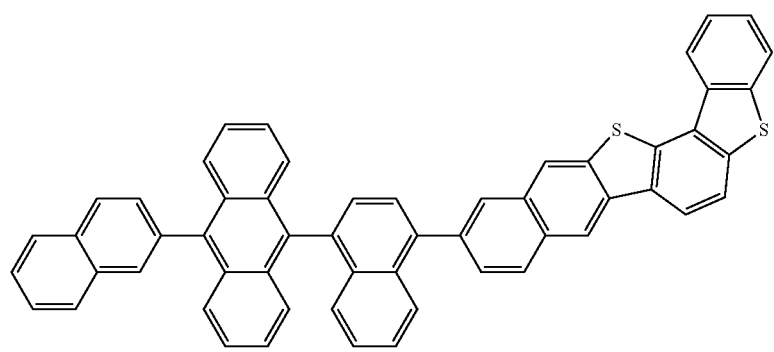
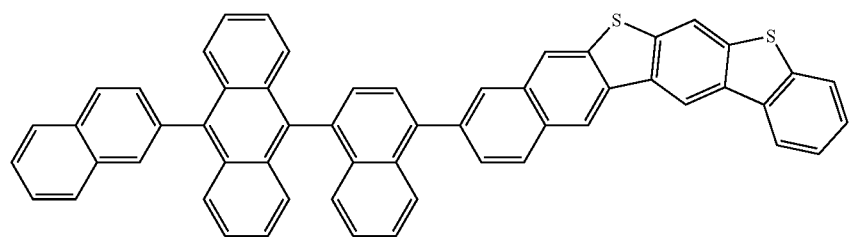

-continued
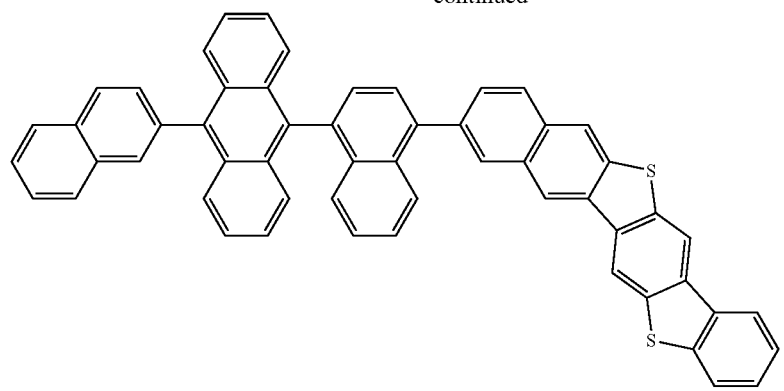
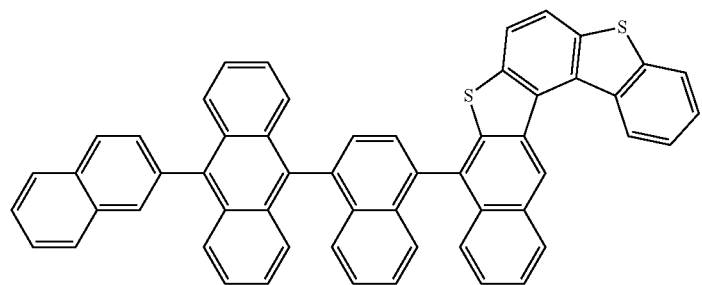
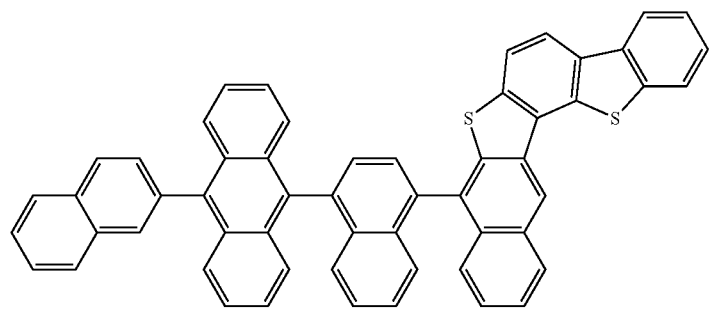
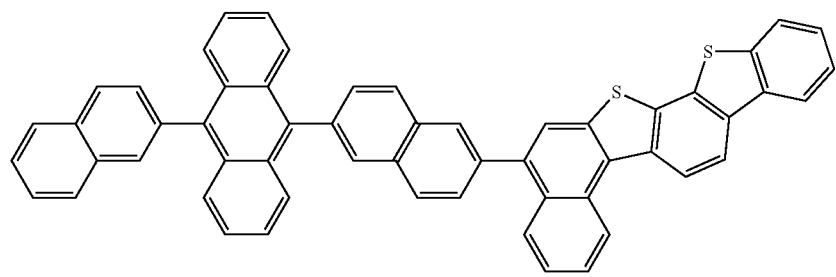
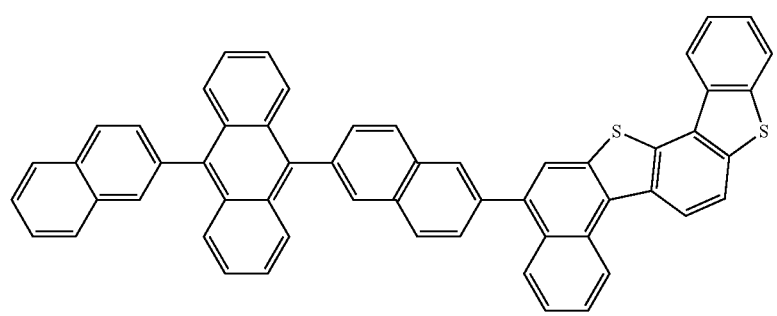

-continued
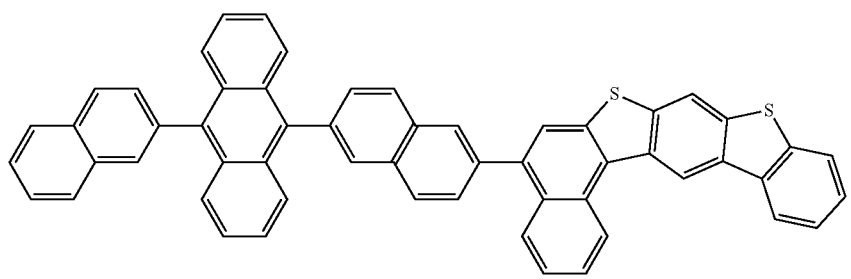

-continued
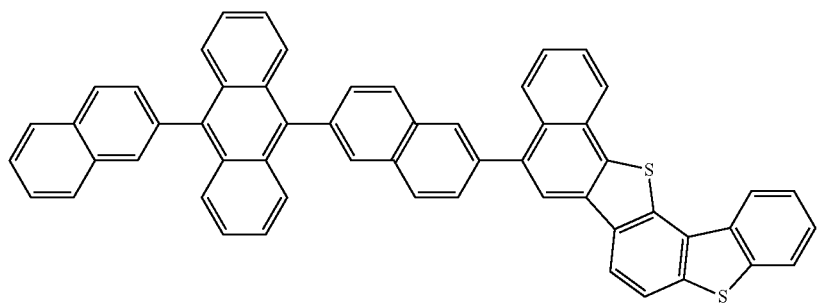
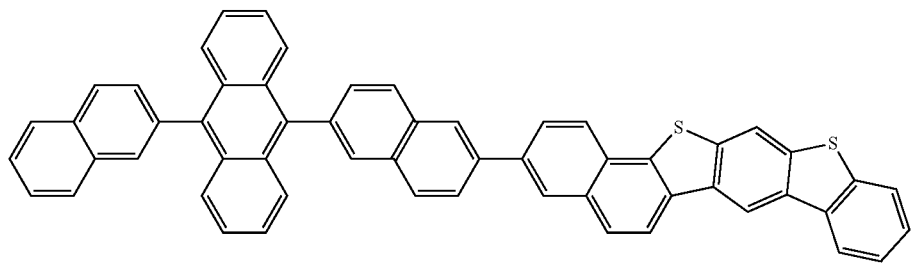
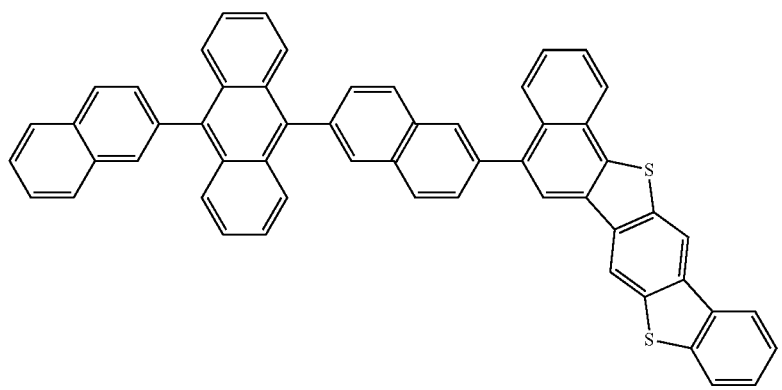
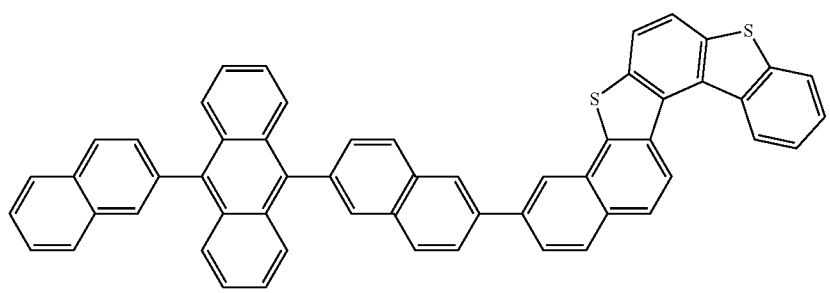
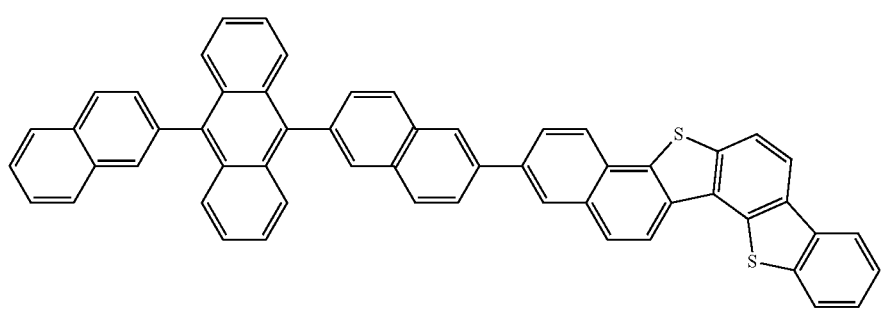

-continued
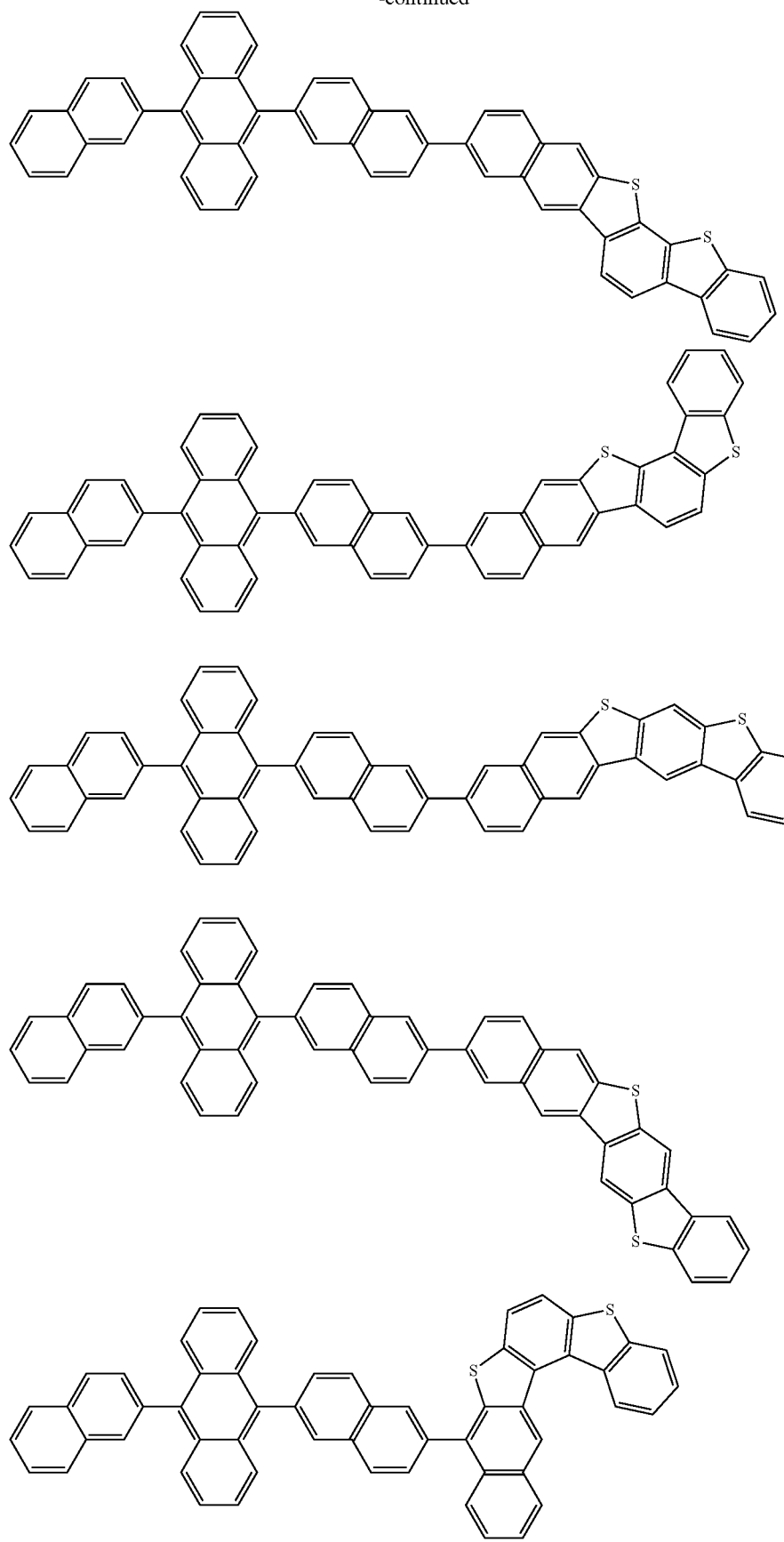

-continued
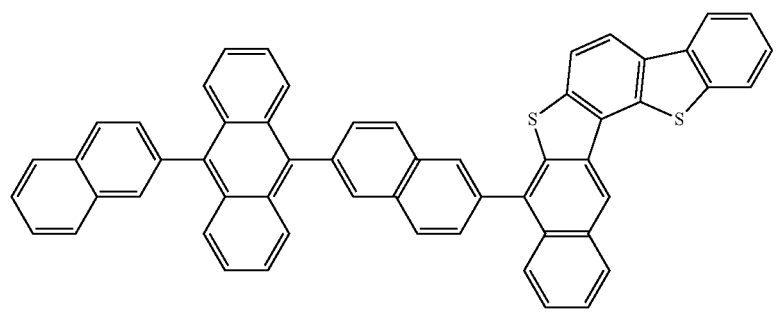
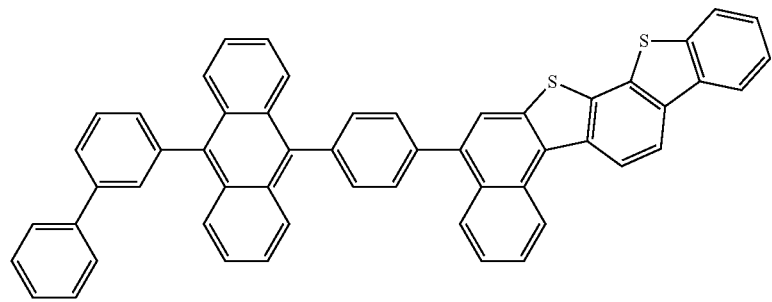
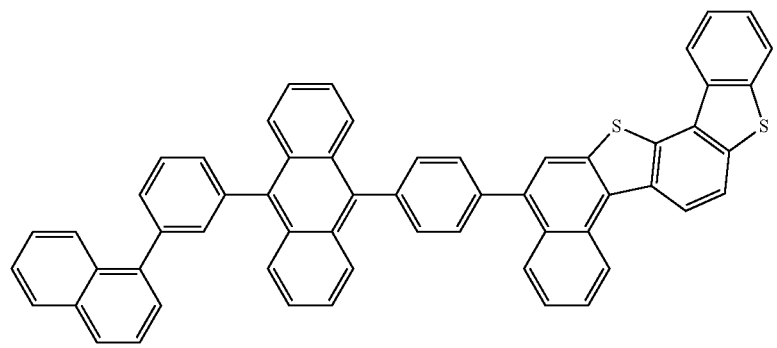
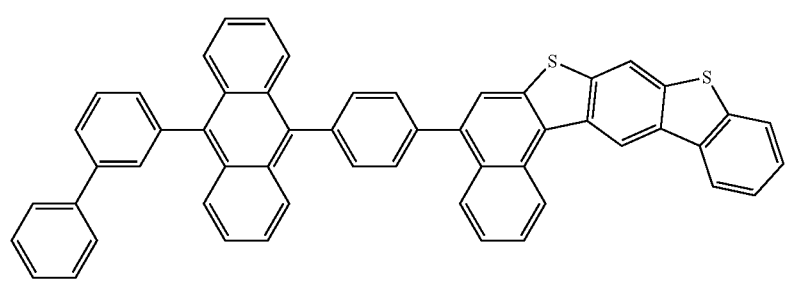
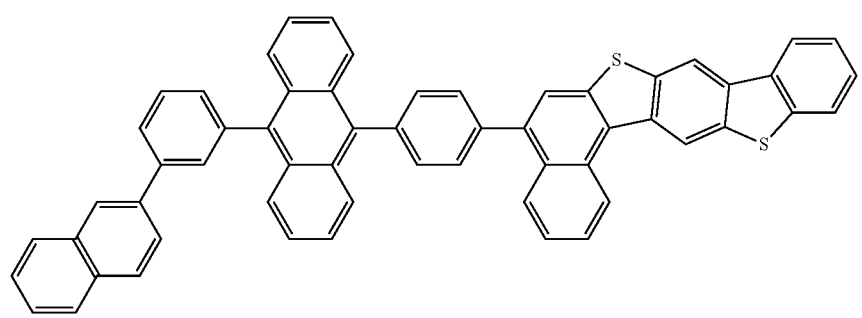

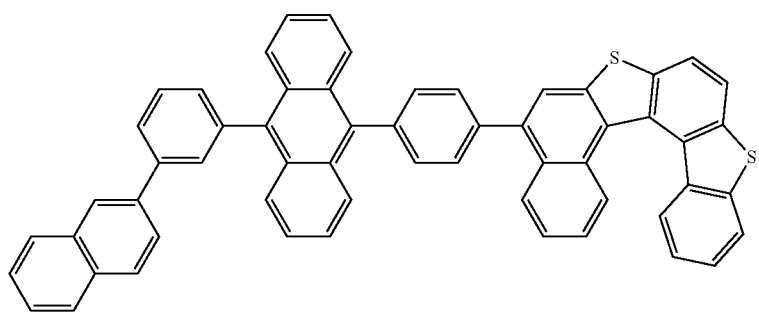
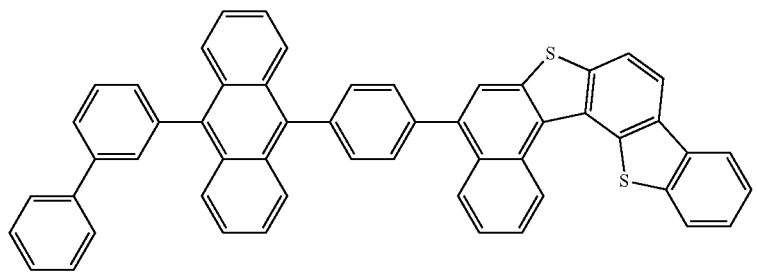
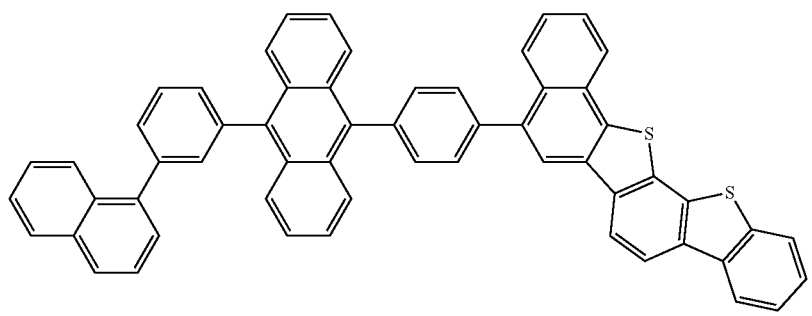
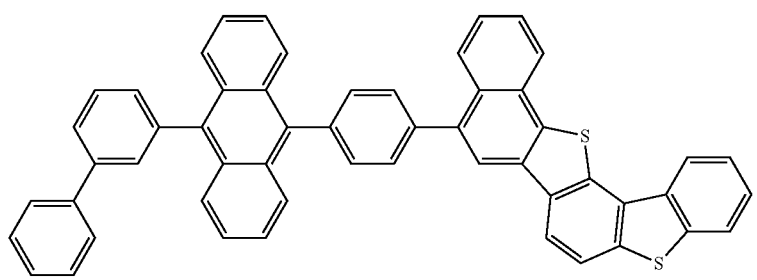
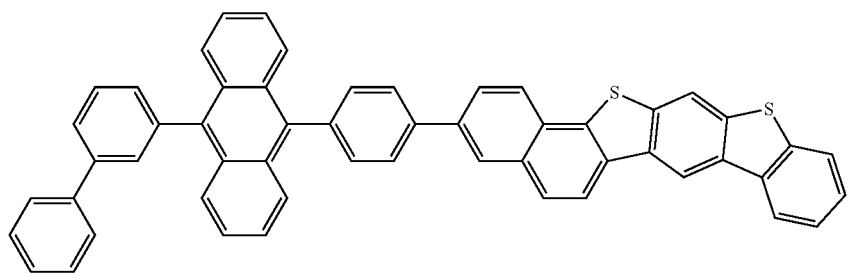

-continued
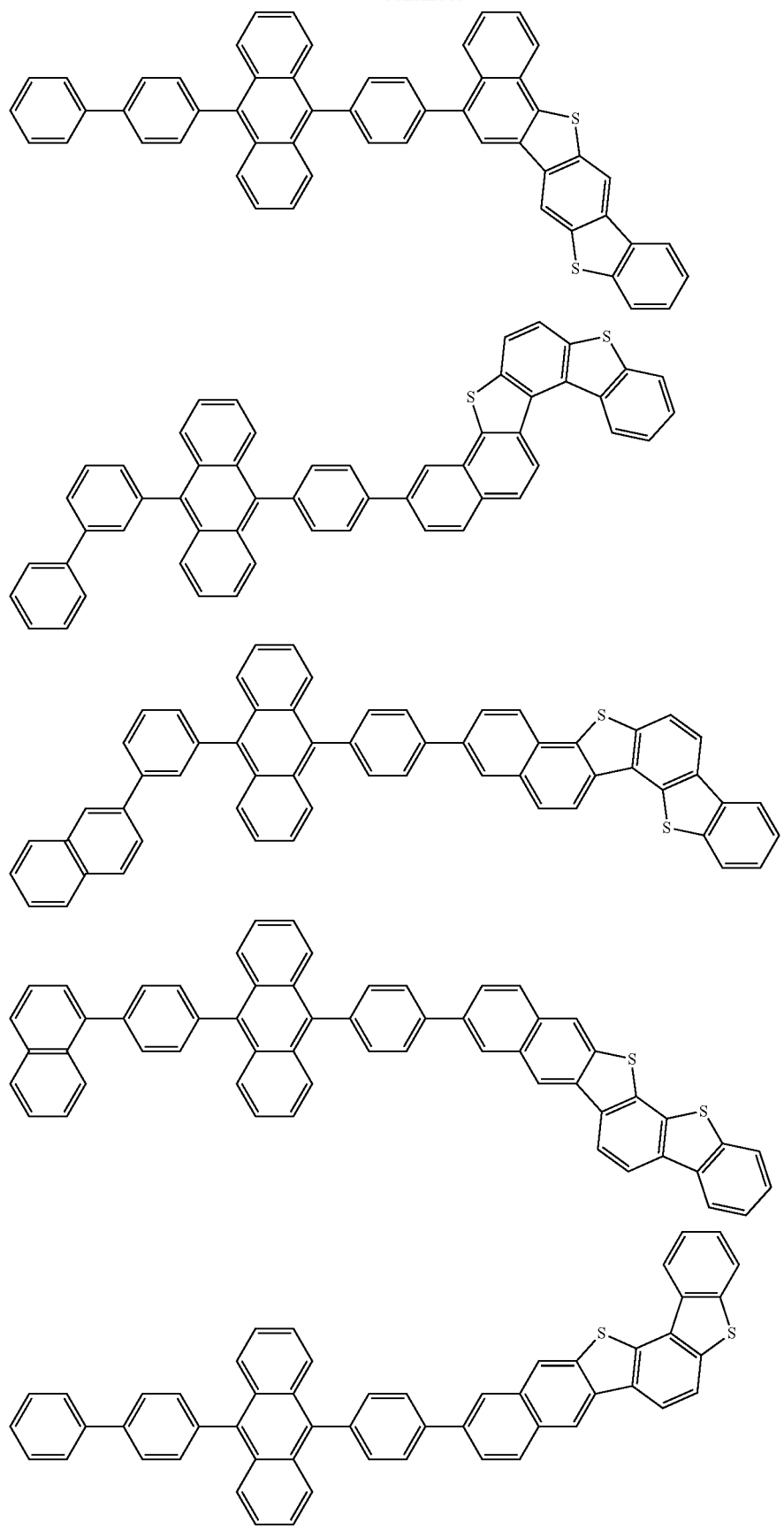

-continued
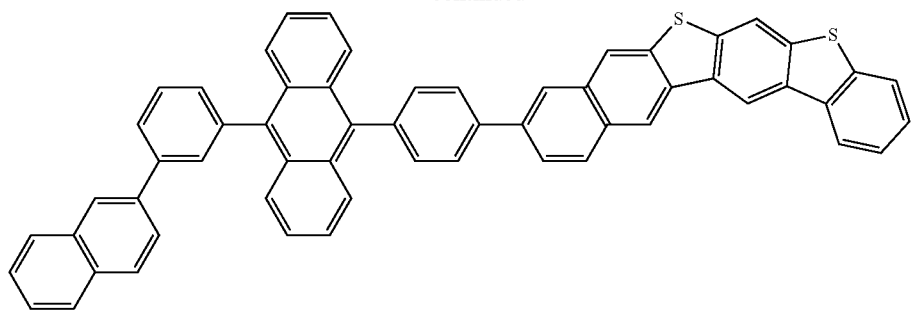
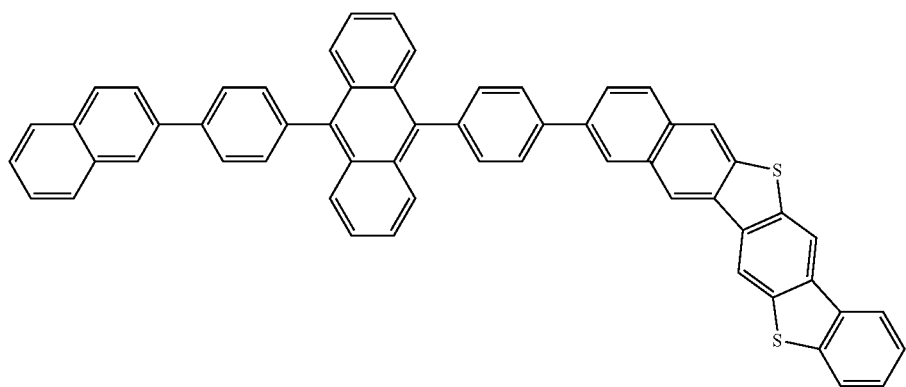
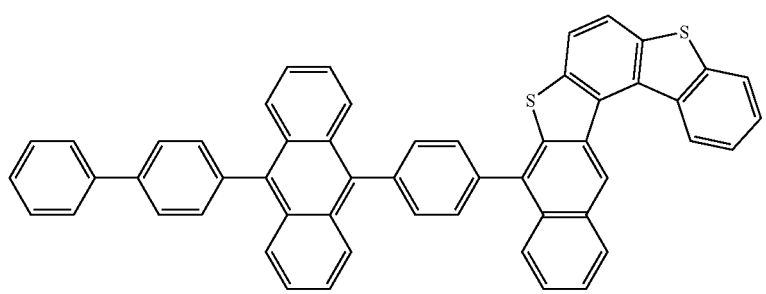
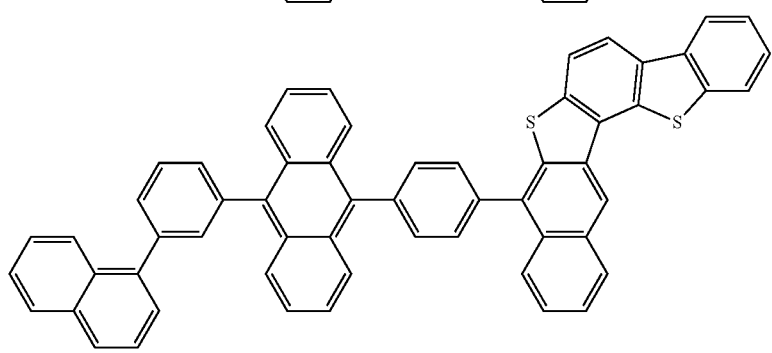
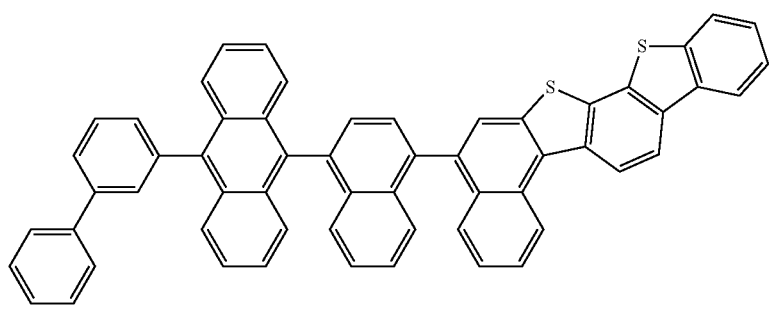

-continued
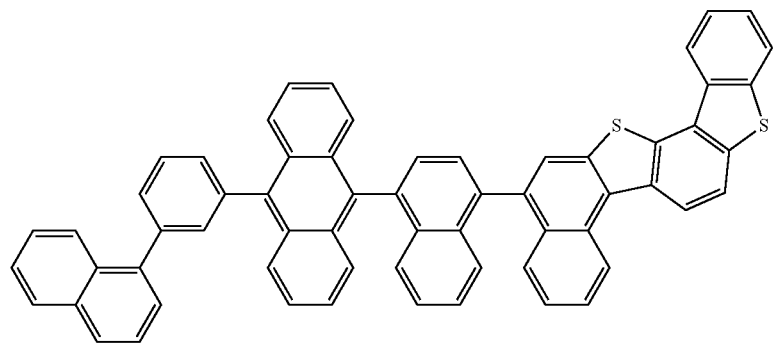
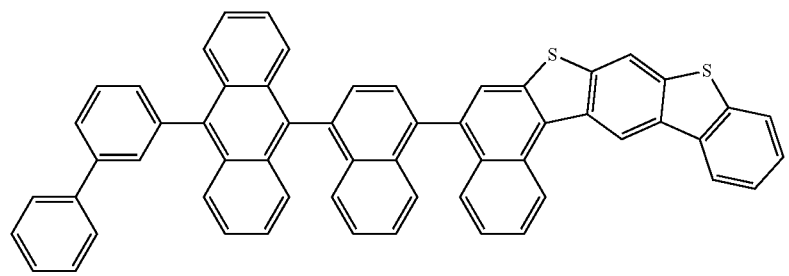
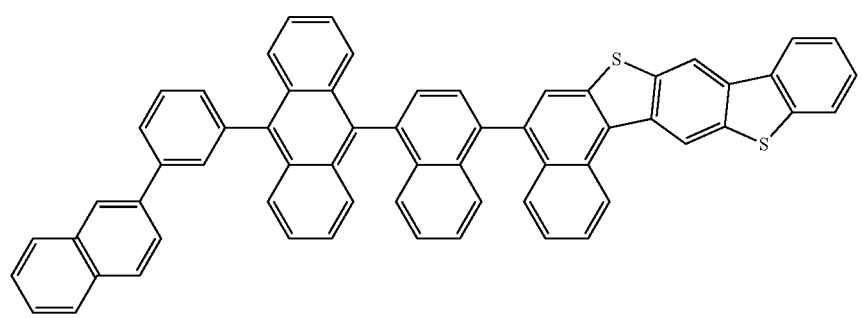
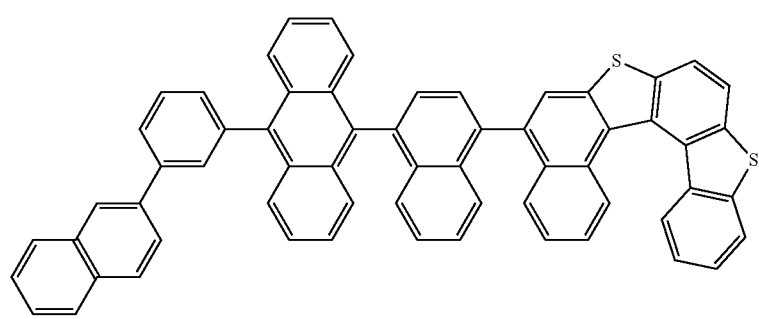
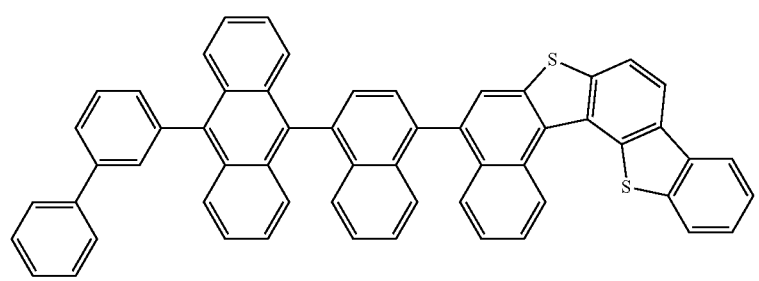

-continued
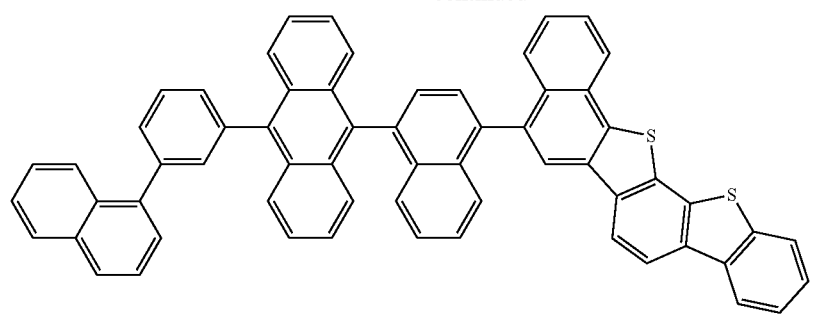
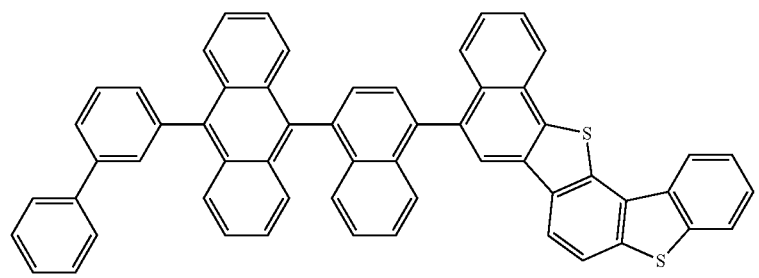
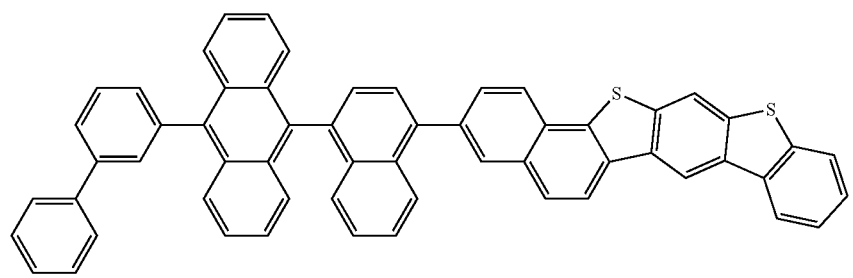
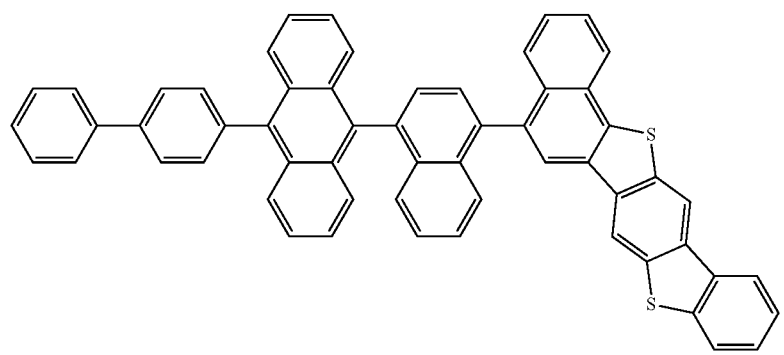
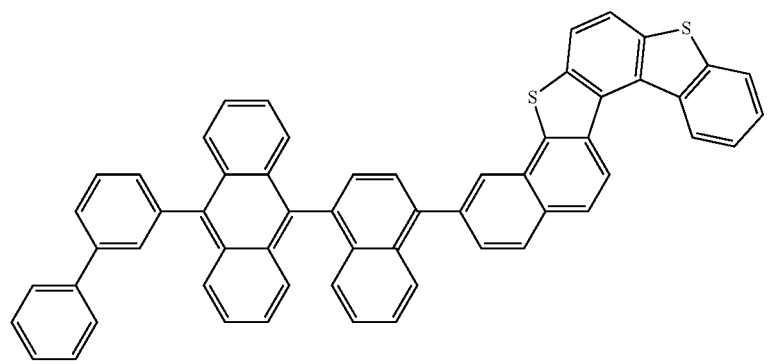

-continued
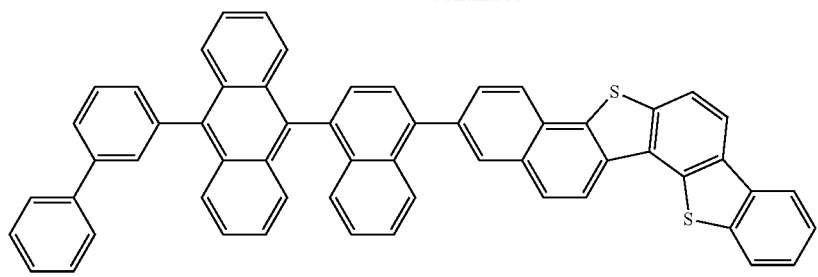
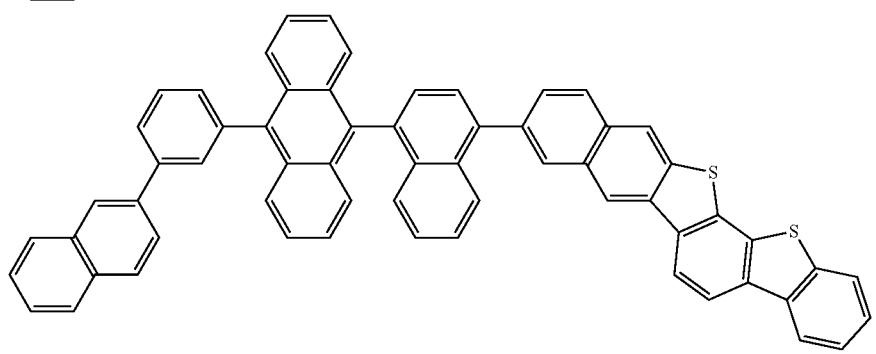
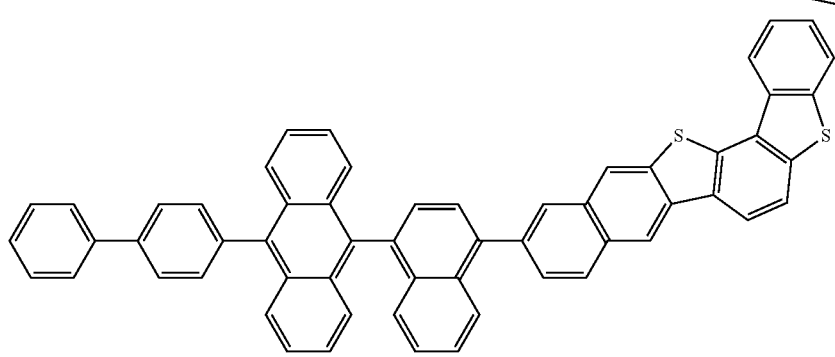
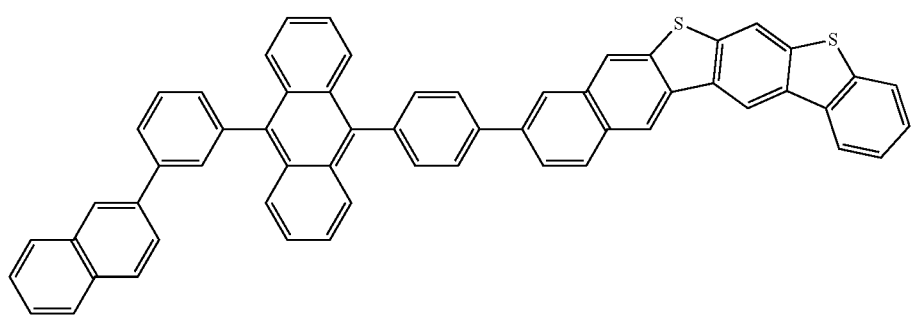
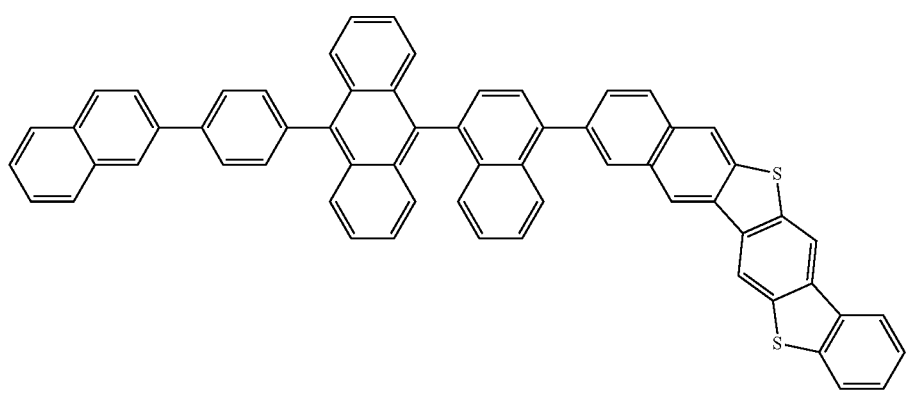

-continued
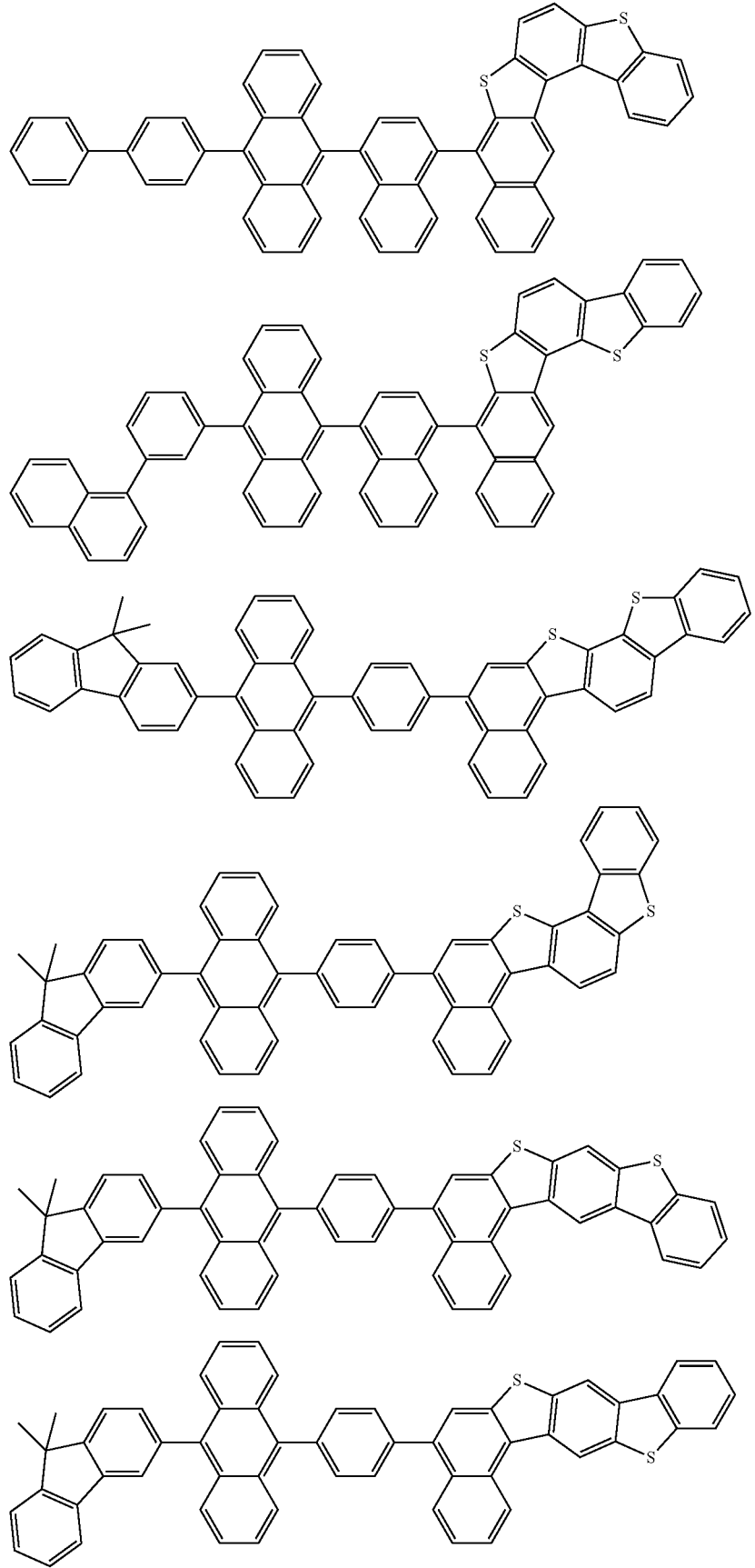

-continued
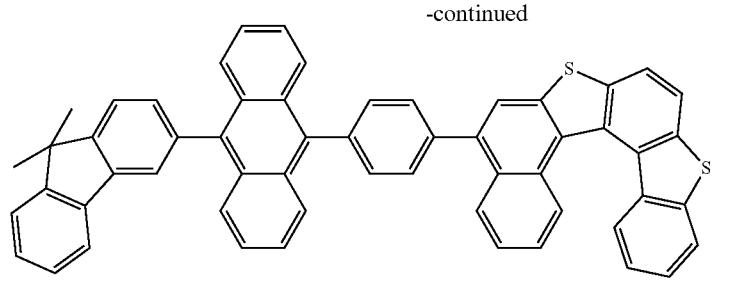
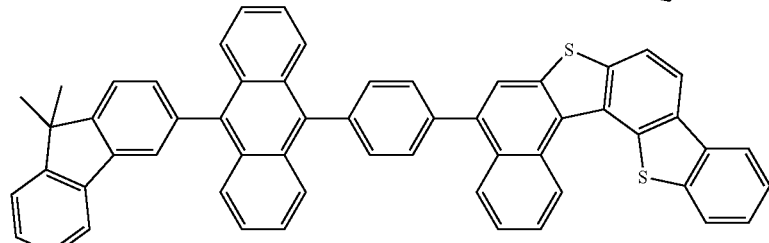
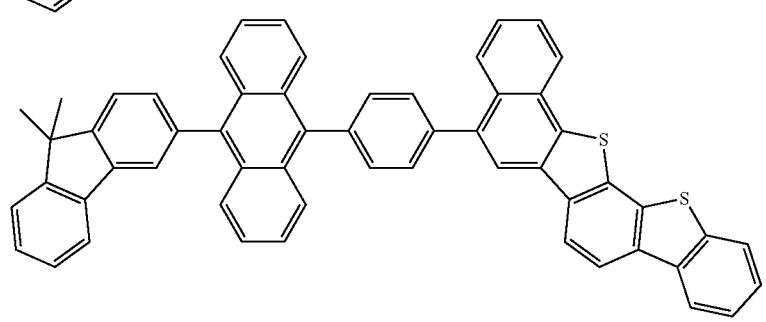
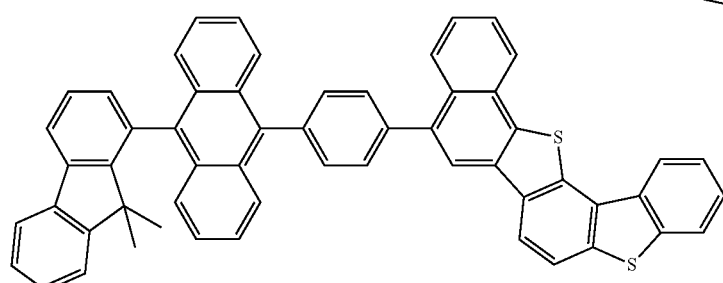
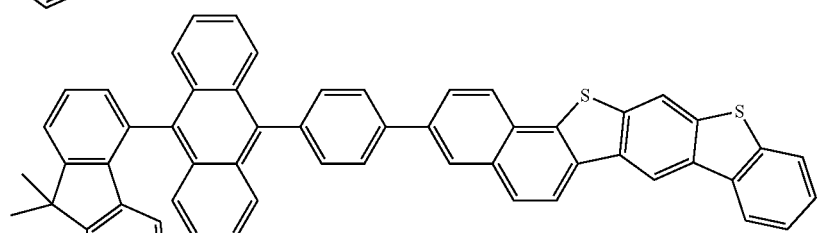
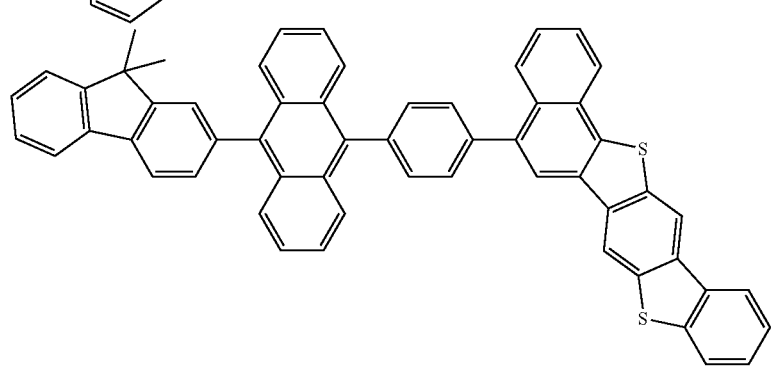

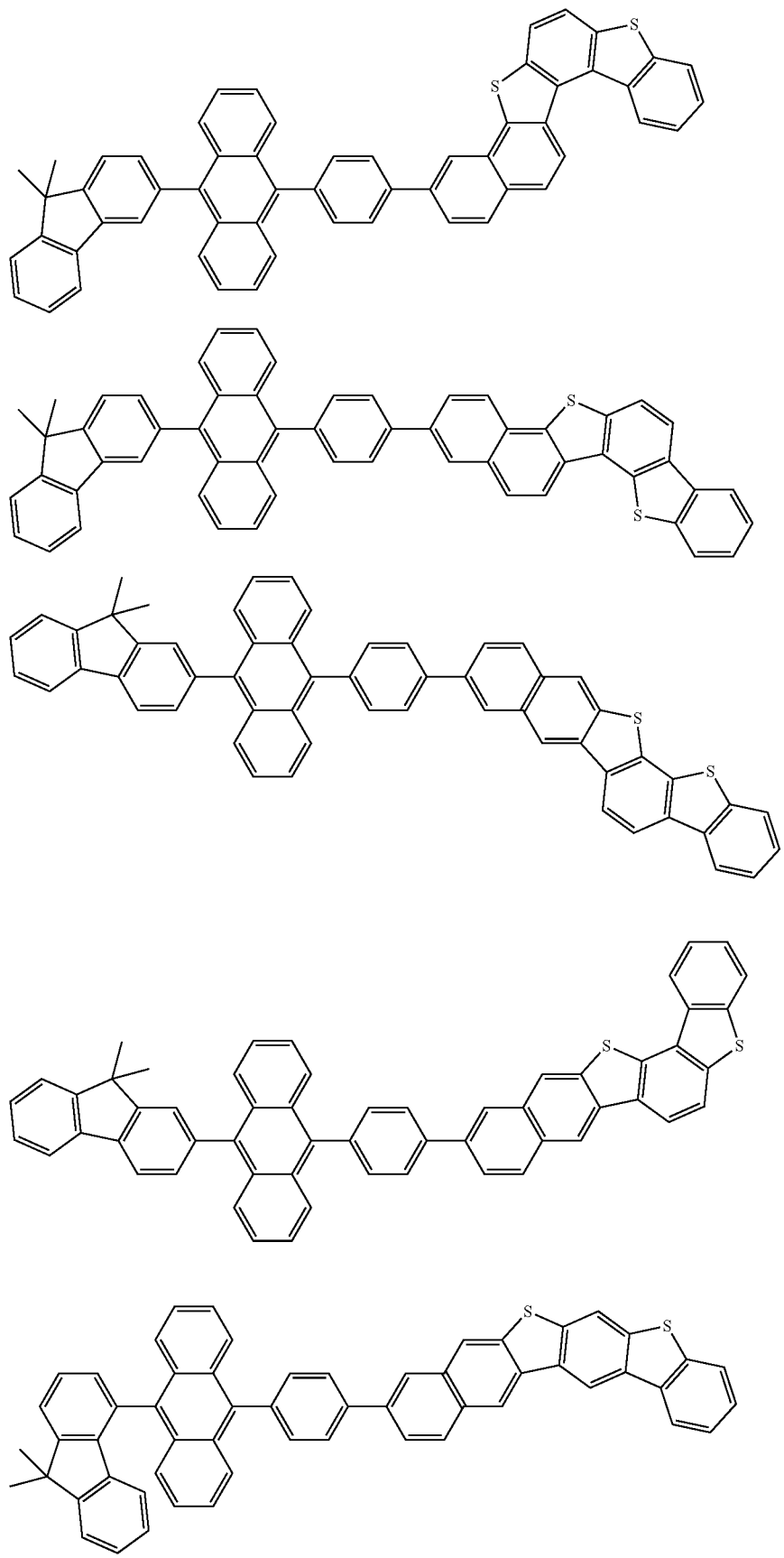

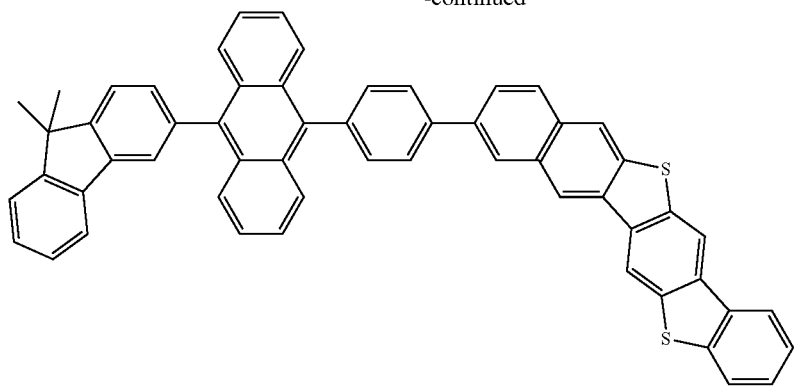
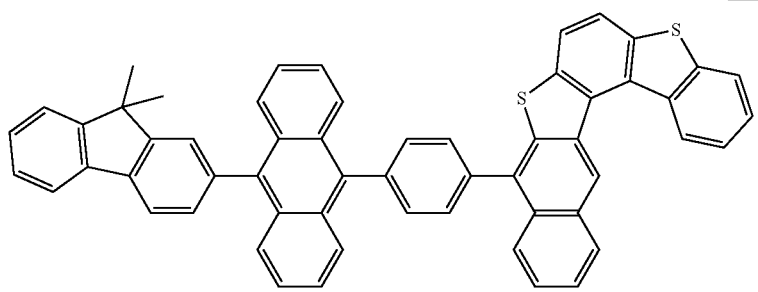
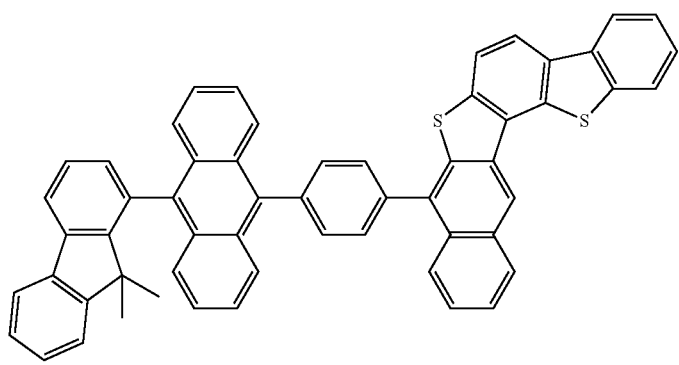
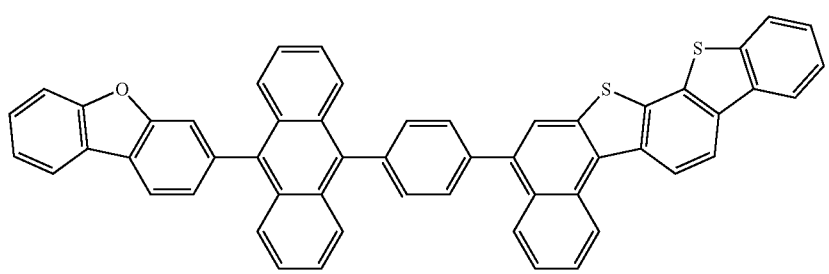
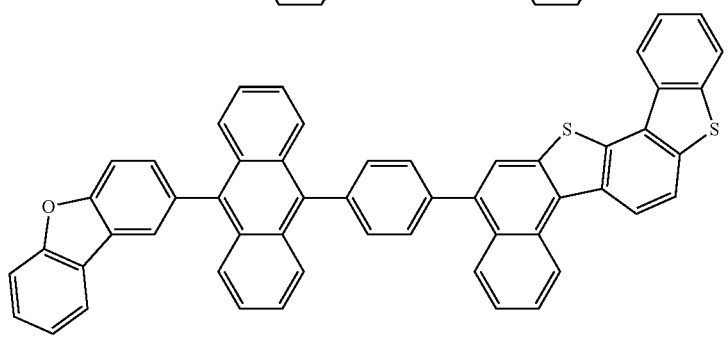

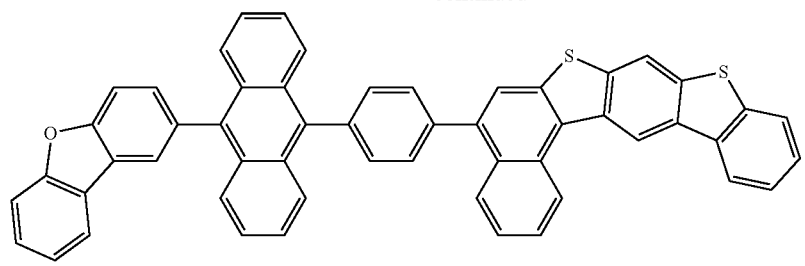
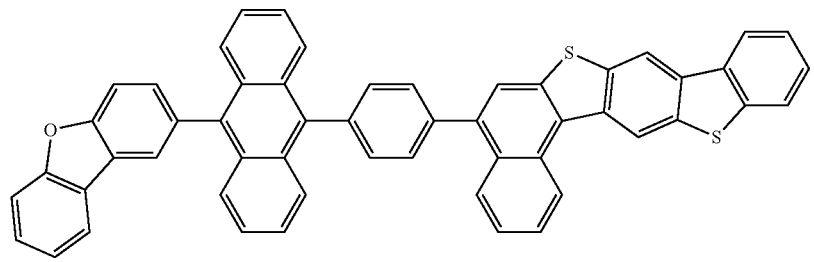
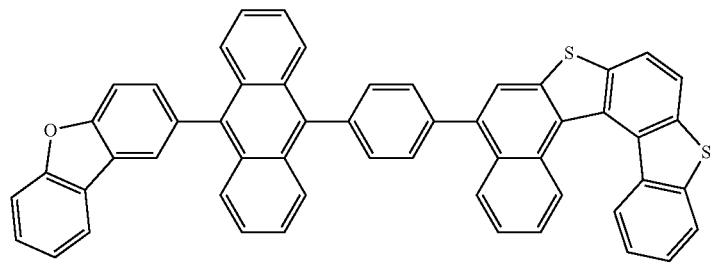
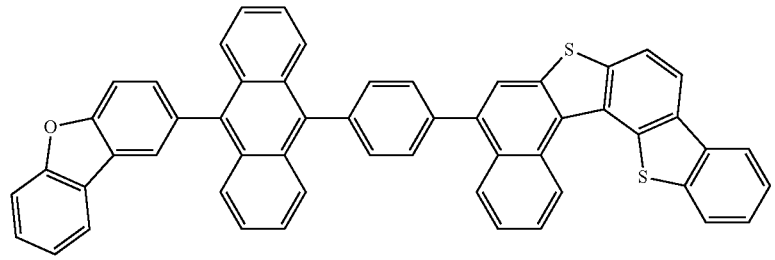
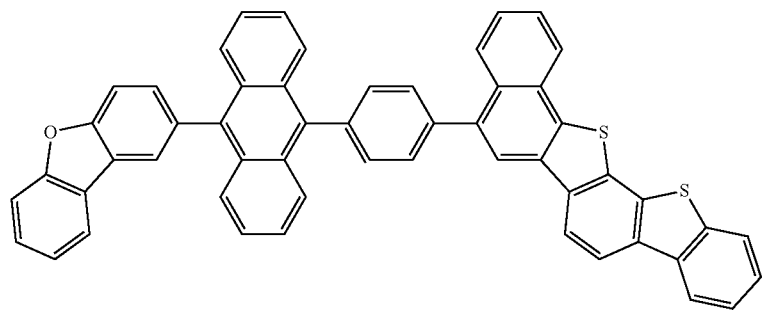
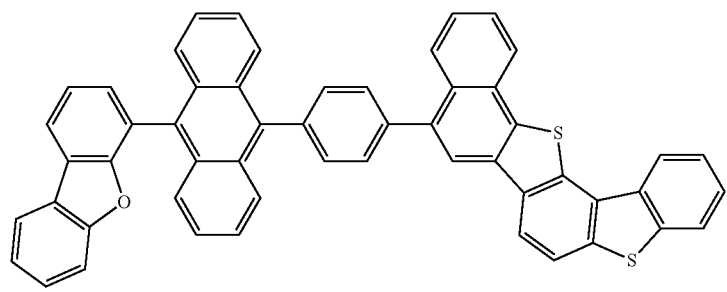

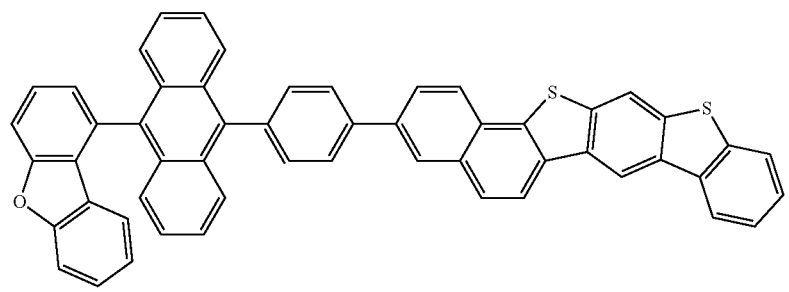
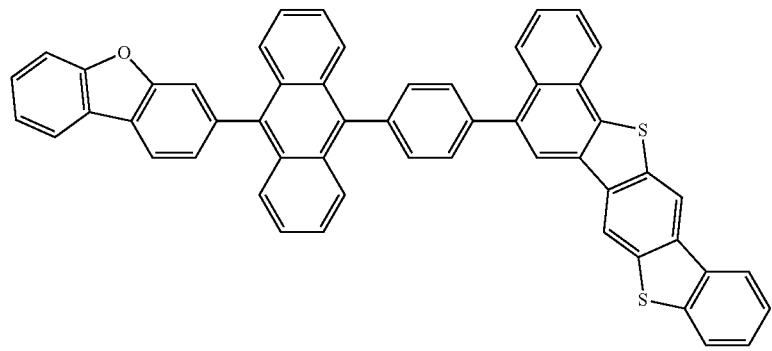
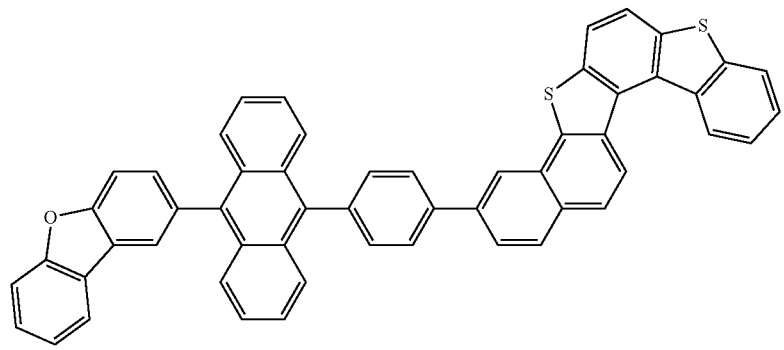
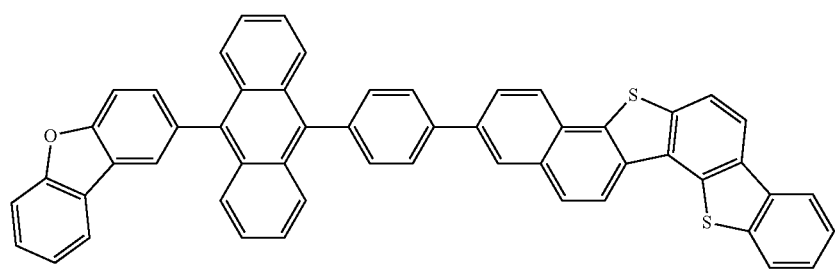
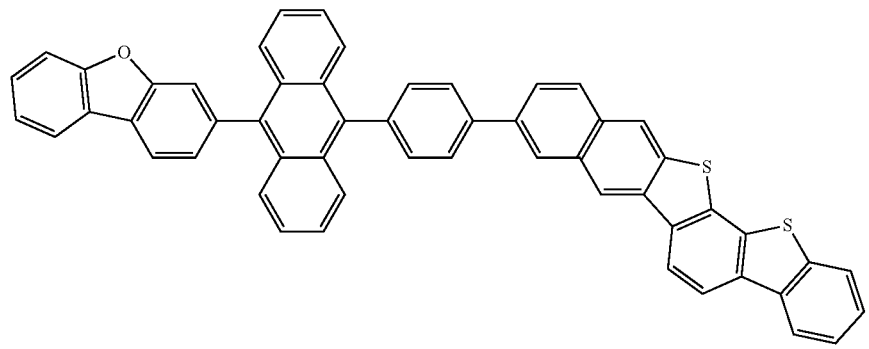

-continued
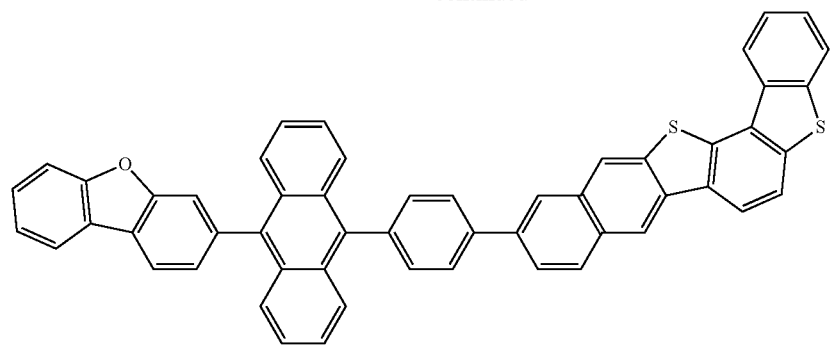
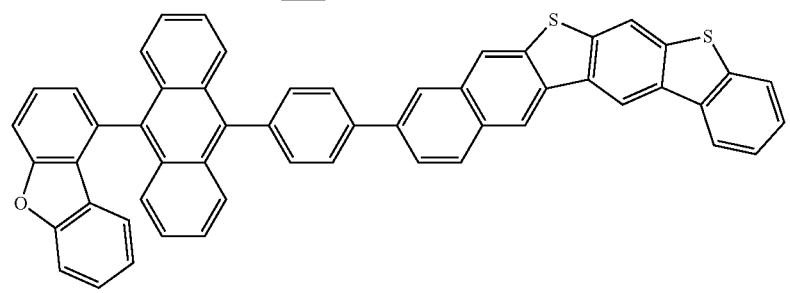
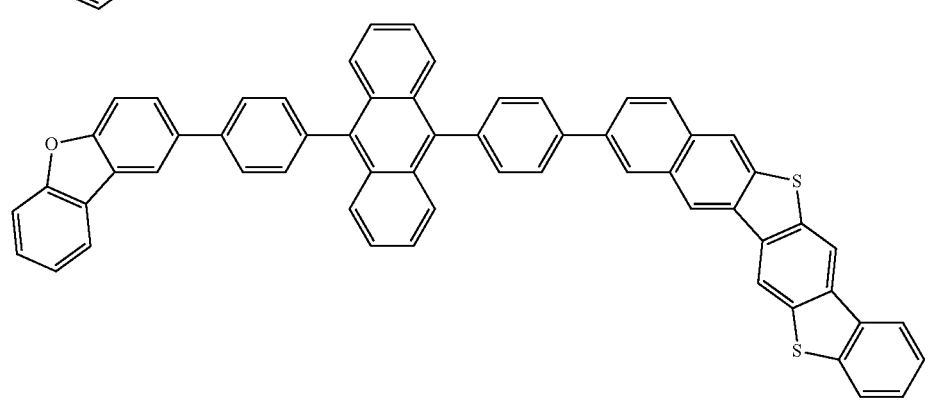
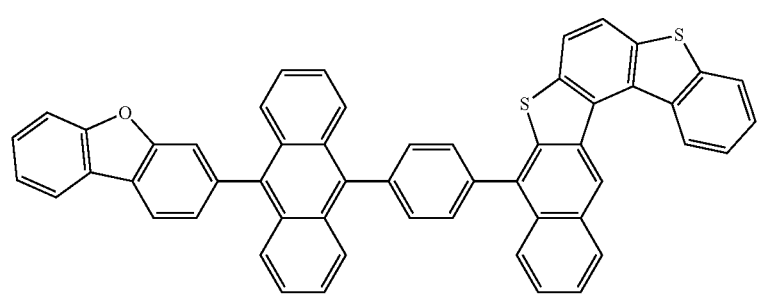
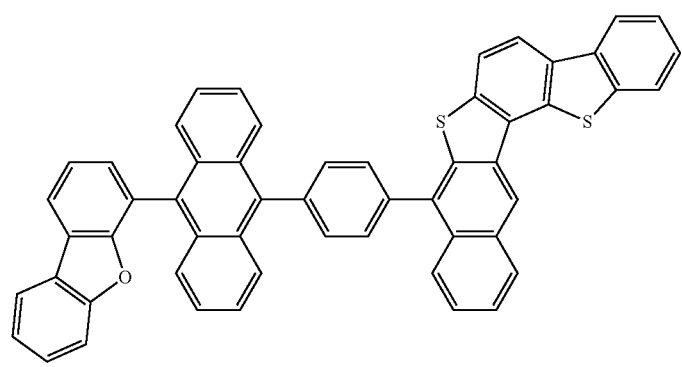

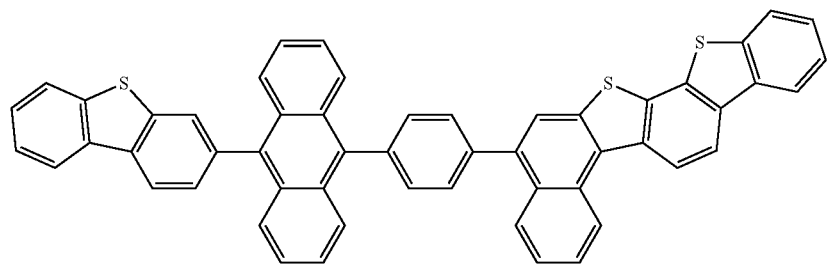
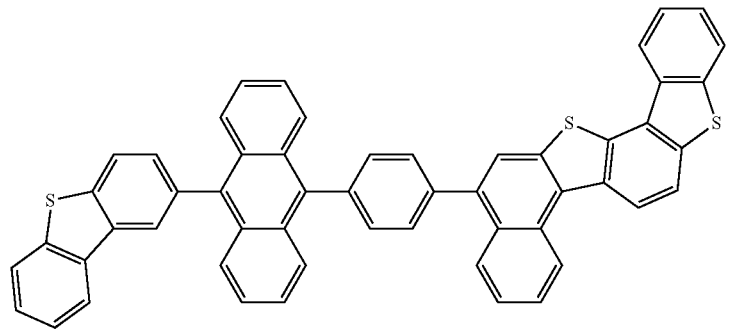
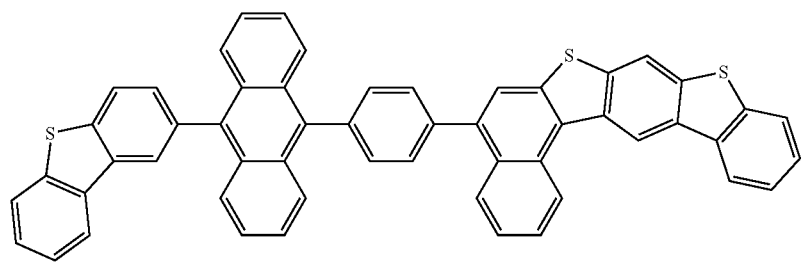
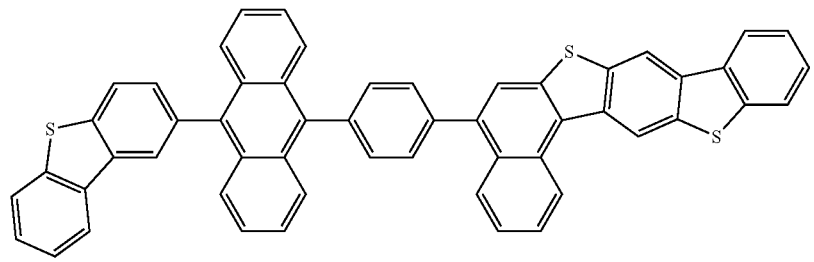
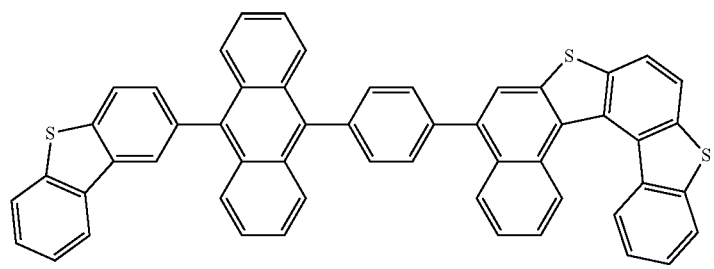
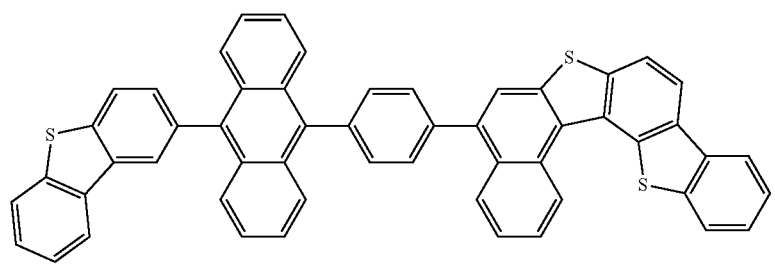

-continued
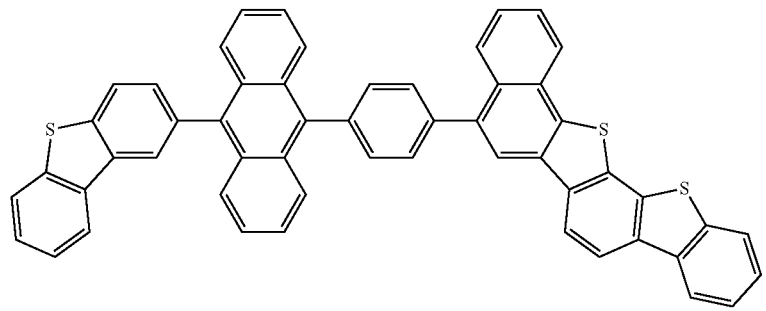
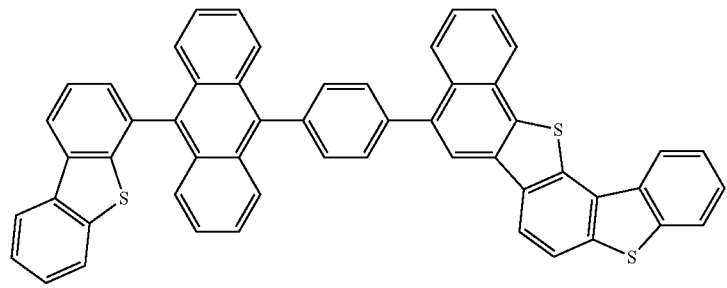
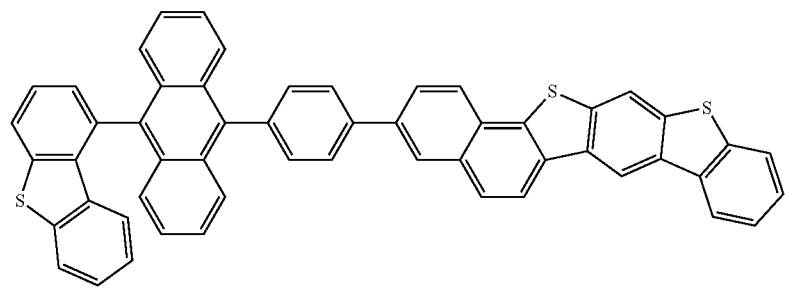
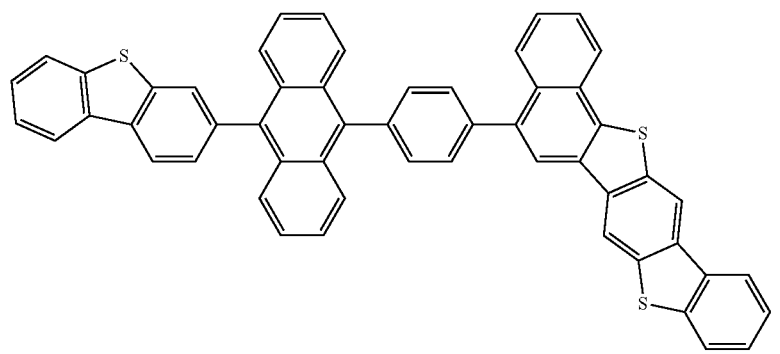
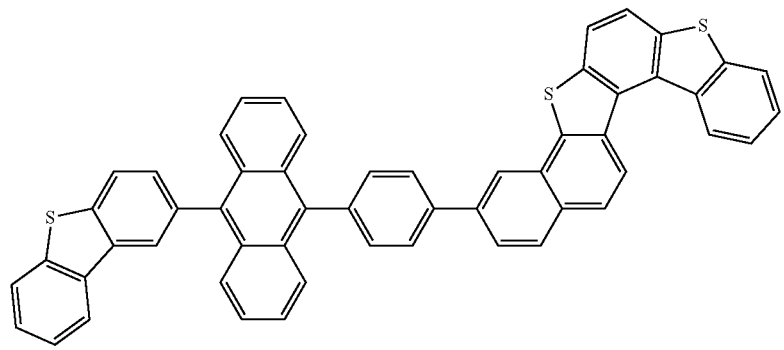

-continued
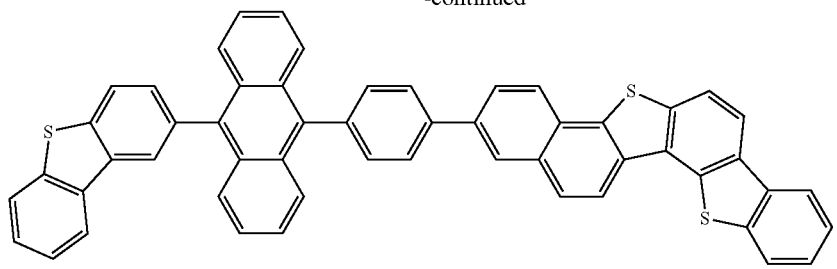
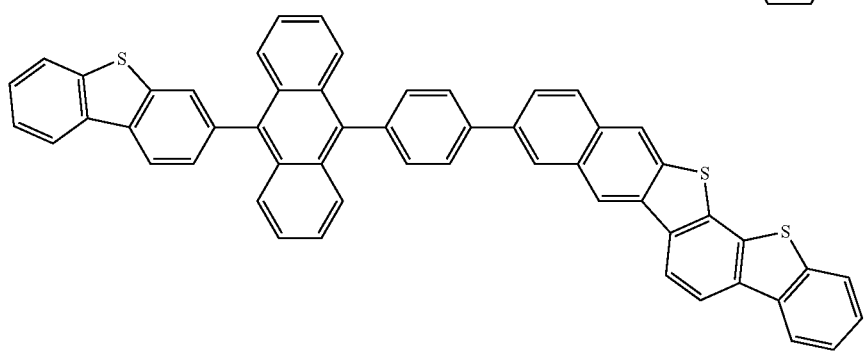
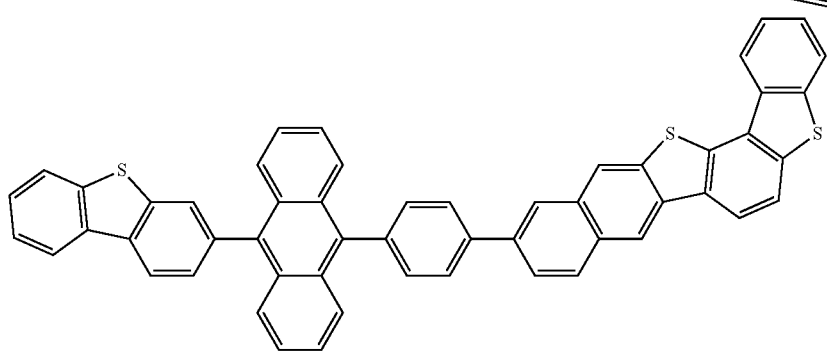
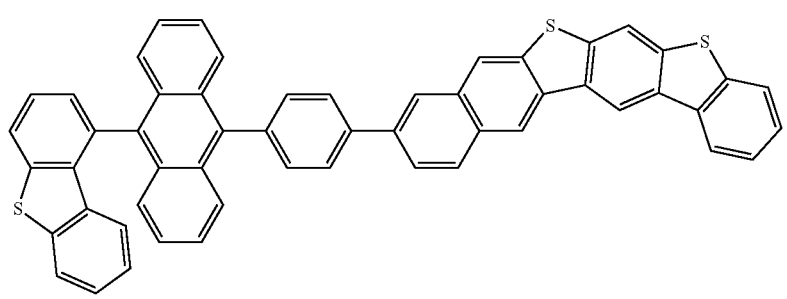
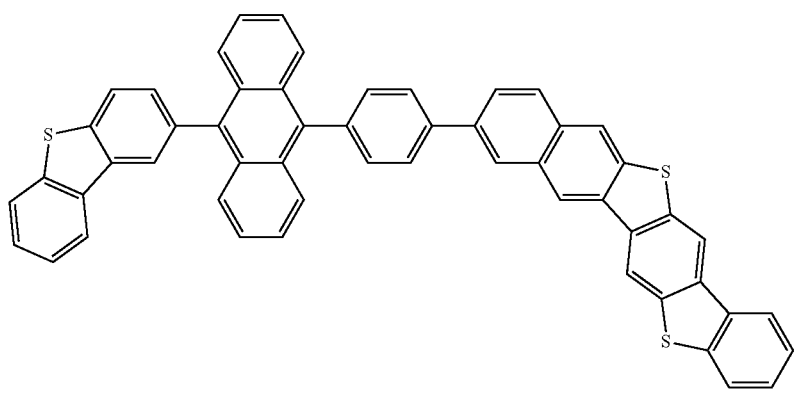

-continued
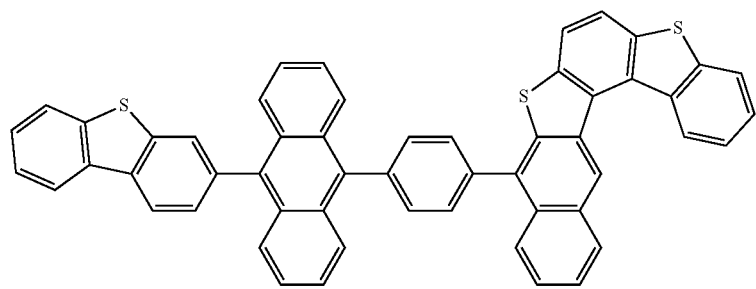
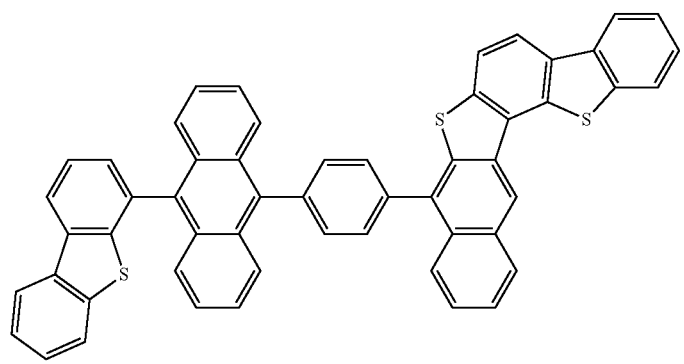
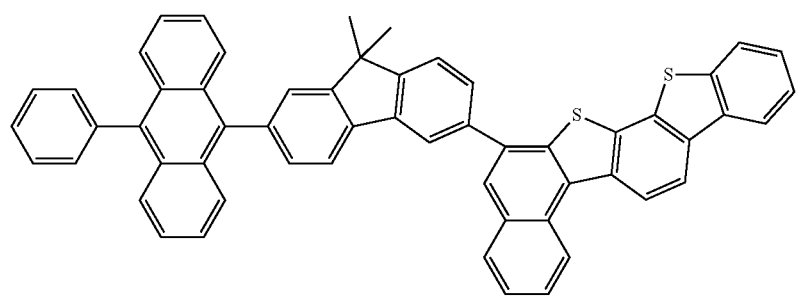
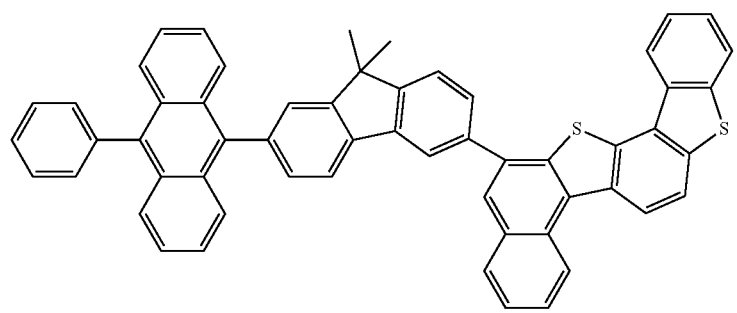
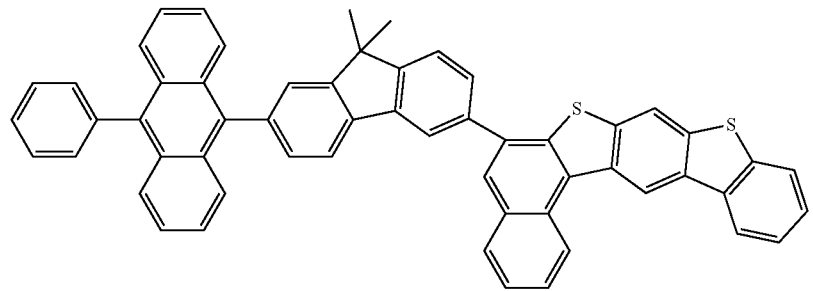

-continued
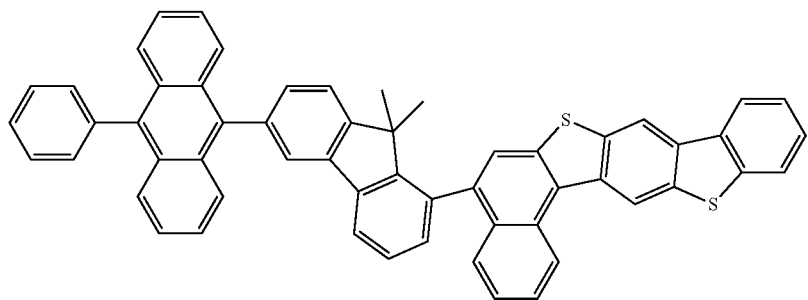
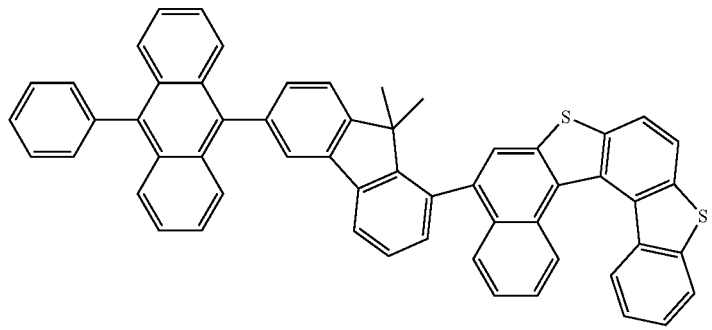
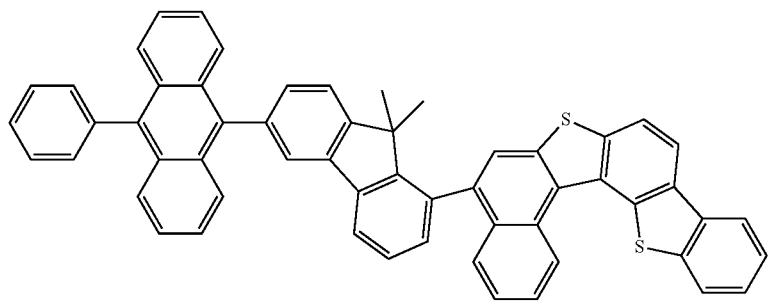
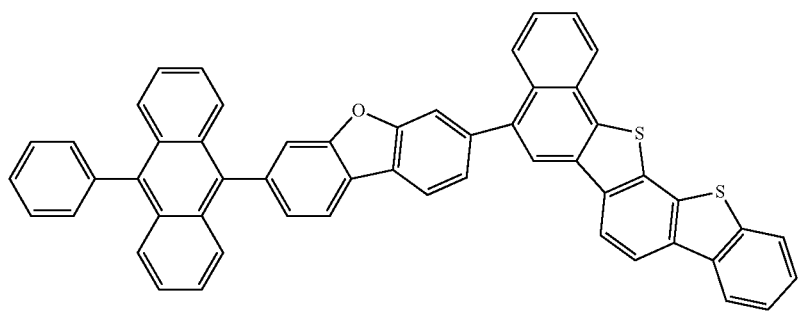
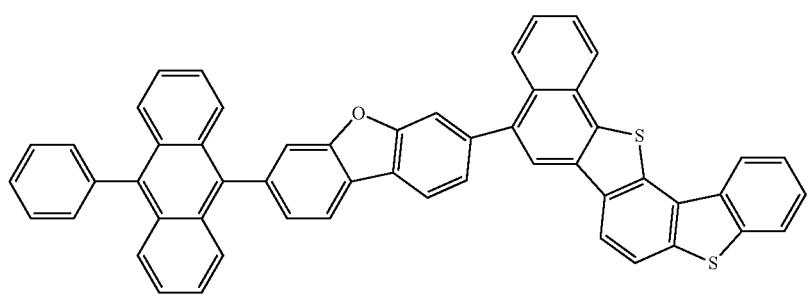

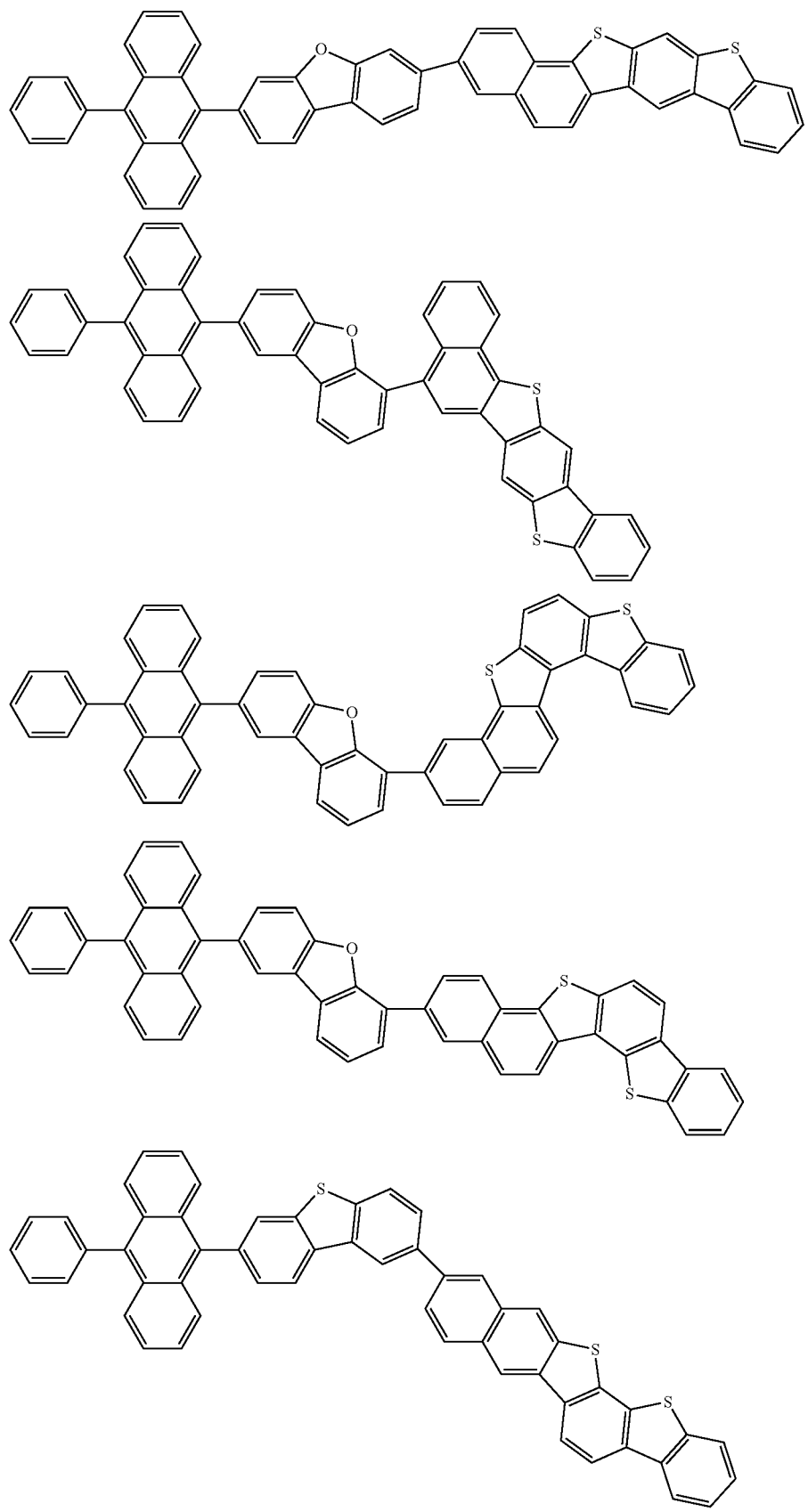

-continued
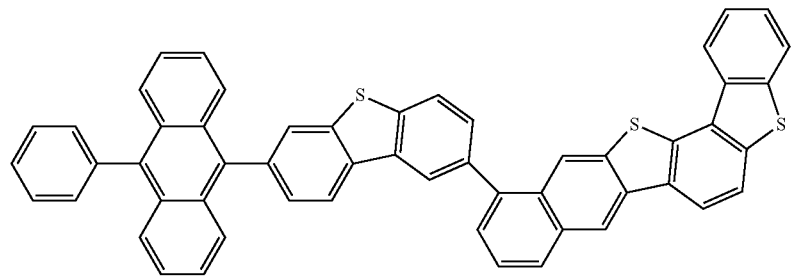
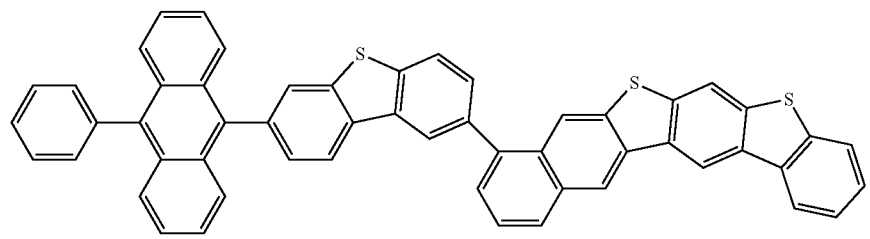
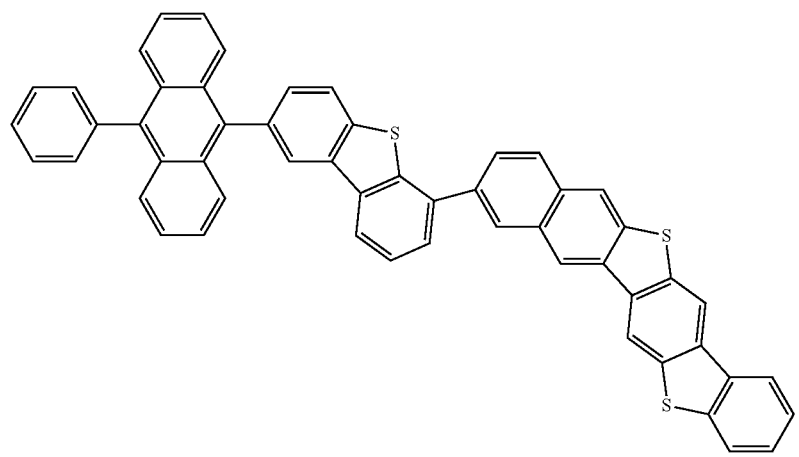
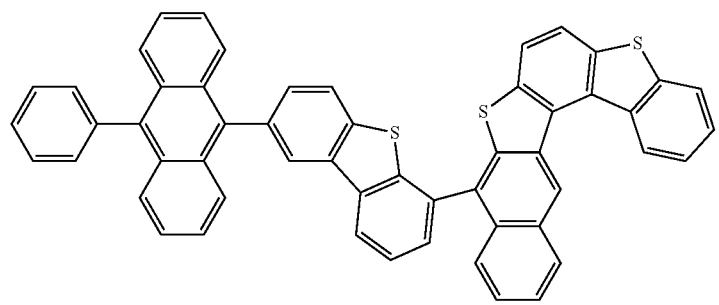
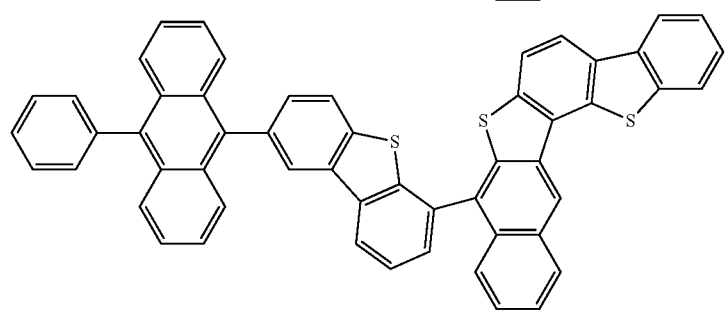

-continued
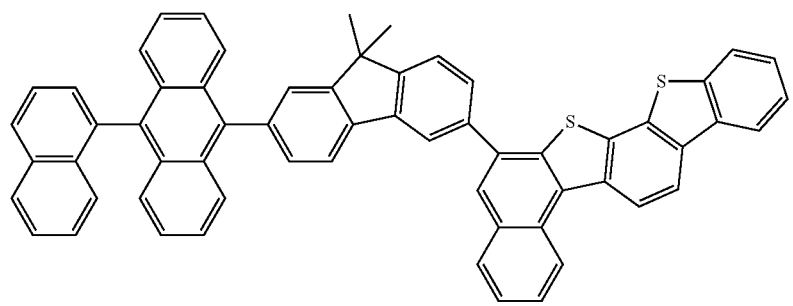
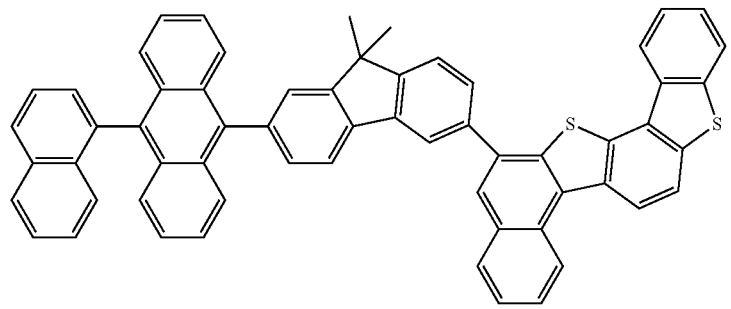
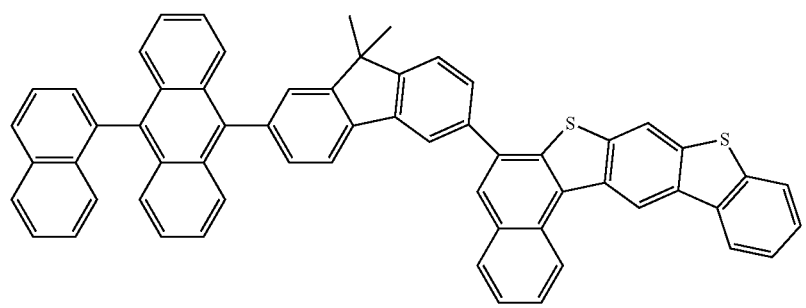
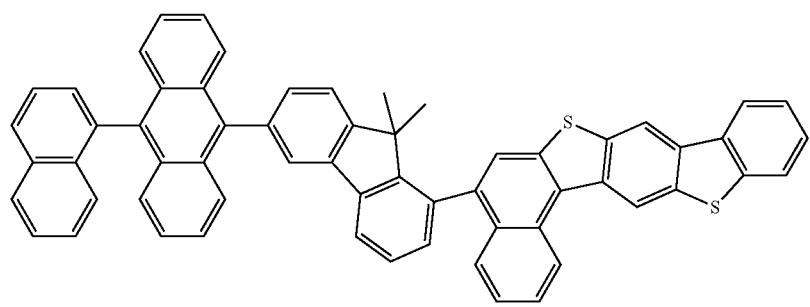
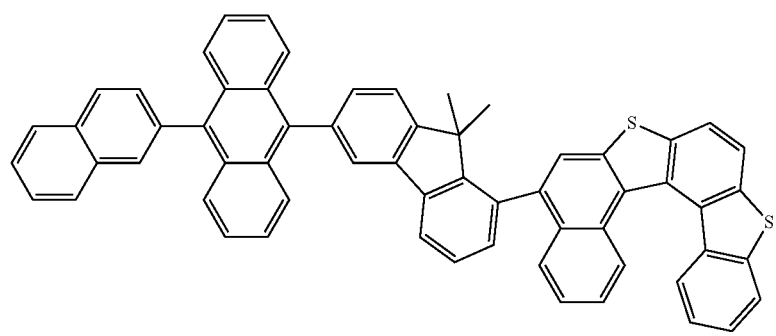

-continued
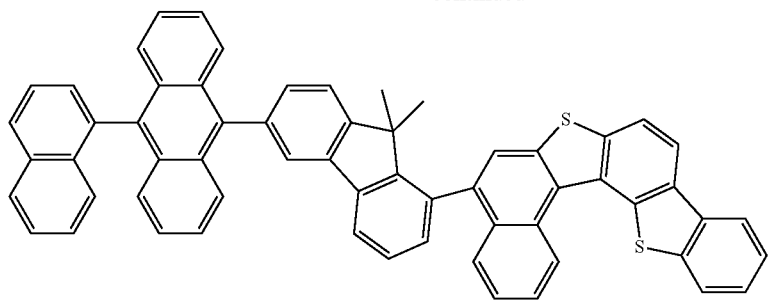
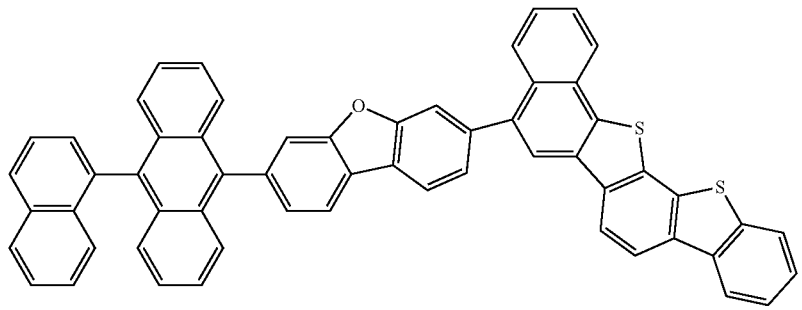
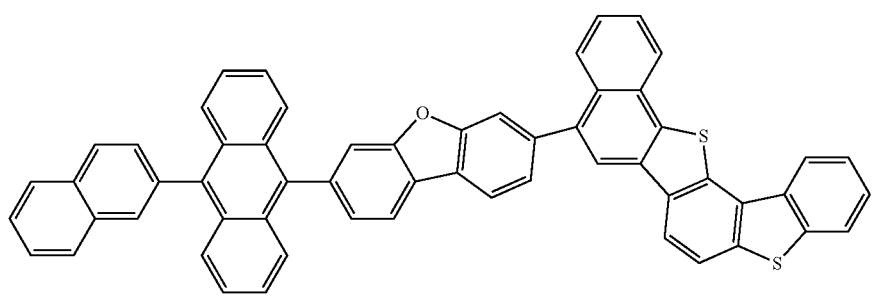
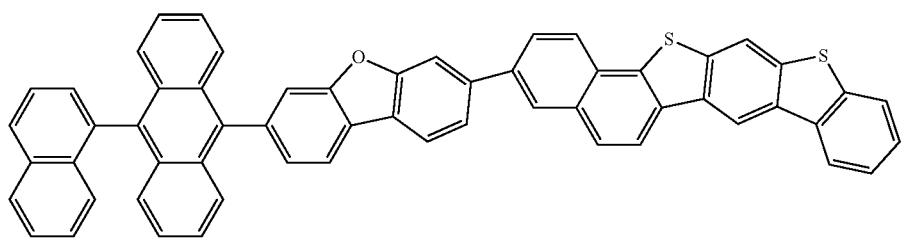
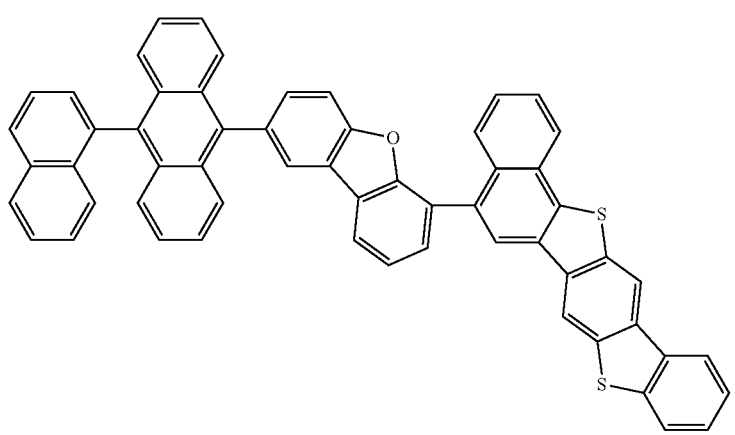

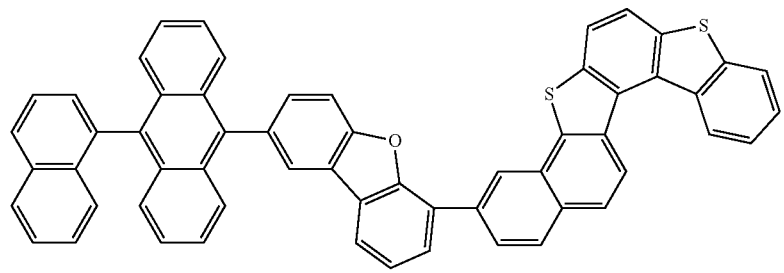

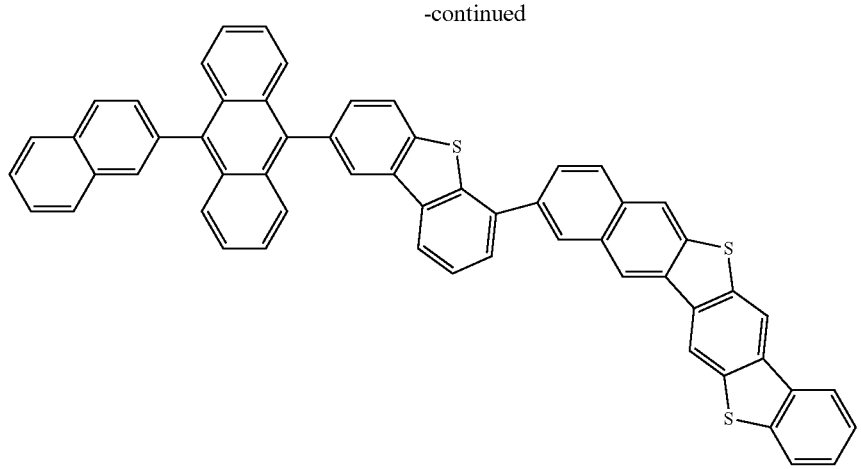
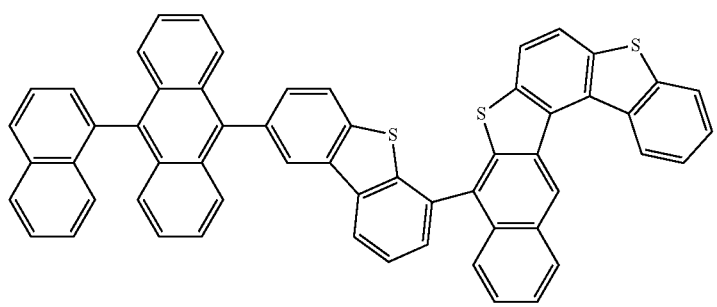
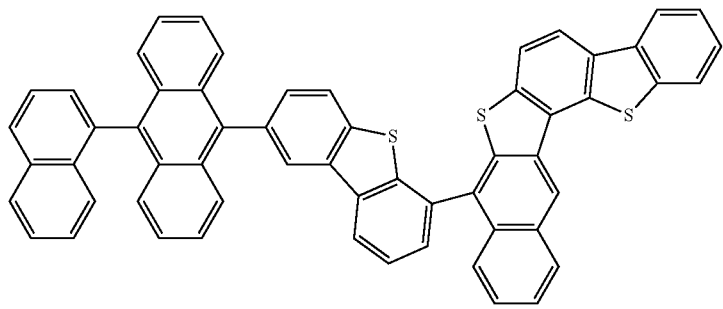
According to one or more exemplary embodiments of the present invention, the condensed cyclic compound may be at least one selected from Compounds H1 to H9; however, exemplary embodiments of the present invention are not limited thereto:
H1
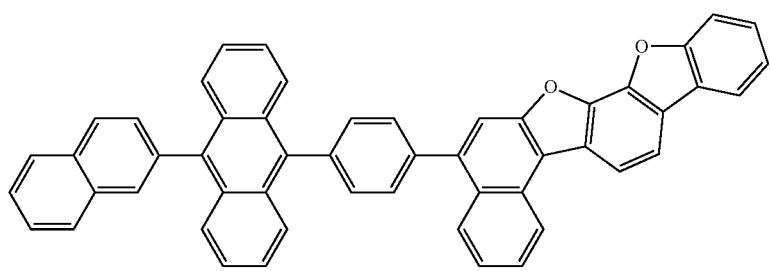

-continued
| | |
|---|---|
| 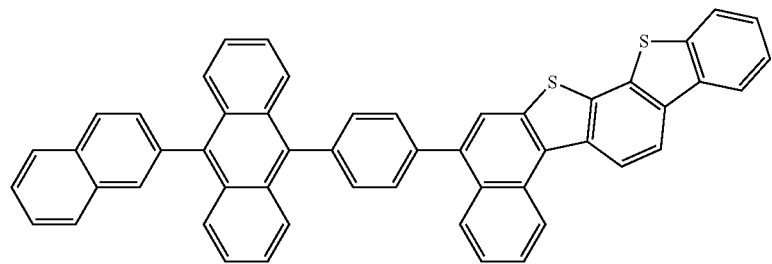 | H2 |
| 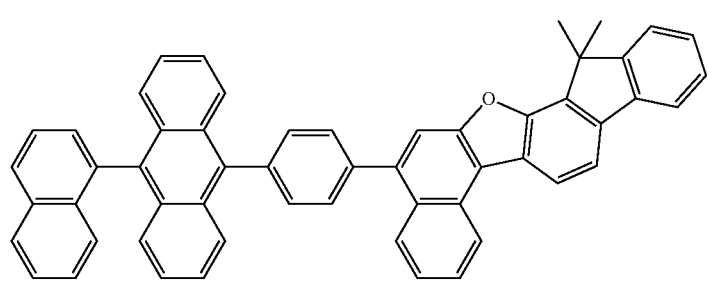 | H3 |
| 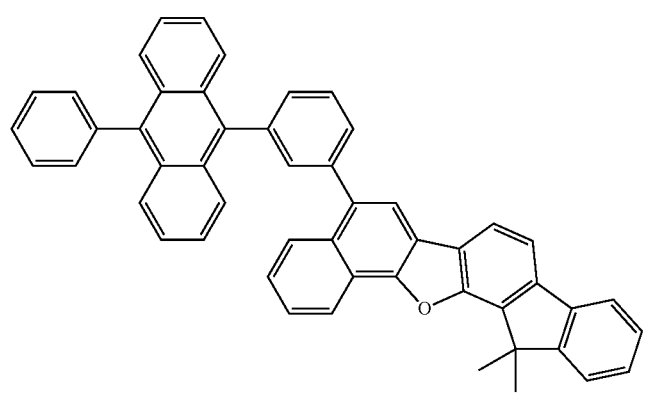 | H4 |
| 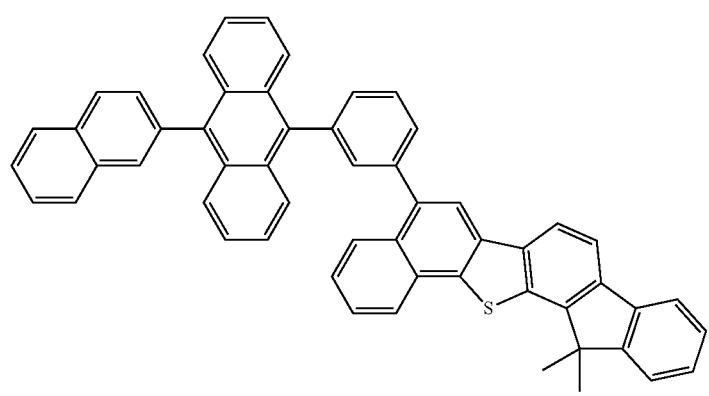 | H5 |
| 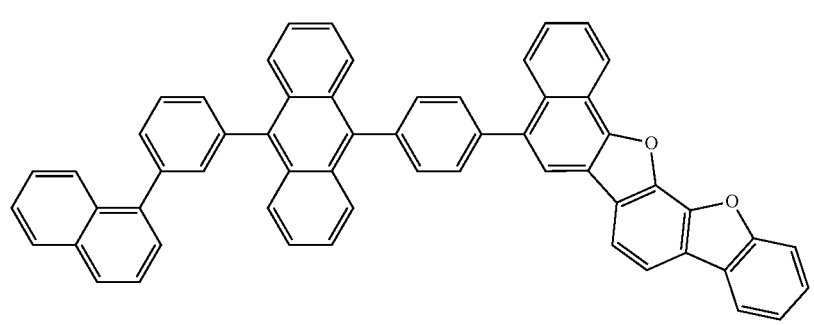 | H6 |

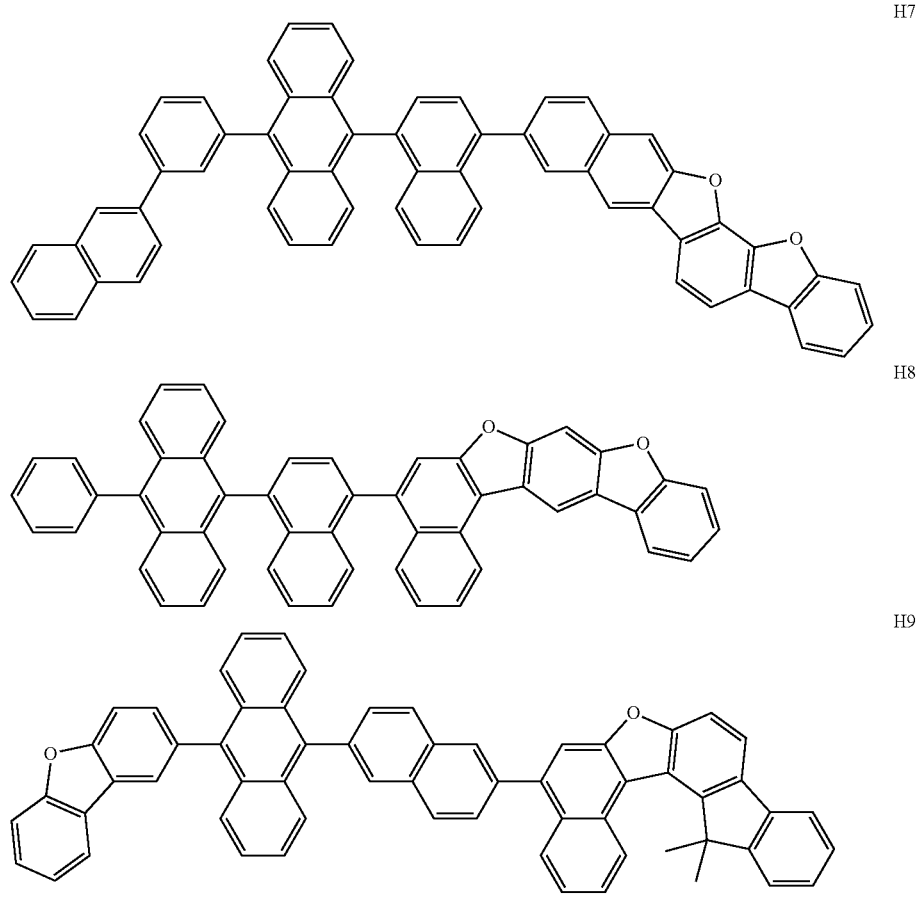

Ring $A_3$ in Formulae 1-1 and 1-2 may be a $C_7$-$C_{60}$ aromatic ring or a $C_1$-$C_{60}$ heteroaromatic ring. For example, a $C_6$ aromatic ring (i.e., a benzene) may be excluded from a list of ring $A_3$. When ring $A_3$ in Formulae 1-1 and 1-2 is a benzene group, although not limited to a specific theory, a size of a molecular structure may be smaller than a size of a condensed cyclic compound structure represented by Formula 1-1 or 1-2. Thus, the dispersion degree of electrons may be relatively low. Therefore, the size of the molecular structure does not contribute to stabilization of a molecular structure.

$T_1$ in Formula 1-1 or 1-2 may be the group represented by Formula 2. The condensed cyclic compound and the group represented by Formula 2 may be linked via $L_2$. When the group represented by Formula 2 is linked to the condensed cyclic compound via $L_2$, the dispersion degree of electrons may be relatively greater than when the group represented by Formula 2 is linked to the condensed cyclic compound not via $L_2$, therefore, contributing to stabilization of the entire molecular structure. Since the entire molecular structure may become three-dimensional, it is possible to have relatively high non-crystallization and relatively increase film characteristics.

The condensed cyclic compound represented by Formula 1-1 or 1-2 may be synthesized by using known organic synthesis methods. A synthesis method of the condensed cyclic compound represented by Formula 1-1 or 1-2 may be recognizable by one of ordinary skill in the art in view of the following Examples.

Figure 1:
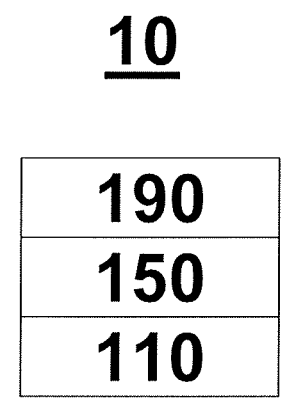

FIG. 1 is a schematic cross-sectional diagram illustrating an organic light-emitting device according to an exemplary embodiment of the present invention. An organic light-emitting device 10 may include a first electrode 110, an organic layer 150, and a second electrode 190.

A structure of the organic light-emitting device 10 according to an exemplary embodiment of the present invention and a method of manufacturing the organic light-emitting device 10 according to an exemplary embodiment of the present invention will be described in more detail below with reference to FIG. 1.

Referring to FIG. 1, a substrate may be disposed below the first electrode 110. Alternatively, the substrate may be disposed above the second electrode 190. The substrate may include a glass substrate or a plastic substrate. The glass substrate and the plastic substrate may each have a relatively high mechanical strength, thermal stability, transparency, surface smoothness, ease of handling, and water-resistance.

The first electrode 110 may be formed by depositing or sputtering a material included in the first electrode 110 on the substrate. When the first electrode 110 is an anode, the material included in the first electrode 110 may include materials with a relatively high work function, which may facilitate hole injection.

The first electrode 110 may be a reflective electrode, a semi-transmissive electrode, or a transmissive electrode. When the first electrode 110 is a transmissive electrode, a material included in the first electrode 110 may include indium tin oxide (ITO), indium zinc oxide (IZO), tin oxide (SnO₂), zinc oxide (ZnO), or any combination thereof; however, exemplary embodiments of the present invention are not limited thereto. When the first electrode 110 is a semi-transmissive electrode or a reflective electrode, a included in the first electrode 110 may include magnesium (Mg), silver (Ag), aluminum (Al), aluminum-lithium (Al—Li), calcium (Ca), magnesium-indium (Mg—In), magnesium-silver (Mg—Ag), or any combination thereof. However, the material included in the first electrode 110 is not limited thereto.

The first electrode 110 may have a single-layered structure. Alternatively, the first electrode 110 may have a multi-layered structure including two or more layers. For example, the first electrode 110 may have a three-layered structure of ITO/Ag/ITO; however, the structure of the first electrode 110 is not limited thereto.

The organic layer 150 may be disposed on the first electrode 110. The organic layer 150 may include an emission layer.

The organic layer 150 may include a condensed cyclic compound represented by Formula 1-1 or 1-2.

The organic layer 150 may include a hole transport region and an electron transport region. The hole transport region may be disposed between the first electrode 110 and the emission layer. The electron transport region may be disposed between the emission layer and the second electrode 190.

The hole transport region may have a single-layered structure including a single layer including a single material. The hole transport region may have a single-layered structure including a single layer including a plurality of different materials. The hole transport region may have a multi-layered structure having a plurality of layers including a plurality of different materials.

The hole transport region may include the condensed cyclic compound represented by Formula 1-1 or 1-2.

The hole transport region may include at least one layer selected from a hole injection layer (HIL), a hole transport layer (HTL), an emission auxiliary layer, and an electron blocking layer (EBL).

For example, the hole transport region may have a single-layered structure. The single layered structure may include a single layer including a plurality of different materials. Alternatively, the hole transport region may have multi-layered structure. The multi-layered structure may include a hole injection layer/hole transport layer structure, a hole injection layer/hole transport layer/emission auxiliary layer structure, a hole injection layer/emission auxiliary layer structure, a hole transport layer/emission auxiliary layer structure, or a hole injection layer/hole transport layer/ electron blocking layer structure. For each structure, the layers may be sequentially stacked on the first electrode 110; however, the structure of the hole transport region is not limited thereto.

The hole transport region may include at least one selected from m-MTDATA, TDATA, 2-TNATA, NPB (NPD), β—NPB, TPD, Spiro-TPD, Spiro-NPB, methylated-NPB, TAPC, HMTPD, 4,4',4"-tris(N-carbazolyl)triphenylamine (TCTA), polyaniline/dodecylbenzenesulfonic acid (Pani/DBSA), PEDOT/PSS (poly(3,4-ethylenedioxythiophene)/poly(4-styrenesulfonate)), polyaniline/camphor sulfonic acid (Pani/CSA), polyaniline/poly(4-styrene-sulfonate) (Pani/PSS), a compound represented by Formula 201, and a compound represented by Formula 202:

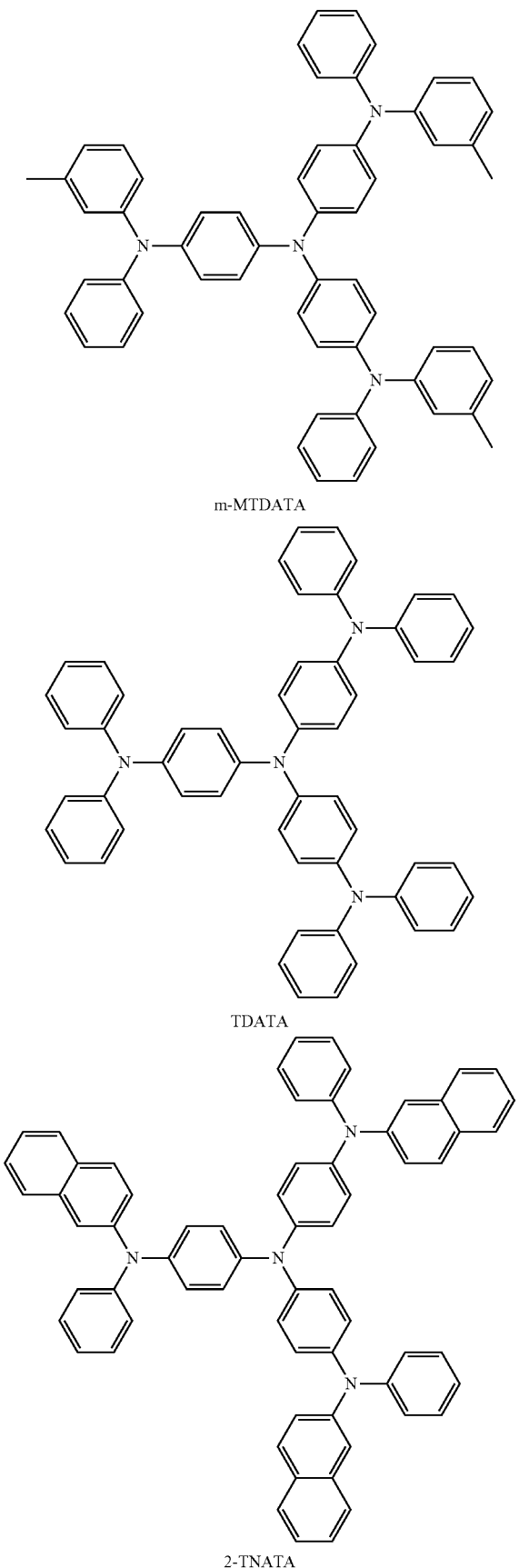

m-MTDATA

TDATA

2-TNATA

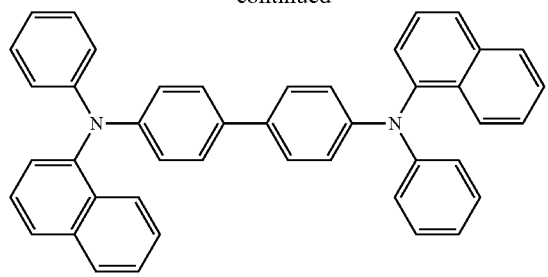

NPB

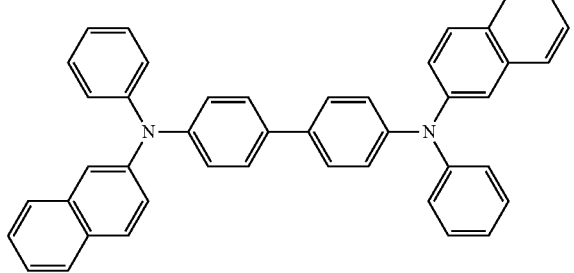

β-NPB

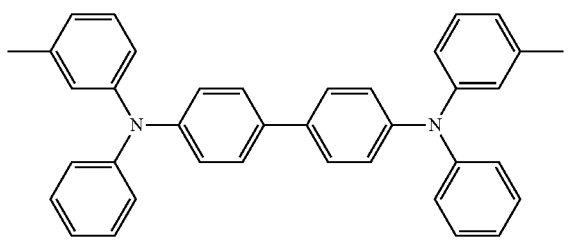

TPD

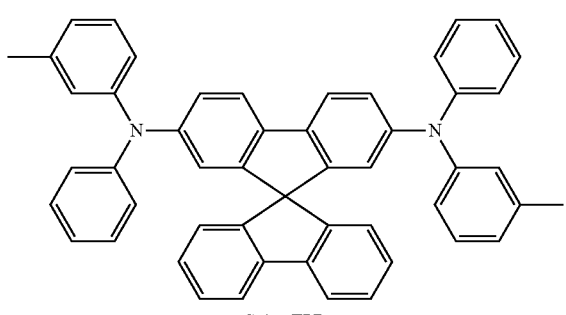

Spiro-TPD

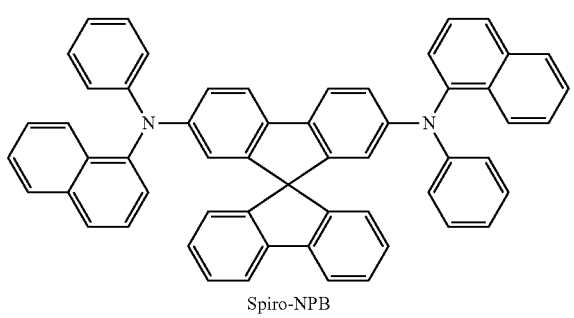

Spiro-NPB

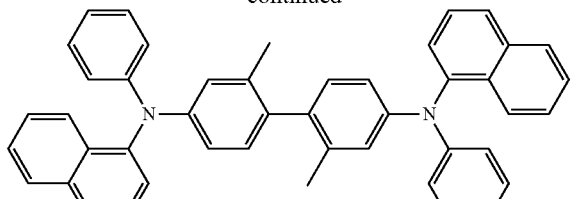

methylated NPB

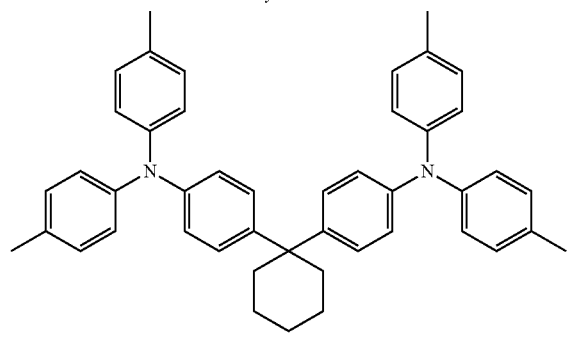

TAPC

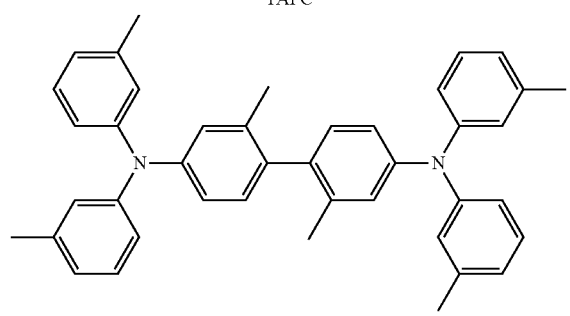

HMTPD

<Formula 201>

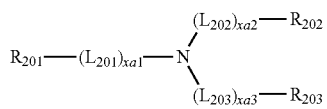

<Formula 202>

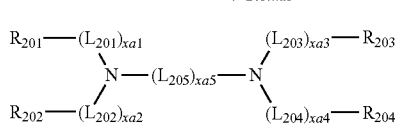

In Formulae 201 and 202:

$L_{201}$ to $L_{204}$ may each independently be selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group.

$L_{205}$ may be selected from *—O—*, *—S—*, *—N($Q_{201}$)-*, a substituted or unsubstituted $C_1$-$C_{20}$ alkylene group, a substituted or unsubstituted $C_2$-$C_{20}$ alkenylene group, a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group.

xa1 to xa4 may each independently be an integer selected from 0 to 3.

xa5 may be an integer selected from 1 to 10.

$R_{201}$ to $R_{204}$ and $Q_{201}$ may each independently be selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group.

For example, in Formula 202, $R_{201}$ and $R_{202}$ may be linked via a single bond, a dimethyl-methylene group, or a diphenyl-methylene group, and $R_{203}$ and $R_{204}$ may be linked via a single bond, a dimethyl-methylene group, or a diphenyl-methylene group. However, exemplary embodiments of the present invention are not limited thereto.

According to one or more exemplary embodiments of the present invention, in Formulae 201 and 202, $L_{201}$ to $L_{205}$ may each independently be selected from:

a phenylene group, a pentalenylene group, an indenylene group, a naphthylene group, an azulenylene group, a heptalenylene group, an indacenylene group, an acenaphthylene group, a fluorenylene group, a spiro-bifluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a thiophenylene group, a furanylene group, a carbazolylene group, an indolylene group, an isoindolylene group, a benzofuranylene group, a benzothiophenylene group, a dibenzofuranylene group, a benzocarbazolylene group, a dibenzocarbazolylene group, a dibenzosilolylene group, and a pyridinylene group; and a phenylene group, a pentalenylene group, an indenylene group, a naphthylene group, an azulenylene group, a heptalenylene group, an indacenylene group, an acenaphthylene group, a fluorenylene group, a spiro-bifluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a thiophenylene group, a furanylene group, a carbazolylene group, an indolylene group, an isoindolylene group, a benzofuranylene group, a benzothiophenylene group, a dibenzofuranylene group, a benzocarbazolylene group, a dibenzocarbazolylene group, a dibenzosilolylene group, and a pyridinylene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, —Si($Q_{31}$)($Q_{32}$)($Q_{33}$), and —N($Q_{31}$)($Q_{32}$).

$Q_{31}$ to $Q_{33}$ may each independently be selected from a $C_1$-$C_{10}$ alkyl group, a $C_1$-$C_{10}$ alkoxy group, a phenyl group, a biphenyl group, a terphenyl group, and a naphthyl group.

According to one or more exemplary embodiments of the present invention, in Formulae 201 and 202, xa1 to xa4 may each independently be an integer selected from 0, 1, or 2.

According to one or more exemplary embodiments of the present invention, xa5 may be an integer selected from 1, 2, 3, and 4.

According to one or more exemplary embodiments of the present invention, $R_{201}$ to $R_{204}$ and $Q_{201}$ may each independently be selected from a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group; and a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, —Si($Q_{31}$)($Q_{32}$)($Q_{33}$), and —N($Q_{31}$)($Q_{32}$).

$Q_{31}$ to $Q_{33}$ may be the same as described above.

According to one or more exemplary embodiments of the present invention, at least one of $R_{201}$ to $R_{203}$ in Formula 201 may each independently be selected from:

a fluorenyl group, a spiro-bifluorenyl group, a carbazolyl group, a dibenzofuranyl group, and a dibenzothiophenyl group; and a fluorenyl group, a spiro-bifluorenyl group, a carbazolyl group, a dibenzofuranyl group, and a dibenzothiophenyl group, each substituted with at least one selected from deuterium, —F, —Cl, —Br, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a naphthyl group, a fluorenyl group, a spiro-bifluorenyl group, a carbazolyl group, a dibenzofuranyl group, and a dibenzothiophenyl group; however, exemplary embodiments of the present invention are not limited thereto.

According to one or more exemplary embodiments of the present invention, in Formula 202, $R_{201}$ and $R_{202}$ may be linked via a single bond and/or i$R_{203}$ and $R_{204}$ may be linked via a single bond.

According to one or more exemplary embodiment of the present invention, at least one of $R_{201}$ to $R_{204}$ in Formula 202 may be selected from:

a carbazolyl group; and a carbazolyl group, substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a naphthyl group, a fluorenyl group, a spiro-bifluorenyl group, a carbazolyl group, a dibenzofuranyl group, and a dibenzothiophenyl group; however, exemplary embodiments of the present invention are not limited thereto.

The compound represented by Formula 201 may be represented by Formula 201A:

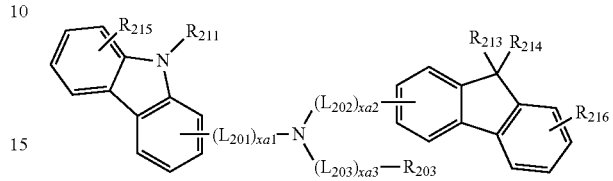

<Formula 201A>

The compound represented by Formula 201 may be represented by Formula 201A(1); however, exemplary embodiments of the present invention are not limited thereto:

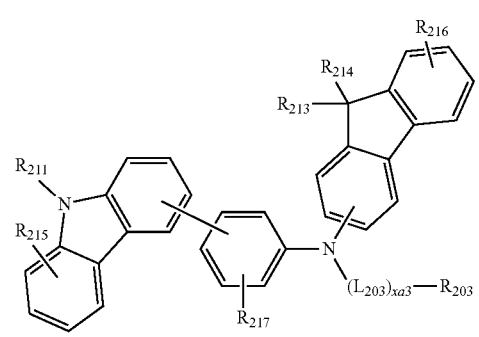

<Formula 201A(1)>

The compound represented by Formula 201 may be represented by Formula 201A-1; however, exemplary embodiments of the present invention are not limited thereto:

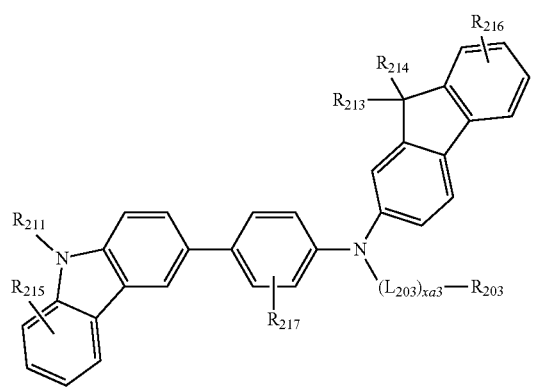

<Formula 201A-1>

According to one or more exemplary embodiments of the present invention, the compound represented by Formula 202 may be represented by Formula 202A:

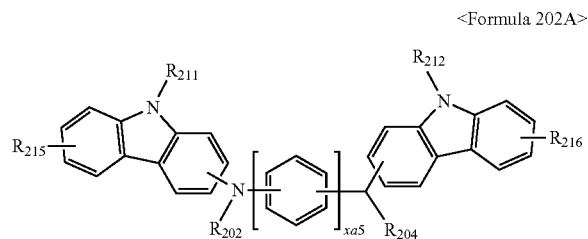

<Formula 202A>

According to one or more exemplary embodiments of the present invention, the compound represented by Formula 202 may be represented by Formula 202A-1:

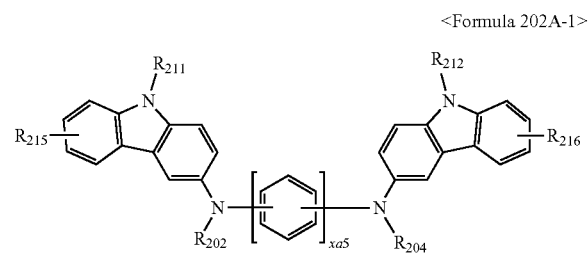

<Formula 202A-1>

In Formulae 201A, 201A(1), 201A-1, 202A, and 202A-1, $L_{201}$ to $L_{203}$, xa1 to xa3, xa5, and $R_{202}$ to $R_{204}$ may each independently be the same as described above.

In Formulae 201A, 201A(1), 201A-1, 202A, and 202A-1, $R_{211}$ and $R_{212}$ may each independently be the same as $R_{203}$.

In Formulae 201A, 201A(1), 201A-1, 202A, and 202A-1, $R_{213}$ to $R_{217}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group.

The hole transport region may include at least one compound selected from Compounds HT1 to HT39; however, exemplary embodiments of the present invention are not limited thereto:

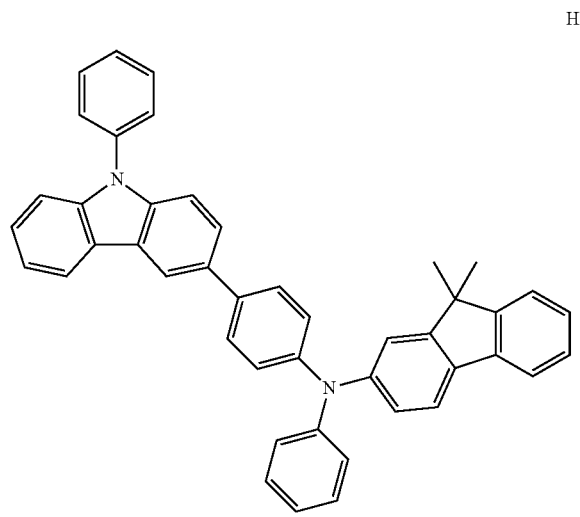

HT1

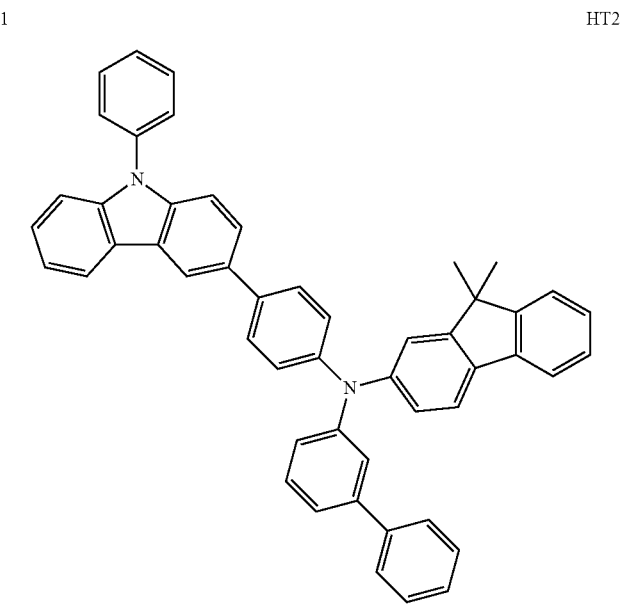

HT2

-continued
HT3
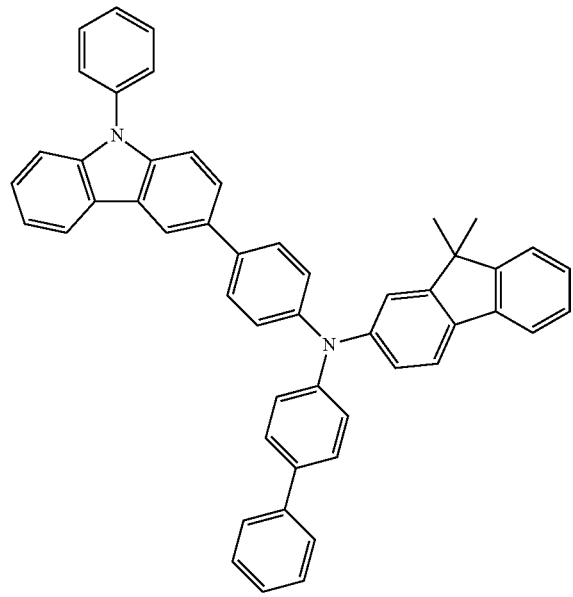
HT4
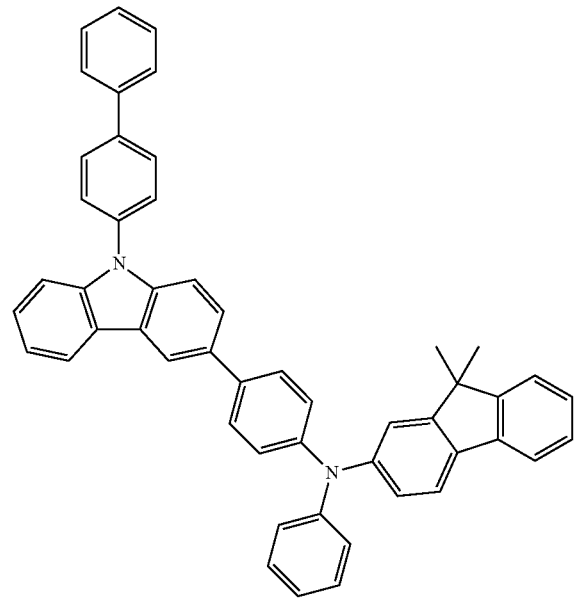
HT5
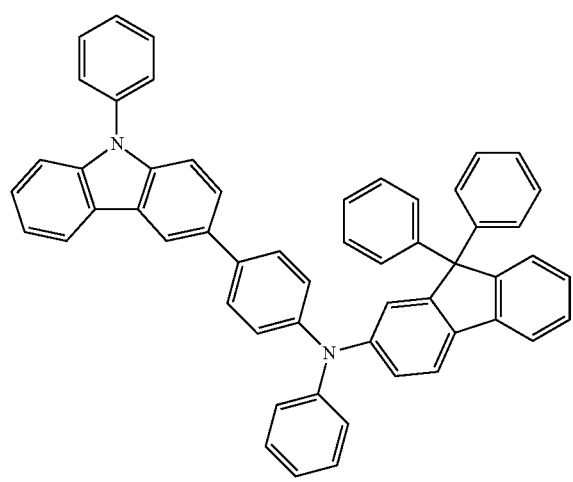
HT6
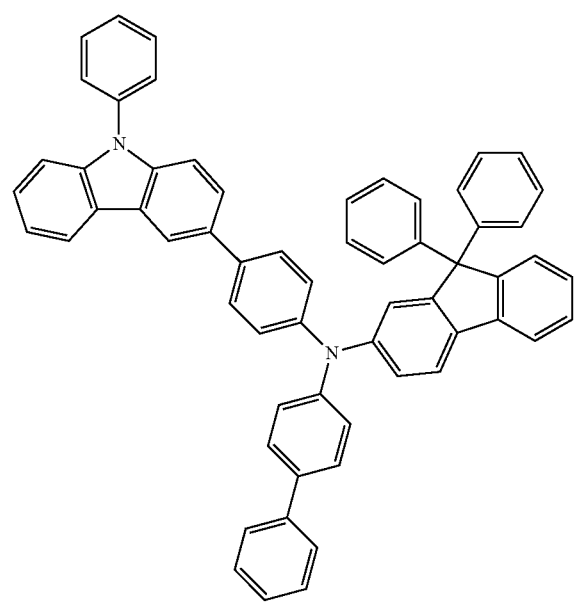

-continued
HT7
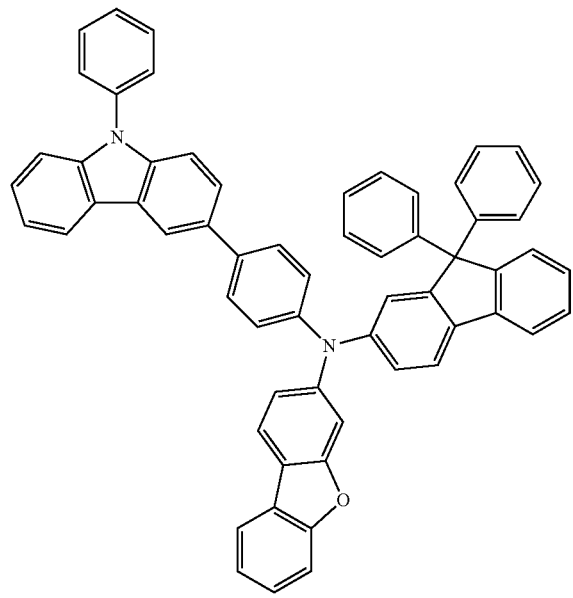
HT8
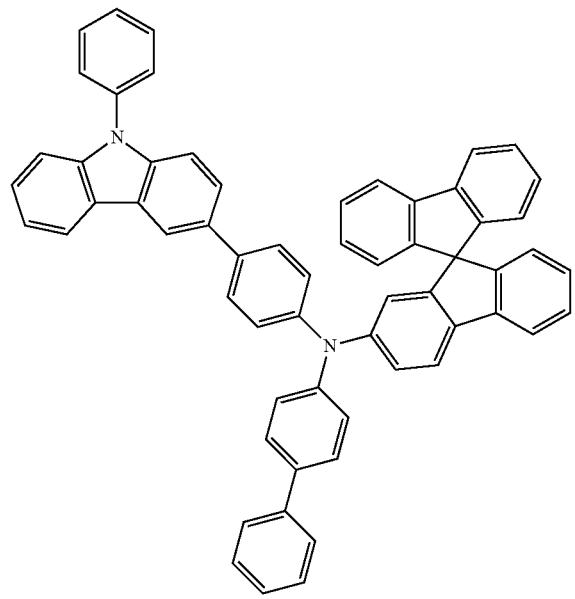
HT9
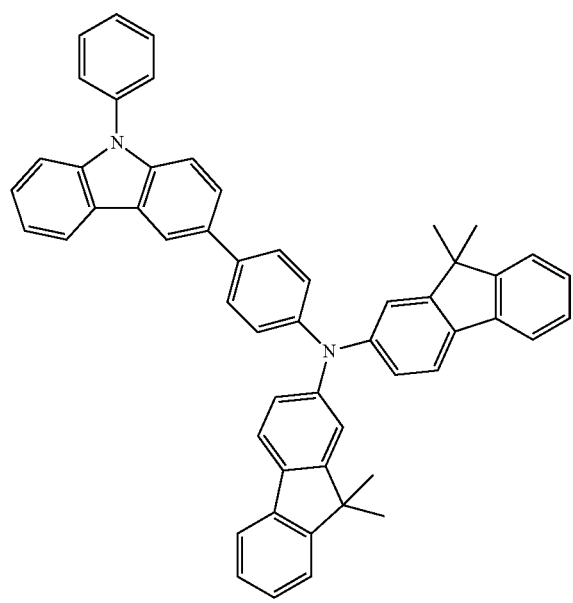
HT10
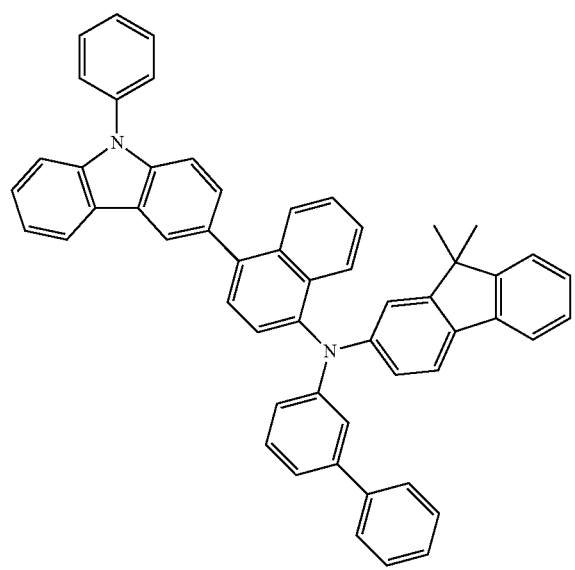

-continued
HT11
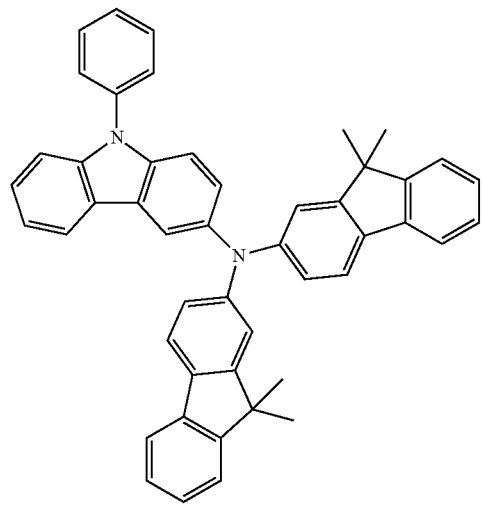
HT12
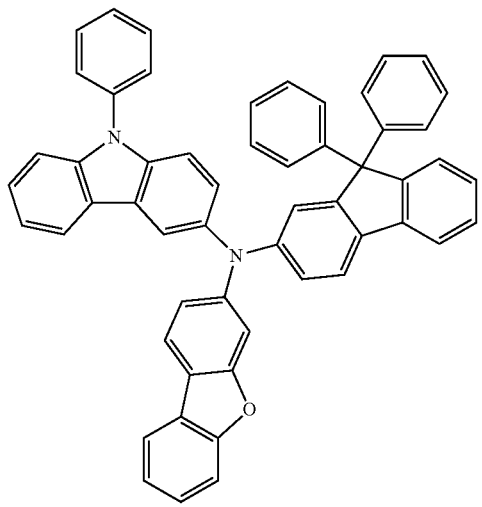
HT13
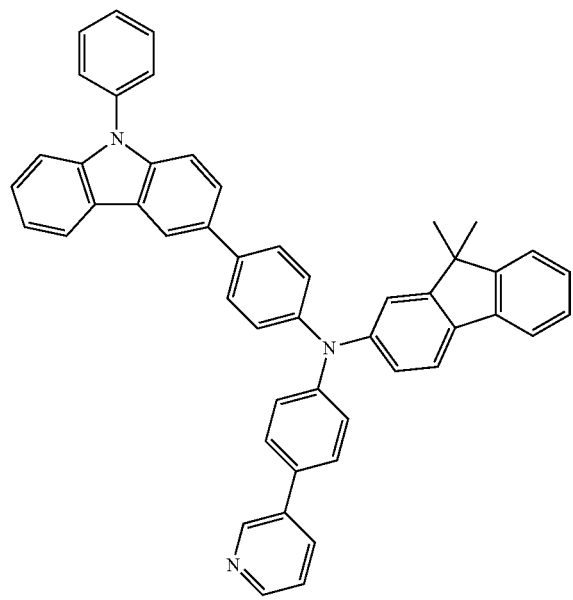
HT14
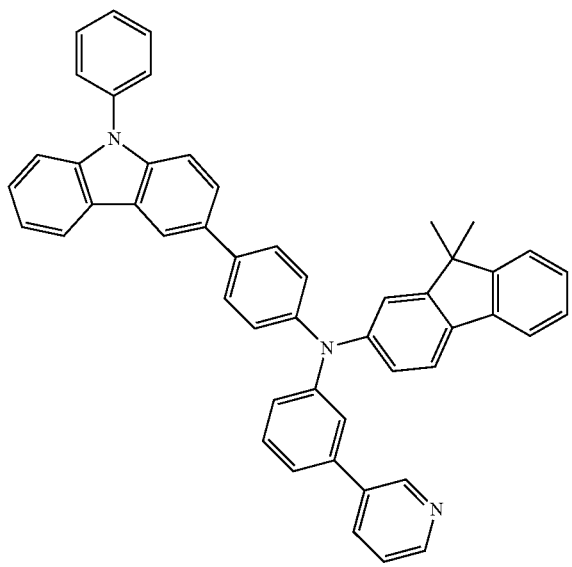
HT15
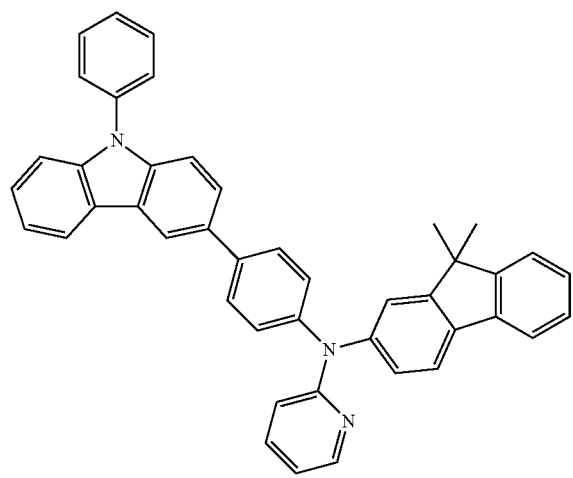
HT16
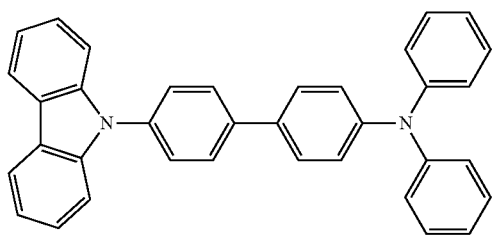

-continued
HT17
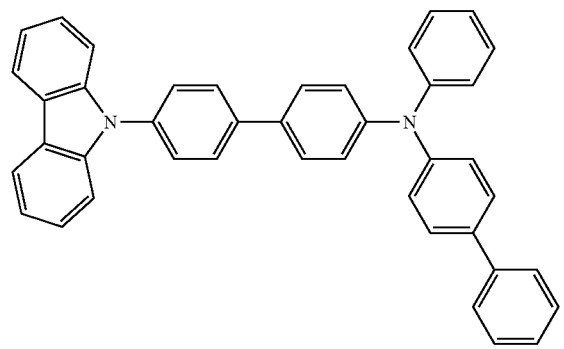
HT18
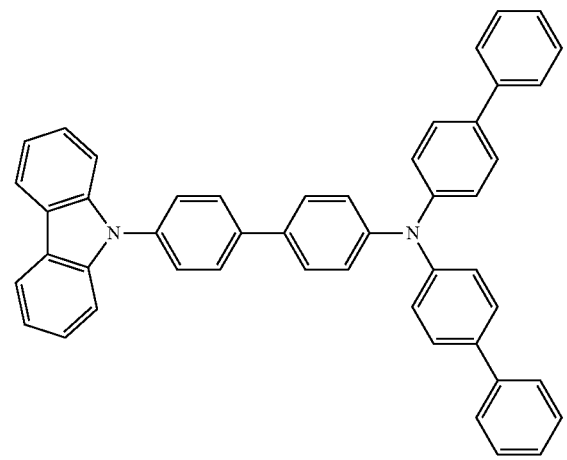
HT19
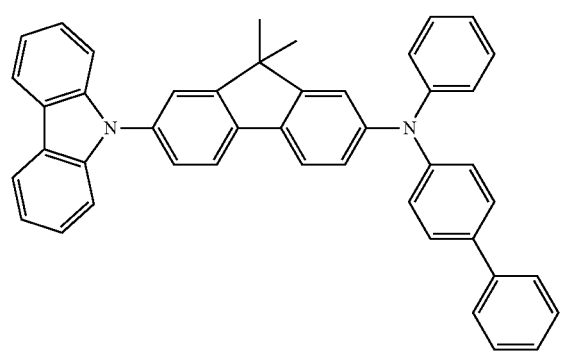
HT20
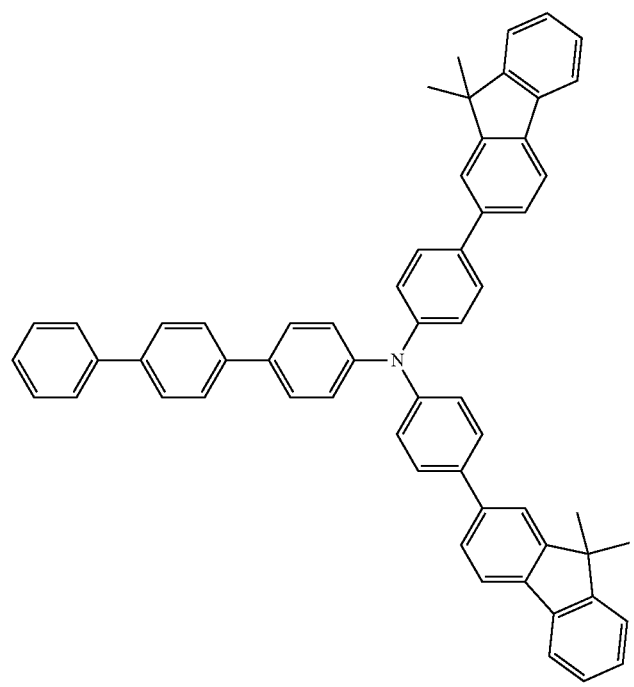

-continued
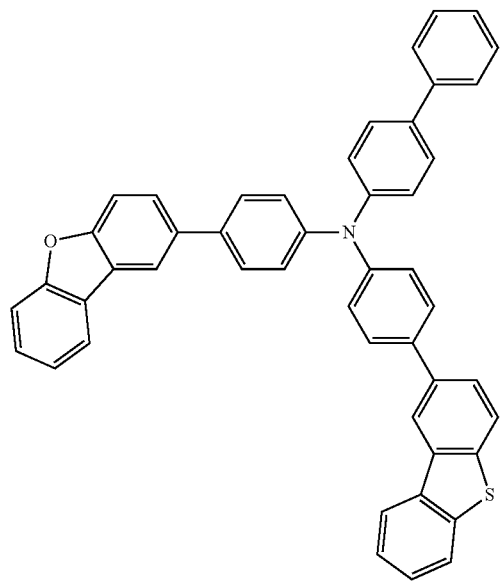
HT21
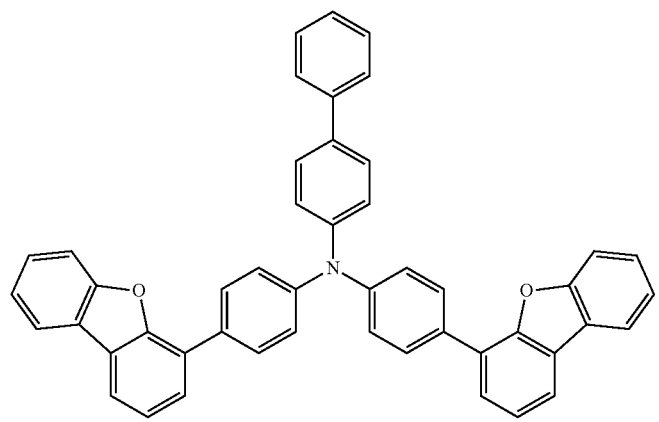
HT22
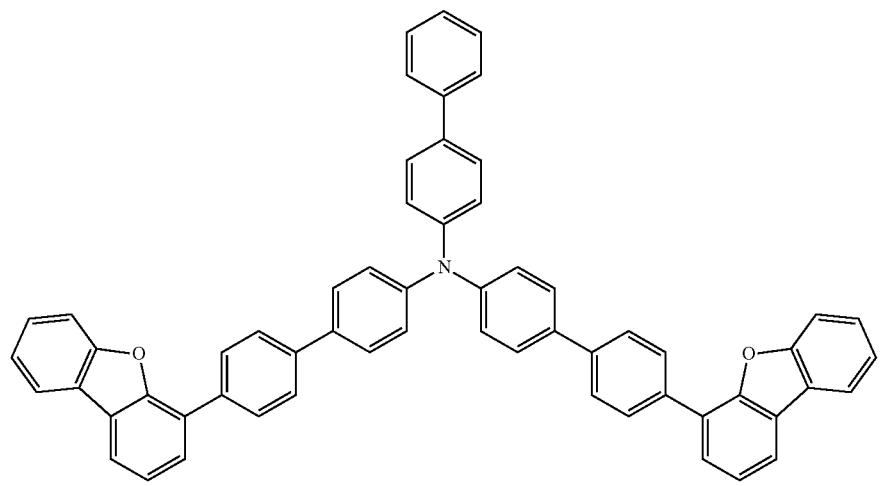
HT23

HT24
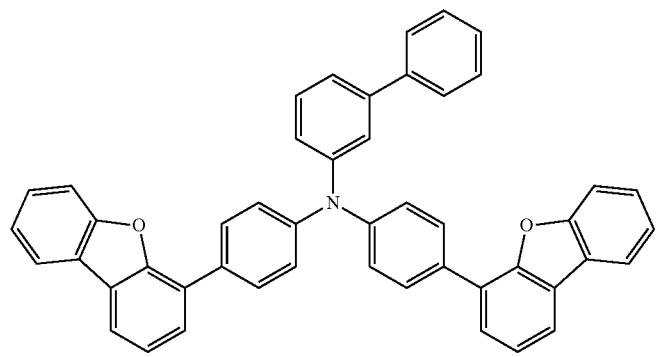
HT25 HT26
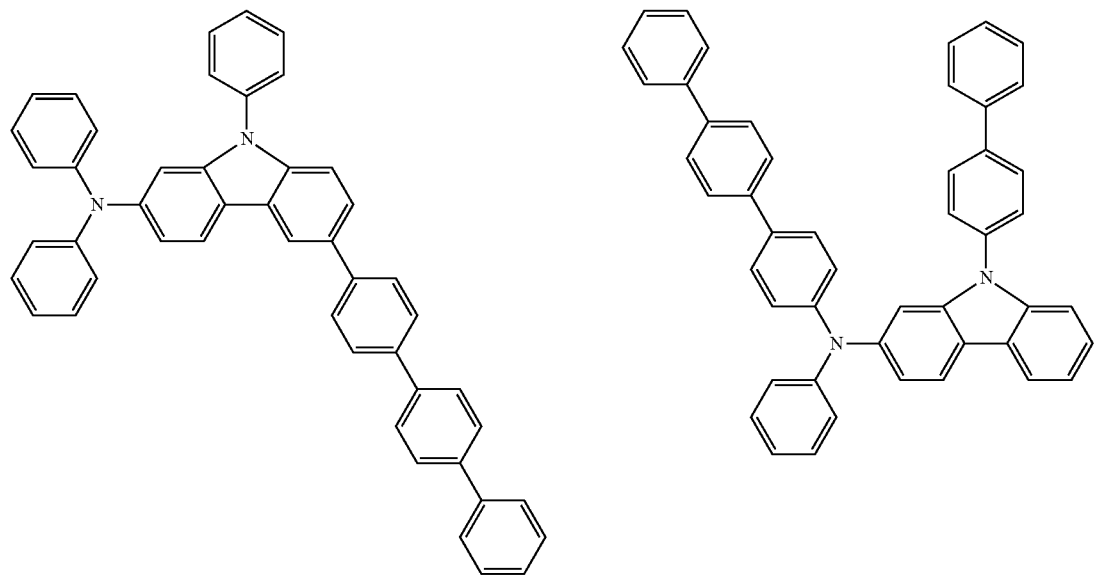
HT27
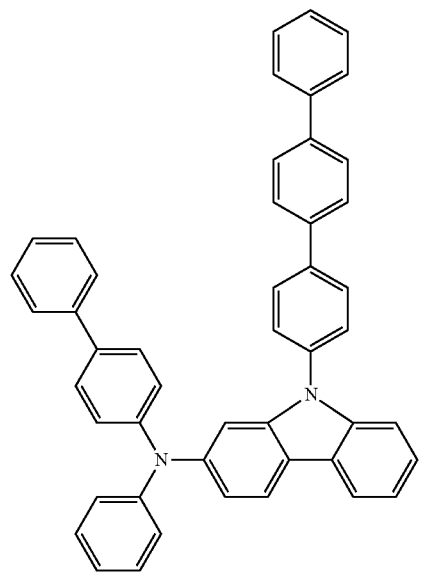

HT28
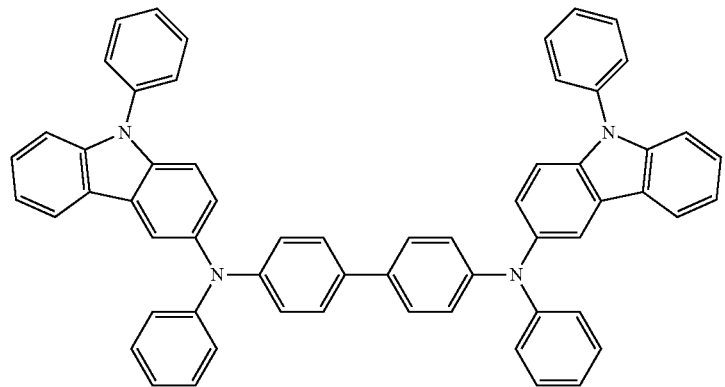
HT29
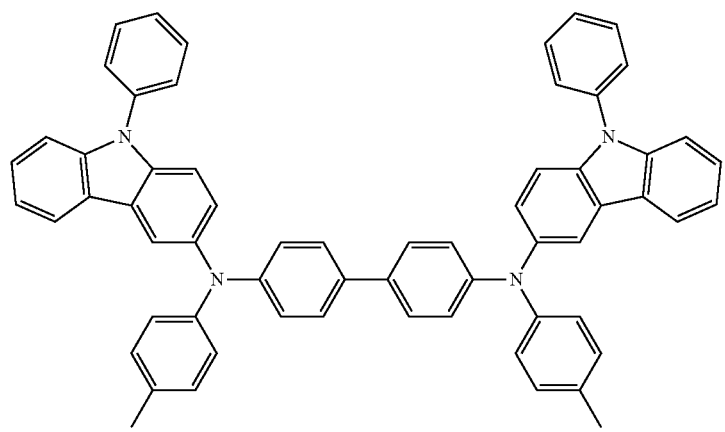
HT30
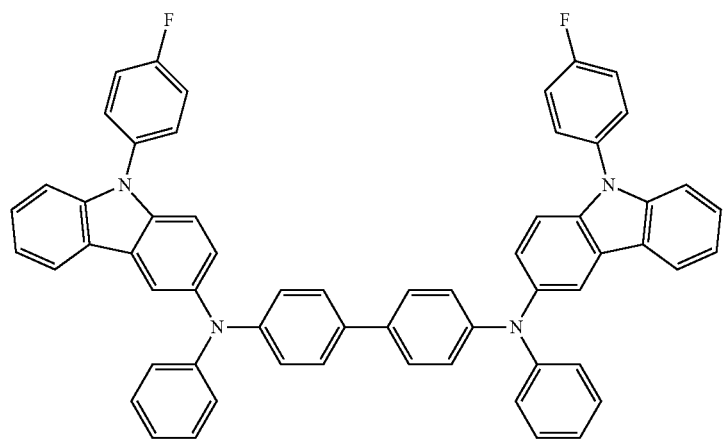

HT31
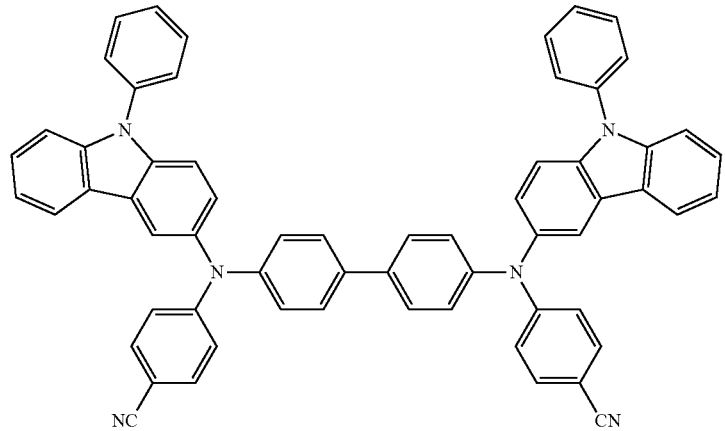
HT32
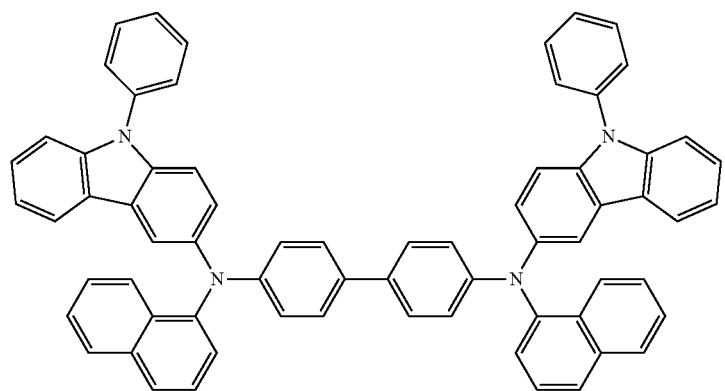
HT33
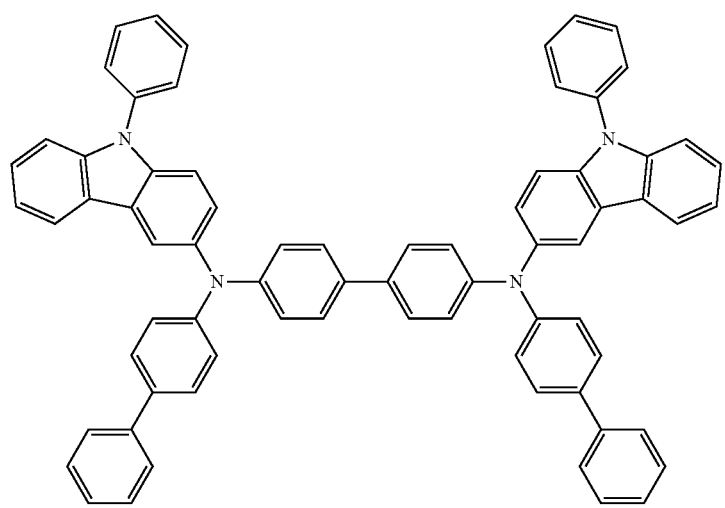

-continued
HT34
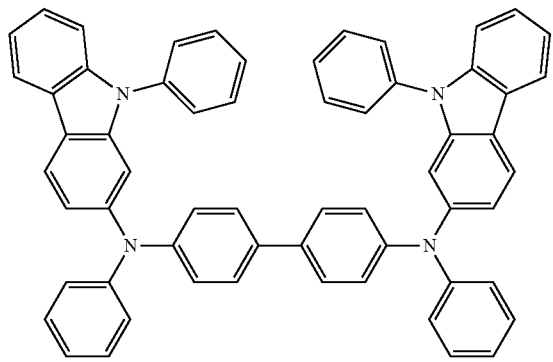
HT35
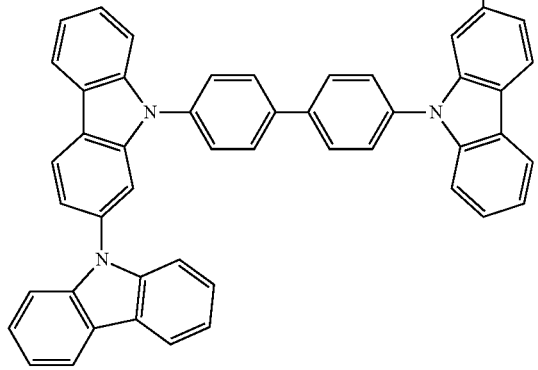
HT36
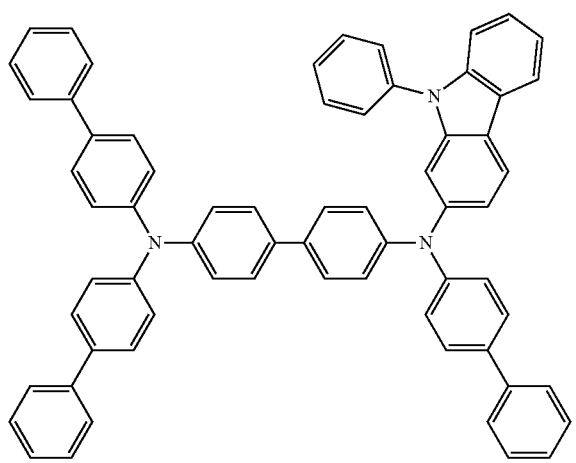
HT37
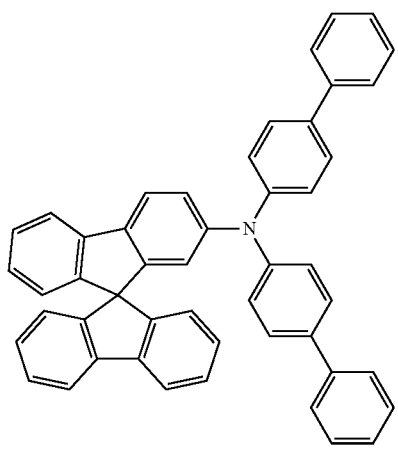
HT38
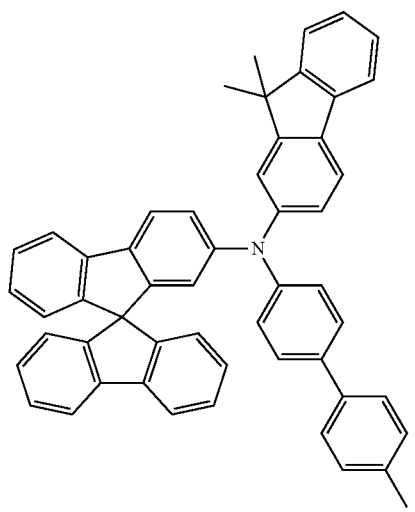
HT39
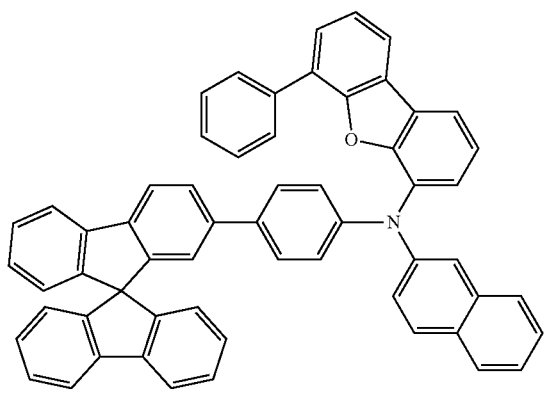

A thickness of the hole transport region may be in a range of from about 100 Å to about 10,000 Å, for example, from about 100 Å to about 1,000 Å. When the hole transport region includes at least one of a hole injection layer and a hole transport layer, the thickness of the hole injection layer may be in a range of from about 100 Å to about 9,000 Å, for example, from about 100 Å to about 1,000 Å, and the thickness of the hole transport layer may be in a range of from about 50 Å to about 2,000 Å, for example, from about 100 Å to about 1,500 Å. When the thicknesses of the hole transport region, the hole injection layer, and the hole transport layer are within these ranges, satisfactory hole transporting characteristics may be obtained without a substantial increase in driving voltage.

The emission auxiliary layer may increase light-emission efficiency by compensating for an optical resonance distance according to the wavelength of light emitted by an emission layer. The electron blocking layer may decrease or prevent the flow of electrons from an electron transport region. The emission auxiliary layer and the electron blocking layer may include materials as described herein.

The hole transport region may include a charge-generation material, which may increase conductive properties of the hole transport region. The charge-generation material may be substantially homogeneously or non-homogeneously dispersed in the hole transport region.

The charge-generation material may be, for example, a p-dopant.

According to one or more exemplary embodiments of the present invention, a lowest unoccupied molecular orbital (LUMO) level of the p-dopant may be −3.5 eV or less.

The p-dopant may include at least one of a quinone derivative, a metal oxide, or a compound including a cyano group; however, exemplary embodiments of the present invention are not limited thereto.

For example, the p-dopant may include at least one selected from:

a quinone derivative, such as tetracyanoquinodimethane (TCNQ) or 2,3,5,6-tetrafluoro-7,7,8,8-tetracyanoquinodimethane (F4-TCNQ);

a metal oxide, such as tungsten oxide or molybdenum oxide;

1,4,5,8,9,11-hexaazatriphenylene-hexacarbonitrile (HAT-CN); and a compound represented by Formula 221; however, exemplary embodiments of the present invention are not limited thereto:

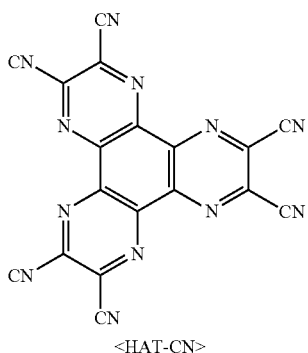

<HAT-CN>

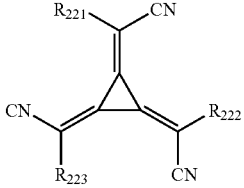

<F4-TCNQ>

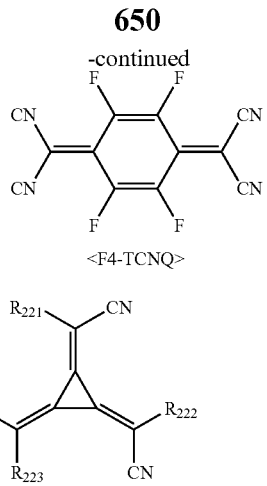

<Formula 221>

In Formula 221:

$R_{221}$ to $R_{223}$ may each independently be selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, provided that at least one selected from $R_{221}$ to $R_{223}$ has at least one substituent selected from a cyano group, —F, —Cl, —Br, —I, a $C_1$-$C_{20}$ alkyl group substituted with —F, a $C_1$-$C_{20}$ alkyl group substituted with —Cl, a $C_1$-$C_{20}$ alkyl group substituted with —Br, and a $C_1$-$C_{20}$ alkyl group substituted with —I.

When the organic light-emitting device 10 is a full color organic light-emitting device, the emission layer may be patterned into a red emission layer, a green emission layer, or a blue emission layer, according to a sub-pixel. According to one or more exemplary embodiments of the present invention, the emission layer may have a stacked structure. The stacked structure may include two or more layers selected from a red emission layer, a green emission layer, and a blue emission layer. The two or more layers may be in direct contact with each other. Alternatively, the two or more layers may be separated from each other. According to one or more exemplary embodiments of the present invention, the emission layer may include two or more materials. The two or more materials may include a red-light emission material, a green-light emission material, or a blue-light emission material. The two or more materials may be mixed with each other in a single layer. The two or more materials mixed with each other in the single layer may emit white light.

The emission layer may include a host and a dopant. The dopant may include at least one of a phosphorescent dopant or a fluorescent dopant.

The emission layer may include the condensed cyclic compound represented by Formula 1-1 or 1-2.

The host may include the condensed cyclic compound represented by Formula 1-1 or 1-2.

The emission layer may include, in addition to the condensed cyclic compound represented by Formula 1-1 or 1-2, a fluorescent dopant.

An amount of the dopant in the emission layer may be in a range of from about 0.01 parts by weight to about 15 parts by weight based on 100 parts by weight of the host; however, exemplary embodiments of the present invention are not limited thereto.

A thickness of the emission layer may be in a range of from about 100 Å to about 1,000 Å, for example, from about 200 Å to about 600 Å. When the thickness of the emission layer is within this range, increased light-emission characteristics may be obtained without a substantial increase in driving voltage.

The phosphorescent dopant may include an organometallic complex represented by Formula 401:

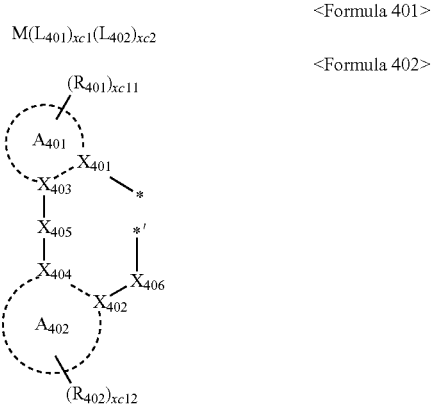

$$M(L_{401})_{xc1}(L_{402})_{xc2} \quad \text{<Formula 401>}$$

<Formula 402>

In Formulae 401 and 402, M may be selected from iridium (Ir), platinum (Pt), palladium (Pd), osmium (Os), titanium (Ti), zirconium (Zr), hafnium (Hf), europium (Eu), terbium (Tb), rhodium (Rh), and thulium (Tm).

In Formulae 401 and 402, $L_{401}$ may be selected from ligands represented by Formula 402. xc1 may be an integer selected from 1, 2, and 3. When xc1 is 2 or greater, at least two or $L_{401}(s)$ may be the same as or different from each other.

In Formulae 401 and 402, $L_{402}$ may be an organic ligand. xc2 may be an integer selected from 0 to 4. When xc2 is 2 or greater, at least two $L_{402}(s)$ may be the same as or different from each other.

In Formulae 401 and 402, $X_{401}$ to $X_{404}$ may each independently be selected from nitrogen (N) and carbon (C).

In Formulae 401 and 402, $X_{401}$ and $X_{403}$ may be linked via a single bond or a double bond. $X_{402}$ and $X_{404}$ may be linked via a single bond or a double bond.

In Formulae 401 and 402, $A_{401}$ and $A_{402}$ may each independently be selected from a $C_5$-$C_{60}$ carbocyclic group and or a $C_1$-$C_{60}$ heterocyclic group.

In Formulae 401 and 402, $X_{405}$ may be selected from a single bond, *—O—*', *—S—*', *—C(=O)—*', *—N($Q_{411}$)-*', *—C($Q_{411}$)($Q_{412}$)-*', *—C($Q_{411}$)=C($Q_{412}$)-*', *—C($Q_{411}$)=*', and *=C($Q_{411}$)=*'. $Q_{411}$ and $Q_{412}$ may be selected from hydrogen, deuterium, a $C_1$-$C_{20}$ alkyl group, a $C_1$-$C_{20}$ alkoxy group, a phenyl group, a biphenyl group, a terphenyl group, and a naphthyl group.

In Formulae 401 and 402, $X_{406}$ may be a single bond, oxygen (O), or sulfur (S).

In Formulae 401 and 402, $R_{401}$ and $R_{402}$ may each independently be selected from hydrogen, deuterium, —F, —Cl, —Br, —I, a hydroxyl group, a cyano group, a nitro group, an amidino group, a hydrazino group, a hydrazono group, a substituted or unsubstituted $C_1$-$C_{20}$ alkyl group, a substituted or unsubstituted $C_1$-$C_{20}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group and a substituted or unsubstituted monovalent non-aromatic condensed heteropolycyclic group, —Si($Q_{401}$)($Q_{402}$)($Q_{403}$), —N($Q_{401}$)($Q_{402}$), —B($Q_{401}$)($Q_{402}$), —C(=O)($Q_{401}$), —S(=O)2($Q_{401}$), and —P(=O)($Q_{401}$)($Q_{402}$), wherein $Q_{401}$ to $Q_{403}$ may each independently be selected from a $C_1$-$C_{10}$ alkyl group, a $C_1$-$C_{10}$ alkoxy group, a $C_6$-$C_{20}$ aryl group, and a $C_1$-$C_{20}$ heteroaryl group.

In Formulae 401 and 402, xc11 and xc12 may each independently be an integer selected from 0 to 10.

In Formula 402, * and *' may each indicate a binding site to M in Formula 401.

According to one or more exemplary embodiments of the present invention, $A_{401}$ and $A_{402}$ in Formula 402 may each independently be selected from a benzene group, a naphthalene group, a fluorene group, a spiro-bifluorene group, an indene group, a pyrrole group, a thiophene group, a furan group, an imidazole group, a pyrazole group, a thiazole group, an isothiazole group, an oxazole group, an isoxazole group, a pyridine group, a pyrazine group, a pyrimidine group, a pyridazine group, a quinoline group, an isoquinoline group, a benzoquinoline group, a quinoxaline group, a quinazoline group, a carbazole group, a benzimidazole group, a benzofuran group, a benzothiophene group, an isobenzothiophene group, a benzoxazole group, an isobenzoxazole group, a triazole group, a tetrazole group, an oxadiazole group, a triazine group, a dibenzofuran group, and a dibenzothiophene group.

In Formula 402, $X_{401}$ may be nitrogen (N), and $X_{402}$ may be carbon (C). Alternatively, $X_{401}$ and $X_{402}$ may each be nitrogen (N).

According to one or more exemplary embodiments of the present invention, $R_{401}$ and $R_{402}$ in Formula 402 may each independently be selected from:

hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from deuterium, —F, —Cl, —Br, —I, a hydroxyl group, a cyano group, a nitro group, an amidino group, a hydrazino group, a hydrazono group, a phenyl group, a naphthyl group, a cyclopentyl group, a cyclohexyl group, an adamantanyl group, a norbornanyl group, and a norbornenyl group;

a cyclopentyl group, a cyclohexyl group, an adamantanyl group, a norbornanyl group, a norbornenyl group, a phenyl group, a biphenyl group, a terphenyl group, a naphthyl group, a fluorenyl group, a pyridinyl group, a pyrazinyl group, a pyrimidinyl group, a pyridazinyl group, a triazinyl group, a quinolinyl group, an isoquinolinyl group, a quinoxalinyl group, a quinazolinyl group, a carbazolyl group, a dibenzofuranyl group, or a dibenzothiophenyl group;

a cyclopentyl group, a cyclohexyl group, an adamantanyl group, a norbornanyl group, a norbornenyl group a phenyl group, a biphenyl group, a terphenyl group, a naphthyl group, a fluorenyl group, a pyridinyl group, a pyrazinyl group, a pyrimidinyl group, a pyridazinyl group, a triazinyl group, a quinolinyl group, an isoquinolinyl group, a quinoxalinyl group, a quinazolinyl group, a carbazolyl group, a dibenzofuranyl group, and a dibenzothiophenyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, an adamantanyl group, a norbornanyl group, a norbornenyl group, a phenyl group, a biphenyl group, a terphenyl group, a naphthyl group, a fluorenyl group, a pyridinyl group, a pyrazinyl group, a pyrimidinyl group, a pyridazinyl group, a triazinyl group, a quinolinyl group, an isoquinolinyl group, a quinoxalinyl group, a quinazolinyl group, a carbazolyl group, a dibenzofuranyl group, and a dibenzothiophenyl group; and —Si($Q_{401}$)($Q_{402}$)($Q_{403}$), —N($Q_{401}$)($Q_{402}$), —B($Q_{401}$)($Q_{402}$), —C(=O)($Q_{401}$), —S(=O)$_2$($Q_{401}$) and —P(=O)($Q_{401}$)($Q_{402}$).

$Q_{401}$ to $Q_{403}$ may each independently be selected from a $C_1$-$C_{10}$ alkyl group, a $C_1$-$C_{10}$ alkoxy group, a phenyl group, a biphenyl group, and a naphthyl group; however, exemplary embodiments of the present invention are not limited thereto.

According to one or more exemplary embodiments of the present invention, when xc1 in Formula 401 is 2 or greater, two $A_{401}$(s) in at least two $L_{401}$(s) may be linked to each other via $X_{407}$, which is a linking group. Alternatively, two $A_{402}$(s) in at least two $L_{401}$(s) may be linked to each other via $X_{408}$, which is a linking group (see, e.g., Compounds PD1 to PD4 and PD7). $X_{407}$ and $X_{408}$ may each independently be selected from a single bond, *—O—*', *—S—*', *—C(=O)—*', *—N($Q_{413}$)-*', *—C($Q_{413}$)($Q_{414}$)-*', and *—C($Q_{413}$)=C($Q_{414}$)-*', in which $Q_{413}$ and $Q_{414}$ may each independently be selected from hydrogen, deuterium, a $C_1$-$C_{20}$ alkyl group, a $C_1$-$C_{20}$ alkoxy group, a phenyl group, a biphenyl group, a terphenyl group, and a naphthyl group; however, exemplary embodiments of the present invention are not limited thereto.

$L_{402}$ in Formula 401 may be selected from a monovalent, divalent, and trivalent organic ligand. For example, $L_{402}$ may be selected from halogen, diketone (for example, acetylacetonate), carboxylic acid (for example, picolinate), —C(=O), isonitrile, —CN, and phosphorus (for example, phosphine, or phosphite); however, exemplary embodiments of the present invention are not limited thereto.

According to one or more exemplary embodiments of the present invention, the phosphorescent dopant may be selected from, for example, Compounds PD1 to PD25; however, exemplary embodiments of the present invention are not limited thereto:

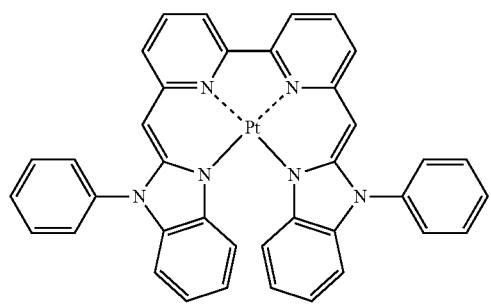
PD1

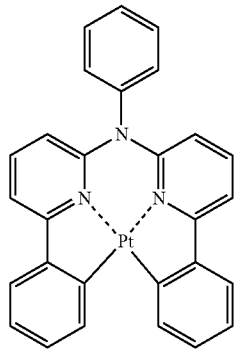
PD2

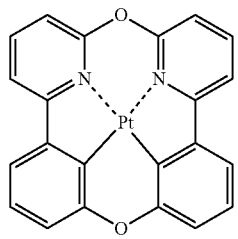
PD3

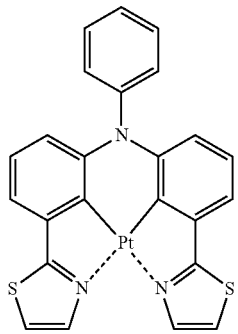
PD4

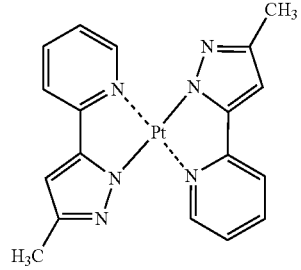
PD5

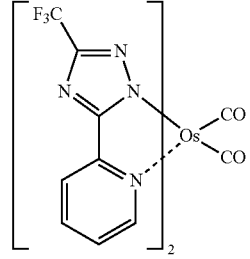
PD6

PD7
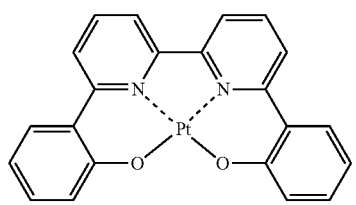
PD8
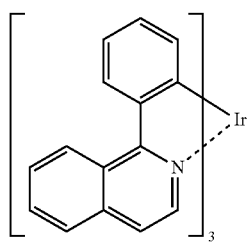
PD9
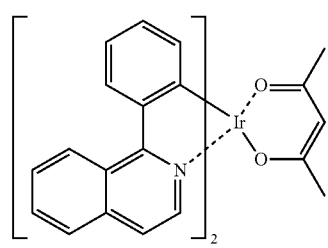
PD10
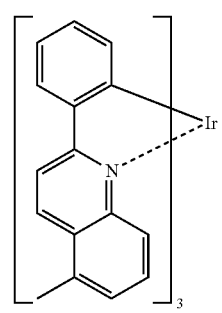
PD11
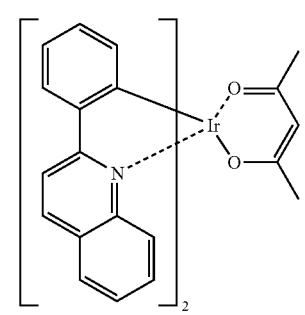
PD12
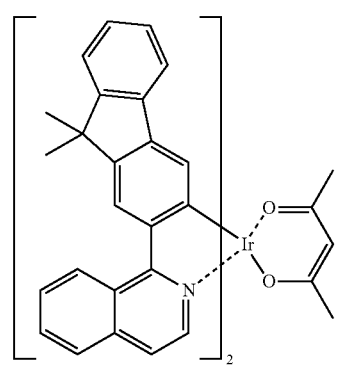
PD13
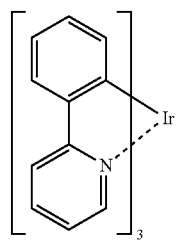
PD14
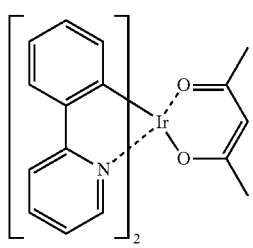
PD15
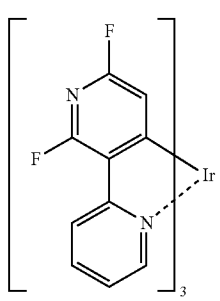
PD16
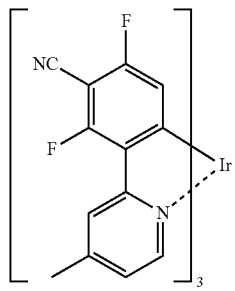

-continued
PD17
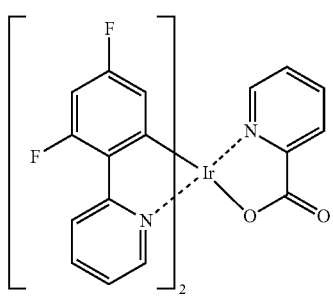
PD18
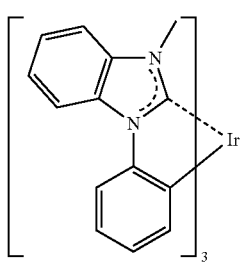
PD19
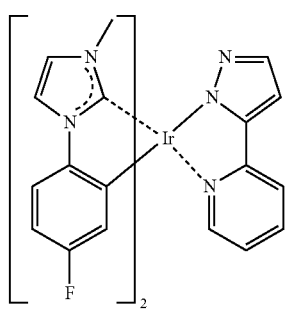
PD20
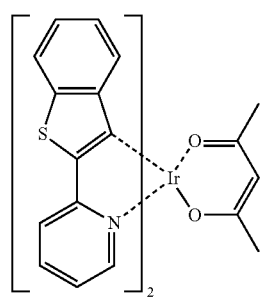
PD21
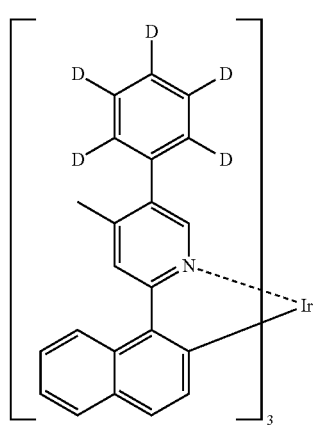
-continued
PD22
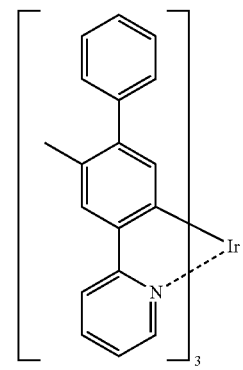
PD23
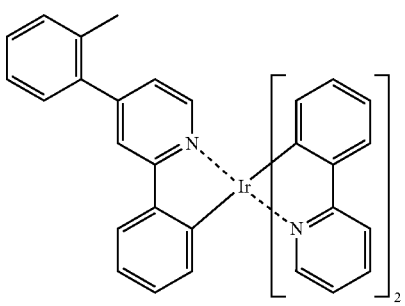
PD24
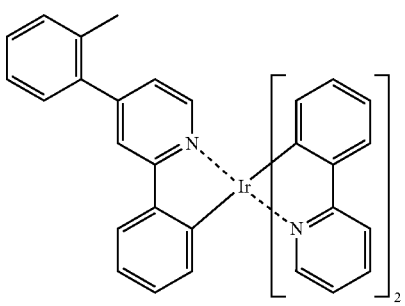
PD25
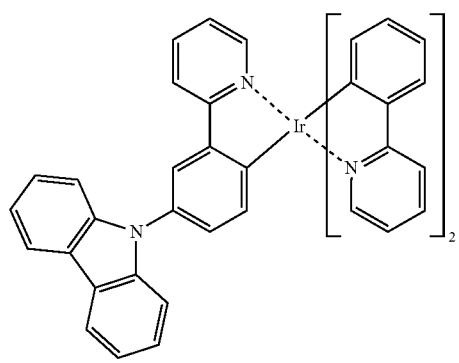
According to one or more exemplary embodiments of the present invention, the fluorescent dopant may include an arylamine compound or a styrylamine compound.
The fluorescent dopant may include a compound represented by Formula 501:

<Formula 501>

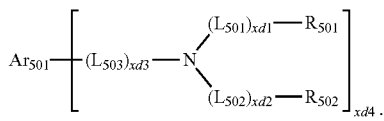

In Formula 501, $Ar_{501}$ may be selected from a substituted or unsubstituted $C_5$-$C_{60}$ carbocyclic group and a substituted or unsubstituted $C_1$-$C_{60}$ heterocyclic group.

In Formula 501, $L_{501}$ to $L_{503}$ may each independently be selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group.

In Formula 501, xd1 to xd3 may each independently be an integer selected from 0 to 3.

In Formula 501, $R_{501}$ and $R_{502}$ may each independently be selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group.

In Formula 501, xd4 may be an integer selected from 1 to 6.

According to one or more exemplary embodiments of the present invention, $Ar_{501}$ in Formula 501 may be selected from:

a naphthalene group, a heptalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, and an indenophenanthrene group; and a naphthalene group, a heptalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, and an indenophenanthrene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, and a naphthyl group.

According to one or more exemplary embodiments of the present invention, $L_{501}$ to $L_{503}$ in Formula 501 may each independently be selected from:

a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, and a pyridinylene group; and a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, and a pyridinylene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group.

According to one or more exemplary embodiments of the present invention, $R_{501}$ and $R_{501}$ in Formula 502 may each independently be selected from:

a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group; and a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, and —Si($Q_{31}$)($Q_{32}$)($Q_{33}$).

$Q_{31}$ to $Q_{33}$ may each be selected from a $C_1$-$C_{10}$ alkyl group, a $C_1$-$C_{10}$ alkoxy group, a phenyl group, a biphenyl group, a terphenyl group, and a naphthyl group.

According to one or more exemplary embodiments of the present invention, xd4 in Formula 501 may be 2; however, exemplary embodiments of the present invention are not limited thereto.

As an example, the fluorescent dopant may be selected from Compounds FD1 to FD22:

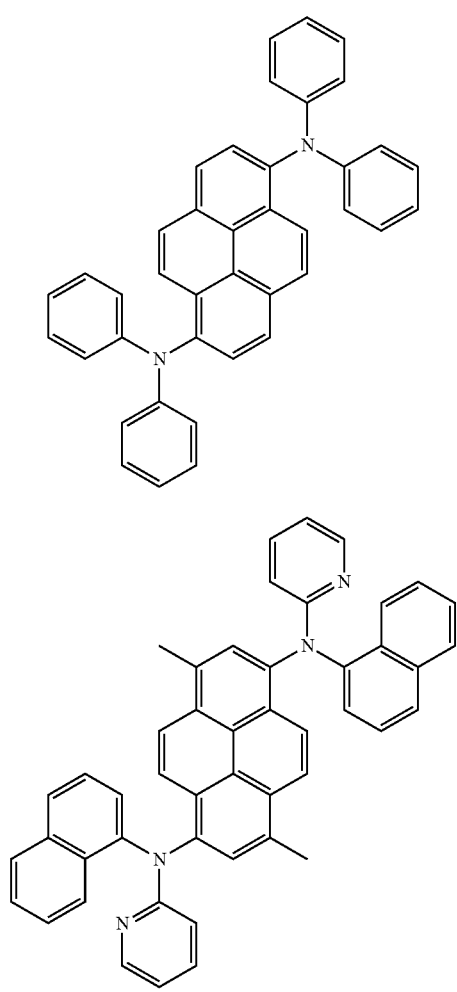

FD1

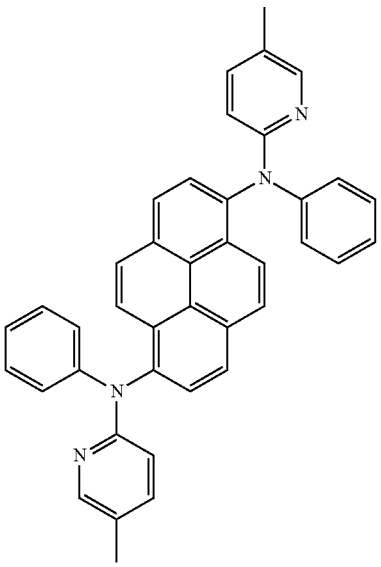

FD3

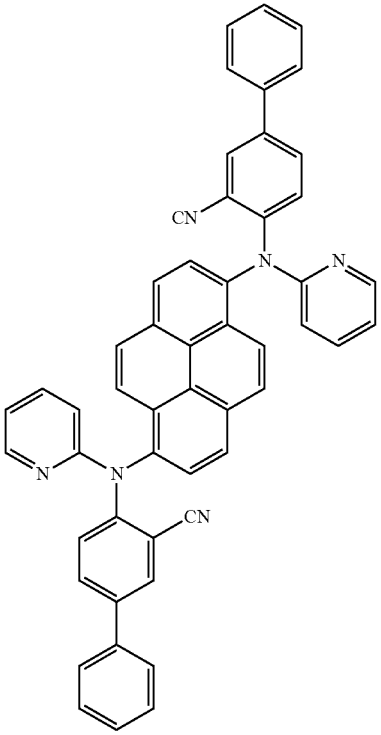

FD4

FD5
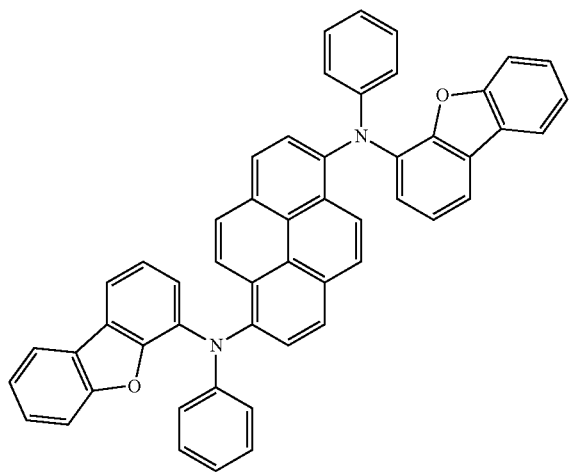
FD6
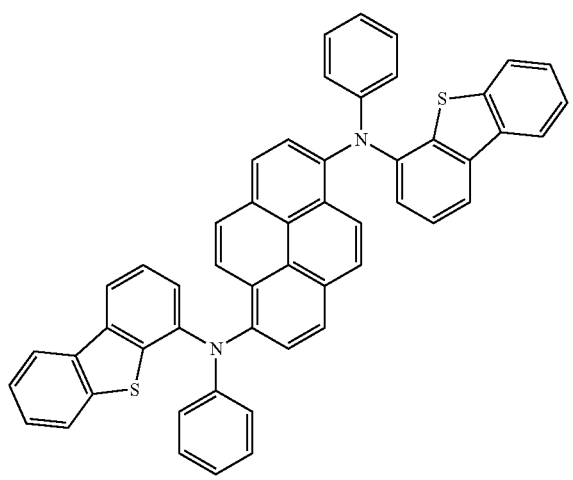
FD7
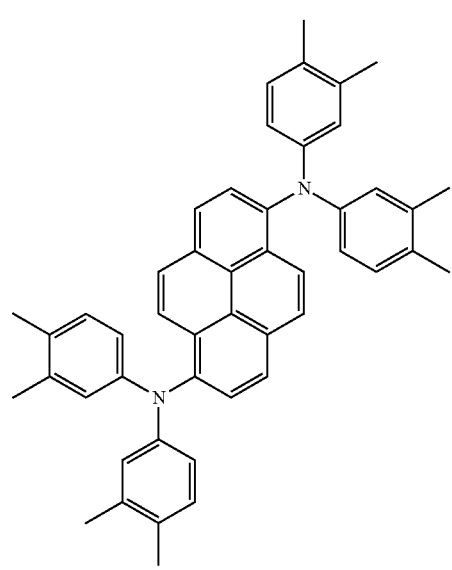
FD8
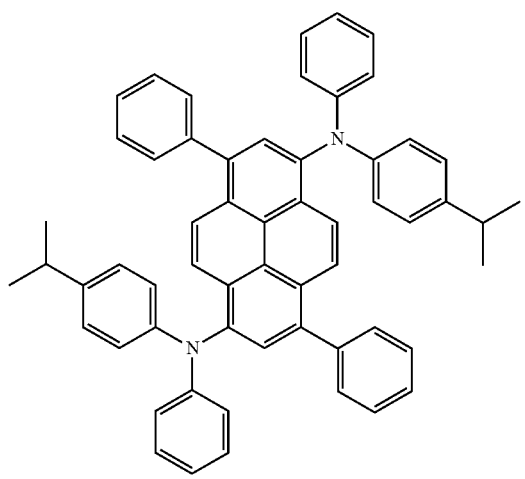
FD9
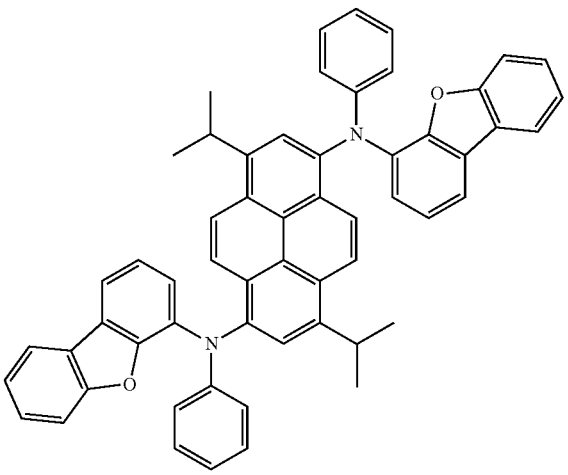
FD10
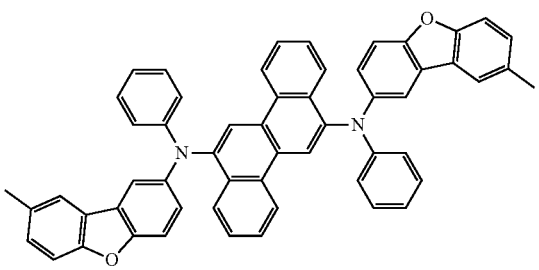
FD11
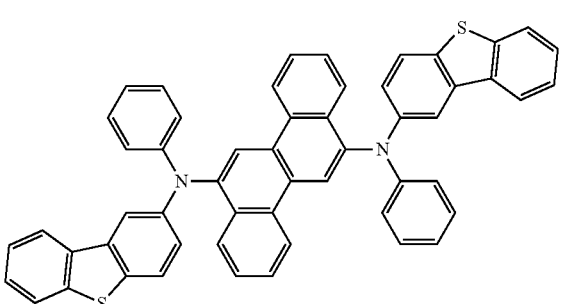

FD12
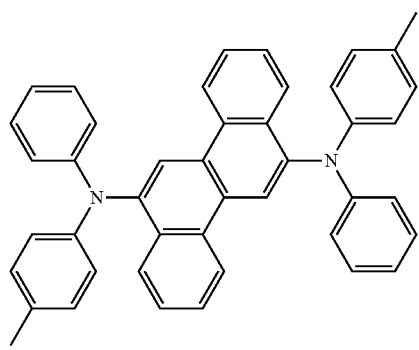
FD13
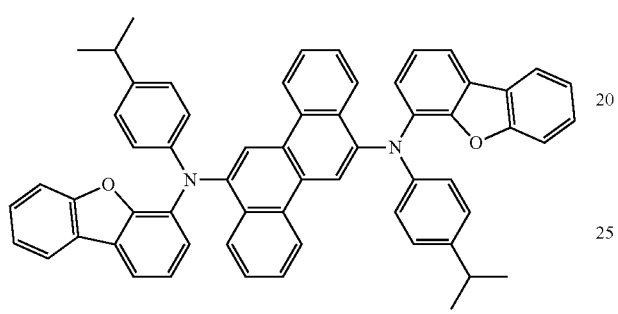
FD14
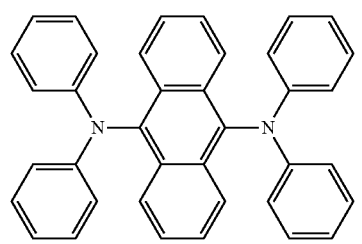
FD15
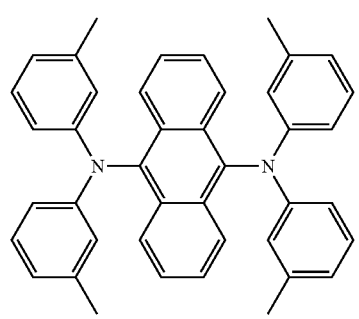
FD16
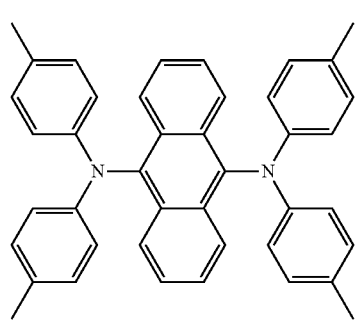
FD17
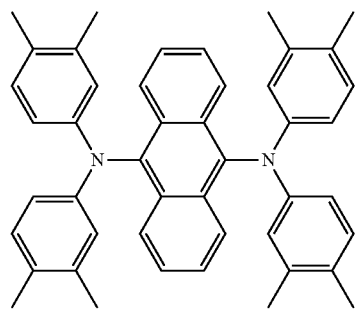
FD18
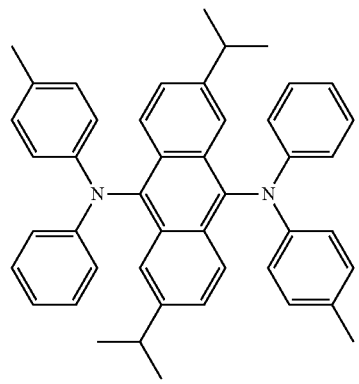
FD19
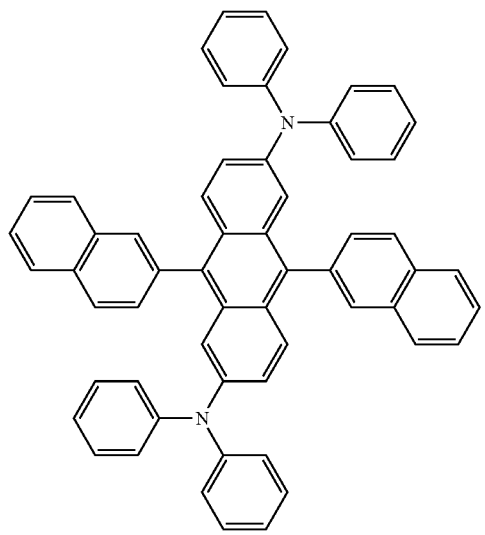

FD20
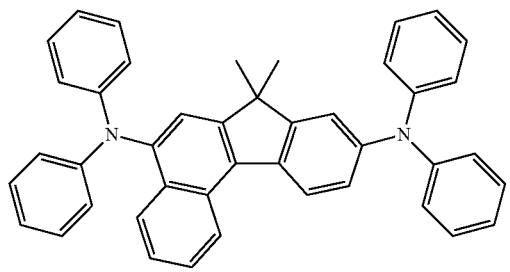
FD21
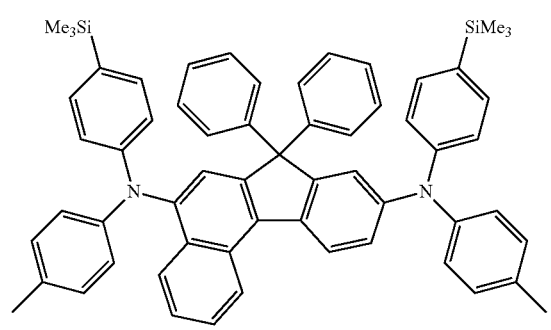
FD22
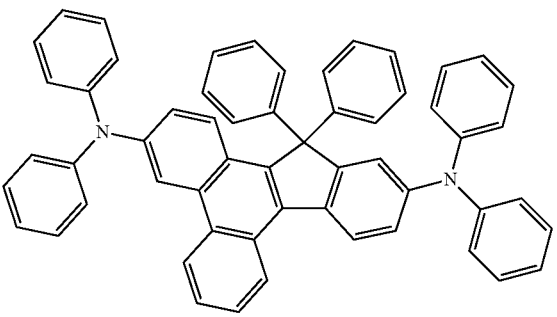
According to one or more exemplary embodiments of the present invention, the fluorescent dopant may be selected from the following compounds; however, exemplary embodiments of the present invention are not limited thereto.
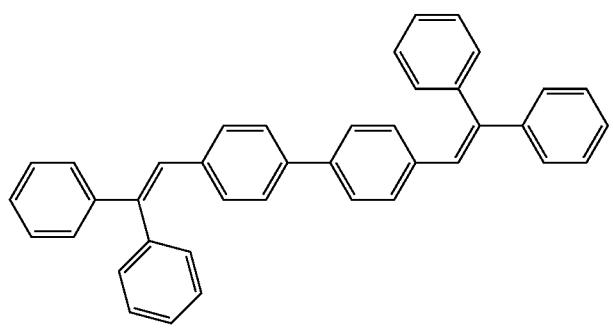
DPVBi
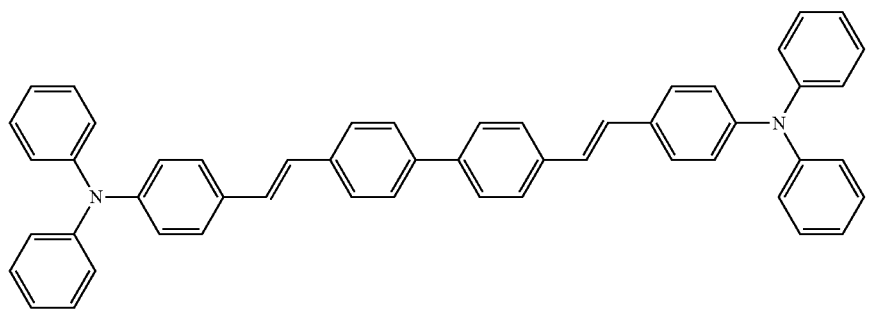
DPAVBi

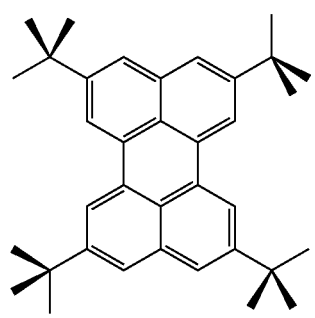
TBPe

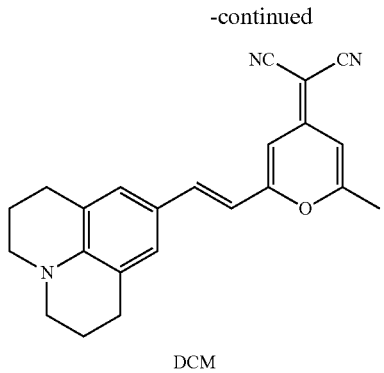
DCM

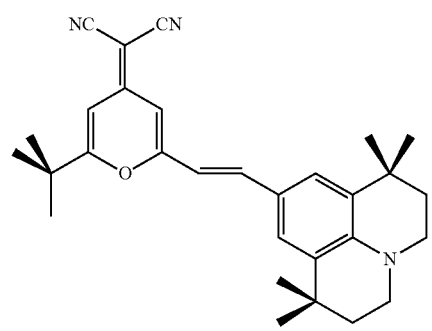
DCJTB

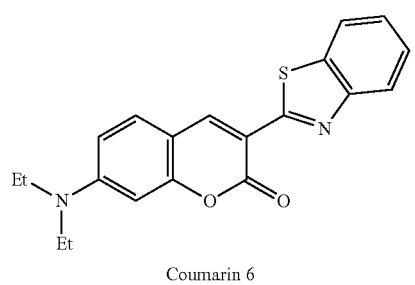
Coumarin 6

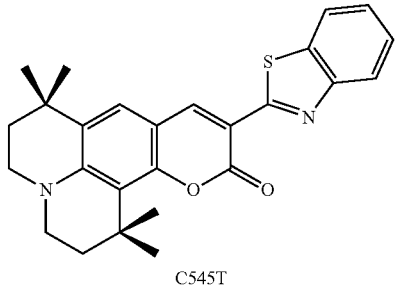
C545T

The electron transport region may have a single-layered structure including a single layer including a single material. The electron transport layer may have a single-layered structure including a single layer including a plurality of different materials. The electron transport layer may have a multi-layered structure having a plurality of layers each including a plurality of different materials.

The electron transport region may include the condensed cyclic compound represented by Formula 1-1 or 1-2.

The electron transport region may include at least one selected from a buffer layer, a hole blocking layer, an electron control layer, an electron transport layer, and an electron injection layer; however, exemplary embodiments of the present invention are not limited thereto.

For example, the electron transport region may have an electron transport layer/electron injection layer structure, a hole blocking layer/electron transport layer/electron injection layer structure, an electron control layer/electron transport layer/electron injection layer structure, or a buffer layer/electron transport layer/electron injection layer structure. For each structure, the layers may be sequentially stacked on an emission layer. However, exemplary embodiments of the structure of the electron transport region are not limited thereto.

The electron transport region, for example, a buffer layer, a hole blocking layer, an electron control layer, or an electron transport layer in the electron transport region, may include a metal-free compound including at least one π electron-depleted nitrogen-containing ring.

The π electron-depleted nitrogen-containing ring may indicate a $C_1$-$C_{60}$ heterocyclic group having at least one *—N=*' moiety as a ring-forming moiety.

For example, the π electron-depleted nitrogen-containing ring may be a 5-membered to 7-membered hetero monocyclic group having at least one *—N=*' moiety. The π electron-depleted nitrogen-containing ring may be a heteropoly cyclic group in which two or more 5-membered to 7-membered hetero monocyclic groups each having at least one *—N=*' moiety are condensed with each other. The π electron-depleted nitrogen-containing ring may be a heteropoly cyclic group in which at least one of 5-membered to 7-membered hetero monocyclic groups, each having at least one *—N=*' moiety, is condensed with at least one $C_5$-$C_{60}$ carbocyclic group.

Examples of the π electron-depleted nitrogen-containing ring include an imidazole, a pyrazole, a thiazole, an isothiazole, an oxazole, an isoxazole, a pyridine, a pyrazine, a pyrimidine, a pyridazine, an indazole, a purine, a quinoline, an isoquinoline, a benzoquinoline, a phthalazine, a naphthyridine, a quinoxaline, a quinazoline, a cinnoline, a phenanthridine, an acridine, a phenanthroline, a phenazine, a benzimidazole, an isobenzothiazole, a benzoxazole, an isobenzoxazole, a triazole, a tetrazole, an oxadiazole, a triazine, thiadiazol, an imidazopyridine, an imidazopyrimidine, or an azacarbazole; however, exemplary embodiments of the present invention are not limited thereto.

For example, the electron transport region may include a compound represented by Formula 601:

$$[Ar_{601}]_{xe11}\text{-}[(L_{601})_{xe1}\text{-}R_{601}]_{xe21}. \quad <\text{Formula 601}>$$

In Formula 601, $Ar_{601}$ may be selected from a substituted or unsubstituted $C_5$-$C_{60}$ carbocyclic group and a substituted or unsubstituted $C_1$-$C_{60}$ heterocyclic group.

In Formula 601, xe11 may be an integer selected from 1, 2, and 3.

In Formula 601, $L_{601}$ may be selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group.

In Formula 601, xe1 may be an integer selected from 0 to 5.

In Formula 601, $R_{601}$ may be selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_{601}$)($Q_{602}$)($Q_{603}$), —C(=O)($Q_{601}$), —S(=O)$_2$($Q_{601}$), and —P(=O)($Q_{601}$)($Q_{602}$).

$Q_{601}$ to $Q_{603}$ may each independently be a $C_1$-$C_{10}$ alkyl group, a $C_1$-$C_{10}$ alkoxy group, a phenyl group, a biphenyl group, a terphenyl group, or a naphthyl group.

In Formula 601, xe21 may be an integer selected from 1 to 5.

According to one or more exemplary embodiments of the present invention, at least one of $Ar_{601}$(s) in the number of xe11 and/or at least one of $R_{601}$(s) in the number of xe21 may include the π electron-depleted nitrogen-containing ring.

According to one or more exemplary embodiments of the present invention, ring $Ar_{601}$ in Formula 601 may be selected from:

a benzene group, a naphthalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, naphthacene group, a picene group, a perylene group, a pentaphene group, an indenoanthracene group, a dibenzofuran group, a dibenzothiophene group, a carbazole group, an imidazole group, a pyrazole group, a thiazole group, an isothiazole group, an oxazole group, an isoxazole group, a pyridine group, a pyrazine group, a pyrimidine group, a pyridazine group, an indazole group, a purine group, a quinoline group, an isoquinoline group, a benzoquinoline group, a phthalazine group, naphthyridine group, a quinoxaline group, a quinazoline group, a cinnoline group, a phenanthridine group, an acridine group, a phenanthroline group, a phenazine group, a benzimidazole group, an iso-benzothiazole group, a benzoxazole group, an isobenzoxazole group, a triazole group, a tetrazole group, an oxadiazole group, a triazine group, thiadiazol group, an imidazopyridine group, an imidazopyrimidine group, and an azacarbazole group; and a benzene group, a naphthalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, naphthacene group, a picene group, a perylene group, a pentaphene group, an indenoanthracene group, a dibenzofuran group, a dibenzothiophene group, a carbazole group, an imidazole group, a pyrazole group, a thiazole group, an isothiazole group, an oxazole group, an isoxazole group, a pyridine group, a pyrazine group, a pyrimidine group, a pyridazine group, an indazole group, a purine group, a quinoline group, an isoquinoline group, a benzoquinoline group, a phthalazine group, naphthyridine group, a quinoxaline group, a quinazoline group, a cinnoline group, a phenanthridine group, an acridine group, a phenanthroline group, a phenazine group, a benzimidazole group, an iso-benzoxazole group, a benzoxazole group, an isobenzoxazole group, a triazole group, a tetrazole group, an oxadiazole group, a triazine group, thiadiazol group, an imidazopyridine group, an imidazopyrimidine group, and an azacarbazole group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, —Si($Q_{31}$)($Q_{32}$)($Q_{33}$), —S(=O)$_2$($Q_{31}$), and —P(=O)($Q_{31}$)($Q_{32}$).

$Q_{31}$ to $Q_{33}$ may each independently be selected from a $C_1$-$C_{10}$ alkyl group, a $C_1$-$C_{10}$ alkoxy group, a phenyl group, a biphenyl group, a terphenyl group, and a naphthyl group.

When xe11 in Formula 601 is 2 or greater, at least two $Ar_{601}$(s) may be linked to each other via a single bond.

According to one or more exemplary embodiments of the present invention, $Ar_{601}$ in Formula 601 may be an anthracene group.

According to one or more exemplary embodiments of the present invention, a compound represented by Formula 601 may be represented by Formula 601-1:

<Formula 601-1>

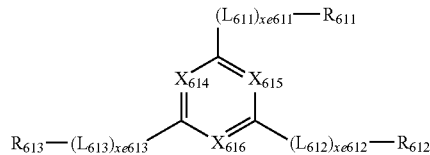

In Formula 601-1, $X_{614}$ may be nitrogen (N) or C($R_{614}$), $X_{615}$ may be nitrogen (N) or C($R_{615}$), $X_{616}$ may be nitrogen (N) or C($R_{616}$), and at least one of $X_{614}$ to $X_{616}$ may be nitrogen (N).

In Formula 601-1, $L_{611}$ to $L_{613}$ may each independently be the same as $L_{601}$.

In Formula 601-1, xe611 to xe613 may each independently be the same as xe1.

In Formula 601-1, $R_{611}$ to $R_{613}$ may be each independently be the same as $R_{601}$.

In Formula 601-1, $R_{614}$ to $R_{616}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, and a naphthyl group.

According to one or more exemplary embodiments of the present invention, $L_{601}$ and $L_{611}$ to $L_{613}$ in Formulae 601 and 601-1 may each independently be selected from:

a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, a pyridinylene group, an imidazolylene group, a pyrazolylene group, a thiazolylene group, an isothiazolylene group, an oxazolylene group, an isoxazolylene group, a thiadiazolylene group, an oxadiazolylene group, a pyrazinylene group, a pyrimidinylene group, a pyridazinylene group, a triazinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a phenanthridinylene group, an acridinylene group, a phenanthrolinylene group, a phenazinylene group, a benzimidazolylene group, an isobenzothiazolylene group, a benzoxazolylene group, an isobenzoxazolylene group, a triazolylene group, a tetrazolylene group, an imidazopyridinylene group, an imidazopyrimidinylene group, and an azacarbazolylene group; and a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, a pyridinylene group, an imidazolylene group, a pyrazolylene group, a thiazolylene group, an isothiazolylene group, an oxazolylene group, an isoxazolylene group, a thiadiazolylene group, an oxadiazolylene group, a pyrazinylene group, a pyrimidinylene group, a pyridazinylene group, a triazinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a phenanthridinylene group, an acridinylene group, a phenanthrolinylene group, a phenazinylene group, a benzimidazolylene group, an isobenzothiazolylene group, a benzoxazolylene group, an isobenzoxazolylene group, a triazolylene group, a tetrazolylene group, an imidazopyridinylene group, an imidazopyrimidinylene group, and an azacarbazolylene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group; however, exemplary embodiments of the present invention are not limited thereto.

According to one or more exemplary embodiments of the present invention, xe1 and xe611 to xe613 in Formulae 601 and 601-1 may each independently be an integer selected from 0, 1, and 2.

According to one or more exemplary embodiments of the present invention, $R_{601}$ and $R_{611}$ to $R_{613}$ in Formula 601 and 601-1 may each independently be selected from:

a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group;

a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group; and —S(=O)$_2$(Q$_{601}$), and —P(=O)(Q$_{601}$)(Q$_{602}$).

Q$_{601}$ and Q$_{602}$ may be the same as described above.

The electron transport region may include at least one compound selected from Compounds ET1 to ET36; however, exemplary embodiments of the present invention are not limited thereto:

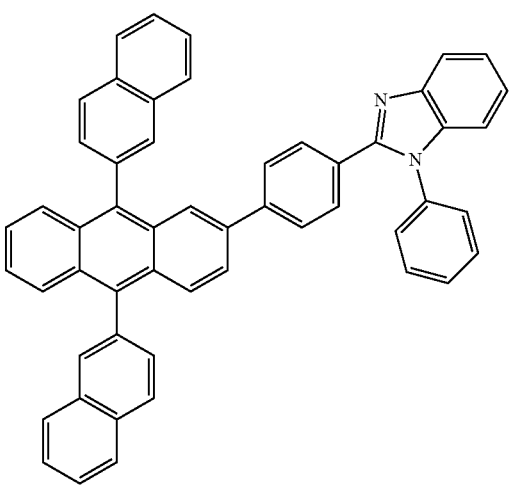

ET1

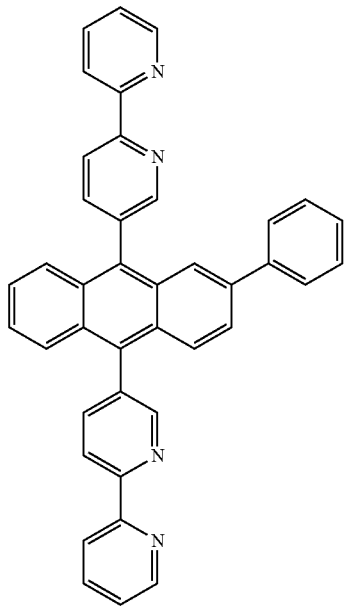

ET2

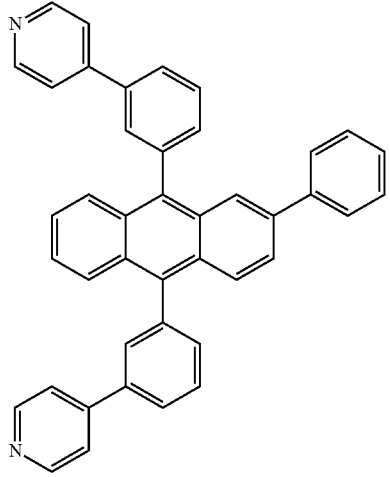

ET3

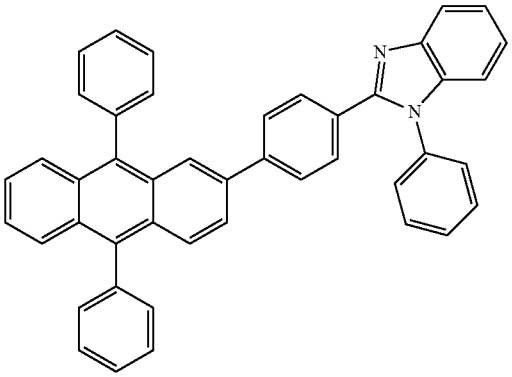

ET4

ET5
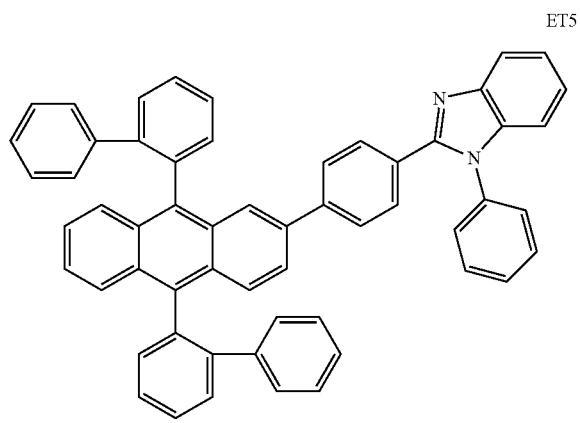
ET6
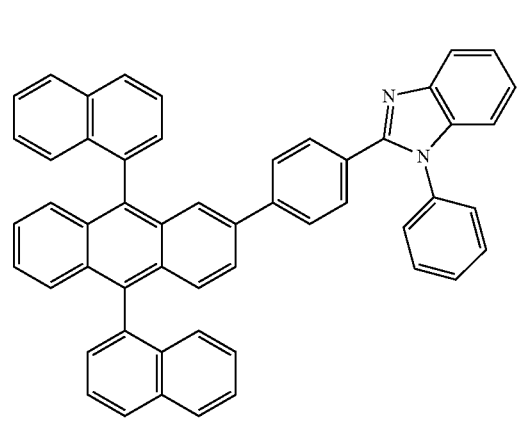
ET7
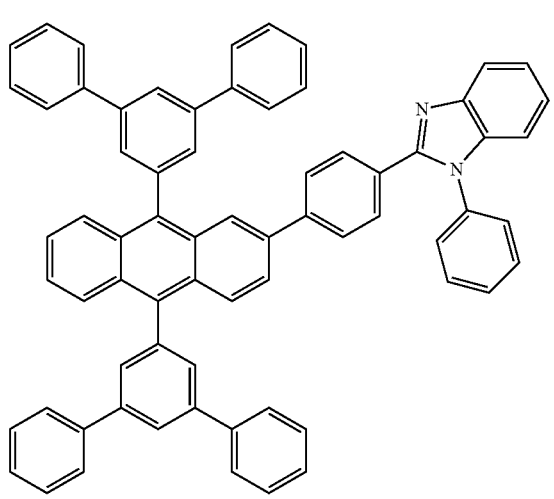
ET8
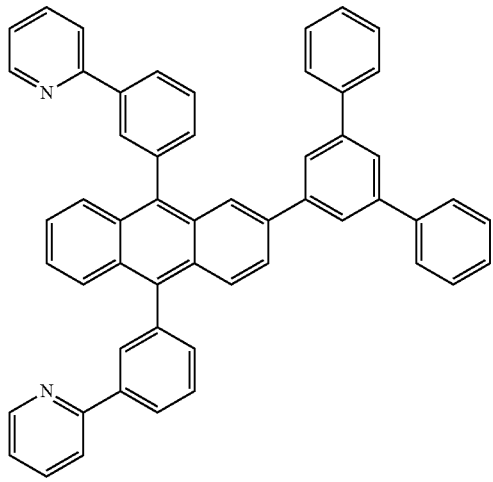
ET9
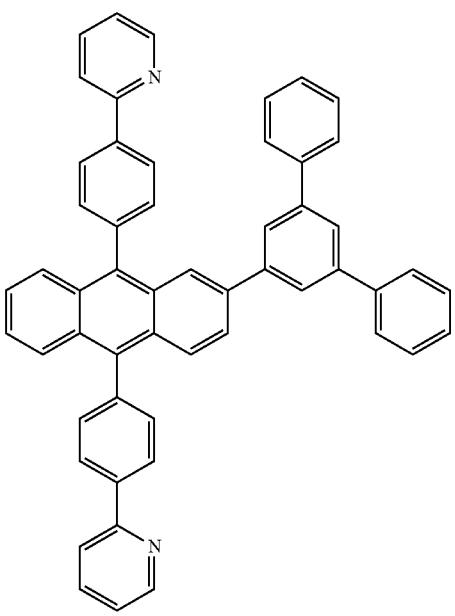

-continued
ET10
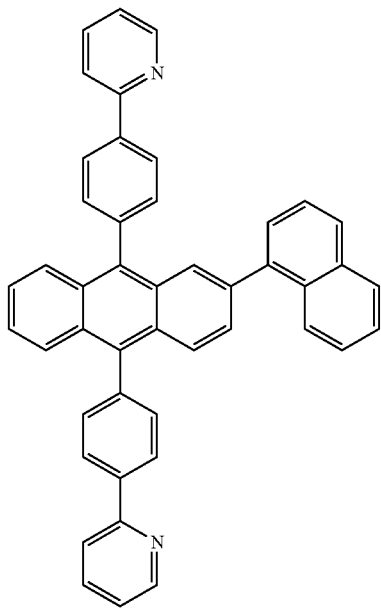
ET11
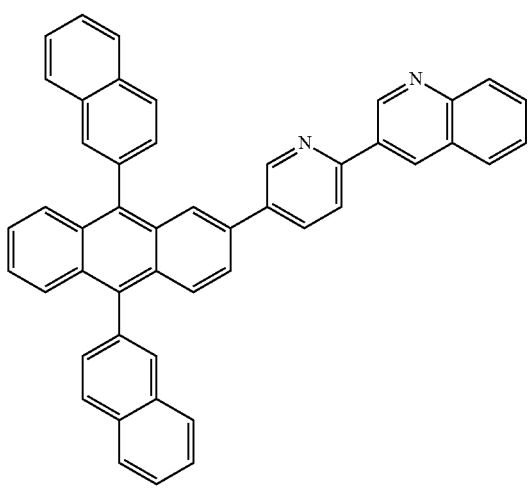
ET12
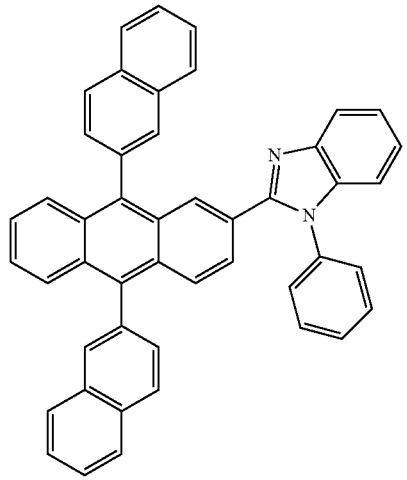
-continued
ET13
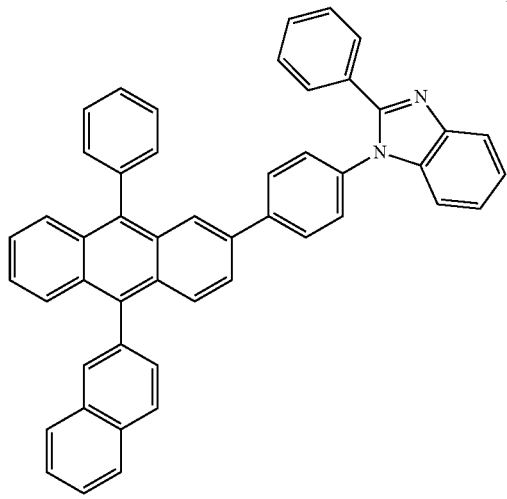
ET14
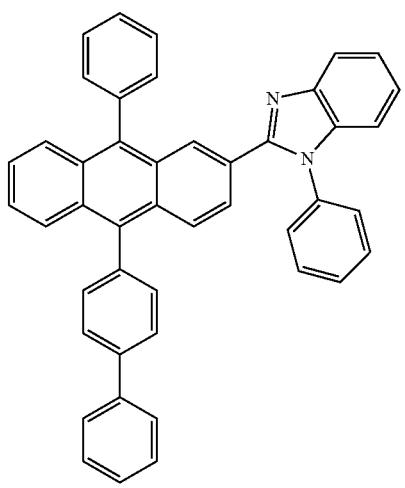
ET15
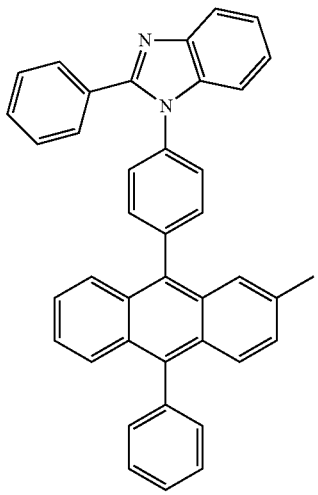

ET16
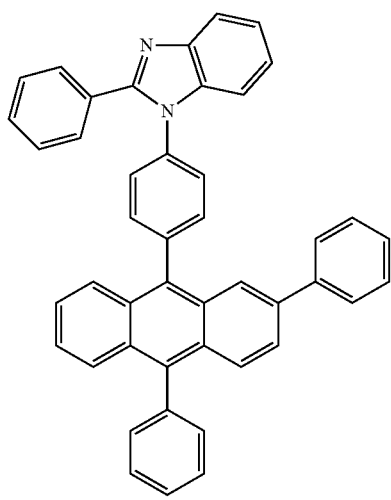
ET17
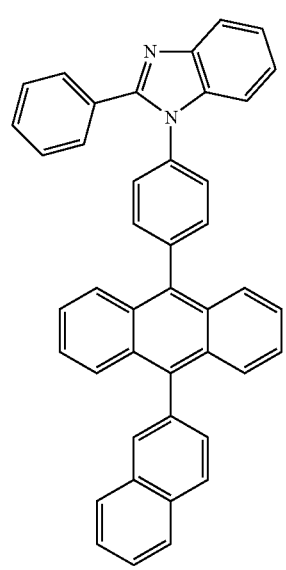
ET18
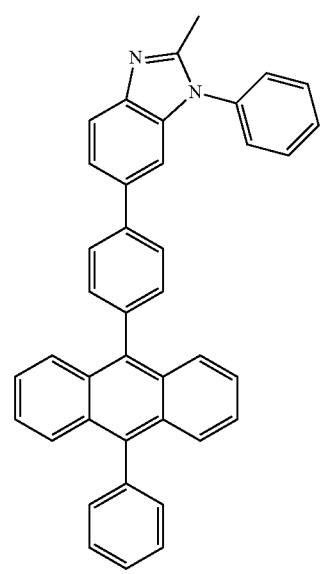
ET19
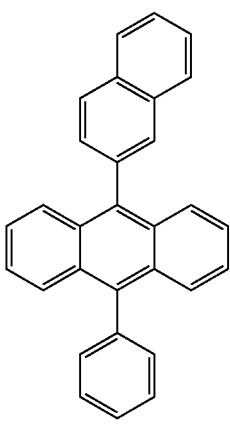
ET20
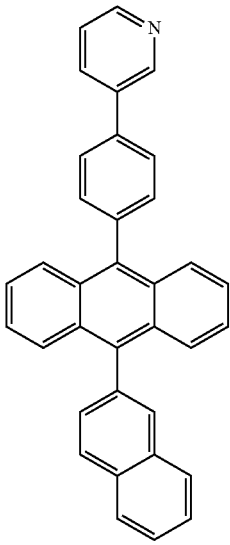
ET21
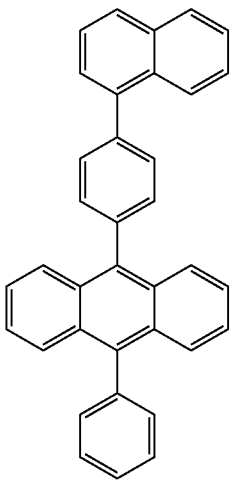

ET22
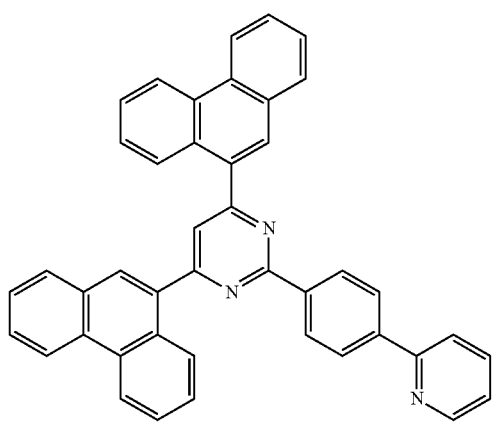
ET25
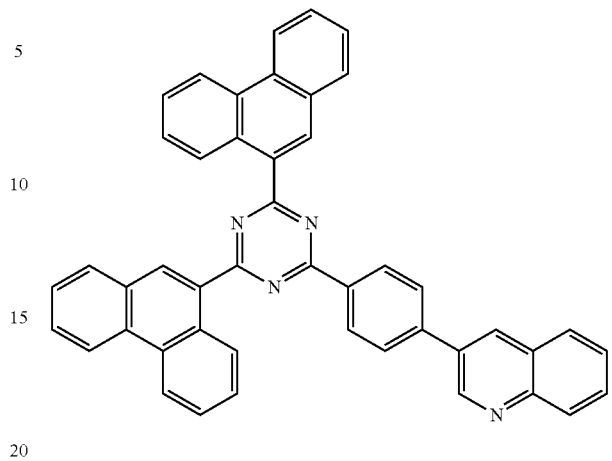
ET23
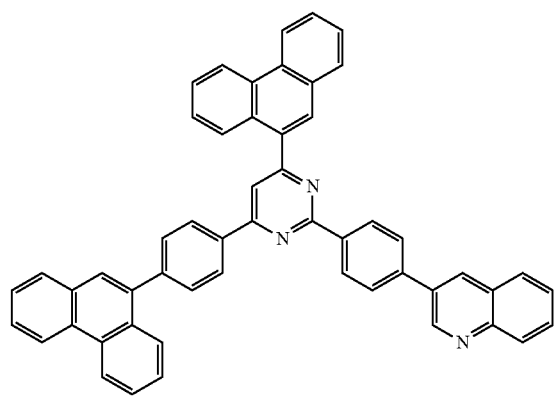
ET26
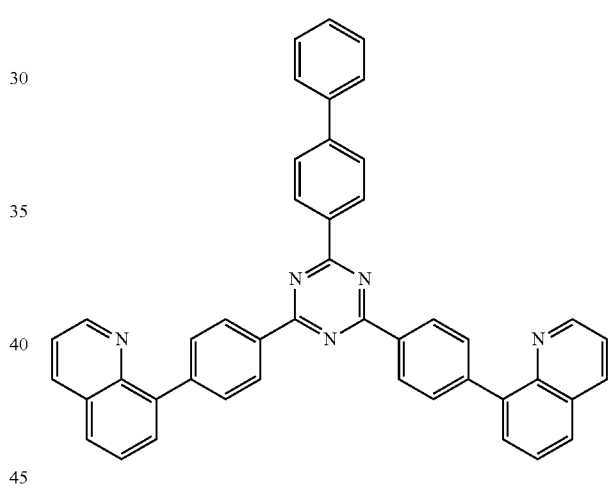
ET24
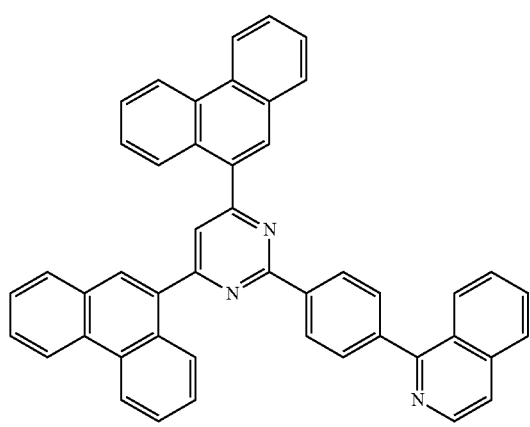
ET27
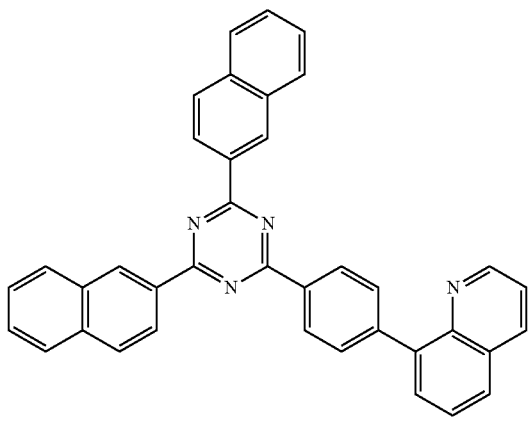

ET28
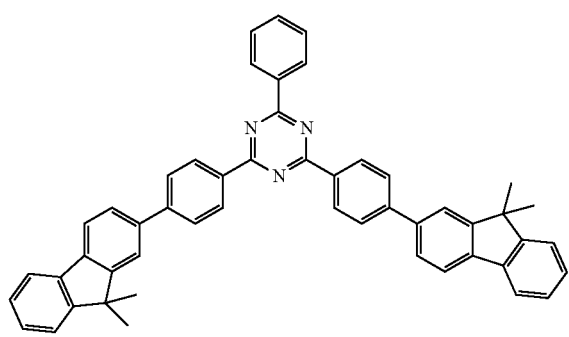
ET29
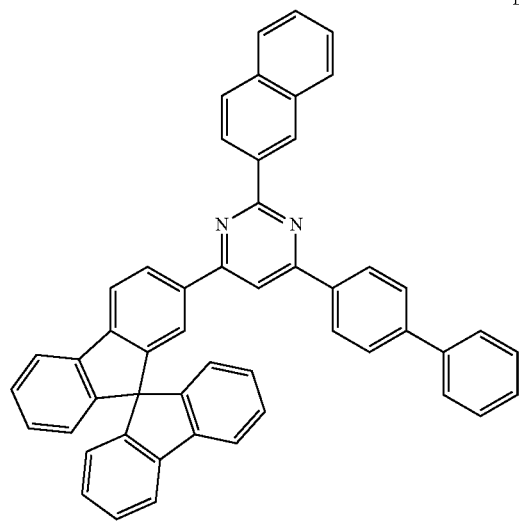
ET30
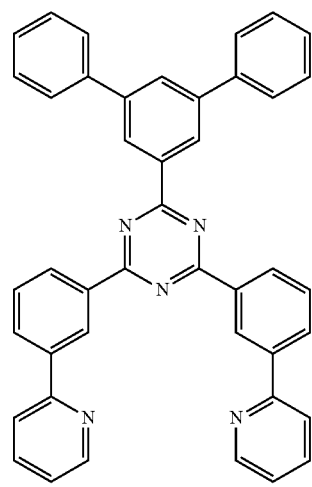
ET31
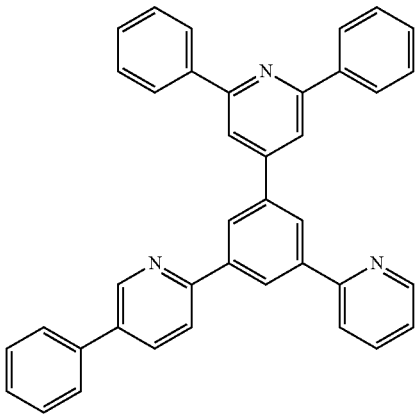
ET32
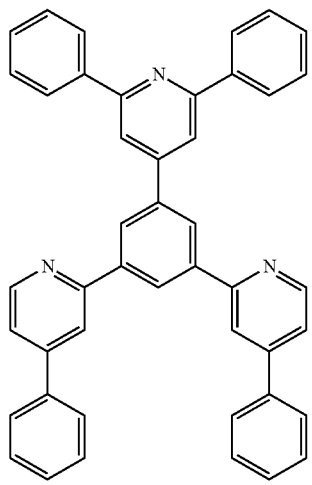
ET33
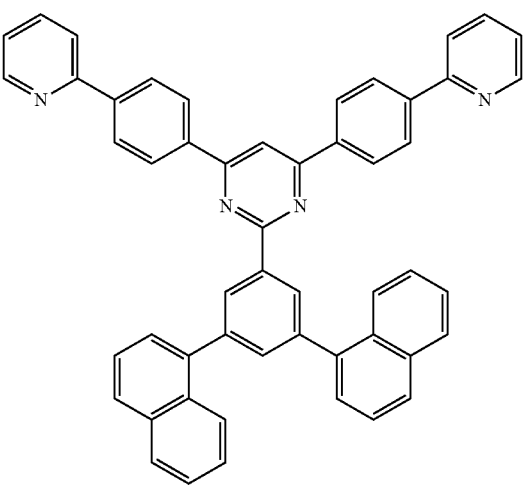

ET34

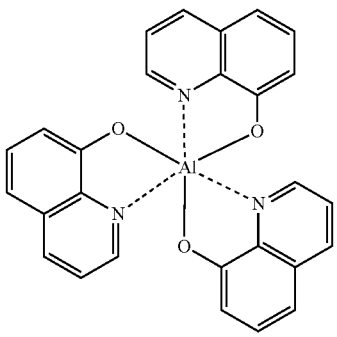

Alq₃

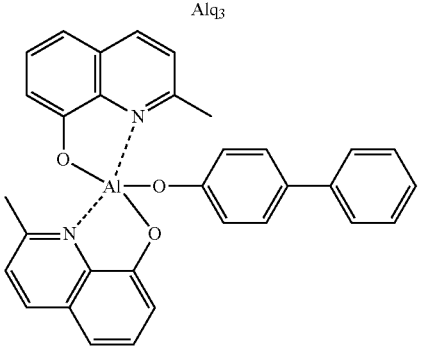

BAlq

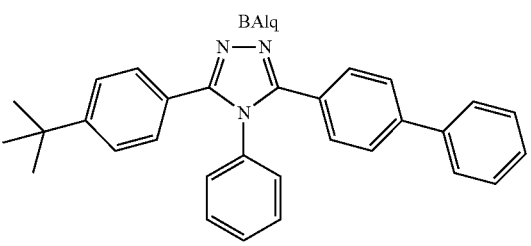

TAZ

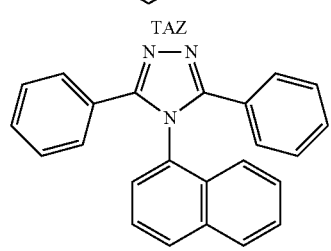

NTAZ

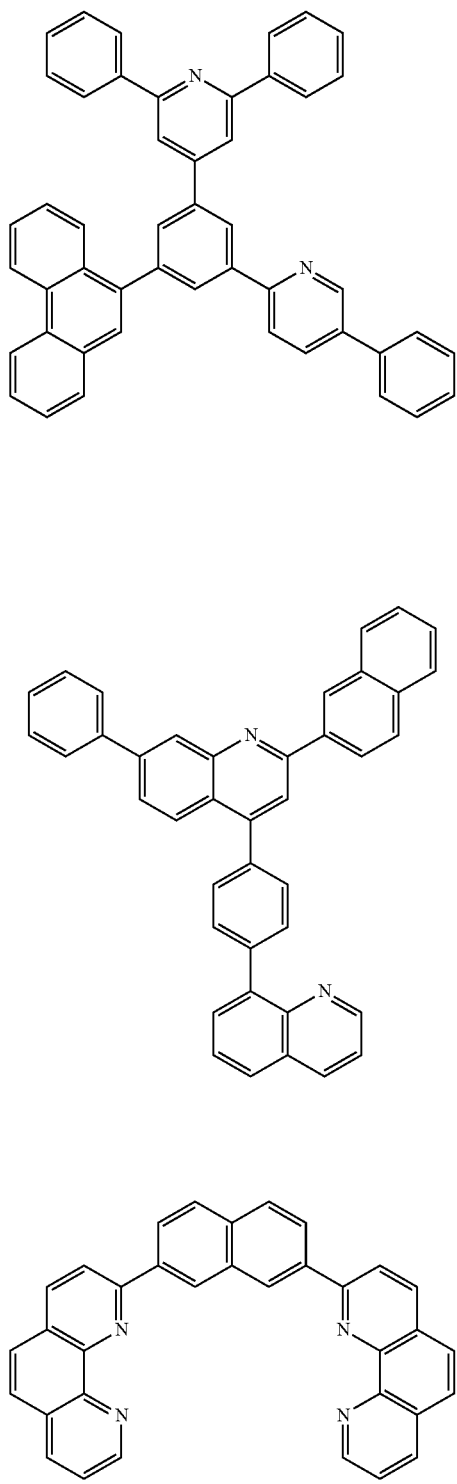

ET35

ET36

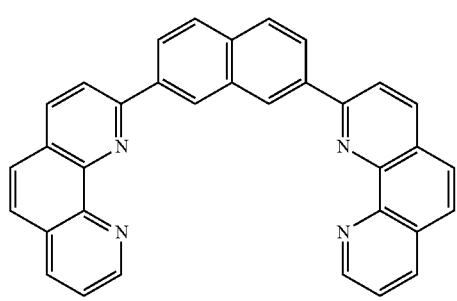

According to one or more exemplary embodiments of the present invention, the electron transport region may include at least one compound selected from 2,9-dimethyl-4,7-diphenyl-1,10-phenanthroline (BCP), 4,7-diphenyl-1,10-phenanthroline (Bphen), Alq3, BAlq, 3-(biphenyl-4-yl)-5-(4-tert-butylphenyl)-4-phenyl-4H-1,2,4-triazole (TAZ), and NTAZ.

A thickness of the buffer layer, the hole blocking layer, or the electron controlling layer may each independently be in a range of from about 20 Å to about 1,000 Å, for example, from about 30 Å to about 300 Å. When the thicknesses of the buffer layer, the hole blocking layer, and the electron control layer are within these ranges, the electron blocking layer may have relatively high electron blocking characteristics and/or electron control characteristics without a substantial increase in driving voltage.

A thickness of the electron transport layer may be in a range of from about 100 Å to about 1,000 Å, for example, from about 150 Å to about 500 Å. When the thickness of the electron transport layer is within the range described above, the electron transport layer may have satisfactory electron transport characteristics without a substantial increase in driving voltage.

The electron transport region, for example, the electron transport layer in the electron transport region, may include a material including metal.

The material including metal may include at least one of an alkali metal complex or an alkaline earth-metal complex. The alkali metal complex may include a metal ion selected from a lithium (Li) ion, a sodium (Na) ion, a potassium (K) ion, a rubidium (Rb) ion, and a caesium (Cs) ion. The alkaline earth-metal complex may include a metal ion selected from a beryllium (Be) ion, a magnesium (Mg) ion, a calcium (Ca) ion, a strontium (Sr) ion, and a barium (Ba) ion. A ligand coordinated with the metal ion of the alkali metal complex or the alkaline earth-metal complex may be selected from a hydroxy quinoline, a hydroxy isoquinoline, a hydroxy benzoquinoline, a hydroxy acridine, a hydroxy phenanthridine, a hydroxy phenylan oxazole, a hydroxy phenylthiazole, a hydroxy diphenylan oxadiazole, a hydroxy diphenylthiadiazol, a hydroxy phenylpyridine, a hydroxy phenylbenzimidazole, a hydroxy phenylbenzothiazole, a bipyridine, a phenanthroline, and a cyclopentadiene; however, exemplary embodiments of the present invention are not limited thereto.

For example, the material including metal may include a lithium (Li) complex. The lithium (Li) complex may include, for example, Compound ET-D1 (lithium quinolate, LiQ) or ET-D2.

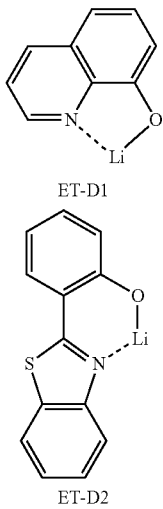

ET-D1

ET-D2

The electron transport region may include an electron injection layer. The electron injection layer may be configured to facilitate injection of electrons from the second electrode 190. The electron injection layer may be in direct contact with the second electrode 190.

The electron injection layer may have a single-layered structure including a single layer including a single material. The electron injection layer may have a single-layered structure including a single layer including a plurality of different materials. The electron injection layer may have a multi-layered structure having a plurality of layers including a plurality of different materials.

The electron injection layer may include alkali metal, alkaline earth metal, rare-earth metal, an alkali metal compound, an alkaline earth-metal compound, a rare-earth metal compound, an alkali metal complex, an alkaline earth-metal complex, a rare-earth metal complex, or any combination thereof.

The alkali metal may be selected from Li, Na, K, Rb, and Cs. According to one or more exemplary embodiments of the present invention, the alkali metal may be Li, Na, or Cs. According to one or more exemplary embodiments of the present invention, the alkali metal may be Li or Cs; however, exemplary embodiments of the present invention are not limited thereto.

The alkaline earth metal may be selected from Mg, Ca, Sr, and Ba.

The rare-earth metal may be selected from Sc, Y, Ce, Tb, Yb, Gd, and Tb.

The alkali metal compound, the alkaline earth-metal compound, and the rare-earth metal compound may be selected from oxides and halides (for example, fluorides, chlorides, bromides, or iodides) of the alkali metal, the alkaline earth-metal, and the rare-earth metal.

The alkali metal compound may be selected from alkali metal oxides, such as $Li_2O$, $Cs_2O$, or $K_2O$, or alkali metal halides, such as LiF, NaF, CsF, KF, LiI, NaI, CsI, and KI. According to one or more exemplary embodiments of the present invention, the alkali metal compound may be selected from LiF, $Li_2O$, NaF, LiI, NaI, CsI, and KI; however, exemplary embodiments of the present invention are not limited thereto.

The alkaline earth-metal compound may be selected from alkaline earth-metal compounds, such as BaO, SrO, CaO, $Ba_xSr_{1-x}O(0<x<1)$, and $Ba_xCa_{1-x}O(0<x<1)$. According to one or more exemplary embodiments of the present invention, the alkaline earth-metal compound may be selected from BaO, SrO, and CaO; however, exemplary embodiments of the present invention are not limited thereto.

The rare-earth metal compound may be selected from $YbF_3$, $ScF_3$, $ScO_3$, $Y_2O_3$, $Ce_2O_3$, $GdF_3$, and $TbF_3$. According to one or more exemplary embodiments of the present invention, the rare-earth metal compound may be selected from $YbF_3$, $ScF_3$, $TbF_3$, $YbI_3$, $ScI_3$, and $TbI_3$; however, exemplary embodiments of the present invention are not limited thereto.

The alkali metal complex, the alkaline earth-metal complex, and the rare-earth metal complex may include an ion of an alkali metal, an alkaline earth-metal, or a rare-earth metal as described above. A ligand coordinated with a metal ion of the alkali metal complex, the alkaline earth-metal complex, or the rare-earth metal complex may each independently be selected from hydroxy quinoline, hydroxy isoquinoline, hydroxy benzoquinoline, hydroxy acridine, hydroxy phenanthridine, hydroxy phenylan oxazole, hydroxy phenylthiazole, hydroxy diphenylan oxadiazole, hydroxy diphenylthiadiazol, hydroxy phenylpyridine, hydroxy phenylbenzimidazole, hydroxy phenylbenzothiazole, bipyridine, phenanthroline, and cyclopentadiene; however, exemplary embodiments of the present invention are not limited thereto.

The electron injection layer may include an alkali metal, an alkaline earth metal, a rare-earth metal, an alkali metal compound, an alkaline earth-metal compound, a rare-earth metal compound, an alkali metal complex, an alkaline earth-metal complex, a rare-earth metal complex, or any combination thereof. According to one or more exemplary embodiments of the present invention, the electron injection layer may include an organic material. When the electron injection layer includes an organic material, an alkali metal, an alkaline earth metal, a rare-earth metal, an alkali metal compound, an alkaline earth-metal compound, a rare-earth metal compound, an alkali metal complex, an alkaline earth-metal complex, a rare-earth metal complex, or any combination thereof may be substantially homogeneously or non-homogeneously dispersed in a matrix including the organic material.

A thickness of the electron injection layer may be in a range of from about 1 Å to about 100 Å, for example, from about 3 Å to about 90 Å. When the thickness of the electron injection layer is within the range described above, the electron injection layer may have satisfactory electron injection characteristics without a substantial increase in driving voltage.

The second electrode 190 may be disposed on the organic layer 150. The organic layer 150 may have a structure as described above. The second electrode 190 may be a cathode. The cathode may be an electron injection electrode. Thus, the second electrode 190 may include a metal, an alloy, an electrically conductive compound, or any combination thereof, which may have a relatively low work function.

The second electrode 190 may include at least one of lithium (Li), silver (Si), magnesium (Mg), aluminum (Al), aluminum-lithium (Al—Li), calcium (Ca), magnesium-indium (Mg—In), magnesium-silver (Mg—Ag), indium tin oxide (ITO), or indium zinc oxide (IZO); however, exemplary embodiments of the present invention are not limited thereto. The second electrode 190 may be a transmissive electrode, a semi-transmissive electrode, or a reflective electrode.

The second electrode 190 may have a single-layered structure. Alternatively, the second electrode 190 may have a multi-layered structure including two or more layers.

Figure 2:
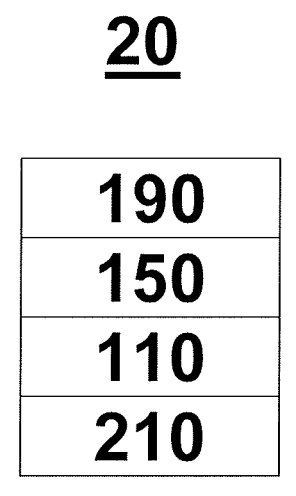

FIG. 2 is a schematic cross-sectional diagram illustrating an organic light-emitting device according to an exemplary embodiment of the present invention. Referring to FIG. 2, an organic light-emitting device 20 may include a first capping layer 210, the first electrode 110, the organic layer 150, and the second electrode 190. The first capping layer 210, the first electrode 110, the organic layer 150, and the second electrode 190 may be sequentially stacked.

Figure 3:
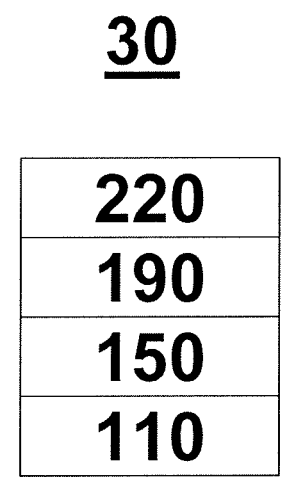

FIG. 3 is a schematic cross-sectional diagram illustrating an organic light-emitting device according to an exemplary embodiment of the present invention. Referring to FIG. 3, an organic light-emitting device 30 may include the first electrode 110, the organic layer 150, the second electrode 190, and a second capping layer 220. The first electrode 110, the organic layer 150, the second electrode 190, and the second capping layer 220 may be sequentially stacked.

Figure 4:
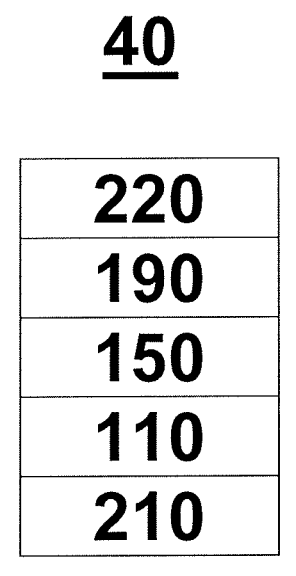

FIG. 4 is a schematic cross-sectional diagram illustrating an organic light-emitting device according to an exemplary embodiment of the present invention. Referring to FIG. 4, an organic light-emitting device 40 may include the first capping layer 210, the first electrode 110, the organic layer 150, the second electrode 190, and the second capping layer 220. The first capping layer 210, the first electrode 110, the organic layer 150, the second electrode 190, and the second capping layer 220 may be sequentially stacked.

In the organic layer 150 of each of the organic light-emitting devices 20 and 40, light generated in an emission layer may pass through the first electrode 110 and the first capping layer 210 toward the outside. The first electrode 110 may be a semi-transmissive or a transmissive electrode. In the organic layer 150 of each of the organic light-emitting devices 30 and 40, light generated in an emission layer may pass through the second electrode 190 and the second capping layer 220 toward the outside. The second electrode 190 may be a semi-transmissive or a transmissive electrode.

The first capping layer 210 and the second capping layer 220 may increase external luminescent efficiency according to the principle of constructive interference.

The first capping layer 210 and the second capping layer 220 may each independently be an organic capping layer including an organic material, an inorganic capping layer including an inorganic material, or a composite capping layer including an organic material and an inorganic material.

At least one of the first capping layer 210 and the second capping layer 220 may include at least one material selected from carbocyclic compounds, heterocyclic compounds, amine-based compounds, porphyrine derivatives, phthalocyanine derivatives, naphthalocyanine derivatives, alkali metal complexes, and alkaline earth-based complexes. The carbocyclic compound, the heterocyclic compound, and the amine-based compound may be substituted with a substituent including at least one element selected from O, N, S, Se, Si, F, Cl, Br, and I. According to one or more exemplary embodiments of the present invention, at least one of the first capping layer 210 and the second capping layer 220 may include an amine-based compound.

According to one or more exemplary embodiments of the present invention, at least one of the first capping layer 210 and the second capping layer 220 may include the condensed cyclic compound represented by Formula 1-1 or 1-2.

According to one or more exemplary embodiments of the present invention, at least one of the first capping layer 210 and the second capping layer 220 may include the compound represented by Formula 201 or the compound represented by Formula 202.

According to one or more exemplary embodiments of the present invention, at least one of the first capping layer 210 and the second capping layer 220 may include a compound selected from Compounds HT28 to HT33 and Compounds CP1 to CP5; however, exemplary embodiments of the present invention are not limited thereto.

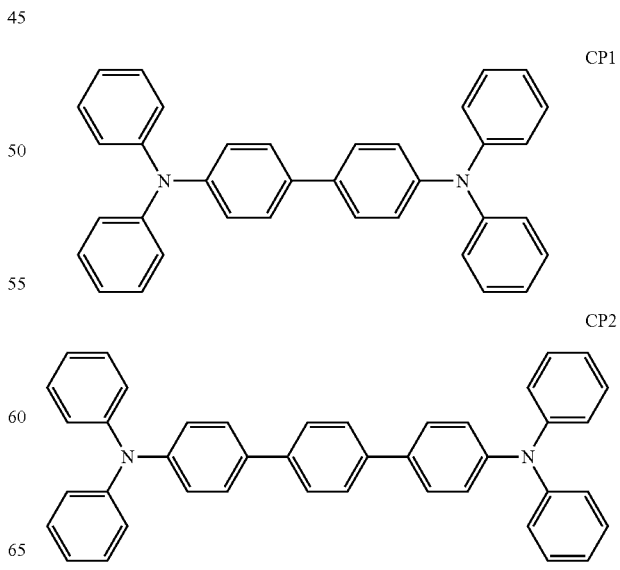

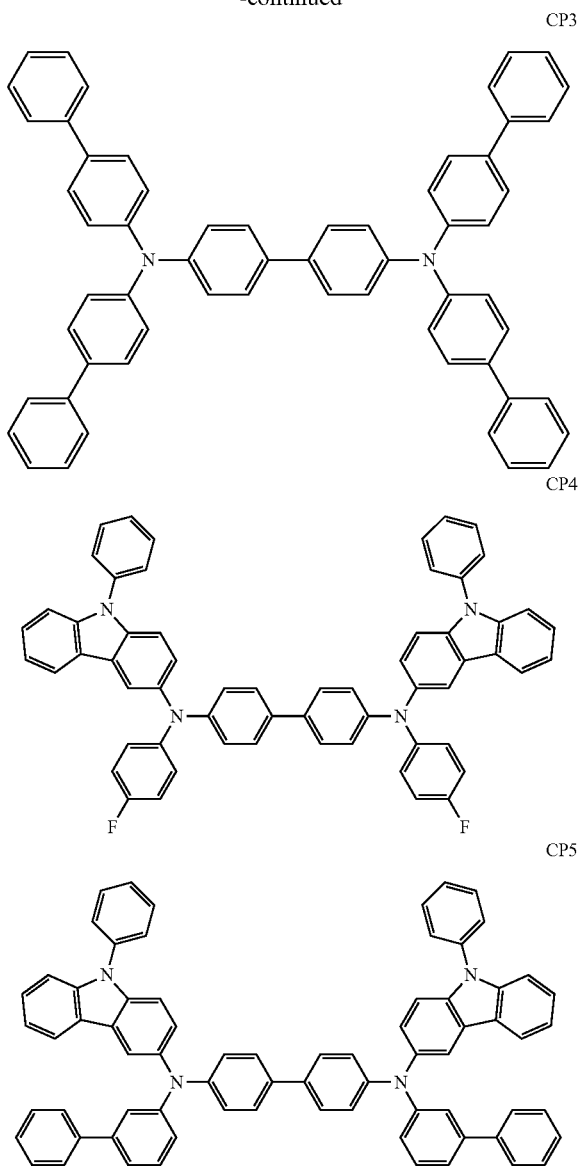

The organic light-emitting device according to some exemplary embodiments of the present invention has been described with reference to FIGS. 1-4. However, exemplary embodiments of the present invention are not limited thereto.

Layers included in the hole transport region, the emission layer, and the electron transport region may be formed by, for example, vacuum deposition, spin coating, casting, Langmuir-Blodgett (LB) deposition, ink-jet printing, laser-printing, or laser-induced thermal imaging (LITI).

When the respective layers of the hole transport region, the emission layer, and the electron transport region are formed by vacuum deposition, for example, the vacuum deposition may be performed at a deposition temperature of from about 100° C. to about 500° C., at a vacuum degree of from about $10^{-8}$ torr to about $10^{-3}$ torr, and at a deposition rate of from about 0.01 Å/sec to about 100 Å/sec by taking into account a compound for forming a layer to be deposited and the structure of a layer to be formed.

When layers included in the hole transport region, the emission layer, and the electron transport region are formed by spin coating, the spin coating may be performed at a coating speed of from about 2,000 rpm to about 5,000 rpm and at a heat treatment temperature of from about 80° C. to about 200° C., depending on a compound to be included in a layer and the structure of each layer to be formed.

The term "$C_1$-$C_{60}$ alkyl group" as used herein refers to a linear or branched saturated aliphatic hydrocarbon monovalent group having 1 to 60 carbon atoms, and non-limiting examples thereof may include a methyl group, an ethyl group, a propyl group, an isobutyl group, a sec-butyl group, a tert-butyl group, a pentyl group, an iso-amyl group, or a hexyl group. The term "$C_1$-$C_{60}$ alkylene group" as used herein refers to a divalent group having the same structure as the $C_1$-$C_{60}$ alkyl group.

The term "$C_2$-$C_{60}$ alkenyl group" as used herein refers to a hydrocarbon group formed by substituting at least one carbon-carbon double bond in the middle or at the terminus of the $C_2$-$C_{60}$ alkyl group, and non-limiting examples thereof may include an ethenyl group, a propenyl group, or a butenyl group. The term "$C_2$-$C_{60}$ alkenylene group" as used herein refers to a divalent group having the same structure as the $C_2$-$C_{60}$ alkenyl group.

The term "$C_2$-$C_{60}$ alkynyl group" as used herein refers to a hydrocarbon group formed by substituting at least one carbon-carbon triple bond in the middle or at the terminus of the $C_2$-$C_{60}$ alkyl group, and non-limiting examples thereof may include an ethynyl group or a propynyl group. The term "$C_2$-$C_{60}$ alkynylene group" as used herein refers to a divalent group having the same structure as the $C_2$-$C_{60}$ alkynyl group.

The term "$C_1$-$C_{60}$ alkoxy group" as used herein refers to a monovalent group represented by —$OA_{101}$, in which $A_{101}$ is the $C_1$-$C_{60}$ alkyl group, and non-limiting examples thereof include a methoxy group, an ethoxy group, or an isopropyloxy group.

The term "$C_3$-$C_{10}$ cycloalkyl group" as used herein refers to a monovalent saturated hydrocarbon monocyclic group having 3 to 10 carbon atoms, and non-limiting examples thereof may include a cyclopropyl group, a cyclobutyl group, a cyclopentyl group, a cyclohexyl group, or a cycloheptyl group. The term "$C_3$-$C_{10}$ cycloalkylene group" as used herein refers to a divalent group having the same structure as the $C_3$-$C_{10}$ cycloalkyl group.

The term "$C_{10}$-$C_{10}$ heterocycloalkyl group" as used herein refers to a monovalent saturated monocyclic group having at least one heteroatom selected from N, O, Si, P, and S as a ring-forming atom and 1 to 10 carbon atoms, and non-limiting examples thereof may include a 1,2,3,4-oxatriazolidinyl group, a tetrahydrofuranyl group, or a tetrahydrothiophenyl group. The term "$C_1$-$C_{10}$ heterocycloalkylene group" as used herein refers to a divalent group having the same structure as the $C_1$-$C_{10}$ heterocycloalkyl group.

The term "$C_3$-$C_{10}$ cycloalkenyl group" as used herein refers to a monovalent monocyclic group that has 3 to 10 carbon atoms and at least one carbon-carbon double bond in the ring thereof and does not have aromaticity, and non-limiting examples thereof may include a cyclopentenyl group, a cyclohexenyl group, or a cycloheptenyl group. The term "$C_3$-$C_{10}$ cycloalkenylene group" as used herein refers to a divalent group having the same structure as the $C_3$-$C_{10}$ cycloalkenyl group.

The term "$C_1$-$C_{10}$ heterocycloalkenyl group" as used herein refers to a monovalent monocyclic group that has at least one heteroatom selected from N, O, Si, P, and S as a ring-forming atom, 1 to 10 carbon atoms, and at least one carbon-carbon double bond in its ring. Non-limiting examples thereof may include a 4,5-dihydro-1,2,3,4-oxatriazolyl group, a 2,3-dihydrofuranyl group, or a 2,3-dihydrothiophenyl group. The term "$C_1$-$C_{10}$ heterocycloalkenylene group" as used herein refers to a divalent group having the same structure as the $C_1$-$C_{10}$ heterocycloalkenyl group.

The term "$C_6$-$C_{60}$ aryl group" as used herein refers to a monovalent group having a carbocyclic aromatic system having 6 to 60 carbon atoms. The term "$C_6$-$C_{60}$ arylene group" as used herein refers to a divalent group having a carbocyclic aromatic system having 6 to 60 carbon atoms. Non-limiting examples of the $C_6$-$C_{60}$ aryl group may include a phenyl group, a naphthyl group, an anthracenyl group, a phenanthrenyl group, a pyrenyl group, or a chrysenyl group. When the $C_6$-$C_{60}$ aryl group and the $C_6$-$C_{60}$ arylene group each include two or more rings, the rings may be chemically bonded to each other.

The term "$C_1$-$C_{60}$ heteroaryl group" as used herein refers to a monovalent group having a heterocyclic aromatic system that has at least one heteroatom selected from N, O, Si, P, and S as a ring-forming atom, in addition to 1 to 60 carbon atoms. The term "$C_1$-$C_{60}$ heteroarylene group" as used herein refers to a divalent group having a heterocyclic aromatic system that has at least one heteroatom selected from N, O, Si, P, and S as a ring-forming atom, in addition to 1 to 60 carbon atoms. Non-limiting examples of the $C_1$-$C_{60}$ heteroaryl group may include a pyridinyl group, a pyrimidinyl group, a pyrazinyl group, a pyridazinyl group, a triazinyl group, a quinolinyl group, or an isoquinolinyl group. When the $C_1$-$C_{60}$ heteroaryl group and the $C_1$-$C_{60}$ heteroarylene group each include two or more rings, the rings may be chemically bonded to each other.

The term "$C_6$-$C_{60}$ aryloxy group" as used herein refers to —$OA_{102}$, in which $A_{102}$ is the $C_6$-$C_{60}$ aryl group. The term "$C_6$-$C_{60}$ arylthio group" as used herein refers to a monovalent group represented by —$SA_{103}$, in which $A_{103}$ is the $C_6$-$C_{60}$ aryl group.

The term "monovalent non-aromatic condensed polycyclic group" as used herein refers to a monovalent group, for example, having 8 to 60 carbon atoms. The monovalent group has two or more rings condensed with each other. Additionally, only carbon atoms are used as a ring-forming atoms. The entire molecular structure has non-aromaticity. An example of the monovalent non-aromatic condensed polycyclic group may include a fluorenyl group. The term "divalent non-aromatic condensed polycyclic group," as used herein, refers to a divalent group having the same structure as the monovalent non-aromatic condensed polycyclic group.

The term "monovalent non-aromatic condensed heteropolycyclic group" as used herein refers to a monovalent group, for example, having 1 to 60 carbon atoms. The monovalent group has two or more rings condensed with each other. The monovalent group has at least one heteroatom selected from N, O, Si, P, and S. Additionally, atoms other than carbon atoms are used as a ring-forming atom. The entire molecular structure has non-aromaticity. A non-limiting example of the monovalent non-aromatic condensed heteropolycyclic group may include a carbazolyl group. The term "divalent non-aromatic condensed heteropolycyclic group" as used herein refers to a divalent group having the same structure as the monovalent non-aromatic condensed heteropolycyclic group.

The term "$C_5$-$C_{60}$ carbocyclic group" as used herein refers to a monocyclic or polycyclic group having 5 to 60 carbon atoms in which a ring-forming atom is a carbon atom only. The $C_5$-$C_{60}$ carbocyclic group may be an aromatic carbocyclic group or a non-aromatic carbocyclic group. The $C_5$-$C_{60}$ carbocyclic group may be a ring, such as a benzene group, a monovalent group, such as a phenyl group, or a divalent group, such as a phenylene group. According to one or more exemplary embodiments of the present invention, depending on the number of substituents connected to the $C_5$-$C_{60}$ carbocyclic group, the $C_5$-$C_{60}$ carbocyclic group may be a trivalent group or a quadrivalent group.

The term "$C_1$-$C_{60}$ heterocyclic group" as used herein refers to a group having the same structure as the $C_1$-$C_{60}$ carbocyclic group, except that as a ring-forming atom, at least one heteroatom selected from N, O, Si, P, and S is used in addition to carbon. The number of carbon atoms may be in a range of 1 to 60.

At least one substituent selected from a substituent(s) of the substituted $C_5$-$C_{60}$ carbocyclic group, the substituted $C_1$-$C_{60}$ heterocyclic group, the substituted $C_3$-$C_{10}$ cycloalkylene group, the substituted $C_1$-$C_{10}$ heterocycloalkylene group, the substituted $C_3$-$C_{10}$ cycloalkenylene group, the substituted $C_1$-$C_{10}$ heterocycloalkenylene group, the substituted $C_6$-$C_{60}$ arylene group, the substituted $C_1$-$C_{60}$ heteroarylene group, the substituted divalent non-aromatic condensed polycyclic group, the substituted divalent non-aromatic condensed heteropolycyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group may be selected from:

deuterium (-D), —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amidino group, a hydrazino group, a hydrazono group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $O_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —$Si(Q_{11})(Q_{12})(Q_{13})$, —$N(Q_{11})(Q_{12})$, —$B(Q_{11})(Q_{12})$, —$C(=O)(Q_{11})$, —$S(=O)_2(Q_{11})$, and —$P(=O)(Q_{11})(Q_{12})$;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{21}$)($Q_{22}$)($Q_{23}$), —N($Q_{21}$)($Q_{22}$), —B($Q_{21}$)($Q_{22}$), —C(=O)($Q_{21}$), —S(=O)$_2$($Q_{21}$), and —P(=O)($Q_{21}$)($Q_{22}$); and —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$).

$Q_{11}$ to $Q_{13}$, $Q_{21}$ to $Q_{23}$, and $Q_{31}$ to $Q_{33}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, a monovalent non-aromatic condensed heteropolycyclic group, a biphenyl group, and a terphenyl group.

The term "Ph" as used herein refers to a phenyl group; the term "Me" as used herein refers to a methyl group; the term "Et" as used herein refers to an ethyl group; the term "ter-Bu" or "But" as used herein refers to a tert-butyl group; and the term "OMe" as used herein refers to a methoxy group.

The term "biphenyl group" as used therein refers to "a phenyl group substituted with a phenyl group." As an example, a "biphenyl group" is a substituted phenyl group having a $C_6$-$C_{60}$ aryl group as a substituent.

The term "terphenyl group" as used herein refers to "a phenyl group substituted with a biphenyl group." As an example, a "terphenyl group" is a substituted phenyl group having a $C_6$-$C_{60}$ aryl group substituted with a $C_6$-$C_{60}$ aryl group as a substituent.

The symbols * and *' as used herein, unless defined otherwise, each refer to a binding site to a neighboring atom in a corresponding formula.

A compound according to one or more exemplary embodiments of the present invention and an organic light-emitting device according to one or more exemplary embodiments of the present invention will be described in more detail below with reference to Synthesis Examples and Examples. However, exemplary embodiments of the present invention are not limited to the Examples described herein. The wording "B was used instead of A" as used in describing Synthesis Examples refers an example in which a molar equivalent of B was used in place of A.

EXAMPLES

Synthesis Example 1: Synthesis of Compound H1

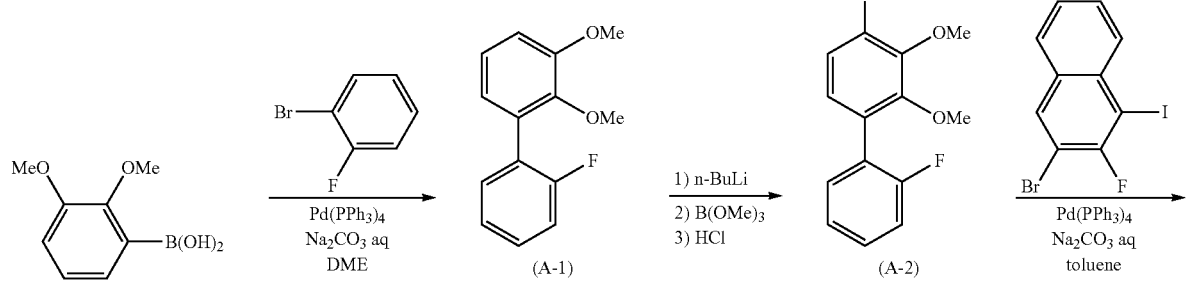

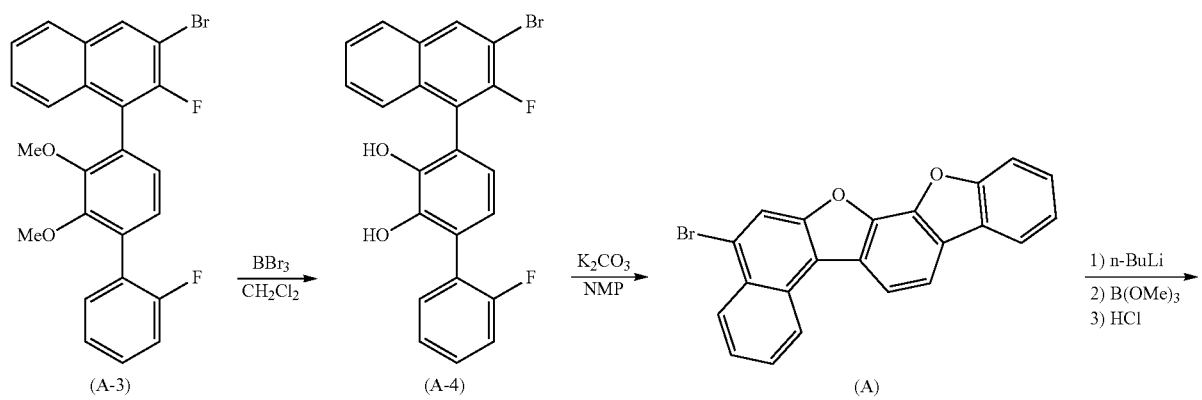

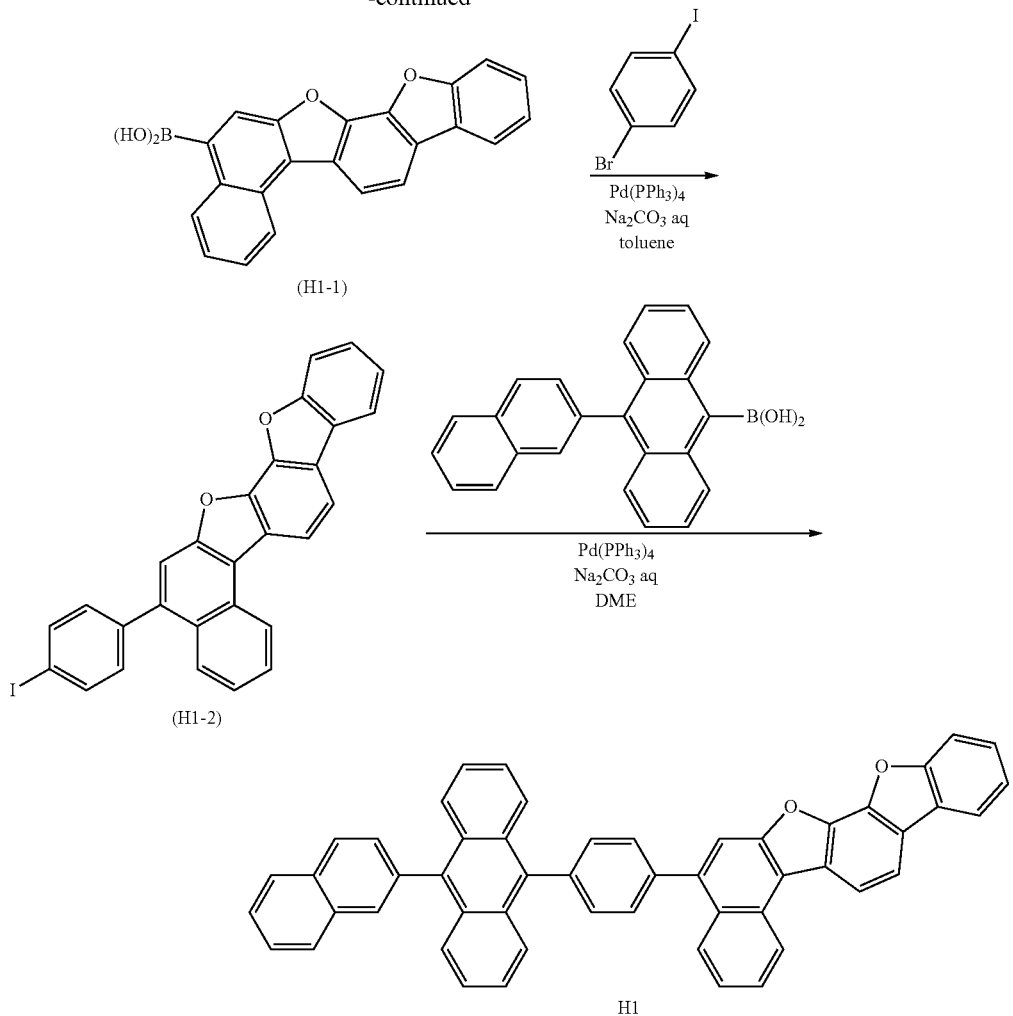

Synthesis of Intermediate (A-1)

Under an argon atmosphere, 22.0 g of 2,3-dimethoxyphenyl boronic acid, 17.5 g of 1-bromo-2-fluorobenzene, 2.32 g of tetrakis(triphenylphosphine)palladium(0), 300 mL of 1,2-dimethoxyethane, and 150 mL of a 2M sodium carbonate aqueous solution were added to a flask, and then, the mixture was heated, refluxed, and stirred for about 8 hours. The mixture was cooled to room temperature, and an aqueous layer was removed therefrom. Then, an organic layer was washed with a saturated saline solution. The organic layer was dried with $SO_4$ and concentrated. The residue obtained therefrom was purified by silica gel column chromatography, thus preparing 19.8 g (85.2%) of Intermediate (A-1).

Synthesis of Intermediate (A-2)

Under an argon atmosphere, 19.8 g of Intermediate (A-1) and 500 mL of anhydrous tetrahydrofuran (THF) were added to a flask, and 60 mL of a hexane solution of 1.6 M n-butyllithium was added thereto. Then, the reaction solution was stirred at room temperature for about 4 hours. The reaction solution was cooled to a temperature of −78° C., and 30 mL of a THF solution of 28.1 g of trimethyl borate was added thereto. Then, the reaction solution was heated to room temperature and stirred for about 8 hours. 200 mL of 10% HCl was added to the reaction solution and was stirred for about 2 hours. An extraction process was performed on the reaction solution by using ether, and an aqueous layer was removed therefrom. Then, an organic layer was washed with a saturated saline solution. The organic layer was dried with $MgSO_4$ and concentrated. The residue obtained therefrom was washed with hexane, thus preparing of 15.3 g (64.9%) of Intermediate (A-2).

Synthesis of Intermediate (A-3)

Under an argon atmosphere, 18.0 g of Intermediate (A-2), 19.2 g of 3-bromo-2-fluoro-1-iodobenzene, 1.28 g of tetrakis(triphenylphosphine)palladium(0), 180 mL of toluene, and 90 mL of a 2M sodium carbonate aqueous solution were added to a flask, and then, the reaction solution was heated, refluxed, and stirred for about 8 hours. After the reaction solution was cooled to room temperature, an extraction process was performed on the reaction solution by using toluene, and an aqueous layer was removed therefrom. Then, an organic layer was washed with a saturated saline solution. The organic layer was dried with $MgSO_4$ and concentrated. The residue obtained therefrom was purified by silica gel column chromatography, thus preparing 19.1 g (76.6%) of Intermediate (A-3).

Synthesis of Intermediate (A-4)

19.2 g of Intermediate (A-3) and 250 mL of dichloromethane (dehydrated) were added to a flask and cooled to a temperature of 0° C. 27.5 g of boron tribromide ($BBr_3$) was added thereto and was stirred at room temperature for about 24 hours. After the reaction was completed, the solution was cooled to a temperature of −78° C. and was quenched with methanol and water. The solution was put in a separating funnel and an extraction process was performed thereon with dichloromethane. The result was dried with MgSO₄ and impurities were removed therefrom through a silica gel short column. A sample obtained by concentrating the solution was vacuum-dried, thus preparing 17.8 g (99.4%) of Intermediate (A-4).

Synthesis of Intermediate (A)

17.8 g of Intermediate (A-4), 300 mL of N-methyl-2-pyrrolidone (dehydrated), and 24.5 g of K₂CO₃ were added to a flask and stirred at a temperature of 200° C. for about 2 hours. After the reaction was completed, the solution was cooled to room temperature. 2 L of toluene was added thereto and the mixed solution was put in a separating funnel. Then, a washing process was performed thereon with water. The mixed solution was dried with MgSO₄ and impurities were removed therefrom through a silica gel short column. Then, the solution was concentrated and recrystallized in a toluene/methanol mixed solvent, thus preparing 10.7 g (66.4%) of Intermediate (A).

Synthesis of Intermediate (H1-1)

10.7 g of Intermediate (A) and 500 mL of THF (dehydrated) were added to a flask and cooled to a temperature of −78° C. 66 mL of n-BuLi (1.6M in hexane) was added thereto, and the mixture was stirred for about 2 hours while being heated to a temperature of 0° C. Then, the mixture was cooled again to a temperature of −78° C. 27.5 g of B(OMe)₃ was added thereto, and the mixture was stirred at a temperature of −78° C. for about 10 minutes and was then stirred at room temperature for about 5 hours. After the reaction was completed, 200 mL of 1N HCl aqueous solution was added thereto and the mixed solution was stirred at room temperature for about 1 hour. The solution was put in a separating funnel and an extraction process was performed thereon with ethyl acetate. The solution was dried with MgSO₄ and washed with concentrated n-hexane, thus preparing 22.9 g (65.1%) of Intermediate (H1-1).

Synthesis of Intermediate (H1-2)

Under an argon atmosphere, 22.9 g of Intermediate (H1-1), 19.8 g of 1-bromo-4-iodobenzene, 1.52 g of tetrakis(triphenylphosphine)palladium(0), 200 mL of toluene, 100 mL of a 2M sodium carbonate aqueous solution were added to a flask, and then, the reaction solution was heated, refluxed, and stirred for about 8 hours. The reaction solution was cooled to room temperature, and an extraction process was performed on the reaction solution by using toluene. An aqueous layer was removed therefrom. Then, an organic layer was dried with MgSO₄ and concentrated. The residue obtained therefrom was purified through silica gel column chromatography, thus preparing 23.9 g (71.9%) of Intermediate (H1-2).

Synthesis of Compound H1

Under an argon atmosphere, 23.9 g of Intermediate (H1-2), 16.4 g of 9-(naphthalene-3-yl)anthracene-10-yl-10-boronic acid, 0.232 g of tetrakis(triphenyl phosphine)palladium(0), 40 mL of 1,2-dimethoxyethane, and 20 mL of a 2M sodium carbonate aqueous solution were added to a flask and refluxed and stirred for about 8 hours. The mixture was cooled to room temperature, and a precipitated solid was filtered and separated. The obtained solid was washed with water and methanol and was recrystallized with toluene, thus preparing 21.0 g (65.4%) of Compound H1. MW=686.81, m/e=686.22.

Synthesis Example 2: Synthesis of Compound H2

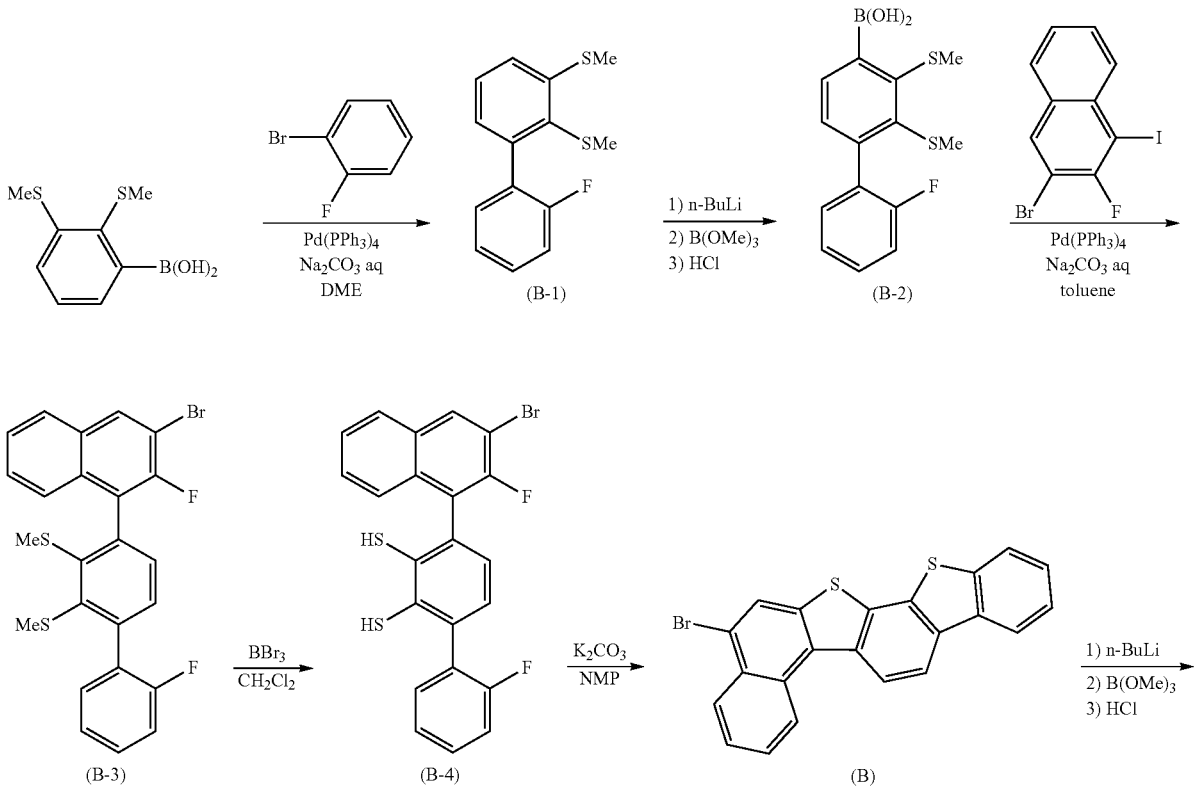

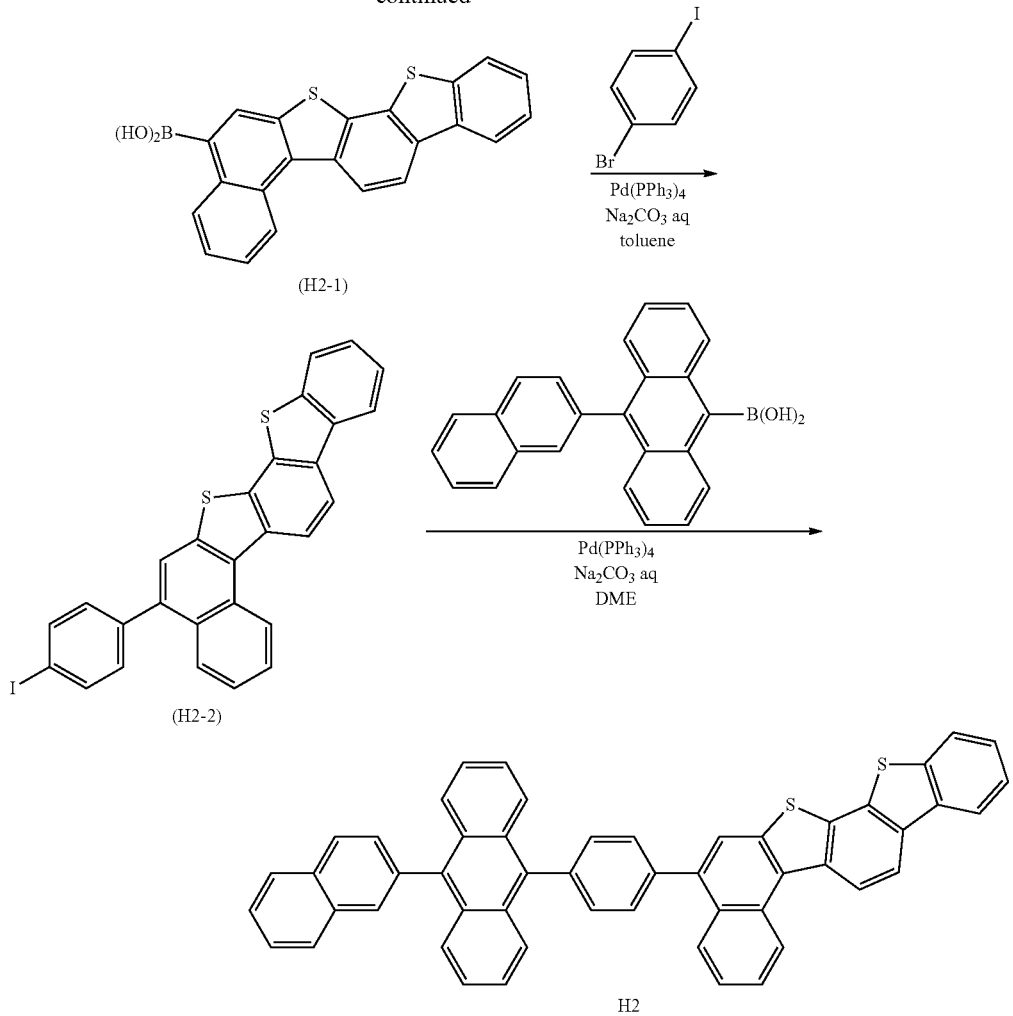

Synthesis of Intermediate (B-1)

Under an argon atmosphere, 20.3 g of 2,3-bis(methylthio)phenyl boronic acid, 17.5 g of 1-bromo-2-fluorobenzene, 2.34 g of tetrakis(triphenylphosphine) palladium(0), 300 mL of 1,2-dimethoxyethane, and 150 mL of a 2M sodium carbonate aqueous solution were added to a flask, and then, the mixture was heated, refluxed, and stirred for about 8 hours. The mixture was cooled to room temperature, and an aqueous layer was removed therefrom. Then, an organic layer was washed with a saturated saline solution. The organic layer was dried with $MgSO_4$ and concentrated. The residue obtained therefrom was purified by silica gel column chromatography, thus preparing 30.9 g (84.9%) of Intermediate (B-1).

Synthesis of Intermediate (B-2)

Under an argon atmosphere, 30.9 g of Intermediate (B-1) and 500 mL of anhydrous THF were added to a flask, and 55 mL of a hexane solution of 1.6M n-butyllithium was added thereto. Then, the reaction solution was stirred at room temperature for about 4 hours. The reaction solution was cooled to a temperature of −78° C., and 30 mL of a THF solution of 28.1 g of trimethyl borate was added thereto. Then, the reaction solution was stirred for about 8 hours while being heated to room temperature. 200 mL of 10% HCl was added to the reaction solution and the mixed solution was stirred for about 2 hours. An extraction process was performed on the reaction solution by using ether and an aqueous layer was removed therefrom. Then, an organic layer was washed with a saturated saline solution. The organic layer was dried with $MgSO_4$ and concentrated. The residue obtained therefrom was washed with hexane, thus preparing 16.8 g (64.1%) of Intermediate (B-2).

Synthesis of Intermediate (B-3)

Under an argon atmosphere, 16.8 g of Intermediate (B-2), 16.5 g of 3-bromo-2-fluoro-1-iodobenzene, 1.28 g of tetrakis(triphenylphosphine)palladium(0), 180 mL of toluene, and 95 mL of a 2M sodium carbonate aqueous solution were added to a flask, and then, the reaction solution was heated, refluxed, and stirred for about 8 hours. After the reaction solution was cooled to room temperature, an extraction process was performed on the reaction solution by using toluene, and an aqueous layer was removed therefrom. Then, an organic layer was washed with a saturated saline solution. The organic layer was dried with $MgSO_4$ and concentrated. The residue obtained therefrom was purified by silica gel column chromatography, thus preparing 20.1 g (75.3%) of Intermediate (B-3).

Synthesis of Intermediate (B-4)

20.1 g of Intermediate (B-3) and 250 mL of dichloromethane (dehydrated) were added to a flask and cooled to a temperature of 0° C. 27.5 g of BBr₃ was added thereto and was stirred at room temperature for about 24 hours. After the reaction was completed, the solution was cooled to a temperature of −78° C. and was quenched with methanol and water. The solution was put in a separating funnel, and an extraction process was performed thereon with MgSO₄ and impurities were removed therefrom through a silica gel short column. A sample obtained by concentrating the solution was vacuum-dried, thus preparing 18.9 g (99.5%) of Intermediate (B-4).

Synthesis of Intermediate (B)

18.9 g of Intermediate (B-4), 300 mL of N-methyl-2-pyrrolidone, and 24.2 g of K₂CO₃ were added to a flask and stirred at a temperature of 200° C. for about 2 hours. After the reaction was completed, the solution was cooled to room temperature. 2 L of toluene was added thereto and the mixed solution was put in a separating funnel. A washing process was performed thereon with water. The mixed solution was dried with MgSO₄ and impurities were removed therefrom through a silica gel short column. Then, the solution was concentrated and recrystallized in a toluene/methanol mixed solvent, thus preparing 11.2 g (65.2%) of Intermediate (B).

Synthesis of Intermediate (H2-1)

24.4 g (63.6%) of Intermediate (H2-1) was synthesized in substantially the same manner as in Synthesis of Intermediate (H1-1), except that Intermediate (B) was used instead of Intermediate (A).

Synthesis of Intermediate (H2-2)

24.9 g (72.1%) of Intermediate (H2-2) was synthesized in substantially the same manner as in Synthesis of Intermediate (H1-2), except that Intermediate (H2-1) was used instead of Intermediate (H1-1).

Synthesis of Compound H2

20.9 g (63.3%) of Compound H2 was synthesized in substantially the same manner as in Synthesis of Compound H1, except that Intermediate (H2-2) was used instead of Intermediate (H1-2). MW=718.93, m/e=718.18.

Synthesis Example 3: Synthesis of Compound H3

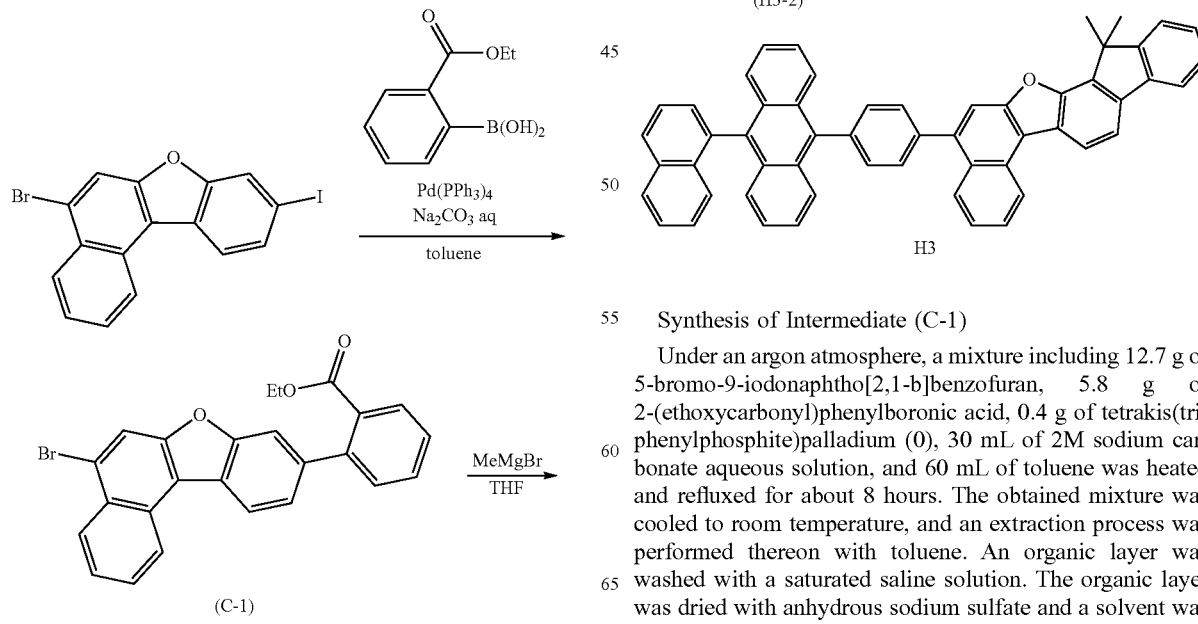

Synthesis of Intermediate (C-1)

Under an argon atmosphere, a mixture including 12.7 g of 5-bromo-9-iodonaphtho[2,1-b]benzofuran, 5.8 g of 2-(ethoxycarbonyl)phenylboronic acid, 0.4 g of tetrakis(triphenylphosphite)palladium (0), 30 mL of 2M sodium carbonate aqueous solution, and 60 mL of toluene was heated and refluxed for about 8 hours. The obtained mixture was cooled to room temperature, and an extraction process was performed thereon with toluene. An organic layer was washed with a saturated saline solution. The organic layer was dried with anhydrous sodium sulfate and a solvent was distilled with reduced pressure. The residue obtained therefrom was purified by silica gel column chromatography, thus preparing 8.7 g (65.4%) of Intermediate (C-1).

Synthesis of Intermediate (C-2)

Under an argon atmosphere, 30 mL of a THF solution of 1M methylmagnesium bromide was ice-cooled and added to 90 mL of a THF solution of 8.7 g of Intermediate (C-1) and was then stirred at room temperature for about 5 hours. Ice water was added to the reaction solution. Then, an extraction process was performed thereon with toluene and an organic layer was washed with a saturated saline solution. The organic layer was dried with anhydrous sodium sulfate and a solvent was distilled with reduced pressure. The residue obtained therefrom was purified by silica gel column chromatography, thus preparing 6.4 g (76.1%) of Intermediate (C-2).

Synthesis of Intermediate (C)

0.7 mL of sulfuric acid was added to 70 mL of acetic acid solution of 6.4 g of Intermediate (C-2), and the mixture was stirred at a temperature of 50° C. for about 8 hours. The obtained mixture was cooled to room temperature and was separated by adding toluene and water thereto. A toluene layer was washed with water and a saturated saline solution. Then, the result was dried with anhydrous sodium sulfate and a solvent was distilled with reduced pressure. The residue obtained therefrom was purified by chromatography, thus preparing 2.1 g (34.8%) of Intermediate (C).

Synthesis of Intermediate (H3-1)

1.2 g (63.4%) of Compound (H3-1) was synthesized in substantially the same manner as in Synthesis of Compound (H1-1), except that Intermediate (C) was used instead of Intermediate (A).

Synthesis of Intermediate (H3-2)

1.2 g (71.8%) of Compound (H3-2) was synthesized in substantially the same manner as in Synthesis of Compound (H1-2), except that Intermediate (H3-1) was used instead of Intermediate (H1-1).

Synthesis of Compound H3

1.0 g (62.9%) of Compound H3 was synthesized in substantially the same manner as in Synthesis of Compound H1, except that Intermediate (H3-2) was used instead of Intermediate (H1-2), and 9-(naphthalene-1-yl)anthracene-10-yl-10-boronic acid was used instead of 9-(naphthalene-3-yl)anthracene-10-yl-10-boronic acid. MW=712.89, m/e=712.28.

Synthesis Example 4: Synthesis of Compound H4

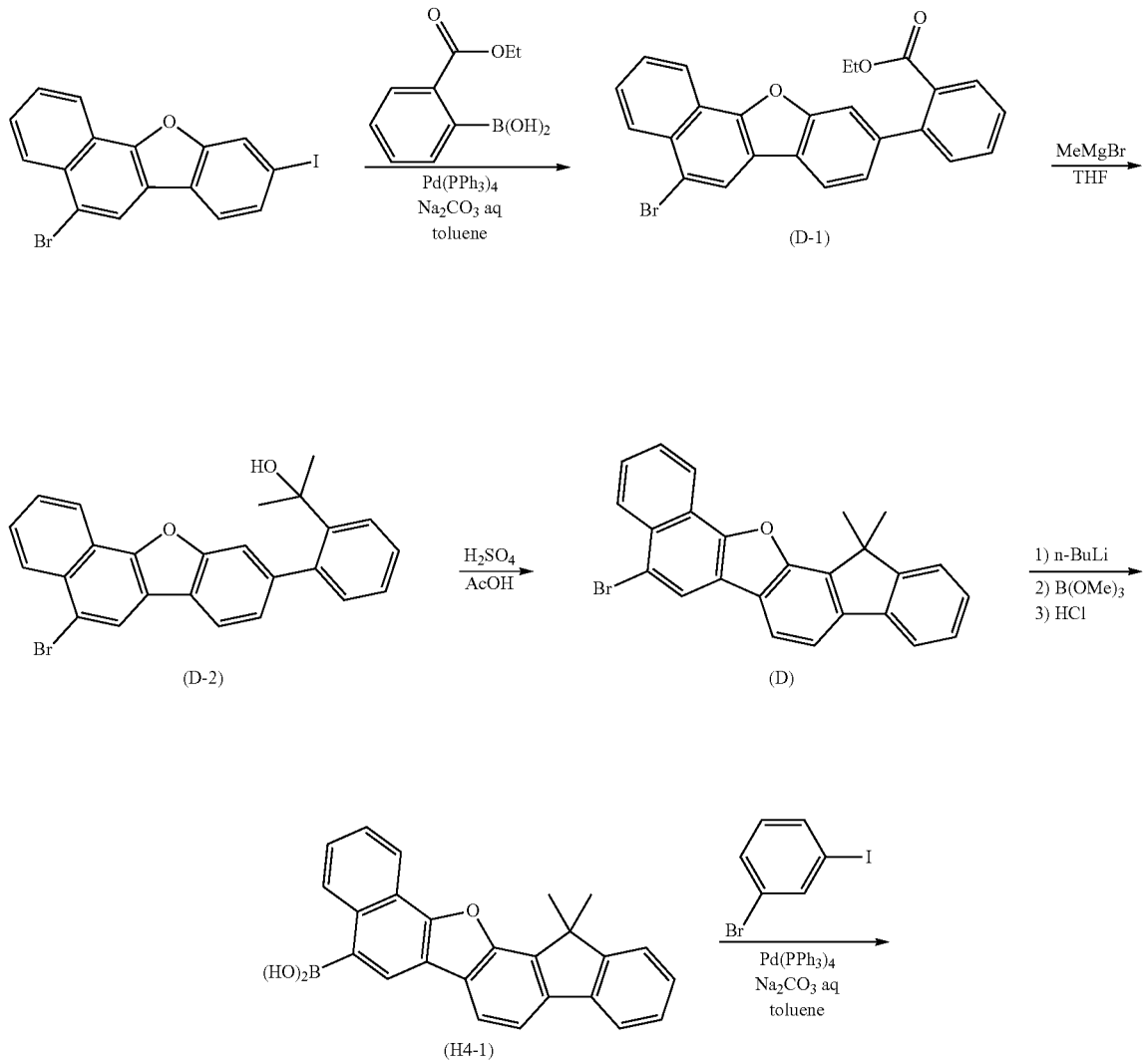

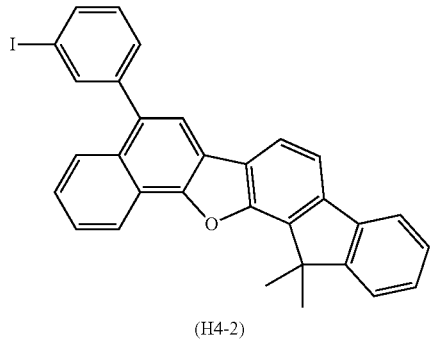

(H4-2)

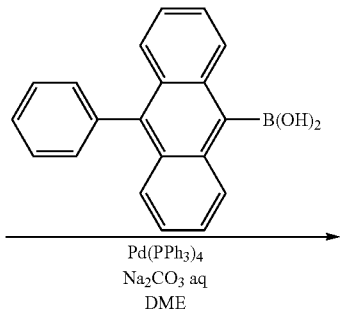

Pd(PPh₃)₄
Na₂CO₃ aq
DME

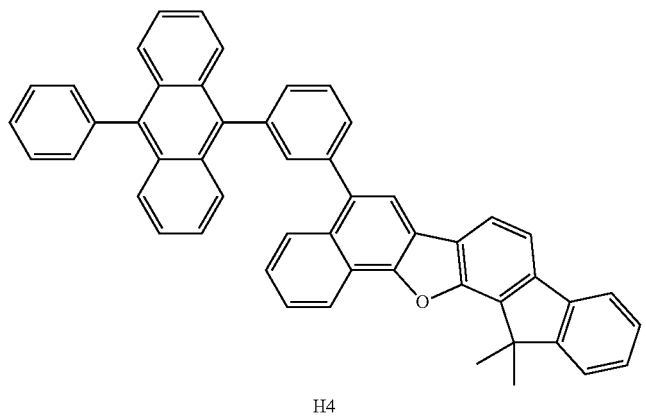

H4

Synthesis of Intermediate (D-1)

Under an argon atmosphere, a mixture including 12.7 g of 5-bromo-9-iodonaphtho[1,2-b]benzofuran, 5.8 g of 2-(ethoxycarbonyl)phenylboronic acid, 0.4 g of tetrakis(triphenylphosphite)palladium(0), 30 mL of 2M sodium carbonate aqueous solution, and 60 mL of toluene was heated and refluxed for about 8 hours. The obtained mixture was cooled to room temperature, and an extraction process was performed thereon with toluene. An organic layer was washed with a saturated saline solution. The organic layer was dried with anhydrous sodium sulfate and a solvent was distilled with reduced pressure. The residue obtained therefrom was purified by silica gel column chromatography, thus preparing 8.8 g (66.2%) of Intermediate (D-1).

Synthesis of Intermediate (D-2)

Under an argon atmosphere, 30 mL of a THF solution of 1M methylmagnesium bromide was ice-cooled and added to 90 mL of a THF solution of 8.8 g of Intermediate (D-1) and was then stirred at room temperature for about 5 hours. Ice water was added to the reaction solution. Then, an extraction process was performed thereon with toluene and an organic layer was washed with a saturated saline solution. The organic layer was dried with anhydrous sodium sulfate and a solvent was distilled with reduced pressure. The residue obtained therefrom was purified by silica gel column chromatography, thus preparing 6.4 g (75.1%) of Intermediate (D-2).

Synthesis of Intermediate (D)

0.7 mL of sulfuric acid was added to 70 mL of acetic acid solution of 6.4 g of Intermediate (D-2), and the mixture was stirred at a temperature of 50° C. for about 8 hours. The obtained mixture was cooled to room temperature and was separated by adding toluene and water thereto. A toluene layer was washed with water and a saturated saline solution. Then, the result was dried with anhydrous sodium sulfate and a solvent was distilled with reduced pressure. The residue obtained therefrom was purified by chromatography, thus preparing 2.2 g (35.3%) of Intermediate (D).

Synthesis of Intermediate (H4-1)

1.3 g (64.5%) of Intermediate (H4-1) was synthesized in substantially the same manner as in Synthesis of Compound (H1-1), except that Intermediate (D) was used instead of Intermediate (A).

Synthesis of Intermediate (H4-2)

1.3 g (72.1%) of Intermediate (H4-2) was synthesized in substantially the same manner as in Synthesis of Intermediate (H1-2), except that Intermediate (H4-1) was used instead of Intermediate (H1-1), and 1-bromo-3-iodobenzene was used instead of 1-bromo-4-iodobenzene.

Synthesis of Compound H4

1.0 g (61.7%) of Compound H4 was synthesized in substantially the same manner as in Synthesis of Compound H1, except that Intermediate (H4-2) was used instead of Intermediate (H1-2), and 9-phenylanthracene-10-yl-10-boronic acid was used instead of 9-(naphthalene-3-yl)anthracene-10-yl-10-boronic acid. MW=662.83, m/e=662.26.

Synthesis Example 5: Synthesis of Compound H5
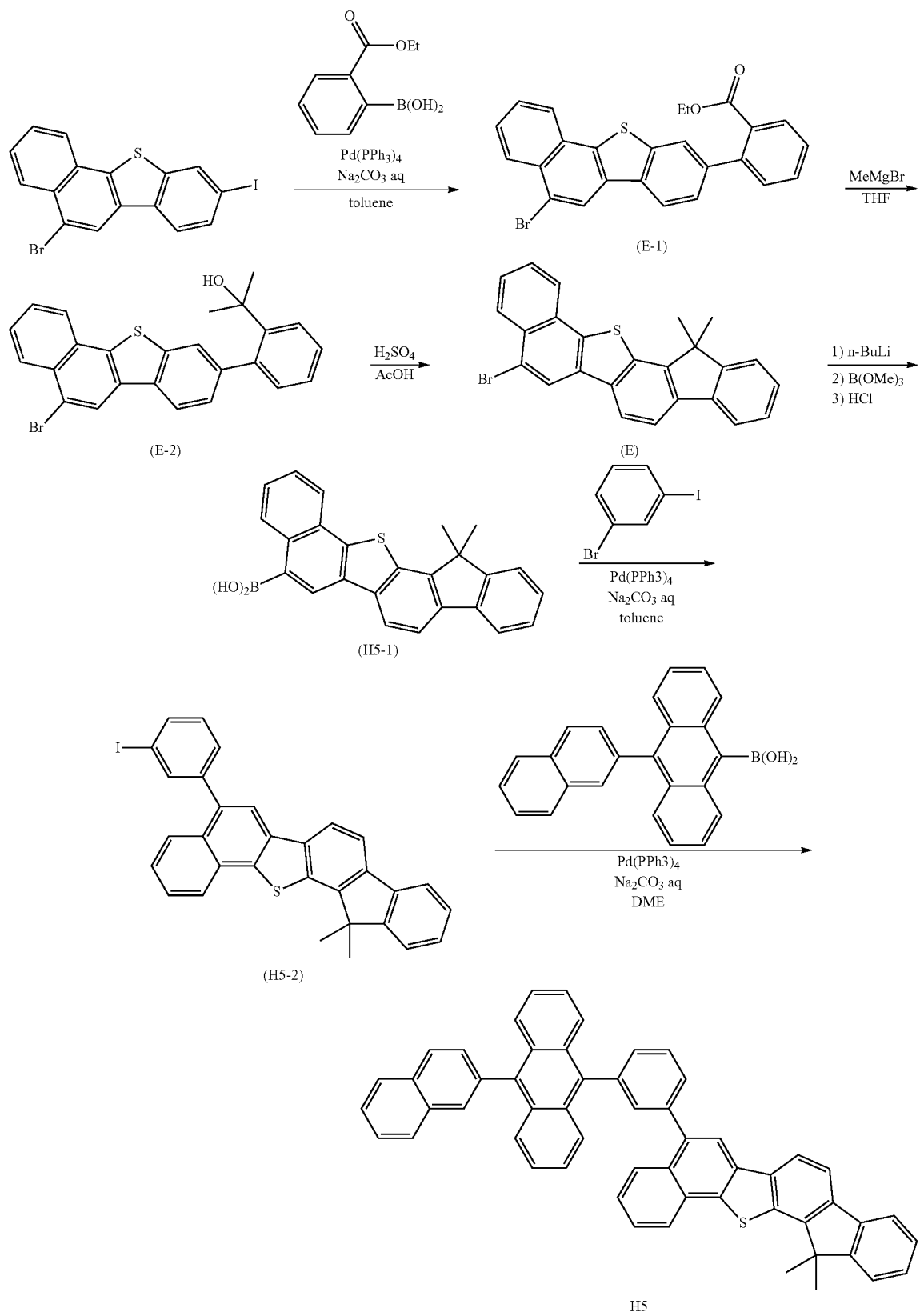

Synthesis of Intermediate (E-1)

Under an argon atmosphere, a mixture including 13.2 g of 5-bromo-9-iodobenzo[b]naphtho[2,1-b]benzothiophene, 5.8 g of 2-(ethoxycarbonyl)phenylboronic acid, 0.4 g of tetrakis(triphenylphosphite)palladium (0), 30 mL of 2M sodium carbonate aqueous solution, and 60 mL of toluene was heated and refluxed for about 8 hours. The obtained mixture was cooled to room temperature, and an extraction process was performed thereon with toluene. An organic layer was washed with a saturated saline solution. The organic layer was dried with anhydrous sodium sulfate and a solvent was distilled with reduced pressure. The residue obtained therefrom was purified by silica gel column chromatography, thus preparing 9.0 g (65.3%) of Intermediate (E-1).

Synthesis of Intermediate (E-2)

Under an argon atmosphere, 30 mL of a THF solution of 1M methylmagnesium bromide was ice-cooled and added to 90 mL of a THF solution of 90 g of Intermediate (E-1) and was then stirred at room temperature for about 5 hours. Ice water was added to the reaction solution. Then, an extraction process was performed thereon with toluene and an organic layer was washed with a saturated saline solution. The organic layer was dried with anhydrous sodium sulfate and a solvent was distilled with reduced pressure. The residue obtained therefrom was purified by silica gel column chromatography, thus preparing 6.5 g (74.5%) of Intermediate (E-2).

Synthesis of Intermediate (E)

0.7 mL of sulfuric acid was added to 70 mL of acetic acid solution of 6.5 g of Intermediate (E-2), and the mixture was stirred at a temperature of 50° C. for about 8 hours. The obtained mixture was cooled to room temperature and was separated by adding toluene and water thereto. A toluene layer was washed with water and a saturated saline solution. Then, the result was dried with anhydrous sodium sulfate and a solvent was distilled with reduced pressure. The residue obtained therefrom was purified by chromatography, thus preparing 2.2 g (34.6%) of Intermediate (E).

Synthesis of Intermediate (H5-1)

1.3 g (63.8%) of Intermediate (H5-1) was synthesized in substantially the same manner as in Synthesis of Intermediate (H1-1), except that Intermediate (E) was used instead of Intermediate (A).

Synthesis of Intermediate (H5-2)

1.3 g (72.8%) of Intermediate (H5-2) was synthesized in substantially the same manner as in Synthesis of Intermediate (H1-2), except that Intermediate (H5-1) was used instead of Intermediate (H1-1), and 1-bromo-3-iodobenzene was used instead of 1-bromo-4-iodobenzene.

Synthesis of Compound H5

1.1 g (62.6%) of Compound H5 was synthesized in substantially the same manner as in Synthesis of Compound H1, except that Intermediate (H5-2) was used instead of Intermediate (H1-2). MW=728.95, m/e=728.25.

Synthesis Example 6: Synthesis of Compound H6

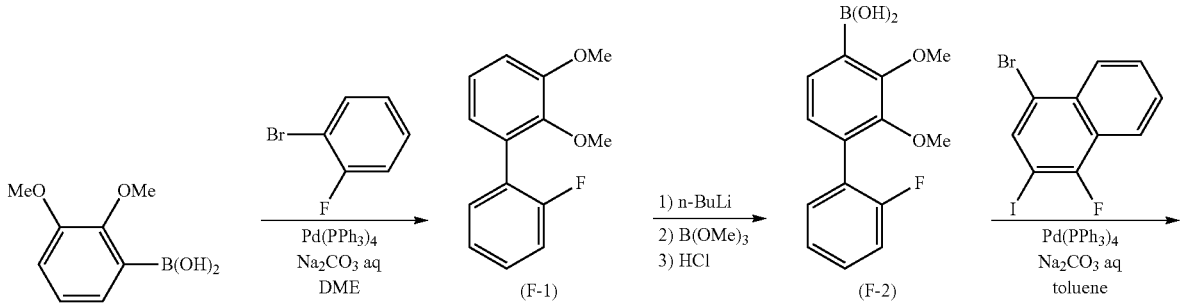

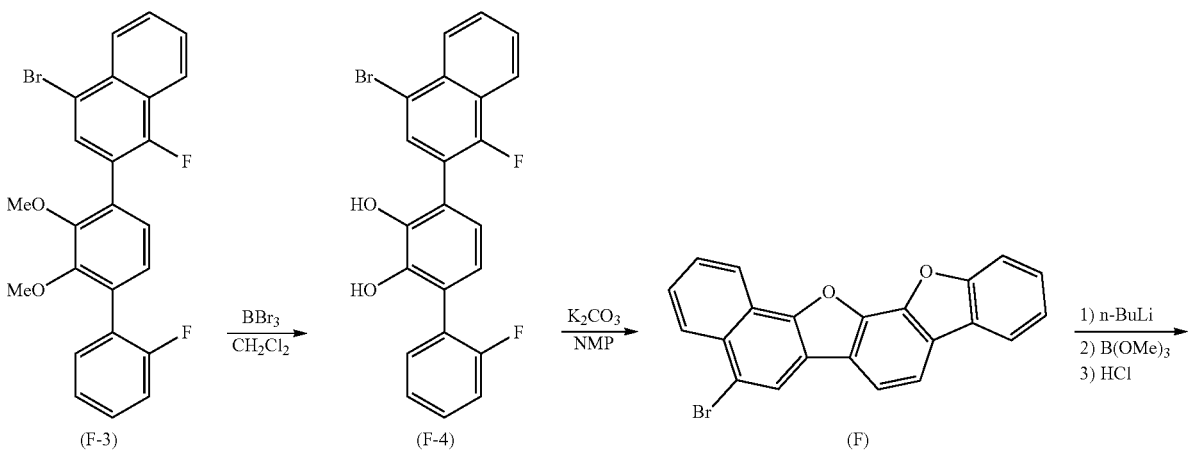

-continued

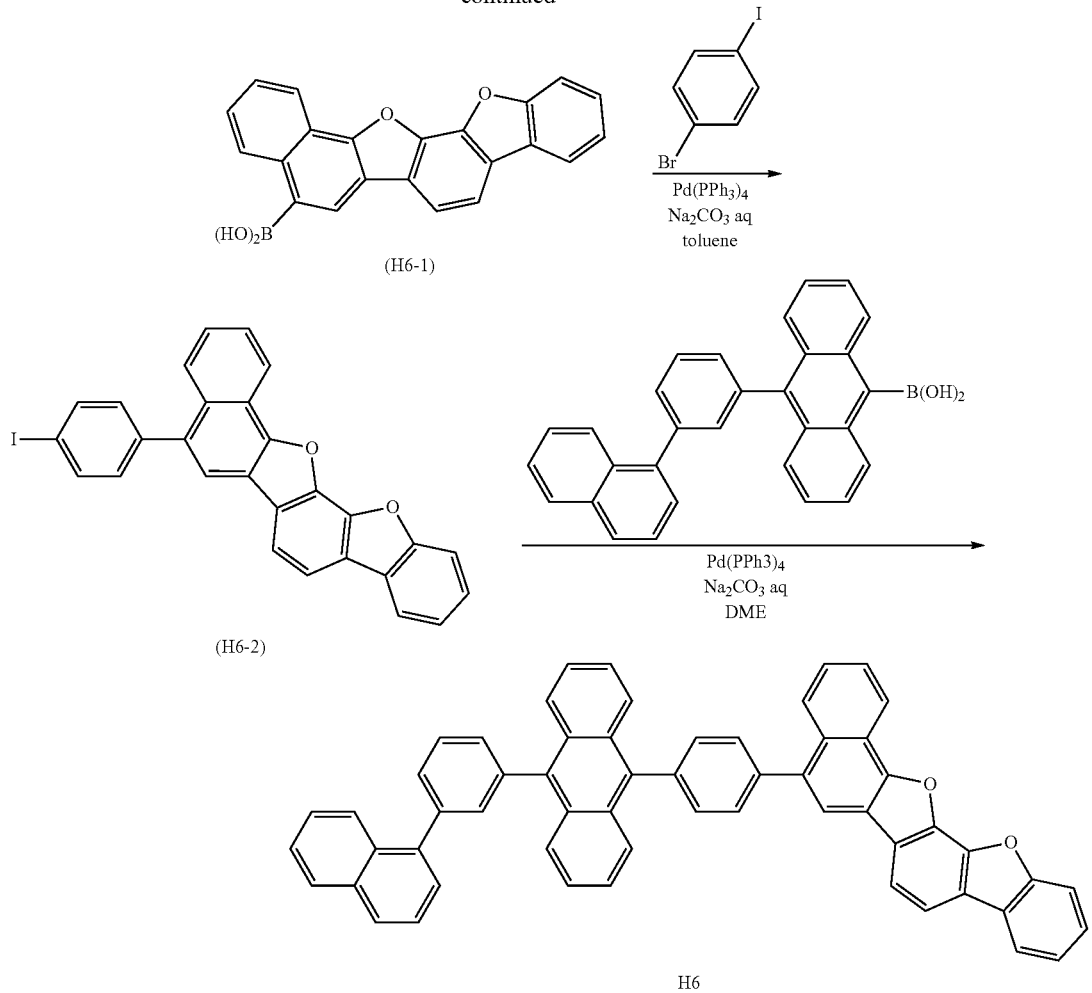

Synthesis of Intermediate (F-1)

Under an argon atmosphere, 17.3 g of 2,3-dimethoxyphenyl boronic acid, 17.5 g of 1-bromo-2-fluorobenzene, 2.34 g of tetrakis(triphenylphosphine)palladium(0), 300 mL of 1,2-dimethoxyethane, and 150 mL of a 2M sodium carbonate aqueous solution were added to a flask, and then, the mixture was heated, refluxed, and stirred for about 8 hours. The mixture was cooled to room temperature, and an aqueous layer was removed therefrom. Then, an organic layer was washed with a saturated saline solution. The organic layer was dried with MgSO₄ and concentrated. The residue obtained therefrom was purified by silica gel column chromatography, thus preparing 18.9 g (85.8%) of Intermediate (F-1).

Synthesis of Intermediate (F-2)

Under an argon atmosphere, 18.9 g of Intermediate (F-1) and 500 mL of anhydrous THF were added to a flask, and 55 mL of a hexane solution of 1.6M n-butyllithium was added thereto. Then, the reaction solution was stirred at room temperature for 4 hours. The reaction solution was cooled to a temperature of −78° C., and 30 mL of a THF solution of 28.1 g of trimethyl borate was added thereto. Then, the reaction solution was stirred for about 8 hours while being heated to room temperature. 200 mL of 10% HCl was added to the reaction solution and the mixed solution was stirred for about 2 hours. An extraction process was performed on the reaction solution by using ether, and an aqueous layer was removed therefrom. Then, an organic layer was washed with a saturated saline solution. The organic layer was dried with MgSO₄ and concentrated. The residue obtained therefrom was washed with hexane, thus preparing 14.3 g (63.9%) of Intermediate (F-2).

Synthesis of Intermediate (F-3)

Under an argon atmosphere, 14.3 g of Intermediate (F-2), 19.2 g of 4-bromo-1-fluoro-2-iodobenzene, 1.28 g of tetrakis(triphenylphosphine)palladium(0), 180 mL of toluene, and 95 mL of a 2M sodium carbonate aqueous solution were added to a flask, and then, the reaction solution was heated, refluxed, and stirred for about 8 hours. After the reaction solution was cooled to room temperature, an extraction process was performed on the reaction solution by using toluene, and an aqueous layer was removed therefrom. Then, an organic layer was washed with a saturated saline solution. The organic layer was dried with MgSO₄ and concentrated. The residue obtained therefrom was purified by silica gel column chromatography, thus preparing 17.9 g (75.6%) of Intermediate (F-3).

Synthesis of Intermediate (F-4)

Under an argon atmosphere, 17.9 g of Intermediate (F-3) and 300 mL of dichloromethane (dehydrated) were added to a flask and was cooled to a temperature of −78° C. 90 mL of dichloromethane solution of 1M BBr₃ was added thereto.

Then, the reaction solution was stirred for about 3 hours while being heated to room temperature. 150 mL of ice water was added to the reaction solution, and an aqueous layer was removed therefrom. Then, an organic layer was dried with MgSO$_4$. The organic layer was concentrated, and a residue obtained therefrom was purified through a silica gel short column, thus preparing 16.7 g (99.5%) of Intermediate (F-4).

Synthesis of Intermediate (F)

16.7 g of Intermediate (F-4), 300 mL of N-methyl-2-pyrrolidone (dehydrated), and 24.2 g of K$_2$CO$_3$ were added to a flask and stirred at a temperature of 200 t for about 2 hours. After the reaction was completed, the solution was cooled to room temperature. 2 L of toluene was added thereto and the mixed solution was put in a separating funnel. Then, a washing process was performed thereon with water. The mixed solution was dried with MgSO$_4$ and impurities were removed therefrom through a silica gel short column. Then, the solution was concentrated and recrystallized in a toluene/methanol mixed solvent, thus preparing 10.1 g (66.8%) of Intermediate (F).

Synthesis of Intermediate (H6-1)

5.9 g (64.9%) of Intermediate (H6-1) was synthesized in substantially the same manner as in Synthesis of Intermediate (H1-1), except that Intermediate (F) was used instead of Intermediate (A).

Synthesis of Intermediate (H6-2)

6.0 g (69.6%) of Intermediate (H6-2) was synthesized in substantially the same manner as in Synthesis of Intermediate (H1-2), except that Intermediate (H6-1) was used instead of Intermediate (H1-1).

Synthesis of Compound H6

5.8 g (64.3%) of Compound H6 was synthesized in substantially the same manner as in Synthesis of Compound H1, except that Intermediate (H6-2) was used instead of Intermediate (H1-2), and 9-(3-(naphthalene-1-yl)phenyl)anthracene-10-yl-10-boronic acid was used instead of 9-(naphthalene-3-yl)anthracene-10-yl-10-boronic acid. MW=762.91, m/e=762.26.

Synthesis Example 7: Synthesis of Compound H7

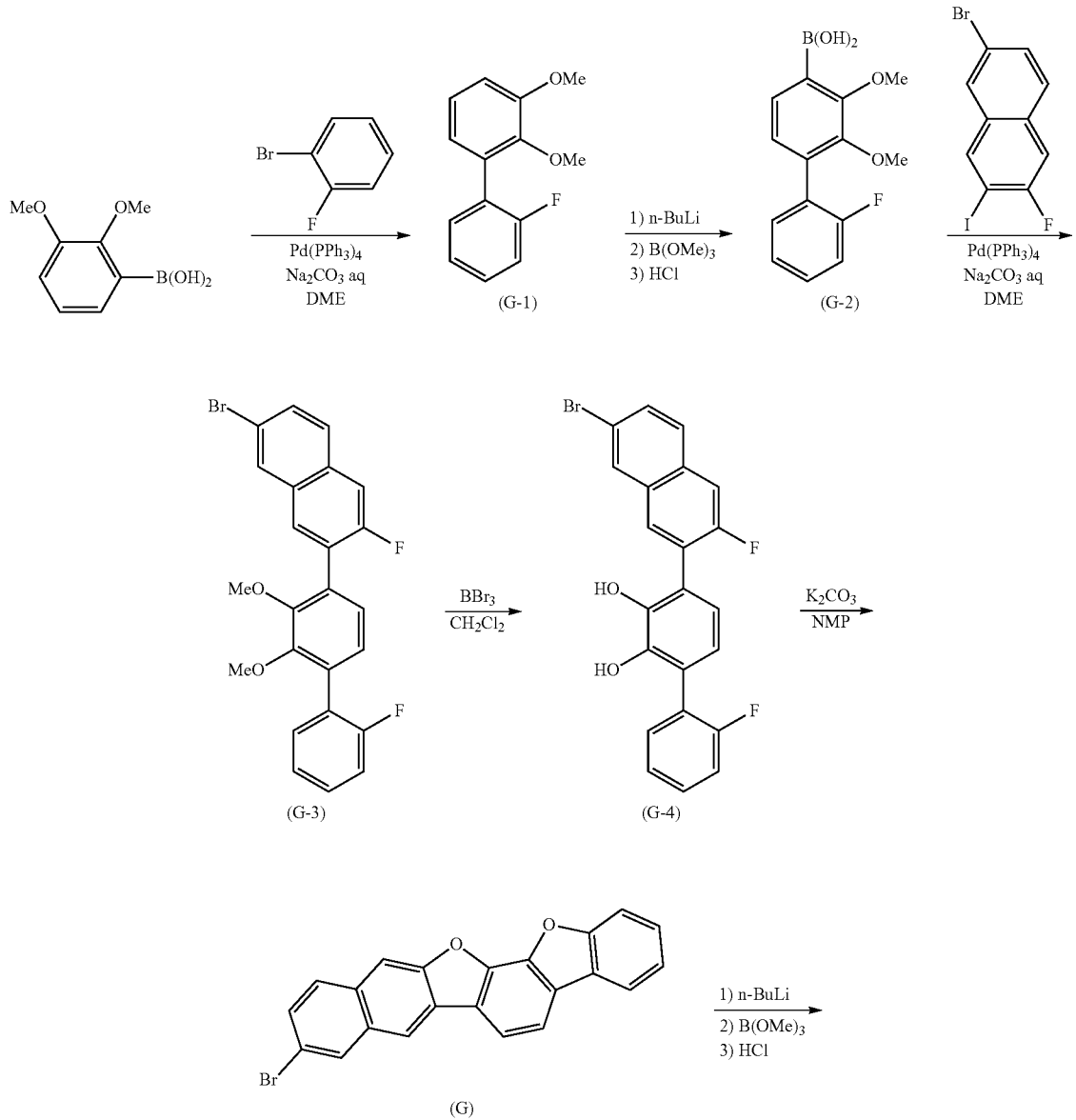

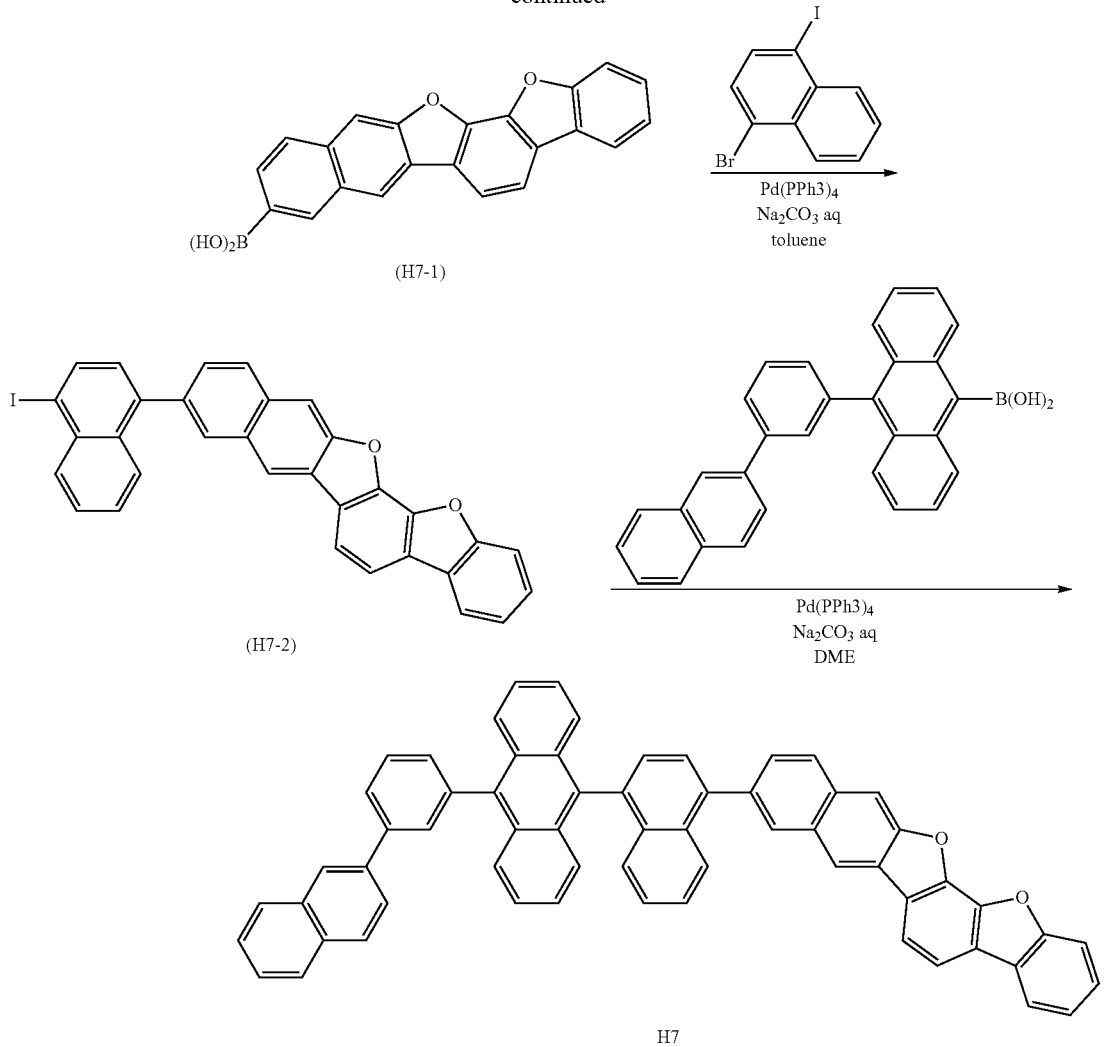

Synthesis of Intermediate (G-1)

Under an argon atmosphere, 17.3 g of 2,3-dimethoxyphenyl boronic acid, 17.5 g of 1-bromo-2-fluorobenzene, 2.34 g of tetrakis(triphenylphosphine)palladium(0), 300 mL of 1,2-dimethoxyethane, and 150 mL of a 2M sodium carbonate aqueous solution were added to a flask, and then, the mixture was heated, refluxed, and stirred for about 8 hours. The mixture was cooled to room temperature, and an aqueous layer was removed therefrom. Then, an organic layer was washed with a saturated saline solution. The organic layer was dried with MgSO$_4$ and concentrated. The residue obtained therefrom was purified by silica gel column chromatography, thus preparing 18.8 g (85.6%) of Intermediate (G-1).

Synthesis of Intermediate (G-2)

Under an argon atmosphere, 18.8 g of Intermediate (G-1) and 500 mL of anhydrous THF were added to a flask, and 55 mL of a hexane solution of 1.6M n-butyllithium was added thereto. Then, the reaction solution was stirred at room temperature for about 4 hours. The reaction solution was cooled to a temperature of −78° C., and 30 mL of a THF solution of 28.1 g of trimethyl borate was added thereto. Then, the reaction solution was stirred for 8 hours while being heated to room temperature. 200 mL of 10% HCl was added to the reaction solution and the mixed solution was stirred for about 2 hours. An extraction process was performed on the reaction solution by using ether, and an aqueous layer was removed therefrom. Then, an organic layer was washed with a saturated saline solution. The organic layer was dried with MgSO$_4$ and concentrated. The residue obtained therefrom was washed with hexane, thus preparing 14.4 g (64.1%) of Intermediate (G-2).

Synthesis of Intermediate (G-3)

Under an argon atmosphere, 14.4 g of Intermediate (G-2), 19.2 g of 6-bromo-2-fluoro-3-iodonaphthalene, 1.28 g of tetrakis(triphenylphosphine)palladium(0), 180 mL of toluene, and 95 mL of a 2M sodium carbonate aqueous solution were added to a flask, and then, the reaction solution was heated, refluxed, and stirred for about 8 hours. After the reaction solution was cooled to room temperature, an extraction process was performed on the reaction solution by using toluene, and an aqueous layer was removed therefrom. Then, an organic layer was washed with a saturated saline solution. The organic layer was dried with MgSO$_4$ and concentrated. The residue obtained therefrom was purified by silica gel column chromatography, thus preparing 17.9 g (75.6%) of Intermediate (G-3).

Synthesis of Intermediate (G-4)

Under an argon atmosphere, 17.9 g of Intermediate (G-3) and 300 mL of dichloromethane (dehydrated) were added to a flask and was cooled to a temperature of −78° C. 90 mL of dichloromethane solution of 1M BBr₃ was added thereto. Then, the reaction solution was stirred for about 3 hours while being heated to room temperature. 150 mL of ice water was added to the reaction solution, and an aqueous layer was removed therefrom. Then, an organic layer was dried with MgSO₄. The organic layer was concentrated, and a residue obtained therefrom was purified through a silica gel short column, thus preparing 16.7 g (99.6%) of Intermediate (G-4).

Synthesis of Intermediate (G)

16.7 g of Intermediate (G-4), 300 mL of N-methyl-2-pyrrolidone (dehydrated), and 24.2 g of K₂CO₃ were added to a flask and stirred at a temperature of 200° C. for about 2 hours. After the reaction was completed, the solution was cooled to room temperature. 2 L of toluene was added thereto and the mixed solution was put in a separating funnel. Then, a washing process was performed thereon with water. The mixed solution was dried with MgSO₄ and impurities were removed therefrom through a silica gel short column. Then, the solution was concentrated and recrystallized in a toluene/methanol mixed solvent, thus preparing 9.9 g (65.6%) of Intermediate (G).

Synthesis of Intermediate (H7-1)

6.0 g (65.4%) of Intermediate (H7-1) was synthesized in substantially the same manner as in Synthesis of Intermediate (H1-1), except that Intermediate (G) was used instead of Intermediate (A).

Synthesis of Intermediate (H7-2)

6.7 g (70.4%) of Intermediate (H7-2) was synthesized in substantially the same manner as in Synthesis of Intermediate (H1-2), except that Intermediate (H7-1) was instead of Intermediate (H1-1), and 1-bromo-4-iodonaphthalene was used instead of 1-bromo-4-iodobenzene.

Synthesis of Compound H7

6.2 g (63.9%) of Compound H7 was synthesized in substantially the same manner as in Synthesis of Compound H1, except that Intermediate (H7-2) was used instead of Intermediate (H1-2), and 9-(3-(naphthalene-2-yl)phenyl)anthracene-10-yl-10-boronic acid was used instead of 9-(naphthalene-3-yl)anthracene-10-yl-10-boronic acid. MW=812.97, m/e=812.27.

Synthesis Example 8: Synthesis of Compound H8

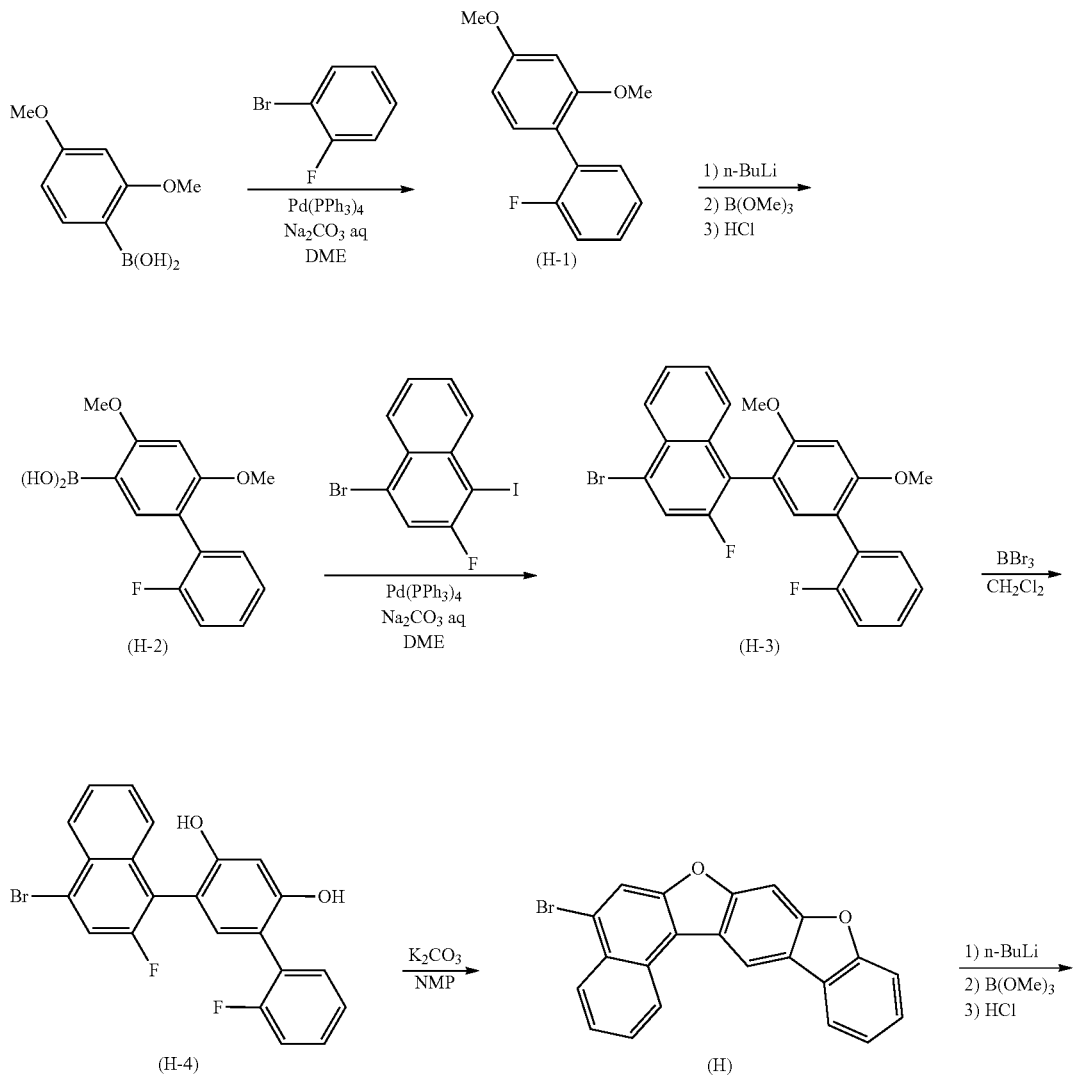

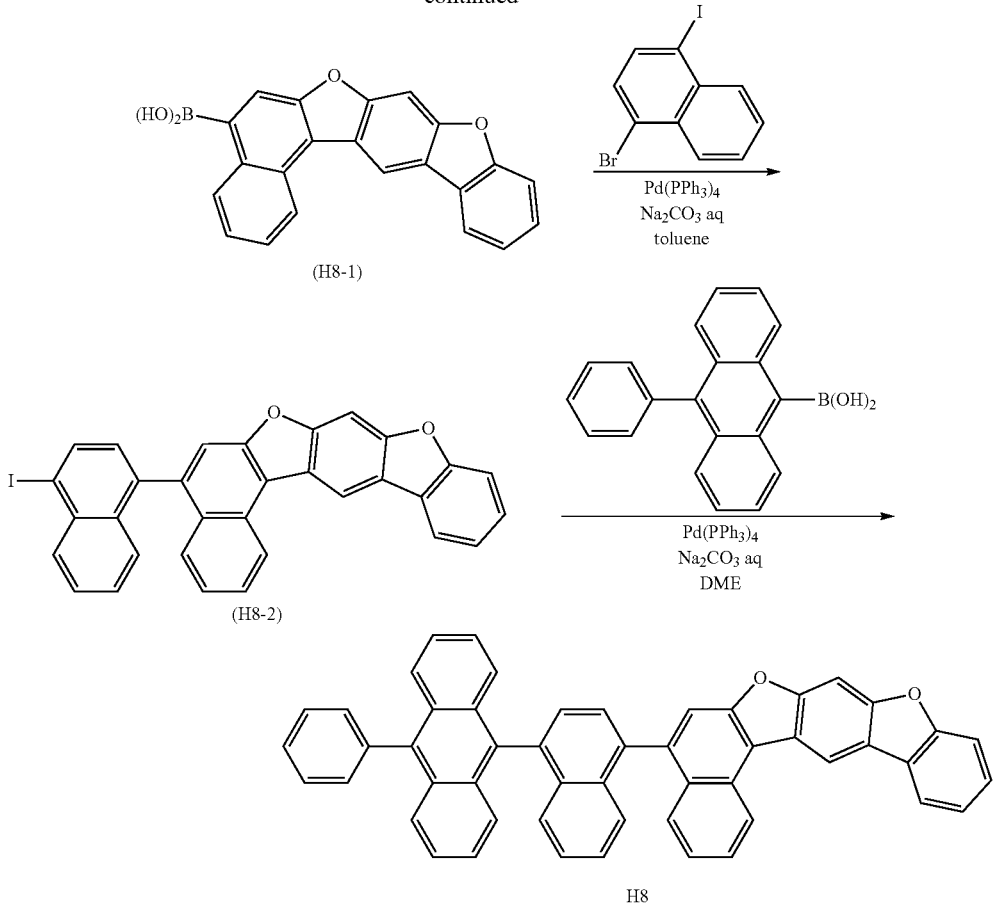

Synthesis of Intermediate (H-1)

Under an argon atmosphere, 17.3 g of 2,4-dimethoxyphenyl boronic acid, 17.5 g of 1-bromo-2-fluorobenzene, 2.34 g of tetrakis(triphenylphosphine)palladium(0), 300 mL of 1,2-dimethoxyethane, and 150 mL of a 2M sodium carbonate aqueous solution were added to a flask, and then, the mixture was heated, refluxed, and stirred for about 8 hours. The mixture was cooled to room temperature, and an aqueous layer was removed therefrom. Then, an organic layer was washed with a saturated saline solution. The organic layer was dried with $MgSO_4$ and concentrated. The residue obtained therefrom was purified by silica gel column chromatography, thus preparing 18.7 g (84.9%) of Intermediate (H-1).

Synthesis of Intermediate (H-2)

Under an argon atmosphere, 18.7 g of Intermediate (H-1) and 500 mL of anhydrous THF were added to a flask, and 55 mL of a hexane solution of 1.6M n-butyllithium was added thereto. Then, the reaction solution was stirred at room temperature for about 4 hours. The reaction solution was cooled to a temperature of −78° C., and 30 mL of a THF solution of 28.1 g of trimethyl borate was added thereto. Then, the reaction solution was stirred for about 8 hours while being heated to room temperature. 200 mL of 10% HCl was added to the reaction solution and the mixed solution was stirred for 2 hours. An extraction process was performed on the reaction solution by using ether, and an aqueous layer was removed therefrom. Then, an organic layer was washed with a saturated saline solution. The organic layer was dried with $MgSO_4$ and concentrated. The residue obtained therefrom was washed with hexane, thus preparing 14.3 g (64.3%) of Intermediate (H-2).

Synthesis of Intermediate (H-3)

Under an argon atmosphere, 14.3 g of Intermediate (H-2), 19.2 g of 4-bromo-2-fluoro-1-iodonaphthalene, 1.28 g of tetrakis(triphenylphosphine)palladium(0), 180 mL of toluene, and 95 mL of a 2M sodium carbonate aqueous solution were added to a flask, and then, the reaction solution was heated, refluxed, and stirred for about 8 hours. After the reaction solution was cooled to room temperature, an extraction process was performed on the reaction solution by using toluene, and an aqueous layer was removed therefrom. Then, an organic layer was washed with a saturated saline solution. The organic layer was dried with $MgSO_4$ and concentrated. The residue obtained therefrom was purified by silica gel column chromatography, thus preparing 17.8 g (75.4%) of Intermediate (H-3).

Synthesis of Intermediate (H-4)

Under an argon atmosphere, 17.9 g of Intermediate (H-3) and 300 mL of dichloromethane (dehydrated) were added to a flask and was cooled to a temperature of −78° C. 90 mL of dichloromethane solution of 1M $BBr_3$ was added thereto. Then, the reaction solution was stirred for about 3 hours while being heated to room temperature. 150 mL of ice water was added to the reaction solution, and an aqueous layer was removed therefrom. Then, an organic layer was dried with $MgSO_4$. The organic layer was concentrated, and a residue obtained therefrom was purified through a silica gel short column, thus preparing of 16.7 g (99.6%) of Intermediate (H-4).

Synthesis of Intermediate (H)

16.7 g of Intermediate (H-4), 300 mL of N-methyl-2-pyrrolidone (dehydrated), and 24.2 g of $K_2CO_3$ were added to a flask and stirred at a temperature of 200° C. for about 2 hours. After the reaction was completed, the solution was cooled to room temperature. 2 L of toluene was added thereto and the mixed solution was put in a separating funnel. Then, a washing process was performed thereon with water. The mixed solution was dried with $MgSO_4$ and impurities were removed therefrom through a silica gel short column. Then, the solution was concentrated and recrystallized in a toluene/methanol mixed solvent, thus preparing 9.7 g (64.3%) of Intermediate (H).

Synthesis of Intermediate (H8-1)

5.7 g (64.5%) of Intermediate (H8-1) was synthesized in substantially the same manner as in Synthesis of Intermediate (H1-1), except that Intermediate (H) was used instead of Intermediate (A).

Synthesis of Intermediate (H8-2)

5.8 g (64.6%) of Intermediate (H8-2) was synthesized in substantially the same manner as in Synthesis of Intermediate (H1-2), except that Intermediate (H8-1) was used instead of Intermediate (H1-1), and 1-bromo-4-iodonaphthalene was used instead of 1-bromo-4-iodobenzene.

Synthesis of Compound H8

4.5 g (63.2%) of Compound H8 was synthesized in substantially the same manner as in Synthesis of Compound H1, except that Intermediate (H8-2) was used instead of Intermediate (H1-2), and 9-phenylanthracene-10-yl-10-boronic acid was used instead of 9-(naphthalene-3-yl)anthracene-10-yl-10-boronic acid. MW=686.81, m/e=686.22.

Synthesis Example 9: Synthesis of Compound H9

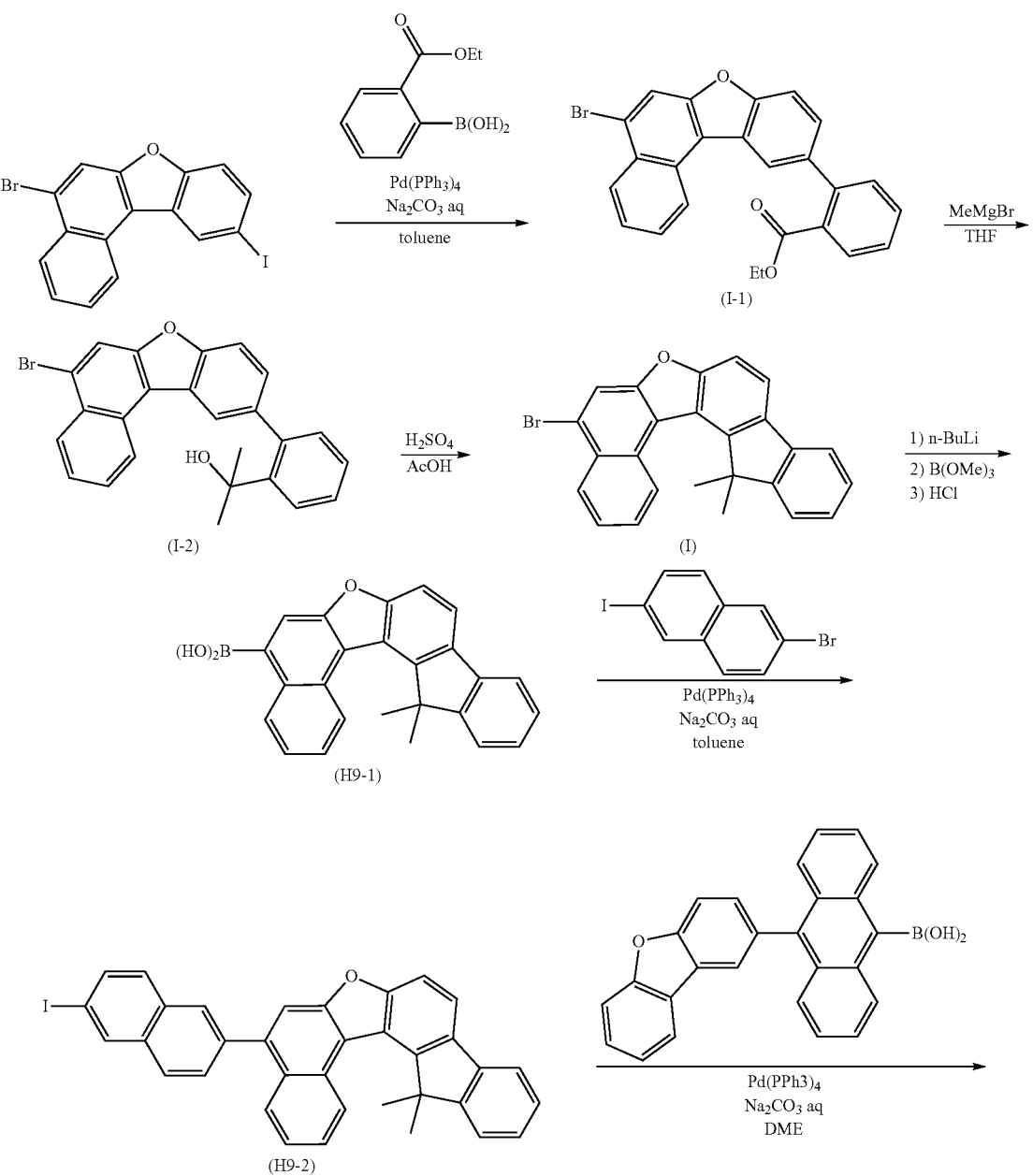

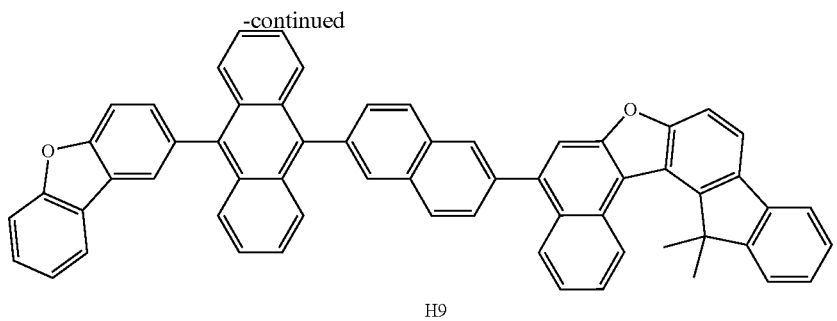

H9

Synthesis of Intermediate (I-1)

Under an argon atmosphere, a mixture including 12.7 g of 5-bromo-10-iodonaphtho[2,1-b]benzofuran, 5.8 g of 2-(ethoxycarbonyl)phenylboronic acid, 0.4 g of tetrakis(triphenylphosphite) palladium(0), 30 mL of 2M sodium carbonate aqueous solution, and 60 mL of toluene was heated and refluxed for about 8 hours. The obtained mixture was cooled to room temperature, and an extraction process was performed thereon with toluene. An organic layer was washed with a saturated saline solution. The organic layer was dried with anhydrous sodium sulfate and a solvent was distilled with reduced pressure. The residue obtained therefrom was purified by silica gel column chromatography, thus preparing 8.6 g (64.6%) of Intermediate (I-1).

Synthesis of Intermediate (I-2)

Under an argon atmosphere, 30 mL of a THF solution of 1M methylmagnesium bromide was ice-cooled and added to 90 mL of a THF solution of 8.6 g of Intermediate (I-1) and was then stirred at room temperature for about 5 hours. Ice water was added to the reaction solution. Then, an extraction process was performed thereon with toluene and an organic layer was washed with a saturated saline solution. The organic layer was dried with anhydrous sodium sulfate and a solvent was distilled with reduced pressure. The residue obtained therefrom was purified by silica gel column chromatography, thus preparing 6.3 g (74.9%) of Intermediate (I-2).

Synthesis of Intermediate (I)

0.7 mL of sulfuric acid was added to 70 mL of acetic acid solution of 6.3 g of Intermediate (I-2), and the mixture was stirred at a temperature of 50° C. for about 8 hours. The obtained mixture was cooled to room temperature and was separated by adding toluene and water thereto. A toluene layer was washed with water and a saturated saline solution. Then, the result was dried with anhydrous sodium sulfate and a solvent was distilled with reduced pressure. The residue obtained therefrom was purified by chromatography, thus preparing 2.1 g (34.6%) of Intermediate (I).

Synthesis of Intermediate (H9-1)

1.2 g (64.9%) of Intermediate (H9-1) was synthesized in substantially the same manner as in Synthesis of Intermediate (H1-1), except that Intermediate (I) was used instead of Intermediate (A).

Synthesis of Intermediate (H9-2)

1.3 g (67.2%) of Intermediate (H9-2) was synthesized in substantially the same manner as in Synthesis of Intermediate (H1-2), except that Intermediate (H9-1) was used instead of Intermediate (H1-1), and 2-bromo-6-iodonaphthalene was used instead of 1-bromo-4-iodobenzene.

Synthesis of Compound H9

1.1 g (64.7%) of Compound H9 was synthesized in substantially the same manner as in Synthesis of Compound H1, except that Intermediate (H9-2) was used instead of Intermediate (H1-2), and 9-(9H-dibenzofuran-2-yl)anthracene-10-yl-10-boronic acid was used instead of 9-(naphthalene-3-yl)anthracene-10-yl-10-boronic acid. MW=802.97, m/e=802.29.

Example 1

An anode was prepared by cutting an ITO glass substrate, on which an ITO layer was deposited to a thickness of 15 Ω/cm$^2$ (1,200 Å), to a size of 50 mm×50 mm×0.7 mm, ultrasonically cleaning the ITO glass substrate (anode) by using isopropyl alcohol and pure water each for about 5 minutes, and exposing the ITO glass substrate (anode) to UV irradiation for about 30 minutes and ozone to clean the ITO glass substrate (anode). Then, the ITO glass substrate (anode) was loaded into a vacuum deposition apparatus.

Compound HT13 was vacuum-deposited on the ITO glass substrate (anode) to form a hole injection layer having a thickness of about 500 Å, and Compound HT3 was vacuum-deposited on the hole injection layer to form a hole transport layer having a thickness of about 450 Å.

Compound H1 (host) and Compound FD1 (dopant) were co-deposited on the hole transport layer at a weight ratio of 95:5 to form an emission layer having a thickness of about 300 Å.

Compound ET1 was deposited on the emission layer to form an electron transport layer having a thickness of about 250 Å. LiF was deposited on the electron transport layer to form an electron injection layer having a thickness of about 50 Å. Al was vacuum-deposited on the electron injection layer to form a cathode having a thickness of about 1,500 Å. Thus, an organic light-emitting device was formed.

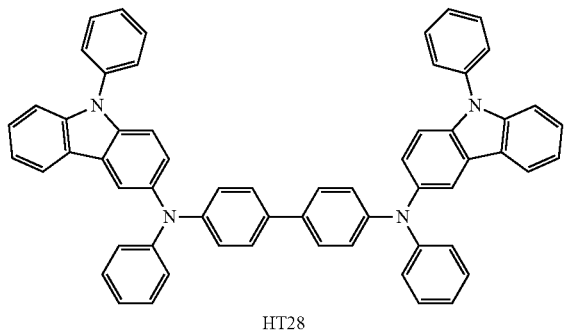

HT28

729
-continued

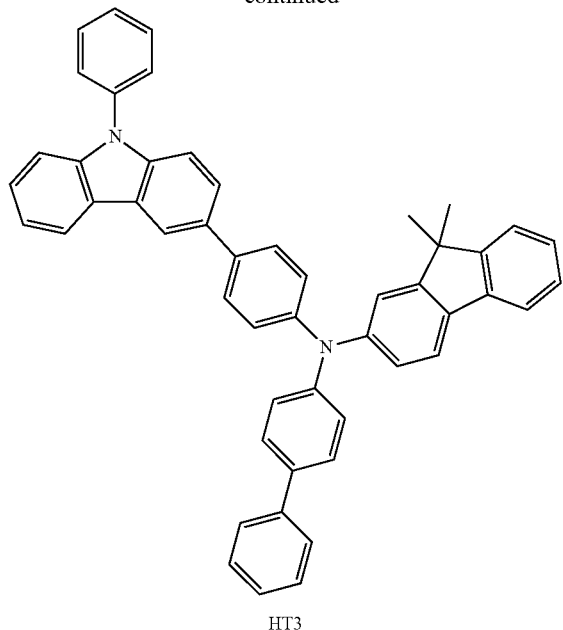

HT3

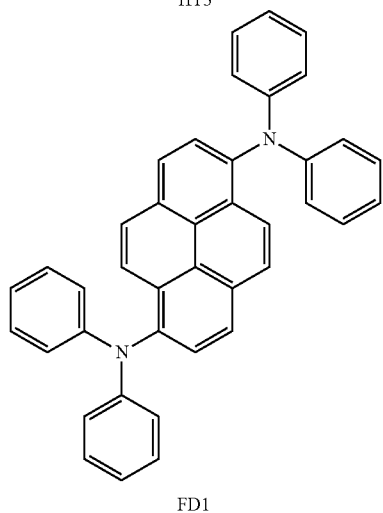

FD1

730
-continued

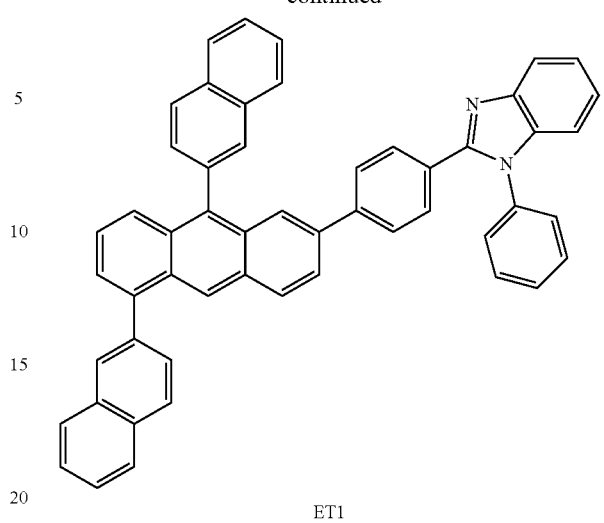

ET1

Examples 2 to 9 and Comparative Examples 1 to 4

Organic light-emitting devices of Examples 2 to 9 and Comparative Examples 1 to 4 were manufactured in substantially the same manner as in Example 1, except that Compounds shown in Table 1 were each used in forming an emission layer.

Evaluation Example 1

The efficiency (cd/A) and lifespan ($T_{80}$) data of the organic light-emitting devices manufactured according to Examples 1 to 9 and Comparative Examples 1 to 4 were evaluated by using a Keithley SMU 236 and a luminance meter PR650, and results thereof are shown in Table 1. The lifespan ($T_{80}$) indicates an amount of time that lapsed when luminance was 80% of initial luminance (100%) after the organic light-emitting devices were driven at the current density of 50 mA/cm².

TABLE 1

| | Material for host | Efficiency (cd/A) | Lifespan (hr @ 50 mA/cm²) |
|---|---|---|---|
| Example 1 | H1 | 5.2 | 110 |
| Example 2 | H2 | 5.1 | 100 |
| Example 3 | H3 | 5.3 | 90 |
| Example 4 | H4 | 5.2 | 100 |
| Example 5 | H5 | 5.1 | 90 |
| Example 6 | H6 | 5.1 | 100 |
| Example 7 | H7 | 5.1 | 90 |
| Example 8 | H8 | 5.0 | 110 |
| Example 9 | H9 | 5.2 | 100 |
| Comparative Example 1 | Compound A | 4.5 | 50 |
| Comparative Example 2 | Compound B | 4.7 | 80 |
| Comparative Example 3 | Compound C | 4.9 | 70 |
| Comparative Example 4 | Compound D | 5.0 | 90 |

TABLE 1-continued
| Material for host | Efficiency (cd/A) | Lifespan (hr @ 50 mA/cm²) |
| --- | --- | --- |
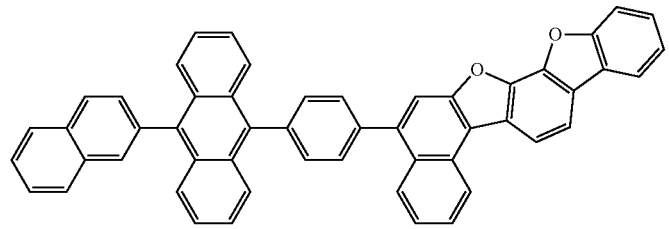 [SMILES: c1ccc2cc(-c3c4ccccc4c(-c4ccc(-c5cc6oc7c(ccc8c9ccccc9oc87)c6c6ccccc56)cc4)c4ccccc34)ccc2c1]
H1
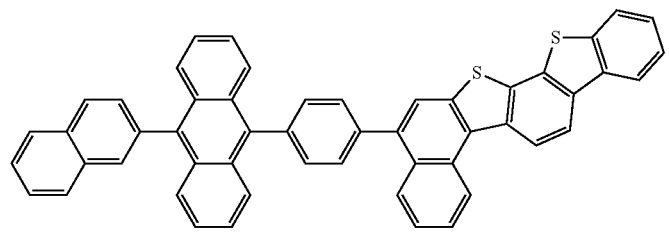
H2
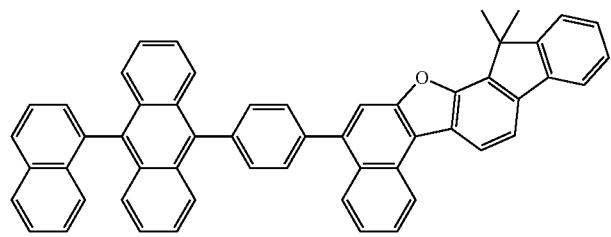 [SMILES: CC1(C)c2ccccc2-c2ccc3c(oc4cc(-c5ccc(-c6c7ccccc7c(-c7cccc8ccccc78)c7ccccc67)cc5)c5ccccc5c43)c21]
H3
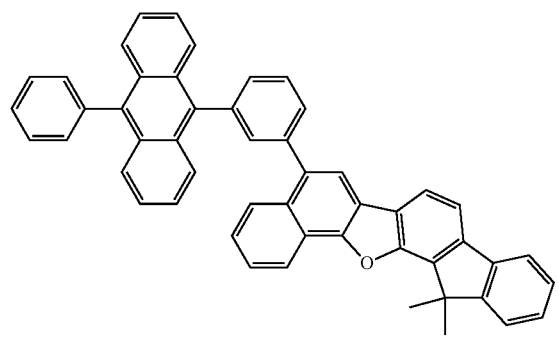 [SMILES: CC1(C)c2ccccc2-c2ccc3c(oc4c5ccccc5c(-c5cccc(-c6c7ccccc7c(-c7ccccc7)c7ccccc67)c5)cc34)c21]
H4
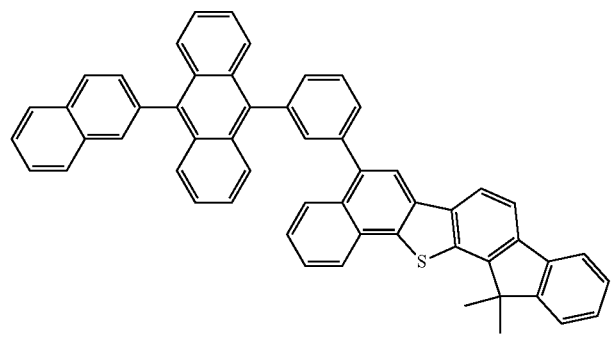 [SMILES: CC1(C)c2ccccc2-c2ccc3c(sc4c5ccccc5c(-c5cccc(-c6c7ccccc7c(-c7ccc8ccccc8c7)c7ccccc67)c5)cc34)c21]
H5

TABLE 1-continued
| Material for host | Efficiency (cd/A) | Lifespan (hr @ 50 mA/cm$^2$) |
| --- | --- | --- |
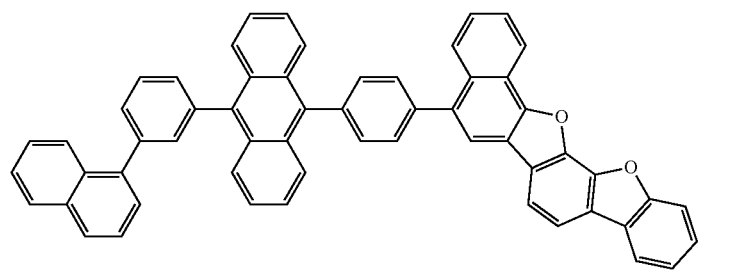 [SMILES: c1cc(-c2cccc3ccccc23)cc(-c2c3ccccc3c(-c3ccc(-c4cc5c6ccc7c8ccccc8oc7c6oc5c5ccccc45)cc3)c3ccccc23)c1]
H6
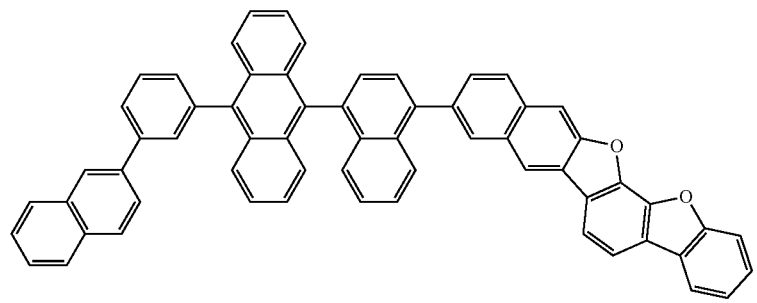 [SMILES: c1cc(-c2ccc3ccccc3c2)cc(-c2c3ccccc3c(-c3ccc(-c4ccc5cc6oc7c(ccc8c9ccccc9oc87)c6cc5c4)c4ccccc34)c3ccccc23)c1]
H7
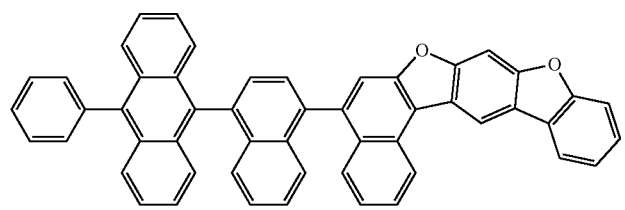 [SMILES: c1ccc(-c2c3ccccc3c(-c3ccc(-c4cc5oc6cc7oc8ccccc8c7cc6c5c5ccccc45)c4ccccc34)c3ccccc23)cc1]
H8
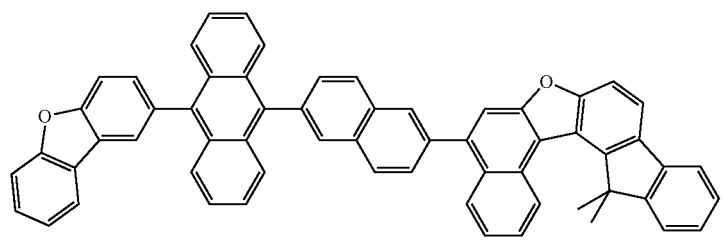 [SMILES: CC1(C)c2ccccc2-c2ccc3oc4cc(-c5ccc6cc(-c7c8ccccc8c(-c8ccc9oc%10ccccc%10c9c8)c8ccccc78)ccc6c5)c5ccccc5c4c3c21]
H9
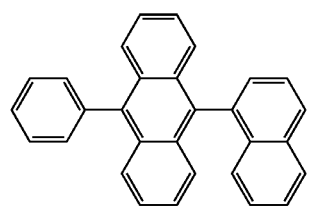 [SMILES: c1ccc(-c2c3ccccc3c(-c3cccc4ccccc34)c3ccccc23)cc1]
A
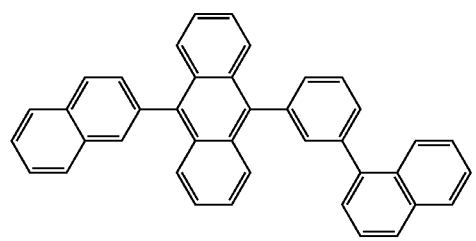 [SMILES: c1cc(-c2cccc3ccccc23)cc(-c2c3ccccc3c(-c3ccc4ccccc4c3)c3ccccc23)c1]
B TABLE 1-continued

| Material for host | Efficiency (cd/A) | Lifespan (hr @ 50 mA/cm²) |
|---|---|---|

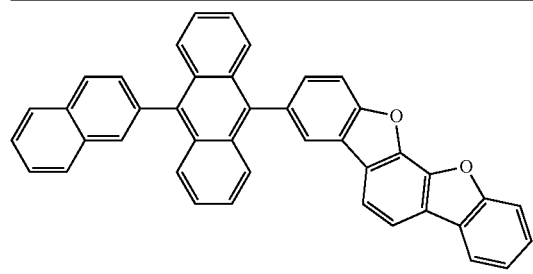
C

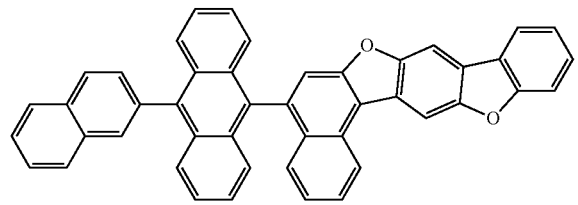 [SMILES: c1ccc2cc(-c3c4ccccc4c(-c4cc5oc6cc7c(cc6c5c5ccccc45)oc4ccccc47)c4ccccc34)ccc2c1]
D

Referring to Table 1, the organic light-emitting devices of Examples 1 to 9 had relatively high efficiency and lifespan characteristics, compared to those of Comparative Examples 1 to 4.

According to one or more exemplary embodiments of the present invention, an organic light-emitting device including the condensed cyclic compound represented by Formula 1-1 or 1-2 may have relatively high efficiency and a relatively long lifespan.

It should be understood that one or more exemplary embodiments of the present invention described herein should be considered in a descriptive sense only and not for purposes of limitation. Descriptions of features or aspects within each exemplary embodiment of the present invention should typically be considered as available for other similar features or aspects in other exemplary embodiments of the present invention.

While one or more exemplary embodiments of the present invention have been described with reference to the figures, it will be understood by those of ordinary skill in the art that various changes in form and details may be made therein without departing from the spirit and scope of the present invention.

What is claimed is:

1. A condensed cyclic compound represented by one selected from Formulae 1(1)-1 to 1(7)-1 and 1(10)-1 to 1(18)-1 used in an emission layer of an organic light-emitting device:

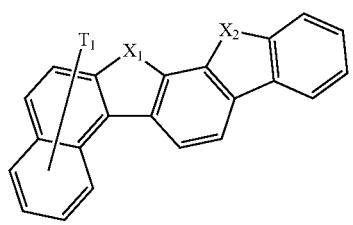
1(1)-1

-continued

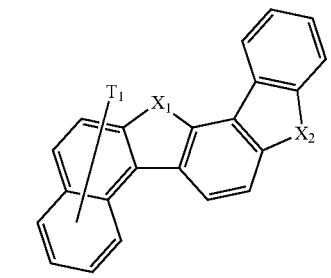
1(2)-1

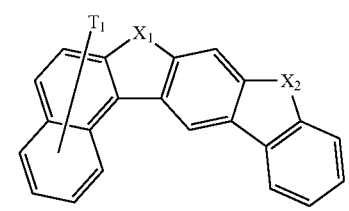
1(3)-1

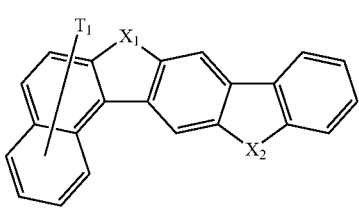
1(4)-1

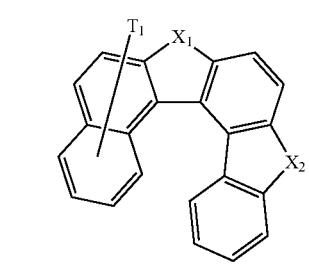
1(5)-1

737
-continued

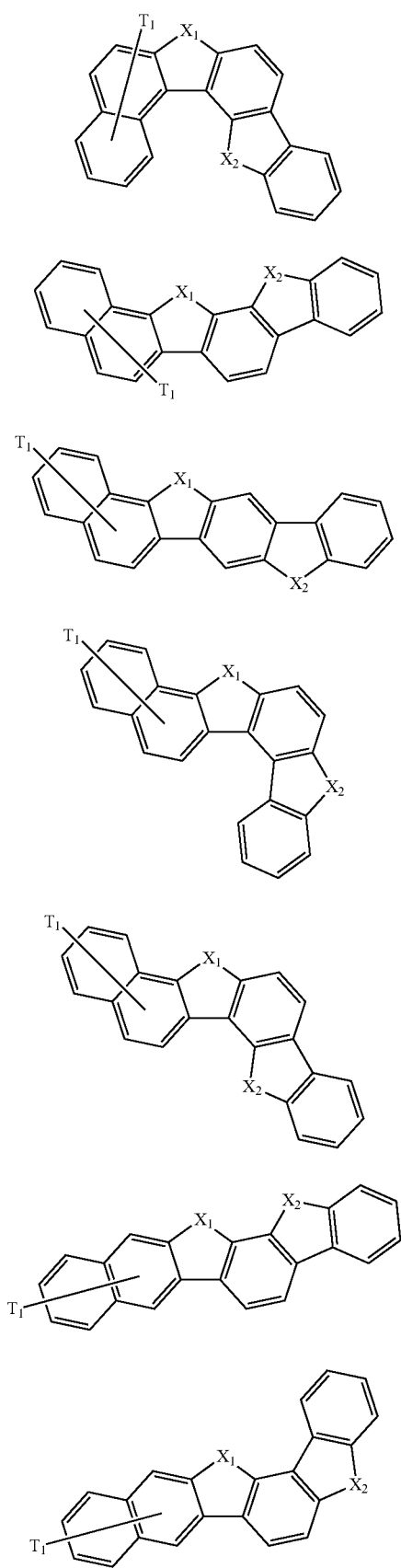

1(6)-1

1(7)-1

1(10)-1

1(11)-1

1(12)-1

1(13)-1

1(14)-1

738
-continued

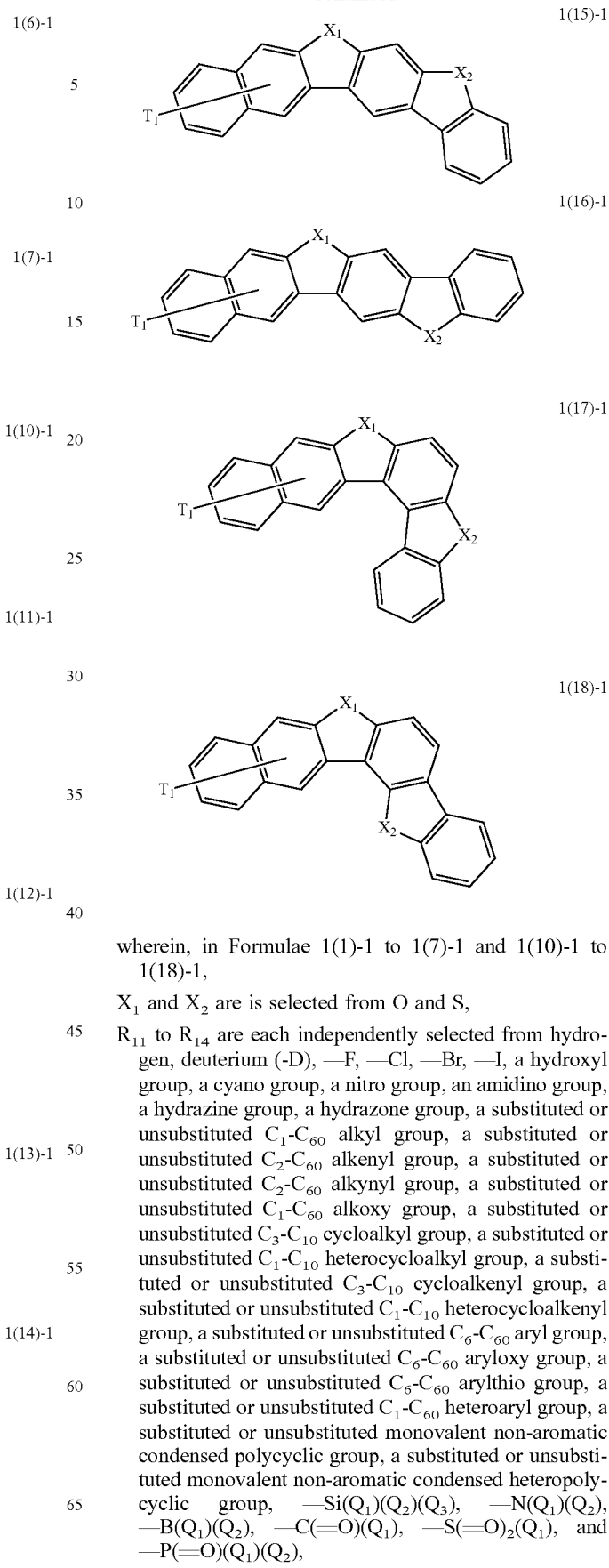

1(15)-1

1(16)-1

1(17)-1

1(18)-1 wherein, in Formulae 1(1)-1 to 1(7)-1 and 1(10)-1 to 1(18)-1, $X_1$ and $X_2$ are is selected from O and S, $R_{11}$ to $R_{14}$ are each independently selected from hydrogen, deuterium (-D), —F, —Cl, —Br, —I, a hydroxyl group, a cyano group, a nitro group, an amidino group, a hydrazine group, a hydrazone group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), —N($Q_1$)($Q_2$), —B($Q_1$)($Q_2$), —C(=O)($Q_1$), —S(=O)$_2$($Q_1$), and —P(=O)($Q_1$)($Q_2$), $T_1$ is a group represented by Formula 2A(1),

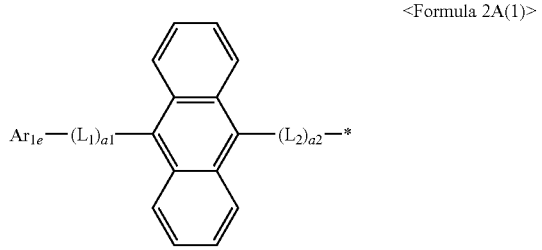

<Formula 2A(1)> wherein, in Formula 2A(1), $L_1$ and $L_2$ are each independently selected from a substituted or unsubstituted $C_3$-$C_{10}$ cycloalkylene, a substituted or unsubstituted $C_1$-$C_{10}$ heterocycloalkylene, a substituted or unsubstituted $C_3$-$C_{10}$ cycloalkenylene, a substituted or unsubstituted $C_1$-$C_{10}$ heterocycloalkenylene, a substituted or unsubstituted $C_6$-$C_{60}$ arylene, a substituted or unsubstituted $C_1$-$C_{60}$ heteroarylene, a substituted or unsubstituted divalent non-aromatic condensed polycyclic group, and a substituted or unsubstituted divalent non-aromatic condensed heteropolycyclic group, a1 is an integer selected from 0, 1, 2, and 3, and a2 is an integer selected from 1, 2, and 3, wherein in Formulae 1(1)-1, 1(7)-1 and 1(13)-1, if $X_1$ and $X_2$ are O, $L_2$ is not a phenylene group, $Ar_{1e}$ is selected from hydrogen, deuterium (-D), —F, —Cl, —Br, —I, a hydroxyl group, a cyano group, a nitro group, an amidino group, a hydrazino group, a hydrazone group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_4$)($Q_5$)($Q_6$), —N($Q_4$)($Q_5$), —B($Q_4$)($Q_5$), —C(=O)($Q_4$), —S(=O)$_2$($Q_4$), and —P(=O)($Q_4$)($Q_5$), at least one substituent selected from a substituent(s) of the substituted $C_3$-$C_{10}$ cycloalkylene group, the substituted $C_1$-$C_{10}$ heterocycloalkylene group, the substituted cycloalkenylene group, the substituted $C_1$-$C_{10}$ heterocycloalkenylene group, the substituted $C_6$-$C_{60}$ arylene group, the substituted $C_1$-$C_{60}$ heteroarylene group, the substituted divalent non-aromatic condensed polycyclic group, the substituted divalent non-aromatic condensed heteropolycyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group is selected from:

deuterium (-D), —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amidino group, a hydrazino group, a hydrazono group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{11}$)($Q_{12}$)($Q_{13}$), —N($Q_{11}$)($Q_{12}$), —B($Q_{11}$)($Q_{12}$), —C(=O)($Q_{11}$), —S(=O)$_2$($Q_{11}$), and —P(=O)($Q_{11}$)($Q_{12}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{21}$)($Q_{22}$)($Q_{23}$), —N($Q_{21}$)($Q_{22}$), —B($Q_{21}$)($Q_{22}$), —C(=O)($Q_{21}$), —S(=O)$_2$($Q_{21}$), and —P(=O)($Q_{21}$)($Q_{22}$); and —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$), $Q_1$ to $Q_6$, $Q_{11}$ to $Q_{13}$, $Q_{21}$ to $Q_{23}$, and $Q_{31}$ to $Q_{33}$ are each independently selected from hydrogen, deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, a monovalent non-aromatic condensed heteropolycyclic group, a biphenyl group, and a terphenyl group, and

* indicates a binding site to a neighboring atom.

2. The condensed cyclic compound of claim 1, wherein, in Formulae 1(3)-1 to 1(5)-1, 1(7)-1 and 1(10)-1 to 1(18)-1,
$X_1$ and $X_2$ are S;
$X_1$ is O and $X_2$ is S;
$X_1$ and $X_2$ are O;
$X_1$ is S and $X_2$ is O.

3. The condensed cyclic compound of claim 1, wherein, in Formulae 1(1)-1 to 1(7)-1 and 1(10)-1 to 1(18)-1, $R_{11}$ to $R_{14}$ are each independently selected from:
hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, and a $C_1$-$C_{20}$ alkoxy group;
—Si($Q_1$)($Q_2$)($Q_3$), —N($Q_1$)($Q_2$), and —B($Q_1$)($Q_2$);
a phenyl group, a biphenyl group, a terphenyl group, a naphthyl group, a fluorenyl group, a phenanthrenyl group, an anthracenyl group, a fluoranthenyl group, a triphenylenyl group, a pyrenyl group, a chrysenyl group, a thiophenyl group, a furanyl group, a carbazolyl group, a benzofuranyl group, a benzothiophenyl group, a dibenzofuranyl group, a dibenzothiophenyl group, a benzocarbazolyl group, and a dibenzocarbazolyl group; and
a phenyl group, a biphenyl group, a terphenyl group, a naphthyl group, a fluorenyl group, a phenanthrenyl group, an anthracenyl group, a fluoranthenyl group, a triphenylenyl group, a pyrenyl group, a chrysenyl group, a thiophenyl group, a furanyl group, a carbazolyl group, a dibenzofuranyl group, a dibenzothiophenyl group, a benzocarbazolyl group, and a dibenzocarbazolyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a phenanthrenyl group, an anthracenyl group, a fluoranthenyl group, a triphenylenyl group, a pyrenyl group, a chrysenyl group, a thiophenyl group, a furanyl group, a carbazolyl group, a dibenzofuranyl group, a dibenzothiophenyl group, a benzocarbazolyl group, a dibenzocarbazolyl group, and —Si($Q_{31}$)($Q_{32}$)($Q_{33}$),
wherein $Q_1$ to $Q_3$ and $Q_{31}$ to $Q_{33}$ are each independently selected from a $C_1$-$C_{10}$ alkyl group, a $C_1$-$C_{10}$ alkoxy group, a phenyl group, a biphenyl group, a terphenyl group, and a naphthyl group.

4. The condensed cyclic compound of claim 1, wherein, in Formula 2A(1),
$L_1$ and $L_2$ are each independently selected from:
a phenylene group, a pentalenylene group, an indenylene group, a naphthylene group, an azulenylene group, a heptalenylene group, an indacenylene group, an acenaphthylene group, a fluorenylene group, a spiro-bifluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a pyrrolylene group, a thiophenylene group, a furanylene group, a carbazolylene group, a benzofuranylene group, a benzothiophenylene group, a dibenzofuranylene group, a dibenzothiophenylene group, a benzocarbazolylene group, and a dibenzocarbazolylene group; and
a phenylene group, a pentalenylene group, an indenylene group, a naphthylene group, an azulenylene group, a heptalenylene group, an indacenylene group, an acenaphthylene group, a fluorenylene group, a spiro-bifluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a pyrrolylene group, a thiophenylene group, a furanylene group, a carbazolylene group, a benzofuranylene group, a benzothiophenylene group, a dibenzofuranylene group, a dibenzothiophenylene group, a benzocarbazolylene group, and a dibenzocarbazolylene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, a benzofuranyl group, a benzothiophenyl group, a dibenzofuranyl group, a dibenzothiophenyl group, a benzocarbazolyl group, and a dibenzocarbazolyl group.

5. The condensed cyclic compound of claim 1, wherein $L_1$ and $L_2$ in Formula 2A(1) are each independently selected from groups represented by Formulae 3-1 to 3-22:

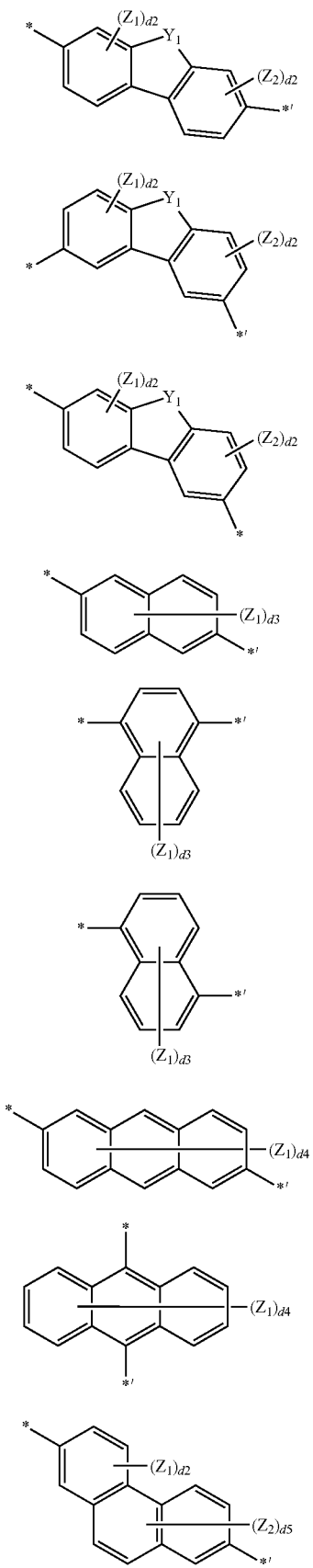
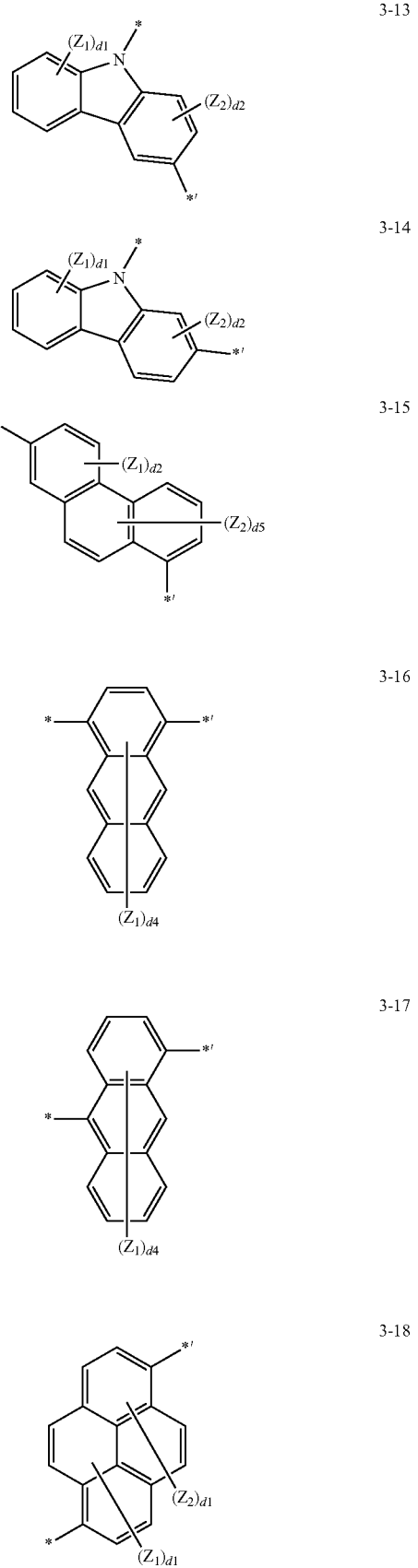

-continued 3-19
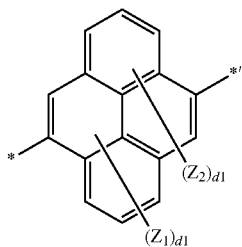

3-20
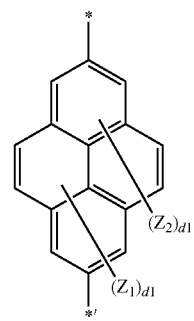

3-21
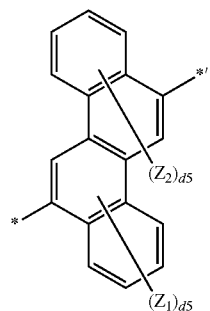

3-22
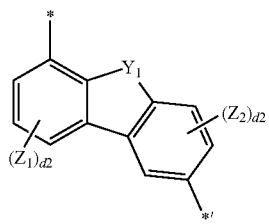

wherein, in Formulae 3-1 to 3-22, $Y_1$ is selected from O, S, $C(Z_3)(Z_4)$, $N(Z_5)$, and $Si(Z_6)(Z_7)$, $Z_1$ to $Z_2$ are each independently selected from hydrogen, deuterium, —F, —Cl, —Br, —I, a hydroxyl group, a cyano group, a nitro group, an amidino group, a hydrazino group, a hydrazone group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a carbazolyl group, and —$Si(Q_{31})(Q_{32})(Q_{33})$, $Q_{31}$ to $Q_{33}$ are each independently selected from a $C_1$-$C_{10}$ alkyl group, a $C_1$-$C_{10}$ alkoxy group, a phenyl group, a naphthyl group, a biphenyl group, and a terphenyl group, and d1 is an integer selected from 1 to 4,
d2 is an integer selected from 1 to 3,
d3 is an integer selected from 1 to 6,
d4 is an integer selected from 1 to 8,
d5 is an integer selected from 1 to 5, and
* and *' each indicate a binding site to a neighboring atom.

6. The condensed cyclic compound of claim 1, wherein $L_1$ and $L_2$ in Formula 2A(1) are each independently selected from groups represented by Formulae 4-1 to 4-35:

4-1
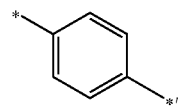

4-2
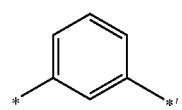

4-3
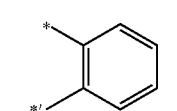

4-4
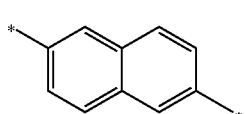

4-5
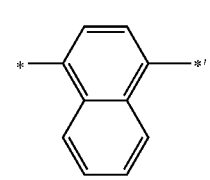

4-6
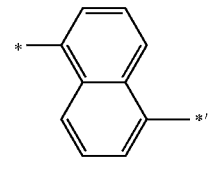

4-7
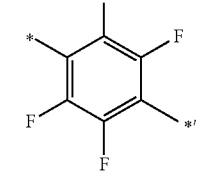

4-8
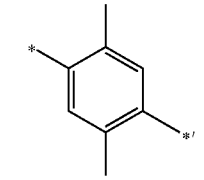

4-9
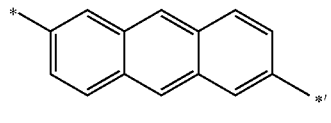

4-10
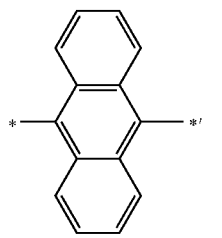
4-11
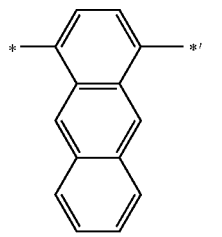
4-12
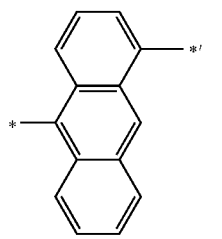
4-13
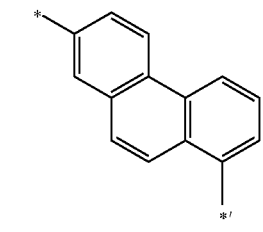
4-14
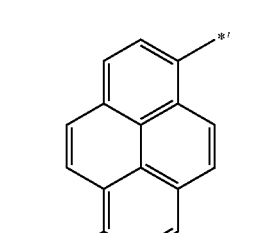
4-15
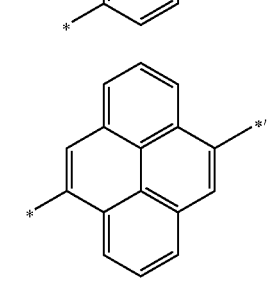
4-16
4-17
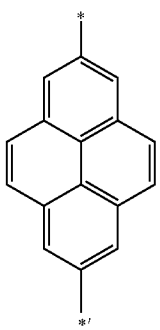
4-18
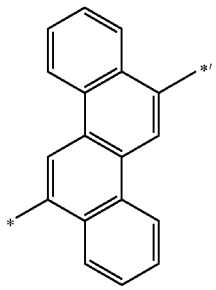
4-19
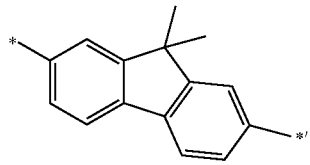
4-20
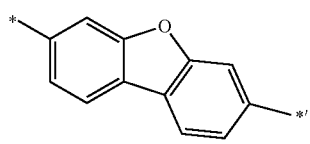
4-21
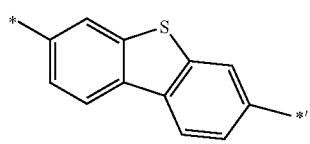
4-22
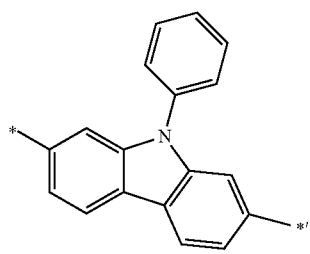
4-23
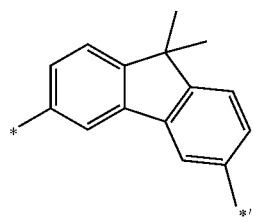

4-24
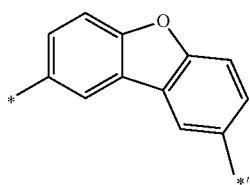
4-25
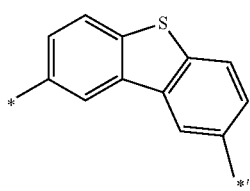
4-26
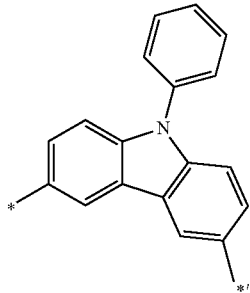
4-27
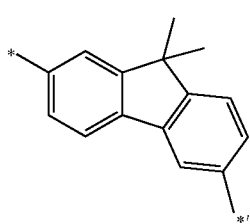
4-28
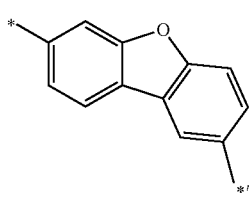
4-29
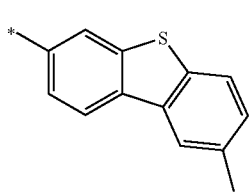
4-30
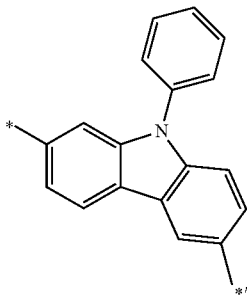
4-31
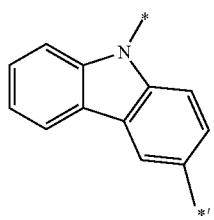
4-32
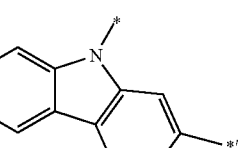
4-33
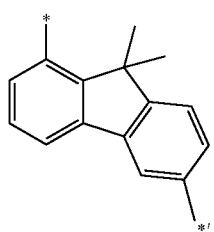
4-34
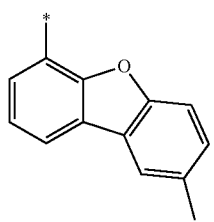
4-35
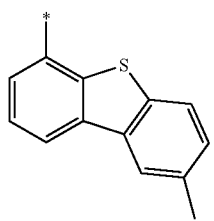
wherein * and *' in Formulae 4-1 and 4-35 each indicate a binding site to a neighboring atom.
7. The condensed cyclic compound of claim 1, wherein, in Formula 2A(1), a1 is an integer selected from 0 and 1 and a2 is an integer selected from 1 and 2.

8. The condensed cyclic compound of claim 1, wherein $Ar_{1e}$ in Formula 2A(1) is selected from:

hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, and a $C_1$-$C_{20}$ alkoxy group;

a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, a benzofuranyl group, a benzothiophenyl group, a dibenzofuranyl group, a dibenzothiophenyl group, a benzocarbazolyl group, a dibenzocarbazolyl group, and a dibenzosilolyl group; and a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a napthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, a benzofuranyl group, a benzothiophenyl group, a dibenzofuranyl group, a dibenzothiophenyl group, a benzocarbazolyl group, a dibenzocarbazolyl group, and a dibenzosilolyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, a benzofuranyl group, a benzothiophenyl group, a dibenzofuranyl group, a dibenzothiophenyl group, a benzocarbazolyl group, a dibenzocarbazolyl group, and a dibenzosilolyl group, and —Si($Q_{31}$)($Q_{32}$)($Q_{33}$), wherein $Q_{31}$ to $Q_{33}$ are each independently selected from a $C_1$-$C_{10}$ alkyl group, a $C_1$-$C_{10}$ alkoxy group, a phenyl group, a naphthyl group, a biphenyl group, and a terphenyl group.

9. The condensed cyclic compound of claim 1, wherein $Ar_{1e}$ in Formula 2A(1) is selected from:

hydrogen, deuterium, —F, —Cl, —Br, —I, a hydroxyl group, a cyano group, a nitro group, an amidino group, a hydrazino group, a hydrazone group, a $C_1$-$C_{10}$ alkyl group, and a $C_1$-$C_{10}$ alkoxy group; and groups represented by Formulae 5-1 to 5-16:

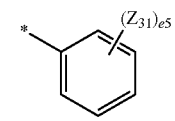

5-1

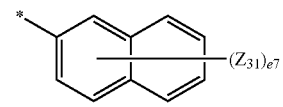

5-2

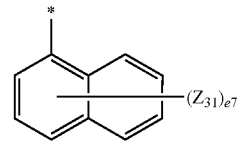

5-3

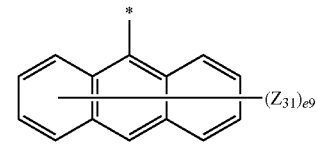

5-4

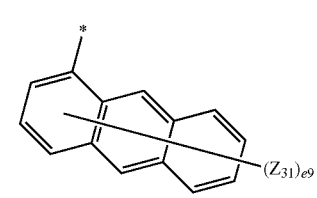

5-5

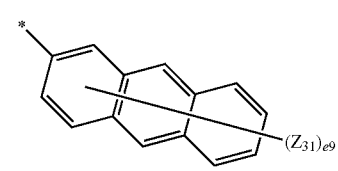

5-6

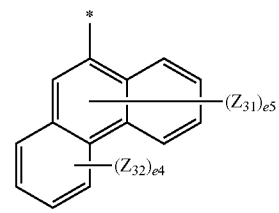

5-7

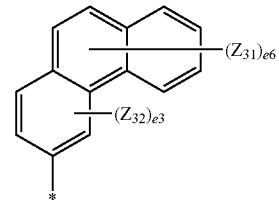

5-8

-continued

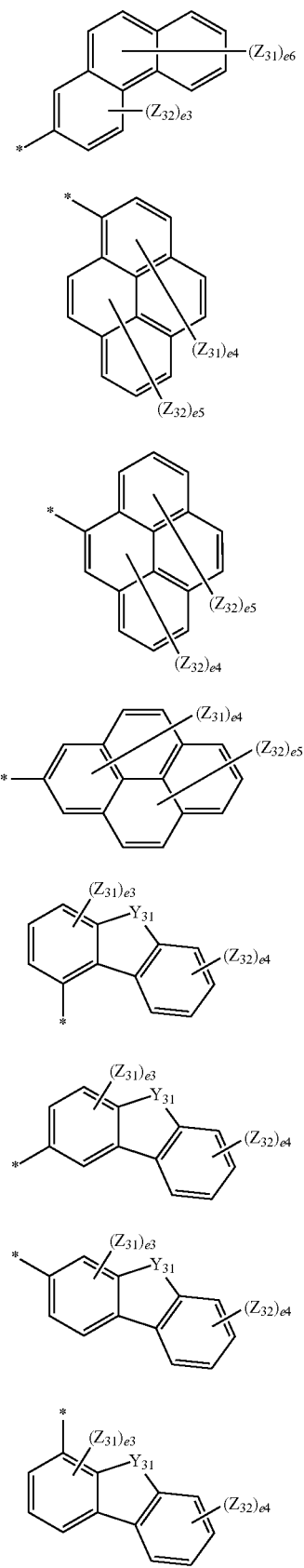

5-9

5-10

5-11

5-12

5-13

5-14

5-15

5-16 wherein, in Formulae 5-1 to 5-16, $Y_{31}$ is selected from O, S, $C(Z_{33})(Z_{34})$, $N(Z_{35})$, and $Si(Z_{36})(Z_{37})$, $Z_{31}$ to $Z_{37}$ are each independently selected from:

hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, and a $C_1$-$C_{20}$ alkoxy group;

a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a triphenylenyl group, a pyrenyl group, a chrysenyl group, a thiophenyl group, a furanyl group, a carbazolyl group, a benzofuranyl group, a benzothiophenyl group, a dibenzofuranyl group, and a dibenzothiophenyl group; and a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a triphenylenyl group, a pyrenyl group, a chrysenyl group, a thiophenyl group, a furanyl group, a carbazolyl group, a benzofuranyl group, a benzothiophenyl group, a dibenzofuranyl group, and a dibenzothiophenyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a triphenylenyl group, a pyrenyl group, a chrysenyl group, a thiophenyl group, a furanyl group, a carbazolyl group, a benzofuranyl group, a benzothiophenyl group, a dibenzofuranyl group, and a dibenzothiophenyl group, e3 is an integer selected from 1 to 3,
e4 is an integer selected from 1 to 4,
e5 is an integer selected from 1 to 5,
e6 is an integer selected from 1 to 6,
e7 is an integer selected from 1 to 7, and
e9 is an integer selected from 1 to 9.

10. The condensed cyclic compound of claim 1, wherein $Ar_{1e}$ in Formula 2A(1) is selected from:

hydrogen, deuterium, —F, —Cl, —Br, —I, a hydroxyl group, a cyano group, a nitro group, an amidino group, a hydrazino group, a hydrazono group, a $C_1$-$C_{10}$ alkyl group, and a $C_1$-$C_{10}$ alkoxy group; and groups represented by Formulae 6-1 to 6-44:

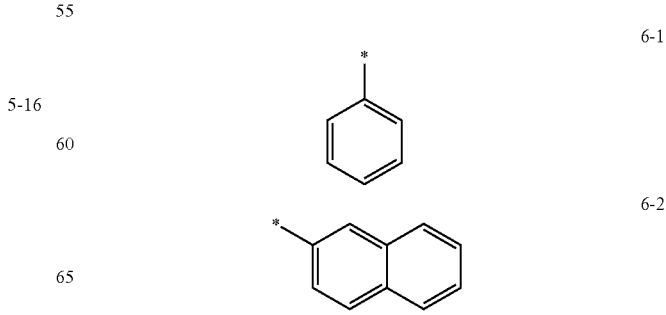

755 756
-continued -continued
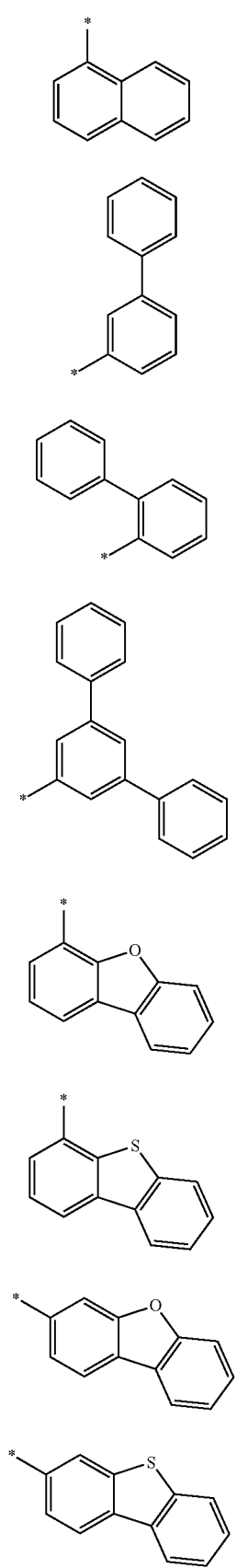
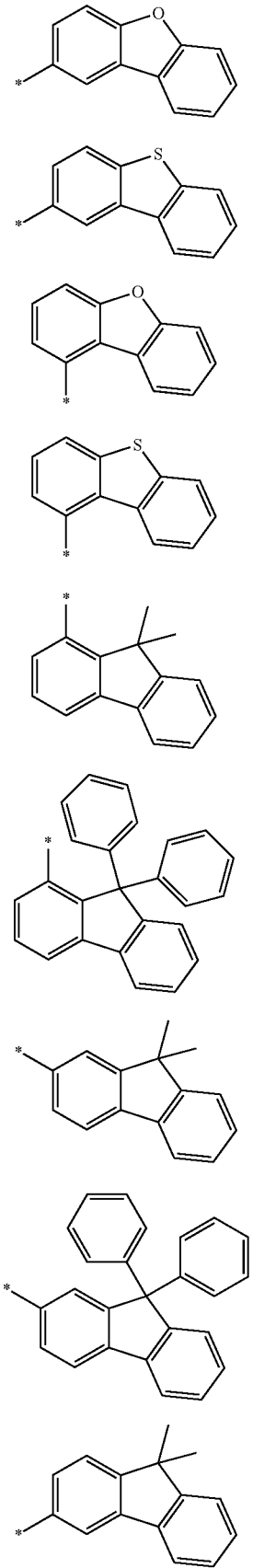
6-3
6-4
6-5
6-6
6-7
6-8
6-9
6-10
6-11
6-12
6-13
6-14
6-15
6-16
6-17
6-18
6-19

6-20 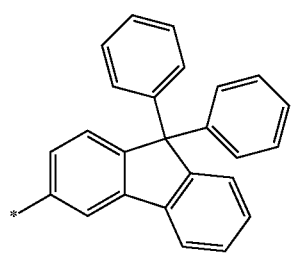
6-21 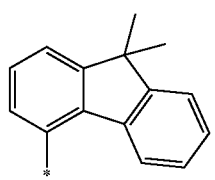
6-22 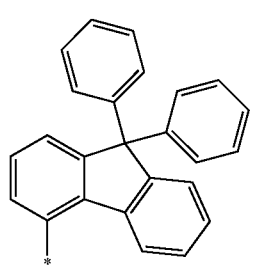
6-23 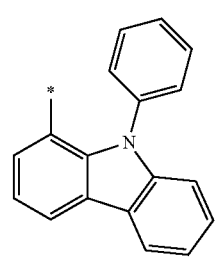
6-24 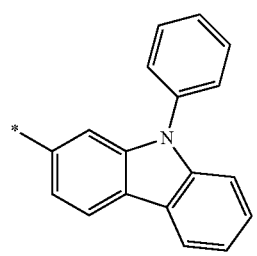
6-25 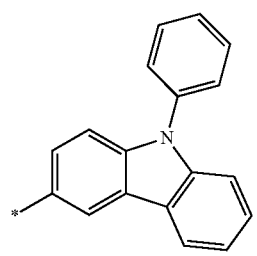
6-26 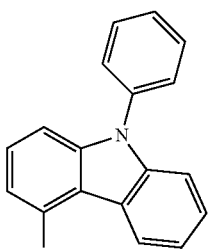
6-27 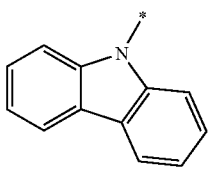
6-28 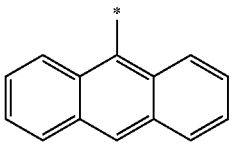
6-29 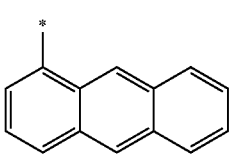
6-30 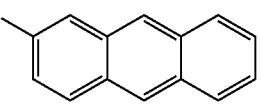
6-31 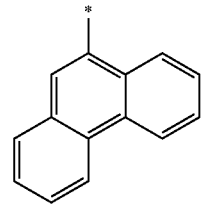
6-32 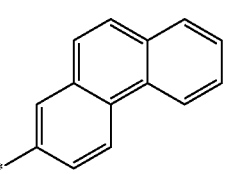
6-33 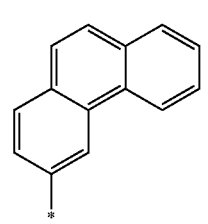

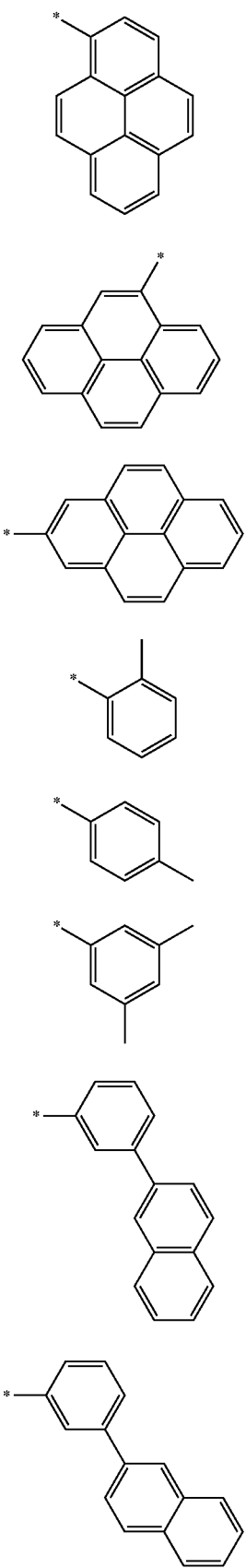

wherein * in Formulae 6-1 to 644 indicates a binding site to a neighboring atom.

11. An organic light-emitting device comprising:
a first electrode;
a second electrode facing the first electrode; and
an organic layer disposed between the first electrode and the second electrode, the organic layer comprising an emission layer,
wherein the organic layer comprises a host having at least one condensed cyclic compound represented by Formulae 1(1)-1 to 1(7)-1 and 1(10)-1 to 1(18)-1 of claim 1.

12. The organic light-emitting device of claim 11, wherein the emission layer comprises the host having at least one condensed cyclic compound represented by Formulae 1(1)-1 to 1(7)-1 and 1(10)-1 to 1(18)-1 of claim 1.

13. The organic light-emitting device of claim 12, wherein the emission layer further comprises a fluorescent dopant.

14. The organic light-emitting device of claim 11, wherein the first electrode is an anode,
the second electrode is a cathode, and
the organic layer comprises a hole transport region disposed between the first electrode and the emission layer, and an electrode transport region disposed between the emission layer and the second electrode, wherein
the hole transport region comprises at least one of a hole injection layer, a hole transport layer, a buffer layer, and an electron blocking layer, and
wherein the electron transport region comprises at least one of a hole blocking layer, an electron transport layer, and an electron injection layer.

15. The organic light-emitting device of claim 14, wherein the electron transport region comprises at least one condensed cyclic compound represented by Formulae 1(1)-1 to 1(7)-1 and 1(10)-1 to 1(18)-1 of claim 1.

16. The organic light-emitting device of claim 11, wherein the organic light-emitting device further includes a first capping layer disposed below the first electrode.

17. The condensed cyclic compound of claim 1, wherein the condensed cyclic compound is represented by one selected from Formulae 1(3)-1, 1(5)-1, 1(6)-1, 1(11)-1, 1(15)-1, 1(16)-1, 1(17)-1.

18. The condensed cyclic compound of claim 1, wherein $X_1$ is different from $X_2$.

* * * * *